US008222028B2

(12) United States Patent
Zieler et al.

(10) Patent No.: US 8,222,028 B2
(45) Date of Patent: Jul. 17, 2012

(54) PLANTS MODIFIED WITH MINI-CHROMOSOMES

(75) Inventors: Helge Zieler, Del Mar, CA (US); Gary W. Rudgers, Indianapolis, IN (US); Daphne Preuss, Chicago, IL (US); Gregory P. Copenhaver, Chapel Hill, NC (US); Michael H. Pauly, Del Mar, CA (US)

(73) Assignee: Chromatin, Inc., Chicago, IL (US)

( * ) Notice: Subject to any disclaimer, the term of this patent is extended or adjusted under 35 U.S.C. 154(b) by 715 days.

(21) Appl. No.: 12/066,175

(22) PCT Filed: Sep. 7, 2006

(86) PCT No.: PCT/US2006/034669
§ 371 (c)(1),
(2), (4) Date: Oct. 22, 2008

(87) PCT Pub. No.: WO2007/030510
PCT Pub. Date: Mar. 15, 2007

(65) Prior Publication Data
US 2009/0222947 A1    Sep. 3, 2009

Related U.S. Application Data

(60) Provisional application No. 60/715,976, filed on Sep. 8, 2005.

(51) Int. Cl.
*C12N 15/82* (2006.01)
*C12N 15/00* (2006.01)
*C12N 15/10* (2006.01)
*A01H 5/00* (2006.01)

(52) U.S. Cl. .............. 435/320.1; 800/278; 800/295; 800/300.1; 435/468; 536/23.1

(58) Field of Classification Search .............. None
See application file for complete search history.

(56) References Cited

U.S. PATENT DOCUMENTS

| | | |
|---|---|---|
| 4,889,806 A | 12/1989 | Olson et al. |
| 5,270,201 A | 12/1993 | Richards et al. |
| 5,288,625 A | 2/1994 | Hadlaczky et al. |
| 5,316,931 A | 5/1994 | Donson et al. |
| 5,491,076 A | 2/1996 | Carrington et al. |
| 5,530,187 A | 6/1996 | Lamb et al. |
| 5,589,379 A | 12/1996 | Kridl et al. |
| 5,650,303 A | 7/1997 | Kridl et al. |
| 5,695,967 A | 12/1997 | Van Bokkelen et al. |
| 5,712,134 A | 1/1998 | Hadlaczky et al. |
| 5,721,118 A | 2/1998 | Scheffler |
| 5,733,744 A | 3/1998 | Hamilton |
| 5,766,885 A | 6/1998 | Carrington et al. |
| 5,866,793 A | 2/1999 | Baga et al. |
| 5,869,294 A | 2/1999 | Harrington et al. |
| 5,877,402 A | 3/1999 | Maliga et al. |
| 5,891,625 A | 4/1999 | Buchardt et al. |
| 5,891,691 A | 4/1999 | Hadlaczky et al. |
| 5,925,808 A | 7/1999 | Oliver et al. |
| 5,977,439 A | 11/1999 | Hamilton |
| 5,977,441 A | 11/1999 | Oliver et al. |
| 6,025,155 A | 2/2000 | Hadlaczky et al. |
| 6,077,697 A | 6/2000 | Hadlaczky et al. |
| 6,127,171 A | 10/2000 | Slilaty et al. |
| 6,156,953 A | 12/2000 | Preuss et al. |
| 6,162,963 A | 12/2000 | Kucherlapati et al. |
| 6,265,211 B1 | 7/2001 | Choo et al. |
| 6,277,608 B1 | 8/2001 | Hartley et al. |
| 6,277,632 B1 | 8/2001 | Harney |
| 6,291,243 B1 | 9/2001 | Fogarty et al. |
| 6,337,431 B1 | 1/2002 | Tricoli et al. |
| 6,348,353 B1 | 2/2002 | Harrington et al. |
| 6,365,377 B1 | 4/2002 | Patten et al. |
| 6,369,296 B1 | 4/2002 | Ratcliff et al. |
| 6,376,234 B1 | 4/2002 | Grimsley et al. |
| 6,376,745 B1 | 4/2002 | Atabekov et al. |
| 6,388,168 B1 | 5/2002 | Maliga et al. |
| 6,391,639 B1 | 5/2002 | Schenk et al. |
| 6,455,315 B1 | 9/2002 | Baszczynski et al. |
| 6,472,586 B1 | 10/2002 | Maliga et al. |
| 6,475,798 B2 | 11/2002 | Fogarty et al. |
| 6,495,318 B2 | 12/2002 | Harney |
| 6,514,693 B1 | 2/2003 | Lansdorp |
| 6,573,427 B1 | 6/2003 | Atabekov et al. |

(Continued)

FOREIGN PATENT DOCUMENTS

EP    0320500    6/1989
(Continued)

OTHER PUBLICATIONS

Ananiev et al 2009 Chromosoma 118:157-177.*
Adam et al., Retrofitting YACs for direct DNA transfer into plant cells, *Plant J.* 11:1349-58 (1997).
Broun et al., Characterization and genetic mapping of simple repeat sequences in the tomato genome, *Mol. Gen. Genet.* 250: 39-49 (1996).
Ganal et al., A molecular and cytogenetic survey of major repeated DNA sequences in tomato (*Lycopersicon esculentum*), *Mol. Gen. Genet.* 213: 262-8 (1988).
Zabel et al., Towards the construction of artificial chromosomes for tomato, 609-24, 1985.
Abdullah et al, "Efficient Plant Regeneration from Rice Protoplasts through Somatic Embryogenesis," *BioTechnology* 4: 1087-1090 (1986).

(Continued)

*Primary Examiner* — Brent T Page
(74) *Attorney, Agent, or Firm* — Marshall, Gerstein & Borun LLP

(57) ABSTRACT

The invention is generally related to methods of generating plants transformed with novel autonomous mini-chromosomes. Mini-chromosomes with novel compositions and structures are used to transform plants cells which are in turn used to generate the plant. Methods for generating the plant include methods for delivering the mini-chromosome into plant cell to transform the cell, methods for selecting the transformed cell, and methods for isolating plants transformed with the mini-chromosome. Plants generated in the present invention contain novel genes introduced into their genome by integration into existing chromosomes.

60 Claims, No Drawings

U.S. PATENT DOCUMENTS

| | | | |
|---|---|---|---|
| 2001/0008025 | A1 | 7/2001 | Hadlaczky et al. |
| 2002/0028513 | A1 | 3/2002 | Fogarty et al. |
| 2002/0034814 | A1 | 3/2002 | Atabekov et al. |
| 2002/0059660 | A1 | 5/2002 | Tricoli et al. |
| 2002/0072097 | A1 | 6/2002 | Delcardayre et al. |
| 2002/0076811 | A1 | 6/2002 | Okazaki et al. |
| 2002/0094574 | A1 | 7/2002 | Hartley et al. |
| 2002/0108146 | A1 | 8/2002 | Pang et al. |
| 2002/0111930 | A1 | 8/2002 | Battles |
| 2002/0123053 | A1 | 9/2002 | Luo et al. |
| 2002/0123145 | A1 | 9/2002 | Ow |
| 2002/0128457 | A1 | 9/2002 | Anderson et al. |
| 2002/0132348 | A1 | 9/2002 | Bradshaw et al. |
| 2002/0151058 | A1 | 10/2002 | Perkins et al. |
| 2002/0155530 | A1 | 10/2002 | Szybalski et al. |
| 2002/0160410 | A1 | 10/2002 | Hadlaczky et al. |
| 2002/0160970 | A1 | 10/2002 | Hadlaczky et al. |
| 2002/0172997 | A1 | 11/2002 | Hartley et al. |
| 2002/0174453 | A1 | 11/2002 | Daniell et al. |
| 2002/0192819 | A1 | 12/2002 | Hartley et al. |
| 2003/0003435 | A1 | 1/2003 | DeJong et al. |
| 2003/0003466 | A1 | 1/2003 | Harrington et al. |
| 2003/0022204 | A1 | 1/2003 | Landsorp |
| 2003/0032186 | A1 | 2/2003 | Jorgensen et al. |
| 2003/0033617 | A1 | 2/2003 | Hadlaczky et al. |
| 2003/0041353 | A1 | 2/2003 | Daniell et al. |
| 2003/0049665 | A1 | 3/2003 | Szybalski et al. |
| 2003/0064509 | A1 | 4/2003 | Marynen et al. |
| 2003/0077804 | A1 | 4/2003 | Byrd et al. |
| 2003/0083293 | A1 | 5/2003 | Hadlaczky et al. |
| 2003/0084482 | A1 | 5/2003 | Hall et al. |
| 2003/0088081 | A1 | 5/2003 | Maliga et al. |
| 2003/0097678 | A1 | 5/2003 | Kushinov et al. |
| 2003/0101480 | A1 | 5/2003 | Hadlaczky et al. |
| 2003/0108914 | A1 | 6/2003 | Hadlaczky |
| 2003/0124561 | A1 | 7/2003 | Mach et al. |
| 2007/0271629 | A1 | 11/2007 | Ananiev et al. |

FOREIGN PATENT DOCUMENTS

| | | |
|---|---|---|
| EP | 0338266 | 10/1989 |
| EP | 0442174 | 8/1991 |
| EP | 0552829 | 7/1993 |
| EP | 0959134 | 11/1999 |
| WO | WO-89/09219 | 5/1989 |
| WO | WO-91/02066 | 2/1991 |
| WO | WO-91/13994 | 9/1991 |
| WO | WO-92/07080 | 4/1992 |
| WO | WO-93/05165 | 3/1993 |
| WO | WO-95/02319 | 1/1995 |
| WO | WO-95/12669 | 5/1995 |
| WO | WO-96/40965 | 12/1996 |
| WO | WO-97/06250 | 2/1997 |
| WO | WO-97/14026 | 4/1997 |
| WO | WO-97/40183 | 10/1997 |
| WO | WO-98/02562 | 1/1998 |
| WO | WO-98/08964 | 3/1998 |
| WO | WO-98/37223 | 8/1998 |
| WO | WO-98/51790 | 11/1998 |
| WO | WO-98/54342 | 12/1998 |
| WO | WO-98/55637 | 12/1998 |
| WO | WO-99/21977 | 5/1999 |
| WO | WO-99/67374 | 12/1999 |
| WO | WO-00/06715 | 2/2000 |
| WO | WO-00/07431 | 2/2000 |
| WO | WO-00/40723 | 7/2000 |
| WO | WO-00/46350 | 8/2000 |
| WO | WO-00/52155 | 9/2000 |
| WO | WO-00/52183 | 9/2000 |
| WO | WO-00/55325 | 9/2000 |
| WO | WO-00/75289 | 12/2000 |
| WO | WO-00/75299 | 12/2000 |
| WO | WO-00/78985 | 12/2000 |
| WO | WO-01/00858 | 1/2001 |
| WO | WO-01/05962 | 1/2001 |
| WO | WO-01/11020 | 2/2001 |
| WO | WO-01/20011 | 3/2001 |
| WO | WO-01/27241 | 4/2001 |
| WO | WO-01/29241 | 4/2001 |
| WO | WO-01/59091 | 8/2001 |
| WO | WO-01/78976 | 8/2001 |
| WO | WO-01/64024 | 9/2001 |
| WO | WO-01/77357 | 10/2001 |
| WO | WO-02/00842 | 1/2002 |
| WO | WO-02/04629 | 1/2002 |
| WO | WO-02/08409 | 1/2002 |
| WO | WO-02/29068 | 4/2002 |
| WO | WO-02/50288 | 6/2002 |
| WO | WO-02/057464 | 7/2002 |
| WO | WO-02/059296 | 8/2002 |
| WO | WO-02/059330 | 8/2002 |
| WO | WO-02/067655 | 9/2002 |
| WO | WO-02/072849 | 9/2002 |
| WO | WO-02/081710 | 10/2002 |
| WO | WO-02/086144 | 10/2002 |
| WO | WO-02/086146 | 10/2002 |
| WO | WO-02/096923 | 12/2002 |
| WO | WO-03/028014 | 4/2003 |
| WO | WO-2005/010142 | 2/2005 |
| WO | WO-2005/010187 | 2/2005 |
| WO | WO-2005/083096 | 9/2005 |
| WO | WO-2007/137114 | 11/2007 |

OTHER PUBLICATIONS

Abel et al., "Delay of Disease Development in Transgenic Plants that Express the Tobacco Mosaic Virus Coat Protein Gene," *Science 232*: 738-743 (1986).

Alfenito et al., "Molecular Characterization of a Maize B Chromosome Centric Sequence," *Genetics 135*: 589-597 (1993).

Alonso-Blanco et al., "Development of AFLP Based Linkage Map of Ler, Col And Cvi *Arabidopsis thaliana* Ecotypes and Construction of a Ler/Cvi Recombinant Inbred Line Population," *The Plant Journal 14*: 259-271 (1998).

Ananiev et al., "Chromosome-specific Molecular Organization of Maize (*Zea mays* L.) Centromeric Regions," *Proc. Natl. Acad. Sci. USA 95*: 13073-13078 (1998).

Ananiev et al., "A Knob-Associated Tandem Repeat in Maize Capable of Forming Fold-back DNA Segments: Are Chromosome Knobs Megatransposons?," *Proc. Natl. Acad. Sci. USA. 95*: 10785-10790 (1998).

Ananiev et al., "Complex Structure of Knob DNA on Maize Chromosome 9: Retrotransposon Invasion into Heterochromatin," *Genetics 149*: 2025-2037 (1998).

Ananiev et al., "Complex Structure of Knobs and Centromeric Regions in Maize Chromosomes," *Tsitol Genet. 34*: 11-5 (2000).

Aragon-Alcaide et al., "A Cereal Centromeric Sequence," *Chromosoma 105*: 261-8 (1996).

Araki et al., "Site-specific Recominanse, R, Encoded by Yeast Plasmid pSR1," *J. Mol. Biol.* 225: 25-37 (1992).

Areshchenkova et al., "Long Tomato Microsatellites are Predominantly Associated with Centromeric Regions," *Genome 42*: 536-44 (1999).

Armstrong et al., "Physical Mapping of DNA Repetitive Sequences to Mitotic and Meiotic Chromosomes of *Brassica oleracea* var. *alboglabra* by Fluorescence in situ Hybridization," *Heredity 81*: 666-673 (1998).

Barki-Golan et al., "Studies on Growth Inhibition by Lectins of *Penicillia* and *Aspergilli*," *Arch. Microbiol.* 116: 119-124 (1978).

Baum et al., "The Centromeric K-Type Repeat and the Central Core are Together Sufficient to Establish a Functional *Schizosaccharomyces pombe* Centromere," *Molecular Biology of the Cell 5*: 747-761 (1994).

Bell et al., "Assignment of 30 Microsatellite Loci to the Linkage Map of *Arabidopsis*," *Genomics 19*: 137-144 (1994).

Bernal-Lupo et al., "Changes in Soluble Carbohydrates During Seed Storage," *Plant Physiol. 98*: 1207-1210 (1992).

Berzal-Herranz et al., "In Vitro Selection of Active Hairpin Ribozymes by Sequential RNA-Catalyzed Cleavage and Ligation Reactions," *Genes & Development 6*: 129-134 (1992).

Bevan et al., "Clearing a Path Through the Jungle: Progress in *Arabidopsis* Genomics," *BioEssays 21*: 110-120 (1999).

Bevan et al., "Structure and Transcription of the Nopaline Synthase Gene Region of T-DNA," *Nucleic Acids Research 11*: 369-385 (1983).

Birchler, "Do These Sequences Make CENs Yet?" *Genome Research 7*: 1035-1037 (1997).

Blackman et al., "Maturation Proteins and Sugars in Dessiccation Tolerance of Developing Soybean Seeds," *Plant Physiol. 100*: 225-230 (1992).

Bloom, "The Centromere Frontier: Kinetochore Components, Microtubule-Based Motility, and the CEN-Value Paradox," *Cell 73*: 621-624 (1993).

Bol et al., "Plant Pathogenesis-related Proteins Induced by Virus Infection," *Annu. Rev. Phytopath. 28*: 113-138 (1990).

Bowler et al., "Superoxide Dismutase and Stress Tolerance," *Annu. Rev. Plant Physiol. Plant Mol. Biol. 43*: 83-116 (1992).

Brandes et al., "Multiple Repetitive DNA Sequences in the Paracentromeric Regions of *Arabidopsis thaliana* L.," *Chromosome Res. 5*: 238-46 (1997).

Branson et al., "Potential for Utilizing Resistance from Relatives of Cultivated Crops," *Proceedings North Central Branch Entomological Society of America 27*: 9195 (1972).

Brisson et al., "Expression of a Bacterial Gene in Plants by Using a Viral Vector," *Nature 310*: 511-516 (1984).

Broach et al., "Transformation in Yeast: Development of a Hybrid Cloning Vector and Isolation of the CAN1 Gene," *Gene 8*: 121-133 (1979).

Broekaert et al., "A Chitin-Binding Lectin from Stinging Nettle Rhizomes with Antifungal Properties," *Science 245*: 1100-1102 (1989).

Buchowicz, J., "Nuclear Extrachromosomal DNA of Higher Plants," *Acta Biochim Pol. 44*: 13-19 (1977).

Burke et al., "Cloning of Large Segments of Exogenous DNA into Yeast by Means of Artificial Chromosome Vectors," *Science 236*: 806-812 (1987).

Bytebier et al., "T-DNA Organization in Tumor Cultures and Transgenic Plants of the Monocotyledon *Asparagus officinalis*," *Proc. Natl. Acad. Sci. USA 84*: 5345-5349 (1987).

Callis et al., "Introns Increase Gene Expression in Cultured Maize Cells," *Genes & Development 1*: 1183-1200 (1987).

Cambareri et al., "Structure of the Chromosome VII Centromere Region in *Neurospora crassa*: Degenerate Transposons and Simple Repeats," *Molecular and Cellular Biology 18*: 5465-5477 (1998).

Campbell, "The Production and Characterization of Rodent and Human Hybridomas," *Laboratory Techniques in Biochemistry and Molecular Biology 13*: 75-83 (1984).

Capecchi, "High Efficiency Transformation by Direct Microinjection of DNA into Cultured Mammalian Cells," *Cell 22*: 479-488 (1980).

Carbon et al., "Centromere Structure and Function in Budding and Fission Yeasts," *The New Biologist 2*: 10-19 (1990).

Carbon et al., "Structural and Functional Analysis of a Yeast Centromere (CEN3)," *J. Cell Sci. Suppl. 1*, 43-58 (1984).

Carbon et al., Recombinant Molecules: Impact on Science and Society, Raven Press: 335-378 (1977).

Carpenter et al., "On the Control of the Distribution of Meiotic Exchange in *Drosophila melanogaster*," *Genetics 101*: 81-89 (1982).

Cech et al., "In Vitro Splicing of the Ribosomal RNA Precursor of Tetrahymena: Involvement of a Guanosine Nucleotide in the Excision of the Intervening Sequence," *Cell 27*: 487-496 (1981).

Cepko et al., "Construction and Applications of a Highly Transmissible Murine Retrovirus Shuttle Vector," *Cell 37*: 1053-1062 (1984).

Chandler et al., "Two Regulatory Genes of the Maize Anthocyanin Pathway are Homologous: Isolation of B Utilizing R Genomic Sequences," *The Plant Cell 1*: 1175-1183 (1989).

Chang et al., "Restriction Fragment Length Polymorphism Linkage Map for *Arabidopsis thaliana*," *Proc. Natl. Acad. Sci USA 85*: 6856-6860 (1988).

Charlesworth et al., "The Evolution of Restricted Recombination and the Accumulation of Repeated DNA Sequences," *Genetics 112*: 947-962 (1986).

Charlesworth et al., "The Evolutionary Dynamics of Repetitive DNA in Eukaryotes," *Nature 371*: 215-220 (1994).

Cheng et al., "Functional Rice Centromeres are Marked by a Satellite Repeat and a Centromere-Specific Retrotransposon," *Plant Cell. 14*: 1691-1704 (2002).

Choi et al., "Construction and Characterization of a Bacterial Artificial Chromosome Library of *Arabidopsis thaliana*," *Plant Molecular Biology Reporter 13*: 124-129 (1995).

Choo, "Turning on the Centromere," *Nature Genetics 18*: 3-4 (1998).

Choo, "Why Is the Centromere So Cold?" *Genome Research 8*: 81-82 (1998).

Chowrira et al., "In Vitro and in Vivo Comparison of Hammerhead, Hairpin, and Hepatitis Delta Virus Self-processing Ribozyme Cassettes," *The Journal of Biological Chemistry 269*: 25856-25864 (1994).

Christou et al., "Stable Transformation of Soybean Callus by DNA-Coated Gold Particles," *Plant Physiol. 87*: 671-674 (1988).

Chu et al., "Separation of Large DNA Molecules by Contour-Clamped Homogenous Electric Fields," *Science 234*: 1582-1585 (1986).

Chye et al., "Characterization of *TSCL*, a Nonviral Retroposon from *Arabidopsis thaliana*," *Plant Molecular Biology 35*: 893-904 (1997).

Clapp, "Somatic Gene Therapy into Hemotopoietic Cells," *Clinics in Perinatology 20*: 155-168 (1993).

Clarke et al., "Centromeres: Proteins, Protein Complexes, and Repeated Domains at Centromeres of Simple Eukaryotes," *Genetics and Development 8*: 212-218 (1998).

Clarke et al., "Analysis of Centromeric DNA in the Fission Yeast *Schizosaccharomyces pombe*," *Proc. Natl. Acad. Sci. USA 83*: 8253-8257 (1986).

Clarke et al., "Isolation of a Yeast Centromere and Construction of Functional Small Circular Chromosomes," *Nature 287*: 504-509 (1980).

Cohen et al., "Construction of Biologically Functional Bacterial Plasmids in Vitro," *Proc. Nat. Acad. Sci. USA 70*: 3240-3244 (1973).

Conkling et al., "Isolation of Transcriptionally Regulated Root-Specific Genes from Tobacco," *Current Opinion Plant Physiol. 93*: 1203-1211 (1990).

Copenhaver, et al., "Centromeres in the Genomic Era: Unraveling Paradoxes," *Plant Biology 2*: 104-108 (1999).

Copenhaver et al., "Assaying Genome-wide Recombination and Centromere Functions with *Arabidopsis* tetrads," *Proc. Natl. Acad. Sci. USA, 95*: 247-252 (1998).

Copenhaver et al., "Tetrad Analysis in Higher Plants: A Budding Technology," *Plant Physiol., 124*: 7-16 (2000).

Copenhaver et al., "RFLP and Physical Mapping with an rDNA-specific Endonuclease Reveals that Nucleolus Organizer Regions of *Arabidopsis thaliana* Adjoin the Telemores on Chromosomes 2 and 4," *Plant Journal 9*: 259-276 (1996).

Copenhaver et al., "Genetic Definition and Sequence Analysis of *Arabidopsis* Centromeres," *Science 286*: 2468-2474 (1999).

Copenhaver et al., "Two-dimensional RFLP analyses Reveal Megabase-sized Clusters of rRNA Gene Variants in *Arabidopsis thaliana*, Suggesting Local Spreading of Variants as the Mode for Gene Homogenization During Concerted Evolution," *The Plant Journal 9*: 273-282 (1996).

Copenhaver et al., "Use of RFLPs Larger than 100 kbp to Map Position and Internal Organization of the Nucleolus Organizer Region on Chromosome 2 in *Arabidopsis thaliana*," *Plant Journal 7*: 273-286 (1995).

Copenhaver, "Using *Arabidopsis* to Understand Centromere Function: Progress and Prospects," *Chromosome Res. 2993*: 11: 255-62 (2003).

Coxson et al., "Pulse Release of Sugars and Polyols from Canopy Bryophytes in Tropical Montane Rain Forest (Guadeloupe, French West Indies)," *Biotropica 24*:121-133 (1992).

Creusot et al., "The CIC Library: A Large Insert YAC Library for Genome Mapping in *Arabidopsis thaliana*," *The Plant Journal 8*: 763-770 (1995).

Cristou et al., "Stable Transformation of Soybean Callus by DNA-Coated Gold Particles, " *Plant Physiol. 87*: 671-674 (1988).

Cuozzo et al., "Viral Protection in Transgenic Tobacco Plants Expressing the Cucumber Mosaic Virus Coat Protein or Its Antisense RNA," *BioTechnology 6*: 549-557 (1988).

Curiel et al., "High-efficiency Gene Transfer Mediated by Adenovirus Coupled to DNA-polylysine Complexes," *Hum. Gen. Ther. 3*: 147-154 (1992).

Curiel et al., "Adenovirus Enhancement of Transferrin-Polylysine-Mediated Gene Delivery," *Proc. Natl. Acad. Sci. USA* 88: 8850-8854 (1991).
Cutler et al., "Winter Flounder Antifreeze Protein Improves the Cold Hardiness of Plant Tissues," *J. Plant Physiol.* 135: 351-354 (1989).
Czapla et al., "Effect of Plant Lectins on the Larval Development of European Corn Borer (*Lepidoptera: Pyralidae*) and Southern Corn Rootworm (*Coleoptera: Chrysomelidae*)," *J. Econ Entomol* 83: 2480-2485 (1990).
Davies et al., "Leaf Senescence in a Nonyellowing Mutant of *Festuca pratensis*," *Plant Physiol.* 93: 588-595 (1990).
Dellaporta et al., "Molecular Cloning of the Maize R-nj Allele by Transposon Tagging with Ac": Chromosome Structure and Function: Impact of New Concepts, 18$^{th}$ Stadler Genetics Symposium 11: 263-282 (1988).
Dennis et al., "Knob Heterochromatin Homology in Maize and Its Relatives," *J. Mol. Evol.* 20: 341-350 (1984).
Depicker et al., "A Negative Selection Scheme for Tobacco Protoplast-Derived Cells Expressing the T-DNA Gene 2," *Plant Cell Reports* 7: 63-66 (1988).
Di Laurenzio et al., "The Scarecrow Gene Regulates an Asymmetric Cell Division that Is Essential for Generating the Radial Organization of the *Arabidopsis* Root," *Cell*, 86: 423-433 (1996).
Discussion with David Baltimore as Moderator, "Recombinant Molecules: Impact on Science and Society": 337-352, New York, 1977.
Donahue et al., "The Nucleotide Sequence of the *HIS4* Region of Yeast," *Gene.* 18: 47-59 (1982).
Dong et al., "Rice (*Oryza sativa*) Centromeric Regions Consist of Complex DNA," *Proc. Natl. Acad. Sci. USA* 95: 8135-40 (1998).
Dure III et al., "Common Amino Acid Sequence Domains Among the LEA Proteins of Higher Plants," *Plant Molecular Biology* 12: 475-486 (1989).
duSart et al., "A Functional Neo-centromere Formed Through Activation of a Latent Human Centromere and Consisting of Non-alpha Satellite DNA," *Nature Genetics* 16: 144-153 (1997).
Earnshaw et al, "Proteins of the Inner and Outer Centromere of Mitotic Chromosomes," *Genome* 31: 541-552 (1989).
Earnshaw et al., "When is a Centromere Not a Kinetochore?" *Journal of Cell Science* 99: 1-4 (1991).
Ebert et al., "Identification of an Essential Upstream Element in the Nopaline Synthase Promoter by Stable and Transient Assays," *Proc. Natl. Acad. Sci. USA* 84: 5745-5749 (1987).
Ecker, "PFGE and YAC Analysis of the *Arabidopsis* Genome," *Methods I*: 186-194 (1990).
Eglitis et al., "Retroviral Vectors for Introduction of Genes into Mammalian Cells," *Bio Techniques* 6: 608-614 (1988).
Eglitis et al.,"Retroviral-mediated Gene Transfer into Hemapoietic Cells," *Avd. Exp. Med. Biol.* 241: 19-27 (1988).
Enomoto et al., "Mapping of the *pin* Locus Coding for a Site-Specific Recombinase that Causes Flagellar-Phase Variation in *Escherichia coli* K-12," *Journal of Bacteriology* 156: 663-668 (1983).
Erdmann et al., "Glycosylglycerol Accumulation During Salt Acclimination of Two Unicellular Cyanobacteria," *Journal of General Microbiology* 138: 363-368 (1992).
Ferrin et al., "Selective Cleavage of Human DNA: RecA-Assisted Restriction Endonuclease (RARE) Cleavage," *Science* 254: 1494-1497 (1991).
Fitzpatrick, "Pleiotropic Gene Found in Barley Plant" *Gen. Engineering News* 13(5): 1, 22 (1993).
Fleig. et al., "Functional Selection for the Centromere DNA from Yeast Chromosome VIII," *Nuc. Acids. Res* 23: 922-924 (1995).
Forster et al., "Self-Cleavage of Plus and Minus RNAs of a Virusoid and a Structural Model for the Active Sites," *Cell 49*: 211-220 (1987).
Fraley et al., "The SEV Sysem: A New Disarmed TI Plasmid Vector System for Plant Transformation," *BioTechnology* 3: 629-635 (1985).
Fransz et al., "Cytogenetics for the Model System *Arabidopsis thaliana*," *The Plant Journal* 13: 867-876 (1998).
Fransz et al., "Integrated Cytogenetic Map of Chromosome Arm 4S of *A. thaliana*: Structural Organization of Heterochromatic Knob and Centromere Region," *Cell.* 100: 367-76 (2000).
Frary et al., "Molecular Mapping of the Centromeres of Tomato Chromosomes 7 and 9," *Mol Gen Genet.*, 250: 295-304 (1996).

Fromm et al., "Expression of Genes Transferred into Monocot and Dicot Plant Cells by Electroporation," *Proc. Nat. Acad. Sci. USA* 82: 5824-5828 (1985).
Fromm et al., "Stable Transformation of Maize After Gene Transfer by Electroporation," *Nature 319*: 791-793 (1986).
Fujimara et al, "Regeneration of Rice Plants from Protoplasts,"*Plant Tissue Culture Letters 2*: 74 (1985).
Fukui et al.., "Physical Arrangement of Retrotransposon-Related Repeats in Centromeric Regions of Wheat," *Plant Cell Physiology*, 42: 189-96 (2004).
Fynan et al., "DNA Vaccines: Protective Immunizations by Parenteral, Mucosal, and Gene-Gun Inoculations," *Proc. Nat. Acad. Sci. USA* 90: 11478-11482 (1993).
Gatehouse et al., "Effect of Seed Lectins from *Phaseolus vulgaris* on the Development of Larvae of *Callosobruchus maculatus*; Mechanism of Toxicity," *J. Sci. Food. Agric.* 35: 373-380 (1984).
Gefter et al., "A Simple Method for Polyethylene Glycol-promoted Hybridization of Mouse Myeloma Cells," *Somatic Cell Genet.* 3: 231-236 (1977).
GenBank Accession No. AF013103, 1997.
GenBank Accession No. AF049110, 1998.
GenBank Accession No. AF050437, 1998.
GenBank Accession No. AF050438, 1998.
GenBank Accession No. AF050452, 1998.
GenBank Accession No. AF050453, 1998.
GenBank Accession No. AF071126, 1998.
GenBank Accession No. AF078917, 1998.
GenBank Accession No. AF078922, 1998.
GenBank Accession No. AF078923, 1998.
GenBank Accession No. AF090447, 2001.
GenBank Accession No. AF123535, 1999.
GenBank Accession No. AF242891, 2001.
GenBank Accession No. AF273104, 2002.
GenBank Accession No. AF448416, 2002.
GenBank Accession No. AY129008, 2002.
GenBank Accession No. AY173950, 2003.
GenBank Accession No. AY321491, 2006.
GenBank Accession No. K01868, 1984.
GanBank Accession No. K02202, 1984.
GenBank Accession No. M35408, 1981.
GenBank Accession No. X01365, 1981.
GenBank Accession No. U39642, 1995.
Gerlach et al., "Construction of a Plant Disease Resistance Gene from the Satellite RNA of Tobacco Ringspot Virus," *Nature* 328: 802-805 (1987).
Gindullis et al., "The Large-Scale Organization of the Centromeric Region in *Beta* Species," *Genome Res.* 11: 253-65 (2001).
Gindullis, et al., "Construction and Characterization of a BAC Library for the Molecular Dissection of a Single Wild Beet Centromere and Sugar Beet (*Beta vulfaris*)," *Genome Analysis*, 44: 846-55 (2001).
Giordano et al., "Identification by Denaturing High-Performance Liquid Chromatography of Numerous Polymorphisms in a Candidate Region for Multiple Sclerosis Susceptibility," *Genomics*, 56: 247-253 (1999).
Goding, *Monoclonal Antibodies: Principles and Practice*, Academic Press, Orlando, Florida, 60-74 (1986).
Golic et al., "The FLP Recombinase of Yeast Catalyzes Site-Specific Recombinatioin in the *Drosophila* Genome" *Cell* 59: 499-509 (1989).
Goring et al., "Transformation of a Partial Nopaline Synthase Gene into Tobacco Suppresses the Expression of a Resident Wild-type Gene," *Proc. Natl. Acad. Aci. USA* 88, 1770-1774 (1991).
Graham et al., "Transformation of Rat Cells by DNA of Human Adenovirus 5," *Virology* 54: 536-539 (1973).
Grellet et al., "Organization and Evolution of a Higher Plant Alphoid-like Satellite DNA Sequence," *J. Mol. Biol.* 187: 495-507(1986).
Grill et al., "Construction and Characterization of a Yeast Artificial Chromosome Library of *Arabidopsis* Which is Suitable for Chromosome Walking," *Mol. Gen. Genet.* 226: 484-490 (1991).

Guerrero et al., "Turgo-Responsive Gene Transcription and RNA Levels Increase Rapidly When Pea Shoots Are Wilted. Sequence and Expression of Three Inducible Genes," *Plant Molecular Biology 15*: 11-26 (1990).

Gupta et al., "Increased Resistance to Oxidative Stress in Transgenic Plants that Overexpress Chloroplastic Cu/Zn Superoxide Dismutase," *Proc. Natl. Acad. Sci. USA 90*: 1629-1633 (1993).

Gutierrez-Marcos et al., "Three Members of a Novel Small Gene-Family from *Arabidopsis thaliana* Able to Complement Functionally an *Escherichia coli* Mutant Defective in PAPS Reducatase Activity Encode Proteins with a Thioredoxin-like Domain and "APS Reductase" Activity," *Proc. Natl. Acad. Sci USA 93*: 13377-133824 (1996).

Haaf et al., "Integration of Human Satellite DNA into Simian Chromosomes: Centromere Protein Binding and Disruption of Normal Chromosome Segregation," *Cell 70*: 681-696 (1992).

Hadlaczky et al., "Centromere Formation in Mouse Cells Cotransformed with Human DNA and a Dominant Marker Gene," *Proc. Natl. Acad. Sci., USA 88*: 8106-8110 (1991).

Hauge et al., "Mapping the *Arabidopsis* Genome," Symp. Society for Experimental Biology, 45: 45-56 (1991).

Hall, et al., "The Rapidly Evolving Field of Plant Centromeres," Department of Molecular Genetics and Cell Biology, The University of Chicago, Chicago, Illinois 60637, USA, *Curr. Opin Plant Biol. 7108*-14 (2002).

Hamilton et al., "Stable Transfer of Intact High Molecular Weight DNA into Plant Chromosones," *Proc. Natl. Acad. Sci. USA 93*: 9975-9979(1996).

Hamilton, "A Binary BAC System for Plant Transformation with High-Molecular-Weight DNA," *Gene 4*: 200: 107-116 (1997).

Hammock et al., "Expression and Effects of the Juvenile Hormone Esterase in a Baculovirus Vector," *Nature 344*: 458-463 (1990).

Harrington et al.,"Formation of de novo Centromeres and Construction of First-generation Human Artificial Microchromosomes," *Nature Genetics 15*: 345-354 (1997).

Harrison et al., "Centromeric Repetitive DNA Sequences in the Genus *Brassica*," *Theor. Appl. Genet.*, 90: 157-165 (1995).

Haseloff et al., "Removal of a Cryptic Intron and Subcellular Localization of Green Fluorescent Protein Are Required to Mark Transgenic *Arabidopsis* Plants Brightly," *Proc. Natl. Acad. Sci. USA 94*: 2122-2127 (1997).

Hegemann et al., "The Ceontromere of Budding Yeast," *BioEssays 15*: 451-460 (1998).

Heller et al., "Mini-Chromosomes Derived from the Human Y Chromosome by Telomere Directed Chromosome Breakage," *Proc. Natl. Acad. Sci. USA 93*: 7125-7130 (1996).

Hemenway et al., "Analysis of the Mechanism of Protection in Transgenic Plants Expressing the Potato Virus X Coat Protein or its Antisense RNA," *The EMBO Journal 7*: 1273-1280 (1988).

Heslop-Harrison et al., "Polymorphisms and Genomic Organization of Repetitive DNA from Centromeric Regions of *Arabidopsis* Chromosomes," *Plant Cell. 11*: 31-42 (1999).

Hilder et al., "A Novel Mechanism of Insect Resistance Engineered into Tobacco," *Nature 330*: 160-163 (1987).

Hinchee et al., "Production of Transgenic Soybean Plants Using Agrobacterium-Mediated DNA Transfer," *BioTechnologly 6*: 915-922 (1988).

Hoess et al., "P1 Site-Specific Recombination: Nucleotide Sequence of the Recombining Sites," *Proc. Nat. Acad. Sci. USA 79*: 3398-3402 (1982).

Houben et al., "DNA and Proteins of Plant Centromeres," *Current Opinion in Plant Biology 6*: 554-560 (2003).

Hsiao et al., "High-Frequency Transformation of Yeast by Plasmids Containing the Cloned Yeast ARG4 Gene," *Proc. Nat. Acad. Sci. USA 76*: 3829-3833 (1979).

Hudakova et al., "Sequence Organization of Barley Centromeres," *Nucleic Acids Resources, 29*: 5029-35 (2001).

Hudspeth et al., "Structure and Expression of the Maize Gene Encoding the Phosphoenolpyruvate Carboxylase Isozyme Involved in $C_4$ Photosynthesis," *Plant Molecular Biology 12*: 579-589 (1989).

Hwang et al., "Identification and Map Position of YAC Clones Comprising One-third of the *Arabidopsis* genome," *The Plant Journal 1*: 367-374 (1991).

Ikeda, et al., "Genetic Studies of Avermectin Biosynthesis in *Streptomyces avermitilis*," *Journal of Bacteriology 16*: 5615-5621 (1987).

Ikeno, et al., "Construction of YAC-based Mammalian Artificial Chromosomes," *Nature Biotechnology 16*: 431-439 (1998).

Ikuta et al., "The Alpha-Amylase Gene as a Marker for Gene Cloning: Direct Screening of Recombinant Clones," *BioTechnology 8*: 241-242 (1990).

Inohara et al., "Two Genes, *atp*C1 and *atp*C2, for the Subunit of *Arabidopsis thaliana* Chloroplast ATP Synthase," *The Journal of Biological Chemistry 266*: 7333-7338 (1991).

Jiang et al., "A Conserved Repetitive DNA Element Located in the Centromeres of Cereal Chromosomes," *Proc Nall Acad Sci USA.*, 93: 4210-4213 (1996).

Jiang et al., "A Molecular View of Plant Centromeres," *Trends in Plant Science 8*: 570-575 (2003).

Jin et al., Maize-Centromeres: Organization and Functional Adaptation in the Genetic Background of Oat, Department of Horticulture, University of Wisconsin-Madison, Madison, Wisconsin 53706, USA, *Plant Cell. 16*: 57-81 (2004).

Johnston et al., "Gene Gun Transfection of Animal Cells and Genetic Immunization," *Methods in Cell Biology 43*: 353-363 (1994).

Jones et al., "T-DNA Structure and Gene Expression in Petunia Plants Transformed by *Agrobacterium tumafaciens* C58 Derivatives," *Mol. Gen. Genet. 207*: 478-485 (1987).

Jones et al., "High Level Expression of Introduced Chimaeric Genes in Regenerated Transformed Plants," *The EMBO Journal 4*: 2411-2418 (1985).

Jorgensen et al., "T-DNA is Organized Predominantly in Inverted Repeat Structures in Plants Transformed with *Agrobacterium tumafaciens* C58 Derivatives," *Mol. Gen. Genet. 207*: 471-477 (1987).

Jouanin et al., "Localization and Restriction Maps of Replication Origin Regions of the Plasmids of *Agrobacterium rhizogenes* Strain $A_4$," *Mol. Gen. Genet. 201*: 370-374 (1985).

Joyce, "RNA Evolution and the Origins of Life," *Nature 338*: 217-224 (1989).

Karpen, "Position-effect Variegation and the New Biology of Heterochromatin," *Current Opinion in Genetics and Development 4*: 281-291 (1994).

Karsten et al., "Polyol Content of *Bostrychia* and *Stictosiphonia* (*Rhodomelaceae, Rhodophyta*) from Field and Culture," *Botanica Marina 35*: 11-19 (1992).

Kaasen et al., "Molecular Cloning and Physical Mapping of the otsBA Genes, Which Encode the Osmoregulatory Trehalose Pathway of *Escherichia coli*: Evidence that Transcription is Activated by KatF (AppR)," *Journal of Bacteriology 174*: 889-898 (1992).

Kaszás et al., "Misdivision Analysis of Centromere Structure in Maize," *The EMBO Journal 15*: 5246-5255 (1996).

Kato et al., "Foreign DNA Introduced by Calcium Phosphate is Integrated into Repetitive DNA Elements of the Mouse L Cell Genome," *Molecular and Cellular Biology 6*: 1787-1795 (1986).

Katz et al., "Cloning and Expression of the Tyrosinase Gene from *Streptomyces antibioticus* in *Streptomyces lividans*," Journal of General Microbiology 129: 2703-2714 (1983).

Kim et al., "Three-Dimensional Model of the Active Site of the Self-Splicing rRNA Precursor of Tetrahymena," *Proc. Nat. Acad. Sci. USA 84*: 8788-8792 (1987).

Kishii, et al., "A Tandem Repetitive Sequence Located in the Centromeric Region of Common Wheat (*Triticum aestivum*) Chromosomes," *Chromosome Resources*, 9: 417-28 (2001).

Klee et al., "Vectors for Transformation of Higher Plants," *BioTechnology 3*: 637-642 (1985).

Klein et al., "High-Velocity Microprojectiles for Delivering Nucleic Acids into Living Cells," *Nature 327*: 70-73 (1987).

Klein et al., "Stable Genetic Transformation of Intact Nicotiana Cells by the Particle Bombardment Process," *Proc. Nat. Acad. Sci. USA 85*: 8502-8505 (1988).

Kohler et al., "Continous Cultures of Fused Cells Secreting Antibody of Predefined Specificity," *Nature 256*: 495-497 (1975).

Kohler et al., "Derivation of Specific Antibody-Producing Tissue Culture and Tumor Lines by Cell Fusion," *Eur. J. Immunol. 6*: 511-519 (1976).

Kolchinsky et al., "A Major Satellite DNA of Soybean is a 92-base Pairs Tandem Repeat" *Theor. Appl. Genet. 90*: 621-626 (1995).

Konieczny et al.," A Superfamily of *Arabidopsis thaliana* Retrotransposons," *Genetics 127*: 801-809 (1991).

Konieczny et al., "A Procedure for Mapping *Arabidopsis* Mutations Using Co-dominant Ectotype-specific PCR-based Markers," *The Plant Journal 4*: 403-310 (1993).

Koorneef et al., "Trisomics in *Arabidopsis thaliana* and the Location of Linkage Groups," *Genetica 61*: 41-46 (1983).

Koorneef ,"Linkage Map of *Arabidopsis thaliana* (2n=10)," In S.J. O'Brien, ed., Genetic Maps 1987: A Compilation of Linkage and Restriction Maps of Genetically Studied Organisms, 742-745 (1987).

Koorneef, "The Use of Telotrisomics for Centromere Mapping in *Arabidopsis thaliana* (L.) Heynh.," *Genetica 62*: 33-40 (1983).

Koster et al., "Sugars and Desiccation Tolerance in Seeds," *Plant Physiol. 88*: 829-832 (1988).

Kotani et al., "Structural Analysis and Complete Physical Map of *Arabidopsis thaliana* Chromosome 5 Including Centromeric Telomeric Regions," *DNA Research 6*: 381-386 (1999).

Kuhn et al., "Clustered tRNA Genes in *Schizosaccharomyces pombe* Centromeric DNA Sequence Repeats," *Proc. Nat. Acad. Sci. USA 88*: 1306-1310 (1991).

Kumekawa et al., "The Size and Sequence Organization of the Centromeric Region of *Arabiodpsis thaliana* Chromosome 5," *DNA Resources, 7*: 315-21 (2000).

Kurata et al.,, "Rice Genome Organization: The Centromere and Genome Interactions," *Ann Bot 90*: 427-35 (2002).

Kyte et al., "A Simple Method for Displaying the Hydropathic Character of a Protein," *J. Mol. Biol. 157*: 105-132 (1982).

Lakshmikumarin et al., "Isolation and Characterization of a Highly Repetitive DNA of *Brassica campestris*," *Plant Molecular Biology 14*: 447-448 (1990).

Lawton et al., "Expression of a Soybean -conclycinin Gene under the Control of the Cauliflower Mosaic Virus 35S and 19S Promoters in Transformed Petunia Tissues;" *Plant Molecular Biology 9*: 315-324 (1987).

Lechner et al., "A 240 kd Multisubunit Protein Complex, CBF3, Is a Major Component of the Budding Yeast Centromere," *Cell 64*: 717-725 (1991).

Lee et al., "Use of Cloned *mtl* Genes of *Escherichia coli* to Introduce *mtl* Deletion Mutations into the Chromosome," *Journal of Bacterialogy 153*: 685-692 (1983).

Levings III, "The Texas Cytoplasm of Maize: Cytoplasmic Male Sterility and Disease Susceptibility," *Science 250*:942-947 (1990).

Li et al., "Direct Electrophoretic Detection of the Allelic State of Single DNA Molecules in Human Sperm by Using the Polymerase Chain Reaction," *Proc. Natl. Acad. Sci. USA 87*: 4580-4584 (1990).

Li et al., "CUE1: A Mesophyll Cell-Specific Positive Regulator of Light-Controlled Gene Expression in *Arabidopsis*," *The Plant Cell 7*: 1599-1610 (1995).

Lieber et al., "Selection of Efficient Cleavage Sites in Target RNAs by Using a Ribozyme Expression Library," *Molecular and Cellular Biology* 15: 540-551 (1995).

Lin et al., "Sequence and Analysis of Chromosome 2 of the Plant *Arabidopsis thaliana*," *Nature 402*: 761-768 (1999).

Liu, Y.G., et al., "Complementation of Plant Mutants with Large Genomic DNA Fragments by a Transformation-Competent Artificial Chromosome Vector Accelerates Positional Cloning," *Proc. Natl. Acad. Sci. USA 96*: 6535-6540 (1999).

Lohe et al., "Return of the H-word (heterochromatin)," *Current Opinion in Genetics and Development 5*: 746-755 (1995).

Loomis et al., "Cyroprotective Capacity of End Products of Anaerobic Metabolism," *The Journal of Experimental Zoology 252*: 9-15 (1989).

Lorz et al., "Gene Transfer to Cereal Cells Mediated by Protoplast Transformation," *Mol. Gen. Genet. 199*: 178-182 (1985).

Louis, "Corrected Sequence for the Right Telomere of *Saccharomyces cerevisiae* Chromosome III," *Yeast 10*: 271-274 (1994).

Lu et al., "High Efficiency Retroviral Mediated Gene Transduction into Single Isolated Immature and Replatable CD34$^{3+}$ Hemotopoietic Stem/Progenitor Cells from Human Umbilical Cord Blood," *J. Ex. Med. 178*: 2089-2096 (1993).

Maeser et al., "The Gin Recombinase of Phase Mu Can Catalyse Site-Specific Recombination in Plant Protoplasts," *Mol. Gen. Genet 230*: 170-176 (1991).

Mahtani et al., "Physical and Genetic Mapping of the Human X Chromosome Centromere: Repression of Recombination," *Genome Research 8*: 100-110 (1998).

Maloy, S.R., Experimental Techniques in Bacterial Genetics , Jones and Bartlett, *Ann. N.Y. Acad. Sci.* 646 (1991). Table of Contents only.

Maluszynska et al., "Localization of Tandemly Repeated DNA Sequences in *Arabidopsis thaliana*," *The Plant Journal 1*: 159-166 (1991).

Maluszynska et al., Molecular Cytogenetics of the Genus *Arabidopsis*: In situ Localization of rDNA Sites, Chromosome Numbers and Diversity in Centromeric Heterochromatin,: *Annals of Botany 71*: 479-484 (1993).

Marcotte et al., "Regulation of a Wheat Promoter by Abscisic Acid in Rice Protoplasts" *Nature 335*: 454 (1988).

Mariani et al., "Induction of Male Sterility in Plants by a Chimaeric Ribonuclease Gene," *Nature 357*: 737-741 (1990).

Marra et al., "A Map for Sequence Analysis of the *Arabidopsis thaliana* Genome," *Nature Genetics 22*: 265-270 (1999).

Martinex-Zapater et al., "A Highly Repeated DNA Sequence in *Arabidopsis thaliana*," *Mol. Gen. Genet 204*: 417-423 (1986).

Matsuura et al., "The *sre* Gene (ORF459) Encodes a Site-Specific Recombinase Responsible for Integration of the R4 Phage Genome," *Journal of Baceteriology 178*: 3374-3376 (1996).

McCabe et al., "Stable Transformation of Soybean (*Glycine max*) by Particle Acceleration," *BioTechnology 6*: 924-926 (1988).

Michel et al.., Modeling of the Three-dimensional Architecture of Group I Catalytic Introns Based on Comparative Sequence Analysis,: *J. Mol. Biol. 216*: 585-610 (1990).

Miller et al., "Retrotransposon-Related DNA Sequences in the Centromeres of Grass Chromosomes," *Genetics 150*: 1615-23 (1998).

Mortimer et al., "Genetic Mapping in *Saccharomyces cerevisiae*," Department of Biophysics and Medical Physics and Donner Laboratory, University of Califomia at Berkeley: 11-26 (1981).

Mozo et al., "A Complete BAC-based Physical Map of the *Arabidopsis thaliana* Genome," *Nature Genetics 22*: 271-275 (1999).

Mozo et al., "Construction and Characterization of the IGF *Arabidopsis* BAC Library," *Mol. Gen. Genet. 258*: 562-570 (1998).

Mundy et al. "Abscisic Acid and Water-stress Induce the Expression of a Novel Rice Gene," *The EMBO Journal 7*: 2279-2286 (1988).

Murakami et al., "The Bialaphos Biosynthetic Genes of *Streptomyces hygroscopicus*: Molecular Cloning and Characterization of the Gene Cluster," *Mol. Gen. Genet. 205*: 42-50 (1986).

Murata et al., "Physical Mapping of the 5S Ribosomal RNA Genes in *Arabidopsis thaliana* by Multi-Color Fluorescence in situ Hybridization with Cosmid Clones," *The Plant Journal 12*: 31-37 (1997).

Murata et al., "Centromeric Repetitive Sequences in *Arabiidopsis thaliana*," *Jpn J Genet. 69*: 361-370 (1994).

Murdock et al., "Biological Efects of Plant Lectins on the Cowpea Weevil," *Phytochemistry 29*: 85-89 (1990).

Murphy et al., "Localization of Centromere Function in a *Drosophila* Minichromosome," *Cell 82*: 599-609 (1995).

Murray et al., "Construction of Artificial Chromosomes in Yeast," *Nature 305*: 189-193(1983).

Mysore et al., "An *Arabidopsis* Histone H2A Mutant is Deficient in *Agrobacterium* T-DNA Integration," *Proc. Natl. Acad, Sci USA 97*: 948-953 (2000).

Mysore et al., "*Arabidopsis* Ecotypes and Mutants That Are Recalcritant to Agrobacterium Root Transformation Are Susceptible to Germ-line Transformation," *The Plant Journal 21*: 9-16 (2000).

Nagaki et al., "Molecular and Cytological Analysis of Large Tracks of Centrometic DNA Reveal the Structure and Evolutionary Dynamics of Maize Centromeres," *Genetics 163*: 759-70 (2003).

Nagaki et al., "Sequencing of a Rice Centromere Uncovers Active Genes", *Nature Genet. 36*: 138-145 (2004).

Nakamura et al., "Construction of an 800-KB Contig in the Near-Centromeric Region of the Rice Blast Resistance Gene *Pi-ta2* Using a Highly Representative Rice BAC Library," *Mol Gen Genet 254*: 611-620 (1997).

Napoli et al., "Introduction of a Chimeric Chalcone Synthase Gene into Petunia Results in Reversible Co-Suppression of Homologous Genes in trans," *The Plant Cell 2*: 279-298 (1990).
Negrutiu, et al. "Plant Protoplasts as Genetic Tool: Selectable Markers for Developmental Studies," *Int. J. Dev. Biol. 36*: 73-84 (1992).
Nester et al., "Crown Gall: A Molecular and Physiological Analysis," *Ann Rev. Plant Physiol 35*: 387-413(1984).
Nicklas, "The Forces That Move Chromosomes in Mitosis," *Ann. Rev. Biophys. Biophys. Chem. 17*: 431-449 (1988).
Nonomura et al., "Organization of the 1.9-KB Repeat Unit RCE1 in the Centromeric Region of Rice Chromosomes," *Mol Gen Genet. 261*: 1-10 (1999).
Nonomura, et al., "The Centromere Composition of Multiple Repetitive Sequences on Rice," *Chromosome 5, 110*: 284-91 (2001).
Noutoshi et al., "Designing of Plant Artificial Chromosome (PAC) by Using the Chlorella Smallest Chromosome as a Model System," *Nucleic Acids Symp. Ser. 37*: 143-4 (1997).
Nussbaum et al., "Construction and Propagation of a Defective Simian Virus 40 Genome Bearing an Operator from Bacteriophage," *Proc. Nat. Acad. Sci. USA 73*: 1068-1072 (1976).
Odell et al., "Identification of DNA Sequences Required for Activity of the Cauliflower Mosaic Virus 35S Promoter," *Nature 313*: 810-812 (1985).
Ohmori et al., "Nucleotide Sequence of the Region Required for Maintenance of Colicin E1 Plasmid," *Mol. Gen. Genet. 176*: 161-170 (1979).
Omirulleh et al., "Activity of a Chimeric Promoter with the Doubled CaMV 35S Enhancer Element in Protoplast-derived Cells and Transgenic Plants in Maize," *Plant Molecular Biology 21*: 415-428 (1993).
Ow et al., "Transient and Stable Expression of the Firefly Luciferase Gene in Plant Cells and Transgenic Plants," *Science 234*: 856-859 (1986).
Page et al., "Characterization of a Maize Chromosome 4 Centromeric Sequence: Evidence for an Evolutionary Relationship with the B Chromosome Centromere," *Genetics 159*: 291-301 (2001).
Palukaitis et al., "Characterization of a Viroid Associated with Avocado Sunblotch Disease," *Virology 99*: 145-151 (1979).
Peacock et al., "Highly Repeated DNA Sequence Limited to Knob Heterochromatin in Maize," *Proc. Nat. Acad. Sci. USA 78*: 4490-4494 (1981).
Pelissier et al., "DNA Regions Flanking the Major *Arabidopsis thaliana* Satellite Are Principally Enriched in *Athila* Retroelement Sequences," *Genetica 97*: 141-151 (1996).
Pelissier et al., "Athila, A New Retroelement from *Arabidopsis thaliana.*," *Plant Mol. Biol. 29*: 441-552 (1995).
Perkins, "The Detection of Linkage in Tetrad Analysis," *Genetics 38*: 187-197 (1953).
Perlak et al., "Modification of the Coding Sequence Enhances Plant Expression of Insect Control Protein Genes," *Proc. Natl. Acad. Sci USA 88*: 3324-3328 (1991).
Perriman et al., "Extended Target-Site Specificity for a Hammerhead Ribozyme," *Gene 113*: 157-163 (1992).
Peterson et al., "Production of Transgenic Mice with Yeast Artificial Chromosomes," *TIG 13*: 61-66 (1997).
Phi-Van et al., "The Chicken Lysozyme 5' Matrix Attachment Region Increases Transcription from a Heterologous Promoter in Heterologous Cells and Dampens Position Effects on the Expression of Transfected Genes," *Molecular and Cellular Biology 10*: 2302-2307 (1990).
Piatowski et al., "Characterization of Five Abscisic Acid-Responsive cDNA Clones Isolated from the Dessication-Tolerant Plant *Craterostigma plantagineum* and Their Relationship to Other Water-Stress Genes," *Plant Physiol. 94*: 1682-1688 (1990).
Potrykus et al., "Direct Gene Transfer to Cells of a Graminaceous Monocot," *Mol. Gen. Genet. 199*: 183-188 (1985).
Prasher et al., "Cloning and Expression of the cDNA Coding for Aequorin, a Bioluminescent Calcium-binding Protein," *Biochem Biophys. Res. Commun 126*: 1259-1268 (1985).
Presting et al., "A *Ty3/gypsy* Retrotransposon-Like Sequence Localizes to the Centromeric Regions of Cereal Chromosomes," *Plant J. 16*: 721-8 (1998).

Preuss et al., "Tetrad Analysis Possible in *Arabidopsis* with Mutation of the QUARTET (QRT) Genes," *Science 264*: 1458-1460 (1994).
Price et al.,"Systematic Relationships of *Arabidopsis*: A Molecular and Morphological Perspective," in Somerville, C. and Meyerowitz, E. (eds.), *Arabidopsis*, Cold Spring Harbor Press, New York (1995) pp. 7-19.
Prody et al.,"Autolytic Processing of Dimeric Plant Virus Satellite RNA," *Science 231*: 1577-80 (1986).
Puechberty, J., "Genetic and Physical Analyses of the Centromeric and Pericentromeric Regions of Human Chromosome 5: Recombination Across 5cen," *Genomics 56*: 274-87 (1999).
Rathore et al., "Use of *bar* as a Selectable Marker Gene and for the Production of Herbicide-Resistant Rice Plants from Protoplasts," *Plant Molecular Biology 21*: 871-884 (1993).
Rattner et al., "The Structure of the Mammalian Centromere," *BioEssays 13*: 51-56 (1991).
Ravatn et al., "Int-B13, An Unusual Site-Specific Recombinase of the Bacteriophage P4 Integrase Family, Is Responsible for Chromosomal Insertion of the 105-Kilobase *c/c* Element of *Pseudomonas* sp. Strain B13," *Journal of Bacteriology 180*: 5505-5514, 1998.
Reed et al.,"Carbohydrate Accumulation and Osmotic Stress in Cyanobacteria," *J. Gen. Microbiology 130*: 1-4 (1984).
Reichel et al., "Enhanced Green Fluorescence by the Expression of an Aequorea victoria Green Fluorescent Protein Mutant in Mono- and Dicotyledonous Plant Cells," *Proc. Nat. Acad. Sci. USA 93*: 5888-5893 (1996).
Reinhold-Hurek et al., "Self-splicing Introns in tRNA Genes of Widely Divergent Bacteria," *Nature 357*: 173-176 (1990).
Rensburg et al., "Proline Accumulation as Drought-tolerance Selection Criterion: Its Relationship to Membrane Integrity and Chloroplast Ultrastructure in *Nicotiana tabacum* L.," *J. Plant Physiol. 141*: 188-194 (1993).
Richards et al., "The Centomere Region of *Arabidopsis thaliana* Chromosome 1 Contains Telomere-Similar Sequences," *Nucleic Acids Research 19*: 3351-3357 (1991).
Richards et al., "Isolation of a Higher Eukaryotic Telomere from *Arabidopsis thaliana,"* Cell 53*: 127-136 (1988).
Richards et al.,"Plant Centromeres: Structure and Control," *Curr Opin Plant Biol.1*: 130-135 (1998).
Rieder, "The Formation, Structure, and Composition of the Mammalian Kinetochore and Kinetochore Fiber," New York State Department of Health, Division of Laboratories and Research, *Intl. Rev. Cytol.79*: 1-58 (1982).
Rogers et al., "Improved Vectors for Plant Transformation: Expression Cassette Vectors and New Selectable Markers," *Methods in Enzymology 153*: 253-277, 1987.
Rosenberg et al., ""RFLP Subtraction": A Method for Making Libraries of Polymorphic Markers," *Proc. Natl. Acad. Sci. USA 91*: 6113-6117 (1994).
Rosenfeld, "Human artificial chromosomes get real," *Nature Genetics 15*: 333-335 (1997).
Round et al., "*Arabidopsis thaliana* Centromere Regions: Genetic Map Positions and Repetitive DNA Structure," *Genome Research 7*: 1045-1053 (1997).
Sasnauskas et al., "Molecular Cloning and Analysis of Autonomous Replicating Sequence of *Candida maltosa*," *Yeast 8*: 253-259 (1992).
Sauer, "Functional Expression of the *cre-lox* Site-Specific Recombination System in the Yeast *Saccharomyces cerevisiae*," *Molecular and Cellular Biology 7*: 2087-2096 (1987).
Schmidt et al., "Analysis of Clones Carrying Repeated DNA Sequences in Two YAC Libraries of *Arabidopsis thaliana* DNA," *The Plant Journal 5*: 735-744 (1994).
Schmidt et al., "Physical Map and Organization of *Arabidopsis thaliana* Chromosome 4," *Science, 270*: 480-483 (1995).
Schwartz et al., "New Techniques for Purifying Large DNAs and Studying Their Properties and Packaging," Department of Human Genetics and Development, Columbia University: 189-195, 1983.
Schweizer et al., "Species-specific DNA sequences for identification of somatic hybrids between *Lycopersicon esculentim* and *Solanum acaule,"* Theor. Appl. Genet 75*: 679-684 (1988).
Sears et al., "Cytogenic Studies in *Arabidopsis thaliana*," Department of Genetics, University of Missouri, *Can. J. Genet. Cytol. 12*: 217-223 (1970).

Shagan et al., "Nucleotide Sequence of an *Arabidopsis thaliana* Turgor-Responsive cDNA Clone Encoding TMP-A, a Transmembrane Protein Containing the Major Intrinsic Protein Motif," *Plant Physiol. 101*: 1397-1398 (1993).
Sheen et al., "Green-flourescent Protein as a New Vital Marker in Plant Cells," *The Plant Journal 8*: 777-784 (1985).
Simoens et a.l, "Characterization of Highly Repetitive Sequences of *Arabidopsis thaliana*," *Nucleic Acids Research 16*: 6753-6766 (1988).
Singh et al., "Centromere Mapping and Orientation of the Molecular Linkage Mao of Rice (*Oryza sativa* L.)," *Proc Natl Acad Sci USA. 93*: 6163-6168 (1996).
Smith et al., "Expression of Truncated Tomato Polygalacturonase Gene Inhibits Expression of the Endogenous Gene in Transgenic Plants," *Mol. Gen. Genet. 224*: 447-481 (1990).
Smithies et al., "Insertion of DNA Sequences into the Human Chromosomal—Globin Locus by Homologous Recombination," *Nature 317*: 230-234 (1985).
Smyth, "New *Arabidopsis* Mutations that Result in All Four Products of Meiosis Being Held Together as a Tetrad of Fused Pollen Grains May Facilitate Genetic Mapping and Lead to New Insights into Pollen Biology," *Current Biology 4*: 851-853 (1994).
Somerville et al., "Plant Functional Genomics," *Science 285*: 380-383 (1999).
Spielmann et al., "T-DNA Structure in Transgenic Tobacco Plants with Multiple Independent Integration Sites," *Mol. Gen. Genet. 205*: 34-43 (1986).
Stalker et al., "Herbicide Resistance in Transgenic Plants Expressing a Bacterial Detoxification Gene," *Science 242*: 419-423 (1988).
Steifel et al., Herbicide Resistance in Transgenic Plants Expressing a Bacterial Detoxification Gene,: *Nature 341*: 343 (1989).
Stinchomb et al., "Isolation and Characterisation of a Yeast Chromosomal Replicator," *Nature 282*: 39-43 (1979).
Stone et al., "*LEAFY COTYLEDON2* Encodes a B3 Domain Transcription Factor that Induces Embryo Development," *Proc. Natl. Acad. Sci. USA*, 98:11806-11811 (2001).
Stougaard, "Substrate-Dependent Negative Selection in Plants Using a Bacterial Cytosine Deaminase Gene," *The Plant Journal 3*: 755-761 (1993).
Sullivan et al., "Isolation and Characterization of a Maize Chlorophyll a/b Binding protein Gene that Produces High Levels of mRNA in the Dark," *Mol. Gen. Genet. 215*: 431-440 (1980).
Sun et al., "Human Artificial Episomal Chromosomes for Cloning Large DNA Fragments in Human Cells," *Nature Genetics 8*: 33-41 (1994).
Sun et al., "Molecular Structure of a Functional *Drosophila* Centromere," *Cell 91*: 1007-1019 (1997).
Sutcliffe, "Nucleotide Sequence of the Ampicillin Resistance Gene of *Escherichia coli* Plasmid pBR322," *Proc. Natl Acad. Sci USA 75*: 3737-3741 (1978).
Symington et al., "Meiotic Recombination Within the Centromere of a Yeast Chromosome," *Cell 52*: 237-240 (1988).
Symons, "Avocado Sunblotch Viroid: Primary Sequence and Proposed Secondary Structure," *Nucleic Acids Research 9*: 6527-6537 (1981).
Symons, "Small Catalytic RNAs," *Annu. Rev. Biochem 61*: 641-671 (1992).
Tarczynski et al., "Expression of a Bacerial mtID Gene in Transgenic Tobacco Leads to Production and Accumulation of Mannitol," *Proc. Nat. Acad. Sci. USA 89*:2600-2604 (1992).
Tarczynski et al., "Stress Protection of Transgenic Tobacco by Production of the Osmolyte Mannitol," *Science 259*: 508-510 (1993).
Tavoletti et al., "Half Tetrad Analysis in Alfalfa Using Multiple Restriction Fragment Length Polymorphism Markers," *Proc. Natl. Acad. Sci. Online 93*: 10918-10922 (1996).
Thillet et al., "Site-directed Mutagenesis of Mouse Dihydrofolate Reductase. Mutants with Increased Resistance to Methotrexate and Trimethoprim," *J. Biol. Chem 263*: 12500-12508 (1988).
Thomas et al., "High-Frequency Targeting of Genes to Specific Sites in the Mammalian Genome," *Cell 44*: 419-428 (1986).
Thomas et al., "Viable Molecular Hybrids of Bacteriophage Lambda and Eukaryotic DNA," *Proc. Nat. Acad. Sci. USA 71*: 4579 (1974).

Thompson et al., "Identification and Distribution of Seven Classes of Middle-Repetitive DNA in the *Arabidopsis thaliana* Genome," *Nucleic Acids Research 24*: 3017-3022 (1996).
Thompson et al., "Decreased Expression of BRCA1 Accelerates Growth and Is Often Present During Sporadic Breast Cancer Progression," *Nature Genet. 9*: 444-450 (1995).
Thompson et al., "A Novel Repetitive Sequence Associated with the Centrometric Regions of *Arabidopsis thaliana* Chromosomes," *Mol Gen Genet 253*: 247-252, (1996).
Tian et al., "Expression of the Green Fluorescent Protein Gene in Conifer Tissues," *Plant Cell Reports 16*: 267-271 (1997).
Tominaga, "The Site-specific Recombinase Encoded by pinD in *Shigella dysenteriae* is due to the presence of a defective Mu prophase," *Microbiol. 143*: 2057-2063 (1997).
Toriyama et al., "Haploid and Diploid Plant Regeneration from Protoplasts of Another Callus in Rice," *Theor Appl. Genet. 73*: 16-19 (1986).
Tsay et al., "Identification of a Mobile Endogenous Transposon in *Arabidopsis thaliana*," *Science 260*: 342-344 (1993).
Tugal et al., "*Arabidopsis* 22-Kilodalton Peroxisomal Membrane Protein, Nucleotide Sequence Analysis and Biochemical Characterization," *Plant Physiology 120*: 309-320 (1999).
Twell et al., "Promoter Analysis of Genes that Are Coordinately Expressed During Pollen-Specific Enhancer Sequences and Shared Regulatory Elements," *Genes Dev. 5*: 496-507 (1991).
Twell et al., "Transient Expression of Chimeric Genes Delivered Pollen by Microprojectile Bombardment," *Plant Physiol. 91*: 1270-1274 (1989).
Tyler-Smith et al., "Localization of DNA Sequences Required for Human Centromere Function Through an Analysis of Rearranged Y Chromosomes," *Nature Genetics 5*: 368-375 (1993).
Tyler-Smith et al., "Mammalian Chromosome Structure," *Current Opin. Genetic Dev. 3*: 390-397 (1993).
Uchimiya et al., "Expression of a Foreign Gene in Callus Derived from DNA-treated Protoplasts of Rice," *Mol. Gen. Genet. 204*: 204 (1986).
Vahedian et al., "Genomic Organization and Evolution of the Soybean SB92 Satellite Sequence," *Plant Molecular Biology 29*: 857-862 (1995).
Valvekens et al., "*Agrobacterium tumefaciens*-Mediated Transformation of *Arabidopsis thaliana* Root Explants by Using Kanamycin Selection," *Proc. Natl. Acad. Sci. USA 85*: 5536-5540 (1988).
Van der Krol et al., "Flavonoid Genes in Petunia: Addition of a Limited Number of Gene Copies May Lead to a Suppression of Gene Expression," *Plant Cell 2*: 291-299 (1990).
Van't Hof et al., "The Size and Number of Replicon Families of Chromosomal DNA of *Arabidopsis thaliana*," *Chromosoma 68*: 269-285 (1978).
Vasil et al., "Herbicide Resistant Fertile Transgenic Wheat Plants Obtained by Microprojectile Bombardment of Regenerable Embryogenic Callus," *BioTechnology 10*: 667-674 (1992).
Vasil, "Progress in the Regeneration and Genetic Manipulation of Cereal Crops," *BioTechnology 6*: 397-402 (1988).
Vernon et al., "A Novel Methyl Transferase Induced by Osmotic Stress in the Faculative Halophyte *Mesembryanthemum crystallinum*," *The EMBO Journal 11*: 2077-2085 (1992).
Voytas et al., "A Copia-Like Transposable Element Family in *Arabidopsis thaliana*," *Nature 336*: 242-244 (1988).
Wagner et al., "Coupling of Adenovirus to Transferrin-Polylysine/DNA Complexes Greatly Enhances Receptor-Mediated Gene Delivery and Expression of Transfected Genes," *Proc. Natl. Acad. Sci. USA*, 89: 6099-6103(1992).
Walker et al., "DNA Sequences Required for Anaerobic Expression of the Maize Alcohol Dehydrogenase 1 Gene," *Proc. Nat. Acad. Sci. USA 84*: 6624-6628 (1987).
Wang et al., "Characterization of cis-Acting Elements Regulating Transcription from the Promoter of a Constitutively Active Rice Actin Gene," *Molecular and Cellular Biology*: 3399-3406 (1992).
Weide et al., "Paracentromeric Sequences on Tomato Chromosome 6 Show Homology to Human Satellite III and to the Mammalian CENP-B Binding Box," *Mol. Gen. Genet. 259*: 190-197 (1998).
Wensink et al., A System for Mapping DNA Sequences in the Chromosomes of *Drosophila melanogaster*. , *Cell 3*: 315-325 (1974).

Wevrick et al. "Partial Deletion of Alpha Satellite DNA Associated with Reduced Amounts of the Centromere Protein CENP-B in a Mitotically Stable Human Chromosome Rearrangement," *Molecular and Cellular Biology 102*: 6374-6380 (1990).

Whitehouse et al., "Mapping Chromosome Centromeres by the Analysis of Unordered Tetrads," *Nature* 4205: 893 (1950).

Wigler et al., "Transfer of Purified Herpes Virus Thymidine Kinase Gene to Cultured Mouse Cells," *Cell 11*: 223-232 (1977).

Willard, "Centromeres of mammalian chromosomes," *TIG 6(12)*: 410-416 (1990).

Willard, "Centromeres: The Missing Link in the Development of Human Artificial Chromosomes," *Genetics & Development 8*: 219-225 (1998).

Wolter et al., "Chilling Sensitivity of *Arabidopsis thaliana* with Genetically Engineered Membrane Lipids," *The EMBO Journal 11*: 4685-4692 (1992).

Wong et al., "Electric Field Mediated Gene Transfer," *Biochim. Biophys. Res. Commun. 107*: 584-587 (1982).

Wright et al., "Multiple Non-LTR Retrotransposons in the Genome of *Arabidopsis thaliana*," *Genetics 142*: 569-578 (1996).

Wu et al., "Composition and Structure of the Centromeric Region of Rice Chromosome 8," *Plant Cell 16*: 967-76 (2004).

Xia et al., "Genomic Organization of the *canrep* Repetitive DNA in *Brassica juncea*," *Plant Molecular Biology 26*: 817-832 (1994).

Xia et al., Structure and Evolution of a Highly Repetitive DNA Sequence from *Brassica napus*, Plant Molecular Biology 21: 213-224 (1993).

Xiang, et al. "The Anti-*nptyll* Gene," *Plant Physiol. 102*: 287-293 (1993).

Xu et al., "Expression of a Late Embryogenesis Abundant Protein Gene, HVA1, from Barley Confers Tolerance to Water Deficit and Salt Stress in Transgenic Rice," *Plant Physiol.* 110: 249-257 (1996).

Yamada et al., "Plant Regeneration from Protoplast-derived Callus of Rice," *Plant Cell Rep. 4*: 85 (1986).

Yamaguchi-Shinozaki et al., "Molecular Cloning and Characterization of 9 cDNAs for Genes that Are Responsive to a Desiccation in *Arabidopsis thaliana*: Sequence Analysis of One cDNA Clone that Encodes a Putative Transmembrane Channel Protein," *Plant Cell Physiol. 33*: 217-224 (1992).

Yang et al., "Maize Sucrose Synthase-1 Promoter Directs Phloem Cell-specific Expression of Gus Gene in Transgenic Tobacco Plants," *Proc. Natl. Acad. Sci. USA 87*: 4144-4148 (1990).

Yen et al., "CENP-E, a Novel Human Centomere-Associated Protein Required for Progression from Metaphase to Anaphase," *The EMBO Journal 10*: 1245-1254 (1991).

Young et al., "Organization of Coding Sequences in *Drosophila melanogaster*," *J. Supramolecular Struct.*, S1: 211 (1977).

Young et al., Eukaryotic Genetic Systems ICNUCLA Symposia on Molecular and Cellular Biology VII: 315-331 (1977).

Yuan et al., "Selection of Guide Sequences That Direct Efficient Cleavage of mRNA by Human Ribonuclease P," *Science 263*: 1269-1273 (1994).

Yuan et al., "Targeted cleavage of mRNA by human RNase P," *Proc. Natl. Acad. Sci. USA 89*: 8006-8010 (1992).

Zatloukal et al., "Transferinfection: A Highly Efficient Way to Express Gene Constructs in Eukaryotic Cells," *Ann. N.Y. Acad. Sci. 660*: 136-153, 1992.

Zentgraf, "Telomere-binding Proteins of *Arabidopsis thaliana*," *Plant Molecular Biology 27*: 467-475 (1995).

Zhang et al., "Molecular Cloning, Nucleotide Sequence, and Function of a Site-Specific Recombinase Encoded in the Major 'Pathogenicity Island' of *Salmonella typhi*," *Gene 202*: 139-146 (1997).

Zhang et al., "*Zea mays* B Chromosome Centromere Repeat Sequence *Zea_mays*_MBsC216 pMBsC216," (unpublished), 1999.

Zukowski et al., "Chromogenic Identification of Genetic Regulatory Signals in *Bacillus subtilis* Based on Expression of a Cloned *Pseudomonas* Gene," *Proc. Natl. Acad. Sci., USA 80*: 1101-1105 (1983).

Zuo et al., "The *WUSCHEL* Gene Promotes Vegetative-to-Embryonic Transition in *Arabidopsis*," *Plant J.*, 30:349-359 (2002).

Iwabuchi et al., Molecular and cytological characterization of repetitive DNA sequences in brassica. *Theor. Appl. Genet.* 81(3): 349-55 (1991).

EMBL Accession No. AC138570, *Zea mays* genetic clone ZM16H10, finished contig 37375, complete sequence, Jan. 11, 2003.

EMBL Accession No. AC185251, *Zea mays* chromosome 4 clone CH201-478E6; ZMMBBc0478E06, Apr. 15, 2006.

EMBL Accession No. AY530257, *Zea mays* clone CentC42 centromeric repeat sequence, Feb. 28, 2004.

* cited by examiner

PLANTS MODIFIED WITH MINI-CHROMOSOMES

This application claims priority to U.S. Provisional Patent Application No. 60/715,976, filed Sep. 8, 2005 which is incorporated by reference herein in its entirety.

BACKGROUND OF THE INVENTION

Two general approaches are used for introduction of new genetic information ("transformation") into cells. One approach is to introduce the new genetic information as part of another DNA molecule, referred to as an "episomal vector," or "mini-chromosome", which can be maintained as an independent unit (an episome) apart from the host chromosomal DNA molecule(s). Episomal vectors contain all the necessary DNA sequence elements required for DNA replication and maintenance of the vector within the cell. Many episomal vectors are available for use in bacterial cells (for example, see Maniatis et al., "Molecular Cloning: a Laboratory Manual," Cold Spring Harbor Laboratory, Cold Spring Harbor, N.Y. 1982). However, only a few episomal vectors that function in higher eukaryotic cells have been developed. Higher eukaryotic episomal vectors were primarily based on naturally occurring viruses. In higher plant systems gemini viruses are double-stranded DNA viruses that replicate through a double-stranded intermediate upon which an episomal vector could be based, although the gemini virus is limited to an approximately 800 bp insert. Although an episomal plant vector based on the Cauliflower Mosaic Virus has been developed, its capacity to carry new genetic information also is limited (Brisson et al., Nature, 310:511, 1984.).

The other general method of genetic transformation involves integration of introduced DNA sequences into the recipient cell's chromosomes, permitting the new information to be replicated and partitioned to the cell's progeny as a part of the natural chromosomes. The introduced DNA usually is broken and joined together in various combinations before it is integrated at random sites into the cell's chromosome (see, for example Wigler et al., Cell, 11:223, 1977). Common problems with this procedure are the rearrangement of introduced DNA sequences and unpredictable levels of expression due to the location of the transgene in the genome or so called "position effect variegation" (Shingo et al., Mol. Cell. Biol., 6:1787, 1986). Further, unlike episomal DNA, integrated DNA cannot normally be precisely removed. A more refined form of integrative transformation can be achieved by exploiting naturally occurring viruses that integrate into the host's chromosomes as part of their life cycle, such as retroviruses (see Chepko et al., Cell, 37:1053, 1984).

One common genetic transformation method used in higher plants is based on the transfer of bacterial DNA into plant chromosomes that occurs during infection by the phytopathogenic soil bacterium *Agrobacterium* (see Nester et al., Ann. Rev. Plant Phys., 35:387-413, 1984). By substituting genes of interest for the naturally transferred bacterial sequences (called T-DNA), investigators have been able to introduce new DNA into plant cells. However, even this more "refined" integrative transformation system is limited in three major ways. First, DNA sequences introduced into plant cells using the *Agrobacterium* T-DNA system are frequently rearranged (see Jones et al., Mol. Gen. Genet., 207:478, 1987). Second, the expression of the introduced DNA sequences varies between individual transformants (see Jones et al., Embo J., 4:2411-2418, 1985). This variability is presumably caused by rearranged sequences and the influence of surrounding sequences in the plant chromosome (i.e., position effects), as well as methylation of the transgene. Finally, insertion of extra elements into the genome can disrupt the genes, promoters or other genetic elements necessary for normal plant growth and function.

Another widely used technique to genetically transform plants involves the use of microprojectile bombardment. In this process, a nucleic acid containing the desired genetic elements to be introduced into the plant is deposited on or in small metallic particles, e.g., tungsten, platinum, or preferably gold, which are then delivered at a high velocity into the plant tissue or plant cells. However, similar problems arise as with *Agrobacterium*-mediated gene transfer, and as noted above expression of the inserted DNA can be unpredictable and insertion of extra elements into the genome can disrupt and adversely impact plant processes.

One attractive alternative to commonly used methods of transformation is the use of an artificial chromosome. Artificial chromosomes are man-made linear or circular DNA molecules constructed in part from cis-acting DNA sequence elements that provide replication and partitioning of the constructed chromosomes (see Murray et al., Nature, 305:189-193, 1983). Desired elements include: (1) origin of replication, which are the sites for initiation of DNA replication, (2) Centromeres (site of kinetochore assembly and responsible for proper distribution of replicated chromosomes into daughter cells at mitosis or meiosis), and (3) if the chromosome is linear, telomeres (specialized DNA structures at the ends of linear chromosomes that function to stabilize the ends and facilitate the complete replication of the extreme termini of the DNA molecule). An additional desired element is a chromatin organizing sequence. It is well documented that centromere function is crucial for stable chromosomal inheritance in almost all eukaryotic organisms (reviewed in Nicklas 1988). The centromere accomplishes this by attaching, via centromere binding proteins, to the spindle fibers during mitosis and meiosis, thus ensuring proper gene segregation during cell divisions.

The essential chromosomal elements for construction of artificial chromosomes have been precisely characterized in lower eukaryotic species, and more recently in mouse and human. Autonomous replication sequences (ARSs) have been isolated from unicellular fungi, including *Saccharomyces cerevisiae* (brewer's yeast) and *Schizosaccharomyces pombe* (see Stinchcomb et al., 1979 and Hsiao et al., 1979). An ARS behaves like an origin of replication allowing DNA molecules that contain the ARS to be replicated in concert with the rest of the genome after introduction into the cell nuclei of these fungi. DNA molecules containing these sequences replicate, but in the absence of a centromere they are not partitioned into daughter cells in a controlled fashion that ensures efficient chromosome inheritance.

Artificial chromosomes have been constructed in yeast using the three cloned essential chromosomal elements (see Murray et al., Nature, 305:189-193, 1983). None of the essential components identified in unicellular organisms, however, function in higher eukaryotic systems. For example, a yeast CEN sequence will not confer stable inheritance upon vectors transformed into higher eukaryotes.

In contrast to the detailed studies done in yeast, less is known about the molecular structure of functional centromeric DNA of higher eukaryotes. Ultrastructural studies indicate that higher eukaryotic kinetochores, which are specialized complexes of proteins that form on the centromere during late prophase, are large structures (mammalian kinetochore plates are approximately 0.3 μm in diameter) which possess multiple microtubule attachment sites (reviewed in Rieder, 1982). It is therefore possible that the centromeric DNA regions of these organisms will be correspondingly large, although the minimal amount of DNA necessary for centromere function may be much smaller.

While the above studies have been useful in elucidating the structure and function of centromeres, it was not known whether information derived from lower eukaryotic or mammalian higher eukaryotic organisms would be applicable to plants. There exists a need for cloned centromeres from higher eukaryotic organisms, particularly plant organisms, which would represent a first step in production of artificial chromosomes. There further exists a need for plant cells, plants, seeds and progeny containing functional, stable, and autonomous artificial chromosomes capable of carrying a large number of different genes and genetic elements.

SUMMARY OF THE INVENTION

In one aspect, the present invention addresses mini-chromosomes comprising a centromere having one or more selected repeated nucleotide sequences and adchromosomal *Zea mays* (corn) plants comprising a mini-chromosome of the invention. The invention provides for the mini-chromosomes, described in further detail herein, having a centromere comprising a selected repeated nucleotide sequence derived from *Zea mays*.

In another aspect, the invention is based on the production of modified plants, containing functional, stable, autonomous mini-chromosomes. Such mini-chromosomes have been shown herein to be meiotically transmitted to progeny. The present invention particularly addresses adchromosmoal *Zea mays* (corn) plants. The invention provides for adchromosomal plants, described in further detail herein, comprising a mini-chromosome, wherein said mini-chromosome preferably has a transmission efficiency during mitotic division of at least 90%, for example, at least 95%. Additionally, these adchromosomal plants may comprise a mini-chromosome having a transmission efficiency during meiotic division of, e.g., at least 80%, at least 85%, at least 90% or at least 95%.

In one embodiment, the mini-chromosomes of the invention comprise a centromere comprising any one of (a) a repeated nucleotide sequence derived from (i.e. is a fragment or variant of) the sequence denoted as CentC, an exemplary sequence of which is provided as GenBank Accession No. AY1290008 (SEQ ID NO: 77), (b) a fragment derived from the sequence denoted as CRM, an exemplary sequence of which is provided as GenBank Accession No. AY129008, or (c) a fragment derived from the sequence denoted as CentA, an exemplary sequence of which is provided as GenBank Accession No. AF078917 (SEQ ID NO: 79), or combinations thereof. Such a sequence or fragment derived from CentC, CRM or CentA preferably hybridizes under highly selective conditions to a representative CentC, CRM or CentA sequence, respectively, or retains at least 70%, 75%, 80%, 85%, 90% or 95% overall identity over the length of the sequence or fragment to a representative CentC, CRM or CentA sequence.

Particularly, the invention provides for mini-chromosomes comprising centromeres having the CentC repeated nucleotide sequence of SEQ ID NO: 70, SEQ ID NO: 71 or variants thereof, e.g. the variants provided in Tables 17 and 22. The invention further provides for mini-chromosomes comprising centromeres having a repeated nucleotide sequence that hybridizes to SEQ ID NO: 70 or SEQ ID NO: 71 under highly selective conditions comprising 0.02 M to 0.15 M NaCl at temperatures of about 50° C. to 70° C., or alternatively comprising 0.5×SSC and 0.25% SDS at 65° C. for 15 minutes, followed by a wash at 65° C. for a half hour. The invention also provides for mini-chromosomes comprising a repeated nucleotide sequence that is at least 70%, 75%, 80%, 85% 90% or 95% identical to SEQ ID NO: 70 or SEQ ID NO: 71. For example, a CentC variant may utilize any nucleotide displayed at a particular base position in Table 17 or 22 together with any nucleotide displayed at any other base position in Table 17 or 22 in any combination, provided that the sequence of the CentC variant retains overall identity over its length of at least 70% to SEQ ID NO: 70 or 71, or would hybridize under highly selective conditions to SEQ ID NO: 70 or 71.

In another embodiment, the invention provides for mini-chromosomes comprising centromeres having a CRM repeated nucleotide sequence that is a fragment of SEQ ID NO: 78 or variant thereof. Such fragments of CRM preferably include at least 30, 40, 50, 60, 70, 80, 90, 100, 125, 150, 175, 200, 225, 250, 275, 300, 350, 400, 450, or 500 bp of CRM, most preferably at least 50 bp of CRM. The invention further provides for mini-chromosomes comprising centromeres having a variant CRM repeated nucleotide sequence that hybridizes to SEQ ID NO: 78 under highly selective conditions comprising 0.02 M to 0.15 M NaCl at temperatures of about 50° C. to 70° C., or alternatively comprising 0.5×SSC and 0.25% SDS at 65° C. for 15 minutes, followed by a wash at 65° C. for a half hour. Exemplary fragments of CRM include nucleotides 1-515 (515 bp), nucleotides 1-930 (930 bp), nucleotides 1-1434 (1434 bp), nucleotides 1508-3791 (2284 bp), nucleotides 1508-5417 (3910 bp), nucleotides 2796-2890 (95 bp), nucleotides 2796-2893 (98 bp), nucleotides 4251-4744 (494 bp), nucleotides 4626-4772 (147 bp), nucleotides 4945-6236 (1295 bp), nucleotides 4983-5342 (360 bp), nucleotides 5487-5569 (83 bp), nucleotides 5757-6212 (456 bp), nucleotides 5765-7571 (1807 bp), nucleotides 6529-6653 (125 bp), nucleotides 6608-6658 (51 bp), nucleotides 6638-7571 (934 bp) and/or nucleotides 6640-7156 (517 bp) of SEQ ID NO: 78. The invention also provides for mini-chromosomes comprising a repeated nucleotide sequence that retains overall identity over its length of at least 70%, 75%, 80%, 85% 90% or 95% to SEQ ID NO: 78. The invention contemplates fragments of CRM ranging in size up to 51 bp, 83 bp, 95 bp, 98 bp, 125 bp, 147 bp, 360 bp, 456 bp, 494 bp, 515 bp, 517 bp, 930 bp, 934 bp, 1295 bp, 1434 bp, 1807 bp, 2284 bp or 3910 bp in length.

The invention also provides for mini-chromosomes comprising centromeres having a CentA repeated nucleotide sequence that is a fragment of SEQ ID NO: 79 or variant thereof. Exemplary fragments of CentA are up to 512 bp or 513 bp in length (see Table 15 below) or range in size from 50 to 512 bp or 50 to 513 bp. The invention further provides for mini-chromosomes comprising centromeres having a variant CentA repeated nucleotide sequence that hybridizes to SEQ ID NO: 79 under highly selective conditions comprising 0.02 M to 0.15 M NaCl at temperatures of about 50° C. to 70° C., or alternatively comprising 0.5×SSC and 0.25% SDS at 65° C. for 15 minutes, followed by a wash at 65° C. for a half hour. The invention also provides for mini-chromosomes comprising a repeated nucleotide sequences that retains overall identity over its length of at least 70%, 75%, 80%, 85%, 90% or 95% to SEQ ID NO: 79.

In another embodiment, the centromeres of any of the preceding mini-chromosomes comprise a combination of two or more of the repeated nucleotides sequences described herein, including those derived from CentC, CRM or CentA sequences. The invention provides for mini-chromosomes having a centromere comprising (a) a first repeated nucleotide sequence that hybridizes under highly selective conditions comprising 0.02 M to 0.15 M NaCl at temperatures of about 50° C. to 70° C., or alternatively comprising 0.5×SSC and 0.25% SDS at 65° C. for 15 minutes, followed by a wash at 65° C. for a half hour, to the nucleotide sequence of either SEQ ID NO: 70 or SEQ ID NO: 71, and (b) a second repeated nucleotide sequence that hybridizes under highly selective conditions comprising 0.02 M to 0.15 M NaCl at temperatures of about 50° C. to 70° C., or alternatively comprising 0.5×SSC and 0.25% SDS at 65° C. for 15 minutes, followed by a wash at 65° C. for a half hour, to the nucleotide sequence of SEQ ID NO: 78. Preferably the second repeated nucleotide sequence comprises at least 50 base pairs of SEQ ID NO: 78. Alternatively, the second nucleotide sequence can hybridize under highly selective conditions to the nucleotide sequence of SEQ ID NO: 79. In particular, the invention contemplates mini-chromosomes having a centromere comprising the repeated nucleotide sequence of SEQ ID NO: 70 or a variant thereof and a 50 bp fragment of SEQ ID NO: 78. The invention also contemplates mini-chromosomes having a centromere comprising the repeated nucleotide sequence of SEQ ID NO: 71 or a variant thereof and a 50 bp fragment of SEQ ID NO: 78.

The invention contemplates mini-chromosomes having centromeres comprising at least 50 bp of the contig segments identified in Tables 14 an d18 as homologous to any of the following sequences: Mo17 locus bz (GenBank Accession No. AY664416), rust resistance gene rp3-1 (GenBank Accession No. AY5704035), coliphage phi-X174 (Genbank Accession No. J02482), 40S ribosomal protein S8 (GenBank Accession No. AY530951), gag-pol (GenBank Accession No. AF464738), retrotransposon (GenBank Accession No. AY574035), Mo17 locus 9008 (GenBank Accession No. AY664418), alpha zein gene cluster (GenBank Accession No. AF090447), Mo17 locus 9009 (GenBank Accession No. AY664419), B73 locus 9002 (GenBank Accession No. AY664413), *Magnaporthe grisea* (GenBank Accession No. XM_367004), yeast 26S ribosomal RNA (GenBank Accession No. AY046113), Tn1 (GenBank Accession No. AF162223), and polynucleotides having the sequence of any of SEQ ID NO: 79, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87 and SEQ ID NO: 88. The invention also contemplates mini-chromosomes having a centromere comprising a fragment or a variant of any of these nucleotide sequences.

The invention further contemplates that, for any of the contig fragments identified in any of the tables herein by their beginning and ending nucleotide numbers, isolated nucleic acids may be prepared (including single stranded or double stranded) that retain exact identity to the identified fragment or complement thereof, or that are further fragments or variants thereof that preferably retain ability to hybridize to the original identified fragment. Such isolated nucleic acids are used, e.g., as components of mini-chromosomes of the invention, as probes to isolate centromere sequences for use in mini-chromosomes of the invention, or for transcription of desired complementary strands.

The invention also contemplates mini-chromosomes having a centromere comprising one or more of the following simple repeat sequences: AT-rich repeat, (GCA)$_n$ repeat, GA-rich repeat, CT-rich repeat, T-rich or (TTTTC)$_n$ repeat.

In another embodiment, any of the preceding mini-chromosomes comprise centromeres having n copies of a repeated nucleotide sequence, wherein n is less than 1000, or less than 500, 250 or 100. In exemplary embodiments, the centromeres of the mini-chromosomes of the invention comprise n copies of a repeated nucleotide sequence, wherein n is at least 5, wherein n is at least 15, wherein n is at least 25, wherein n is at least 50 and wherein n is at least 100.

In additional exemplary embodiments, the centromeres of the mini-chromosomes of the invention comprise n copies of a repeated nucleotide sequence where n ranges from 5 to 15, 5 to 25, 5 to 50, 5 to 100, 5 to 250, 5 to 500, 5 to 1000, 15 to 25, 15 to 50, 15 to 100, 15 to 250, 15 to 500, 15 to 1000, 25 to 50, 25 to 100, 25 to 250, 25 to 500, 25 to 1000, 50 to 100, 50 to 250, 50 to 500, 50 to 1000, 100 to 250, 100 to 500, 100 to 1000, 250 to 500, 250 to 1000, or 500 to 1000.

According to the rough sequence assembly described in Example 6, BAC clones ZB19 has long stretches of CentC repeat and BAC clone ZP113 has long stretches of CentC repeats and/or CRM repeats. For example, the BAC clone ZB19 has stretches of 50 copies of CentC repeats in about 7.5 kb of the nucleotide sequence of contig 30 (SEQ ID NO: 50) and 70 copies of CentC repeats in about 10.5 kb of the nucleotide sequence of contig 31 (SEQ ID NO: 51). The BAC clone ZB113 has stretches of 7 copies of CentC repeats in about 1 kb of the nucleotide sequence of contig 4 (SEQ ID NO: 55), 13 copies of CentC repeats in 1.5 kb of the nucleotide sequence of contig 8 (SEQ ID NO: 59), 24 copies of CentC repeats in about 3.5 kb of the nucleotide sequence of contig 11 (SEQ ID NO: 62), 70 copies of CentC repeats in about 10.7 kb of the nucleotide sequence of contig 15 (SEQ ID NO: 66), 85 copies of CentC repeats in about 13.5 kb of the nucleotide sequence of contig 17 (SEQ ID NO: 68), and 68 copies of CentC repeats in about 20 kb of the nucleotide sequence of contig 18 (SEQ ID NO: 69). In addition, BAC clone ZB113 has 10 copies of CRM repeats and 20 copies of CentC repeats in about 8.5 kb of the nucleotide sequence of contig 14 (SEQ ID NO: 65). BAC clone ZB113 has 11 copies of CRM repeat and 1 copies of CentA repeat in 15.5 kb of the nucleotide sequence of contig 16 (SEQ ID NO: 67). These are examples of stretches of repeated nucleotide sequence in two functional mini-chromosomes.

The invention contemplates mini-chromosomes having a centromere comprising any of the following: at least 5, 6, 7, 8, 9 or 10 repeated nucleotide sequences in about 1.3 kb of nucleotide sequence, at least 15, 20, 25, 30, 35 or 37 repeated nucleotide sequences in about 5.5 kb of nucleotide sequence; or at least 40, 45, 50, 55, 60, 65, 70, 75 or 76 repeated nucleotide sequences in about 13.5 kb of nucleotide sequence.

In an embodiment of the invention, any of the preceding mini-chromosomes comprising a centromere having at least 5 consecutive repeated nucleotide sequences in head to tail orientation. The invention also provides for any of the preceding mini-chromosomes comprising a centromere having at least 5 repeated nucleotide sequences that are consecutive. Consecutive repeated nucleotide sequences may be in any orientation, e.g. head to tail, tail to tail, or head to head, and need not be directly adjacent to each other (e.g., may be 1-50 bp apart).

The invention further provides for any of the preceding mini-chromosomes comprising a centromere having at least 5 of the consecutive repeated nucleotide sequences separated by less than n number of nucleotides, wherein n ranges from 1 to 10, or 1 to 20, or 1 to 30, or 1 to 40, or 1 to 50 or wherein n is less than 10 bp or n is less than 20 bp or n is less than 30 bp or n is less than 40 bp or n is less than 50 bp.

In one embodiment, the mini-chromosomes of the invention are 1000 kilobases or less in length. In exemplary embodiments, the mini-chromosome is 600 kilobases or less in length or 500 kilobases or less in length.

In another embodiment, the mini-chromosomes of the invention comprises a site for site-specific recombination.

In another embodiment, the invention provides for the mini-chromosome, further comprising a centromeric nucleic acid insert that comprises artificially synthesized repeated nucleotide sequences. These artificially synthesized repeated nucleotide sequences may be derived from natural centromere sequences, combinations or fragments of natural centromere sequences including a combination of repeats of different lengths, a combination of different sequences, a combination of both different repeat lengths and different sequences, a combination of repeats from two or more plant species, a combination of different artificially synthesized sequences or a combination of natural centromere sequence(s) and artificially synthesized sequence(s).

The invention also provides for a mini-chromosome, wherein the mini-chromosome is derived from a donor clone or a centromere clone and has substitutions, deletions, insertions, duplications or arrangements of one or more nucleotides in the mini-chromosome compared to the nucleotide sequence of the donor clone or centromere clone. In one embodiment, the mini-chromosome is obtained by passage of the mini-chromosome through one or more hosts. In another embodiment, the mini-chromosome is obtained by passage of the mini-chromosome through two or more different hosts. The host may be selected from the group consisting of viruses, bacteria, yeasts, plants, prokaryotic organisms, or eukaryotic organisms. In another embodiment, the mini-chromosome is obtained from a donor clone by in vitro methods that introduce sequence variation during template-based replication of the donor clone, or its complementary sequence. In one embodiment this variation may be introduced by a DNA-dependent DNA polymerase. In a further embodiment a minichromosome derived by an in vitro method may be further modified by passage of the mini-chromosome through one or more hosts.

The invention also provides for mini-chromosomes that preferably have a transmission efficiency during mitotic division of at least 90%, for example, at least 95%. Additionally, these adchromosomal mini-chromosomes have a transmission efficiency during meiotic division of, e.g., at least 80%, at least 85%, at least 90% or at least 95%.

The invention also provides for a mini-chromosome, wherein the mini-chromosome comprises one or more exogenous nucleic acids. In further exemplary embodiments, the mini-chromosome comprises at least two or more, at least three or more, at least four or more, at least five or more or at least ten or more exogenous nucleic acids.

In one embodiment, at least one exogenous nucleic acid of any of the preceding mini-chromosomes of a plant is operably linked to a heterologous regulatory sequence functional in plant cells. The invention provides for exogenous nucleic acids linked to a plant regulatory sequence. The invention also provides for exogenous nucleic acids linked to a non-plant regulatory sequence, such as an arthropod, viral, bacterial, vertebrate or yeast regulatory sequence. Exemplary regulatory sequences comprise any one of SEQ ID NOS: 1 to 20 or a functional fragment or variant thereof.

In another embodiment, the mini-chromosome comprises an exogenous nucleic acid that confers herbicide resistance, insect resistance, disease resistance, or stress resistance on the plant. The invention provides for mini-chromosomes comprising an exogenous nucleic acid that confers resistance to phosphinothricin or glyphosate herbicide. The invention also provides for mini-chromosomes comprising an exogenous nucleic acid that encodes a phosphinothricin acetyltransferase, glyphosate acetyltransferase, acetohydroxyadic synthase or a mutant enolpyruvylshikimate phosphate (EPSP) synthase.

The invention also provides for mini-chromosomes comprising an exogenous nucleic acid that encodes a *Bacillus thuringiensis* toxin gene or *Bacillus cereus* toxin gene. The invention further provides for mini-chromosomes comprising an exogenous nucleic acid that confers resistance to drought, heat, chilling, freezing, excessive moisture, ultraviolet light, ionizing radiation, toxins, pollution, mechanical stress or salt stress. The invention also provides for a mini-chromosome that comprises an exogenous nucleic acid that confers resistance to a virus, bacteria, fungi or nematode.

In another embodiment, the mini-chromosome comprises an exogenous nucleic acid conferring herbicide resistance, an exogenous nucleic acid conferring insect resistance, and at least one additional exogenous nucleic acid.

The invention provides for mini-chromosomes comprising an exogenous nucleic acid selected from the group consisting of a nitrogen fixation gene, a plant stress-induced gene, a nutrient utilization gene, a gene that affects plant pigmentation, a gene that encodes an antisense or ribozyme molecule, a gene encoding a secretable antigen, a toxin gene, a receptor gene, a ligand gene, a seed storage gene, a hormone gene, an enzyme gene, an interleukin gene, a clotting factor gene, a cytokine gene, an antibody gene, a growth factor gene, a transcription factor gene, a transcriptional repressor gene, a DNA-binding protein gene, a recombination gene, a DNA replication gene, a programmed cell death gene, a kinase gene, a phosphatase gene, a G protein gene, a cyclin gene, a cell cycle control gene, a gene involved in transcription, a gene involved in translation, a gene involved in RNA processing, a gene involved in RNAi, an organellar gene, a intracellular trafficking gene, an integral membrane protein gene, a transporter gene, a membrane channel protein gene, a cell wall gene, a gene involved in protein processing, a gene involved in protein modification, a gene involved in protein degradation, a gene involved in metabolism, a gene involved in biosynthesis, a gene involved in assimilation of nitrogen or other elements or nutrients, a gene involved in controlling carbon flux, gene involved in respiration, a gene involved in photosynthesis, a gene involved in light sensing, a gene involved in organogenesis, a gene involved in embryogenesis, a gene involved in differentiation, a gene involved in meiotic drive, a gene involved in self incompatibility, a gene involved in development, a gene involved in nutrient, metabolite or mineral transport, a gene involved in nutrient, metabolite or mineral storage, a calcium-binding protein gene, or a lipid-binding protein gene.

The invention also provides for a mini-chromosome comprising an exogenous enzyme gene selected from the group consisting of a gene that encodes an enzyme involved in metabolizing biochemical wastes for use in bioremediation, a gene that encodes an enzyme for modifying pathways that produce secondary plant metabolites, a gene that encodes an enzyme that produces a pharmaceutical, a gene that encodes an enzyme that improves changes the nutritional content of a plant, a gene that encodes an enzyme involved in vitamin synthesis, a gene that encodes an enzyme involved in carbohydrate, polysaccharide or starch synthesis, a gene that encodes an enzyme involved in mineral accumulation or availability, a gene that encodes a phytase, a gene that encodes an enzyme involved in fatty acid, fat or oil synthesis, a gene that encodes an enzyme involved in synthesis of chemicals or plastics, a gene that encodes an enzyme involved in synthesis of a fuel and a gene that encodes an enzyme involved in synthesis of a fragrance, a gene that encodes an enzyme involved in synthesis of a flavor, a gene that encodes an enzyme involved in synthesis of a pigment or dye, a gene that encodes an enzyme involved in synthesis of a hydrocarbon, a gene that encodes an enzyme involved in synthesis of a structural or fibrous compound, a gene that encodes an enzyme involved in synthesis of a food additive, a gene that encodes an enzyme involved in synthesis of a chemical insecticide, a gene that encodes an enzyme involved in synthesis of an insect repellent, or a gene controlling carbon flux in a plant.

In another embodiment of the invention, any of the preceding mini-chromosomes comprise a telomere.

The invention also provides embodiments wherein any of the preceding mini-chromosomes are linear or circular.

In one embodiment, the invention provides for corn plant cells comprising any of the preceding mini-chromosomes. The invention also provides for corn plant tissue and corn plants comprising these cells. The invention further provides for corn seed obtained from the corn plants of the invention.

In another embodiment, the invention provides for adchromosomal *Zea mays* (corn) plants comprising any of the preceding mini-chromosomes. In addition, the invention provides for corn plant cells, tissues and seeds obtained from the adchromosomal plants.

In one embodiment of the invention, any of the preceding adchromosomal plants are a monocotyledon. In another embodiment of the invention, any of the preceding adchromosomal plants are a dicotyledone. The invention also provides that the adchromosomal plants of the invention are, e.g., crop plants, cereal plants, vegetable crops, field crops, fruit and vine crops, wood or fiber crops or ornamental plants. The invention also provides exemplary adchromosomal plants that are *Zea* species.

Another embodiment of the invention is a part of any of the preceding adchromosomal plants. Exemplary plant parts of the invention include a pod, root, cutting, tuber, stem, stalk, fruit, berry, nut, flower, leaf, bark, wood, epidermis, vascular tissue, organ, protoplast, crown, callus culture, petiole, petal, sepal, stamen, stigma, style, bud, meristem, cambium, cortex, pith, sheath, silk or embryo. Other exemplary plant parts are a meiocyte or gamete or ovule or pollen or endosperm of any of the preceding adchromosomal plants. Other exemplary plant parts are a seed, embryo or propagule of any of the preceding adchromosomal plants.

An embodiment of the invention is a progeny of any of the preceding adchromosomal plants of the invention. These progeny of the invention may be the result of self-breeding, cross-breeding, apomyxis or clonal propagation. In exemplary embodiments, the invention also provides for progeny that comprise a mini-chromosome that is descended from a parental mini-chromosome that contained a centromere less than 150 kilobases in length, less than 100 kilobases in length or less than 50 kilobases in length.

In another aspect, the invention provides for methods of making a mini-chromosome for use in any of the preceding adchromosomal plants of the invention. These methods comprise identifying a centromere nucleotide sequence in a genomic DNA library using a multiplicity of diverse probes, and constructing a mini-chromosome comprising the centromere nucleotide sequence. These methods may further comprise determining hybridization scores for hybridization of the multiplicity of diverse probes to genomic clones within the genomic nucleic acid library, determining a classification for genomic clones within the genomic nucleic acid library according to the hybridization scores for at least two of the diverse probes, and selecting one or more genomic clones within one or more classifications for constructing the mini-chromosome.

In exemplary embodiments, the step of determining a classification for genomic clones within the genomic nucleic acid library may utilize the hybridization scores for at least 3, 4, 5, 6, 7, 8, 9, 10, 11, 12, 13, 14, 15, 16, 17, 18, 19, 20, 21, 22, 23, 24, 25, 26, 27, 28, 29 or 30 or more different probes. A classification may comprise a pattern of high, medium or low hybridization scores to various probes.

Exemplary embodiments of probes useful in this method include a probe that hybridizes to the centromere region of a chromosome, a probe that hybridizes to satellite repeat DNA, a probe that hybridizes to retroelement DNA, a probe that hybridizes to portions of genomic DNA that are heavily methylated, a probe that hybridizes to arrays of tandem repeats in genomic DNA, a probe that hybridizes to telomere DNA or a probe that hybridizes to a pseudogene. Other exemplary probes include, a probe that hybridizes to ribosomal DNA, a probe that hybridizes to mitochondrial DNA, or a probe that hybridizes to chloroplast DNA, for which preferably a classification comprises a low hybridization score for hybridization to said probe.

Another aspect of the invention provides for methods of making any one of the preceding adchromosomal plants comprising delivering a mini-chromosome to a plant cell using a biolistic method, wherein a particle suitable for use in biolistic method is delivered in a liquid with the mini-chromosome, and regenerating a plant from the plant cell. The liquid may further comprise a divalent ion and a di- or poly-amine. In exemplary embodiments, the liquid comprises water, CaCl2, and spermidine, and the particles are gold particles. Suitable alternatives to spermidine are, e.g., spermine or other aliphatic or conjugated di- or poly-amines such as 1,5-diaminopentane, 1,6-diaminohexane, 1,7-diaminoheptane, 1,8-diaminooctane, histamine or related molecules.

A further aspect of the invention provides for methods of making any of the preceding adchromosomal plant comprising co-delivering to a plant cell a mini-chromosome and a nucleic acid encoding a growth inducing gene, wherein said nucleic acid is not part of the mini-chromosome, and regenerating a plant from the plant cell. The invention further provides for methods comprising co-delivering a nucleic acid encoding a growth inducing gene is not expressed or alternatively is not present in the regenerated plant. The invention also provides for methods wherein the co-delivered nucleic acid encodes a growth inducing gene expressed during regeneration. The growth inducing gene may be a plant growth regulator gene, an organogenesis-promoting gene, an embryogenesis-promoting gene or regeneration-promoting gene, such as *Agrobacterium tumefaciens* isopentenyl transferase gene, *Agrobacterium rhizogenes* isopentenyl transferase gene, *Agrobacterium tumefaciens* indole-3-acetamide hydrolase (IAAH) gene or *Agrobacterium tumefaciens* tryptophan-2-monooxygenase (IAAM) gene.

Another aspect of the invention provides for methods of using any of the preceding adchromosomal plants for a food product, a pharmaceutical product or chemical product, according to which a suitable exogenous nucleic acid is expressed in adchromosomal plants or plant cells and the plant or plant cells are grown. The plant may secrete the product into its growth environment or the product may be contained within the plant, in which case the plant is harvested and desirable products are extracted.

Thus, the invention contemplates methods of using any of the preceding adchromosomal plants to produce a modified food product, for example, by growing a plant that expresses a exogenous nucleic acid that alters the nutritional content of the plant, and harvesting or processing the corn plant.

The invention also contemplates methods of using any of the preceding adchromosomal plants to produce a recombinant protein, by growing a plant comprising a mini-chromosome that comprises an exogenous nucleic acid encoding the recombinant protein. Optionally the plant is harvested and the desired recombinant protein is isolated from the plant. Exemplary recombinant proteins include pharmaceutical proteins or industrial enzymes.

The invention also contemplates methods of using any of the preceding adchromosomal plants to produce a recombinant protein, by growing a plant comprising a mini-chromosome that comprises an exogenous nucleic acid encoding an enzyme involved in synthesis of the chemical product. Optionally the plant is harvested and the desired chemical product is isolated from the plant. Exemplary chemical products include pharmaceutical products.

Sequences of the Invention

The following table indicates the identity of the SEQ ID NOs in the sequence listing:
SEQ ID NOS: 1-6—*Drosophila melanogaster* promoter sequences
SEQ ID NOS: 7-20 *Saccharomyces cerevisia* promoter sequences
SEQ ID NOS: 21-51—contigs 1-31 of ZB19
SEQ ID NOS: 52-69-contigs 1-18 of ZB113
SEQ ID NO 70—Consensus repeat sequence of CentC from ZB19
SEQ ID NO 71—Consensus repeat sequence of CentC from ZB113
SEQ ID NO 72—Consensus repeat sequence of repeat SmO-TOT00200215.1 from ZB113
SEQ ID NO 73—Consensus repeat sequence of repeat SmO-TOT00200215.2 from ZB113
SEQ ID NO 74—Consensus repeat sequence of repeat SmO-TOT00200480 from ZB113
SEQ ID NO 75—Consensus repeat sequence of repeat SmO-TOT00200588 from ZB113
SEQ ID NO: 76—Full length sequence of CentC (GenBank Accession no. AY321491)
SEQ ID NO: 77—Full length sequence of CRM (GenBank Accession no. AY129008)
SEQ ID NO: 78—Full length sequence of CentA (GenBank Accession no. AF078917)
SEQ ID NOS: 79-88—Additional sequences from ZB19 and ZB113

DETAILED DESCRIPTION OF THE INVENTION

While this invention is susceptible of embodiment in many different forms, and will be described herein in detail, specific embodiments thereof with the understanding that the present disclosure is to be considered as an exemplification of the principles of the invention and is not intended to limit the invention to the specific embodiments illustrated.

In another aspect, the invention is based on the production of modified plants, containing functional, stable, autonomous mini-chromosomes. Such mini-chromosomes have been shown herein to be meiotically transmitted to progeny. The present invention particularly addresses adchromosmoal *Zea mays* (corn) plants. The invention provides for adchromosomal plants, described in further detail herein, comprising a mini-chromosome, wherein said mini-chromosome preferably has a transmission efficiency during mitotic division of at least 90%, for example, at least 95%. Additionally, these adchromosomal plants may comprise a mini-chromosome having a transmission efficiency during meiotic division of, e.g., at least 80%, at least 85%, at least 90% or at least 95%.

One aspect of the invention is related to plants containing functional, stable, autonomous mini-chromosomes, preferably carrying one or more nucleic acids exogenous to the cell. Such plants carrying mini-chromosomes are contrasted to transgenic plants whose genome has been altered by chromosomal integration of an exogenous nucleic acid. Preferably, expression of the exogenous nucleic acid, either constitutively or in response to a signal which may be a challenge or a stimulus, e.g. tissue specific expression or time specific expression, results in an altered phenotype of the plant.

The invention provides for mini-chromosomes comprising at least 1, 2, 3, 4, 5, 6, 7, 8, 9, 10, 11, 12, 13, 14, 15, 16, 17, 18, 19, 20, 21, 22, 23, 24, 25, 30, 35, 40, 45, 50, 60, 70, 80, 90, 100, 110, 120, 130, 140, 150, 250, 500, 1000 or more exogenous nucleic acids.

The invention contemplates that any plants, including but not limited to monocots, dicots, gymnosperm, field crops, vegetable crops, fruit and vine crops, or any specific plants named herein, may be modified by carrying autonomous mini-chromosomes as described herein. A related aspect of the invention is plant parts or plant tissues, including pollen, silk, endosperm, ovule, seed, embryo, pods, roots, cuttings, tubers, stems, stalks, fruit, berries, nuts, flowers, leaves, bark, whole plant, plant cell, plant organ, protoplast, cell culture, or any group of plant cells organized into a structural and functional unit, any cells of which carry mini-chromosomes.

A related aspect of the invention is adchromosomal plant parts or plant tissues, including pollen, silk, endosperm, ovule, seed, embryo, pods, roots, cuttings, tubers, stems, stalks, crown, callus culture, petiole, petal, sepal, stamen, stigma, style, bud, fruit, berries, nuts, flowers, leaves, bark, wood, whole plant, plant cell, plant organ, protoplast, cell culture, or any group of plant cells organized into a structural and functional unit. In one preferred embodiment, the exogenous nucleic acid is primarily expressed in a specific location or tissue of a plant, for example, epidermis, vascular tissue, meristem, cambium, cortex, pith, leaf, sheath, flower, root or seed. Tissue-specific expression can be accomplished with, for example, localized presence of the mini-chromosome, selective maintenance of the mini-chromosome, or with promoters that drive tissue-specific expression.

Another related aspect of the invention is meiocytes, pollen, ovules, endosperm, seed, somatic embryos, apomyctic embryos, embryos derived from fertilization, vegetative propagules and progeny of the originally adchromosomal plant and of its filial generations that retain the functional, stable, autonomous mini-chromosome. Such progeny include clonally propagated plants, embryos and plant parts as well as filial progeny from self- and cross-breeding, and from apomyxis.

Preferably the mini-chromosome is transmitted to subsequent generations of viable daughter cells during mitotic cell division with a transmission efficiency of at least 60%, 70%, 80%, 85%, 90%, 95%, 96%, 97%, 98%, or 99%. More preferably, the mini-chromosome is transmitted to viable gametes during meiotic cell division with a transmission efficiency of at least 60%, 70%, 80%, 85%, 90%, 95%, 96%, 97%, 98%, or 99% when more than one copy of the mini-chromosome is present in the gamete mother cells of the plant. Preferably, the mini-chromosome is transmitted to viable gametes during meiotic cell division with a transmission frequency of at least 20%, 30%, 40%, 45%, 46%, 47%, 48%, or 49% when one copy of the mini-chromosome is present in the gamete mother cells of the plant. For production of seeds via sexual reproduction or by apomyxis the mini-chromosome is preferably transferred into at least 60%, 70%, 80%, 85%, 90%, 95%, 96%, 97%, 98%, or 99% of viable embryos when cells of the plant contain more than one copy of the mini-chromosome. For production of seeds via sexual reproduction or by apomyxis from plants with one mini-chromosome per cell, the mini-chromosome is preferably transferred into at least 20%, 30%, 40%, 45%, 46%, 47%, 48%, or 49% of viable embryos.

Preferably, a mini-chromosome that comprises an exogenous selectable trait or exogenous selectable marker can be employed to increase the frequency in subsequent generations of adchromosomal cells, tissues, gametes, embryos, endosperm, seeds, plants or progeny. More preferably, the frequency of transmission of mini-chromosomes into viable cells, tissues, gametes, embryos, endosperm, seeds, plants or progeny can be at least 95%, 96%, 97%, 98%, 99% or 99.5% after mitosis or meiosis by applying a selection that favors the survival of adchromosomal cells, tissues, gametes, embryos, endosperm, seeds, plants or progeny over such cells, tissues, gametes, embryos, endosperm, seeds, plants or progeny lacking the mini-chromosome.

Transmission efficiency may be measured as the percentage of progeny cells or plants that carry the mini-chromosome as measured by one of several assays taught herein including detection of reporter gene fluorescence, PCR detection of a sequence that is carried by the mini-chromosome, RT-PCR detection of a gene transcript for a gene carried on the mini-chromosome, Western analysis of a protein produced by a gene carried on the mini-chromosome, Southern analysis of the DNA (either in total or a portion thereof) carried by the mini-chromosome, fluorescence in situ hybridization (FISH) or in situ localization by repressor binding, to name a few. Any assay used to detect the presence of the mini-chromosome (or a portion of the mini-chromosome) may be used to measure the efficiency of a parental cell or plant transmits the mini-chromosome to its progeny. Efficient transmission as measured by some benchmark percentage should indicate the degree to which the mini-chromosome is stable through the mitotic and meiotic cycles.

Plants of the invention may also contain chromosomally integrated exogenous nucleic acid in addition to the autonomous mini-chromosomes. The adchromosomal plants or plant parts, including plant tissues of the invention may include plants that have chromosomal integration of some portion of the mini-chromosome (e.g. exogenous nucleic acid or centromere sequences) in some or all cells the plant. The plant, including plant tissue or plant cell is still characterized as adchromosomal despite the occurrence of some chromosomal integration. In one aspect of the invention, the autonomous mini-chromosome can be isolated from integrated exogenous nucleic acid by crossing the adchromosomal plant containing the integrated exogenous nucleic acid with plants producing some gametes lacking the integrated exogenous nucleic acid and subsequently isolating offspring of the cross, or subsequent crosses, that are adchromosomal but lack the integrated exogenous nucleic acid. This independent segregation of the mini-chromosome is one measure of the autonomous nature of the mini-chromosome.

Another aspect of the invention relates to methods for producing and isolating such adchromosomal plants containing functional, stable, autonomous mini-chromosomes.

In one embodiment, the invention contemplates improved methods for isolating native centromere sequences. In another embodiment, the invention contemplates methods for generating variants of native or artificial centromere sequences by passage through bacterial or plant or other host cells.

In a further embodiment, the invention contemplates methods for delivering the mini-chromosome into plant cells or tissues to transform the cells or tissues.

In yet another embodiment, the invention contemplates improved methods for regenerating plants, including methods for co-delivery of growth inducing genes with mini-chromosomes. The growth delivery genes include *Agrobacterium tumefaciens* or *Arhizogenes* isopentenyl transferase (IPT) genes involved in cytokinin biosynthesis, plant isopentenyl transferase (IPT) genes involved in cytokinin biosynthesis (from any plant), *Agrobacterium tumefaciens* IAAH, IAAM genes involved in auxin biosynthesis (indole-3-acetamide hydrolase and tryptophan-2-monooxygenase, respectively), *Agrobacterium rhizogenes* rolA, rolB and rolC genes involved in root formation, *Agrobacterium tumefaciens* Aux1, Aux2 genes involved in auxin biosynthesis (indole-3-acetamide hydrolase or tryptophan-2-monooxygenase genes), *Arabidopsis thaliana* leafy cotyledon genes (e.g. Lec1, Lec2) promoting embryogenesis and shoot formation (see Stone et al., Proc. Natl. Acad. Sci. USA 98: 11806-11811), *Arabidopsis thaliana* ESR1 gene involved in shoot formation (see Banno et al., Plant Cell 13: 2609-2618), *Arabidopsis thaliana* PGA6/WUSCHEL gene involved in embryogenesis (see Zuo et al., Plant J. 30: 349-359).

In yet a further embodiment, the invention contemplates methods for selecting modified plant cells or plant parts containing mini-chromosomes for regeneration. Such methods include assays for identifying adchromosomal plants or cells by determining that mini-chromosomes within the modified plant cell or plant are functional, stable, and autonomous. Exemplary assays for assessing mini-chromosome performance include lineage-based inheritance assays, use of chromosome loss agents to demonstrate autonomy, exonuclease digestion, global mitotic mini-chromosome inheritance assays (sectoring assays) with or without the use of agents inducing chromosomal loss, assays measuring expression levels of marker genes in the mini-chromosome over time and space in a plant, physical assays for separation of autonomous mini-chromosomes from endogenous nuclear chromosomes of plants, molecular assays demonstrating conserved mini-chromosome structure, such as PCR, Southern blots, mini-chromosome rescue, cloning and characterization of mini-chromosome sequences present in the plant, cytological assays detecting mini-chromosome presence in the cell's genome (e.g. FISH) and meiotic mini-chromosome inheritance assays, which measure the levels of mini-chromosome inheritance into a subsequent generation of plants via meiosis and gametes, embryos, endosperm or seeds.

The invention also contemplates novel methods of screening for adchromosomal plant cells that involve use of relatively low, sub-killing concentrations of selection agent (e.g. sub-killing antibiotic concentrations), and also involve use of a screenable marker (e.g., a visible marker gene) to identify clusters of modified cells carrying the screenable marker, after which these screenable cells are manipulated to homogeneity. Another aspect of the present invention is related to methods of making and compositions of non-plant promoters for expressing genes in plants.

The invention further provides isolated promoter nucleic acid sequences comprising any one of SEQ ID NOS: 1 to 20, or fragments or variants thereof that retain expression-promoting activity. Mini-chromosomes comprising non-plant promoter sequences such as these that are operably linked to plant-expressed genes (e.g., genes that confer a different phenotype on plants), are contemplated as are plants comprising such mini-chromosomes.

Another aspect is related to methods for using exonuclease to enrich for circular mini-chromosome DNA in genomic DNA preparations.

Another aspect of the invention relates to methods for using such adchromosomal plants containing a mini-chromosome for producing food products, pharmaceutical products and chemical products by appropriate expression of exogenous nucleic acid(s) contained within the mini-chromosome(s).

Mini-chromosomes containing centromeres from one plant species, when inserted into plant cells of a different species or even a different genus or family, can be stable, functional and autonomous. Thus, another aspect of the invention is an adchromosomal plant comprising a functional, stable, autonomous mini-chromosome that contains centromere sequence derived from a different taxonomic plant species, or derived from a different taxonomic plant species, genus, family, order or class.

Yet another aspect of the invention provides novel autonomous mini-chromosomes with novel compositions and structures which are used to transform plant cells which are in turn used to generate a plant (or multiple plants). Exemplary mini-chromosomes of the invention are contemplated to be of a size 2000 kb or less in length. Other exemplary sizes of mini-chromosomes include less than or equal to, e.g., 1500 kb, 1000 kb, 900 kb, 800 kb, 700 kb, 600 kb, 500 kb, 450 kb; 400 kb, 350 kb, 300 kb, 250 kb, 200 kb, 150 kb, 100 kb, 80 kb, 60 kb, or 40 kb in length.

In a related aspect, novel centromere compositions as characterized by sequence content, size or other parameters are provided. Preferably, the minimal size of centromeric sequence is utilized in mini-chromosome construction. Exemplary sizes include a centromeric nucleic acid insert derived from a portion of plant genomic DNA, that is less than or equal to 1000 kb, 900 kb, 800 kb, 700 kb, 600 kb, 500 kb, 400 kb, 300 kb, 200 kb, 150 kb, 100 kb, 95 kb, 90 kb, 85 kb, 80 kb, 75 kb, 70 kb, 65 kb, 60 kb, 55 kb, 50 kb, 45 kb, 40 kb, 35 kb, 30 kb, 25 kb, 20 kb, 15 kb, 10 kb, 5 kb, or 2 kb in length. For example, rescued functional variant soybean centromeric sequences have been shown to be less than 30 kb in size. Another related aspect is the novel structure of the mini-chromosome, particularly structures lacking bacterial sequences, e.g., required for bacterial propagation.

In exemplary embodiments, the invention also contemplates mini-chromosomes or other vectors comprising fragments or variants of the genomic DNA inserts of the BAC clones [identified as ZB19, or ZB113] deposited on Feb. 23, 2005 with the American Type Culture Collection (ATCC), P.O. Box 1549 Manassas, Va. 20108, USA, under Accession Nos. PTA-6604 and, PTA-6605, respectively], or naturally occurring descendants thereof, that retain the ability to segregate during mitotic or meiotic division as described herein, as well as adchromosomal plants or parts containing these mini-chromosomes. Other exemplary embodiments include fragments or variants of the genomic DNA inserts of any of the BAC clones identified herein, or descendants thereof, and fragments or variants of the centromeric nucleic acid inserts of any of the vectors or mini-chromosomes identified herein.

In other exemplary embodiments, the invention contemplates mini-chromosomes or other vectors comprising centromeric nucleotide sequence that when hybridized to 1, 2, 3, 4, 5, 6, 7, 8 or more of the probes described in the examples herein, under hybridization conditions described herein, e.g. low, medium or high stringency, provides relative hybridization scores as described in the examples herein. Exemplary stringent hybridization conditions comprise 0.02 M to 0.15 M NaCl at temperatures of about 50° C. to 70° C. or 0.5×SSC 0.25% SDS at 65° for 15 minutes, followed by a wash at 65 degrees for a half hour. Preferably the probes for which relative hybridization scores are described herein as 5/10 or greater are used, and a hybridization signal greater than background for one or more of these probes is used to select clones. Adchromosomal plants or parts containing such mini-chromosomes are contemplated.

The advantages of the present invention include: provision of an autonomous, independent genetic linkage group for accelerating breeding; lack of disruption of host genome; multiple gene "stacking" of large an potentially unlimited numbers of genes; uniform genetic composition exogenous DNA sequences in plant cells and plants containing autonomous mini-chromosomes; defined genetic context for predictable gene expression; higher frequency occurrence and recovery of plant cells and plants containing stably maintained exogenous DNA due to elimination of inefficient integration step; and the ability to eliminate mini-chromosomes in any tissues.

I. Composition of Mini-Chromosomes and Mini-Chromosome Construction

The mini-chromosome vector of the present invention may contain a variety of elements, including (1) sequences that function as plant centromeres, (2) one or more exogenous nucleic acids, including, for example, plant-expressed genes, (3) sequences that function as an origin of replication, which may be included in the region that functions as plant centromere, (4) optionally, a bacterial plasmid backbone for propagation of the plasmid in bacteria, (5) optionally, sequences that function as plant telomeres, (6) optionally, additional "stuffer DNA" sequences that serve to separate the various components on the mini-chromosome from each other, (7) optionally "buffer" sequences such as MARs or SARs, (8) optionally marker sequences of any origin, including but not limited to plant and bacterial origin, (9) optionally, sequences that serve as recombination sites, and (10) "chromatin packaging sequences" such as cohesion and condensing binding sites.

The mini-chromosomes of the present invention may be constructed to include various components which are novel, which include, but are not limited to, the centromere comprising novel repeating centromeric sequences, and the promoters, particularly promoters derived from non-plant species, as described in further detail below.

The mini-chromosomes of the present invention may be constructed to include various components which are novel, which include, but are not limited to, the centromere comprising novel repeating centromeric sequences, and the promoters, particularly promoters derived from non-plant species, as described in further detail below.

Novel Centromere Compositions

The centromere in the mini-chromosome of the present invention may comprise novel repeating centromeric sequences.

Exemplary embodiments of centromere nucleic acid sequences according to the present invention include fragments or variants of the genomic DNA inserts of the BAC clones [identified as ZB19, or ZB113 deposited on Feb. 23, 2005 with the American Type Culture Collection (ATCC), P.O. Box 1549 Manassas, Va. 20108, USA, under Accession Nos. PTA-6604 and PTA-6605, respectively] that retain the ability to segregate during mitotic or meiotic division as described herein. Variants of such sequences include artificially produced modifications as described herein and modifications produced via passaging through one or more bacterial, plant or other host cells as described herein.

Vectors comprising one, two, three, four, five, six, seven, eight, nine, ten, 15 or 20 or more of the elements contained in any of the exemplary vectors described in the examples below are also contemplated.

The invention specifically contemplates the alternative use of fragments or variants (mutants) of any of the nucleic acids described herein that retain the desired activity, including nucleic acids that function as centromeres, nucleic acids that function as promoters or other regulatory control sequences, or exogenous nucleic acids. Variants may have one or more additions, substitutions or deletions of nucleotides within the original nucleotide sequence or consensus sequence. Variants include nucleic acid sequences that are at least 50%, 55%, 60, 65, 70, 75, 80, 81, 82, 83, 84, 85, 86, 87, 88, 89, 90, 91, 92, 93, 94, 95, 96, 97, 98, 99, or 100% identical to the original nucleic acid sequence. Variants also include nucleic acid sequences that hybridize under low, medium, high or very high stringency conditions to the original nucleic acid sequence. Similarly, the specification also contemplates the alternative use of fragments or variants of any of the polypeptides described herein.

The comparison of sequences and determination of percent identity between two nucleotide sequences can be accomplished using a mathematical algorithm. In a preferred embodiment, the percent identity between two amino acid sequences is determined using the Needleman and Wunsch (1970) J. Mol. Biol. 48:444-453 algorithm which has been incorporated into the GAP program in the GCG software package, using either a Blossum 62 matrix or a PAM250 matrix. Preferably parameters are set so as to maximize the percent identity.

As used herein, the term "hybridizes under low stringency, medium stringency, and high stringency conditions" describes conditions for hybridization and washing. Guidance for performing hybridization reactions can be found in Current Protocols in Molecular Biology (1989) John Wiley & Sons, N.Y., 6.3.1-6.3.6, which is incorporated by reference. Aqueous and non-aqueous methods are described in that reference and either can be used. Specific hybridization conditions referred to herein are as follows: 1) low stringency hybridization conditions in 6× sodium chloride/sodium citrate (SSC) at about 45° C., followed by two washes in 0.5× SSC, 0.1% SDS, at least at 50° C.; 2) medium stringency hybridization conditions in 6×SSC at about 45° C., followed by one or more washes in 0.2×SSC, 0.1% SDS at 55° C.; 3) high stringency hybridization conditions in 6×SSC at about 45° C., followed by one or more washes in 0.2×SSC, 0.1% SDS at 65° C. Other exemplary highly selective or stringent hybridization conditions comprise 0.02 M to 0.15 M NaCl at temperatures of about 50° C. to 70° C. or 0.5×SSC 0.25% SDS at 65° for 15 minutes, followed by a wash at 65 degrees for a half hour.

Mini-Chromosome Sequence Content and Structure

Plant-expressed genes from non-plant sources may be modified to accommodate plant codon usage, to insert preferred motifs near the translation initiation ATG codon, to remove sequences recognized in plants as 5' or 3' splice sites, or to better reflect plant GC/AT content. Plant genes typically have a GC content of more than 35%, and coding sequences which are rich in A and T nucleotides can be problematic. For example, ATTTA motifs may destabilize mRNA; plant polyadenylation signals such as AATAAA at inappropriate positions within the message may cause premature truncation of transcription; and monocotyledons may recognize AT-rich sequences as splice sites.

Each exogenous nucleic acid or plant-expressed gene may include a promoter, a coding region and a terminator sequence, which may be separated from each other by restriction endonuclease sites or recombination sites or both. Genes may also include introns, which may be present in any number and at any position within the transcribed portion of the gene, including the 5' untranslated sequence, the coding region and the 3' untranslated sequence. Introns may be natural plant introns derived from any plant, or artificial introns based on the splice site consensus that has been defined for plant species. Some intron sequences have been shown to enhance expression in plants. Optionally the exogenous nucleic acid may include a plant transcriptional terminator, non-translated leader sequences derived from viruses that enhance expression, a minimal promoter, or a signal sequence controlling the targeting of gene products to plant compartments or organelles.

The coding regions of the genes can encode any protein, including but not limited to visible marker genes (for example, fluorescent protein genes, other genes conferring a visible phenotype to the plant) or other screenable or selectable marker genes (for example, conferring resistance to antibiotics, herbicides or other toxic compounds or encoding a protein that confers a growth advantage to the cell expressing the protein) or genes which confer some commercial or agronomic value to the adchromosomal plant. Multiple genes can be placed on the same mini-chromosome vector, limited only by the number of restriction endonuclease sites or site-specific recombination sites present in the vector. The genes may be separated from each other by restriction endonuclease sites, homing endonuclease sites, recombination sites or any combinations thereof. Any number of genes can be present.

The mini-chromosome vector may also contain a bacterial plasmid backbone for propagation of the plasmid in bacteria such as E. coli, A. tumefaciens, or A. rhizogenes. The plasmid backbone may be that of a low-copy vector or in other embodiments it may be desirable to use a mid to high level copy backbone. In one embodiment of the invention, this backbone contains the replicon of the F' plasmid of E. coli. However, other plasmid replicons, such as the bacteriophage P1 replicon, or other low-copy plasmid systems such as the RK2 replication origin, may also be used. The backbone may include one or several antibiotic-resistance genes conferring resistance to a specific antibiotic to the bacterial cell in which the plasmid is present. Bacterial antibiotic-resistance genes include but are not limited to kanamycin-, ampicillin-, chloramphenicol-, streptomycin-, spectinomycin-, tetracycline- and gentamycin-resistance genes.

The mini-chromosome vector may also contain plant telomeres. An exemplary telomere sequence is TTTAGGG or its complement. Telomeres are specialized DNA structures at the ends of linear chromosomes that function to stabilize the ends and facilitate the complete replication of the extreme termini of the DNA molecule (Richards et. al., Cell. 1988 Apr. 8; 53(1):127-36; Ausubel et al., Current Protocols in Molecular Biology, Wiley & Sons, 1997).

Additionally, the mini-chromosome vector may contain "stuffer DNA" sequences that serve to separate the various components on the mini-chromosome (centromere, genes, telomeres) from each other. The stuffer DNA may be of any origin, prokaryotic or eukaryotic, and from any genome or species, plant, animal, microbe or organelle, or may be of synthetic origin. The stuffer DNA can range from 100 bp to 10 Mb in length and can be repetitive in sequence, with unit repeats from 10 to 1,000,000 bp. Examples of repetitive sequences that can be used as stuffer DNAs include but are not limited to: rDNA, satellite repeats, retroelements, transposons, pseudogenes, transcribed genes, microsatellites, tDNA genes, short sequence repeats and combinations thereof. Alternatively, the stuffer DNA can consist of unique, non-repetitive DNA of any origin or sequence. The stuffer sequences may also include DNA with the ability to form boundary domains, such as but not limited to scaffold attachment regions (SARs) or matrix attachment regions (MARs). The stuffer DNA may be entirely synthetic, composed of random sequence. In this case, the stuffer DNA may have any base composition, or any A/T or G/C content. For example, the G/C content of the stuffer DNA could resemble that of the plant (~30-40%), or could be much lower (0-30%) or much higher (40-100%). Alternatively, the stuffer sequences could be synthesized to contain an excess of any given nucleotide such as A, C, G or T. Different synthetic stuffers of different compositions may also be combined with each other. For example a fragment with low G/C content may be flanked or abutted by a fragment of medium or high G/C content, or vice versa.

In one embodiment of the invention, the mini-chromosome has a circular structure without telomeres. In another embodiment, the mini-chromosome has a circular structure with telomeres. In a third embodiment, the mini-chromosome has a linear structure with telomeres, as would result if a "linear" structure were to be cut with a unique endonuclease, exposing the telomeres at the ends of a DNA molecule that contains all of the sequence contained in the original, closed construct with the exception of the an antibiotic-resistance gene. In a fourth embodiment of the invention, the telomeres could be placed in such a manner that the bacterial replicon, backbone sequences, antibiotic-resistance genes and any other sequences of bacterial origin and present for the purposes of propagation of the mini-chromosome in bacteria, can be removed from the plant-expressed genes, the centromere, telomeres, and other sequences by cutting the structure with an unique endonuclease. This results in a mini-chromosome from which much of, or preferably all, bacterial sequences have been removed. In this embodiment, bacterial sequence present between or among the plant-expressed genes or other mini-chromosome sequences would be excised prior to removal of the remaining bacterial sequences by cutting the mini-chromosome with a homing endonuclease and re-ligating the structure such that the antibiotic-resistance gene has been lost. The unique endonuclease site may be the recognition sequence of a homing endonuclease. Alternatively, the endonucleases and their sites can be replaced with any specific DNA cutting mechanism and its specific recognition site such as rare-cutting endonuclease or recombinase and its specific recognition site, as long as that site is present in the mini-chromosomes only at the indicated positions.

Various structural configurations are possible by which mini-chromosome elements can be oriented with respect to each other. A centromere can be placed on a mini-chromosome either between genes or outside a cluster of genes next to one telomere or next to the other telomere. Stuffer DNAs can be combined with these configurations to place the stuffer sequences inside the telomeres, around the centromere between genes or any combination thereof. Thus, a large number of alternative mini-chromosome structures are possible, depending on the relative placement of centromere DNA, genes, stuffer DNAs, bacterial sequences, telomeres, and other sequences. The sequence content of each of these variants is the same, but their structure may be different depending on how the sequences are placed. These variations in architecture are possible both for linear and for circular mini-chromosomes.

Exemplary Centromere Components

Centromere components may be isolated or derived from native plant genome, for example, modified through recombinant techniques or through the cell-based techniques described below. Alternatively, wholly artificial centromere components may be constructed using as a general guide the sequence of native centromeres. Combinations of centromere components derived from natural sources and/or combinations of naturally derived and artificial components are also contemplated. As noted above, centromere sequence from one taxonomic plant species has been shown to be functional in another taxonomic plant species, genus and family.

In one embodiment, the centromere contains n copies of a repeated nucleotide sequence obtained by the methods disclosed herein; wherein n is at least 2. In another embodiment, the centromere contains n copies of interdigitated repeats. An interdigitated repeat is a DNA sequence that consists of two distinct repetitive elements that combine to create a unique permutation. Potentially any number of repeat copies capable of physically being placed on the recombinant construct could be included on the construct, including about 5, 10, 15, 20, 30, 50, 75, 100, 150, 200, 300, 400, 500, 750, 1,000, 1,500, 2,000, 3,000, 5,000, 7,500, 10,000, 20,000, 30,000, 40,000, 50,000, 60,000, 70,000, 80,000, 90,000 and about 100,000, including all ranges in-between such copy numbers. Moreover, the copies, while largely identical, can vary from each other. Such repeat variation is commonly observed in naturally occurring centromeres. The length of the repeat may vary, but will preferably range from about 20 bp to about 360 bp, from about 20 bp to about 250 bp, from about 50 bp to about 225 bp, from about 75 bp to about 210 bp, such as a 92 bp repeat and a 97 bp repeat, from about 100 bp to about 205 bp, from about 125 bp to about 200 bp, from about 150 bp to about 195 bp, from about 160 bp to about 190 and from about 170 bp to about 185 bp including about 180 bp.

The invention contemplates that two or more of these repeated nucleotide sequences, or similar repeated nucleotide sequences, may be oriented head to tail within the centromere. The term "head to tail" refers to multiple consecutive copies of the same or similar repeated nucleotide sequence (e.g., at least 70% identical) that are in the same 5'-3' orientation. The invention also contemplates that two or more of these repeated nucleotide sequences may be consecutive within the centromere. The term "consecutive" refers to the same or similar repeated nucleotide sequences (e.g., at least 70% identical) that follow one after another without being interrupted by other significant sequence elements. Such consecutive repeated nucleotide sequences may be in any orientation, e.g. head to tail, tail to tail, or head to head, and may be separated by n number of nucleotides, wherein n ranges from 1 to 10, or 1 to 20, or 1 to 30, or 1 to 40, or 1 to 50. Exemplary repeated nucleotide sequences derived from corn, and identified by the methods described herein, are CentC, CRM and CentA. An exemplary sequence of CentC is provided as GenBank Accession No. AY1290008 (SEQ ID NO: 77). The consensus sequence of CentC derived from BAC clone ZB19 is set out as SEQ ID NO: 70, and the consensus sequence of CentC derived from BAC clone ZB113 is set out as SEQ ID NO: 71. Variants of these CentC consensus sequences within the BAC clones were identified and are set out in Tables 17 and 22.

An exemplary sequence of CRM is provided as GenBank Accession No. AY129008 (SEQ ID NO: 78). The fragments of SEQ ID NO: 78 that are observed within the BAC clone ZB113 are as follows: nucleotides 1-515, nucleotides 1-930, nucleotides 1-1434, nucleotides 1508-3791, nucleotides 1508-5417, nucleotides 2796-2890, nucleotides 2796-2893, nucleotides 4251-4744, nucleotides 4626-4772, nucleotides 4945-6236, nucleotides 4983-5342, nucleotides 5487-5569, nucleotides 5757-6212, nucleotides 5765-7571, nucleotides 6529-6653, nucleotides 6608-6658, nucleotides 6638-7571 and/or nucleotides 6640-7156 of SEQ ID NO: 78.

An exemplary sequence of CentA is provided as GenBank Accession No. AF078917 (SEQ ID NO: 79). The fragment of SEQ ID NO: 79 that are observed in the BAC clone ZB113 are as follows comprise nucleotides 9589-10101 of SEQ ID NO: 37. (contig 16).

Modification of Centromeres Isolated from Native Plant Genome

Modification and changes may be made in the centromeric DNA segments of the current invention and still obtain a functional molecule with desirable characteristics. The following is a discussion based upon changing the nucleic acids of a centromere to create an equivalent, or even an improved, second generation molecule.

In particular embodiments of the invention, mutated centromeric sequences are contemplated to be useful for increasing the utility of the centromere. It is specifically contemplated that the function of the centromeres of the current invention may be based in part of in whole upon the secondary structure of the DNA sequences of the centromere, modification of the DNA with methyl groups or other adducts, and/or the proteins which interact with the centromere. By changing the DNA sequence of the centromere, one may alter the affinity of one or more centromere-associated protein(s) for the centromere and/or the secondary structure or modification of the centromeric sequences, thereby changing the activity of the centromere. Alternatively, changes may be made in the centromeres of the invention which do not affect the activity of the centromere. Changes in the centromeric sequences which reduce the size of the DNA segment needed to confer centromere activity are contemplated to be particularly useful in the current invention, as would changes which increased the fidelity with which the centromere was transmitted during mitosis and meiosis.

Modification of Centromeres by Passage Through Bacteria, Plant or Other Hosts or Processes In the methods of the present invention, the resulting mini-chromosome DNA sequence may also be a derivative of the parental clone or centromere clone having substitutions, deletions, insertions, duplications and/or rearrangements of one or more nucleotides in the nucleic acid sequence. Such nucleotide mutations may occur individually or consecutively in stretches of 1, 2, 3, 4, 5, 10, 20, 40, 80, 100, 200, 400, 800, 1000, 2000, 4000, 8000, 10000, 50000, 100000, and about 200000, including all ranges in-between.

Variations of mini-chromosomes may arise through passage of mini-chromosomes through various hosts including virus, bacteria, yeast, plant or other prokaryotic or eukaryotic organism and may occur through passage of multiple hosts or individual host. Variations may also occur by replicating the mini-chromosome in vitro.

Derivatives may be identified through sequence analysis, or variations in mini-chromosome molecular weight through electrophoresis such as, but not limited to, CHEF gel analysis, column or gradient separation, or any other methods used in the field to determine and/or analyze DNA molecular weight or sequence content. Alternately, derivatives may be identified by the altered activity of a derivative in conferring centromere function to a mini-chromosome.

Exemplary Exogenous Nucleic Acids Including Plant-Expressed Genes

Of particular interest in the present invention are exogenous nucleic acids which when introduced into plants will alter the phenotype of the plant, a plant organ, plant tissue, or portion of the plant. Exemplary exogenous nucleic acids encode polypeptides involved in one or more important biological properties in plants. Other exemplary exogenous nucleic acids alter expression of exogenous or endogenous genes, either increasing or decreasing expression, optionally in response to a specific signal or stimulus.

As used herein, the term "trait" can refer either to the altered phenotype of interest or the nucleic acid which causes the altered phenotype of interest.

One of the major purposes of transformation of crop plants is to add some commercially desirable, agronomically important traits to the plant. Such traits include, but are not limited to, herbicide resistance or tolerance; insect (pest) resistance or tolerance; disease resistance or tolerance (viral, bacterial, fungal, nematode or other pathogens); stress tolerance and/or resistance, as exemplified by resistance or tolerance to drought, heat, chilling, freezing, excessive moisture, salt stress, mechanical stress, extreme acidity, alkalinity, toxins, UV light, ionizing radiation or oxidative stress; increased yields, whether in quantity or quality; enhanced or altered nutrient acquisition and enhanced or altered metabolic efficiency; enhanced or altered nutritional content and makeup of plant tissues used for food, feed, fiber or processing; physical appearance; male sterility; drydown; standability; prolificacy; starch quantity and quality; oil quantity and quality; protein quality and quantity; amino acid composition; modified chemical production; altered pharmaceutical or nutraceutical properties; altered bioremediation properties; increased biomass; altered growth rate; altered fitness; altered biodegradability; altered $CO_2$ fixation; presence of bioindicator activity; altered digestibility by humans or animals; altered allergenicity; altered mating characteristics; altered pollen dispersal; improved environmental impact; altered nitrogen fixation capability; the production of a pharmaceutically active protein; the production of a small molecule with medicinal properties; the production of a chemical including those with industrial utility; the production of nutraceuticals, food additives, carbohydrates, RNAs, lipids, fuels, dyes, pigments, vitamins, scents, flavors, vaccines, antibodies, hormones, and the like; and alterations in plant architecture or development, including changes in developmental timing, photosynthesis, signal transduction, cell growth, reproduction, or differentiation. Additionally one could create a library of an entire genome from any organism or organelle including mammals, plants, microbes, fungi, or bacteria, represented on mini-chromosomes.

In one embodiment, the modified plant may exhibit increased or decreased expression or accumulation of a product of the plant, which may be a natural product of the plant or a new or altered product of the plant. Exemplary products include an enzyme, an RNA molecule, a nutritional protein, a structural protein, an amino acid, a lipid, a fatty acid, a polysaccharide, a sugar, an alcohol, an alkaloid, a carotenoid, a propanoid, a phenylpropanoid, or terpenoid, a steroid, a flavonoid, a phenolic compound, an anthocyanin, a pigment, a vitamin or a plant hormone. In another embodiment, the modified plant has enhanced or diminished requirements for light, water, nitrogen, or trace elements. In another embodiment the modified plant has an enhance ability to capture or fix nitrogen from its environment. In yet another embodiment, the modified plant is enriched for an essential amino acid as a proportion of a protein fraction of the plant. The protein fraction may be, for example, total seed protein, soluble protein, insoluble protein, water-extractable protein, and lipid-associated protein. The modification may include overexpression, underexpression, antisense modulation, sense suppression, inducible expression, inducible repression, or inducible modulation of a gene.

A brief summary of exemplary improved properties and polypeptides of interest for either increased or decreased expression is provided below.

(i) Herbicide Resistance

A herbicide resistance (or tolerance) trait is a characteristic of a modified plant that is resistant to dosages of an herbicide that is typically lethal to a non-modified plant. Exemplary herbicides for which resistance is useful in a plant include glyphosate herbicides, phosphinothricin herbicides, oxynil herbicides, imidazolinone herbicides, dinitroaniline herbicides, pyridine herbicides, sulfonylurea herbicides, bialaphos herbicides, sulfonamide herbicides and glufosinate herbicides. Other herbicides would be useful as would combinations of herbicide genes on the same mini-chromosome.

The genes encoding phosphinothricin acetyltransferase (bar), glyphosate tolerant EPSP synthase genes, glyphosate acetyltransferase, the glyphosate degradative enzyme gene gox encoding glyphosate oxidoreductase, deh (encoding a dehalogenase enzyme that inactivates dalapon), herbicide resistant (e.g., sulfonylurea and imidazolinone) acetolactate synthase, and bxn genes (encoding a nitrilase enzyme that degrades bromoxynil) are good examples of herbicide resistant genes for use in transformation. The bar gene codes for an enzyme, phosphinothricin acetyltransferase (PAT), which inactivates the herbicide phosphinothricin and prevents this compound from inhibiting glutamine synthetase enzymes. The enzyme 5 enolpyruvylshikimate 3 phosphate synthase (EPSP Synthase), is normally inhibited by the herbicide N (phosphonomethyl)glycine (glyphosate). However, genes are known that encode glyphosate resistant EPSP synthase enzymes. These genes are particularly contemplated for use in plant transformation. The deh gene encodes the enzyme dalapon dehalogenase and confers resistance to the herbicide dalapon. The bxn gene codes for a specific nitrilase enzyme that converts bromoxynil to a non herbicidal degradation product. The glyphosate acetyl transferase gene inactivates the herbicide glyphosate and prevents this compound from inhibiting EPSP synthase.

Polypeptides that may produce plants having tolerance to plant herbicides include polypeptides involved in the shikimate pathway, which are of interest for providing glyphosate tolerant plants. Such polypeptides include polypeptides involved in biosynthesis of chorismate, phenylalanine, tyrosine and tryptophan.

(ii) Insect Resistance

Potential insect resistance (or tolerance) genes that can be introduced include *Bacillus thuringiensis* toxin genes or Bt genes (Watrud et al., In: Engineered Organisms and the Environment, 1985). Bt genes may provide resistance to lepidopteran or coleopteran pests such as European Corn Borer (ECB). Preferred Bt toxin genes for use in such embodiments include the CryIA(b) and CryIA(c) genes. Endotoxin genes from other species of *B. thuringiensis* which affect insect growth or development also may be employed in this regard.

It is contemplated that preferred Bt genes for use in the mini-chromosomes disclosed herein will be those in which the coding sequence has been modified to effect increased expression in plants, and for example, in monocot plants. Means for preparing synthetic genes are well known in the art and are disclosed in, for example, U.S. Pat. No. 5,500,365 and U.S. Pat. No. 5,689,052, each of the disclosures of which are specifically incorporated herein by reference in their entirety. Examples of such modified Bt toxin genes include a synthetic Bt CryIA(b) gene (Perlak et al., Proc. Natl. Acad. Sci. USA, 88:3324-3328, 1991), and the synthetic CryIA(c) gene termed 1800b (PCT Application WO 95/06128). Some examples of other Bt toxin genes known to those of skill in the art are given in Table 1 below.

TABLE 1

*Bacillus thuringiensis* Endotoxin Genes[a]

| New Nomenclature | Old Nomenclature | GenBank Accession |
|---|---|---|
| Cry1Aa | CryIA(a) | M11250 |
| Cry1Ab | CryIA(b) | M13898 |
| Cry1Ac | CryIA(c) | M11068 |
| Cry1Ad | CryIA(d) | M73250 |
| Cry1Ae | CryIA(e) | M65252 |
| Cry1Ba | CryIB | X06711 |
| Cry1Bb | ET5 | L32020 |
| Cry1Bc | PEG5 | Z46442 |
| Cry1Bd | CryE1 | U70726 |
| Cry1Ca | CryIC | X07518 |
| Cry1Cb | CryIC(b) | M97880 |
| Cry1Da | CryID | X54160 |
| Cry1Db | PrtB | Z22511 |
| Cry1Ea | CryIE | X53985 |
| Cry1Eb | CryIE(b) | M73253 |
| Cry1Fa | CryIF | M63897 |
| Cry1Fb | PrtD | Z22512 |
| Cry1Ga | PrtA | Z22510 |
| Cry1Gb | CryH2 | U70725 |
| Cry1Ha | PrtC | Z22513 |
| Cry1Hb |  | U35780 |
| Cry1Ia | CryV | X62821 |
| Cry1Ib | CryV | U07642 |
| Cry1Ja | ET4 | L32019 |
| Cry1Jb | ET1 | U31527 |
| Cry1K |  | U28801 |
| Cry2Aa | CryIIA | M31738 |
| Cry2Ab | CryIIB | M23724 |
| Cry2Ac | CryIIC | X57252 |
| Cry3A | CryIIIA | M22472 |
| Cry3Ba | CryIIIB | X17123 |
| Cry3Bb | CryIIIB2 | M89794 |
| Cry3C | CryIIID | X59797 |
| Cry4A | CryIVA | Y00423 |
| Cry4B | CryIVB | X07423 |
| Cry5Aa | CryVA(a) | L07025 |
| Cry5Ab | CryVA(b) | L07026 |
| Cry6A | CryVIA | L07022 |
| Cry6B | CryVIB | L07024 |
| Cry7Aa | CryIIIC | M64478 |
| Cry7Ab | CryIIICb | U04367 |
| Cry8A | CryIIIE | U04364 |
| Cry8B | CryIIIG | U04365 |
| Cry8C | CryIIIF | U04366 |
| Cry9A | CryIG | X58120 |
| Cry9B | CryIX | X75019 |
| Cry9C | CryIH | Z37527 |
| Cry10A | CryIVC | M12662 |
| Cry11A | CryIVD | M31737 |
| Cry11B | Jeg80 | X86902 |
| Cry12A | CryVB | L07027 |
| Cry13A | CryVC | L07023 |
| Cry14A | CryVD | U13955 |
| Cry15A | 34 kDa | M76442 |
| Cry16A | cbm71 | X94146 |
| Cry17A | cbm71 | X99478 |
| Cry18A | CryBP1 | X99049 |
| Cry19A | Jeg65 | Y08920 |
| Cyt1Aa | CytA | X03182 |
| Cyt1Ab | CytM | X98793 |
| Cyt2A | CytB | Z14147 |
| Cyt2B | CytB | U52043 |

[a]N. Crickmore, D.R. Zeigler, J. Feitelson, E. Schnepf, J. Van Rie, D. Lereclus, J. Baum, and D.H. Dean. Microbiology and Molecular Biology Reviews (1998) Vol 62: 807-813 (and updated on the internet at Professor Crickmore's internet site at the University of Sussex, School of Life Sciences.

Protease inhibitors also may provide insect resistance (Johnson et al., Proc Natl Acad Sci USA. 1989 December; 86(24): 9871-9875.), and will thus have utility in plant transformation. The use of a protease inhibitor II gene, pinII, from tomato or potato is envisioned to be particularly useful. Even more advantageous is the use of a pinII gene in combination with a Bt toxin gene, the combined effect of which has been discovered to produce synergistic insecticidal activity. Other genes which encode inhibitors of the insect's digestive system, or those that encode enzymes or co factors that facilitate the production of inhibitors, also may be useful. This group may be exemplified by oryzacystatin and amylase inhibitors such as those from wheat and barley.

Amylase inhibitors are found in various plant species and are used to ward off insect predation via inhibition of the digestive amylases of attacking insects. Several amylase inhibitor genes have been isolated from plants and some have been introduced as exogenous nucleic acids, conferring an insect resistant phenotype that is potentially useful ("Plants, Genes, and Crop Biotechnology" by Maarten J. Chrispeels and David E. Sadava (2003) Jones and Bartlett Press).

Genes encoding lectins may confer additional or alternative insecticide properties. Lectins are multivalent carbohydrate binding proteins which have the ability to agglutinate red blood cells from a range of species. Lectins have been identified recently as insecticidal agents with activity against weevils, ECB and rootworm (Murdock et al., Phytochemistry, 29:85-89, 1990, Czapla & Lang, J. Econ. Entomol., 83:2480-2485, 1990). Lectin genes contemplated to be useful include, for example, barley and wheat germ agglutinin (WGA) and rice lectins (Gatehouse et al., J. Sci. Food. Agric., 35:373-380, 1984), with WGA being preferred.

Genes controlling the production of large or small polypeptides active against insects when introduced into the insect pests, such as, e.g., lytic peptides, peptide hormones and toxins and venoms, form another aspect of the invention. For example, it is contemplated that the expression of juvenile hormone esterase, directed towards specific insect pests, also may result in insecticidal activity, or perhaps cause cessation of metamorphosis (Hammock et al., Nature, 344:458-461, 1990).

Genes which encode enzymes that affect the integrity of the insect cuticle form yet another aspect of the invention. Such genes include those encoding, e.g., chitinase, proteases, lipases and also genes for the production of nikkomycin, a compound that inhibits chitin synthesis, the introduction of any of which is contemplated to produce insect resistant plants. Genes that code for activities that affect insect molting, such as those affecting the production of ecdysteroid UDP glucosyl transferase, also fall within the scope of the useful exogenous nucleic acids of the present invention.

Genes that code for enzymes that facilitate the production of compounds that reduce the nutritional quality of the host plant to insect pests also are encompassed by the present invention. It may be possible, for instance, to confer insecticidal activity on a plant by altering its sterol composition. Sterols are obtained by insects from their diet and are used for hormone synthesis and membrane stability. Therefore alterations in plant sterol composition by expression of novel genes, e.g., those that directly promote the production of undesirable sterols or those that convert desirable sterols into undesirable forms, could have a negative effect on insect growth and/or development and hence endow the plant with insecticidal activity. Lipoxygenases are naturally occurring plant enzymes that have been shown to exhibit anti nutritional effects on insects and to reduce the nutritional quality of their diet. Therefore, further embodiments of the invention concern modified plants with enhanced lipoxygenase activity which may be resistant to insect feeding.

*Tripsacum dactyloides* is a species of grass that is resistant to certain insects, including corn root worm. It is anticipated that genes encoding proteins that are toxic to insects or are involved in the biosynthesis of compounds toxic to insects will be isolated from *Tripsacum* and that these novel genes will be useful in conferring resistance to insects. It is known that the basis of insect resistance in *Tripsacum* is genetic, because said resistance has been transferred to *Zea mays* via sexual crosses (Branson and Guss, Proceedings North Central Branch Entomological Society of America, 27:91-95, 1972). It is further anticipated that other cereal, monocot or dicot plant species may have genes encoding proteins that are toxic to insects which would be useful for producing insect resistant plants.

Further genes encoding proteins characterized as having potential insecticidal activity also may be used as exogenous nucleic acids in accordance herewith. Such genes include, for example, the cowpea trypsin inhibitor (CpTI; Hilder et al., Nature, 330:160-163, 1987) which may be used as a rootworm deterrent; genes encoding avermectin (Avermectin and Abamectin., Campbell, W. C., Ed., 1989; Ikeda et al., J. Bacteriol., 169:5615-5621, 1987) which may prove particularly useful as a corn rootworm deterrent; ribosome inactivating protein genes; and even genes that regulate plant structures. Modified plants including anti insect antibody genes and genes that code for enzymes that can convert a non toxic insecticide (pro insecticide) applied to the outside of the plant into an insecticide inside the plant also are contemplated.

Polypeptides that may improve plant tolerance to the effects of plant pests or pathogens include proteases, polypeptides involved in anthocyanin biosynthesis, polypeptides involved in cell wall metabolism, including cellulases, glucosidases, pectin methylesterase, pectinase, polygalacturonase, chitinase, chitosanase, and cellulose synthase, and polypeptides involved in biosynthesis of terpenoids or indole for production of bioactive metabolites to provide defense against herbivorous insects. It is also anticipated that combinations of different insect resistance genes on the same minichromosome will be particularly useful.

Vegetative Insecticidal Proteins (VIP) are a relatively new class of proteins originally found to be produced in the vegetative growth phase of the bacterium, *Bacillus cereus*, but do have a spectrum of insect lethality similar to the insecticidal genes found in strains of *Bacillus thuriengensis*. Both the vip1a and vip3A genes have been isolated and have demonstrated insect toxicity. It is anticipated that such genes may be used in modified plants to confer insect resistance ("Plants, Genes, and Crop Biotechnology" by Maarten J. Chrispeels and David E. Sadava (2003) Jones and Bartlett Press).

(iii) Environment or Stress Resistance

Improvement of a plant's ability to tolerate various environmental stresses such as, but not limited to, drought, excess moisture, chilling, freezing, high temperature, salt, and oxidative stress, also can be effected through expression of novel genes. It is proposed that benefits may be realized in terms of increased resistance to freezing temperatures through the introduction of an "antifreeze" protein such as that of the Winter Flounder (Cutler et al., J. Plant Physiol., 135:351-354, 1989) or synthetic gene derivatives thereof. Improved chilling tolerance also may be conferred through increased expression of glycerol 3 phosphate acetyltransferase in chloroplasts (Wolter et al., The EMBO J., 4685-4692, 1992). Resistance to oxidative stress (often exacerbated by conditions such as chilling temperatures in combination with high light intensities) can be conferred by expression of superoxide dismutase (Gupta et al., 1993), and may be improved by glutathione reductase (Bowler et al., Ann Rev. Plant Physiol., 43:83-116, 1992). Such strategies may allow for tolerance to freezing in newly emerged fields as well as extending later maturity higher yielding varieties to earlier relative maturity zones.

It is contemplated that the expression of novel genes that favorably affect plant water content, total water potential, osmotic potential, or turgor will enhance the ability of the plant to tolerate drought. As used herein, the terms "drought resistance" and "drought tolerance" are used to refer to a plant's increased resistance or tolerance to stress induced by a reduction in water availability, as compared to normal circumstances, and the ability of the plant to function and survive in lower water environments. In this aspect of the invention it is proposed, for example, that the expression of genes encoding for the biosynthesis of osmotically active solutes, such as polyol compounds, may impart protection against drought. Within this class are genes encoding for mannitol L phosphate dehydrogenase (Lee and Saier, 1982) and trehalose 6 phosphate synthase (Kaasen et al., J. Bacteriology, 174:889-898, 1992). Through the subsequent action of native phosphatases in the cell or by the introduction and coexpression of a specific phosphatase, these introduced genes will result in the accumulation of either mannitol or trehalose, respectively, both of which have been well documented as protective compounds able to mitigate the effects of stress. Mannitol accumulation in transgenic tobacco has been verified and preliminary results indicate that plants expressing high levels of this metabolite are able to tolerate an applied osmotic stress (Tarczynski et al., Science, 259:508-510, 1993, Tarczynski et al Proc. Natl. Acad. Sci. USA, 89:1-5, 1993).

Similarly, the efficacy of other metabolites in protecting either enzyme function (e.g., alanopine or propionic acid) or membrane integrity (e.g., alanopine) has been documented (Loomis et al., J. Expt. Zoology, 252:9-15, 1989), and therefore expression of genes encoding for the biosynthesis of these compounds might confer drought resistance in a manner similar to or complimentary to mannitol. Other examples of naturally occurring metabolites that are osmotically active and/or provide some direct protective effect during drought and/or desiccation include fructose, erythritol (Coxson et al., Biotropica, 24:121-133, 1992), sorbitol, dulcitol (Karsten et al., Botanica Marina, 35:11-19, 1992), glucosylglycerol (Reed et al., J. Gen. Microbiology, 130:1-4, 1984; Erdmann et al., J. Gen. Microbiology, 138:363-368, 1992), sucrose, stachyose (Koster and Leopold, Plant Physiol., 88:829-832, 1988; Blackman et al., Plant Physiol., 100:225-230, 1992), raffinose (Bernal Lugo and Leopold, Plant Physiol., 98:1207-1210, 1992), proline (Rensburg et al., J. Plant Physiol., 141: 188-194, 1993), glycine betaine, ononitol and pinitol (Vernon and Bohnert, The EMBO J., 11:2077-2085, 1992). Continued canopy growth and increased reproductive fitness during times of stress will be augmented by introduction and expression of genes such as those controlling the osmotically active compounds discussed above and other such compounds. Currently preferred genes which promote the synthesis of an osmotically active polyol compound are genes which encode the enzymes mannitol 1 phosphate dehydrogenase, trehalose 6 phosphate synthase and myoinositol 0 methyltransferase.

It is contemplated that the expression of specific proteins also may increase drought tolerance. Three classes of Late Embryogenic Abundant (LEA) Proteins have been assigned based on structural similarities (see Dure et al., Plant Molecular Biology, 12:475-486, 1989). All three classes of LEAs have been demonstrated in maturing (e.g. desiccating) seeds. Within these 3 types of LEA proteins, the Type II (dehydrin type) have generally been implicated in drought and/or desiccation tolerance in vegetative plant parts (e.g. Mundy and Chua, The EMBO J., 7:2279-2286, 1988; Piatkowski et al., Plant Physiol., 94:1682-1688, 1990; Yamaguchi Shinozaki et al., Plant Cell Physiol., 33:217-224, 1992). Expression of a Type III LEA (HVA 1) in tobacco was found to influence plant height, maturity and drought tolerance (Fitzpatrick, Gen. Engineering News, 22:7, 1993). In rice, expression of the HVA 1 gene influenced tolerance to water deficit and salinity (Xu et al., Plant Physiol., 110:249-257, 1996). Expression of structural genes from any of the three LEA groups may therefore confer drought tolerance. Other types of proteins induced during water stress include thiol proteases, aldolases or transmembrane transporters (Guerrero et al., Plant Molecular Biology, 15:11-26, 1990), which may confer various protective and/or repair type functions during drought stress. It also is contemplated that genes that effect lipid biosynthesis and hence membrane composition might also be useful in conferring drought resistance on the plant.

Many of these genes for improving drought resistance have complementary modes of action. Thus, it is envisaged that combinations of these genes might have additive and/or synergistic effects in improving drought resistance in plants. Many of these genes also improve freezing tolerance (or resistance); the physical stresses incurred during freezing and drought are similar in nature and may be mitigated in similar fashion. Benefit may be conferred via constitutive expression of these genes, but the preferred means of expressing these novel genes may be through the use of a turgor induced promoter (such as the promoters for the turgor induced genes described in Guerrero et al., Plant Molecular Biology, 15:11-26, 1990 and Shagan et al., Plant Physiol., 101:1397-1398, 1993 which are incorporated herein by reference). Spatial and temporal expression patterns of these genes may enable plants to better withstand stress.

It is proposed that expression of genes that are involved with specific morphological traits that allow for increased water extractions from drying soil would be of benefit. For example, introduction and expression of genes that alter root characteristics may enhance water uptake. It also is contemplated that expression of genes that enhance reproductive fitness during times of stress would be of significant value. For example, expression of genes that improve the synchrony of pollen shed and receptiveness of the female flower parts, e.g., silks, would be of benefit. In addition it is proposed that expression of genes that minimize kernel abortion during times of stress would increase the amount of grain to be harvested and hence be of value.

Given the overall role of water in determining yield, it is contemplated that enabling plants to utilize water more efficiently, through the introduction and expression of novel genes, will improve overall performance even when soil water availability is not limiting. By introducing genes that improve the ability of plants to maximize water usage across a full range of stresses relating to water availability, yield stability or consistency of yield performance may be realized.

Polypeptides that may improve stress tolerance under a variety of stress conditions include polypeptides involved in gene regulation, such as serine/threonine-protein kinases, MAP kinases, MAP kinase kinases, and MAP kinase kinase kinases; polypeptides that act as receptors for signal transduction and regulation, such as receptor protein kinases; intracellular signaling proteins, such as protein phosphatases, GTP binding proteins, and phospholipid signaling proteins; polypeptides involved in arginine biosynthesis; polypeptides involved in ATP metabolism, including for example ATPase, adenylate transporters, and polypeptides involved in ATP synthesis and transport; polypeptides involved in glycine betaine, jasmonic acid, flavonoid or steroid biosynthesis; and hemoglobin. Enhanced or reduced activity of such polypeptides in modified plants will provide changes in the ability of a plant to respond to a variety of environmental stresses, such as chemical stress, drought stress and pest stress.

Other polypeptides that may improve plant tolerance to cold or freezing temperatures include polypeptides involved in biosynthesis of trehalose or raffinose, polypeptides encoded by cold induced genes, fatty acyl desaturases and other polypeptides involved in glycerolipid or membrane lipid biosynthesis, which find use in modification of membrane fatty acid composition, alternative oxidase, calcium-dependent protein kinases, LEA proteins or uncoupling protein.

Other polypeptides that may improve plant tolerance to heat include polypeptides involved in biosynthesis of trehalose, polypeptides involved in glycerolipid biosynthesis or membrane lipid metabolism (for altering membrane fatty acid composition), heat shock proteins or mitochondrial NDK.

Other polypeptides that may improve tolerance to extreme osmotic conditions include polypeptides involved in proline biosynthesis.

Other polypeptides that may improve plant tolerance to drought conditions include aquaporins, polypeptides involved in biosynthesis of trehalose or wax, LEA proteins or invertase.

(iv) Disease Resistance

It is proposed that increased resistance (or tolerance) to diseases may be realized through introduction of genes into plants, for example, into monocotyledonous plants such as maize. It is possible to produce resistance to diseases caused by viruses, viroids, bacteria, fungi and nematodes. It also is contemplated that control of mycotoxin producing organisms may be realized through expression of introduced genes. Resistance can be affected through suppression of endogenous factors that encourage disease-causing interactions, expression of exogenous factors that are toxic to or otherwise provide protection from pathogens, or expression of factors that enhance the plant's own defense responses.

Resistance to viruses may be produced through expression of novel genes. For example, it has been demonstrated that expression of a viral coat protein in a modified plant can impart resistance to infection of the plant by that virus and perhaps other closely related viruses (Cuozzo et al., Bio/Technology, 6:549-553, 1988, Hemenway et al., The EMBO J., 7:1273-1280, 1988, Abel et al., Science, 232:738-743, 1986). It is contemplated that expression of antisense genes targeted at essential viral functions may also impart resistance to viruses. For example, an antisense gene targeted at the gene responsible for replication of viral nucleic acid may inhibit replication and lead to resistance to the virus. It is believed that interference with other viral functions through the use of antisense genes also may increase resistance to viruses. Further, it is proposed that it may be possible to achieve resistance to viruses through other approaches, including, but not limited to the use of satellite viruses.

It is proposed that increased resistance to diseases caused by bacteria and fungi may be realized through introduction of novel genes. It is contemplated that genes encoding so called "peptide antibiotics," pathogenesis related (PR) proteins, toxin resistance, or proteins affecting host pathogen interactions such as morphological characteristics will be useful. Peptide antibiotics are polypeptide sequences which are inhibitory to growth of bacteria and other microorganisms. For example, the classes of peptides referred to as cecropins and magainins inhibit growth of many species of bacteria and fungi. It is proposed that expression of PR proteins in plants, for example, monocots such as maize, may be useful in conferring resistance to bacterial disease. These genes are induced following pathogen attack on a host plant and have been divided into at least five classes of proteins (Bol, Linthorst, and Cornelissen, 1990). Included amongst the PR proteins are beta 1,3 glucanases, chitinases, and osmotin and other proteins that are believed to function in plant resistance to disease organisms. Other genes have been identified that have antifungal properties, e.g., UDA (stinging nettle lectin), or hevein (Broakaert et al., 1989; Barkai Golan et al., 1978). It is known that certain plant diseases are caused by the production of phytotoxins. It is proposed that resistance to these diseases would be achieved through expression of a novel gene that encodes an enzyme capable of degrading or otherwise inactivating the phytotoxin. It also is contemplated that expression of novel genes that alter the interactions between the host plant and pathogen may be useful in reducing the ability of the disease organism to invade the tissues of the host plant; e.g., an increase in the waxiness of the leaf cuticle or other morphological characteristics.

Polypeptides useful for imparting improved disease responses to plants include polypeptides encoded by cercosporin induced genes, antifungal proteins and proteins encoded by R-genes or SAR genes.

Agronomically important diseases caused by fungal phytopathogens include: glume or leaf blotch, late blight, stalk/head rot, rice blast, leaf blight and spot, corn smut, wilt, sheath blight, stem canker, root rot, blackleg or kernel rot.

Exemplary plant viruses include tobacco or cucumber mosaic virus, ringspot virus, necrosis virus, maize dwarf mosaic virus, etc. Specific fungal, bacterial and viral pathogens of major crops include, but are not limited to:

RICE: rice brown spot fungus (*Cochliobolus miyabeanus*), rice blast fungus—*Magnaporthe grisea* (*Pyricularia grisea*), *Magnaporthe salvinii* (*Sclerotium oryzae*), *Xanthomomas oryzae* pv. *oryzae*, *Xanthomomas oryzae* pv. *oryzicola*, *Rhizoctonia* spp. (including but not limited to *Rhizoctonia solani*, *Rhizoctonia oryzae* and *Rhizoctonia oryzae-sativae*), *Pseudomonas* spp. (including but not limited to *Pseudomonas plantarii*, *Pseudomonas avenae*, *Pseudomonas glumae*, *Pseudomonas fuscovaginae*, *Pseudomonas alboprecipitans*, *Pseudomonas syringae* pv. *panici*, *Pseudomonas syringae* pv. *syringae*, *Pseudomonas syringae* pv. *oryzae* and *Pseudomonas syringae* pv. *aptata*), *Erwinia* spp. (including but not limited to *Erwinia herbicola*, *Erwinia amylovaora*, *Erwinia chrysanthemi* and *Erwinia carotovora*), *Achyla* spp. (including but not limited to *Achyla conspicua* and *Achyia klebsiana*), *Pythium* spp. (including but not limited to *Pythium dissotocum*, *Pythium irregulare*, *Pythium arrhenomanes*, *Pythium myriotylum*, *Pythium catenulatum*, *Pythium graminicola* and *Pythium spinosum*), *Saprolegnia* spp., *Dictyuchus* spp., *Pythiogeton* spp., *Phytophthora* spp., *Alternaria padwickii*, *Cochliobolus miyabeanus*, *Curvularia* spp. (including but not limited to *Curvularia lunata*, *Curvularia affinis*, *Curvularia clavata*, *Curvularia eragrostidis*, *Curvularia fallax*, *Curvularia geniculata*, *Curvularia inaequalis*, *Curvularia intermedia*, *Curvularia oryzae*, *Curvularia oryzae-sativae*, *Curvularia pallescens*, *Curvularia senegalensis*, *Curvularia tuberculata*, *Curvularia uncinata* and *Curvularia verruculosa*), *Sarocladium oryzae*, *Gerlachia oryzae*, *Fusarium* spp. (including but not limited *Fusarium graminearum*, *Fusarium nivale* and to different pathovars of *Fusarium monoliforme*, including pvs. *fujikuroi* and *zeae*), *Sclerotium rolfsii*, *Phoma exigua*, *Mucor fragilis*, *Trichoderma viride*, *Rhizopus* spp., *Cercospora oryzae*, *Entyloma oryzae*, *Dreschlera gigantean*, *Scierophthora macrospora*, *Mycovellosiella oryzae*, *Phomopsis oryzae-sativae*, *Puccinia graminis*, *Uromyces coronatus*, *Cylindrocladium scoparium*, *Sarocladium oryzae*, *Gaeumannomyces graminis* pv. *graminis*, *Myrothecium verrucaria*, *Pyrenochaeta oryzae*, *Ustilaginoidea virens*, *Neovossia* spp. (including but not limited to *Neovossia horrida*), *Tilletia* spp., *Balansia oryzae-sativae*, *Phoma* spp. (including but not limited to *Phoma sorghina*, *Phoma insidiosa*, *Phoma glumarum*, *Phoma glumicola* and *Phoma oryzina*), *Nigrospora* spp. (including but not limited to *Nigrospora oryzae*, *Nigrospora sphaerica*, *Nigrospora panici* and *Nigrospora padwickii*), *Epiococcum nigrum*, *Phyllostica* spp., *Wolkia decolorans*, *Monascus purpureus*, *Aspergillus* spp., *Penicillium* spp., *Absidia* spp., *Mucor* spp., *Chaetomium* spp., *Dematium* spp., *Monilia* spp., *Streptomyces* spp., *Syncephalastrum* spp., *Verticillium* spp., *Nematospora coryli*, *Nakataea sigmoidea*, *Cladosporium* spp., *Bipolaris* spp., *Coniothyrium* spp., *Diplodia oryzae*, *Exserophilum rostratum*, *Helococera oryzae*, *Melanomma glumarum*, *Metashaeria* spp., *Mycosphaerella* spp., *Oidium* spp., *Pestalotia* spp., *Phaeoseptoria* spp., *Sphaeropsis* spp., *Trematosphaerella* spp., rice black-streaked dwarf virus, rice dwarf virus, rice gall dwarf virus, barley yellow dwarf virus, rice grassy stunt virus, rice hoja blanca virus, rice necrosis mosaic virus, rice ragged stunt virus, rice stripe virus, rice stripe necrosis virus, rice transitory yellowing virus, rice tungro bacilliform virus, rice tungro spherical virus, rice yellow mottle virus, rice tarsonemid mite virus, *Echinochloa* hoja blanca virus, *Echinochloa* ragged stunt virus, orange leaf mycoplasma-like organism, yellow dwarf mycoplasma-like organism, *Aphelenchoides besseyi*, *Ditylenchus angustus*, *Hirschmanniella* spp., *Criconemella* spp., *Meloidogyne* spp., *Heterodera* spp., *Pratylenchus* spp., *Hoplolaimus indicus*.

SOYBEANS: *Phytophthora sojae*, *Fusarium solani* f. sp. Glycines, *Macrophomina phaseolina*, *Fusarium*, *Pythium*, *Rhizoctonia*, *Phialophora gregata*, *Sclerotinia sclerotiorum*, *Diaporthe phaseolorum* var. *sojae*, *Colletotrichum truncatum*, *Phomopsis longicolla*, *Cercospora kikuchii*, *Diaporthe phaseolonum* var. *meridionalis* (and var. *caulivora*), *Phakopsora pachyrhyzi*, *Fusarium solani*, *Microsphaera diffusa*, *Septoria glycines*, *Cercospora kikuchii*, *Macrophomina phaseolina*, *Sclerotinia sclerotiorum*, *Corynespora cassiicola*, *Rhizoctonia solani*, *Cercospora sojina*, *Phytophthora megasperma* fsp. *glycinea*, *Macrophomina phaseolina*, *Fusarium oxysporum*, *Diapothe phaseolorum* var. *sojae* (*Phomopsis sojae*), *Diaporthe phaseolorum* var. *caulivora*, *Sclerotium rolfsii*, *Cercospora kikuchii*, *Cercospora sojina*, *Peronospora manshurica*, *Colletotrichum dematium* (*Colletotichum truncatum*), *Corynespora cassiicola*, *Phyllosticta sojicola*, *Alternaria alternata*, *Pseudomonas syringae* p.v. *glycinea*, *Xanthomonas campestris* p.v. *phaseoli*, *Microspaera diffusa*, *Fusarium semitectum*, *Phialophora gregata*, Soybean mosaic virus, *Glomerella glycines*, Tobacco Ring spot virus, Tobacco Streak virus, *Phakopsora pachyrhizi*, *Pythium aphanidermatum*, *Pythium ultimum*, *Pythium dearyanum*, Tomato spotted wilted virus, *Heterodera glycines*, *Fusarium solani*, Soybean cyst and root knot nematodes.

CORN: *Fusarium moniliforme* var. *subglutinans*, *Erwinia stewartii*, *Fusarium moniliforme*, *Gibberella zeae* (*Fusarium Graminearum*), *Stenocarpella maydi* (*Diplodia maydis*), *Pythium irregulare*, *Pythium debaryanum*, *Pythium graminicola*, *Pythium splendens*, *Pythium ultimum*, *Pythium aphanidermatum*, *Aspergillus flavus*, *Bipolaris maydis* O, T (*cochliobolus heterostrophus*), *Helminthosporium carbonum* I, II, and III (*Cochliobolus carbonum*), *Exserohilum turcicum* I, II and III, *Helminthosporium pedicellatum*, *Physoderma maydis*, *Phyllosticta maydis*, *Kabatie-maydis*, *Cercospora sorghi*, *Ustilago maydis*, *Puccinia sorghi*, *Puccinia polysora*, *Macrophomina phaseolina*, *Penicillium oxalicum*, *Nigrospora oryzae*, *Cladosporium herbarum*, *Curvularia lunata*, *Curvularia inaequalis*, *Curvularia pallescens*, *Clavibacter michiganese* subsp. *Nebraskense*, *Trichoderma viride*, Maize dwarf Mosaic Virus A and B, Wheat Streak Mosaic Virus, Maize Chlorotic Dwarf Virus, *Claviceps sorghi*, *Pseudonomas avenae*, *Erwinia chrysantemi* p.v. *Zea*, *Erwinia corotovora*, *Cornstun spiroplasma*, *Diplodia macrospora*, *Sclerophthora macrospora*, *Peronosclerospora sorghi*, *Peronoscherospora philippinesis*, *Peronosclerospora maydis*, *Peronosclerospora sacchari*, *Spacelotheca reiliana*, *Physopella zea*, *Cephalosporium maydis*, *Caphalosporium acremonium*, Maize Chlorotic Mottle Virus, High Plains Virus, Maize Mosaic Virus, Maize Rayado Fino Virus, Maize Streak Virus, Maize Stripe Virus, Maize Rought Dwarf Virus:

WHEAT: *Pseudomonas syringae* p.v. *atrofaciens*, *Urocystis agropyri*, *Xanthomonas campestris* p.v. *translucens*, *Pseudomonas syringae* p.v. *syringae*, *Alternaria alternata*, *Cladosporium herbarum*, *Fusarium graminearum*, *Fusarium avenaceum*, *Fusarium culmorum*, *Ustilago tritici*, *Ascochyta tritici*, *Cephalosporium gramineum*, *Collotetrichum graminicola*, *Erysiphe graminis* f. sp. *Tritici*, *Puccinia graminis* f. sp. *Tritici*, *Puccinia recondite* f. sp. *tritici*, *puccinia striiformis*, *Pyrenophora triticirepentis*, *Septoria nodorum*, *Septoria tritici*, *Septoria avenae*, *Pseudocercosporella herpotrichoides*, *Rhizoctonia solani*, *Rhizoctonia cerealis*, *Gaeumannomyces graminis* var. *tritici*, *Pythium aphanidermatum*, *Pythium arrhenomanes*, *Pythium ultimum*, *Bipolaris sorokiniana*, Barley Yellow Dwarf Virus, Brome Mosaic Virus, Soil Borne Wheat Mosaic Virus, Wheat Streak Virus, Wheat Spindle Streak Virus, American Wheat Striate Virus, *Claviceps purpurea*, *Tilletia tritici*, *Tilletia laevis*, *Pstilago tritici*, *Tilletia indica*, *Rhizoctonia solani*, *Pythium arrhenomannes*, *Pythium gramicola*, *Pythium aphanidermatum*, High Plains Virus, European Wheat Striate Virus:

CANOLA: *Albugo candida*, *Alternaria brassicae*, *Leptosharia maculans*, *Rhizoctonia solani*, *Sclerotinia sclerotiorum*, *Mycospaerella brassiccola*, *Pythium ultimum*, *Peronospora parasitica*, *Fusarium roseum*, *Fusarium oxysporum*, *Tilletia foetida*, *Tilletia caries*, *Alternaria alternata*:

SUNFLOWER: *Plasmophora halstedii*, *Scherotinia sclerotiorum*, Aster Yellows, *Septoria helianthi*, *Phomopsis helianthi*, *Alternaria helianthi*, *Alternaria zinniae*, *Botrytis cinera*, *Phoma macdonaldii*, *Macrophomina phaseolina*, *Erysiphe cichoracearum*, *Phizopus oryzae*, *Rhizopus arrhizus*, *Rhizopus stolonifer*, *Puccinia helianthi*, *Verticillium Dahliae*, *Erwinia carotovorum* p.v. *carotovora*, *Cephalosporium acremonium*, *Phytophthora cryptogea*, *Albugo tragopogonis*.

SORGHUM: *Exserohilum turcicum*, *Colletotrichum graminicola* (*Glomerella graminicola*), *Cercospora sorghi*, *Gloeocercospora sorghi*, *Ascochyta sorghi*, *Pseudomonas syringae* p.v. *syringae*, *Xanthomonas campestris* p.v. *holcicola*, *Pseudomonas andropogonis*, *Puccinia purpurea*, *Macrophomina phaseolina*, *Periconia circinata*, *Fusarium moniliforme*, *Alternaria alternate*, *Bipolaris sorghicola*, *Helminthosporium sorghicola*, *Curvularia lunata*, *Phoma insidiosa*, *Pseudomonas avenae* (*Pseudomonas alboprecipitans*), *Ramulispora sorghi*, *Ramulispora sorghicola*, *Phyllachara sacchari Sporisorium relianum* (*Sphacelotheca reliana*), *Sphacelotheca cruenta*, *Sporisorium sorghi*, Sugarcane mosaic H, Maize Dwarf Mosaic Virus A & B, *Claviceps sorghi*, *Rhizoctonia solani*, *Acremonium strictum*, *Sclerophthona macrospora*, *Peronosclerospora sorghi*, *Peronosclerospora philippinensis*, *Sclerospora graminicola*, *Fusarium graminearum*, *Fusarium Oxysporum*, *Pythium arrhenomanes*, *Pythium graminicola*.

ALFALFA: *Clavibater michiganensis* subsp. *Insidiosum*, *Pythium ultimum*, *Pythium irregulare*, *Pythium splendens*, *Pythium debaryanum*, *Pythium aphanidermatum*, *Phytophthora megasperma*, *Peronospora trifoliorum*, *Phoma medi-* caginis var. medicaginis, Cercospora medicaginis, Pseudopeziza medicaginis, Leptotrochila medicaginis, Fusarium oxysporum, Rhizoctonia solani, Uromyces striatus, Colletotrichum trifolii race 1 and race 2, Leptosphaerulina briosiana, Stemphylium botryosum, Stagonospora meliloti, Sclerotinia trifoliorum, Alfalfa Mosaic Virus, Verticillium albo-atrum, Xanthomonas campestris p.v. alfalfae, Aphanomyces euteiches, Stemphylium herbarum, Stemphylium alfalfae.

(v) Plant Agronomic Characteristics

Two of the factors determining where crop plants can be grown are the average daily temperature during the growing season and the length of time between frosts. Within the areas where it is possible to grow a particular crop, there are varying limitations on the maximal time it is allowed to grow to maturity and be harvested. For example, a variety to be grown in a particular area is selected for its ability to mature and dry down to harvestable moisture content within the required period of time with maximum possible yield. Therefore, crops of varying maturities are developed for different growing locations. Apart from the need to dry down sufficiently to permit harvest, it is desirable to have maximal drying take place in the field to minimize the amount of energy required for additional drying post harvest. Also, the more readily a product such as grain can dry down, the more time there is available for growth and kernel fill. It is considered that genes that influence maturity and/or dry down can be identified and introduced into plant lines using transformation techniques to create new varieties adapted to different growing locations or the same growing location, but having improved yield to moisture ratio at harvest. Expression of genes that are involved in regulation of plant development may be especially useful.

It is contemplated that genes may be introduced into plants that would improve standability and other plant growth characteristics. Expression of novel genes in plants which confer stronger stalks, improved root systems, or prevent or reduce ear droppage or shattering would be of great value to the farmer. It is proposed that introduction and expression of genes that increase the total amount of photoassimilate available by, for example, increasing light distribution and/or interception would be advantageous. In addition, the expression of genes that increase the efficiency of photosynthesis and/or the leaf canopy would further increase gains in productivity. It is contemplated that expression of a phytochrome gene in crop plants may be advantageous. Expression of such a gene may reduce apical dominance, confer semidwarfism on a plant, or increase shade tolerance (U.S. Pat. No. 5,268, 526). Such approaches would allow for increased plant populations in the field.

(vi) Nutrient Utilization

The ability to utilize available nutrients may be a limiting factor in growth of crop plants. It is proposed that it would be possible to alter nutrient uptake, tolerate pH extremes, mobilization through the plant, storage pools, and availability for metabolic activities by the introduction of novel genes. These modifications would allow a plant, for example, maize to more efficiently utilize available nutrients. It is contemplated that an increase in the activity of, for example, an enzyme that is normally present in the plant and involved in nutrient utilization would increase the availability of a nutrient or decrease the availability of an antinutritive factor. An example of such an enzyme would be phytase. It is further contemplated that enhanced nitrogen utilization by a plant is desirable. Expression of a glutamate dehydrogenase gene in plants, e.g., E. coli gdhA genes, may lead to increased fixation of nitrogen in organic compounds. Furthermore, expression of gdhA in plants may lead to enhanced resistance to the herbicide glufosinate by incorporation of excess ammonia into glutamate, thereby detoxifying the ammonia. It also is contemplated that expression of a novel gene may make a nutrient source available that was previously not accessible, e.g., an enzyme that releases a component of nutrient value from a more complex molecule, perhaps a macromolecule.

Polypeptides useful for improving nitrogen flow, sensing, uptake, storage and/or transport include those involved in aspartate, glutamine or glutamate biosynthesis, polypeptides involved in aspartate, glutamine or glutamate transport, polypeptides associated with the TOR (Target of Rapamycin) pathway, nitrate transporters, nitrate reductases, amino transferases, ammonium transporters, chlorate transporters or polypeptides involved in tetrapyrrole biosynthesis.

Polypeptides useful for increasing the rate of photosynthesis include phytochrome, ribulose bisphosphate carboxylase-oxygenase, Rubisco activase, photosystem I and II proteins, electron carriers, ATP synthase, NADH dehydrogenase or cytochrome oxidase.

Polypeptides useful for increasing phosphorus uptake, transport or utilization include phosphatases or phosphate transporters.

(vii) Male Sterility

Male sterility is useful in the production of hybrid seed. It is proposed that male sterility may be produced through expression of novel genes. For example, it has been shown that expression of genes that encode proteins, RNAs, or peptides that interfere with development of the male inflorescence and/or gametophyte result in male sterility. Chimeric ribonuclease genes that express in the anthers of transgenic tobacco and oilseed rape have been demonstrated to lead to male sterility (Mariani et al., Nature, 347:737-741, 1990).

A number of mutations were discovered in maize that confer cytoplasmic male sterility. One mutation in particular, referred to as T cytoplasm, also correlates with sensitivity to Southern corn leaf blight. A DNA sequence, designated TURF 13 (Levings, Science, 250:942-947, 1990), was identified that correlates with T cytoplasm. It is proposed that it would be possible through the introduction of TURF 13 via transformation, to separate male sterility from disease sensitivity. As it is necessary to be able to restore male fertility for breeding purposes and for grain production, it is proposed that genes encoding restoration of male fertility also may be introduced.

(viii) Altered Nutritional Content

Genes may be introduced into plants to improve or alter the nutrient quality or content of a particular crop. Introduction of genes that alter the nutrient composition of a crop may greatly enhance the feed or food value. For example, the protein of many grains is suboptimal for feed and food purposes, especially when fed to pigs, poultry, and humans. The protein is deficient in several amino acids that are essential in the diet of these species, requiring the addition of supplements to the grain. Limiting essential amino acids may include lysine, methionine, tryptophan, threonine, valine, arginine, and histidine. Some amino acids become limiting only after corn is supplemented with other inputs for feed formulations. The levels of these essential amino acids in seeds and grain may be elevated by mechanisms which include, but are not limited to, the introduction of genes to increase the biosynthesis of the amino acids, decrease the degradation of the amino acids, increase the storage of the amino acids in proteins, or increase transport of the amino acids to the seeds or grain.

Polypeptides useful for providing increased seed protein quantity and/or quality include polypeptides involved in the metabolism of amino acids in plants, particularly polypeptides involved in biosynthesis of methionine/cysteine and lysine, amino acid transporters, amino acid efflux carriers, seed storage proteins, proteases, or polypeptides involved in phytic acid metabolism.

The protein composition of a crop may be altered to improve the balance of amino acids in a variety of ways including elevating expression of native proteins, decreasing expression of those with poor composition, changing the composition of native proteins, or introducing genes encoding entirely new proteins possessing superior composition.

The introduction of genes that alter the oil content of a crop plant may also be of value. Increases in oil content may result in increases in metabolizable-energy-content and density of the seeds for use in feed and food. The introduced genes may encode enzymes that remove or reduce rate-limitations or regulated steps in fatty acid or lipid biosynthesis. Such genes may include, but are not limited to, those that encode acetyl-CoA carboxylase, ACP-acyltransferase, alpha-ketoacyl-ACP synthase, or other well known fatty acid biosynthetic activities. Other possibilities are genes that encode proteins that do not possess enzymatic activity such as acyl carrier protein. Genes may be introduced that alter the balance of fatty acids present in the oil providing a more healthful or nutritive feedstuff. The introduced DNA also may encode sequences that block expression of enzymes involved in fatty acid biosynthesis, altering the proportions of fatty acids present in crops.

Genes may be introduced that enhance the nutritive value of crops, or of foods derived from crops by increasing the level of naturally occurring phytosterols, or by encoding for proteins to enable the synthesis of phytosterols in crops. The phytosterols from these crops can be processed directly into foods, or extracted and used to manufacture food products.

Genes may be introduced that enhance the nutritive value of the starch component of crops, for example by increasing the degree of branching, resulting in improved utilization of the starch in livestock by delaying its metabolism. Additionally, other major constituents of a crop may be altered, including genes that affect a variety of other nutritive, processing, or other quality aspects. For example, pigmentation may be increased or decreased.

Carbohydrate metabolism may be altered, for example by increased sucrose production and/or transport. Polypeptides useful for affecting on carbohydrate metabolism include polypeptides involved in sucrose or starch metabolism, carbon assimilation or carbohydrate transport, including, for example sucrose transporters or glucose/hexose transporters, enzymes involved in glycolysis/gluconeogenesis, the pentose phosphate cycle, or raffinose biosynthesis, or polypeptides involved in glucose signaling, such as SNF1 complex proteins.

Feed or food crops may also possess sub-optimal quantities of vitamins, antioxidants or other nutraceuticals, requiring supplementation to provide adequate nutritive value and ideal health value. Introduction of genes that enhance vitamin biosynthesis may be envisioned including, for example, vitamins A, E, B12, choline, or the like. Mineral content may also be sub-optimal. Thus genes that affect the accumulation or availability of compounds containing phosphorus, sulfur, calcium, manganese, zinc, or iron among others would be valuable.

Numerous other examples of improvements of crops may be used with the invention. The improvements may not necessarily involve grain, but may, for example, improve the value of a crop for silage. Introduction of DNA to accomplish this might include sequences that alter lignin production such as those that result in the "brown midrib" phenotype associated with superior feed value for cattle. Other genes may encode for enzymes that alter the structure of extracellular carbohydrates in the stover, or that facilitate the degradation of the carbohydrates in the non-grain portion of the crop so that it can be efficiently fermented into ethanol or other useful carbohydrates.

It may be desirable to modify the nutritional content of plants by reducing undesirable components such as fats, starches, etc. This may be done, for example, by the use of exogenous nucleic acids that encode enzymes which increase plant use or metabolism of such components so that they are present at lower quantities. Alternatively, it may be done by use of exogenous nucleic acids that reduce expression levels or activity of native plant enzymes that synthesize such components.

Likewise the elimination of certain undesirable traits may improve the food or feed value of the crop. Many undesirable traits must currently be eliminated by special post-harvest processing steps and the degree to which these can be engineered into the plant prior to harvest and processing would provide significant value. Examples of such traits are the elimination of anti-nutritionals such as phytates and phenolic compounds which are commonly found in many crop species. Also, the reduction of fats, carbohydrates and certain phytohormones may be valuable for the food and feed industries as they may allow a more efficient mechanism to meet specific dietary requirements.

In addition to direct improvements in feed or food value, genes also may be introduced which improve the processing of crops and improve the value of the products resulting from the processing. One use of crops is via wetmilling. Thus novel genes that increase the efficiency and reduce the cost of such processing, for example by decreasing steeping time, may also find use. Improving the value of wetmilling products may include altering the quantity or quality of starch, oil, corn gluten meal, or the components of gluten feed. Elevation of starch may be achieved through the identification and elimination of rate limiting steps in starch biosynthesis by expressing increased amounts of enzymes involved in biosynthesis or by decreasing levels of the other components of crops resulting in proportional increases in starch.

Oil is another product of wetmilling, the value of which may be improved by introduction and expression of genes. Oil properties may be altered to improve its performance in the production and use of cooking oil, shortenings, lubricants or other oil-derived products or improvement of its health attributes when used in the food-related applications. Novel fatty acids also may be synthesized which upon extraction can serve as starting materials for chemical syntheses. The changes in oil properties may be achieved by altering the type, level, or lipid arrangement of the fatty acids present in the oil. This in turn may be accomplished by the addition of genes that encode enzymes that catalyze the synthesis of novel fatty acids (e.g. fatty acid elongases, desaturases) and the lipids possessing them or by increasing levels of native fatty acids while possibly reducing levels of precursors or breakdown products. Alternatively, DNA sequences may be introduced which slow or block steps in fatty acid biosynthesis resulting in the increase in precursor fatty acid intermediates. Genes that might be added include desaturases, epoxidases, hydratases, dehydratases, or other enzymes that catalyze reactions involving fatty acid intermediates. Representative examples of catalytic steps that might be blocked include the desaturations from stearic to oleic acid or oleic to linolenic acid resulting in the respective accumulations of stearic and oleic acids. Another example is the blockage of elongation steps resulting in the accumulation of C8 to C12 saturated fatty acids.

Polypeptides useful for providing increased seed oil quantity and/or quality include polypeptides involved in fatty acid and glycerolipid biosynthesis, beta-oxidation enzymes, enzymes involved in biosynthesis of nutritional compounds, such as carotenoids and tocopherols, or polypeptides that increase embryo size or number or thickness of aleurone.

Polypeptides involved in production of galactomannans or arabinogalactans are of interest for providing plants having increased and/or modified reserve polysaccharides for use in food, pharmaceutical, cosmetic, paper and paint industries.

Polypeptides involved in modification of flavonoid/isoflavonoid metabolism in plants include cinnamate-4-hydroxylase, chalcone synthase or flavones synthase. Enhanced or reduced activity of such polypeptides in modified plants will provide changes in the quantity and/or speed of flavonoid metabolism in plants and may improve disease resistance by enhancing synthesis of protective secondary metabolites or improving signaling pathways governing disease resistance.

Polypeptides involved in lignin biosynthesis are of interest for increasing plants' resistance to lodging and for increasing the usefulness of plant materials as biofuels.

(ix) Production or Assimilation of Chemicals or Biological

It may further be considered that a modified plant prepared in accordance with the invention may be used for the production or manufacturing of useful biological compounds that were either not produced at all, or not produced at the same level, in the corn plant previously. Alternatively, plants produced in accordance with the invention may be made to metabolize or absorb and concentrate certain compounds, such as hazardous wastes, thereby allowing bioremediation of these compounds.

The novel plants producing these compounds are made possible by the introduction and expression of one or potentially many genes with the constructs provided by the invention. The vast array of possibilities include but are not limited to any biological compound which is presently produced by any organism such as proteins, nucleic acids, primary and intermediary metabolites, carbohydrate polymers, enzymes for uses in bioremediation, enzymes for modifying pathways that produce secondary plant metabolites such as falconoid or vitamins, enzymes that could produce pharmaceuticals, and for introducing enzymes that could produce compounds of interest to the manufacturing industry such as specialty chemicals and plastics. The compounds may be produced by the plant, extracted upon harvest and/or processing, and used for any presently recognized useful purpose such as pharmaceuticals, fragrances, and industrial enzymes to name a few.

(x) Other Characteristics

Cell cycle modification: Polypeptides encoding cell cycle enzymes and regulators of the cell cycle pathway are useful for manipulating growth rate in plants to provide early vigor and accelerated maturation. Improvements in quality traits, such as seed oil content, may also be obtained by expression of cell cycle enzymes and cell cycle regulators. Polypeptides of interest for modification of cell cycle pathway include cycling and EIF5$\alpha$ pathway proteins, polypeptides involved in polyamine metabolism, polypeptides which act as regulators of the cell cycle pathway, including cyclin-dependent kinases (CDKs), CDK-activating kinases, cell cycle-dependent phosphatases, CDK-inhibitors, Rb and Rb-binding proteins, or transcription factors that activate genes involved in cell proliferation and division, such as the E2F family of transcription factors, proteins involved in degradation of cyclins, such as cullins, and plant homologs of tumor suppressor polypeptides.

Plant growth regulators: Polypeptides involved in production of substances that regulate the growth of various plant tissues are of interest in the present invention and may be used to provide modified plants having altered morphologies and improved plant growth and development profiles leading to improvements in yield and stress response. Of particular interest are polypeptides involved in the biosynthesis, or degradation of plant growth hormones, such as gibberellins, brassinosteroids, cytokinins, auxins, ethylene or abscisic acid, and other proteins involved in the activity, uptake and/or transport of such polypeptides, including for example, cytokinin oxidase, cytokinin/purine permeases, F-box proteins, G-proteins or phytosulfokines.

Transcription factors in plants: Transcription factors play a key role in plant growth and development by controlling the expression of one or more genes in temporal, spatial and physiological specific patterns. Enhanced or reduced activity of such polypeptides in modified plants will provide significant changes in gene transcription patterns and provide a variety of beneficial effects in plant growth, development and response to environmental conditions. Transcription factors of interest include, but are not limited to myb transcription factors, including helix-turn-helix proteins, homeodomain transcription factors, leucine zipper transcription factors, MADS transcription factors, transcription factors having AP2 domains, zinc finger transcription factors, CCAAT binding transcription factors, ethylene responsive transcription factors, transcription initiation factors or UV damaged DNA binding proteins.

Homologous recombination: Increasing the rate of homologous recombination in plants is useful for accelerating the introgression of transgenes into breeding varieties by backcrossing, and to enhance the conventional breeding process by allowing rare recombinants between closely linked genes in phase repulsion to be identified more easily. Polypeptides useful for expression in plants to provide increased homologous recombination include polypeptides involved in mitosis and/or meiosis, DNA replication, nucleic acid metabolism, DNA repair pathways or homologous recombination pathways including for example, recombinases, nucleases, proteins binding to DNA double-strand breaks, single-strand DNA binding proteins, strand-exchange proteins, resolvases, ligases, helicases and polypeptide members of the RAD52 epistasis group.

Non-Protein-Expressing Exogenous Nucleic Acids

Plants with decreased expression of a gene of interest can also be achieved, for example, by expression of antisense nucleic acids, dsRNA or RNAi, catalytic RNA such as ribozymes, sense expression constructs that exhibit cosuppression effects, aptamers or zinc finger proteins.

Antisense RNA reduces production of the polypeptide product of the target messenger RNA, for example by blocking translation through formation of RNA:RNA duplexes or by inducing degradation of the target mRNA. Antisense approaches are a way of preventing or reducing gene function by targeting the genetic material as disclosed in U.S. Pat. Nos. 4,801,540; 5,107,065; 5,759,829; 5,910,444; 6,184,439; and 6,198,026, all of which are incorporated herein by reference. In one approach, an antisense gene sequence is introduced that is transcribed into antisense RNA that is complementary to the target mRNA. For example, part or all of the normal gene sequences are placed under a promoter in inverted orientation so that the 'wrong' or complementary strand is transcribed into a non-protein expressing antisense RNA. The promoter used for the antisense gene may influence the level, timing, tissue, specificity, or inducibility of the antisense inhibition.

Autonomous mini-chromosomes may contain exogenous DNA bounded by recombination sites, for example lox-P sites, that can be recognized by a recombinase, e.g. Cre, and removed from the mini-chromosome. In cases where there is a homologous recombination site or sites in the host genomic DNA, the exogenous DNA excised the mini-chromosome may be integrated into the genome at one of the specific recombination sites and the DNA bounded by the recombination sites will become integrated into the host DNA. The use of a mini-chromosome as a platform for DNA excision or for launching such DNA integration into the host genome may include in vivo induction of the expression of a recombinase encoded in the genomic DNA of a transgenic host, or in a mini-chromosome or other episome.

RNAi gene suppression in plants by transcription of a dsRNA is described in U.S. Pat. No. 6,506,559, U.S. patent application Publication No. 2002/0168707, WO 98/53083, WO 99/53050 and WO 99/61631, all of which are incorporated herein by reference. The double-stranded RNA or RNAi constructs can trigger the sequence-specific degradation of the target messenger RNA. Suppression of a gene by RNAi can be achieved using a recombinant DNA construct having a promoter operably linked to a DNA element comprising a sense and anti-sense element of a segment of genomic DNA of the gene, e.g., a segment of at least about 23 nucleotides, more preferably about 50 to 200 nucleotides where the sense and anti-sense DNA components can be directly linked or joined by an intron or artificial DNA segment that can form a loop when the transcribed RNA hybridizes to form a hairpin structure.

Catalytic RNA molecules or ribozymes can also be used to inhibit expression of the target gene or genes or facilitate molecular reactions. Ribozymes are targeted to a given sequence by hybridization of sequences within the ribozyme to the target mRNA. Two stretches of homology are required for this targeting, and these stretches of homologous sequences flank the catalytic ribozyme structure. It is possible to design ribozymes that specifically pair with virtually any target mRNA and cleave the target mRNA at a specific location, thereby inactivating it. A number of classes of ribozymes have been identified. One class of ribozymes is derived from a number of small circular RNAs that are capable of self-cleavage and replication in plants. The RNAs replicate either alone (viroid RNAs) or with a helper virus (satellite RNAs). Examples include Tobacco Ringspot Virus (Prody et al., *Science,* 231:1577-1580, 1986), Avocado Sunblotch Viroid (Palukaitis et al., *Virology,* 99:145-151, 1979; Symons, *Nucl. Acids Res.,* 9:6527-6537, 1981), and Lucerne Transient Streak Virus (Forster and Symons, *Cell,* 49:211-220, 1987), and the satellite RNAs from velvet tobacco mottle virus, *Solanum* nodiflorum mottle virus and subterranean clover mottle virus. The design and use of target RNA-specific ribozymes is described in Haseloff, et al., Nature 334:585-591 (1988). Several different ribozyme motifs have been described with RNA cleavage activity (Symons, *Annu. Rev. Biochem.,* 61:641-671, 1992). Other suitable ribozymes include sequences from RNase P with RNA cleavage activity (Yuan et al., *Proc. Natl. Acad. Sci. USA,* 89:8006-8010, 1992; Yuan and Altman, *Science,* 263:1269-1273, 1994; U.S. Pat. Nos. 5,168,053 and 5,624,824), hairpin ribozyme structures (Berzal-Herranz et al., *Genes and Devel.,* 6:129-134, 1992; Chowrira et al., *J. Biol. Chem.,* 269:25856-25864, 1994) and Hepatitis Delta virus based ribozymes (U.S. Pat. No. 5,625, 047). The general design and optimization of ribozyme directed RNA cleavage activity has been discussed in detail (Haseloff and Gerlach, 1988, Nature. 1988 Aug. 18; 334 (6183):585-91, Chowrira et al., J. Biol. Chem., 269:25856-25864, 1994).

Another method of reducing protein expression utilizes the phenomenon of cosuppression or gene silencing (for example, U.S. Pat. Nos. 6,063,947; 5,686,649; or 5,283,184; each of which is incorporated herein by reference). Cosuppression of an endogenous gene using a full-length cDNA sequence as well as a partial cDNA sequence are known (for example, Napoli et al., Plant Cell 2:279-289 [1990]; van der Krol et al., Plant Cell 2:291-299 [1990]; Smith et al., Mol. Gen. Genetics 224:477-481 [1990]). The phenomenon of cosuppression has also been used to inhibit plant target genes in a tissue-specific manner.

In some embodiments, nucleic acids from one species of plant are expressed in another species of plant to effect cosuppression of a homologous gene. The introduced sequence generally will be substantially identical to the endogenous sequence intended to be repressed, for example, about 65%, 80%, 85%, 90%, or preferably 95% or greater identical. Higher identity may result in a more effective repression of expression of the endogenous sequence. A higher identity in a shorter than full length sequence compensates for a longer, less identical sequence. Furthermore, the introduced sequence need not have the same intron or exon pattern, and identity of non-coding segments will be equally effective. Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence.

Yet another method of reducing protein activity is by expressing nucleic acid ligands, so-called aptamers, which specifically bind to the protein. Aptamers may be obtained by the SELEX (Systematic Evolution of Ligands by EXponential Enrichment) method. See U.S. Pat. No. 5,270,163, incorporated herein by reference. In the SELEX method, a candidate mixture of single stranded nucleic acids having regions of randomized sequence is contacted with the protein and those nucleic acids having an increased affinity to the target are selected and amplified. After several iterations a nucleic acid with optimal affinity to the polypeptide is obtained and is used for expression in modified plants.

A zinc finger protein that binds a polypeptide-encoding sequence or its regulatory region is also used to alter expression of the nucleotide sequence. Transcription of the nucleotide sequence may be reduced or increased. Zinc finger proteins are, for example, described in Beerli et al. (1998) PNAS 95:14628-14633., or in WO 95/19431, WO 98/54311, or WO 96/06166, all incorporated herein by reference.

Other examples of non-protein expressing sequences specifically envisioned for use with the invention include tRNA sequences, for example, to alter codon usage, and rRNA variants, for example, which may confer resistance to various agents such as antibiotics.

It is contemplated that unexpressed DNA sequences, including novel synthetic sequences, could be introduced into cells as proprietary "labels" of those cells and plants and seeds thereof. It would not be necessary for a label DNA element to disrupt the function of a gene endogenous to the host organism, as the sole function of this DNA would be to identify the origin of the organism. For example, one could introduce a unique DNA sequence into a plant and this DNA element would identify all cells, plants, and progeny of these cells as having arisen from that labeled source. It is proposed that inclusion of label DNAs would enable one to distinguish proprietary germplasm or germplasm derived from such, from unlabelled germplasm.

Exemplary Plant Promoters, Regulatory Sequences and Targeting Sequences

Exemplary classes of plant promoters are described below.

Constitutive Expression promoters: Exemplary constitutive expression promoters include the ubiquitin promoter (e.g., sunflower—Binet et al. Plant Science 79: 87-94 (1991); maize—Christensen et al. Plant Molec. Biol. 12: 619-632 (1989); and *Arabidopsis*—Callis et al., J. Biol. Chem. 265: 12486-12493 (1990) and Norris et al., Plant Mol. Biol. 21: 895-906 (1993)); the CaMV 35S promoter (U.S. Pat. Nos. 5,858,742 and 5,322,938); or the actin promoter (e.g., rice—U.S. Pat. No. 5,641,876; McElroy et al. Plant Cell 2: 163-171 (1990), McElroy et al. Mol. Gen. Genet. 231: 150-160 (1991), and Chibbar et al. Plant Cell Rep. 12: 506-509 (1993)).

Inducible Expression promoters: Exemplary inducible expression promoters include the chemically regulatable tobacco PR-1 promoter (e.g., tobacco—U.S. Pat. No. 5,614,395; *Arabidopsis*—Lebel et al., Plant J. 16: 223-233 (1998); maize—U.S. Pat. No. 6,429,362). Various chemical regulators may be employed to induce expression, including the benzothiadiazole, isonicotinic acid, and salicylic acid compounds disclosed in U.S. Pat. Nos. 5,523,311 and 5,614,395. Other promoters inducible by certain alcohols or ketones, such as ethanol, include, for example, the alcA gene promoter from *Aspergillus nidulans* (Caddick et al. (1998) Nat. Biotechnol 16:177-180). A glucocorticoid-mediated induction system is described in Aoyama and Chua (1997) The Plant Journal 11: 605-612 wherein gene expression is induced by application of a glucocorticoid, for example a dexamethasone. Another class of useful promoters are water-deficit-inducible promoters, e.g. promoters which are derived from the 5' regulatory region of genes identified as a heat shock protein 17.5 gene (HSP 17.5), an HVA22 gene (HVA22), and a cinnamic acid 4-hydroxylase (CA4H) gene of *Zea mays*. Another water-deficit-inducible promoter is derived from the rab-17 promoter as disclosed by Vilardell et al., Plant Molecular Biology, 17(5):985-993, 1990. See also U.S. Pat. No. 6,084,089 which discloses cold inducible promoters, U.S. Pat. No. 6,294,714 which discloses light inducible promoters, U.S. Pat. No. 6,140,078 which discloses salt inducible promoters, U.S. Pat. No. 6,252,138 which discloses pathogen inducible promoters, and U.S. Pat. No. 6,175,060 which discloses phosphorus deficiency inducible promoters.

As another example, numerous wound-inducible promoters have been described (e.g. Xu et al. Plant Molec. Biol. 22: 573-588 (1993), Logemann et al. Plant Cell 1: 151-158 (1989), Rohrmeier & Lehle, Plant Molec. Biol. 22: 783-792 (1993), Firek et al. Plant Molec. Biol. 22: 129-142 (1993), Warner et al. Plant J. 3: 191-201 (1993)). Logemann describe 5' upstream sequences of the potato wun1 gene. Xu et al. show that a wound-inducible promoter from the dicotyledon potato (pin2) is active in the monocotyledon rice. Rohrmeier & Lehle describe maize Wip1 cDNA which is wound induced and which can be used to isolate the cognate promoter. Firek et al. and Warner et al. have described a wound-induced gene from the monocotyledon *Asparagus officinalis*, which is expressed at local wound and pathogen invasion sites.

Tissue-Specific Promoters: Exemplary promoters that express genes only in certain tissues are useful according to the present invention. For example root specific expression may be attained using the promoter of the maize metallothionein-like (MTL) gene described by de Framond (FEBS 290: 103-106 (1991)) and also in U.S. Pat. No. 5,466,785, incorporated herein by reference. U.S. Pat. No. 5,837,848 discloses a root specific promoter. Another exemplary promoter confers pith-preferred expression (see Int'l. Pub. No. WO 93/07278, herein incorporated by reference, which describes the maize trpA gene and promoter that is preferentially expressed in pith cells). Leaf-specific expression may be attained, for example, by using the promoter for a maize gene encoding phosphoenol carboxylase (PEPC) (see Hudspeth & Grula, Plant Molec Biol 12: 579-589 (1989)). Pollen-specific expression may be conferred by the promoter for the maize calcium-dependent protein kinase (CDPK) gene which is expressed in pollen cells (WO 93/07278). U.S. Pat. Appl. Pub. No. 20040016025 describes tissue-specific promoters. Pollen-specific expression may be conferred by the tomato LAT52 pollen-specific promoter (Bate et. al., Plan mol Biol. 1998 July; 37(5):859-69).

See also U.S. Pat. No. 6,437,217 which discloses a root-specific maize RS81 promoter, U.S. Pat. No. 6,426,446 which discloses a root specific maize RS324 promoter, U.S. Pat. No. 6,232,526 which discloses a constitutive maize A3 promoter, U.S. Pat. No. 6,177,611 which discloses constitutive maize promoters, U.S. Pat. No. 6,433,252 which discloses a maize L3 oleosin promoter that are aleurone and seed coat-specific promoters, U.S. Pat. No. 6,429,357 which discloses a constitutive rice actin 2 promoter and intron, U.S. patent application Pub. No. 20040216189 which discloses an inducible constitutive leaf specific maize chloroplast aldolase promoter.

Optionally a plant transcriptional terminator can be used in place of the plant-expressed gene native transcriptional terminator. Exemplary transcriptional terminators are those that are known to function in plants and include the CaMV 35S terminator, the tm1 terminator, the nopaline synthase terminator and the pea rbcS E9 terminator. These can be used in both monocotyledons and dicotyledons.

Various intron sequences have been shown to enhance expression, particularly in monocotyledonous cells. For example, the introns of the maize Adh1 gene have been found to significantly enhance expression. Intron 1 was found to be particularly effective and enhanced expression in fusion constructs with the chloramphenicol acetyltransferase gene (Callis et al., Genes Develop. 1: 1183-1200 (1987)). The intron from the maize bronze1 gene also enhances expression. Intron sequences have been routinely incorporated into plant transformation vectors, typically within the non-translated leader. U.S. Patent Application Publication 2002/0192813 discloses 5', 3' and intron elements useful in the design of effective plant expression vectors.

A number of non-translated leader sequences derived from viruses are also known to enhance expression, and these are particularly effective in dicotyledonous cells. Specifically, leader sequences from Tobacco Mosaic Virus (TMV, the "omega-sequence"), Maize Chlorotic Mottle Virus (MCMV), and Alfalfa Mosaic Virus (AMV) have been shown to be effective in enhancing expression (e.g. Gallie et al. Nucl. Acids Res. 15: 8693-8711 (1987); Skuzeski et al. Plant Molec. Biol. 15: 65-79 (1990)). Other leader sequences known in the art include but are not limited to: picornavirus leaders, for example, EMCV leader (Encephalomyocarditis 5' noncoding region) (Elroy-Stein, O., Fuerst, T. R., and Moss, B. PNAS USA 86:6126-6130 (1989)); potyvirus leaders, for example, TEV leader (Tobacco Etch Virus) (Allison et al., 1986); MDMV leader (Maize Dwarf Mosaic Virus); Virology 154:9-20); human immunoglobulin heavy-chain binding protein (BiP) leader, (Macejak, D. G., and Sarnow, P., Nature 353: 90-94 (1991)); untranslated leader from the coat protein mRNA of alfalfa mosaic virus (AMV RNA 4), (Jobling, S. A., and Gehrke, L., Nature 325:622-625 (1987); tobacco mosaic virus leader (TMV), (Gallie et al., Molecular Biology of RNA, pages 237-256 (1989); or Maize Chlorotic Mottle Virus leader (MCMV) (Lommel et al., Virology 81:382-385 (1991). See also, Della-Cioppa et al., Plant Physiology 84:965-968 (1987).

A minimal promoter may also be incorporated. Such a promoter has low background activity in plants when there is no transactivator present or when enhancer or response element binding sites are absent. One exemplary minimal promoter is the Bz1 minimal promoter, which is obtained from the bronze1 gene of maize. Roth et al., Plant Cell 3: 317 (1991). A minimal promoter may also be created by use of a synthetic TATA element. The TATA element allows recognition of the promoter by RNA polymerase factors and confers a basal level of gene expression in the absence of activation (see generally, Mukumoto (1993) Plant Mol Biol 23: 995-1003; Green (2000) Trends Biochem Sci 25: 59-63).

Sequences controlling the targeting of gene products also may be included. For example, the targeting of gene products to the chloroplast is controlled by a signal sequence found at the amino terminal end of various proteins which is cleaved during chloroplast import to yield the mature protein (e.g. Comai et al. J. Biol. Chem. 263: 15104-15109 (1988)). These signal sequences can be fused to heterologous gene products to effect the import of heterologous products into the chloroplast (van den Broeck, et al. Nature 313: 358-363 (1985)). DNA encoding for appropriate signal sequences can be isolated from the 5' end of the cDNAs encoding the RUBISCO protein, the CAB protein, the EPSP synthase enzyme, the GS2 protein or many other proteins which are known to be chloroplast localized. Other gene products are localized to other organelles such as the mitochondrion and the peroxisome (e.g. Unger et al. Plant Molec. Biol. 13: 411-418 (1989)). Examples of sequences that target to such organelles are the nuclear-encoded ATPases or specific aspartate amino transferase isoforms for mitochondria. Targeting cellular protein bodies has been described by Rogers et al. (Proc. Natl. Acad. Sci. USA 82: 6512-6516 (1985)). In addition, amino terminal and carboxy-terminal sequences are responsible for targeting to the ER, the apoplast, and extracellular secretion from aleurone cells (Koehler & Ho, Plant Cell 2: 769-783 (1990)). Additionally, amino terminal sequences in conjunction with carboxy terminal sequences are responsible for vacuolar targeting of gene products (Shinshi et al. Plant Molec. Biol. 14: 357-368 (1990)).

Another possible element which may be introduced is a matrix attachment region element (MAR), such as the chicken lysozyme A element (Stief, 1989), which can be positioned around an expressible gene of interest to effect an increase in overall expression of the gene and diminish position dependent effects upon incorporation into the plant genome (Stief et al., Nature, 341:343, 1989; Phi-Van et al., Mol. Cell. Biol., 10:2302-2307.1990).

Use of Non-Plant Promoter Regions Isolated from *Drosophila melanogaster* and *Saccharomyces cerevisiae* to Express Genes in Plants The promoter in the mini-chromosome of the present invention can be derived from plant or non-plant species. In a preferred embodiment, the nucleotide sequence of the promoter is derived from non-plant species for the expression of genes in plant cells, including but not limited to dicotyledon plant cells such as tobacco, tomato, potato, soybean, canola, sunflower, alfalfa, cotton and *Arabidopsis*, or monocotyledonous plant cell, such as wheat, maize, rye, rice, turf grass, oat, barley, sorghum, millet, and sugarcane. In one embodiment, the non-plant promoters are constitutive or inducible promoters derived from insect, e.g., *Drosophila Melanogaster* or yeast, e.g., *Saccharomyces cerevisiae*. Table 2 lists the promoters from *Drosophila melanogaster* and *Saccharomyces cerevisiae* that are used to derive the examples of non-plant promoters in the present invention. Promoters derived from any animal, protist, or fungi are also contemplated. SEQ ID NOS: 1-20 are examples of promoter sequences derived from *Drosophila melanogaster* or *Saccharomyces cerevisiae*. These non-plant promoters can be operably linked to nucleic acid sequences encoding polypeptides or non-protein-expressing sequences including, but not limited to, antisense RNA and ribozymes, to form nucleic acid constructs, vectors, and host cells (prokaryotic or eukaryotic), comprising the promoters.

TABLE 2

*Drosophila melanogaster* Promoters
(Information obtained from Flybase S. Tweedle, M. Ashburner, K. Falls, P. Leyland, P. McQuilton, S. Marygold, G. Millburn, D. Osumi-Sutherland, A. Schroeder, R. Seal, H. Zhang, and The FlyBase Consortium.
FlyBase: enhancing Drosophila Gene Ontology annotations.
Nucleic Acids Research (2009) 37: D555-D559)

| SEQ ID NO: | Symbol | Flybase ID | Standard promoter gene name | Gene Product | Chromosome |
|---|---|---|---|---|---|
| 1 | Pgd | FBgn0004654 | Phosphogluconate dehydrogenase | 6-phosphogluconate dehydrogenase | X |
| 2 | Grim | FBgn0015946 | grim | grim-P138 | 3 |
| 3 | Uro | FBgn0003961 | Urate oxidase | Uro-P1 | 2 |
| 4 | Sna | FBgn0003448 | snail | sna-P1 | 2 |
| 5 | Rh3 | FBgn0003249 | Rhodopsin 3 | Rh3 | 3 |
| 6 | Lsp-1 γ | FBgn0002564 | Larval serum protein 1 γ | Lsp1γ-P1 | 3 |

*Saccharomyces cerevisiae* Promoters
(Information obtained from the *Saccharomyces* Genome Database Web site (partial reference: Cherry JM, Ball C, Weng S, Juvik G, Schmidt R, Adler C, Dunn B, Dwight S, Riles L, Mortimer RK, Botstein D Nature 1997 387(6632 Suppl):67-73. Genetic and physical maps of *Saccaromyces cerevisiae*))

| SEQ ID NO: | Symbol | Systematic Name | Standard promoter gene name | Gene Product | Chromosome |
|---|---|---|---|---|---|
| 7 | Tef-2 | YBR118W | TEF2 (Translation elongation factor promtoer) | Translation elongation factor EF-1 alpha | 2 |

TABLE 2-continued

| | | | | | |
|---|---|---|---|---|---|
| 8 | Leu-1 | YGL009C | LEU1 (LEUcine biosynthesis) | isopropylmalate isomerase | 7 |
| 9 | Met16 | YPR167C | METhionine requiring | 3'phosphoadenylylsulfate reductase | 16 |
| 10 | Leu-2 | YCL018W | LEU2 (leucine biosynthesis) | beta-IPM (isopropylmalate) dehydrogenase | 3 |
| 11 | His-4 | YCL030C | HIS4 (HIStidine requiring) | histidinol dehydrogenase | 3 |
| 12 | Met-2 | YNL277W | MET2 (methionine requiring) | L-homoserine-O-acetyltransferase | 14 |
| 13 | Ste-3 | YKL178C | STE3 (alias DAF2 Sterile) | a-factor receptor | 11 |
| 14 | Arg-1 | YOL058W | ARG1(alias ARG10 ARGinine requiring) | arginosuccinate synthetase | 15 |
| 15 | Pgk-1 | YCR012W | PGK1 (phosphoglycerate kinase) | phosphoglycerate kinase | 3 |
| 16 | GPD-1 | YDL022W | GPD1 (alias DAR1/HOR1/OSG OSR5: glycerol-3-phosphate dehydrogenase activity) | glycerol-3-phosphate dehydrogenase | 4 |
| 17 | ADH1 | YOL086C | ADH1 (alias ADC1) | alcohol dehydrogenase | 15 |
| 18 | GPD-2 | YOL059W | GPD2 (alias GPD3: glycerol-3-phosphate dehydrogenase activity | glycerol-3-phosphate dehydrogenase | 15 |
| 19 | Arg-4 | YHR018C | ARGinine requiring | argininosuccinate lyase | 8 |
| 20 | Yat-1 | YAR035W | YAT-1(carnitine acetyltransferase) | carnitine acetyltransferase | 1 |

The present invention relates to methods for producing a polypeptide, comprising cultivating plant material for the production of the polypeptide at any level, wherein the plant host cells comprises a first nucleic acid sequence encoding the polypeptide operably linked to a second nucleic acid sequence comprising a heterologous promoter foreign to the nucleic acid sequence, wherein the promoter comprises a sequence selected from the group consisting of SEQ ID NOS:1 to 20 or subsequences thereof; and mutant, hybrid, or tandem promoters thereof that retain promoter activity.

The present invention also relates to methods for producing non-protein expressed sequences, comprising cultivating plant material for the production of the non-protein expressed sequence, wherein the plant host cell comprises a first nucleic acid sequence encoding the non-protein expressed sequences operably linked to a second nucleic acid sequence comprising a heterologous promoter foreign to the nucleic acid sequence, wherein the promoter comprises a sequence selected from the group consisting of SEQ ID NOS: 1 to 20 or subsequences thereof; and mutant, hybrid, or tandem promoters thereof.

The present invention also relates to isolated promoter sequences and to constructs, vectors, or plant host cells comprising one or more of the promoters operably linked to a nucleic acid sequence encoding a polypeptide or non-protein expressing sequence.

In the methods of the present invention, the promoter may also be a mutant of the promoters having a substitution, deletion, and/or insertion of one or more nucleotides in the nucleic acid sequence of SEQ ID NOS: 1 to 20.

The present invention also relates to methods for obtaining derivative promoters of SEQ ID NOS: 1 to 20.

The techniques used to isolate or clone a nucleic acid sequence comprising a promoter of interest are known in the art and include isolation from genomic DNA. The cloning procedures may involve excision or amplification, for example by polymerase chain reaction, and isolation of a desired nucleic acid fragment comprising the nucleic acid sequence encoding the promoter, insertion of the fragment into a vector molecule, and incorporation of the recombinant vector into the plant cell.

Definitions

The term "adchromosomal" plant or plant part as used herein means a plant or plant part that contains functional, stable and autonomous mini-chromosomes. Adchromosomal plants or plant parts may be chimeric or not chimeric (chimeric meaning that mini-chromosomes are only in certain portions of the plant, and are not uniformly distributed throughout the plant). An adchromosomal plant cell contains at least one functional, stable and autonomous mini-chromosome.

The term "autonomous" as used herein means that when delivered to plant cells, at least some mini-chromosomes are transmitted through mitotic division to daughter cells and are episomal in the daughter plant cells, i.e. are not chromosomally integrated in the daughter plant cells. Daughter plant cells that contain autonomous mini-chromosomes can be selected for further replication using, for example, selectable or screenable markers. During the introduction into a cell of a mini-chromosome, or during subsequent stages of the cell cycle, there may be chromosomal integration of some portion or all of the DNA derived from a mini-chromosome in some cells. The mini-chromosome is still characterized as autonomous despite the occurrence of such events if a plant may be regenerated that contains episomal descendants of the mini-chromosome distributed throughout its parts, or if gametes or progeny can be derived from the plant that contain episomal descendants of the mini-chromosome distributed through its parts.

As used herein, a "centromere" is any DNA sequence that confers an ability to segregate to daughter cells through cell division. In one context, this sequence may produce a transmission efficiency to daughter cells ranging from about 1% to about 100%, including to about 5%, 10%, 20%, 30%, 40%, 50%, 60%, 70%, 80%, 90% or about 95% of daughter cells. Variations in such a transmission efficiency may find important applications within the scope of the invention; for example, mini-chromosomes carrying centromeres that confer 100% stability could be maintained in all daughter cells without selection, while those that confer 1% stability could be temporarily introduced into a transgenic organism, but be eliminated when desired. In particular embodiments of the invention, the centromere may confer stable transmission to daughter cells of a nucleic acid sequence, including a recombinant construct comprising the centromere, through mitotic or meiotic divisions, including through both meiotic and meiotic divisions. A plant centromere is not necessarily derived from plants, but has the ability to promote DNA transmission to daughter plant cells.

As used herein, the term "circular permutations" refer to variants of a sequence that begin at base n within the sequence, proceed to the end of the sequence, resume with base number one of the sequence, and proceed to base n−1. For this analysis, n may be any number less than or equal to the length of the sequence. For example, circular permutations of the sequence ABCD are: ABCD, BCDA, CDAB, and DABC.

The term "co-delivery" as used herein refers to the delivery of two nucleic acid segments to a cell. In co-delivery of plant growth inducing genes and mini-chromosomes, the two nucleic acid segments are delivered simultaneously using the same delivery method. Alternatively, the nucleic acid segment containing the growth inducing gene, optionally as part of an episomal vector, such as a viral vector or a plasmid vector, may be delivered to the plant cells before or after delivery of the mini-chromosome, and the mini-chromosome may carry an exogenous nucleic acid that induces expression of the earlier-delivered growth inducing gene. In this embodiment, the two nucleic acid segments may be delivered separately at different times provided the encoded growth inducing factors are functional during the appropriate time period.

The term "coding sequence" is defined herein as a nucleic acid sequence that is transcribed into mRNA which is translated into a polypeptide when placed under the control of promoter sequences. The boundaries of the coding sequence are generally determined by the ATG start codon located at the start of the open reading frame, near the 5' end of the mRNA, and TAG, TGA or TAA stop codons at the end of the coding sequence, near the 3' end of the mRNA, and in some cases, a transcription terminator sequence located just downstream of the open reading frame at the 3' end of the mRNA. A coding sequence can include, but is not limited to, genomic DNA, cDNA, semisynthetic, synthetic, or recombinant nucleic acid sequences.

As used herein the term "consensus" refers to a nucleic acid sequence derived by comparing two or more related sequences. A consensus sequence defines both the conserved and variable sites between the sequences being compared. Any one of the sequences used to derive the consensus or any permutation defined by the consensus may be useful in construction of mini-chromosomes.

The term "exogenous" when used in reference to a nucleic acid, for example, is intended to refer to any nucleic acid that has been introduced into a recipient cell, regardless of whether the same or similar nucleic acid is already present in such a cell. Thus, as an example, "exogenous DNA" can include an additional copy of DNA that is already present in the plant cell, DNA from another plant, DNA from a different organism, or a DNA generated externally, such as a DNA sequence containing an antisense message of a gene, or a DNA sequence encoding a synthetic or modified version of a gene. An "exogenous gene" can be a gene not normally found in the host genome in an identical context, or an extra copy of a host gene. The gene may be isolated from a different species than that of the host genome, or alternatively, isolated from the host genome but operably linked to one or more regulatory regions which differ from those found in the unaltered, native gene.

The term "functional" as used herein to describe a mini-chromosome means that when an exogenous nucleic acid is present within the mini-chromosome the exogenous nucleic acid can function in a detectable manner when the mini-chromosome is within a plant cell; exemplary functions of the exogenous nucleic acid include transcription of the exogenous nucleic acid, expression of the exogenous nucleic acid, regulatory control of expression of other exogenous nucleic acids, recognition by a restriction enzyme or other endonuclease, ribozyme or recombinase; providing a substrate for DNA methylation, DNA glycolation or other DNA chemical modification; binding to proteins such as histones, helix-loop-helix proteins, zinc binding proteins, leucine zipper proteins, MADS box proteins, topoisomerases, helicases, transposases, TATA box binding proteins, viral protein, reverse transcriptases, or cohesins; providing an integration site for homologous recombination; providing an integration site for a transposon, T-DNA or retrovirus; providing a substrate for RNAi synthesis; priming of DNA replication; aptamer binding; or kinetochore binding. If multiple exogenous nucleic acids are present within the mini-chromosome, the function of one or preferably more of the exogenous nucleic acids can be detected under suitable conditions permitting function thereof.

As used herein, a "library" is a pool of cloned DNA fragments that represents some or all DNA sequences collected, prepared or purified from a specific source. Each library may contain the DNA of a given organism inserted as discrete restriction enzyme generated fragments or as randomly sheared fragments into many thousands of plasmid vectors. For purposes of the present invention, *E. coli*, yeast, and *Salmonella* plasmids are particularly useful for propagating the genome inserts from other organisms. In principle, any gene or sequence present in the starting DNA preparation can be isolated by screening the library with a specific hybridization probe (see, for example, Young et al., In: Eukaryotic Genetic Systems ICN-UCLA Symposia on Molecular and Cellular Biology, VII, 315-331, 1977).

As used herein, the term "linker" refers to a DNA molecule, generally up to 50 or 60 nucleotides long and composed of two or more complementary oligonucleotides that have been synthesized chemically, or excised or amplified from existing plasmids or vectors. In a preferred embodiment, this fragment contains one, or preferably more than one, restriction enzyme site for a blunt cutting enzyme and/or a staggered cutting enzyme, such as BamHI. One end of the linker is designed to be ligatable to one end of a linear DNA molecule and the other end is designed to be ligatable to the other end of the linear molecule, or both ends may be designed to be ligatable to both ends of the linear DNA molecule.

As used herein, a "mini-chromosome" is a recombinant DNA construct including a centromere and capable of transmission to daughter cells. A mini-chromosome may remain separate from the host genome (as episomes) or may integrate into host chromosomes. The stability of this construct through cell division could range between from about 1% to about 100%, including about 5%, 10%, 20%, 30%, 40%, 50%, 60%, 70%, 80%, 90% and about 95%. The mini-chromosome construct may be a circular or linear molecule. It may include elements such as one or more telomeres, origin of replication sequences, stuffer sequences, buffer sequences, chromatin packaging sequences, linkers and genes. The number of such sequences included is only limited by the physical size limitations of the construct itself. It could contain DNA derived from a natural centromere, although it may be preferable to limit the amount of DNA to the minimal amount required to obtain a transmission efficiency in the range of 1-100%. The mini-chromosome could also contain a synthetic centromere composed of tandem arrays of repeats of any sequence, either derived from a natural centromere, or of synthetic DNA. The mini-chromosome could also contain DNA derived from multiple natural centromeres. The mini-chromosome may be inherited through mitosis or meiosis, or through both meiosis and mitosis. As used herein, the term mini-chromosome specifically encompasses and includes the terms "plant artificial chromosome" or "PLAC," or engineered chromosomes or microchromosomes and all teachings relevant to a PLAC or plant artificial chromosome specifically apply to constructs within the meaning of the term mini-chromosome.

The term "non-protein expressing sequence" or "non-protein coding sequence" is defined herein as a nucleic acid sequence that is not eventually translated into protein. The nucleic acid may or may not be transcribed into RNA. Exemplary sequences include ribozymes or antisense RNA.

The term "operably linked" is defined herein as a configuration in which a control sequence, e.g., a promoter sequence, directs transcription or translation of another sequence, for example a coding sequence. For example, a promoter sequence could be appropriately placed at a position relative to a coding sequence such that the control sequence directs the production of a polypeptide encoded by the coding sequence.

"Phenotype" or "phenotypic trait(s)", as used herein, refers to an observable property or set of properties resulting from the expression of a gene. The set of properties may be observed visually or after biological or biochemical testing, and may be constantly present or may only manifest upon challenge with the appropriate stimulus or activation with the appropriate signal.

The term "plant," as used herein, refers to any type of plant. Exemplary types of plants are listed below, but other types of plants will be known to those of skill in the art and could be used with the invention. Modified plants of the invention include, for example, dicots, gymnosperm, monocots, mosses, ferns, horsetails, club mosses, liverworts, hornworts, red algae, brown algae, gametophytes and sporophytes of pteridophytes, and green algae.

The term "crop plant" refers to plants grown for agricultural or commercial rather than experimental purposes and specifically excludes *Arabidopsis thaliana*. Some plants grown for experimental purposes may take on commercial importance when used to produce pharmaceutical or chemical products. Centromeres "derived from crop plants" according to the present invention specifically exclude centromeres that are fragments of naturally occurring *Arabidopsis thaliana* centromeres or naturally occurring descendants thereof. Centromeres derived from crop plants include variants (mutants) of *Arabidopsis thaliana* centromeres, or artificial centromeres synthesized based on nucleotide sequences of *Arabidopsis thaliana* centromeres.

A common class of plants exploited in agriculture are vegetable crops, including artichokes, kohlrabi, arugula, leeks, asparagus, lettuce (e.g., head, leaf, romaine), bok choy, malanga, broccoli, melons (e.g., muskmelon, watermelon, crenshaw, honeydew, cantaloupe), brussels sprouts, cabbage, cardoni, carrots, napa, cauliflower, okra, onions, celery, parsley, chick peas, parsnips, chicory, chinese cabbage, peppers, collards, potatoes, cucumber plants (marrows, cucumbers), pumpkins, cucurbits, radishes, dry bulb onions, rutabaga, eggplant, salsify, escarole, shallots, endive, garlic, spinach, green onions, squash, greens, beet (sugar beet or fodder beet), sweet potatoes, swiss chard, horseradish, tomatoes, kale, turnips, or spices.

Other types of plants frequently finding commercial use include fruit and vine crops such as apples, grapes, apricots, cherries, nectarines, peaches, pears, plums, prunes, quince, almonds, chestnuts, filberts, pecans, pistachios, walnuts, citrus, blueberries, boysenberries, cranberries, currants, loganberries, raspberries, strawberries, blackberries, grapes, avocados, bananas, kiwi, persimmons, pomegranate, pineapple, tropical fruits, pomes, melon, mango, papaya, or lychee.

Modified wood and fiber or pulp plants of particular interest include, but are not limited to maple, oak, cherry, mahogany, poplar, aspen, birch, beech, spruce, fir, kenaf, pine, walnut, cedar, redwood, chestnut, acacia, bombax, alder, eucalyptus, catalpa, mulberry, persimmon, ash, honeylocust, sweetgum, privet, sycamore, magnolia, sourwood, cottonwood, mesquite, buckthorn, locust, willow, elderberry, teak, linden, bubinga, basswood or elm.

Modified flowers and ornamental plants of particular interest, include, but are not limited to, roses, petunias, pansy, peony, olive, begonias, violets, phlox, nasturtiums, irises, lilies, orchids, vinca, philodendron, poinsettias, opuntia, cyclamen, magnolia, dogwood, azalea, redbud, boxwood, *Viburnum*, maple, elderberry, hosta, agave, asters, sunflower, pansies, hibiscus, morning glory, alstromeria, zinnia, geranium, *Prosopis*, artemesia, clematis, delphinium, dianthus, gallium, coreopsis, iberis, lamium, poppy, lavender, leucophyllum, sedum, salvia, verbascum, digitalis, penstemon, savory, pythrethrum, or oenothera. Modified nut-bearing trees of particular interest include, but are not limited to pecans, walnuts, macadamia nuts, hazelnuts, almonds, or pistachios, cashews, pignolas or chestnuts.

Many of the most widely grown plants are field crop plants such as evening primrose, meadow foam, corn (field, sweet, popcorn), hops, jojoba, peanuts, rice, safflower, small grains (barley, oats, rye, wheat, etc.), sorghum, tobacco, kapok, leguminous plants (beans, lentils, peas, soybeans), oil plants (rape, mustard, poppy, olives, sunflowers, coconut, castor oil plants, cocoa beans, groundnuts, oil palms), fibre plants (cotton, flax, hemp, jute), lauraceae (cinnamon, camphor), or plants such as coffee, sugarcane, cocoa, tea, or natural rubber plants.

Still other examples of plants include bedding plants such as flowers, cactus, succulents or ornamental plants, as well as trees such as forest (broad-leaved trees or evergreens, such as conifers), fruit, ornamental, or nut-bearing trees, as well as shrubs or other nursery stock.

Modified crop plants of particular interest in the present invention include, but are not limited to, soybean (*Glycine max*), cotton, canola (also known as rape), wheat, sunflower, sorghum, alfalfa, barley, safflower, millet, rice, tobacco, fruit and vegetable crops or turfgrasses. Exemplary cereals include maize, wheat, barley, oats, rye, millet, sorghum, rice triticale, secale, einkorn, spelt, emmer, teff, milo, flax, gramma grass, *Tripsacum* sp., or teosinte. Oil-producing plants include plant species that produce and store triacylglycerol in specific organs, primarily in seeds. Such species include soybean (*Glycine max*), rapeseed or canola (including *Brassica napus, Brassica rapa* or *Brassica campestris*), *Brassica juncea, Brassica carinata*, sunflower (*Helianthus annus*), cotton (*Gossypium hirsutum*), corn (*Zea mays*), cocoa (*Theobroma* cacao), safflower (*Carthamus tinctorius*), oil palm (*Elaeis guineensis*), coconut palm (*Cocos nucifera*), flax (*Linium usitatissimum*), castor (*Ricinus communis*) or peanut (*Arachis hypogaea*).

The term "plant part" as used herein includes pollen, silk, endosperm, ovule, seed, embryo, pods, roots, cuttings, tubers, stems, stalks, fruit, berries, nuts, flowers, leaves, bark, wood, whole plant, plant cell, plant organ, epidermis, vascular tissue, protoplast, cell culture, crown, callus culture, petiole, petal, sepal, stamen, stigma, style, bud, meristem, cambium, cortex, pith, sheath or any group of plant cells organized into a structural and functional unit. In one preferred embodiment, the exogenous nucleic acid is expressed in a specific location or tissue of a plant, for example, epidermis, vascular tissue, meristem, cambium, cortex, pith, leaf, sheath, flower, root or seed.

The term "promoter" is defined herein as a DNA sequence that allows the binding of RNA polymerase (including but not limited to RNA polymerase I, RNA polymerase II and RNA polymerase III from eukaryotes) and directs the polymerase to a downstream transcriptional start site of a nucleic acid sequence encoding a polypeptide to initiate transcription. RNA polymerase effectively catalyzes the assembly of messenger RNA complementary to the appropriate DNA strand of the coding region.

A "promoter operably linked to a heterologous gene" is a promoter that is operably linked to a gene that is different from the gene to which the promoter is normally operably linked in its native state. Similarly, an "exogenous nucleic acid operably linked to a heterologous regulatory sequence" is a nucleic acid that is operably linked to a regulatory control sequence to which it is not normally linked in its native state.

The term "hybrid promoter" is defined herein as parts of two or more promoters that are fused together to generate a sequence that is a fusion of the two or more promoters, which is operably linked to a coding sequence and mediates the transcription of the coding sequence into mRNA.

The term "tandem promoter" is defined herein as two or more promoter sequences each of which is operably linked to a coding sequence and mediates the transcription of the coding sequence into mRNA.

The term "constitutive active promoter" is defined herein as a promoter that allows permanent stable expression of the gene of interest.

The term "Inducible promoter" is defined herein as a promoter induced by the presence or absence of biotic or an abiotic factor.

The term "polypeptide" does not refer to a specific length of the encoded product and, therefore, encompasses peptides, oligopeptides, and proteins. The term "exogenous polypeptide" is defined as a polypeptide which is not native to the plant cell, a native polypeptide in which modifications have been made to alter the native sequence, or a native polypeptide whose expression is quantitatively altered as a result of a manipulation of the plant cell by recombinant DNA techniques.

As used herein, the term "pseudogene" refers to a non-functional copy of a protein-coding gene; pseudogenes found in the genomes of eukaryotic organisms are often inactivated by mutations and are thus presumed to be non-essential to that organism; pseudogenes of reverse transcriptase and other open reading frames found in retroelements are abundant in the centromeric regions of *Arabidopsis* and other organisms and are often present in complex clusters of related sequences.

As used herein the term "regulatory sequence" refers to any DNA sequence that influences the efficiency of transcription or translation of any gene. The term includes, but is not limited to, sequences comprising promoters, enhancers and terminators.

As used herein the term "repeated nucleotide sequence" refers to any nucleic acid sequence of at least 25 bp present in a genome or a recombinant molecule, other than a telomere repeat, that occurs at least two or more times and that are preferably at least 80% identical either in head to tail or head to head orientation either with or without intervening sequence between repeat units.

As used herein, the term "retroelement" or "retrotransposon" refers to a genetic element related to retroviruses that disperse through an RNA stage; the abundant retroelements present in plant genomes contain long terminal repeats (LTR retrotransposons) and encode a polyprotein gene that is processed into several proteins including a reverse transcriptase. Specific retroelements (complete or partial sequences) can be found in and around plant centromeres and can be present as dispersed copies or complex repeat clusters. Individual copies of retroelements may be truncated or contain mutations; intact retroelements are rarely encountered.

As used herein the term "satellite DNA" refers to short DNA sequences (typically<1000 bp) present in a genome as multiple repeats, mostly arranged in a tandemly repeated fashion, as opposed to a dispersed fashion. Repetitive arrays of specific satellite repeats are abundant in the centromeres of many higher eukaryotic organisms.

As used herein, a "screenable marker" is a gene whose presence results in an identifiable phenotype. This phenotype may be observable under standard conditions, altered conditions such as elevated temperature, or in the presence of certain chemicals used to detect the phenotype. The use of a screenable marker allows for the use of lower, sub-killing antibiotic concentrations and the use of a visible marker gene to identify clusters of transformed cells, and then manipulation of these cells to homogeneity. Preferred screenable markers of the present include genes that encode fluorescent proteins that are detectable by a visual microscope such as the fluorescent reporter genes DsRed, ZsGreen, ZsYellow, AmCyan, Green Fluorescent Protein (GFP). An additional preferred screenable marker gene is lac.

The invention also contemplates novel methods of screening for adchromosomal plant cells that involve use of relatively low, sub-killing concentrations of a selection agent (e.g. sub-killing antibiotic concentrations), and also involve use of a screenable marker (e.g., a visible marker gene) to identify clusters of modified cells carrying the screenable marker, after which these screenable cells are manipulated to homogeneity. As used herein, a "selectable marker" is a gene whose presence results in a clear phenotype, and most often a growth advantage for cells that contain the marker. This growth advantage may be present under standard conditions, altered conditions such as elevated temperature, specialized media compositions, or in the presence of certain chemicals such as herbicides or antibiotics. Use of selectable markers is described, for example, in Broach et al. Gene, 8:121-133, 1979. Examples of selectable markers include the thymidine kinase gene, the cellular adenine phosphoribosyltransferase gene and the dihydrylfolate reductase gene, hygromycin phosphotransferase genes, the bar gene, neomycin phosphotransferase genes and phosphomannose isomerase, among others. Preferred selectable markers in the present invention include genes whose expression confer antibiotic or herbicide resistance to the host cell, or proteins allowing utilization of a carbon source not normally utilized by plant cells. Expression of one of these markers should be sufficient to enable the maintenance of a vector within the host cell, and facilitate the manipulation of the plasmid into new host cells. Of particular interest in the present invention are proteins conferring cellular resistance to kanamycin, G 418, paramomycin, hygromycin, bialaphos, and glyphosate for example, or proteins allowing utilization of a carbon source, such as mannose, not normally utilized by plant cells.

The term "stable" as used herein means that the mini-chromosome can be transmitted to daughter cells over at least 8 mitotic generations. Some embodiments of mini-chromosomes may be transmitted as functional, autonomous units for less than 8 mitotic generations, e.g. 1, 2, 3, 4, 5, 6, or 7. Preferred mini-chromosomes can be transmitted over at least 8, 9, 10, 11, 12, 13, 14, 15, 16, 17, 18, 18, 19, 20, 21, 22, 23, 24, 25, 26, 27, 28, 29 or 30 generations, for example, through the regeneration or differentiation of an entire plant, and preferably are transmitted through meiotic division to gametes. Other preferred mini-chromosomes can be further maintained in the zygote derived from such a gamete or in an embryo or endosperm derived from one or more such gametes. A "functional and stable" mini-chromosome is one in which functional mini-chromosomes can be detected after transmission of the mini-chromosomes over at least 8 mitotic generations, or after inheritance through a meiotic division. During mitotic division, as occurs occasionally with native chromosomes, there may be some non-transmission of mini-chromosomes; the mini-chromosome may still be characterized as stable despite the occurrence of such events if an adchromosomal plant that contains descendants of the mini-chromosome distributed throughout its parts may be regenerated from cells, cuttings, propagules, or cell cultures containing the mini-chromosome, or if an adchromosomal plant can be identified in progeny of the plant containing the mini-chromosome.

As used herein, a "structural gene" is a sequence which codes for a polypeptide or RNA and includes 5' and 3' ends. The structural gene may be from the host into which the structural gene is transformed or from another species. A structural gene will preferably, but not necessarily, include one or more regulatory sequences which modulate the expression of the structural gene, such as a promoter, terminator or enhancer. A structural gene will preferably, but not necessarily, confer some useful phenotype upon an organism comprising the structural gene, for example, herbicide resistance. In one embodiment of the invention, a structural gene may encode an RNA sequence which is not translated into a protein, for example a tRNA or rRNA gene.

As used herein, the term "telomere" or "telomere DNA" refers to a sequence capable of capping the ends of a chromosome, thereby preventing degradation of the chromosome end, ensuring replication and preventing fusion to other chromosome sequences. Telomeres can include naturally occurring telomere sequences or synthetic sequences. Telomeres from one species may confer telomere activity in another species. An exemplary telomere DNA is a heptanucleotide telomere repeat TTTAGGG (and its complement) found in the majority of plants.

"Transformed," "transgenic," "modified," and "recombinant" refer to a host organism such as a plant into which an exogenous or heterologous nucleic acid molecule has been introduced, and includes meiocytes, seeds, zygotes, embryos, endosperm, or progeny of such plant that retain the exogenous or heterologous nucleic acid molecule but which have not themselves been subjected to the transformation process.

When the phrase "transmission efficiency" of a certain percent is used, transmission percent efficiency is calculated by measuring mini-chromosome presence through one or more mitotic or meiotic generations. It is directly measured as the ratio (expressed as a percentage) of the daughter cells or plants demonstrating presence of the mini-chromosome to parental cells or plants demonstrating presence of the mini-chromosome. Presence of the mini-chromosome in parental and daughter cells is demonstrated with assays that detect the presence of an exogenous nucleic acid carried on the mini-chromosome. Exemplary assays can be the detection of a screenable marker (e.g. presence of a fluorescent protein or any gene whose expression results in an observable phenotype), a selectable marker, or PCR amplification of any exogenous nucleic acid carried on the mini-chromosome.

Constructing Mini-Chromosomes by Site-Specific Recombination

Plant mini-chromosomes may be constructed using site-specific recombination sequences (for example those recognized by the bacteriophage P1 Cre recombinase, or the bacteriophage lambda integrase, or similar recombination enzymes). A compatible recombination site, or a pair of such sites, is present on both the centromere containing DNA clones and the donor DNA clones. Incubation of the donor clone and the centromere clone in the presence of the recombinase enzyme causes strand exchange to occur between the recombination sites in the two plasmids; the resulting mini-chromosomes contain centromere sequences as well as mini-chromosome vector sequences. The DNA molecules formed in such recombination reactions is introduced into *E. coli*, other bacteria, yeast or plant cells by common methods in the field including, but not limited to, heat shock, chemical transformation, electroporation, particle bombardment, whiskers, or other transformation methods followed by selection for marker genes including chemical, enzymatic, color, or other marker present on either parental plasmid, allowing for the selection of transformants harboring mini-chromosomes.

II. Methods of Detecting and Characterizing Mini-Chromosomes in Plant Cells or of Scoring Mini-Chromosome Performance in Plant Cells:

Identification of candidate centromere fragments by probing BAC libraries Centromere clones are identified from a large genomic insert library such as a Bacterial Artificial Chromosome library. Probes are labeled using nick-translation in the presence of radioactively labeled dCTP, dATP, dGTP or dTTP as in, for example, the commercially available Rediprime kit (Amersham) as per the manufacturer's instructions. Other labeling methods familiar to those skilled in the art could be substituted. The libraries are screened and deconvoluted. Genomic clones are screened by probing with small centromere-specific clones. Other embodiments of this procedure would involve hybridizing a library with other centromere sequences. Of the BAC clones identified using this procedure, a representative set are identified as having high hybridization signals to some probes, and optionally low hybridization signals to other probes. These are selected, the bacterial clones grown up in cultures and DNA prepared by methods familiar to those skilled in the art such as alkaline lysis. The DNA composition of purified clones is surveyed using for example fingerprinting by digesting with restriction enzymes such as, but not limited to, HinfI or HindIII. In a preferred embodiment the restriction enzyme cuts within the tandem centromere satellite repeat (see below). A variety of clones showing different fingerprints are selected for conversion into mini-chromosomes and inheritance testing. It can also be informative to use multiple restriction enzymes for fingerprinting or other enzymes which can cleave DNA.

Fingerprinting Analysis of BACs and Mini-Chromosomes

Centromere function may be associated with large tandem arrays of satellite repeats. To assess the composition and architecture of the centromere BACs, the candidate BACs are digested with a restriction enzyme, such as HindIII, which cuts with known frequency within the consensus sequence of the unit repeat of the tandemly repeated centromere satellite. Digestion products are then separated by agarose gel electrophoresis. Large insert clones containing a large array of tandem repeats will produce a strong band of the unit repeat size, as well as less intense bands at 2× and 3× the unit repeat size, and further multiples of the repeat size. These methods are well-known and there are many possible variations known to those skilled in the art.

Determining Sequence Composition of Mini-Chromosomes by Shotgun Cloning/Sequencing, Sequence Analysis To determine the sequence composition of the mini-chromosome, the insert is sequenced. To generate DNA suitable for sequencing mini-chromosomes are fragmented, for example by using a random shearing method (such as sonication, nebulization, etc). Other fragmentation techniques may also be used such as enzymatic digestion. These fragments are then cloned into a plasmid vector and sequenced. The resulting DNA sequence is trimmed of poor-quality sequence and of sequence corresponding to the plasmid vector. The sequence is then compared to the known DNA sequences using an algorithm such as BLAST to search a sequence database such as GenBank.

To determine the consensus of the satellite repeat in the mini-chromosome, the sequences containing satellite repeat are aligned using a DNA sequence alignment program such as ContigExpress from Vector NTI. The sequences may also be aligned to previously determined repeats for that species. The sequences are trimmed to unit repeat length using the consensus as a template. Sequences trimmed from the ends of the alignment are realigned with the consensus and further trimmed until all sequences are at or below the consensus length. The sequences are then aligned with each other. The consensus is determined by the frequency of a specific nucleotide at each position; if the most frequent base is three times more frequent than the next most frequent base, it was considered the consensus.

Methods for determining consensus sequence are well known in the art, see, e.g., U.S. Pat. App. Pub. No. 20030124561; Hall & Preuss (2002). These methods, including DNA sequencing, assembly, and analysis, are well-known and there are many possible variations known to those skilled in the art. Other alignment parameters may also be useful such as using more or less stringent definitions of consensus.

Non-Selective Mini-Chromosome Mitotic Inheritance Assays

The following list of assays and potential outcomes illustrates how various assays can be used to distinguish autonomous events from integrated events.

Assay #1: Transient Assay

Mini-chromosomes are tested for their ability to become established as chromosomes and their ability to be inherited in mitotic cell divisions. In this assay, mini-chromosomes are delivered to plant cells, for example suspension cells in liquid culture. The cells used can be at various stages of growth. In this example, a population in which some cells were undergoing division was used. The mini-chromosome is then assessed over the course of several cell divisions, by tracking the presence of a screenable marker, e.g. a visible marker gene such as a fluorescent protein. Mini-chromosomes that are inherited well may show an initial delivery into many single cells; after several cell divisions, these single cells divide to form clusters of mini-chromosome-containing cells. Other exemplary embodiments of this method include delivering mini-chromosomes to other mitotic cell types, including roots and shoot meristems.

Assay #2: Non-Lineage Based Inheritance Assays on Modified Transformed Cells and Plants Mini-chromosome inheritance is assessed on modified cell lines and plants by following the presence of the mini-chromosome over the course of multiple cell divisions. An initial population of mini-chromosome containing cells is assayed for the presence of the mini-chromosome, by the presence of a marker gene, including but not limited to a fluorescent protein, a colored protein, a protein assayable by histochemical assay, and a gene affecting cell morphology. All nuclei are stained with a DNA-specific dye including but not limited to DAPI, Hoechst 33258, OliGreen, Giemsa YOYO, or TOTO, allowing a determination of the number of cells that do not contain the mini-chromosome. After the initial determination of the percent of cells carrying the mini-chromosome, the cells are allowed to divide over the course of several cell divisions. The number of cell divisions, n, is determined by a method including but not limited to monitoring the change in total weight of cells, and monitoring the change in volume of the cells or by directly counting cells in an aliquot of the culture. After a number of cell divisions, the population of cells is again assayed for the presence of the mini-chromosome. The loss rate per generation is calculated by the equation:

$$\text{Loss rate per generation} = 1 - (F/I)^{1/n}$$

The population of mini-chromosome-containing cells may include suspension cells, roots, leaves, meristems, flowers, or any other tissue of modified plants, or any other cell type containing a mini-chromosome.

These methods are well-known and there are many possible variations known to those skilled in the art; they have been used before with human cells and yeast cells.

Assay #3: Lineage Based Inheritance Assays on Modified Cells and Plants

Mini-chromosome inheritance is assessed on modified cell lines and plants by following the presence of the mini-chromosome over the course of multiple cell divisions. In cell types that allow for tracking of cell lineage, including but not limited to root cell files, trichomes, and leaf stomata guard cells, mini-chromosome loss per generation does not need to be determined statistically over a population, it can be discerned directly through successive cell divisions. In other manifestations of this method, cell lineage can be discerned from cell position, or methods including but not limited to the use of histological lineage tracing dyes, and the induction of genetic mosaics in dividing cells.

In one simple example, the two guard cells of the stomata are daughters of a single precursor cell. To assay mini-chromosome inheritance in this cell type, the epidermis of the leaf of a plant containing a mini-chromosome is examined for the presence of the mini-chromosome by the presence of a marker gene, including but not limited to a fluorescent protein, a colored protein, a protein assayable by histochemical assay, and a gene affecting cell morphology. The number of loss events in which one guard cell contains the mini-chromosome (L) and the number of cell divisions in which both guard cells contain the mini-chromosome (B) are counted. The loss rate per cell division is determined as L/(L+B). Other lineage-based cell types are assayed in similar fashion. These methods are well-known and there are many possible variations known to those skilled in the art; they have been used before with yeast cells.

Lineal mini-chromosome inheritance may also be assessed by examining root files or clustered cells in callus over time. Changes in the percent of cells carrying the mini-chromosome will indicate the mitotic inheritance.

Assay #4: Inheritance Assays on Modified Cells and Plants in the Presence of Chromosome Loss Agents Any of the above three assays can be done in the presence of chromosome loss agents (including but not limited to colchicine, colcemid, caffeine, etopocide, nocodazole, oryzalin, trifluran). It is likely that an autonomous mini-chromosome will prove more susceptible to loss induced by chromosome loss agents; therefore, autonomous mini-chromosomes should show a lower rate of inheritance in the presence of chromosome loss agents. These methods have been used to study chromosome loss in fruit flies and yeast; there are many possible variations known to those skilled in the art.

III. Transformation of Plant Cells and Plant Regeneration

Various methods may be used to deliver DNA into plant cells. These include biological methods, such as *Agrobacterium, E. coli*, and viruses, physical methods such as biolistic particle bombardment, nanocopoiea device, the Stein beam gun, silicon carbide whiskers and microinjection, electrical methods such as electroporation, and chemical methods such as the use of poly-ethylene glycol and other compounds known to stimulate DNA uptake into cells. Examples of these techniques are described by Paszkowski et al., EMBO J. 3: 2717-2722 (1984), Potrykus et al., Mol. Gen. Genet. 199: 169-177 (1985), Reich et al., Biotechnology 4: 1001-1004 (1986), and Klein et al., Nature 327: 70-73 (1987). Transformation using silicon carbide whiskers, e.g. in maize, is described in Brisibe, J. Exp. Bot. 51(343):187-196 (2000) and Dunwell, Methods Mol. Biol. 111:375-82 (1999) and U.S. Pat. No. 5,464,765.

*Agrobacterium*-Mediated Delivery

*Agrobacterium*-mediated transformation is one method for introducing a desired genetic element into a plant. Several *Agrobacterium* species mediate the transfer of a specific DNA known as "T-DNA" that can be genetically engineered to carry a desired piece of DNA into many plant species. Plasmids used for delivery contain the T-DNA flanking the nucleic acid to be inserted into the plant. The major events marking the process of T-DNA mediated pathogenesis are induction of virulence genes, processing and transfer of T-DNA.

There are three common methods to transform plant cells with *Agrobacterium*. The first method is co-cultivation of *Agrobacterium* with cultured isolated protoplasts. This method requires an established culture system that allows culturing protoplasts and plant regeneration from cultured protoplasts. The second method is transformation of cells or tissues with *Agrobacterium*. This method requires (a) that the plant cells or tissues can be modified by *Agrobacterium* and (b) that the modified cells or tissues can be induced to regenerate into whole plants. The third method is transformation of seeds, apices or meristems with *Agrobacterium*. This method requires exposure of the meristematic cells of these tissues to *Agrobacterium* and micropropagation of the shoots or plan organs arising from these meristematic cells.

Those of skill in the art are familiar with procedures for growth and suitable culture conditions for *Agrobacterium* as well as subsequent inoculation procedures. Liquid or semisolid culture media can be used. The density of the *Agrobacterium* culture used for inoculation and the ratio of *Agrobacterium* cells to explant can vary from one system to the next, as can media, growth procedures, timing and lighting conditions.

Transformation of dicotyledons using *Agrobacterium* has long been known in the art, and transformation of monocotyledons using *Agrobacterium* has also been described. See, WO 94/00977 and U.S. Pat. No. 5,591,616, both of which are incorporated herein by reference. See also, Negrotto et al., Plant Cell Reports 19: 798-803 (2000), incorporated herein by reference.

A number of wild-type and disarmed strains of *Agrobacterium tumefaciens* and *Agrobacterium rhizogenes* harboring Ti or Ri plasmids can be used for gene transfer into plants. Preferably, the *Agrobacterium* hosts contain disarmed Ti and Ri plasmids that do not contain the oncogenes that cause tumorigenesis or rhizogenesis. Exemplary strains include *Agrobacterium tumefaciens* strain C58, a nopaline-type strain that is used to mediate the transfer of DNA into a plant cell, octopine-type strains such as LBA4404 or succinamopine-type strains, e.g., EHA101 or EHA105. The use of these strains for plant transformation has been reported and the methods are familiar to those of skill in the art.

U.S. Application No. 20040244075 published Dec. 2, 2004 describes improved methods of *Agrobacterium*-mediated transformation. The efficiency of transformation by *Agrobacterium* may be enhanced by using a number of methods known in the art. For example, the inclusion of a natural wound response molecule such as acetosyringone (AS) to the *Agrobacterium* culture has been shown to enhance transformation efficiency with *Agrobacterium tumefaciens* (Shahla et al., (1987) Plant Molec. Biol. 8:291-298). Alternatively, transformation efficiency may be enhanced by wounding the target tissue to be modified or transformed. Wounding of plant tissue may be achieved, for example, by punching, maceration, bombardment with microprojectiles, etc. (See e.g., Bidney et al., (1992) Plant Molec. Biol. 18:301-313).

In addition, a recent method described by Broothaerts, et. al. (Nature 433: 629-633, 2005) expands the bacterial genera that can be used to transfer genes into plants. This work involved the transfer of a disarmed Ti plasmid without T-DNA and another vector with T-DNA containing the marker enzyme beta-glucuronidase, into three different bacteria. Gene transfer was successful and this method significantly expands the tools available for gene delivery into plants.

Microprojectile Bombardment Delivery

Another widely used technique to genetically transform plants involves the use of microprojectile bombardment. In this process, a nucleic acid containing the desired genetic elements to be introduced into the plant is deposited on or in small dense particles, e.g., tungsten, platinum, or preferably 1 micron gold particles, which are then delivered at a high velocity into the plant tissue or plant cells using a specialized biolistics device. Many such devices have been designed and constructed; one in particular, the PDS1000/He sold by Bio-Rad, is the instrument most commonly used for biolistics of plant cells. The advantage of this method is that no specialized sequences need to be present on the nucleic acid molecule to be delivered into plant cells; delivery of any nucleic acid sequence is theoretically possible.

For the bombardment, cells in suspension are concentrated on filters or solid culture medium. Alternatively, immature embryos, seedling explants, or any plant tissue or target cells may be arranged on solid culture medium. The cells to be bombarded are positioned at an appropriate distance below the microprojectile stopping plate.

Various biolistics protocols have been described that differ in the type of particle or the manner in which DNA is coated onto the particle. Any technique for coating microprojectiles that allows for delivery of transforming DNA to the target cells may be used. For example, particles may be prepared by functionalizing the surface of a gold oxide particle by providing free amine groups. DNA, having a strong negative charge, will then bind to the functionalized particles.

Parameters such as the concentration of DNA used to coat microprojectiles may influence the recovery of transformants containing a single copy of the transgene. For example, a lower concentration of DNA may not necessarily change the efficiency of the transformation but may instead increase the proportion of single copy insertion events. In this regard, ranges of approximately 1 ng to approximately 10 µg (10,000 ng), approximately 5 ng to 8 µg or approximately 20 ng, 50 ng, 100 ng, 200 ng, 500 ng, 1 µg, 2 µg, 5 µg, or 7 µg of transforming DNA may be used per each 1.0-2.0 mg of starting 1.0 micron gold particles.

Other physical and biological parameters may be varied, such as manipulation of the DNA/microprojectile precipitate, factors that affect the flight and velocity of the projectiles, manipulation of the cells before and immediately after bombardment (including osmotic state, tissue hydration and the subculture stage or cell cycle of the recipient cells), the orientation of an immature embryo or other target tissue relative to the particle trajectory, and also the nature of the transforming DNA, such as linearized DNA or intact supercoiled plasmids. One may particularly wish to adjust physical parameters such as DNA concentration, gap distance, flight distance, tissue distance, and helium pressure.

The particles delivered via biolistics can be "dry" or "wet." In the "dry" method, the mini-chromosome DNA-coated particles such as gold are applied onto a macrocarrier (such as a metal plate, or a carrier sheet made of a fragile material such as mylar) and dried. The gas discharge then accelerates the macrocarrier into a stopping screen, which halts the macrocarrier but allows the particles to pass through; the particles then continue their trajectory until they impact the tissue being bombarded. For the "wet" method, the droplet containing the mini-chromosome DNA-coated particles is applied to the bottom part of a filter holder, which is attached to a base which is itself attached to a rupture disk holder used to hold the rupture disk to the helium egress tube for bombardment. The gas discharge directly displaces the DNA/gold droplet from the filter holder and accelerates the particles and their DNA cargo into the tissue being bombarded. The wet biolistics method has been described in detail elsewhere but has not previously been applied in the context of plants (Mialhe et al., Mol Mar Biol Biotechnol. 4(4):275-831995). The concentrations of the various components for coating particles and the physical parameters for delivery can be optimized using procedures known in the art.

A variety of plant cells/tissues are suitable for transformation, including immature embryos, scutellar tissue, suspension cell cultures, immature inflorescence, shoot meristem, epithelial peels, nodal explants, callus tissue, hypocotyl tissue, cotyledons, roots, and leaves, meristem cells, and gametic cells such as microspores, pollen, sperm and egg cells. It is contemplated that any cell from which a fertile plant may be regenerated is useful as a recipient cell. Callus may be initiated from tissue sources including, but not limited to, immature embryos, seedling apical meristems, microspore-derived embryos, roots, hypocotyls, cotyledons and the like. Those cells which are capable of proliferating as callus also are recipient cells for genetic transformation.

Any suitable plant culture medium can be used. Examples of suitable media would include but are not limited to MS-based media (Murashige and Skoog, Physiol. Plant, 15:473-497, 1962) or N6-based media (Chu et al., Scientia Sinica 18:659, 1975) supplemented with additional plant growth regulators including but not limited to auxins such as picloram (4-amino-3,5,6-trichloropicolinic acid), 2,4-D (2,4-dichlorophenoxyacetic acid), naphalene-acetic acid (NAA) and dicamba (3,6-dichloroanisic acid), cytokinins such as BAP (6-benzylaminopurine) and kinetin, and gibberellins. Other media additives can include but are not limited to amino acids, macroelements, iron, microelements, vitamins and organics, carbohydrates, undefined media components such as casein hydrolysates, an appropriate gelling agent such as a form of agar, a low melting point agarose or Gelrite if desired. Those of skill in the art are familiar with the variety of tissue culture media, which when supplemented appropriately, support plant tissue growth and development and are suitable for plant transformation and regeneration. These tissue culture media can either be purchased as a commercial preparation, or custom prepared and modified. Examples of such media would include but are not limited to Murashige and Skoog (Mursahige and Skoog, Physiol. Plant, 15:473-497, 1962), N6 (Chu et al., Scientia Sinica 18:659, 1975), Linsmaier and Skoog (Linsmaier and Skoog, Physio. Plant., 18:100, 1965), Uchimiya and Murashige (Uchimiya and Murashige, Plant Physiol. 15:473, 1962), Gamborg's B5 media (Gamborg et al., Exp. Cell Res., 50:151, 1968), D medium (Duncan et al., Planta, 165:322-332, 1985), Mc-Cown's Woody plant media (McCown and Lloyd, HortScience 6:453, 1981), Nitsch and Nitsch (Nitsch and Nitsch, Science 163:85-87, 1969), and Schenk and Hildebrandt (Schenk and Hildebrandt, Can. J. Bot. 50:199-204, 1972) or derivations of these media supplemented accordingly. Those of skill in the art are aware that media and media supplements such as nutrients and growth regulators for use in transformation and regeneration and other culture conditions such as light intensity during incubation, pH, and incubation temperatures can be varied.

Those of skill in the art are aware of the numerous modifications in selective regimes, media, and growth conditions that can be varied depending on the plant system and the selective agent. Typical selective agents include but are not limited to antibiotics such as geneticin (G418), kanamycin, paromomycin or other chemicals such as glyphosate or other herbicides. Consequently, such media and culture conditions disclosed in the present invention can be modified or substituted with nutritionally equivalent components, or similar processes for selection and recovery of transgenic events, and still fall within the scope of the present invention.

Mini-Chromosome Delivery without Selection

The Mini-chromosome is delivered to plant cells or tissues, e.g., plant cells in suspension to obtain stably modified callus clones for inheritance assay. Suspension cells are maintained in a growth media, for example Murashige and Skoog (MS) liquid medium containing an auxin such as 2,4-dichlorophenoxyacetic acid (2,4-D). Cells are bombarded using a particle bombardment process, such as the helium-driven PDS-1000/He system, and propagated in the same liquid medium to permit the growth of modified and non-modified cells. Portions of each bombardment are monitored for formation of fluorescent clusters, which are isolated by micromanipulation and cultured on solid medium. Clones modified with the mini-chromosome are expanded and homogenous clones are used in inheritance assays, or assays measuring mini-chromosome structure or autonomy.

Mini-Chromosome Transformation with Selectable Marker Gene

Isolation of mini-chromosome-modified cells in bombarded calluses or explants can be facilitated by the use of a selectable marker gene. The bombarded tissues are transferred to a medium containing an appropriate selective agent for a particular selectable marker gene. Such a transfer usually occurs between 0 and about 7 days after bombardment. The transfer could also take place any number of days after bombardment. The amount of selective agent and timing of incorporation of such an agent in selection medium can be optimized by using procedures known in the art. Selection inhibits the growth of non-modified cells, thus providing an advantage to the growth of modified cells, which can be further monitored by tracking the presence of a fluorescent marker gene or by the appearance of modified explants (modified cells on explants may be green under light in selection medium, while surrounding non-modified cells are weakly pigmented). In plants that develop through shoot organogenesis (e.g. *Brassica*, tomato or tobacco), the modified cells can form shoots directly, or alternatively, can be isolated and expanded for regeneration of multiple shoots transgenic for the mini-chromosome. In plants that develop through embryogenesis (e.g. corn or soybean), additional culturing steps may be necessary to induce the modified cells to form an embryo and to regenerate in the appropriate media.

Useful selectable marker genes are well known in the art and include, for example, herbicide and antibiotic resistance genes including but not limited to neomycin phosphotransferase II (conferring resistance to kanamycin, paramomycin and G418), hygromycin phosphotransferase (conferring resistance to hygromycin), 5-enolpyruvylshikimate-3-phosphate synthase (EPSPS, conferring resistance to glyphosate), phosphinothricin acetyltransferase (conferring resistance to phosphinothricin/bialophos), MerA (conferring resistance to mercuric ions). Selectable marker genes may be transformed using standard methods in the art.

The first step in the production of plants containing novel genes involves delivery of DNA into a suitable plant tissue (described in the previous section) and selection of the tissue under conditions that allow preferential growth of any cells containing the novel genes. Selection is typically achieved with a selectable marker gene present in the delivered DNA, which may be a gene conferring resistance to an antibiotic, herbicide or other killing agent, or a gene allowing utilization of a carbon source not normally metabolized by plant cells. For selection to be effective, the plant cells or tissue need to be grown on selective medium containing the appropriate concentration of antibiotic or killing agent, and the cells need to be plated at a defined and constant density. The concentration of selective agent and cell density are generally chosen to cause complete growth inhibition of wild type plant tissue that does not express the selectable marker gene; but allowing cells containing the introduced DNA to grow and expand into adchromosomal clones. This critical concentration of selective agent typically is the lowest concentration at which there is complete growth inhibition of wild type cells, at the cell density used in the experiments. However, in some cases, sub-killing concentrations of the selective agent may be equally or more effective for the isolation of plant cells containing mini-chromosome DNA, especially in cases where the identification of such cells is assisted by a visible marker gene (e.g., fluorescent protein gene) present on the mini-chromosome.

In some species (e.g., tobacco or tomato), a homogenous clone of modified cells can also arise spontaneously when bombarded cells are placed under the appropriate selection. An exemplary selective agent is the neomycin phosphotransferase II (nptII) marker gene, which is commonly used in plant biotechnology and confers resistance to the antibiotics kanamycin, G418 (geneticin) and paramomycin. In other species, or in certain plant tissues or when using particular selectable markers, homogeneous clones may not arise spontaneously under selection; in this case the clusters of modified cells can be manipulated to homogeneity using the visible marker genes present on the mini-chromosomes as an indication of which cells contain mini-chromosome DNA.

Regeneration of Adchromosomal Plants from Explants to Mature, Rooted Plants

For plants that develop through shoot organogenesis (e.g. *Brassica*, tomato and tobacco), regeneration of a whole plant involves culturing of regenerable explant tissues taken from sterile organogenic callus tissue, seedlings or mature plants on a shoot regeneration medium for shoot organogenesis, and rooting of the regenerated shoots in a rooting medium to obtain intact whole plants with a fully developed root system. These plants are potted in soil and grown to maturity in a greenhouse.

For plant species, such corn and soybean, regeneration of a whole plant occurs via an embryogenic step that is not necessary for plant species where shoot organogenesis is efficient. In these plants the explant tissue is cultured on an appropriate media for embryogenesis, and the embryo is cultured until shoots form. The regenerated shoots are cultured in a rooting medium to obtain intact whole plants with a fully developed root system. These plants are potted in soil and grown to maturity in a greenhouse.

Explants are obtained from any tissues of a plant suitable for regeneration. Exemplary tissues include hypocotyls, internodes, roots, cotyledons, petioles, cotyledonary petioles, leaves and peduncles, prepared from sterile seedlings or mature plants.

Explants are wounded (for example with a scalpel or razor blade) and cultured on a shoot regeneration medium (SRM) containing Murashige and Skoog (MS) medium as well as a cytokinin, e.g., 6-benzylaminopurine (BA), and an auxin, e.g., α-naphthaleneacetic acid (NAA), and an anti-ethylene agent, e.g., silver nitrate ($AgNO_3$). For example, 2 mg/L of BA, 0.05 mg/L of NAA, and 2 mg/L of $AgNO_3$ can be added to MS medium for shoot organogenesis. The most efficient shoot regeneration is obtained from longitudinal sections of internode explants.

Shoots regenerated via organogenesis are rooted in a MS medium containing low concentrations of an auxin such as NAA. Plants are potted and grown in a greenhouse to sexual maturity for seed harvest.

To regenerate a whole plant with a mini-chromosome, explants are pre-incubated for 1 to 7 days (or longer) on the shoot regeneration medium prior to bombardment with mini-chromosome (see below). Following bombardment, explants are incubated on the same shoot regeneration medium for a recovery period up to 7 days (or longer), followed by selection for transformed shoots or clusters on the same medium but with a selective agent appropriate for a particular selectable marker gene (see below).

Method of Co-Delivering Growth Inducing Genes to Facilitate Isolation of Adchromosomal Plant Cell Clones Another method used in the generation of cell clones containing mini-chromosomes involves the co-delivery of DNA containing genes that are capable of activating growth of plant cells, or that promote the formation of a specific organ, embryo or plant structure that is capable of self-sustaining growth. In one embodiment, the recipient cell receives simultaneously the mini-chromosome, and a separate DNA molecule encoding one or more growth promoting, organogenesis-promoting, embryogenesis-promoting or regeneration-promoting genes. Following DNA delivery, expression of the plant growth regulator genes stimulates the plant cells to divide, or to initiate differentiation into a specific organ, embryo, or other cell types or tissues capable of regeneration. Multiple plant growth regulator genes can be combined on the same molecule, or co-bombarded on separate molecules. Use of these genes can also be combined with application of plant growth regulator molecules into the medium used to culture the plant cells, or of precursors to such molecules that are converted to functional plant growth regulators by the plant cell's biosynthetic machinery, or by the genes delivered into the plant cell.

The co-bombardment strategy of mini-chromosomes with separate DNA molecules encoding plant growth regulators transiently supplies the plant growth regulator genes for several generations of plant cells following DNA delivery. During this time, the mini-chromosome may be stabilized by virtue of its centromere, but the DNA molecules encoding plant growth regulator genes, or organogenesis-promoting, embryogenesis-promoting or regeneration-promoting genes will tend to be lost. The transient expression of these genes, prior to their loss, may give the cells containing mini-chromosome DNA a sufficient growth advantage, or sufficient tendency to develop into plant organs, embryos or a regenerable cell cluster, to outgrow the non-modified cells in their vicinity, or to form a readily identifiable structure that is not formed by non-modified cells. Loss of the DNA molecule encoding these genes will prevent phenotypes from manifesting themselves that may be caused by these genes if present through the remainder of plant regeneration. In rare cases, the DNA molecules encoding plant growth regulator genes will integrate into the host plant's genome or into the mini-chromosome.

Under a different embodiment of this invention, the genes promoting plant cell growth may be genes promoting shoot formation or embryogenesis, or giving rise to any identifiable organ, tissue or structure that can be regenerated into a plant. In this case, it may be possible to obtain embryos or shoots harboring mini-chromosomes directly after DNA delivery, without the need to induce shoot formation with growth activators supplied into the medium, or lowering the growth activator treatment necessary to regenerate plants. The advantages of this method are more rapid regeneration, higher transformation efficiency, lower background growth of non-modified tissue, and lower rates of morphologic abnormalities in the regenerated plants (due to shorter and less intense treatments of the tissue with chemical plant growth activators added to the growth medium).

Determination of Mini-Chromosome Structure an Autonomy in Adchromosomal Plants and Tissues The structure and autonomy of the mini-chromosome in adchromosomal plants and tissues can be determined by methods including but not limited to: conventional and pulsed-field Southern blot hybridization to genomic DNA from modified tissue subjected or not subjected to restriction endonuclease digestion, dot blot hybridization of genomic DNA from modified tissue hybridized with different mini-chromosome specific sequences, mini-chromosome rescue, exonuclease activity, PCR on DNA from modified tissues with probes specific to the mini-chromosome, or Fluorescence In Situ Hybridization to nuclei of modified cells. Table below summarizes these methods.

| Assay | Assay details | Potential outcome | Interpretation |
|---|---|---|---|
| Southern blot | Restriction digest of genomic DNA* compared to purified mini-C | Native sizes and pattern of bands | Autonomous or integrated via CEN fragment |
| | | Altered sizes or pattern of bands | Integrated or rearranged |
| CHEF gel Southern blot | Restriction digest of genomic DNA compared to purified mini-C | Native sizes and pattern of bands | Autonomous or integrated via CEN fragment |
| | | Altered sizes or pattern of bands | Integrated or rearranged |
| | Native genomic DNA (no digest) | Mini-C band migrating ahead of genomic DNA | Autonomous circles or linears present in plant |
| | | Mini-C band co-migrating with genomic DNA | Integrated |
| | | >1 mini-C bands observed | Various possibilities |
| Exonuclease assay | Exonuclease digestion of genomic DNA followed by detection of circular mini chromosome by PCR, dot blot, or restriction digest (optional), electrophoresis and southern blot (useful for circular mini-chromosomes) | Signal strength close to that w/o exonuclease | Autonomous circles present |
| | | No signal or signal strength lower that w/o exonuclease | Integrated |
| Mini-chromosome rescue | Transformation of plant genomic DNA into E. coli followed by selection for antibiotic resistance genes on mini-C | Colonies isolated only from mini-C plants with mini-Cs, not from controls; mini-C structure matches that of the parental mini-C | Autonomous circles present, native mini-C structure |
| | | Colonies isolated only from mini-C plants with mini-Cs, not from controls; mini-C structure different from parental mini-C | Autonomous circles present, rearranged mini-C structure OR mini-Cs integrated via centromere fragment |
| | | Colonies observed both in mini-C-modified plants and in controls | Various possibilities |
| PCR | PCR amplification of various parts of the mini-chromosome | All mini-c parts detected by PCR | Complete mini-C sequences present in plant |
| | | Subset of mini-c parts detected by PCR | Partial mini-C sequences present in plant |
| FISH | Detection of mini-chromosome sequences in mitotic or meiotic nuclei by fluorescence in situ | Mini-C sequences detected, free of genome | autonomous |
| | | Mini-C sequences detected, associated with genome | integrated |

| Assay | Assay details | Potential outcome | Interpretation |
|---|---|---|---|
| | hybridization | Mini-C sequences detected, both free and associated with genome | Both autonomous and integrated mini-C sequences present |
| | | No mini-C sequences detected | Mini-C DNA not visible by FISH |

Furthermore, mini-chromosome structure can be examined by characterizing mini-chromosomes 'rescued' from adchromosomal cells. Circular mini-chromosomes that contain bacterial sequences for their selection and propagation in bacteria can be rescued from an adchromosomal plant or plant cell and re-introduced into bacteria. If no loss of sequences has occurred during replication of the mini-chromosome in plant cells, the mini-chromosome is able to replicate in bacteria and confer antibiotic resistance. Total genomic DNA is isolated from the adchromosomal plant cells by any method for DNA isolation known to those skilled in the art, including but not limited to a standard cetyltrimethylammonium bromide (CTAB) based method (Current Protocols in Molecular Biology (1994) John Wiley & Sons, N.Y., 2.3) The purified genomic DNA is introduced into bacteria (e.g., *E. coli*) using methods familiar to one skilled in the art (for example heat shock or electroporation). The transformed bacteria are plated on solid medium containing antibiotics to select bacterial clones modified with mini-chromosome DNA. Modified bacterial clones are grown up, the plasmid DNA purified (by alkaline lysis for example), and DNA analyzed by restriction enzyme digestion and gel electrophoresis or by sequencing. Because plant-methylated DNA containing methylcytosine residues will be degraded by wild-type strains of *E. coli*, bacterial strains (e.g. DH10B) deficient in the genes encoding methylation restriction nucleases (e.g. the mcr and mrr gene loci in *E. coli*) are best suited for this type of analysis. Mini-chromosome rescue can be performed on any plant tissue or clone of plant cells modified with a mini-chromosome.

Mini-Chromosome Autonomy Demonstration by In Situ Hybridization (ISH)

To assess whether the mini-chromosome is autonomous from the native plant chromosomes, or has integrated into the plant genome, In Situ Hybridization is carried out (Fluorescent In Situ Hybridization or FISH is particularly well suited to this purpose). In this assay, mitotic or meiotic tissue, such as root tips or meiocytes from the anther, possibly treated with metaphase arrest agents such as colchicines is obtained, and standard FISH methods are used to label both the centromere and sequences specific to the mini-chromosome. For example, a *Zea* centromere is labeled using a probe from a sequence that labels all *Zea* centromeres, attached to one fluorescent tag (Molecular Probes Alexafluor 568, for example), and sequences specific to the mini-chromosome are labeled with another fluorescent tag (Alexafluor 488, for example). All centromere sequences are detected with the first tag; only mini-chromosomes are detected with both the first and second tag. Chromosomes are stained with a DNA-specific dye including but not limited to DAPI, Hoechst 33258, OliGreen, Giemsa YOYO, and TOTO. An autonomous mini-chromosome is visualized as a body that shows hybridization signal with both centromere probes and mini-chromosome specific probes and is separate from the native chromosomes.

Determination of Gene Expression Levels

The expression level of any gene present on the mini-chromosome can be determined by methods including but not limited to one of the following. The mRNA level of the gene can be determined by Northern Blot hybridization, Reverse Transcriptase-Polymerase Chain Reaction, binding levels of a specific RNA-binding protein, in situ hybridization, or dot blot hybridization.

The protein level of the gene product can be determined by Western blot hybridization, Enzyme-Linked Immunosorbant Assay (ELISA), fluorescent quantitation of a fluorescent gene product, enzymatic quantitation of an enzymatic gene product, immunohistochemical quantitation, or spectroscopic quantitation of a gene product that absorbs a specific wavelength of light.

Use of Exonuclease to Isolate Circular Mini-Chromosome DNA from Genomic DNA:

Exonucleases may be used to obtain pure mini-chromosome DNA, suitable for isolation of mini-chromosomes from *E. coli* or from plant cells. The method assumes a circular structure of the mini-chromosome. A DNA preparation containing mini-chromosome DNA and genomic DNA from the source organism is treated with exonuclease, for example lambda exonuclease combined with *E. coli* exonuclease I, or the ATP-dependent exonuclease (Qiagen Inc). Because the exonuclease is only active on DNA ends, it will specifically degrade the linear genomic DNA fragments, but will not affect the circular mini-chromosome DNA. The result is mini-chromosome DNA in pure form. The resultant mini-chromosome DNA can be detected by a number of methods for DNA detection known to those skilled in the art, including but not limited to PCR, dot blot followed by hybridization analysis, and southern blot followed by hybridization analysis. Exonuclease treatment followed by detection of resultant circular mini-chromosome may be used as a method to determine mini-chromosome autonomy.

Structural Analysis of Mini-Chromosomes by BAC-End Sequencing:

BAC-end sequencing procedures, known to those skilled in the art, can be applied to characterize mini-chromosome clones for a variety of purposes, such as structural characterization, determination of sequence content, and determination of the precise sequence at a unique site on the chromosome (for example the specific sequence signature found at the junction between a centromere fragment and the vector sequences). In particular, this method is useful to prove the relationship between a parental mini-chromosome and the mini-chromosomes descended from it and isolated from plant cells by mini-chromosome rescue, described above.

Methods for Scoring Meiotic Mini-Chromosome Inheritance

A variety of methods can be used to assess the efficiency of meiotic mini-chromosome transmission. In one embodiment of the method, gene expression of genes encoded by the mini-chromosome (marker genes or non-marker genes) can be scored by any method for detection of gene expression known to those skilled in the art, including but not limited to visible methods (e.g. fluorescence of fluorescent protein markers, scoring of visible phenotypes of the plant), scoring resistance of the plant or plant tissues to antibiotics, herbicides or other selective agents, by measuring enzyme activity of proteins encoded by the mini-chromosome, or measuring non-visible plant phenotypes, or directly measuring the RNA and protein products of gene expression using microarray, northern blots, in situ hybridization, dot blot hybridization, RT-PCR, western blots, immunoprecipitation, Enzyme-Linked Immunosorbant Assay (ELISA), immunofluorescence and radio-immunoassays (RIA). Gene expression can be scored in the post-meiotic stages of microspore, pollen, pollen tube or female gametophyte, or the post-zygotic stages such as embryo, seed, or progeny seedlings and plants. In another embodiment of the method, the mini-chromosome can de directly detected or visualized in post-meiotic, zygotic, embryonal or other cells in by a number of methods for DNA detection known to those skilled in the art, including but not limited to fluorescence in situ hybridization, in situ PCR, PCR, southern blot, or by mini-chromosome rescue described above.

FISH Analysis of Mini-Chromosome Copy Number in Meiocytes, Roots or Other Tissues of Adchromosomal Plants The copy number of the mini-chromosome can be assessed in any cell or plant tissue by In Situ Hybridization (Fluorescent In Situ Hybridization or FISH is particularly well suited to this purpose). In an exemplary assay, standard FISH methods are used to label the centromere, using a probe which labels all chromosomes with one fluorescent tag (Molecular Probes Alexafluor 568, for example), and to label sequences specific to the mini-chromosome with another fluorescent tag (Alexafluor 488, for example). All centromere sequences are detected with the first tag; only mini-chromosomes are detected with both the first and second tag. Nuclei are stained with a DNA-specific dye including but not limited to DAPI, Hoechst 33258, OliGreen, Giemsa YOYO, and TOTO. Mini-chromosome copy number is determined by counting the number of fluorescent foci that label with both tags.

Induction of Callus and Roots from Adchromosomal Plants Tissues for Inheritance Assays Mini-chromosome inheritance is assessed using callus and roots induced from transformed plants. To induce roots and callus, tissues such as leaf pieces are prepared from adchromosomal plants and cultured on a Murashige and Skoog (MS) medium containing a cytokinin, e.g., 6-benzylaminopurine (BA), and an auxin, e.g., α-naphthaleneacetic acid (NAA). Any tissue of an adchromosomal plant can be used for callus and root induction, and the medium recipe for tissue culture can be optimized using procedures known in the art.

Clonal Propagation of Adchromosomal Plants

To produce multiple clones of plants from a mini-chromosome-transformed plant, any tissue of the plant can be tissue-cultured for shoot organogenesis using regeneration procedures described under the section regeneration of plants from explants to mature, rooted plants (see above). Alternatively, multiple auxiliary buds can induced from a mini-chromosome-modified plant by excising the shoot tip, which can be rooted and subsequently be grown into a whole plant; each auxiliary bud can be rooted and produce a whole plant.

Scoring of Antibiotic- or Herbicide Resistance in Seedlings and Plants (Progeny of Self- and Out-Crossed Transformants Progeny seeds harvested from mini-chromosome-modified plants can be scored for antibiotic- or herbicide resistance by seed germination under sterile conditions on a growth media (for example Murashige and Skoog (MS) medium) containing an appropriate selective agent for a particular selectable marker gene. Only seeds containing the mini-chromosome can germinate on the medium and further grow and develop into whole plants. Alternatively, seeds can be germinated in soil, and the germinating seedlings can then be sprayed with a selective agent appropriate for a selectable marker gene. Seedlings that do not contain mini-chromosome do not survive; only seedlings containing mini-chromosome can survive and develop into mature plants.

Genetic Methods for Analyzing Mini-Chromosome Performance:

In addition to direct transformation of a plant with a mini-chromosome, plants containing a mini-chromosome can be prepared by crossing a first plant containing the functional, stable, autonomous mini-chromosome with a second plant lacking the mini-chromosome.

Fertile plants modified with mini-chromosomes can be crossed to other plant lines or plant varieties to study mini-chromosome performance and inheritance. In the first embodiment of this method, pollen from an adchromosomal plant can be used to fertilize the stigma of a non-adchromosomal plant. Mini-chromosome presence is scored in the progeny of this cross using the methods outlines in the preceding section. In the second embodiment, the reciprocal cross is performed by using pollen from a non-adchromosomal plant to fertilize the flowers of a adchromosomal plant. The rate of mini-chromosome inheritance in both crosses can be used to establish the frequencies of meiotic inheritance in male and female meiosis. In the third embodiment of this method, the progeny of one of the crosses just described are back-crossed to the non-adchromosomal parental line, and the progeny of this second cross are scored for the presence of genetic markers in the plant's natural chromosomes as well as the mini-chromosome. Scoring of a sufficient marker set against a sufficiently large set of progeny allows the determination of linkage or co-segregation of the mini-chromosome to specific chromosomes or chromosomal loci in the plant's genome. Genetic crosses performed for testing genetic linkage can be done with a variety of combinations of parental lines; such variations of the methods described are known to those skilled in the art.

It should be understood that various changes and modifications to the presently preferred embodiments described herein will be apparent to those skilled in the art. Such changes and modifications can be made without departing from the spirit and scope of the present invention and without diminishing its intended advantages. It is therefore intended that such changes and modifications be covered by the appended claims.

Example 1

Corn Centromere Discovery

BAC Library Construction

Two Bacterial Artificial Chromosome (BAC) libraries were constructed from corn genomic DNA. The corn genomic DNA was isolated from corn variety B73 and digested with the restriction enzymes BstYI or MboI. These enzymes were chosen because they are methylation insensitive and therefore can be used to enrich BAC libraries for centromere DNA sequences.

Probe Identification and Selection

Twenty-three groups of corn repetitive genomic or plastid sequences, including specific centromere-localized sequences, were initially compiled as candidate probes for hybridization with the BAC libraries (Table 3). These probes represented various classes of corn repetitive sequences including satellite repeats (heterochromatic/centromere-specific), retroelements, rDNA, B chromosome-specific repeats, chloroplast and mitochondrion DNA, hypermethylated or hypomethylated DNA fractions, and telomeric DNA.

TABLE 3

Maize Repetitive Sequences and Bac Library Probes

| Class | Class Name | Primers | Description | Reference | Comment | GenBank accession |
|---|---|---|---|---|---|---|
| 1 | CR (centromeric retro-transposalable) element | CRJM-001 and 002 | gypsy-type localized to cen all cereals. CentC and CRM co-IP with CEN H3 | Aragon-Alcaide al 1996, Jiang et 1996, Zhong et al 2002 | aka CRM, pSau3A9 (from *sorghum*), CRR (from rice) | AY1290008 |
| 2 | CentA | CHR 15 and one other | centromere retrotransposon, includes MCS1A and B | | AF082532 Similar sequence | AF078917 |
| 3 | Huck | CRJM-005 and 006 | Ty3/gypsy | | (most frequent) | AF050438 |
| 4 | Grande | CRJM-056 and 057 | Ty3/gypsy | | | AF050437 |
| 5 | Cinful | CRJM-007 and 008 | Ty3/gypsy | | | AF049110 |
| 6 | Ji/Prem2 | LTR-5 CRJM 011 and 012 gag 014, and one another | Ty1/copia | | | from alpha zein seq |
| 7 | Opie | | Ty1/copia | | 5' LTR | AF050453 |
| 8 | Tekay | CRJM-009 and 010 | | | 3' LTR | AF050452 |
| 9 | alpha zein | | | | | AF090447 |
| 10 | adh | | | | | AF123535 |
| 11 | bz | | | | | AF448416 |
| 12 | knob 180 | CHR 11 and one other | | | many sequences! | gi\|168710\|gb\| M32521.1\| MZEZMA |
| 13 | MZEHETRO | CRJM-015 and 016 | maize heterochromatic repeat (knob) | Peacock et al PNAS. 78, 4490-4494 (1981) | | M35408 |
| 14 | TR-1 | CHR 13 and and one other | Knob-specific | Hsu et al 2002 | 3 lengths, multi types. Type 1 BLASTs to all 3. Cuts w/RI | AF071126 |
| 15 | CentC | CHR 17 and and one other | 156 bp | | all match well | AY321491 (Cent C27) AF078923 158a AF078922 156a |
| | | CRJM-019 and 020 | | | | |
| 16 | Cent4 | CRJM-021 and 022 | Chromosome 4 repeat homologous to B-chromosome cen repeat | Page et al, 2001 | | AF242891 |
| 17 | pZmBs and K5 | S67586 | B-specific repeats; B73 has no B chromosomes | Alfenito and Birchler 1993; Kaszas and Birchler 1993, 1998 | | AY173950 |
| 18 | rDNA | CRJM-023 and 024 | maize intergenic spacer | | | AF013103 |
| | | CRJM-025 and 026 | maize 5S | | | AF273104 |
| | | CRJM-027 and 028 | maize 17S | | | K0220 |
| 19 | chloroplast | CHHZ211 and 212 | *Arabidiosis* | | | |
| | | CRJM-030 and 031 | maize xpl rDNAs | | | X01365 |
| 20 | mito | CHHZ214 and 215 | *Arabidiosis* | | | |
| | | CRJM-032 and 033 | maize mito 26S rDNA | | | K01868 |
| 21 | Hypermethylated fraction | purified | | | | complex mixture |
| 22 | Hypomethylated fraction | purified | | | | complex mixture |
| 23 | telomere | | sub-telomeric repeat | | U39641 | U39642 |

Twelve probes were picked to interrogate the BAC libraries. These probes represent different groups of commonly found repetitive sequences in the corn genome. The twelve probes selected are shown in Tables 3 and 4 and were: CentC (#15), Cent4 (#16), MZEHETRO (#13), TR-1 (#14), CentA (#2), CR (#1), Huck (#3), Grande (#4), 17S rDNA (#18), 5S rDNA (#18); B cen (#17), and xplmito (#19 and #20). The primers used to amplify these probes are identified in Table 4. Probes were prepared and labeled with standard molecular methods.

Grande. Class II (HiC HiA) BAC clones had strong hybridization to both CentC and CentA, but low hybridization to CR. Class III (HiCR HiC) BAC clones had strong hybridization to both CentC and CR, but low hybridization to CentA. Class IV (HiA HiC HiCR) BAC clones had strong hybridization to CentC, CentA, and CR. Class V (HiC Hi17s) BAC clones had strong hybridization to CentC and 17S rDNA. Class VI (Hi4) BAC clones had strong hybridization to Cent4. Class VII (HiTr1 LoHet) BAC clones had strong hybridization to TR-1 but low hybridization to MZEHETRO. Class

TABLE 4

Classification of maize BAC Clones Containing Centromeric DNA

| | | Probe Hybridization Range | | | | | | | | | | | |
|---|---|---|---|---|---|---|---|---|---|---|---|---|---|
| Class | Class Properties | CentC | CentA | CR | Huck | Grande | 17S rDNA | Cent4 | TR-1 | MZE HETRO | 5S rDNA | B cen | xplmito | # clones identified |
| I | HiC LoA | >=7 | <7 | <7 | <7 | <6 | N/A | N/A | N/A | N/A | N/A | N/A | N/A | 61 |
| II | HiC HiA | >=7 | >=6 | <7 | <=10 | <=10 | N/A | N/A | N/A | N/A | N/A | N/A | N/A | 61 |
| III | HiCR HiC | >=7 | <6 | >=6 | <=10 | <=10 | N/A | N/A | N/A | N/A | N/A | N/A | N/A | 30 |
| IV | HiA HiC HiCR | >=7 | >6 | >=6 | <=10 | <=10 | N/A | N/A | N/A | N/A | N/A | N/A | N/A | 30 |
| V | HiC Hi17s | >=7 | >0 | >0 | >0 | >0 | >5 | N/A | N/A | N/A | N/A | N/A | N/A | 30 |
| VI | Hi4 | >0 | >0 | >0 | >0 | N/A | N/A | >5 | N/A | N/A | N/A | N/A | N/A | 17 |
| VII | HiTr1 LoHe | >0 | >0 | N/A | N/A | N/A | >0 | N/A | >6 | <6 | N/A | N/A | N/A | 31 |
| VIII | LoTr1 HiHe | >0 | >0 | N/A | N/A | N/A | >0 | N/A | <5 | >7 | N/A | N/A | N/A | 31 |
| IX | HiTr1 HiHe | >0 | >0 | N/A | N/A | N/A | >0 | N/A | >6 | >6 | N/A | N/A | N/A | 24 |
| Total | | | | | | | | | | | | | | 315 |

* Values represent hybridization intensities of an individual BAC to each probe on a scale of 1 to 10. Values were normalized.

Library Interrogation and Data Analysis

The BAC clones from the libraries were spotted onto filters for further analysis. The filters were hybridized with each of the 12 probes to identify specific BAC clones that contain DNA from the group of sequences represented by the probe(s). Exemplary hybridization conditions: 0.5×SSC 0.25% SDS at 65 degrees for 15 minutes, followed by a wash at 65 degrees for a half hour.

A total of 92,160 BAC clones from the two libraries (36,864 BAC clones from 2 filters from the BstYI library and 55,296 clones from 3 filters from the MboI library) were interrogated with each of the 12 probes described above, and the hybridization intensities of the BAC clones with each probe were scanned to quantitate hybridization intensity for each clone. Scores of 1 to 10 (based on the hybridization intensities, with 10 being the strongest hybridization) were imported into a relational database, for classification. The database contained a total of 24 tables, 12 from each library used in the interrogation. Each table contained the hybridization scores of each BAC clone from the BstYI or MboI library, to one of the 12 probes. Data analysis was carried out using standard SQL (Structured Query Language) routines to find BACs that contain different groups of repetitive sequences.

Classification and Selection of BAC Clones for Mini-Chromosome Construction

BAC clones containing centromeric/heterochromatic DNA were identified by their hybridization scores to different probes. The goal was to select BAC clones that contained a diverse set of various repetitive sequences. Nine classes of centromeric BAC clones were eventually chosen to cover the broadest possible range of centromeric/heterochromatic sequences for mini-chromosome construction. Detailed descriptions of each class and probe hybridization values for each class are shown in Table 4.

Class I (HiC LoA) BAC clones had strong hybridization to probe CentC, but low hybridization to CentA, CR, Huck and VIII (LoTr1 HiHet) BAC clones had strong hybridization to MZEHETRO but low hybridization to TR-1. Class IX (HiTr1 HiHet) BAC clones had strong hybridization to both TR-1 and MZEHETRO.

A number of representative clones from each class were chosen to yield a total of 315 BAC clones for further analysis by restriction digest fingerprinting. The number of clones chosen in each class is shown in Table 4.

The 315 BAC clones were fingerprinted based on restriction sites found in the centromere specific sequence(s). Fingerprinting was used to evaluate the sequence composition of the large numbers of BAC clones and to compare their similarity to each other by comparing the restriction enzyme digest fragment patterns. A sequence with a tandem repeated sequence will show a single intense band of unit repeat size when digested with a restriction enzyme that cuts within the unit repeat. Second, BAC clones with similar sequences will show similar patterns of restriction fragments in a digest.

BAC DNA was extracted from bacteria using methods familiar to those in the art. Restriction enzymes HpaII and MspI were used to digest BAC clones in Classes I through VI, and restriction enzyme NdeI was used to digest BAC clones in classes VII through IX.

Z. mays BACs ZB19 and ZB113 were deposited with the American Type Culture Collection (ATCC) on Feb. 22, 2005 and assigned accession nos. PTA-6604 and PTA-6605. ZB19 was classified as "class 1" or "HiCLoA when characterized with the restriction endonucleases HpaII, MspI and fingerprint class CL/SL, sm. ZB113 was classified as "class 4" or "HiA, HiC and HiCR and fingerprint class CL/SL.

Example 2

Construction of Maize Mini-Chromosomes

The 315 BAC clones identified in Example 1 were grown up and DNA was extracted for mini-chromosome construction using NucleoBond™ Purification Kit (Clontech). To determine the molecular weight of centromere fragments in the BAC libraries, a frozen sample of bacteria harboring a BAC clone was grown in selective liquid media and the BAC DNA harvested using a standard alkaline lysis method. The recovered BAC DNA was restriction digested and resolved on an agarose gel. Centromere fragment size was determined by comparing to a molecular weight standard.

For each BAC, two types of mini-chromosomes were generated, differing only by the promoter used to express the DsRed gene. Corn ADH promoter was used to express DsRed in mini-chromosomes constructed with pCHR667 and the *Arabidopsis* UBQ10 promoter was used to express DsRed in mini-chromosomes constructed with pCHR758. Mini-chromosome genetic elements within the pCHR667 and pCHR758 vectors are set out in Table 5 and 6, respectively.

TABLE 5

Donor Components of pCHR667

| Genetic Element | Size (base pair) | Location (bp) | Details |
| --- | --- | --- | --- |
| ADH Corn Promoter | 1189 | 14-1202 | PCR amplified maize promoter alcohol dehydrogenase 1 (ADH-1) for expression of DsRed in maize (used primers CRJM-42/43) |
| Maize ADH Intron | 579 | 1216-1794 | PCR amplified maize ADH intron with AUG mutation for stabilization of DsRed2 gene transcript and increase protein expression level (used primers CRJM-72/73) |
| DsRed2 + NLS | 780 | 1817-2596 | Nuclear localized red fluorescent protein from *Discosoma* sp. (Matz, M et. al *Nat Biotechnol* 1999 Dec; 17(12): 1227). |
| ADH Terminator | 203 | 2725-2927 | Amplified maize terminator using primers CRJM-46/47 |
| Bacterial Kanamycin | 817 | 3066-3882 | Bacterial kanamycin selectable marker |
| Rps16A terminator | 489 | 4065-4553 | Amplified from *Arabidopsis thaliana* 40S ribosomal protein S16 for termination of NptII gene |
| NPTII | 795 | 4617-5411 | Neomycin phosphotransferase II plant selectable marker |
| UBQ10 intron | 359 | 5439-5798 | PCR amplified *Arabidopsis thaliana* intron from UBQ10 gene (At4g05320) for stabilization of NptII gene transcript and increase protein expression level |
| YAT1 yeast promoter | 2000 | 5812-7811 | PCR amplified YAT1 promoter from chromosome I of *Saccharomyces cerevisiae* for expression of NptII in maize |
| LoxP | 34 | 10341-10374 and 7829-7862 | Recombination site for Cre mediated recombination (Arenski et. al 1983, Abremski et. al 1984) |

TABLE 6

Donor Components of pCHR758

| Genetic Element | Size (base pair) | Location (bp) | Details |
| --- | --- | --- | --- |
| UBQ10 promoter | 2038 | 14-2051 | *Arabidopsis thaliana* polyubiquitin promoter (At4g05320) |
| DsRed2 + NLS | 780 | 2088-2867 | Nuclear localized red fluorescent protein from *Discosoma* sp. (Matz, M et. al *Nat Biotechnol* 1999 Dec; 17(12): 1227). |
| Pyruvate kinase terminator | 332 | 3002-3333 | *Arabidopsis thaliana* pyruvate kinase terminator (At5g52920) |
| Bacterial Kanamycin | 817 | 3478-4294 | Bacterial kanamycin selectable marker |
| Rps16A terminator | 489 | 4477-4965 | Amplified from *Arabidopsis thaliana* 40S ribosomal protein S16 for termination of NptII gene |
| NPTII | 795 | 5029-5823 | Neomycin phosphotransferase II plant selectable marker |
| UBQ10 intron | 359 | 5851-6210 | PCR amplified *Arabidopsis thaliana* intron from UBQ10 gene (At4g05320) for stabilization of NptII gene transcript and increase protein expression level |
| YAT1 yeast promoter | 2000 | 6224-8223 | PCR amplified YAT1 promoter from chromosome I of *Saccharomyces cerevisiae* for expression of NptII in maize |

TABLE 6-continued

Donor Components of pCHR758

| Genetic Element | Size (base pair) | Location (bp) | Details |
|---|---|---|---|
| LoxP | 34 | 8243-8276 & 10755-10788 | Recombination site for Cre mediated recombination (Arenski et. al 1983, Abremski et. al 1984) |

Corn mini-chromosomes were constructed by following a two-step procedure: Step 1: Preparation of donor DNA for retrofitting with BAC centromere vectors and Step 2: Cre-Lox Recombination-BAC and Donor DNA to generate the mini-chromosome. A total of 230 corn mini-chromosomes were constructed using this assembly process, and were subsequently tested in several different corn cell lines.

Preparation of Donor DNA for Retrofitting

Cre recombinase-mediated exchange was used to construct mini-chromosomes by combining the plant centromere fragments cloned in pBeloBAC11 with a donor plasmid (i.e. pCHR667 or pCHR758, Tables 7 & 8). The recipient BAC vector carrying the plant centromere fragment contained a loxP recombination site; the donor plasmid contained two such sites, flanking the sequences to be inserted into the recipient BAC.

Cre recombinase-mediated exchange was used to construct mini-chromosomes by combining the plant centromere fragments cloned in pBeloBAC11 with a donor plasmid (i.e. pCHR667 & pCHR758, Table 5 & 6). The recipient BAC vector carrying the plant centromere fragment contained a loxP recombination site; the donor plasmid contained two such sites, flanking the sequences to be inserted into the recipient BAC. Mini-chromosomes were constructed using a two-step method. First, the donor plasmid was linearized to allow free contact between the two loxP site; in this step the backbone of the donor plasmid is eliminated. In the second step, the donor molecules were combined with centromere BACs and were treated with Cre recombinase, generating circular mini-chromosomes with all the components of the donor and recipient DNA. Mini-chromosomes were delivered into E. coli and selected on medium containing kanamycin and chloramphenicol. Only vectors that successfully cre recombined and contained both selectable markers survived in the medium. Mini-chromosomes were extracted from bacteria and restriction digested to verify DNA composition and calculate centromere insert size.

To determine the molecular weight of the centromere fragments in the mini-chromosomes, three bacterial colonies from each transformation event were independently grown in selective liquid media and the mini-chromosome DNA harvested using a standard alkaline lysis method. The recovered mini-chromosome was restriction digested and resolved on an agarose gel. Centromere fragment size was determined by comparing to a molecular weight standard. If variation in centromere size was noted, the mini-chromosome with the largest centromere insert was used for further experimentation. Selection of Corn Cell Clones Stably Containing Mini-chromosome DNA Functional Testing of Mini-Chromosomes Using Transient Assays Maize mini-chromosomes were tested in several corn cell lines including PC1117, HiII, and BMS, and the procedure was optimized for antibiotic selection, cell pre-treatments, and bombardment conditions. All assays were transient and fluorescent cells were counted at several time points. Preliminary results identified several mini-chromosomes that successfully generated fluorescent cell clusters.

Example 3

Mini-Chromosome Delivery into Maize Cells

Various methods have been used to deliver DNA into plant cells. These include biological methods, such as viruses, physical methods such as biolistic particle bombardment and silicon carbide whiskers, electrical methods such as electroporation, and chemical methods such as the use of polyethylene glycol and other compounds known to stimulate DNA uptake into cells. Biolistic particle bombardment have been the methods that have found most widespread use in plant biotechnology.

Biolistic Particle Delivery of Mini-Chromosomes

A biolistic particle delivery method was used to transfer corn mini-chromosomes into a number of different corn tissues including suspension cells, plate-grown calli, and immature embryos. For the purpose of transient delivery or selection of stable cell culture modified with a corn mini-chromosome, suspension cells were used for delivery using wet or dry gold delivery methods. An example of such a suspension culture is the publicly available line, PC1117.

Wet Bombardment

A biolistic delivery method using wet gold particles kept in an aqueous DNA suspension was adapted from the teachings of Milahe and Miller (Biotechniques 16: 924-931, 1994) and used to transform corn cells. To prepare the wet gold particles for bombardment, 1.0 μm gold particles were washed by mixing with 100% ethanol on a vortex followed by spinning the particles in a microfuge at 4000 rpm in order to remove supernatant. Subsequently, the gold particles were washed with sterile distilled water three times, followed by spinning in a microfuge to remove supernatant. The washed gold particles are resuspend in sterile distilled water at a final concentration of 90 mg per ml and stored at 4° C. until use. For bombardment, the gold particle suspension (90 mg/ml) was then mixed rapidly with 1 μg/μl DNA solution (in dH$_2$O or TE), 2.5 M CaCl$_2$, and 1 M spermidine. DNA/gold mixture was left at room temperature and used for bombardment within 2-4 hours.

For bombardment of corn cells, the cells were harvested by centrifugation (1200 rpm for 2 minutes) on the day of bombardment. The cells were plated onto 50 mm circular polyester screen cloth disks placed on petri plates with solid medium. The solid medium used was the same medium that the cells are normally grown in, plus 0.26% gelrite, or 0.6% tissue culture agar, added before autoclaving. Approximately 1.5 ml packed cells were placed on each filter disk, and spread out in a very even spot approximately 1 inch in diameter.

Bombardment of the cells was carried out in the BioRad PDS-1000/He Biolistic Particle Delivery System (BioRad). The DNA/gold suspension was resuspended and immediately inserted onto the grid of the filter holder. A 50 mm circular polyester screen cloth disk with the cells was placed into a fresh 60 mm petri dish with the same medium and the cells were covered with a 10×10 cm square of sterile nylon or Dacron chiffon netting. A metal cylinder was inserted into the petri dish and used to push the netting down to the bottom of the dish. This weight prevents the cells from being dislodged from the plate during bombardment. The petri dish containing the cells was then placed onto the sample holder, and positioned in the sample chamber of the gene gun and bombarded with the DNA/gold suspension. After the bombardment, the cells were scraped off the filter circle in the petri dish containing solid medium with a sterile spatula and transferred to fresh medium in a 125 ml blue-capped glass bottle. The bottles were transferred onto a shaker and grown while shaking at 150 rpm.

Suspensions of the maize cell line PC117 were bombarded with wet gold particles containing DNA from BAC clones ZB10, ZB18, ZB19 and ZB99. After bombardment, all cells were returned to liquid culture and allowed to grow for three days prior to plating in selection media. Subsequently, the transfected cells were grown in selection medium containing various concentrations of antibiotics. The selection media contained either an increasing concentration of kanamycin (25, 50, 75, 100, 125 and 150 µg/ml) or G418 (10, 20, 35, 50, 75 and 100 µg/ml). The growth of clones in the selection medium indicated expression of the selection gene within the mini-chromosome and suggests a functional centromere within the mini-chromosome. These results are summarized in Table 7.

TABLE 7

| Construct | # bombardments | # clones isolated |
|---|---|---|
| ZB10R2-1 | 2 | 0 |
| ZB18R3-1 | 2 | 0 |
| ZB19R2-1 | 12 | 9 |
| ZB99R1-1 | 12 | 1 |

Dry Bombardment

A biolistic delivery method using dry gold particles was also carried out to deliver mini-chromosomes to corn embryos. For this method, 5 µg of mini-chromosome DNA was precipitated onto 3 mg of sterilized and washed 0.6µ gold particles. The DNA-containing gold particles were resuspended in cold sterile water containing 2.5 M $CaCl_2$. The mixture was lightly vortexed, and then filter-sterilized 0.1 M Spermidine (free base) was added to the mixture. Subsequently, the mixture was lightly vortexed and allowed to precipitate on ice for an hour, with vortexing about every 10 minutes. The precipitated DNA was then washed with 100% ethanol, resuspended in 100% ethanol which was allowed to fully evaporate prior to bombardment.

Immature embryos were excised onto N6 based medium (Chu's N6 medium with 25 µM silver nitrate) 3-5 days prior to day of bombardment. The embryos were osmotically adjusted approximately 4 hours prior to bombardment. This osmotic medium is composed of Chu's N6 Basal medium with the addition of 25 µM silver nitrate, 36.4 g/l sorbitol, and 36.4 g/l mannitol. Embryos were arranged scutellar side up in an open ring that had the same diameter as the plate stage in the gun.

The embryos were bombarded using the BioRad PDS-1000/He Biolistic Particle Delivery System. For this bombardment, the rupture disk rating was 1100 psi with one shot per plate of embryos. The distance from the rupture disk to the macrocarrier was ¼ inch. After bombardment, the plates of embryos were incubated in a dark incubator overnight at 27° C. The following day, the bombarded tissue was transferred to selection medium, Chu's N6 with 200-250 mg/l Paromomycin or 25-35 mg/l G418 (Geneticin), and cultured in the dark. During this transfer, any emerging coleoptiles were removed from the immature embryos.

Approximately 2-3 weeks after bombardment, all tissue was transferred to fresh selective medium at a higher selection pressure of 250-300 mg/l Paromomycin or 35-50 mg/l G418. At this transfer, the callus was separated into approximately 2-3 mm segments. The callus that was proliferating and showed dsRed activity after at least two subcultures was regenerated. Regeneration was initiated when the amount of healthy callus suggested that a minimum of three plants can be regenerated from that event.

For regeneration, the callus was transferred to R1 medium (MS medium with 20 g/l sucrose and 5 mg/l 6-benzyl-aminopurine). Plates were then incubated at 27° C. in the dark for 3-7 days. Tissue was then moved to R2 medium (MS medium with 60 g/l sucrose) with either 10 mg/l G418 or 50 mg/l Paromomycin and placed under low light at 26° C. When leaf tissue reached the top of the petri dish, developing plantlets were transferred to R3 medium (MS medium with 15 gl/l sucrose) with either 10 mg/l G418 or 50 mg/l under higher light intensity at 26° C. to continue plant growth and allow substantial root development. Plantlets were then transferred into moistened soilless mix under a humi-dome to maintain high humidity in a growth chamber for one week prior to being transplanted into the greenhouse.

Example 4

Selection of Corn Cell Clones Stably Containing Mini-Chromosome DNA

Use of Visible Marker Genes

The presence of visible marker genes allowed for visual selection of Corn cells stably containing mini-chromosome DNA because any modified cells or cell clusters were readily identified by virtue of fluorescent protein expression. In addition, the use of fluorescent protein expression allowed for the use of sub-killing concentrations of selective agent during growth of plant tissue on selective medium. This flexibility allowed for the use of a wider range of antibiotic concentrations than possible in the absence of a visible marker gene, without having to consider the amount of background growth observed in wild type plant tissue. As a result, the adchromosomal cell clones were isolated with use of certain selectable marker genes, and under conditions that might not be effective in standard selection experiments as practiced in the industry. These selections were typically done at lower antibiotic concentrations than practiced elsewhere, and resulted in higher levels of background growth. Fluorescent cell clusters can be visually identified after one to several weeks of growth on selective media. Clusters of cells stably containing mini-chromosomes were identified by visual observation of fluorescence in the cells in a darkened room.

Manipulation of Adchromosomal Tissue to Homogeneity

After identifying clusters of fluorescent cells, physical manipulations were carried out to allow for the preferential expansion of cells harboring the delivered mini-chromosomes. Non-fluorescent tissue surrounding the fluorescent clusters was trimmed to avoid overgrowth of fluorescent cells by non-fluorescent ones, while retaining a minimum tissue size capable of rapid growth. These manipulations were performed under sterile conditions with the use of a fluorescence stereomicroscope that allows for visualization of the fluorescent cells and cell clumps in the larger pieces of tissue. In between the mechanical purification steps, the tissue was allowed to grow on appropriate media, either in the presence or absence of selection. Over time, a pure population of fluorescent cells was obtained.

Method of Co-Delivering Growth Inducing Genes to Facilitate Isolation of Adchromosomal Plant Cell Clones Another method used in the generation of cell clones containing mini-chromosomes involved the co-delivery of DNA containing genes that are capable of activating growth of plant cells. In this method, the cell receiving DNA receives simultaneously the mini-chromosome, and a separate NA molecule encoding one or more growth promoting genes. Following DNA delivery, expression of the plant growth regulator genes stimulates the plant cells to divide, or to initiate differentiation into a specific organ, embryo, or other cell types or tissues capable of regeneration. Multiple plant growth regulator genes are combined on the same molecule, or co-bombarded on separate molecules. Use of these genes can also be combined with application of plant growth regulator molecules into the medium used to culture the plant cells, or of precursors to such molecules that are converted to functional plant growth regulators by the plant cell's biosynthetic machinery, or by the genes delivered into the plant cell.

The co-bombardment strategy of mini-chromosomes with separate DNA molecules encoding plant growth regulators transiently supplies the plant growth regulator genes for several generations of plant cells following DNA delivery. During this time, the mini-chromosome may be stabilized by virtue of its centromere, but the DNA molecules encoding plant growth regulator genes will tend to be lost. In rare cases, the DNA molecules encoding plant growth regulator genes will integrate into the host plant's genome or into the mini-chromosome.

Example 5

Regeneration of Adchromosomal Corn Plants

A total of 125 corn mini-chromosomes were prepared as described herein and are shown in Table 8.

TABLE 8

| BAC Number ZB | Mini-chromosome Number | | Bac Number ZB | Mini-chromosome Number | |
|---|---|---|---|---|---|
| | 667 donor vector | 758 donor vector | | 667 donor vector | 758 donor vector |
| 5 | ZB5R1-1 | | 30 | | ZB130R2-1 |
| 6 | ZB6R1-1 | ZB6R2-1 | 31 | | ZB131R2-2 |
| 7 | ZB7R1-1 | ZB7R2-2 | 37 | | ZB137R2-3 |
| 8 | ZB8R1-2 | ZB8R2-1 | 44 | | ZB144R2-1 |
| 9 | ZB9R1-1 | | 45 | | ZB145R2-2 |
| 10 | ZB10R2-1 | ZB10R3-1 | 46 | | ZB146R2-1 |
| 13 | ZB13R1-1 | ZB13R2-1 | 47 | | ZB147R2-2 |
| 14 | ZB14R1-1 | ZB14R2-1 | 50 | | ZB150R2-1 |
| 18 | ZB18R2-1 | ZB18R3-1 | 56 | ZB156R1-1 | ZB156R2-1 |
| 19 | ZB19R1-1 | ZB19R2-1 | 57 | ZB157R1-2 | |
| 20 | ZB20R1-1 | | 58 | ZB158R1-2 | ZB158R2-3 |
| 21 | ZB21R2-1 | | 67 | | ZB167R2-1 |
| 24 | ZB24R2-1 | | 75 | ZB175R1-1 | ZB175R2-1 |
| 25 | | ZB25R2-1 | 77 | ZB177R1-1 | ZB177R2-1 |
| 29 | ZB29R1-1 | | 78 | ZB178R1-1 | ZB178R2-1 |
| 32 | | ZB32R3-1 | 99 | ZB199R1-1 | ZB199R2-1 |
| 34 | | ZB34R3-1 | 07 | ZB207R1-1 | |
| 44 | | ZB44R2-2 | 11 | ZB211R3-1 | |
| 49 | | ZB49R2-1 | 32 | ZB232R1-1 | ZB232R2-1 |
| 64 | ZB64R1-1 | ZB64R2-2 | 33 | ZB233R1-1 | ZB233R2-1 |
| 65 | ZB65R1-1 | | 35 | ZB235R1-1 | ZB235R2-1 |
| 66 | ZB66R1-1 | | 38 | | ZB238R2-1 |
| 71 | ZB71R1-3 | | 43 | | ZB243R2-1 |

TABLE 8-continued

| BAC Number ZB | Mini-chromosome Number | | Bac Number ZB | Mini-chromosome Number | |
|---|---|---|---|---|---|
| | 667 donor vector | 758 donor vector | | 667 donor vector | 758 donor vector |
| 72 | ZB72R1-2 | | 48 | | ZB248R2-1 |
| 73 | ZB73R1-3 | ZB73R2-1 | 53 | | ZB253R2-1 |
| 80 | | ZB80R2-1 | 58 | ZB258R2-1 | ZB258R3-2 |
| 81 | | ZB81R2-1 | 59 | ZB259R2-2 | |
| 82 | ZB82R1-2 | ZB82R2-1 | 60 | ZB260R2-2 | |
| 94 | ZB94R1-1 | ZB94R2-1 | 61 | ZB261R2-1 | |
| 96 | ZB96R1-1 | ZB96R2-1 | 65 | ZB265R2-1 | |
| 98 | ZB98R1-3 | ZB98R2-1 | 71 | | ZB271R3-2 |
| 99 | ZB99R1-1 | ZB99R2-1 | 79 | | ZB279R3-1 |
| 100 | ZB100R1-2 | ZB100R2-3 | 82 | | ZB282R2-2 |
| 101 | ZB101R1-2 | ZB101R2-2 | 91 | | ZB291R3-1 |
| | | ZB104R2-1 | 93 | ZB293R1-1 | |
| 105 | ZB105R1-1 | ZB105R2-1 | 95 | ZB295R1-3 | ZB295R2-1 |
| 106 | ZB106R1-1 | ZB106R2-2 | 96 | ZB296R1-2 | ZB296R2-1 |
| 108 | ZB108R1-2 | ZB108R2-1 | 97 | ZB297R1-3 | ZB297R2-2 |
| 109 | ZB109R1-1 | ZB109R2-1 | 98 | ZB298R1-1 | |
| 113 | ZB113R1-1 | ZB113R2-1 | 05 | ZB305R1-2 | ZB305R2-1 |
| 120 | ZB120R1-1 | | 08 | ZB308R1-1 | ZB308R2-2 |
| 122 | ZB122R1-3 | ZB122R2-1 | | | |
| 123 | ZB123R1-1 | | | | |
| 124 | ZB124R1-1 | | | | |
| 129 | | ZB129R2-2 | | | |

The biolistic delivery method described above was used to deliver the mini-chromosomes into a number of different corn tissues including suspension cells, plate-grown calli, and immature embryos. For the purpose of transient delivery or selection of stable cell culture modified with a corn mini-chromosome, suspension cells were used for delivery using wet or dry gold delivery methods. An example of such a suspension culture is the publicly available line, PC1117.

To obtain trans-chromosomal corn plants modified with corn mini-chromosomes, standard protocols for corn tissue culture and transformation are followed. Such protocols include the Maize Embryo/Callus Bombardment Protocols available at Iowa Statue University, College of Agriculture web site.

The transformation process involves the preparation of regenerable tissues such as immature embryos from corn cultivars such as Hill, pre-culture of embryos on an auxin-enriched medium, delivery of miniC's into immature embryos or embryogenic calli, selection and isolation of fluorescent cell clusters, expansion of cell clusters and formation of transchromosomal embryos, maturation and regeneration of embryos into whole plants.

Example 6

Sequence Analysis of Centromeres

Two BAC clones (ZB19 and ZB113) were sequenced and the centromere sequences were analyzed using conventional methods. Briefly, the BAC DNA was purified from E. coli, sheared and cloned into standard cloning vectors to create a shotgun library. Clones in the library were sequenced as reads 500-900 bp in length. Individual reads were trimmed to remove sequence of poor quality (phred score of <20) and to remove sequences derived from the cloning vector used to generate the shotgun library. The remaining sequence information was then filtered to remove E. coli sequences, which inevitably contaminate the BAC DNA prep, and sequences corresponding to the known vector component of each mini-chromosome.

The filtered reads and sequences were then analyzed with a variety of tools to establish sequence content and to locate repetitive DNA sequences. Contig assemblies were recomputed with phredPhrap. The following programs were used extensively: phred/phrap and consed (Ewing B, Green P: Basecalling of automated sequencer traces using phred. II. Error probabilities. Genome Research 8:186-194 (1998); Ewing B, Hillier L, Wendl M, Green P: Basecalling of automated sequencer traces using phred. I. Accuracy assessment. Genome Research 8:175-185 (1998); Gordon, David. "Viewing and Editing Assembled Sequences Using Consed", in Current Protocols in Bioinformatics, A. D. Baxevanis and D. B. Davison, eds, New York: John Wiley & Co., 2004, 11.2.1-11.2.43; Gordon D, Desmarais C, Green P: Automated finishing with Autofinish. Genome Res 11:614-625 (2001); and Gordon D, Abaiian C, Green P: Consed: a graphical tool for sequence finishing. Genome Research 8:195-202 (1998); and ReapeatMasker (available at the Institute of Systems Biology website). The following databases were used to identify maize sequences: Genbank, RepeatMasker Libraries (repeatmaskerlibraries20050523.tar.gz), TIGR databases "characterized.sub.--02202004.fasta", "uncharacterized-.sub.--02202004.fasta", "RECON_prediction.sub.--02202004.fasta" which are accessible at the TIGR web site.

As described in detail below, repeat CentC is highly represented in the sequence of both ZB19 and ZB113. These fingerprint analysis classified BAC clone ZB19 as "class 1" or "HiC,LoA" and BAC clone ZB113 as "class 4" or "HiA, HiC and HiCR" (see Table 4 above). The repeated sequence CRM was also highly represented in ZB113.

The full length sequence of CentC is set out in GenBank Accession No. AY321491 (SEQ ID NO: 77). The full length sequence of CRM is set out in GenBank Accession No. AY129008 (SEQ ID NO: 78). The full length sequence of CentA is set out in Genbank Accession No. AF078917 (SEQ ID NO: 79).

Characterization of ZB19

The nucleotide sequence of ZB19 was assembled into 31 contigs with a combined trimmed length of 64 kb. ZB19 contigs numbered 1-31 correspond to SEQ ID NOS: 21-51, respectively.

When examining all contigs, only the two largest contigs, 30 and 31, showed significant numbers of high and low quality matches among various sequencing reads. Alternatively, all but three contigs (16, 17 and 22) show nearly complete matches to TIGR maize database entries. Large numbers of sequence regions within contig 30 have significant matches to sequence regions in contig 31. Given the small number of inconsistent forward/reverse pairs, this does not suggest a misassembly but rather that both contigs 30 and 31 share large numbers of common maize sequence. Other distinct sequence similarities were evident between contigs 7 and 29, and contigs 17 and 22.

The sequence analysis of ZB19 indicated that 0.47% of the sequence is simple repeats and low complexity sequence (e.g. AT-rich, (CGA)n, GA-rich and CT-rich), 14% vector sequence, 1.15% *E. coli* sequence, 83% sequence is present in the TIGR maize database, 1.10% uncharacterized sequence and 28.91% CentC repeat. About 19.4 kb of the sequence was true repeat sequences, meaning those sequences are repeated within the BAC ZB19 sequence.

ZB19 has 39 simple repeat bases (0.06%) and 257 low complexity bases (0.39%) contained within contigs 16, 24, 25, and 28. This low simple repeat content is summarized in Table 9.

TABLE 9

ZB19 Simple Repeat Content

| Contig (length) | Contig Match | | | | Simple |
|---|---|---|---|---|---|
| | begin | end | length | % diverge | repeat |
| ZB19.Contig16 (2303) | 1572 | 1597 | 25 | 0 | AT_rich |
| ZB19.Contig24 (2816) | 708 | 747 | 39 | 17.5 | (CGA)n |
| ZB19.Contig25 (2997) | 60 | 87 | 27 | 3.6 | AT_rich |
| ZB19.Contig25 (2997) | 2518 | 2552 | 34 | 11.4 | GA-rich |
| ZB19.Contig28 (3308) | 1121 | 1292 | 171 | 32.4 | CT-rich |
| | | | 296 | | |
| | | | 0.47% | | |

The ZB19 contigs are set out as SEQ ID NOS: 21-51 respectively. These contigs were compared to the NCBI database at the National Institute of Health Web Site using BLAST. Results of the BLAST comparison are set out in Table 10.

TABLE 10

ZB19 Genbank Homology

| Contig (length) | Contig Alignment | | | | Genbank | | | |
|---|---|---|---|---|---|---|---|---|
| | begin | end | length | % id | begin | end | Accession # | Homologous feature |
| ZB19.Contig1 (1500) | 1 | 1500 | 1501 | 97.07 | 191344 | 189846 | AY664416 | Mo17 locus bz |
| ZB19.Contig2 (1708) | 545 | 1451 | 918 | 86.06 | 14246 | 13335 | AY574035 | rust resistance rp3-1 |
| ZB19.Contig3 (118) | 1 | 118 | 118 | 100 | 4877 | 4760 | J02482 | Coliphage phi-X174 |
| ZB19.Contig4 (194) | 1 | 194 | 194 | 100 | 980 | 1173 | J02482 | Coliphage phi-X174 |
| ZB19.Contig5 (1176) | 28 | 1148 | 1122 | 97.15 | 8181 | 7060 | AY664416 | Mo17 locus bz |
| ZB19.Contig6 (731) | | | | | | | "NA" | "pCHR758mcv" |
| ZB19.Contig7 (1325) | 560 | 1311 | 756 | 92.33 | 3387 | 2633 | AY530951 | 40S ribosomal protein S8 |
| ZB19.Contig8 (77) | | | | | | | "NA" | "low quality" |
| ZB19.Contig9 (153) | | | | | | | "NA" | "*E. coli*" |
| ZB19.Contig10 (1424) | 23 | 1412 | 1396 | 91.55 | 42422 | 41034 | AF464738 | putative gag-pol |
| ZB19.Contig11 (78) | | | | | | | "NA" | "*E. coli*" |
| ZB19.Contig12 (1743) | 561 | 1532 | 974 | 90.04 | 40272 | 41239 | AY574035 | rust resistance rp3-1 |
| ZB19.Contig13 (1528) | 853 | 1301 | 449 | 91.31 | 1 | 448 | AY574035 | retrotransposon |
| ZB19.Contig14 (460) | | | | | | | "NA" | "*E. coli*" |
| ZB19.Contig15 (234) | 1 | 234 | 234 | 99.57 | 669 | 436 | J02482 | Coliphage phi-X174 |
| ZB19.Contig16 (2303) | | | | | | | "NA" | "pCHR758mcv" |
| ZB19.Contig17 (1638) | | | | | | | "NA" | "pCHR758mcv" |
| ZB19.Contig18 (1869) | 132 | 1719 | 1590 | 84.97 | 37117 | 35528 | AY664418 | Mo17 locus 9008 |
| ZB19.Contig19 (2133) | 1055 | 2109 | 1055 | 97.63 | 309950 | 308897 | AF090447 | alpha zein gene cluster |

TABLE 10-continued

ZB19 Genbank Homology

| Contig (length) | Contig Alignment | | | | Genbank | | | |
|---|---|---|---|---|---|---|---|---|
| | begin | end | length | % id | begin | end | Accession # | Homologous feature |
| ZB19.Contig20 (1536) | 93 | 1505 | 1422 | 83.97 | 400455 | 401871 | AY664419 | Mo17 locus 9009 |
| ZB19.Contig21 (1614) | 261 | 1556 | 1296 | 96.91 | 238900 | 237606 | AY664418 | Mo17 locus 9008 |
| ZB19.Contig22 (2563) | | | | | | | "NA" | "pCHR758mcv" |
| ZB19.Contig23 (2753) | 695 | 2625 | 1938 | 85.19 | 33521 | 35457 | AY664418 | Mo17 locus 9008 |
| ZB19.Contig23 (2753) | 187 | 680 | 496 | 82.26 | 32998 | 33492 | AY664418 | Mo17 locus 9008 |
| ZB19.Contig23 (2753) | 31 | 148 | 119 | 82.35 | 170387 | 170505 | AY664418 | Mo17 locus 9008 |
| ZB19.Contig24 (2816) | 748 | 2788 | 2046 | 96.19 | 308241 | 306197 | AF090447 | alpha zein gene cluster |
| ZB19.Contig24 (2816) | 136 | 707 | 572 | 94.76 | 308852 | 308282 | AF090447 | alpha zein gene cluster |
| ZB19.Contig25 (2997) | 31 | 770 | 746 | 86.6 | 113462 | 114199 | AY574035 | rust resistance rp3-1 |
| ZB19.Contig25 (2997) | 849 | 1560 | 720 | 86.67 | 104886 | 105601 | AY574035 | rust resistance rp3-1 |
| ZB19.Contig26 (2897) | 482 | 2861 | 2380 | 91.18 | 89258 | 86886 | AY664416 | Mo17 locus bz |
| ZB19.Contig26 (2897) | 35 | 463 | 430 | 93.72 | 93544 | 93117 | AY664416 | Mo17 locus bz |
| ZB19.Contig27 (2845) | 38 | 2822 | 2790 | 92.29 | 75093 | 72309 | AY664416 | Mo17 locus bz |
| ZB19.Contig28 (3308) | 157 | 2297 | 2142 | 91.83 | 116223 | 118359 | AY664413 | B73 locus 9002 |
| ZB19.Contig28 (3308) | 2308 | 2372 | 65 | 92.31 | 118385 | 118446 | AY664413 | B73 locus 9002 |
| ZB19.Contig29 (4998) | 27 | 1161 | 1135 | 96.3 | 189722 | 188588 | AY664416 | Mo17 locus bz |
| ZB19.Contig29 (4998) | 1161 | 1429 | 271 | 93.36 | 195008 | 195276 | AY664416 | Mo17 locus bz |
| ZB19.Contig29 (4998) | 1430 | 2298 | 870 | 92.41 | 31346 | 30482 | AY664416 | Mo17 locus bz |
| ZB19.Contig29 (4998) | 2094 | 4994 | 2903 | 92.08 | 30851 | 27961 | AY664416 | Mo17 locus bz |
| ZB19.Contig30 (8151) | | | | | | | "NA" | "CentC-like TIGR identified" |
| ZB19.Contig31 (10813) | | | | | | | "NA" | "CentC-like TIGR identified" |

The identity, distribution and frequency of repeats within the centromere sequences of ZB19 are set out in Table 11. The repeats were identified by comparing the contigs to the TIGR maize database of the Institute of Genomic Research Web Site. Results of this comparison is summarized in Table 11. Percent divergence is defined as the percentage of a sequence (% of the total number of nucleotides) that is different from another sequence, with nucleotide mismatches are classified as differences.

Nearly all of contigs 4, 8, 11, 14, 15 and 18 match repeat elements without gaps apart from 155 bases on the 5' end of contig 2, a 454 bp gap in the middle of contig 16 and the 3' 1071 bp of contig 17. Sequence regions from ZB19 are identified by 75 named TIGR maize sequence database records. Among these, 23 records are CentC variants and many are multiply represented. The remaining 52 records are not CentC and are either uniquely represented or multiply represented by non-overlapping fragments.

TABLE 11

TIGR Maize Sequence Content in ZB19

| Contig (length) | Contig Match | | | | Maize repeat DB | TIGR |
|---|---|---|---|---|---|---|
| | begin | end | length | % diverge | identifier | homology |
| ZB19.Contig1 (1500) | 1 | 1447 | 1446 | 15.2 | SiTERTOOT0149 | put. retrotrans. |
| ZB19.Contig1 (1500) | 1152 | 1483 | 331 | 13 | SgTERTOOT03898 | put. retrotrans. |
| ZB19.Contig2 (1708) | 30 | 205 | 175 | 17.8 | SgCMCMOOT00130 | centromere-related |
| ZB19.Contig2 (1708) | 212 | 1474 | 1262 | 11.8 | SmOTOT00101839 | family_4154_C17 |
| ZB19.Contig2 (1708) | 1475 | 1700 | 225 | 17 | SgTERTOOT30294 | put. retrotrans. |
| ZB19.Contig2 (1708) | 1475 | 1676 | 201 | 15.2 | SgTERTOOT31072 | put. retrotrans. |
| ZB19.Contig5 (1176) | 10 | 121 | 111 | 9.8 | SgTERTOOT01453 | put. retrotrans. |
| ZB19.Contig5 (1176) | 22 | 1148 | 1126 | 4.7 | SiTERTOOT0208 | put. retrotrans. |
| ZB19.Contig5 (1176) | 977 | 1169 | 192 | 19.2 | SgTERT00100386 | put. retrotrans. |
| ZB19.Contig7 (1325) | 30 | 606 | 576 | 4.9 | SgTERTOOT19733 | put. retrotrans. |
| ZB19.Contig7 (1325) | 560 | 1325 | 765 | 5.6 | SgTERTOOT00141 | put. retrotrans. |
| ZB19.Contig10 (1424) | 12 | 117 | 105 | 9.5 | SgTERTOOT00426 | put. retrotrans. |
| ZB19.Contig10 (1424) | 23 | 1421 | 1398 | 7.1 | SiTERTOOT0207 | put. retrotrans. |
| ZB19.Contig12 (1743) | 1 | 218 | 217 | 5.5 | SiTERTOOT0090 | put. retrotrans. |
| ZB19.Contig12 (1743) | 219 | 1590 | 1371 | 10.9 | SgTERTOOT03659 | put. retrotrans. |
| ZB19.Contig12 (1743) | 1589 | 1743 | 154 | 22.1 | SgTERTOOT29480 | put. retrotrans. |
| ZB19.Contig13 (1528) | 21 | 105 | 84 | 28.2 | SmOTOT00101761 | family_3909_C1 |
| ZB19.Contig13 (1528) | 43 | 805 | 762 | 13.8 | SmOTOT00200539 | family_18_C52 |
| ZB19.Contig13 (1528) | 688 | 819 | 131 | 13.6 | SmOTOT00200521 | family_18_C35 |
| ZB19.Contig13 (1528) | 822 | 1528 | 706 | 5 | SiTERTOOT0162 | put. retrotrans. |
| ZB19.Contig18 (1869) | 16 | 347 | 331 | 9.3 | SmOTOT00201263 | family_457_C3 |
| ZB19.Contig18 (1869) | 33 | 417 | 384 | 20 | SmOTOT00100906 | family_21444_C1 |
| ZB19.Contig18 (1869) | 418 | 1175 | 757 | 13.2 | SiTERTOOT0109 | put. retrotrans. |
| ZB19.Contig18 (1869) | 418 | 1083 | 665 | 8.4 | SgTERTOOT23750 | put. retrotrans. |
| ZB19.Contig18 (1869) | 986 | 1848 | 862 | 32 | SgTERTOOT01238 | put. retrotrans. |
| ZB19.Contig19 (2133) | 1055 | 2109 | 1054 | 2.3 | SiTERTOOT0192 | put. retrotrans. |
| ZB19.Contig20 (1536) | 23 | 1319 | 1296 | 18.9 | SiTERTOOT0103 | put. retrotrans. |
| ZB19.Contig20 (1536) | 1320 | 1508 | 188 | 9.5 | SmOTOT00101322 | family_2963_C1 |
| ZB19.Contig21 (1614) | 51 | 647 | 596 | 21.1 | SgTERTOOT16518 | put. retrotrans. |
| ZB19.Contig21 (1614) | 131 | 1608 | 1477 | 5.3 | SiTERTOOT0172 | put. retrotrans. |

TABLE 11-continued

TIGR Maize Sequence Content in ZB19

| Contig (length) | Contig Match | | | | Maize repeat DB identifier | TIGR homology |
|---|---|---|---|---|---|---|
| | begin | end | length | % diverge | | |
| ZB19.Contig23 (2753) | 7 | 63 | 56 | 13.2 | SmOTOT00200682 | family_21_C7 |
| ZB19.Contig23 (2753) | 22 | 189 | 167 | 10.7 | SmOTOT00100741 | family_1920_C6 |
| ZB19.Contig23 (2753) | 190 | 547 | 357 | 26.1 | SgTERT00T18326 | put. retrotrans. |
| ZB19.Contig23 (2753) | 250 | 399 | 149 | 7.5 | SmOTOT00200636 | family_20_C20 |
| ZB19.Contig23 (2753) | 399 | 632 | 233 | 9 | SmOTOT00201628 | family_73_C1 |
| ZB19.Contig23 (2753) | 640 | 1305 | 665 | 32.8 | SgTERT00T02327 | put. retrotrans. |
| ZB19.Contig23 (2753) | 710 | 1116 | 406 | 32.4 | SgTERT00T26280 | put. retrotrans. |
| ZB19.Contig23 (2753) | 804 | 1364 | 560 | 31.6 | SiTERT00T0139 | put. retrotrans. |
| ZB19.Contig23 (2753) | 1050 | 1247 | 197 | 14.1 | SmOTOT00201653 | family_766_C5 |
| ZB19.Contig23 (2753) | 1271 | 1403 | 132 | 15.8 | SmOTOT00201649 | family_766_C1 |
| ZB19.Contig23 (2753) | 1405 | 1691 | 286 | 11.8 | SmOTOT00201691 | family_79_C1 |
| ZB19.Contig23 (2753) | 1756 | 2702 | 946 | 35.8 | SgTERT00T00119 | put. retrotrans. |
| ZB19.Contig23 (2753) | 1903 | 2039 | 136 | 13.1 | SmOTOT00200145 | family_1251_C1 |
| ZB19.Contig23 (2753) | 2230 | 2626 | 396 | 31.8 | SgTERT00T00404 | put. retrotrans. |
| ZB19.Contig24 (2816) | 14 | 2788 | 2774 | 6 | SiTERT00T0192 | put. retrotrans. |
| ZB19.Contig25 (2997) | 22 | 2767 | 2745 | 21.6 | SiTERT00T0310 | put. retrotrans. |
| ZB19.Contig25 (2997) | 2498 | 2970 | 472 | 25.4 | SgTERT00T26929 | put. retrotrans. |
| ZB19.Contig25 (2997) | 2875 | 2981 | 106 | 15.9 | SgTERT00T08404 | put. retrotrans. |
| ZB19.Contig26 (2897) | 28 | 463 | 435 | 2.8 | SgTERT00T22255 | put. retrotrans. |
| ZB19.Contig26 (2897) | 480 | 2871 | 2391 | 3.7 | SiTERT00T0162 | put. retrotrans. |
| ZB19.Contig27 (2845) | 7 | 2823 | 2816 | 6.3 | SiTERT00T0162 | put. retrotrans. |
| ZB19.Contig28 (3308) | 27 | 2368 | 2341 | 18.9 | SiTERT00T0157 | put. retrotrans. |
| ZB19.Contig29 (4998) | 29 | 1161 | 1132 | 21.8 | SiTERT00T0310 | put. retrotrans. |
| ZB19.Contig29 (4998) | 1162 | 1429 | 267 | 2.6 | SgTERT00T17469 | put. retrotrans. |
| ZB19.Contig29 (4998) | 1430 | 4994 | 3564 | 8.7 | SiTERT00T0170 | put. retrotrans. |
| ZB19.Contig29 (4998) | 2032 | 4998 | 2966 | 1.9 | SiTERT00T0172 | put. retrotrans. |
| ZB19.Contig30 (8151) | 74 | 233 | 159 | 31.8 | SiTERT00T0296 | |
| ZB19.Contig30 (8151) | 368 | 500 | 132 | 6 | SgCMCM00200161 | CentC |
| ZB19.Contig30 (8151) | 501 | 655 | 154 | 2.6 | SgCMCM00200034 | CentC |
| ZB19.Contig30 (8151) | 656 | 810 | 154 | 5.8 | SgCMCM00200282 | CentC |
| ZB19.Contig30 (8151) | 811 | 966 | 155 | 5.8 | SgCMCM00200175 | Cent |
| ZB19.Contig30 (8151) | 967 | 1121 | 154 | 3.2 | SgCMCM00200034 | CentC |
| ZB19.Contig30 (8151) | 1122 | 1276 | 154 | 6.5 | SgCMCM00200356 | CentC |
| ZB19.Contig30 (8151) | 1277 | 1431 | 154 | 5.8 | SgCMCM00200034 | CentC |
| ZB19.Contig30 (8151) | 1432 | 1587 | 155 | 3.9 | SgCMCM00200282 | CentC |
| ZB19.Contig30 (8151) | 1588 | 1743 | 155 | 5.8 | SgCMCM00200175 | CentC |
| ZB19.Contig30 (8151) | 1744 | 1898 | 154 | 4.5 | SgCMCM00200034 | CentC |
| ZB19.Contig30 (8151) | 1899 | 2053 | 154 | 3.2 | SgCMCM00200034 | CentC |
| ZB19.Contig30 (8151) | 2054 | 2208 | 154 | 3.9 | SgCMCM00200356 | CentC |
| ZB19.Contig30 (8151) | 2209 | 2363 | 154 | 4.5 | SgCMCM00200034 | CentC |
| ZB19.Contig30 (8151) | 2364 | 2518 | 154 | 3.2 | SgCMCM00200356 | CentC |
| ZB19.Contig30 (8151) | 2519 | 2674 | 155 | 3.9 | SgCMCM00200228 | CentC |
| ZB19.Contig30 (8151) | 2675 | 2829 | 154 | 3.2 | SgCMCM00200034 | CentC |
| ZB19.Contig30 (8151) | 2830 | 2984 | 154 | 3.2 | SgCMCM00200145 | CentC |
| ZB19.Contig30 (8151) | 2985 | 3139 | 154 | 3.9 | SgCMCM00200034 | CentC |
| ZB19.Contig30 (8151) | 3140 | 3295 | 155 | 1.9 | SgCMCM00200034 | CentC |
| ZB19.Contig30 (8151) | 3296 | 3452 | 156 | 1.9 | SgCMCM00200034 | CentC |
| ZB19.Contig30 (8151) | 3453 | 3607 | 154 | 3.9 | SgCMCM00200034 | CentC |
| ZB19.Contig30 (8151) | 3608 | 3763 | 155 | 1.9 | SgCMCM00200034 | CentC |
| ZB19.Contig30 (8151) | 3764 | 3918 | 154 | 4.5 | SgCMCM00200034 | CentC |
| ZB19.Contig30 (8151) | 3919 | 4073 | 154 | 1.9 | SgCMCM00200034 | CentC |
| ZB19.Contig30 (8151) | 4074 | 4227 | 153 | 2.6 | SgCMCM00200092 | CentC |
| ZB19.Contig30 (8151) | 4228 | 4382 | 154 | 3.9 | SgCMCM00200034 | CentC |
| ZB19.Contig30 (8151) | 4383 | 4538 | 155 | 2.6 | SgCMCM00200034 | CentC |
| ZB19.Contig30 (8151) | 4539 | 4693 | 154 | 3.9 | SgCMCM00200034 | CentC |
| ZB19.Contig30 (8151) | 4694 | 4848 | 154 | 2.6 | SgCMCM00200034 | CentC |
| ZB19.Contig30 (8151) | 4849 | 5003 | 154 | 3.9 | SgCMCM00200356 | CentC |
| ZB19.Contig30 (8151) | 5004 | 5158 | 154 | 5.8 | SgCMCM00200034 | CentC |
| ZB19.Contig30 (8151) | 5159 | 5314 | 155 | 4.5 | SgCMCM00200526 | CentC |
| ZB19.Contig30 (8151) | 5315 | 5468 | 153 | 3.9 | SgCMCM00200034 | CentC |
| ZB19.Contig30 (8151) | 5469 | 5624 | 155 | 5.8 | SgCMCM00200034 | CentC |
| ZB19.Contig30 (8151) | 5625 | 5779 | 154 | 3.2 | SgCMCM00200228 | CentC |
| ZB19.Contig30 (8151) | 5780 | 5934 | 154 | 3.2 | SgCMCM00200034 | CentC |
| ZB19.Contig30 (8151) | 5935 | 6089 | 154 | 3.9 | SgCMCM00200145 | CentC |
| ZB19.Contig30 (8151) | 6090 | 6244 | 154 | 3.9 | SgCMCM00200034 | CentC |
| ZB19.Contig30 (8151) | 6245 | 6399 | 154 | 4.5 | SgCMCM00200145 | CentC |
| ZB19.Contig30 (8151) | 6400 | 6555 | 155 | 3.2 | SgCMCM00200034 | CentC |
| ZB19.Contig30 (8151) | 6556 | 6710 | 154 | 4.5 | SgCMCM00200034 | CentC |
| ZB19.Contig30 (8151) | 6711 | 6865 | 154 | 1.9 | SgCMCM00200034 | CentC |
| ZB19.Contig30 (8151) | 6866 | 7020 | 154 | 3.9 | SgCMCM00200356 | CentC |
| ZB19.Contig30 (8151) | 7021 | 7175 | 154 | 4.5 | SgCMCM00200009 | CentC |
| ZB19.Contig30 (8151) | 7176 | 7330 | 154 | 2.6 | SgCMCM00200228 | CentC |
| ZB19.Contig30 (8151) | 7331 | 7485 | 154 | 5.2 | SgCMCM00200034 | CentC |
| ZB19.Contig30 (8151) | 7486 | 7640 | 154 | 5.2 | SgCMCM00200026 | CentC |

TABLE 11-continued

TIGR Maize Sequence Content in ZB19

| Contig (length) | Contig Match | | | | Maize repeat DB identifier | TIGR homology |
|---|---|---|---|---|---|---|
| | begin | end | length | % diverge | | |
| ZB19.Contig30 (8151) | 7642 | 7796 | 154 | 1.9 | SgCMCM00200034 | CentC |
| ZB19.Contig30 (8151) | 7797 | 7952 | 155 | 4.5 | SgCMCM00200034 | CentC |
| ZB19.Contig30 (8151) | 7954 | 8107 | 153 | 4.6 | SgCMCM00200372 | CentC |
| ZB19.Contig31 (10813) | 23 | 167 | 144 | 4.8 | SgCMCM00200030 | CentC |
| ZB19.Contig31 (10813) | 168 | 322 | 154 | 3.9 | SgCMCM00200356 | CentC |
| ZB19.Contig31 (10813) | 323 | 477 | 154 | 2.6 | SgCMCM00200034 | CentC |
| ZB19.Contig31 (10813) | 478 | 632 | 154 | 3.9 | SgCMCM00200034 | CentC |
| ZB19.Contig31 (10813) | 633 | 788 | 155 | 2.6 | SgCMCM00200034 | CentC |
| ZB19.Contig31 (10813) | 789 | 943 | 154 | 3.2 | SgCMCM00200034 | CentC |
| ZB19.Contig31 (10813) | 944 | 1098 | 154 | 3.9 | SgCMCM00200145 | CentC |
| ZB19.Contig31 (10813) | 1100 | 1254 | 154 | 3.9 | SgCMCM00200034 | CentC |
| ZB19.Contig31 (10813) | 1255 | 1409 | 154 | 2.6 | SgCMCM00200228 | CentC |
| ZB19.Contig31 (10813) | 1410 | 1565 | 155 | 5.8 | SgCMCM00200034 | CentC |
| ZB19.Contig31 (10813) | 1566 | 1720 | 154 | 3.9 | SgCMCM00200356 | CentC |
| ZB19.Contig31 (10813) | 1721 | 1875 | 154 | 2.6 | SgCMCM00200034 | CentC |
| ZB19.Contig31 (10813) | 1876 | 2031 | 155 | 4.5 | SgCMCM00200034 | CentC |
| ZB19.Contig31 (10813) | 2032 | 2186 | 154 | 2.6 | SgCMCM00200034 | CentC |
| ZB19.Contig31 (10813) | 2187 | 2342 | 155 | 5.1 | SgCMCM00200034 | CentC |
| ZB19.Contig31 (10813) | 2343 | 2497 | 154 | 3.9 | SgCMCM00200090 | CentC |
| ZB19.Contig31 (10813) | 2498 | 2649 | 151 | 3.3 | SgCMCM00200260 | CentC |
| ZB19.Contig31 (10813) | 2650 | 2804 | 154 | 1.9 | SgCMCM00200356 | CentC |
| ZB19.Contig31 (10813) | 2805 | 2959 | 154 | 1.9 | SgCMCM00200034 | CentC |
| ZB19.Contig31 (10813) | 2960 | 3114 | 154 | 4.5 | SgCMCM00200034 | CentC |
| ZB19.Contig31 (10813) | 3115 | 3270 | 155 | 3.2 | SgCMCM0O200034 | CentC |
| ZB19.Contig31 (10813) | 3271 | 3425 | 154 | 3.2 | SgCMCM00200034 | CentC |
| ZB19.Contig31 (10813) | 3426 | 3580 | 154 | 2.6 | SgCMCM00200034 | CentC |
| ZB19.Contig31 (10813) | 3581 | 3734 | 153 | 3.9 | SgCMCM00200159 | CentC |
| ZB19.Contig31 (10813) | 3735 | 3890 | 155 | 4.5 | SgCMCM00200034 | CentC |
| ZB19.Contig31 (10813) | 3891 | 4045 | 154 | 1.9 | SgCMCM00200034 | CentC |
| ZB19.Contig31 (10813) | 4047 | 4201 | 154 | 5.2 | SgCMCM00200026 | CentC |
| ZB19.Contig31 (10813) | 4202 | 4356 | 154 | 3.2 | SgCMCM00200090 | CentC |
| ZB19.Contig31 (10813) | 4357 | 4513 | 156 | 2.6 | SgCMCM00200034 | CentC |
| ZB19.Contig31 (10813) | 4514 | 4668 | 154 | 6.5 | SgCMCM00200179 | CentC |
| ZB19.Contig31 (10813) | 4669 | 4823 | 154 | 3.2 | SgCMCM00200034 | CentC |
| ZB19.Contig31 (10813) | 4824 | 4978 | 154 | 5.2 | SgCMCM00200034 | CentC |
| ZB19.Contig31 (10813) | 4979 | 5133 | 154 | 3.9 | SgCMCM00200034 | CentC |
| ZB19.Contig31 (10813) | 5135 | 5289 | 154 | 5.2 | SgCMCM00200026 | CentC |
| ZB19.Contig31 (10813) | 5290 | 5444 | 154 | 3.2 | SgCMCM00200090 | CentC |
| ZB19.Contig31 (10813) | 5445 | 5601 | 156 | 2.6 | SgCMCM00200034 | CentC |
| ZB19.Contig31 (10813) | 5602 | 5756 | 154 | 6.5 | SgCMCM00200179 | CentC |
| ZB19.Contig31 (10813) | 5757 | 5911 | 154 | 3.2 | SgCMCM00200034 | CentC |
| ZB19.Contig31 (10813) | 5912 | 6066 | 154 | 5.2 | SgCMCM00200034 | CentC |
| ZB19.Contig31 (10813) | 6068 | 6221 | 153 | 3.9 | SgCMCM00200034 | CentC |
| ZB19.Contig31 (10813) | 6222 | 6376 | 154 | 4.5 | SgCMCM00200356 | CentC |
| ZB19.Contig31 (10813) | 6377 | 6533 | 156 | 7.1 | SgCMCM00200282 | CentC |
| ZB19.Contig31 (10813) | 6534 | 6686 | 152 | 5.9 | SgCMCM00200026 | CentC |
| ZB19.Contig31 (10813) | 6687 | 6840 | 153 | 4.5 | SgCMCM00200090 | CentC |
| ZB19.Contig31 (10813) | 6841 | 6995 | 154 | 3.9 | SgCMCM00200034 | CentC |
| ZB19.Contig31 (10813) | 6996 | 7150 | 154 | 2.6 | SgCMCM00200104 | CentC |
| ZB19.Contig31 (10813) | 7151 | 7305 | 154 | 3.2 | SgCMCM00200034 | CentC |
| ZB19.Contig31 (10813) | 7306 | 7460 | 154 | 3.2 | SgCMCM00200356 | CentC |
| ZB19.Contig31 (10813) | 7461 | 7616 | 155 | 4.5 | SgCMCM00200034 | CentC |
| ZB19.Contig31 (10813) | 7617 | 7771 | 154 | 3.9 | SgCMCM00200145 | CentC |
| ZB19.Contig31 (10813) | 7772 | 7925 | 153 | 3.2 | SgCMCM00200034 | CentC |
| ZB19.Contig31 (10813) | 7926 | 8081 | 155 | 2.6 | SgCMCM00200034 | CentC |
| ZB19.Contig31 (10813) | 8083 | 8236 | 153 | 4.5 | SgCMCM00200356 | CentC |
| ZB19.Contig31 (10813) | 8237 | 8392 | 155 | 5.8 | SgCMCM00200282 | CentC |
| ZB19.Contig31 (10813) | 8393 | 8547 | 154 | 3.2 | SgCMCM00200034 | CentC |
| ZB19.Contig31 (10813) | 8548 | 8703 | 155 | 3.9 | SgCMCM00200258 | CentC |
| ZB19.Contig31 (10813) | 8704 | 8859 | 155 | 3.9 | SgCMCM00200058 | CentC |
| ZB19.Contig31 (10813) | 8860 | 9015 | 155 | 4.5 | SgCMCM00200034 | CentC |
| ZB19.Contig31 (10813) | 9016 | 9170 | 154 | 3.9 | SgCMCM00200090 | CentC |
| ZB19.Contig31 (10813) | 9171 | 9324 | 153 | 3.9 | SgCMCM00200034 | CentC |
| ZB19.Contig31 (10813) | 9325 | 9479 | 154 | 4.5 | SgCMCM00200228 | CentC |
| ZB19.Contig31 (10813) | 9480 | 9634 | 154 | 3.2 | SgCMCM00200034 | CentC |
| ZB19.Contig31 (10813) | 9635 | 9789 | 154 | 1.3 | SgCMCM00200092 | CentC |
| ZB19.Contig31 (10813) | 9790 | 9917 | 127 | 3.1 | SgCMCM00200234 | CentC |
| ZB19.Contig31 (10813) | 9914 | 10011 | 97 | 2.1 | SgCMCM00200032 | CentC |
| ZB19.Contig31 (10813) | 10012 | 10165 | 153 | 2.6 | SgCMCM00200034 | CentC |
| ZB19.Contig31 (10813) | 10167 | 10320 | 153 | 3.2 | SgCMCM00200356 | CentC |
| ZB19.Contig31 (10813) | 10325 | 10476 | 151 | 2.6 | S8CMCM00200150 | CentC |
| ZB19.Contig31 (10813) | 10477 | 10631 | 154 | 2.6 | SgCMCM00200034 | CentC |
| ZB19.Contig31 (10813) | 10632 | 10785 | 153 | 4.5 | SgCMCM00200092 | CentC |

The contigs of ZB19 consist of sequence that is not repeated within the library apart from all of contig 31 and all but the very 5' end of contig 30 and perhaps a small 400 base repeat in the middle of contig 29. The repeat regions extend approximately 8 and 10 kb in contigs 30 and 31, respectively. Since the repeated regions are apparent both when compared to self and the reverse complement, the larger repeat region consists of many smaller repeat regions that occur both in the forward and reverse direction.

The consensus sequence of the CentC repeat present in ZB19 is set out as SEQ ID NO: 70. The variants of the CentC repeats present in ZB19 are set out in Table 12 where the most common base is indicated. Where the most common base occurs less than 60% of the time, the percent occurrence of each base is reported.

TABLE 12

| CentC consensus and Variation in ZB19 | |
|---|---|
| 1 | T |
| 2 | G (C: 4/G: 96) |
| 3 | G (A: 9/G: 91) |
| 4 | T (A: 3/T: 97) |
| 5 | T (C: 4/T: 96) |
| 6 | C (C: 81/G: 3/T: 16) |
| 7 | C (A: 3/C: 85/G: 1/T: 11) |
| 8 | G (A: 5/G: 95) |
| 9 | G (A: 2/G: 97) |
| 10 | T (G: 1/T: 99) |
| 11 | G (G: 98/T: 2) |
| 12 | G (C: 1/G: 99) |
| 13 | C (A: 1/C: 99) |
| 14 | A (A: 94/C: 3/G: 2) |
| 15 | A (A: 97/C: 2/G: 1) |
| 16 | A (A: 98/G: 2) |
| 17 | A |
| 18 | A (A: 99/C: 1/—: 1) |
| 19 | C (A: 2/C: 97/T: 1) |
| 20 | T (A: 4/C: 3/T: 94) |
| 21 | C (C: 91/T: 9) |
| 22 | G (A: 7/G: 90/T: 3) |
| 23 | T (C: 2/T: 98) |
| 24 | G (C: 3/G: 93/—: 4) |
| 25 | C (A: 4/C: 90/G: 1/T: 4) |
| 26 | H (A: 24/C: 3/T: 55/—: 18) |
| 27 | T (A: 2/G: 3/T: 95) |
| 28 | T (A: 1/G: 1/T: 99) |
| 29 | D (A: 12/G: 27/T: 53/—: 8) |
| 30 | W (A: 48/T: 52) |
| 31 | M (A: 55/C: 1/—: 44) |
| 32 | T (A: 4/C: 1/T: 92/—: 3) |
| 33 | T (T: 1/—: 99) |
| 34 | G |
| 35 | C (C: 99/T: 1) |
| 36 | A |
| 37 | C (A: 3/C: 97) |
| 38 | Y (C: 26/T: 3/—: 71) |
| 39 | C (C: 99/—: 1) |
| 40 | C (C: 93/G: 1/T: 1/—: 4) |
| 41 | C (C: 79/G: 2/T: 2/—: 18) |
| 42 | G (A: 3/C: 1/G: 96) |
| 43 | A (A: 99/G: 1) |
| 44 | C (A: 3/C: 95/T: 3) |
| 45 | A |
| 46 | C (A: 1/C: 96/T: 3) |
| 47 | C |
| 48 | C (C: 97/G: 1/T: 3) |
| 49 | G (G: 1/—: 99) |
| 50 | G (A: 3/G: 92/T: 5) |
| 51 | T (A: 2/T: 98) |
| 52 | T (T: 99) |
| 53 | T (G: 2/T: 98) |
| 54 | T (C: 1/T: 98/—: 1) |
| 55 | C (C: 91/T: 9/—: 1) |
| 56 | G (A: 1/G: 99) |
| 57 | G (A: 10/G: 90) |
| 58 | G (G: 1/—: 99) |
| 59 | A (A: 97/T: 3) |
| 60 | A (A: 99/T: 1) |
| 61 | T |
| 62 | G (A: 4/G: 96) |
| 63 | G |
| 64 | G (A: 3/G: 89/T: 8) |
| 65 | T |
| 66 | G |
| 67 | A |
| 68 | C (C: 96/T: 4) |
| 69 | G (A: 4/G: 96) |
| 70 | T (C: 1/T: 99) |
| 71 | G |
| 72 | C (C: 93/G: 2/T: 5) |
| 73 | G (A: 4/G: 90/T: 6) |
| 74 | G (A: 6/G: 94) |
| 75 | C |
| 76 | A (A: 95/G: 5) |
| 77 | A |
| 78 | C (A: 1/C: 99) |
| 79 | G (A: 3/G: 97) |
| 80 | A |
| 81 | A |
| 82 | A |
| 83 | T |
| 84 | T (A: 1/G: 1/T: 99) |
| 85 | G (A: 4/G: 96) |
| 86 | C (A: 3/C: 94/T: 3) |
| 87 | G (A: 3/G: 97) |
| 88 | C (A: 2/C: 91/G: 1/T: 5/—: 2) |
| 89 | G (A: 4/G: 96) |
| 90 | A (A: 98/T: 2) |
| 91 | A |
| 92 | A (A: 99/C: 1) |
| 93 | C |
| 94 | C (A: 4/C: 96) |
| 95 | A |
| 96 | C (A: 1/C: 96/T: 3) |
| 97 | C (A: 3/C: 92/T: 5) |
| 98 | C (A: 1/C: 99) |
| 99 | C (A: 25/C: 74/—: 1) |
| 100 | A |
| 101 | A |
| 102 | C (C: 3/—: 97) |
| 103 | A |
| 104 | C (A: 1/C: 99/T: 1) |
| 105 | A (A: 97/T: 3) |
| 106 | A (A: 1/—: 99) |
| 107 | T |
| 108 | G (A: 1/G: 94/T: 4) |
| 109 | A (A: 64/C: 1/G: 26/T: 8) |
| 110 | G |
| 111 | T (G: 1/T: 99) |
| 112 | T |
| 113 | T (T: 98/—: 2) |
| 114 | T (T: 98/—: 2) |
| 115 | G (A: 3/G: 94/T: 3/—: 1) |
| 116 | G |
| 117 | A (A: 99/G: 1) |
| 118 | C |
| 119 | C (A: 2/C: 96/T: 3) |
| 120 | T (A: 3/T: 97) |
| 121 | A (A: 90/G: 1/T: 9) |
| 122 | A (A: 99/T: 1) |
| 123 | A |
| 124 | G (C: 1/G: 99) |
| 125 | T (C: 1/T: 99) |
| 126 | A |
| 127 | G (A: 4/G: 96) |
| 128 | T (G: 1/T: 99) |
| 129 | G (A: 2/G: 92/T: 6) |
| 130 | G (G: 72/T: 28) |
| 131 | A |
| 132 | T (G: 6/T: 94) |
| 133 | T (C: 1/T: 99) |
| 134 | G (C: 3/G: 97) |
| 135 | G (A: 2/C: 3/G: 95/T: 1) |
| 136 | G (G: 97/T: 3) |

TABLE 12-continued

CentC consensus and Variation in ZB19

| | |
|---|---|
| 137 | C (A: 2/C: 98) |
| 138 | A (A: 97/C: 2/G: 1) |
| 139 | T |
| 140 | G (A: 3/G: 96/T: 1) |
| 141 | T |
| 142 | T |
| 143 | C (C: 94/T: 6) |
| 144 | G (A: 4/G: 94/T: 3) |
| 145 | T (T: 99) |
| 146 | T |
| 147 | G |
| 148 | C (C: 97/T: 3) |
| 149 | G (A: 2/G: 97/—: 1) |
| 150 | A (A: 96/C: 4) |
| 151 | A (A: 97/T: 3) |
| 152 | A |
| 153 | A |
| 154 | A |
| 155 | C (A: 4/C: 67/G: 3/T: 25/—: 1) |
| 156 | G (A: 13/G: 84/—: 3) |
| 157 | A |
| 158 | A (A: 98/T: 2) |
| 159 | G (G: 99/T: 1) |
| 160 | A |
| 161 | A |
| 162 | A (A: 99/G: 1) |
| 163 | T (C: 1/G: 1/T: 97) |
| 164 | G (C: 1/G: 99) |
| 165 | R (A: 45/G: 55) |
| 166 | T |
| 167 | T |
| 168 | C |
| 169 | Y (C: 41/T: 59) |
| 170 | G (A: 30/G: 70) |
| 171 | G (A: 14/G: 86) |
| 172 | T |
| 153 | mean length |
| 3.8 | std |

Characterization of ZB113

The nucleotide sequence of ZB113 was assembled into 18 contigs with a combined trimmed length of 90 kb. ZB113 contigs 1-18 correspond to SEQ ID NOS: 52-69, respectively.

All but three contigs (9, 12, and 13c) of ZB113 showed significant numbers of mostly high and some low quality matches to various sequencing reads; and all but contigs 12 and 13 showed significant matches to TIGR maize database entries. With the large numbers of inconsistent forward/reverse pairs present within the contigs there may be a number of misassemblies present. Notably, contig 17 might be falsely assembled sequence fragments belonging to contigs 14, 15, and 18. Many large regions of similarity exist between the contigs. Notably, an approximately 1.3 kb region on the 3' end of contig 18 is present several times on the 5' end of contig 18 as well as covering nearly all of contigs 15 and 17, and the 3' half of contig 14.

The sequence analysis of ZB19 indicated that 0.23% of the sequence is simple repeats and low complexity sequence (e.g. AT-rich, T-rich and (TTTTC)n), 17% vector sequence, 78% sequence is present in the TIGR maize database, 4.40% uncharacterized sequence, 47.55% CentC repeat, 0.57% CentA repeat and 31.73% of CRM repeat. About 42.3 kb of the sequence was true repeat sequence, meaning those sequences are repeated within the BAC ZB19 sequence.

ZB113 has 64 simple repeat bases (0.07%) and 145 low complexity bases (0.16%) contained within contigs 12, 13, 16, and 18. This low simple repeat content is summarized in Table 13.

TABLE 13

ZB113 Simple Repeat Content

| | Contig Match | | | % di- | Simple |
|---|---|---|---|---|---|
| Contig (length) | begin | end | length | verge | repeat |
| ZB113.Contig12 (5594) | 1466 | 1488 | 22 | 0 | AT_rich |
| ZB113.Contig12 (5594) | 2391 | 2423 | 32 | 0 | AT_rich |
| ZB113.Contig13 (5111) | 3730 | 3755 | 25 | 0 | AT_rich |
| ZB113.Contig16 (15540) | 3933 | 3995 | 62 | 22.2 | T-rich |
| ZB113.Contig18 (20048) | 16200 | 16263 | 63 | 11.3 | (TTTTC)n |
| | | | 204 | | |

The ZB113 contigs are set out as SEQ ID NOS: 52-69, respectively. These contigs were compared to the NCBI database at the National Institute of Health Web Site using BLAST. Results of the BLAST comparison are set out in Table 14.

TABLE 14

ZB113 GenBank Homology

| | Contig Alignment | | | | Genbank | | | |
|---|---|---|---|---|---|---|---|---|
| Contig (length) | begin | end | length | % id | begin | end | Accession # | Homologous feature |
| ZB113.Contig1 (864) | | | | | | | "NA" | "pCHR758mcv" |
| ZB113.Contig2 (835) | 366 | 547 | 182 | 96.15 | 27727 | 27546 | AC116034 | Zea mays clone |
| ZB113.Contig2 (835) | 587 | 703 | 117 | 99.15 | 21738 | 21622 | AC116034 | Zea mays clone |
| ZB113.Contig2 (835) | 743 | 835 | 93 | 91.4 | 21581 | 21491 | AC116034 | Zea mays clone |
| ZB113.Contig2 (835) | 234 | 279 | 46 | 100 | 27870 | 27825 | AC116034 | Zea mays clone |
| ZB113.Contig2 (835) | 168 | 215 | 48 | 97.92 | 28900 | 28853 | AC116034 | Zea mays clone |
| ZB113.Contig2 (835) | 317 | 344 | 28 | 100 | 27917 | 27890 | AC116034 | Zea mays clone |
| ZB113.Contig3 (903) | 137 | 732 | 598 | 97.99 | 1 | 597 | XM_367004 | Magnaporthe grisea |
| ZB113.Contig4 (1110) | | | | | | | "NA" | "CentC-like TIGR identified" |
| ZB113.Contig5 (586) | | | | | | | "NA" | "pCHR758mcv" |
| ZB113.Contig6 (857) | | | | | | | "NA" | "pCHR758mcv" |
| ZB113.Contig7 (119) | 20 | 95 | 76 | 96.05 | 264 | 339 | AY046113 | yeast 26S ribosomal RNA |
| ZB113.Contig8 (1510) | | | | | | | "NA" | "CentC-like TIGR identified" |
| ZB113.Contig9 (1785) | | | | | | | "NA" | "pCHR758mcv" |
| ZB113.Contig10 (867) | 1 | 831 | 831 | 98.92 | 8132 | 8957 | AF162223 | Tn10 |
| ZB113.Contig11 (3369) | | | | | | | "NA" | "CentC-like TIGR identified" |
| ZB113.Contig12 (5594) | | | | | | | "NA" | "pCHR758mcv" |
| ZB113.Contig13 (5111) | | | | | | | "NA" | "pCHR758mcv" |
| ZB113.Contig14 (8559) | 57 | 4643 | | | | | "NA" | "CRM retrotrans-like TIGR identified" |
| ZB113.Contig14 (8559) | 4643 | 7938 | | | | | "NA" | "CentC-like TIGR identified" |
| ZB113.Contig14 (8559) | 7937 | 8511 | | | | | "NA" | "CRM retrotrans-like TIGR identified" |

TABLE 14-continued

ZB113 GenBank Homology

| Contig (length) | Contig Alignment | | | | Genbank | | | |
|---|---|---|---|---|---|---|---|---|
| | begin | end | length | % id | begin | end | Accession # | Homologous feature |
| ZB113.Contig15 (10771) | | | | | | | "NA" | "CentC-like TIGR identified" |
| ZB113.Contig16 (15540) | 37 | 9786 | | | | | "NA" | "CRM retrotrans-like TIGR identified" |
| ZB113.Contig16 (15540) | 9589 | 10101 | | | | | "NA" | "CentA-like TIGR identified" |
| ZB113.Contig16 (15540) | 9916 | 12079 | | | | | "NA" | "CRM retrotrans-like TIGR identified" |
| ZB113.Contig16 (15540) | 12080 | 12436 | | | | | "NA" | "pCHR758mcv" |
| ZB113.Contig16 (15540) | 12533 | 14274 | | | | | "NA" | "CRM retrotrans-like TIGR identified" |
| ZB113.Contig16 (15540) | 14274 | 15203 | | | | | "NA" | "pCHR758mcv" |
| ZB113.Contig16 (15540) | 15203 | 15404 | | | | | "NA" | "CRM retrotrans-like TIGR identified" |
| ZB113.Contig16 (15540) | 15404 | 15540 | | | | | "NA" | "pCHR758mcv" |
| ZB113.Contig17 (14443) | | | | | | | "NA" | "CentC-like TIGR identified" |
| ZB113.Contig18 (20048) | 57 | 7388 | | | | | "NA" | "CentC-like TIGR identified" |
| ZB113.Contig18 (20048) | 7389 | 10554 | | | | | "NA" | "CRM retrotrans-like TIGR identified" |
| ZB113.Contig18 (20048) | 10512 | 10664 | | | | | "No Match" | None |
| ZB113.Contig18 (20048) | 10633 | 20015 | | | | | "NA" | "CentC-like TIGR identified" |

The identity, distribution and frequency of repeats within the centromere sequences of ZB113 is set out in Table 15. The contigs were also compared to the TIGR maize database at the Institute of Genomic Research Web Site. Results of this comparison are summarized in Table 15. Sequence regions from ZB113 are identified by 54 named TIGR maize sequence database records. Among these, 38 records are CentC variants and many are multiply represented. The remaining 16 records are not CentC and are either uniquely represented or multiply represented by non-overlapping fragments, apart from SmOTOT00200141, SmOTOT00200215, SmOTOT00200264, SmOTOT00200480, SmOTOT00201588.

TABLE 15

ZB113 TIGR Maize Sequence Content

| Contig (length) | Contig Match | | | | Maize Repeat DB | TIGR |
|---|---|---|---|---|---|---|
| | begin | end | length | % diverge | Identifier | homology |
| ZB113.Contig2 (835) | 156 | 384 | 228 | 2.2 | SmOTOT00200480 | family_1868_C1 |
| ZB113.Contig2 (835) | 390 | 698 | 308 | 1.9 | SmOTOT00200215 | family_1380_C2 |
| ZB113.Contig2 (835) | 700 | 748 | 48 | 2.1 | SmOTOT00200303 | family_14706_C1 |
| ZB113.Contig2 (835) | 745 | 835 | 90 | 6.7 | SmOTOT00200264 | family_1431_C3 |
| ZB113.Contig4 (1110) | 78 | 233 | 155 | 3.2 | SgCMCM00200034 | CentC |
| ZB113.Contig4 (1110) | 234 | 369 | 135 | 4.4 | SgCMCM00200034 | CentC |
| ZB113.Contig4 (1110) | 370 | 524 | 154 | 1.9 | SgCMCM00200228 | CentC |
| ZB113.Contig4 (1110) | 525 | 678 | 153 | 1.3 | SgCMCM00200173 | CentC |
| ZB113.Contig4 (1110) | 679 | 833 | 154 | 2.6 | SgCMCM00200034 | CentC |
| ZB113.Contig4 (1110) | 834 | 988 | 154 | 1.3 | SgCMCM00200228 | CentC |
| ZB113.Contig4 (1110) | 989 | 1060 | 71 | 0 | SgCMCM00200173 | CentC |
| ZB113.Contig8 (1510) | 5 | 37 | 32 | 3 | SgCMCM00200269 | CentC |
| ZB113.Contig8 (1510) | 38 | 192 | 154 | 1.9 | SgCMCM00200034 | CentC |
| ZB113.Contig8 (1510) | 193 | 346 | 153 | 1.9 | SgCMCM00200228 | CentC |
| ZB113.Contig8 (1510) | 347 | 501 | 154 | 1.9 | SgCMCM00200034 | CentC |
| ZB113.Contig8 (1510) | 502 | 656 | 154 | 1.9 | SgCMCM00200228 | CentC |
| ZB113.Contig8 (1510) | 657 | 811 | 154 | 1.3 | SgCMCM00200099 | CentC |
| ZB113.Contig8 (1510) | 812 | 966 | 154 | 3.2 | SgCMCM00200034 | CentC |
| ZB113.Contig8 (1510) | 967 | 1122 | 155 | 1.3 | SgCMCM00200530 | CentC |
| ZB113.Contig8 (1510) | 1123 | 1277 | 154 | 3.9 | SgCMCM00200058 | CentC |
| ZB113.Contig8 (1510) | 1279 | 1433 | 154 | 2.6 | SgCMCM00200034 | CentC |
| ZB113.Contig8 (1510) | 1434 | 1471 | 37 | 13.2 | SgCMCM00200214 | CentC |
| ZB113.Contig8 (1510) | 1434 | 1467 | 33 | 8.8 | SgCMCM00200257 | CentC |
| ZB113.Contig8 (1510) | 1434 | 1460 | 26 | 0 | SgCMCM00200350 | CentC |
| ZB113.Contig10 (867) | 1 | 831 | 830 | 0.5 | SmOTOT00102689 | family_7207_C1 |
| ZB113.Contig11 (3369) | 52 | 177 | 125 | 1.6 | SgCMCM00200034 | CentC |
| ZB113.Contig11 (3369) | 178 | 332 | 154 | 1.9 | SgCMCM00200034 | CentC |
| ZB113.Contig11 (3369) | 333 | 486 | 153 | 2.6 | SgCMCM00200017 | CentC |
| ZB113.Contig11 (3369) | 487 | 641 | 154 | 1.9 | SgCMCM00200034 | CentC |
| ZB113.Contig11 (3369) | 642 | 797 | 155 | 1.3 | SgCMCM00200099 | CentC |
| ZB113.Contig11 (3369) | 798 | 954 | 156 | 3.8 | SgCMCM00200014 | CentC |
| ZB113.Contig11 (3369) | 958 | 1115 | 157 | 5.8 | SgCMCM00200034 | CentC |
| ZB113.Contig11 (3369) | 1116 | 1270 | 154 | 2.6 | SgCMCM00200034 | CentC |
| ZB113.Contig11 (3369) | 1271 | 1425 | 154 | 1.9 | SgCMCM00200034 | CentC |
| ZB113.Contig11 (3369) | 1426 | 1579 | 153 | 1.9 | SgCMCM00200228 | CentC |
| ZB113.Contig11 (3369) | 1580 | 1735 | 155 | 1.9 | SgCMCM00200228 | CentC |
| ZB113.Contig11 (3369) | 1736 | 1890 | 154 | 2.6 | SgCMCM00200228 | CentC |
| ZB113.Contig11 (3369) | 1891 | 2046 | 155 | 0.6 | SgCMCM00200095 | CentC |
| ZB113.Contig11 (3369) | 2047 | 2201 | 154 | 1.3 | SgCMCM00200228 | CentC |
| ZB113.Contig11 (3369) | 2202 | 2358 | 156 | 1.9 | SgCMCM00200026 | CentC |

TABLE 15-continued

ZB113 TIGR Maize Sequence Content

| Contig (length) | Contig Match begin | end | length | % diverge | Maize Repeat DB Identifier | TIGR homology |
|---|---|---|---|---|---|---|
| ZB113.Contig11 (3369) | 2359 | 2513 | 154 | 2.6 | SgCMCM00200034 | CentC |
| ZB113.Contig11 (3369) | 2514 | 2669 | 155 | 2.6 | SgCMCM00200034 | CentC |
| ZB113.Contig11 (3369) | 2670 | 2824 | 154 | 0 | SgCMCM00200228 | CentC |
| ZB113.Contig11 (3369) | 2825 | 2979 | 154 | 1.9 | SgCMCM00200228 | CentC |
| ZB113.Contig11 (3369) | 2980 | 3135 | 155 | 0.6 | SgCMCM00200095 | CentC |
| ZB113.Contig11 (3369) | 3136 | 3290 | 154 | 2.6 | SgCMCM00200034 | CentC |
| ZB113.Contig11 (3369) | 3291 | 3328 | 37 | 13.2 | SgCMCM00200214 | CentC |
| ZB113.Contig11 (3369) | 3291 | 3324 | 33 | 8.8 | SgCMCM00200257 | CentC |
| ZB113.Contig11 (3369) | 3291 | 3317 | 26 | 0 | SgCMCM00200095 | CentC |
| ZB113.Contig14 (8559) | 57 | 1862 | 1805 | 0.6 | SiCMCMOOT0036 | CRM |
| ZB113.Contig14 (8559) | 1895 | 2046 | 151 | 1.3 | SmOTOT00201588 | family_6912_C1 |
| ZB113.Contig14 (8559) | 2035 | 2541 | 506 | 24.5 | SiCMCMOOT0036 | CRM |
| ZB113.Contig14 (8559) | 2524 | 3249 | 725 | 1.4 | SmOTOT00200264 | family_1431_C3 |
| ZB113.Contig14 (8559) | 3179 | 3581 | 402 | 23 | SmOTOT00101933 | family_4330_C5 |
| ZB113.Contig14 (8559) | 3296 | 3604 | 308 | 1.9 | SmOTOT00200215 | family_1380_C2 |
| ZB113.Contig14 (8559) | 3610 | 4066 | 456 | 2.5 | SmOTOT00200480 | family_1868_C1 |
| ZB113.Contig14 (8559) | 3968 | 4277 | 309 | 25.4 | SiCMCMOOT0036 | CRM |
| ZB113.Contig14 (8559) | 4245 | 4643 | 398 | 0.8 | SmOTOT00200141 | family_1241_C3 |
| ZB113.Contig14 (8559) | 4643 | 5076 | 433 | 3 | SgTERTOOT02246 | put. retrotrans. |
| ZB113.Contig14 (8559) | 5077 | 5234 | 157 | 2.6 | SgCMCM00200102 | CentC |
| ZB113.Contig14 (8559) | 5235 | 5390 | 155 | 0.6 | SgCMCM00200099 | CentC |
| ZB113.Contig14 (8559) | 5391 | 5545 | 154 | 1.9 | SgCMCM00200034 | CentC |
| ZB113.Contig14 (8559) | 5546 | 5700 | 154 | 1.9 | SgCMCM00200228 | CentC |
| ZB113.Contig14 (8559) | 5701 | 5855 | 154 | 1.9 | SgCMCM00200228 | CentC |
| ZB113.Contig14 (8559) | 5856 | 6011 | 155 | 1.3 | SgCMCM00200095 | CentC |
| ZB113.Contig14 (8559) | 6012 | 6166 | 154 | 3.9 | SgCMCM00200034 | CentC |
| ZB113.Contig14 (8559) | 6167 | 6321 | 154 | 1.9 | SgCMCM00200034 | CentC |
| ZB113.Contig14 (8559) | 6322 | 6476 | 154 | 0.7 | SgCMCM00200228 | CentC |
| ZB113.Contig14 (8559) | 6477 | 6631 | 154 | 1.9 | SgCMCM00200228 | CentC |
| ZB113.Contig14 (8559) | 6632 | 6787 | 155 | 0.6 | SgCMCM00200095 | CentC |
| ZB113.Contig14 (8559) | 6788 | 6942 | 154 | 1.9 | SgCMCM00200228 | CentC |
| ZB113.Contig14 (8559) | 6943 | 7097 | 154 | 1.9 | SgCMCM00200034 | CentC |
| ZB113.Contig14 (8559) | 7098 | 7252 | 154 | 1.9 | SgCMCM00200034 | CentC |
| ZB113.Contig14 (8559) | 7253 | 7409 | 156 | 2.5 | SgCMCM00200026 | CentC |
| ZB113.Contig14 (8559) | 7410 | 7565 | 155 | 0.6 | SgCMCM00200095 | CentC |
| ZB113.Contig14 (8559) | 7566 | 7720 | 154 | 1.9 | SgCMCM00200034 | CentC |
| ZB113.Contig14 (8559) | 7721 | 7875 | 154 | 1.9 | SgCMCM00200034 | CentC |
| ZB113.Contig14 (8559) | 7876 | 7938 | 62 | 3.2 | SgCMCM00200356 | CentC |
| ZB113.Contig14 (8559) | 7937 | 8511 | 574 | 11.5 | SiCMCMOOT0036 | put. retrotrans. |
| ZB113.Contig16 (15540) | 37 | 5452 | 5415 | 1.7 | SiCMCMOOT0036 | put. retrotrans. |
| ZB113.Contig16 (15540) | 5453 | 8994 | 3541 | 25.8 | SiCMCMOOT0036 | put. retrotrans. |
| ZB113.Contig16 (15540) | 8955 | 9353 | 398 | 0.8 | SmOTOT00200141 | family_1241_C3 |
| ZB113.Contig16 (15540) | 9317 | 9520 | 203 | 28.6 | SiCMCMOOT0033 | centromeric repeat |
| ZB113.Contig16 (15540) | 9532 | 9786 | 254 | 17.7 | SgTERTOOT02246 | put. retrotrans. |
| ZB113.Contig16 (15540) | 9589 | 10101 | 512 | 17.1 | SiTERTOOT0090 | CentA |
| ZB113.Contig16 (15540) | 9916 | 12079 | 2163 | 21.6 | SiCMCMOOT0036 | CRM |
| ZB113.Contig16 (15540) | 12533 | 12567 | 34 | 6.1 | SmOTOT00101153 | family_26265_C1 |
| ZB113.Contig16 (15540) | 12537 | 12812 | 275 | 17.4 | SmOTOT00102620 | family_68_C5 |
| ZB113.Contig16 (15540) | 12815 | 13013 | 198 | 18.6 | SmOTOT00100244 | family_1167_C2 |
| ZB113.Contig15 (10771) | 62 | 216 | 154 | 1.9 | SgCMCM00200224 | CentC |
| ZB113.Contig15 (10771) | 217 | 371 | 154 | 1.3 | SgCMCM00200034 | CentC |
| ZB113.Contig15 (10771) | 372 | 526 | 154 | 3.2 | SgCMCM00200034 | CentC |
| ZB113.Contig15 (10771) | 527 | 682 | 155 | 2.6 | SgCMCM00200034 | CentC |
| ZB113.Contig15 (10771) | 683 | 837 | 154 | 1.9 | SgCMCM00200228 | CentC |
| ZB113.Contig15 (10771) | 838 | 994 | 156 | 1.9 | SgCMCM00200026 | CentC |
| ZB113.Contig15 (10771) | 995 | 1150 | 155 | 1.3 | SgCMCM00200095 | CentC |
| ZB113.Contig15 (10771) | 1151 | 1305 | 154 | 3.2 | SgCMCM00200034 | CentC |
| ZB113.Contig15 (10771) | 1306 | 1460 | 154 | 1.9 | SgCMCM00200034 | CentC |
| ZB113.Contig15 (10771) | 1461 | 1615 | 154 | 1.9 | SgCMCM00200228 | CentC |
| ZB113.Contig15 (10771) | 1616 | 1770 | 154 | 1.3 | SgCMCM00200228 | CentC |
| ZB113.Contig15 (10771) | 1771 | 1926 | 155 | 0.6 | SgCMCM00200095 | CentC |
| ZB113.Contig15 (10771) | 1927 | 2081 | 154 | 2.6 | SgCMCM00200034 | CentC |
| ZB113.Contig15 (10771) | 2082 | 2236 | 154 | 1.9 | SgCMCM00200034 | CentC |
| ZB113.Contig15 (10771) | 2237 | 2391 | 154 | 2.6 | SgCMCM00200228 | CentC |
| ZB113.Contig15 (10771) | 2392 | 2547 | 155 | 0.6 | SgCMCM00200095 | CentC |
| ZB113.Contig15 (10771) | 2548 | 2702 | 154 | 2.6 | SgCMCM00200034 | CentC |
| ZB113.Contig15 (10771) | 2703 | 2857 | 154 | 1.9 | SgCMCM00200034 | CentC |
| ZB113.Contig15 (10771) | 2858 | 3012 | 154 | 0.7 | SgCMCM00200228 | CentC |
| ZB113.Contig15 (10771) | 3013 | 3167 | 154 | 1.3 | SgCMCM00200228 | CentC |
| ZB113.Contig15 (10771) | 3168 | 3323 | 155 | 0.6 | SgCMCM00200095 | CentC |
| ZB113.Contig15 (10771) | 3324 | 3478 | 154 | 1.9 | SgCMCM00200034 | CentC |
| ZB113.Contig15 (10771) | 3479 | 3633 | 154 | 1.9 | SgCMCM00200034 | CentC |
| ZB113.Contig15 (10771) | 3634 | 3788 | 154 | 0.7 | SgCMCM00200228 | CentC |
| ZB113.Contig15 (10771) | 3789 | 3943 | 154 | 1.3 | SgCMCM00200228 | CentC |

TABLE 15-continued

ZB113 TIGR Maize Sequence Content

| Contig (length) | Contig Match | | | | Maize Repeat DB Identifier | TIGR homology |
|---|---|---|---|---|---|---|
| | begin | end | length | % diverge | | |
| ZB113.Contig15 (10771) | 3944 | 4099 | 155 | 1.3 | SgCMCM00200095 | CentC |
| ZB113.Contig15 (10771) | 4100 | 4254 | 154 | 2.6 | SgCMCM00200034 | CentC |
| ZB113.Contig15 (10771) | 4255 | 4409 | 154 | 1.9 | SgCMCM00200034 | CentC |
| ZB113.Contig15 (10771) | 4410 | 4564 | 154 | 0.7 | SgCMCM00200228 | CentC |
| ZB113.Contig15 (10771) | 4565 | 4719 | 154 | 0.7 | SgCMCM00200034 | CentC |
| ZB113.Contig15 (10771) | 4720 | 4874 | 154 | 1.9 | SgCMCM00200228 | CentC |
| ZB113.Contig15 (10771) | 4875 | 5029 | 154 | 1.9 | SgCMCM00200228 | CentC |
| ZB113.Contig15 (10771) | 5030 | 5185 | 155 | 1.3 | SgCMCM00200095 | CentC |
| ZB113.Contig15 (10771) | 5186 | 5340 | 154 | 3.2 | SgCMCM00200034 | CentC |
| ZB113.Contig15 (10771) | 5341 | 5495 | 154 | 1.3 | SgCMCM00200034 | CentC |
| ZB113.Contig15 (10771) | 5496 | 5649 | 153 | 1.3 | SgCMCM00200002 | CentC |
| ZB113.Contig15 (10771) | 5650 | 5806 | 156 | 1.3 | SgCMCM00200026 | CentC |
| ZB113.Contig15 (10771) | 5807 | 5961 | 154 | 1.9 | SgCMCM00200034 | CentC |
| ZB113.Contig15 (10771) | 5962 | 6115 | 153 | 0 | SgCMCM00200530 | CentC |
| ZB113.Contig15 (10771) | 6116 | 6270 | 154 | 4.5 | SgCMCM00200058 | CentC |
| ZB113.Contig15 (10771) | 6272 | 6426 | 154 | 3.2 | SgCMCM00200034 | CentC |
| ZB113.Contig15 (10771) | 6427 | 6581 | 154 | 1.3 | SgCMCM00200034 | CentC |
| ZB113.Contig15 (10771) | 6582 | 6737 | 155 | 1.9 | SgCMCM00200099 | CentC |
| ZB113.Contig15 (10771) | 6738 | 6891 | 153 | 1.3 | SiCMCM0020001 | CentC |
| ZB113.Contig15 (10771) | 6892 | 7048 | 156 | 1.3 | SgCMCM00200026 | CentC |
| ZB113.Contig15 (10771) | 7049 | 7203 | 154 | 1.3 | SgCMCM00200034 | CentC |
| ZB113.Contig15 (10771) | 7204 | 7358 | 154 | 1.3 | SgCMCM00200034 | CentC |
| ZB113.Contig15 (10771) | 7359 | 7513 | 154 | 2.6 | SgCMCM00200034 | CentC |
| ZB113.Contig15 (10771) | 7514 | 7668 | 154 | 1.3 | SgCMCM00200017 | CentC |
| ZB113.Contig15 (10771) | 7669 | 7825 | 156 | 1.3 | SgCMCM00200026 | CentC |
| ZB113.Contig15 (10771) | 7826 | 7980 | 154 | 2.6 | SgCMCM00200034 | CentC |
| ZB113.Contig15 (10771) | 7981 | 8135 | 154 | 1.9 | SgCMCM00200034 | CentC |
| ZB113.Contig15 (10771) | 8136 | 8290 | 154 | 1.9 | SgCMCM00200034 | CentC |
| ZB113.Contig15 (10771) | 8291 | 8445 | 154 | 1.3 | SgCMCM00200228 | CentC |
| ZB113.Contig15 (10771) | 8446 | 8600 | 154 | 1.9 | SgCMCM00200228 | CentC |
| ZB113.Contig15 (10771) | 8601 | 8757 | 156 | 0.6 | SgCMCM00200026 | CentC |
| ZB113.Contig15 (10771) | 8758 | 8912 | 154 | 2.6 | SgCMCM00200034 | CentC |
| ZB113.Contig15 (10771) | 8913 | 9067 | 154 | 1.9 | SgCMCM00200034 | CentC |
| ZB113.Contig15 (10771) | 9068 | 9223 | 155 | 2.6 | SgCMCM00200228 | CentC |
| ZB113.Contig15 (10771) | 9224 | 9378 | 154 | 2.6 | SgCMCM00200034 | CentC |
| ZB113.Contig15 (10771) | 9379 | 9533 | 154 | 1.9 | SgCMCM00200099 | CentC |
| ZB113.Contig15 (10771) | 9534 | 9688 | 154 | 2.6 | SgCMCM00200034 | CentC |
| ZB113.Contig15 (10771) | 9689 | 9842 | 153 | 0 | SgCMCM00200530 | CentC |
| ZB113.Contig15 (10771) | 9843 | 9997 | 154 | 3.9 | SgCMCM00200058 | CentC |
| ZB113.Contig15 (10771) | 9999 | 10153 | 154 | 3.2 | SgCMCM00200034 | CentC |
| ZB113.Contig15 (10771) | 10154 | 10308 | 154 | 1.3 | SgCMCM00200034 | CentC |
| ZB113.Contig15 (10771) | 10309 | 10464 | 155 | 1.9 | SgCMCM00200034 | CentC |
| ZB113.Contig15 (10771) | 10465 | 10619 | 154 | 3.2 | SgCMCM00200044 | CentC |
| ZB113.Contig15 (10771) | 10620 | 10759 | 139 | 9.1 | SgCMCM00200311 | CentC |
| ZB113.Contig15 (10771) | 10620 | 10726 | 106 | 3.7 | SgCMCM00200152 | CentC |
| ZB113.Contig17 (14443) | 1 | 91 | 90 | 9.9 | SgCMCM00200454 | CentC |
| ZB113.Contig17 (14443) | 13 | 91 | 78 | 0 | SgCMCM00200530 | CentC |
| ZB113.Contig17 (14443) | 92 | 246 | 154 | 1.9 | SgCMCM00200034 | CentC |
| ZB113.Contig17 (14443) | 247 | 402 | 155 | 1.3 | SgCMCM00200099 | CentC |
| ZB113.Contig17 (14443) | 403 | 561 | 158 | 2.6 | SgCMCM00200102 | CentC |
| ZB113.Contig17 (14443) | 562 | 716 | 154 | 2.6 | SgCMCM00200034 | CentC |
| ZB113.Contig17 (14443) | 717 | 870 | 153 | 1.3 | SgCMCM00200173 | CentC |
| ZB113.Contig17 (14443) | 871 | 1025 | 154 | 1.9 | SgCMCM00200228 | CentC |
| ZB113.Contig17 (14443) | 1026 | 1161 | 135 | 4.4 | SgCMCM00200034 | CentC |
| ZB113.Contig17 (14443) | 1162 | 1317 | 155 | 2.6 | SgCMCM00200034 | CentC |
| ZB113.Contig17 (14443) | 1318 | 1472 | 154 | 1.3 | SgCMCM00200034 | CentC |
| ZB113.Contig17 (14443) | 1473 | 1627 | 154 | 1.9 | SgCMCM00200034 | CentC |
| ZB113.Contig17 (14443) | 1628 | 1782 | 154 | 0.7 | SgCMCM00200034 | CentC |
| ZB113.Contig17 (14443) | 1783 | 1937 | 154 | 1.3 | SgCMCM00200224 | CentC |
| ZB113.Contig17 (14443) | 1938 | 2093 | 155 | 2.6 | SgCMCM00200014 | CentC |
| ZB113.Contig17 (14443) | 2094 | 2249 | 155 | 1.3 | SgCMCM00200102 | CentC |
| ZB113.Contig17 (14443) | 2250 | 2405 | 155 | 1.9 | SgCMCM00200079 | CentC |
| ZB113.Contig17 (14443) | 2406 | 2560 | 154 | 2.6 | SgCMCM00200228 | CentC |
| ZB113.Contig17 (14443) | 2561 | 2715 | 154 | 0 | SgCMCM00200034 | CentC |
| ZB113.Contig17 (14443) | 2716 | 2870 | 154 | 3.2 | SgCMCM00200034 | CentC |
| ZB113.Contig17 (14443) | 2871 | 3025 | 154 | 1.9 | SgCMCM00200224 | CentC |
| ZB113.Contig17 (14443) | 3026 | 3180 | 154 | 2.6 | SgCMCM00200034 | CentC |
| ZB113.Contig17 (14443) | 3181 | 3337 | 156 | 1.9 | SgCMCM00200026 | CentC |
| ZB113.Contig17 (14443) | 3338 | 3492 | 154 | 1.3 | SgCMCM00200228 | CentC |
| ZB113.Contig17 (14443) | 3493 | 3647 | 154 | 1.3 | SgCMCM00200228 | CentC |
| ZB113.Contig17 (14443) | 3648 | 3802 | 154 | 1.9 | SgCMCM00200034 | CentC |
| ZB113.Contig17 (14443) | 3803 | 3957 | 154 | 3.2 | SgCMCM00200034 | CentC |
| ZB113.Contig17 (14443) | 3958 | 4114 | 156 | 0.6 | SgCMCM00200026 | CentC |
| ZB113.Contig17 (14443) | 4115 | 4269 | 154 | 0.7 | SgCMCM00200228 | CentC |

TABLE 15-continued

ZB113 TIGR Maize Sequence Content

| Contig (length) | Contig Match | | | | Maize Repeat DB Identifier | TIGR homology |
|---|---|---|---|---|---|---|
| | begin | end | length | % diverge | | |
| ZB113.Contig17 (14443) | 4270 | 4424 | 154 | 1.3 | SgCMCM00200228 | CentC |
| ZB113.Contig17 (14443) | 4425 | 4579 | 154 | 6.5 | SgCMCM00200224 | CentC |
| ZB113.Contig17 (14443) | 4580 | 4734 | 154 | 0.7 | SgCMCM00200224 | CentC |
| ZB113.Contig17 (14443) | 4735 | 4894 | 159 | 0 | SgCMCM00200500 | CentC |
| ZB113.Contig17 (14443) | 4895 | 5049 | 154 | 2.6 | SgCMCM00200068 | CentC |
| ZB113.Contig17 (14443) | 5050 | 5204 | 154 | 0.7 | SgCMCM00200228 | CentC |
| ZB113.Contig17 (14443) | 5205 | 5359 | 154 | 0.7 | SgCMCM00200228 | CentC |
| ZB113.Contig17 (14443) | 5360 | 5515 | 155 | 1.3 | SgCMCM00200034 | CentC |
| ZB113.Contig17 (14443) | 5516 | 5670 | 154 | 1.3 | SgCMCM00200228 | CentC |
| ZB113.Contig17 (14443) | 5671 | 5826 | 155 | 0.6 | SgCMCM00200095 | CentC |
| ZB113.Contig17 (14443) | 5827 | 5981 | 154 | 1.3 | SgCMCM00200228 | CentC |
| ZB113.Contig17 (14443) | 5982 | 6136 | 154 | 1.9 | SgCMCM00200228 | CentC |
| ZB113.Contig17 (14443) | 6137 | 6292 | 155 | 0.6 | SgCMCM00200095 | CentC |
| ZB113.Contig17 (14443) | 6293 | 6447 | 154 | 1.3 | SgCMCM00200228 | CentC |
| ZB113.Contig17 (14443) | 6448 | 6602 | 154 | 0.7 | SgCMCM00200228 | CentC |
| ZB113.Contig17 (14443) | 6603 | 6757 | 154 | 1.9 | SgCMCM00200034 | CentC |
| ZB113.Contig17 (14443) | 6758 | 6912 | 154 | 1.3 | SgCMCM00200034 | CentC |
| ZB113.Contig17 (14443) | 6913 | 7067 | 154 | 2.6 | SgCMCM00200034 | CentC |
| ZB113.Contig17 (14443) | 7068 | 7224 | 156 | 1.3 | SgCMCM00200026 | CentC |
| ZB113.Contig17 (14443) | 7225 | 7379 | 154 | 0 | SgCMCM00200228 | CentC |
| ZB113.Contig17 (14443) | 7380 | 7533 | 153 | 1.9 | SgCMCM00200228 | CentC |
| ZB113.Contig17 (14443) | 7534 | 7688 | 154 | 1.9 | SgCMCM00200034 | CentC |
| ZB113.Contig17 (14443) | 7689 | 7843 | 154 | 2.6 | SgCMCM00200034 | CentC |
| ZB113.Contig17 (14443) | 7844 | 7998 | 154 | 2.6 | SgCMCM00200034 | CentC |
| ZB113.Contig17 (14443) | 8000 | 8154 | 154 | 3.9 | SgCMCM00200058 | CentC |
| ZB113.Contig17 (14443) | 8155 | 8310 | 155 | 1.3 | SgCMCM00200530 | CentC |
| ZB113.Contig17 (14443) | 8311 | 8465 | 154 | 3.2 | SgCMCM00200034 | CentC |
| ZB113.Contig17 (14443) | 8466 | 8621 | 155 | 0.6 | SgCMCM00200099 | CentC |
| ZB113.Contig17 (14443) | 8622 | 8780 | 158 | 2.6 | SgCMCM00200102 | CentC |
| ZB113.Contig17 (14443) | 8781 | 8935 | 154 | 1.9 | SgCMCM00200034 | CentC |
| ZB113.Contig17 (14443) | 8936 | 9089 | 153 | 0 | SgCMCM00200173 | CentC |
| ZB113.Contig17 (14443) | 9090 | 9244 | 154 | 0.7 | SgCMCM00200228 | CentC |
| ZB113.Contig17 (14443) | 9245 | 9399 | 154 | 1.9 | SgCMCM00200034 | CentC |
| ZB113.Contig17 (14443) | 9400 | 9554 | 154 | 1.9 | SgCMCM00200034 | CentC |
| ZB113.Contig17 (14443) | 9555 | 9709 | 154 | 1.9 | SgCMCM00200034 | CentC |
| ZB113.Contig17 (14443) | 9710 | 9864 | 154 | 0.7 | SgCMCM00200034 | CentC |
| ZB113.Contig17 (14443) | 9865 | 10017 | 152 | 1.3 | SgCMCM00200026 | CentC |
| ZB113.Contig17 (14443) | 10018 | 10171 | 153 | 1.3 | SgCMCM00200002 | CentC |
| ZB113.Contig17 (14443) | 10172 | 10327 | 155 | 1.3 | SgCMCM00200099 | CentC |
| ZB113.Contig17 (14443) | 10328 | 10482 | 154 | 2.6 | SgCMCM00200034 | CentC |
| ZB113.Contig17 (14443) | 10483 | 10637 | 154 | 0.7 | SgCMCM00200034 | CentC |
| ZB113.Contig17 (14443) | 10638 | 10794 | 156 | 1.3 | SgCMCM00200026 | CentC |
| ZB113.Contig17 (14443) | 10795 | 10948 | 153 | 1.3 | SgCMCM00200005 | CentC |
| ZB113.Contig17 (14443) | 10949 | 11104 | 155 | 1.3 | SgCMCM00200099 | CentC |
| ZB113.Contig17 (14443) | 11105 | 11259 | 154 | 1.3 | SgCMCM00200034 | CentC |
| ZB113.Contig17 (14443) | 11260 | 11414 | 154 | 2.6 | SgCMCM00200034 | CentC |
| ZB113.Contig17 (14443) | 11416 | 11570 | 154 | 3.9 | SgCMCM00200058 | CentC |
| ZB113.Contig17 (14443) | 11571 | 11724 | 153 | 0 | SgCMCM00200530 | CentC |
| ZB113.Contig17 (14443) | 11725 | 11879 | 154 | 1.9 | SgCMCM00200034 | CentC |
| ZB113.Contig17 (14443) | 11880 | 12035 | 155 | 0.6 | SgCMCM00200099 | CentC |
| ZB113.Contig17 (14443) | 12036 | 12194 | 158 | 2.6 | SgCMCM00200102 | CentC |
| ZB113.Contig17 (14443) | 12195 | 12351 | 156 | 3.2 | SgCMCM00200026 | CentC |
| ZB113.Contig17 (14443) | 12352 | 12506 | 154 | 0.7 | SgCMCM00200228 | CentC |
| ZB113.Contig17 (14443) | 12507 | 12661 | 154 | 1.3 | SgCMCM00200228 | CentC |
| ZB113.Contig17 (14443) | 12662 | 12816 | 154 | 3.9 | SgCMCM00200224 | CentC |
| ZB113.Contig17 (14443) | 12817 | 12911 | 94 | 3.2 | SgCMCM00200025 | CentC |
| ZB113.Contig17 (14443) | 12911 | 13372 | 461 | 3 | SgTERT00T02573 | put. retrotrans. |
| ZB113.Contig18 (20048) | 57 | 212 | 155 | 0.6 | SgCMCM00200095 | CentC |
| ZB113.Contig18 (20048) | 213 | 367 | 154 | 3.2 | SgCMCM00200034 | CentC |
| ZB113.Contig18 (20048) | 368 | 522 | 154 | 1.9 | SgCMCM00200034 | CentC |
| ZB113.Contig18 (20048) | 523 | 677 | 154 | 1.3 | SgCMCM00200228 | CentC |
| ZB113.Contig18 (20048) | 678 | 832 | 154 | 2.6 | SgCMCM00200228 | CentC |
| ZB113.Contig18 (20048) | 833 | 988 | 155 | 0.6 | SgCMCM00200095 | CentC |
| ZB113.Contig18 (20048) | 989 | 1143 | 154 | 3.2 | SgCMCM00200034 | CentC |
| ZB113.Contig18 (20048) | 1144 | 1298 | 154 | 1.3 | SgCMCM00200034 | CentC |
| ZB113.Contig18 (20048) | 1299 | 1453 | 154 | 2.6 | SgCMCM00200034 | CentC |
| ZB113.Contig18 (20048) | 1454 | 1609 | 155 | 1.9 | SgCMCM00200079 | CentC |
| ZB113.Contig18 (20048) | 1610 | 1765 | 155 | 1.3 | SgCMCM00200102 | CentC |
| ZB113.Contig18 (20048) | 1766 | 1921 | 155 | 0 | SgCMCM00200099 | CentC |
| ZB113.Contig18 (20048) | 1922 | 2077 | 155 | 2.6 | SgCMCM00200014 | CentC |
| ZB113.Contig18 (20048) | 2078 | 2232 | 154 | 2.6 | SgCMCM00200224 | CentC |
| ZB113.Contig18 (20048) | 2233 | 2387 | 154 | 1.9 | SgCMCM00200017 | CentC |
| ZB113.Contig18 (20048) | 2388 | 2542 | 154 | 2.6 | SgCMCM00200034 | CentC |
| ZB113.Contig18 (20048) | 2543 | 2697 | 154 | 2.6 | SgCMCM00200017 | CentC |

TABLE 15-continued

ZB113 TIGR Maize Sequence Content

| Contig (length) | Contig Match begin | end | length | % diverge | Maize Repeat DB Identifier | TIGR homology |
|---|---|---|---|---|---|---|
| ZB113.Contig18 (20048) | 2698 | 2852 | 154 | 1.9 | SgCMCM00200034 | CentC |
| ZB113.Contig18 (20048) | 2853 | 3007 | 154 | 0.7 | SgCMCM00200228 | CentC |
| ZB113.Contig18 (20048) | 3008 | 3161 | 153 | 0 | SgCMCM00200173 | CentC |
| ZB113.Contig18 (20048) | 3162 | 3317 | 155 | 1.9 | SgCMCM00200156 | CentC |
| ZB113.Contig18 (20048) | 3318 | 3473 | 155 | 0 | SgCMCM00200167 | CentC |
| ZB113.Contig18 (20048) | 3474 | 3629 | 155 | 3.2 | SgCMCM00200014 | CentC |
| ZB113.Contig18 (20048) | 3630 | 3784 | 154 | 2.6 | SgCMCM00200017 | CentC |
| ZB113.Contig18 (20048) | 3785 | 3940 | 155 | 0 | SgCMCM00200034 | CentC |
| ZB113.Contig18 (20048) | 3941 | 4096 | 155 | 1.3 | SgCMCM00200104 | CentC |
| ZB113.Contig18 (20048) | 4097 | 4251 | 154 | 1.3 | SgCMCM00200034 | CentC |
| ZB113.Contig18 (20048) | 4252 | 4406 | 154 | 1.3 | SgCMCM00200169 | CentC |
| ZB113.Contig18 (20048) | 4407 | 4562 | 155 | 2.6 | SgCMCM00200034 | CentC |
| ZB113.Contig18 (20048) | 4563 | 4718 | 155 | 2.6 | SgCMCM00200102 | CentC |
| ZB113.Contig18 (20048) | 4719 | 4874 | 155 | 0 | SgCMCM00200099 | CentC |
| ZB113.Contig18 (20048) | 4875 | 5027 | 152 | 2 | SgCMCM00200005 | CentC |
| ZB113.Contig18 (20048) | 5028 | 5183 | 155 | 1.9 | SgCMCM00200095 | CentC |
| ZB113.Contig18 (20048) | 5184 | 5339 | 155 | 1.3 | SgCMCM00200034 | CentC |
| ZB113.Contig18 (20048) | 5340 | 5494 | 154 | 0.7 | SgCMCM00200034 | CentC |
| ZB113.Contig18 (20048) | 5495 | 5649 | 154 | 0.7 | SgCMCM00200034 | CentC |
| ZB113.Contig18 (20048) | 5650 | 5804 | 154 | 0 | SgCMCM00200169 | CentC |
| ZB113.Contig18 (20048) | 5805 | 5959 | 154 | 1.9 | SgCMCM00200224 | CentC |
| ZB113.Contig18 (20048) | 5960 | 6115 | 155 | 1.3 | SiCMCM0020001 | CentC |
| ZB113.Contig18 (20048) | 6116 | 6271 | 155 | 3.2 | SgCMCM00200034 | CentC |
| ZB113.Contig18 (20048) | 6272 | 6426 | 154 | 2.6 | SgCMCM00200034 | CentC |
| ZB113.Contig18 (20048) | 6427 | 6581 | 154 | 3.2 | SgCMCM00200169 | CentC |
| ZB113.Contig18 (20048) | 6582 | 6737 | 155 | 1.9 | SgCMCM00200034 | CentC |
| ZB113.Contig18 (20048) | 6738 | 6892 | 154 | 3.2 | SgCMCM00200034 | CentC |
| ZB113.Contig18 (20048) | 6893 | 7047 | 154 | 1.9 | SgCMCM00200034 | CentC |
| ZB113.Contig18 (20048) | 7048 | 7202 | 154 | 4.5 | SgCMCM00200034 | CentC |
| ZB113.Contig18 (20048) | 7203 | 7388 | 185 | 1.1 | SgCMCM00200225 | CentC |
| ZB113.Contig18 (20048) | 7389 | 7548 | 159 | 0 | SgCMCM00200500 | CentC |
| ZB113.Contig18 (20048) | 7549 | 7703 | 154 | 0.7 | SgCMCM00200224 | CentC |
| ZB113.Contig18 (20048) | 7704 | 7858 | 154 | 0.7 | SgCMCM00200005 | CentC |
| ZB113.Contig18 (20048) | 7859 | 7951 | 92 | 4.3 | SgCMCM00200012 | CentC |
| ZB113.Contig18 (20048) | 7952 | 8370 | 418 | 2 | SmOTOT00200141 | family_1241_C3 |
| ZB113.Contig18 (20048) | 8338 | 8646 | 308 | 25.2 | SiCMCMOOT0036 | CRM |
| ZB113.Contig18 (20048) | 8549 | 8927 | 378 | 5.5 | SmOTOT00200480 | family_1868_C1 |
| ZB113.Contig18 (20048) | 8789 | 8949 | 160 | 4.5 | SmOTOT00200480 | family_1868_C1 |
| ZB113.Contig18 (20048) | 8955 | 9262 | 307 | 2.9 | SmOTOT00200215 | family_1380_C2 |
| ZB113.Contig18 (20048) | 8974 | 9371 | 397 | 25.5 | SmOTOT00101933 | family_4330_C5 |
| ZB113.Contig18 (20048) | 9309 | 10034 | 725 | 2.2 | SmOTOT00200264 | family_1431_C3 |
| ZB113.Contig18 (20048) | 10017 | 10554 | 537 | 27.1 | SiCMCMOOT0036 | CRM |
| ZB113.Contig18 (20048) | 10512 | 10664 | 152 | 26.4 | SmOTOT00201588 | family_6912_C1 |
| ZB113.Contig18 (20048) | 10633 | 13769 | 3136 | 25.3 | SiCMCMOOT0036 | CRM |
| ZB113.Contig18 (20048) | 13802 | 13931 | 129 | 0.8 | SmOTOT00101774 | family_3931_C1 |
| ZB113.Contig18 (20048) | 13932 | 17719 | 3787 | 2.5 | SiCMCMOOT0036 | CRM |
| ZB113.Contig18 (20048) | 17718 | 17780 | 62 | 4.8 | SgCMCM00200021 | CentC |
| ZB113.Contig18 (20048) | 17781 | 17936 | 155 | 1.9 | SgCMCM00200095 | CentC |
| ZB113.Contig18 (20048) | 17937 | 18091 | 154 | 1.9 | SgCMCM00200228 | CentC |
| ZB113.Contig18 (20048) | 18092 | 18246 | 154 | 1.9 | SgCMCM00200034 | CentC |
| ZB113.Contig18 (20048) | 18247 | 18401 | 154 | 1.9 | SgCMCM00200034 | CentC |
| ZB113.Contig18 (20048) | 18402 | 18556 | 154 | 2.6 | SgCMCM00200034 | CentC |
| ZB113.Contig18 (20048) | 18557 | 18711 | 154 | 0.7 | SgCMCM00200034 | CentC |
| ZB113.Contig18 (20048) | 18712 | 18868 | 156 | 1.3 | SgCMCM00200026 | CentC |
| ZB113.Contig18 (20048) | 18869 | 19022 | 153 | 1.3 | SiCMCM0020001 | CentC |
| ZB113.Contig18 (20048) | 19023 | 19177 | 154 | 1.3 | SgCMCM00200099 | CentC |
| ZB113.Contig18 (20048) | 19178 | 19333 | 155 | 2.6 | SgCMCM00200014 | CentC |
| ZB113.Contig18 (20048) | 19334 | 19489 | 155 | 0.6 | SgCMCM00200099 | CentC |
| ZB113.Contig18 (20048) | 19490 | 19647 | 157 | 3.9 | SgCMCM00200058 | CentC |
| ZB113.Contig18 (20048) | 19648 | 19802 | 154 | 3.2 | SgCMCM00200044 | CentC |
| ZB113.Contig18 (20048) | 19803 | 19958 | 155 | 0.6 | SgCMCM00200099 | CentC |
| ZB113.Contig18 (20048) | 19959 | 20015 | 56 | 8.8 | SgCMCM00200457 | CentC |
| ZB113.Contig18 (20048) | 19959 | 20000 | 41 | 2.4 | SgCMCM00200498 | CentC |

The ZB113 contigs 4, 8, 11, 15, and 17 consist of nearly all repeated sequence, contig 14 has an approximately 4 kb stretch of repeated sequence within its 3' half, and contig 18 has a 5 kb and 3 kb of repeated sequence on its 5' and 3' ends. The repeated regions are apparent both when compared to self and the reverse complement, therefore the larger repeat regions consists of many smaller repeat regions that occur both in the forward and reverse direction.

The consensus sequence of the CentC repeat represented in ZB113 is set out as SEQ ID NO: 71. The variants of the CentC repeats present in ZB113 are set out in Table 16 where the most common base is indicated. Where the most common base occurs less than 60% of the time, the percent occurrence of each base is reported.

TABLE 16

| | ZB113 CentC consensus sequence and variants |
|---|---|
| 1 | C |
| 2 | C |
| 3 | A |
| 4 | T |
| 5 | T (G: 0/T: 100) |
| 6 | T (C: 2/G: 0/T: 98) |
| 7 | C (A: 0/C: 92/T: 8) |
| 8 | T (A: 0/C: 0/T: 100) |
| 9 | T (C: 1/G: 1/T: 98/—: 0) |
| 10 | C (A: 1/C: 84/G: 3/T: 12) |
| 11 | G (A: 1/G: 97/T: 2) |
| 12 | T |
| 13 | T |
| 14 | T (G: 0/T: 100) |
| 15 | T (A: 0/T: 100) |
| 16 | T (C: 0/T: 100) |
| 17 | K (G: 0/T: 0/—: 99) |
| 18 | C (A: 0/C: 95/G: 1/T: 3/—: 0) |
| 19 | G (A: 6/C: 0/G: 89/T: 5) |
| 20 | C (A: 0/C: 78/G: 0/T: 21) |
| 21 | M (A: 2/C: 1/—: 97) |
| 22 | A (A: 2/—: 98) |
| 23 | A (A: 99/C: 0/—: 0) |
| 24 | A (A: 97/C: 1/—: 2) |
| 25 | C (C: 90/G: 3/T: 5/—: 2) |
| 26 | G (A: 3/G: 97) |
| 27 | A (A: 97/G: 3/T: 0) |
| 28 | A (A: 98/G: 0/T: 0/—: 1) |
| 29 | C (A: 1/C: 75/G: 1/—: 23) |
| 30 | V (A: 8/C: 2/G: 0/—: 90) |
| 31 | M (A: 0/C: 17/—: 83) |
| 32 | M (A: 17/C: 6/—: 78) |
| 33 | A (A: 75/—: 25) |
| 34 | T (G: 0/T: 99/—: 0) |
| 35 | G (C: 0/G: 99/T: 0) |
| 36 | C (C: 100/T: 0) |
| 37 | C (A: 1/C: 98/G: 0/T: 1) |
| 38 | C (A: 2/C: 84/G: 7/T: 5/—: 2) |
| 39 | B (C: 1/G: 0/T: 0/—: 98) |
| 40 | H (A: 0/C: 0/T: 0/—: 99) |
| 41 | A (A: 100/C: 0/G: 0) |
| 42 | A (A: 99/T: 1) |
| 43 | T (C: 3/T: 97) |
| 44 | C (A: 0/C: 83/G: 0/T: 1/—: 15) |
| 45 | C (C: 99/G: 0/T: 0) |
| 46 | N (A: 0/C: 16/G: 0/T: 0/—: 83) |
| 47 | A (A: 99/C: 1) |
| 48 | C (C: 97/G: 2/T: 1) |
| 49 | T (A: 0/C: 0/T: 99) |
| 50 | W (A: 50/T: 50) |
| 51 | A (A: 99/C: 1/T: 1) |
| 52 | C (C: 99/T: 1) |
| 53 | T (A: 0/T: 100) |
| 54 | T (A: 1/T: 99/—: 0) |
| 55 | T (T: 100/—: 0) |
| 56 | W (A: 1/T: 1/—: 98) |
| 57 | A (A: 0/—: 100) |
| 58 | A (A: 99/G: 1) |
| 59 | G (A: 0/C: 6/G: 94) |
| 60 | G (A: 7/C: 0/G: 92/T: 1/—: 0) |
| 61 | D (A: 1/G: 0/T: 1/—: 99) |
| 62 | T (A: 0/C: 0/T: 99) |
| 63 | C (A: 8/C: 91/G: 0/T: 1) |
| 64 | C (C: 99/T: 0/—: 0) |
| 65 | A (A: 99/C: 0/G: 0/—: 0) |
| 66 | A (A: 99/C: 0/G: 0) |
| 67 | A (A: 100/T: 0) |
| 68 | A |
| 69 | A (A: 2/—: 98) |
| 70 | C (A: 0/C: 99/T: 1) |
| 71 | T (C: 0/T: 100) |
| 72 | C (C: 100/T: 0) |
| 73 | A (A: 100/G: 0) |
| 74 | T (A: 0/C: 0/G: 0/T: 99) |

TABLE 16-continued

| | ZB113 CentC consensus sequence and variants |
|---|---|
| 75 | K (G: 35/T: 1/—: 64) |
| 76 | G (A: 0/G: 64/T: 35/—: 0) |
| 77 | T (A: 0/C: 0/G: 0/T: 64/—: 35) |
| 78 | T |
| 79 | T (G: 1/T: 99/—: 0) |
| 80 | G (A: 1/C: 0/G: 88/T: 8/—: 4) |
| 81 | G (A: 5/G: 95) |
| 82 | G (A: 1/G: 94/T: 5) |
| 83 | G (A: 2/G: 98) |
| 84 | D (A: 0/G: 2/T: 3/—: 95) |
| 85 | T (A: 0/G: 5/T: 95) |
| 86 | G (A: 0/C: 0/G: 99) |
| 87 | G (A: 2/C: 0/G: 94/T: 3) |
| 88 | D (A: 0/G: 0/T: 8/—: 91) |
| 89 | T |
| 90 | T (G: 0/T: 100) |
| 91 | T (C: 1/T: 89/—: 10) |
| 92 | C (A: 0/C: 95/G: 0/T: 4) |
| 93 | G (A: 6/C: 0/G: 86/T: 8) |
| 94 | C (A: 1/C: 98/G: 1/T: 1) |
| 95 | G (A: 37/C: 0/G: 63) |
| 96 | C (A: 1/C: 99/G: 0/T: 0) |
| 97 | A (A: 99/T: 1) |
| 98 | A (A: 94/G: 6/T: 0) |
| 99 | R (A: 0/G: 0/—: 99) |
| 100 | T |
| 101 | T (G: 0/T: 100) |
| 102 | T |
| 103 | C (A: 0/C: 81/G: 1/T: 18/—: 0) |
| 104 | G (A: 0/C: 0/G: 97/T: 2) |
| 105 | R (A: 0/G: 1/—: 99) |
| 106 | T (T: 1/—: 99) |
| 107 | T (G: 0/T: 100) |
| 108 | T (A: 0/T: 100) |
| 109 | G (C: 0/G: 99/T: 0) |
| 110 | T (C: 16/T: 84) |
| 111 | C (A: 0/C: 99/T: 0) |
| 112 | G (A: 4/C: 0/G: 96) |
| 113 | C (A: 0/C: 99/G: 1) |
| 114 | A (A: 98/G: 1/T: 0) |
| 115 | C (A: 0/C: 97/T: 3) |
| 116 | G (A: 1/G: 99) |
| 117 | T |
| 118 | C (C: 97/T: 3) |
| 119 | T (T: 0/—: 100) |
| 120 | C (C: 0/—: 100) |
| 121 | A |
| 122 | C |
| 123 | C (C: 93/T: 7) |
| 124 | C (C: 99/T: 1) |
| 125 | A |
| 126 | T (A: 0/T: 100) |
| 127 | T (G: 0/T: 100) |
| 128 | T (T: 0/—: 100) |
| 129 | C |
| 130 | C (C: 69/G: 0/T: 31) |
| 131 | G (A: 1/G: 99) |
| 132 | A |
| 133 | A |
| 134 | A |
| 135 | A |
| 136 | M (A: 1/C: 25/—: 74) |
| 137 | C (A: 1/C: 72/G: 18/—: 10) |
| 138 | G (A: 1/G: 96/T: 3) |
| 139 | G (A: 5/G: 95) |
| 140 | G (G: 75/T: 8/—: 17) |
| 141 | T (C: 0/T: 100) |
| 142 | G (A: 24/G: 76) |
| 143 | T (C: 0/T: 100) |
| 144 | C (C: 97/G: 2/T: 0) |
| 145 | G (A: 14/G: 86) |
| 146 | G (G: 83/T: 11/—: 6) |
| 147 | G (A: 4/G: 96/T: 0) |
| 148 | K (G: 55/T: 8/—: 37) |
| 149 | K (G: 4/T: 0/—: 96) |
| 150 | T (G: 1/T: 99) |
| 151 | G (A: 0/G: 100) |
| 152 | C (A: 4/C: 96) |

TABLE 16-continued

ZB113 CentC consensus sequence and variants

| | |
|---|---|
| 153 | A (A: 100/T: 0) |
| 154 | T (A: 0/C: 1/T: 99) |
| 155 | A |
| 156 | C (A: 3/C: 68/—: 29) |
| 157 | A |
| 158 | A (A: 96/G: 4) |
| 159 | A |
| 160 | G |
| 161 | C |
| 162 | A (A: 99/T: 1) |
| 163 | C |
| 164 | G (A: 1/G: 99) |
| 165 | A (A: 97/C: 3) |
| 166 | G (A: 1/G: 98/—: 1) |
| 167 | T |
| 168 | T (G: 1/T: 99) |
| 169 | T |
| 170 | T |
| 171 | T |
| 172 | G (G: 99/T: 1) |
| 173 | T (T: 0/—: 100) |
| 174 | C |
| 175 | C |
| 176 | A |
| 177 | C (C: 98/G: 2) |
| 178 | C (A: 2/C: 97/T: 1) |
| 179 | G (A: 3/G: 97) |
| 180 | G |
| 181 | A |
| 182 | A |
| 183 | C |
| 184 | C (C: 99/T: 1) |
| 185 | A |
| 186 | T |
| 187 | C |
| 188 | T |
| mean length | 155 |
| stdev | 1.5 |

The sequence of the CRM retrotransposon (SEQ ID NO: 77) was blasted against the contigs of ZB113 and filtered for hits with alignment lengths greater than 50 to determine the representation of CRM in ZB113. The representation of CRM within ZB113 is summarized in Table 17.

TABLE 17

CRM Fragments in ZB113

| Contig | CRM begin | CRM end | % identity | Contig match begin | Contig match end |
|---|---|---|---|---|---|
| ZB113.fasta.screen.Contig14 | 1 | 930 | 99.3 | 933 | 1862 |
| ZB113.fasta.screen.Contig14 | 1 | 515 | 99.8 | 7937 | 8451 |
| ZB113.fasta.screen.Contig14 | 2796 | 2893 | 91.1 | 2132 | 2035 |
| ZB113.fasta.screen.Contig14 | 5765 | 7571 | 90.9 | 57 | 1862 |
| ZB113.fasta.screen.Contig14 | 6640 | 7156 | 83.7 | 7936 | 8451 |
| ZB113.fasta.screen.Contig16 | 1 | 1434 | 99.4 | 5452 | 4019 |
| ZB113.fasta.screen.Contig16 | 1508 | 5417 | 99.6 | 3947 | 37 |
| ZB113.fasta.screen.Contig16 | 4251 | 4744 | 99.3 | 6565 | 7058 |
| ZB113.fasta.screen.Contig16 | 4626 | 4772 | 80.1 | 12043 | 11897 |
| ZB113.fasta.screen.Contig16 | 4945 | 6236 | 80.8 | 11724 | 10433 |
| ZB113.fasta.screen.Contig16 | 4983 | 5342 | 80.0 | 7297 | 7656 |
| ZB113.fasta.screen.Contig16 | 5487 | 5569 | 80.6 | 7801 | 7883 |
| ZB113.fasta.screen.Contig16 | 5757 | 6213 | 85.7 | 8071 | 8527 |
| ZB113.fasta.screen.Contig16 | 6529 | 6653 | 86.8 | 10140 | 10016 |
| ZB113.fasta.screen.Contig16 | 6608 | 6658 | 82.4 | 8922 | 8972 |
| ZB113.fasta.screen.Contig16 | 6638 | 7572 | 84.3 | 5455 | 4522 |
| ZB113.fasta.screen.Contig18 | 1 | 1434 | 99.0 | 17719 | 16288 |
| ZB113.fasta.screen.Contig18 | 1508 | 3791 | 99.4 | 16214 | 13932 |
| ZB113.fasta.screen.Contig18 | 2796 | 2890 | 99.7 | 10426 | 10520 |
| ZB113.fasta.screen.Contig18 | 4251 | 4744 | 80.3 | 11782 | 12275 |
| ZB113.fasta.screen.Contig18 | 4983 | 5342 | 79.8 | 12514 | 12873 |
| ZB113.fasta.screen.Contig18 | 5487 | 5569 | 80.6 | 13018 | 13100 |
| ZB113.fasta.screen.Contig18 | 5757 | 6213 | 88.0 | 13288 | 13744 |
| ZB113.fasta.screen.Contig18 | 6640 | 7572 | 82.1 | 17720 | 16789 |

Five unique repeats were identified in the nucleotide sequence of ZB113 (SmOTOT00200141, SmOTOT00200215 (2 variants), SmOTOT00200264, SmOTOT00200480, SmOTOT00201588 and analyzed for variation in a manner similar to CentC. The repeat SmOTOT00200141 was too large for analysis with source reads matching a wide variety of locations. The consensus sequence of SmOTOT00200215 are set out as SEQ ID NO: 72 and SEQ ID NO: 73. The consensus of SmOTOT00200480 is set out as SEQ ID NO: 74. The consensus of SmOTOT00201588 is set out as SEQ ID NO: 75. The variants of the unique repeats are set out in Tables 18-20 respectively where the most common base is indicated. Where the most common base occurs less than 60% of the time, the percent occurrence of each base is reported.

The sequences were queried against GenBank, which returned no feature specific hit. SmOTOT00200215.1 (SEQ ID NO: 72) and SmOTOT00200480 (SEQ ID NO: 74) and SmOTOT00201588 (SEQ ID NO: 75) matched a clone from *Zea mays* (AC116034), and SmOTOT00200215.2 (SEQ ID NO: 73) returned no matches.

TABLE 18

SmOTOT00200215.1 Variation in ZB113

| | |
|---|---|
| 1 | T |
| 2 | T |
| 3 | T |
| 4 | C |
| 5 | A |
| 6 | T |
| 7 | C |
| 8 | C |
| 9 | C |
| 10 | G |
| 11 | G |
| 12 | T |
| 13 | C |
| 14 | G |
| 15 | T |
| 16 | T |
| 17 | T |
| 18 | T |
| 19 | T |
| 20 | A |
| 21 | G (A: 17/G: 83) |
| 22 | A |
| 23 | A |
| 24 | C |
| 25 | A |
| 26 | T |
| 27 | A |
| 28 | A |
| 29 | C |
| 30 | T |
| 31 | T |
| 32 | G |
| 33 | A |
| 34 | G |
| 35 | G |
| 36 | T |

TABLE 18-continued

SmOTOT00200215.1 Variation in ZB113

| | |
|---|---|
| 37 | A |
| 38 | C |
| 39 | C |
| 40 | T |
| 41 | T |
| 42 | C |
| 43 | C |
| 44 | G |
| 45 | T |
| 46 | A |
| 47 | A |
| 48 | A |
| 49 | C |
| 50 | C |
| 51 | G |
| 52 | G |
| 53 | G |
| 54 | C |
| 55 | A |
| 56 | T |
| 57 | A |
| 58 | A |
| 59 | C |
| 60 | T |
| 61 | T |
| 62 | T |
| 63 | T |
| 64 | C |
| 65 | G |
| 66 | C |
| 67 | T |
| 68 | C |
| 69 | G |
| 70 | G |
| 71 | G |
| 72 | T |
| 73 | G |
| 74 | T |
| 75 | C |
| 76 | C |
| 77 | A |
| 78 | A |
| 79 | A |
| 80 | A |
| 81 | A |
| 82 | A |
| 83 | T |
| 84 | C |
| 85 | T |
| 86 | G |
| 87 | A |
| 88 | A |
| 89 | A |
| 90 | T |
| 91 | T |
| 92 | T |
| 93 | T |
| 94 | T |
| 95 | A |
| 96 | T (C: 17/T: 83) |
| 97 | A |
| 98 | G |
| 99 | G |
| 100 | A |
| 101 | G |
| 102 | C |
| 103 | T |
| 104 | A (A: 83/T: 17) |
| 105 | G |
| 106 | T |
| 107 | T |
| 108 | G |
| 109 | A |
| 110 | C |
| 111 | A |
| 112 | C |
| 113 | C |
| 114 | A |
| 115 | T |
| 116 | T |
| 117 | C |
| 118 | T (G: 17/T: 83) |
| 119 | G |
| 120 | A |
| 121 | G |
| 122 | G |
| 123 | C |
| 124 | C |
| 125 | G |
| 126 | G |
| 127 | C |
| 128 | C |
| 129 | A |
| 130 | A |
| 131 | A |
| 132 | C |
| 133 | T |
| 134 | C (C: 83/G: 17) |
| 135 | A |
| 136 | C |
| 137 | C |
| 138 | T |
| 139 | A (A: 83/T: 17) |
| 140 | C (C: 83/T: 17) |
| 141 | G |
| 142 | G |
| 143 | T |
| 144 | C |
| 145 | T |
| 146 | G |
| 147 | T |
| 148 | T |
| 149 | T |
| 150 | G |
| 151 | G |
| 152 | G |
| 153 | G |
| 154 | T |
| 155 | T |
| 156 | C |
| 157 | G |
| 158 | A |
| mean length | 156 |
| stdev | 2.9 |

TABLE 19

SmOTOT00200215.2 Variation in ZB113

| | |
|---|---|
| 1 | A |
| 2 | C |
| 3 | A |
| 4 | A |
| 5 | A |
| 6 | C |
| 7 | C |
| 8 | G |
| 9 | A |
| 10 | G |
| 11 | T |
| 12 | C |
| 13 | A |
| 14 | A |
| 15 | C |
| 16 | G |
| 17 | G |
| 18 | Y (C: 50/T: 50) |
| 19 | C |
| 20 | G (G: 80/T: 20) |
| 21 | T |
| 22 | T (C: 40/T: 60) |
| 23 | T (C: 20/T: 80) |
| 24 | C |

TABLE 19-continued

| SmOTOT00200215.2 Variation in ZB113 | |
|---|---|
| 25 | C (C: 80/T: 20) |
| 26 | T (G: 17/T: 83) |
| 27 | T |
| 28 | G (G: 67/T: 33) |
| 29 | T (A: 33/T: 67) |
| 30 | T (G: 17/T: 83) |
| 31 | T |
| 32 | T |
| 33 | T (C: 17/T: 83) |
| 34 | C (C: 67/T: 33) |
| 35 | T (C: 33/T: 67) |
| 36 | C (C: 83/G: 17) |
| 37 | C (C: 67/T: 33) |
| 38 | T |
| 39 | T |
| 40 | C (C: 83/G: 17) |
| 41 | G |
| 42 | G |
| 43 | T |
| 44 | T |
| 45 | A (A: 67/T: 17/—: 17) |
| 46 | A (A: 17/—: 83) |
| 47 | C (C: 17/—: 83) |
| 48 | C (A: 17/C: 67/G: 17) |
| 49 | G |
| 50 | A |
| 51 | A |
| 52 | A |
| 53 | A |
| 54 | A |
| 55 | A |
| 56 | A |
| 57 | A |
| 58 | A |
| 59 | C |
| 60 | A (A: 83/C: 17) |
| 61 | G (A: 17/G: 83) |
| 62 | V (A: 33/C: 33/G: 33) |
| 63 | A |
| 64 | A |
| 65 | A |
| 66 | A |
| 67 | A |
| 68 | A |
| 69 | A |
| 70 | A |
| 71 | A |
| 72 | A (A: 33/—: 67) |
| 73 | M (A: 17/C: 17/—: 67) |
| 74 | C (A: 17/C: 83) |
| 75 | A |
| 76 | A |
| 77 | A |
| 78 | C |
| 79 | C |
| 80 | G |
| 81 | A |
| 82 | G |
| 83 | T |
| 84 | C |
| 85 | M (A: 17/C: 17/—: 67) |
| 86 | A |
| 87 | A |
| 88 | C |
| 89 | G (G: 67/—: 33) |
| 90 | A (A: 67/—: 33) |
| 91 | C (C: 67/—: 33) |
| 92 | C (C: 67/—: 33) |
| 93 | G (G: 67/—: 33) |
| 94 | G (G: 17/—: 83) |
| 95 | C (C: 17/—: 83) |
| 96 | C (C: 17/—: 83) |
| 97 | C (C: 83/T: 17) |
| 98 | T |
| 99 | T (C: 17/T: 83) |
| 100 | C |
| 101 | C |
| 102 | T |
| 103 | T |
| 104 | G |
| 105 | T |
| 106 | T |
| 107 | T |
| 108 | T |
| 109 | T |
| 110 | C |
| 111 | T |
| 112 | C |
| 113 | C |
| 114 | T |
| 115 | T |
| 116 | C |
| 117 | G |
| 118 | G |
| 119 | T |
| 120 | T |
| 121 | A |
| 122 | C |
| 123 | D (A: 50/G: 33/T: 17) |
| 124 | T |
| 125 | A (A: 67/C: 33) |
| 126 | A |
| 127 | A |
| 128 | A |
| 129 | A |
| 130 | A |
| 131 | A |
| 132 | A |
| 133 | C |
| 134 | A |
| 135 | G |
| 136 | A |
| 137 | A (A: 67/—: 33) |
| 138 | A (A: 67/—: 33) |
| 139 | C (C: 67/—: 33) |
| 140 | A (A: 67/—: 33) |
| 141 | A (A: 67/—: 33) |
| 142 | A |
| 143 | A |
| 144 | A |
| 145 | A |
| 146 | A |
| 147 | A |
| 148 | A |
| 149 | G |
| 150 | A |
| 151 | A (A: 67/T: 33) |
| 152 | A |
| 153 | A |
| 154 | C |
| 155 | G |
| 156 | A |
| 157 | A |
| 158 | G |
| 159 | G |
| 160 | A |
| 161 | G |
| 162 | A |
| 163 | A |
| 164 | G (A: 33/G: 67) |
| 165 | G |
| 166 | G |
| 167 | A |
| 168 | T |
| 169 | A |
| 170 | C |
| 171 | G |
| 172 | G |
| 173 | T |
| 174 | T |
| 175 | G |
| 176 | T |
| 153 | |
| 3.6 | |

TABLE 20

| SmOTOT00200480 | Variation in ZB113 |
|---|---|
| 1 | G |
| 2 | A |
| 3 | C |
| 4 | G |
| 5 | T |
| 6 | A |
| 7 | A |
| 8 | C |
| 9 | C |
| 10 | G |
| 11 | A |
| 12 | A |
| 13 | G |
| 14 | G |
| 15 | A |
| 16 | G |
| 17 | A |
| 18 | A |
| 19 | A |
| 20 | A |
| 21 | A |
| 22 | Y (C: 50/T: 50) |
| 23 | A |
| 24 | A |
| 25 | G |
| 26 | G |
| 27 | A |
| 28 | R (A: 50/G: 50) |
| 29 | A |
| 30 | C |
| 31 | G |
| 32 | A |
| 33 | T |
| 34 | G |
| 35 | T |
| 36 | T |
| 37 | G |
| 38 | A |
| 39 | C |
| 40 | T |
| 41 | C |
| 42 | G |
| 43 | G |
| 44 | T |
| 45 | T |
| 46 | T |
| 47 | G |
| 48 | T |
| 49 | G |
| 50 | G |
| 51 | Y (C: 50/T: 50) |
| 52 | G |
| 53 | T |
| 54 | G |
| 55 | A |
| 56 | T |
| 57 | C |
| 58 | A |
| 59 | A |
| 60 | A |
| 61 | Y (C: 50/T: 50) |
| 62 | G |
| 63 | G |
| 64 | R (A: 50/G: 50) |
| 65 | A |
| 66 | G |
| 67 | A |
| 68 | T |
| 69 | G |
| 70 | R (A: 50/G: 50) |
| 71 | T |
| 72 | G |
| 73 | G |
| 74 | C |
| 75 | G |
| 76 | G |
| 77 | C |
| 78 | G |
| 79 | C |
| 80 | T |
| 81 | A |
| 82 | G |
| 83 | G |
| 84 | R (A: 50/G: 50) |
| 85 | T |
| 86 | T |
| 87 | T |
| 88 | G |
| 89 | A |
| 90 | A |
| 91 | T |
| 92 | G |
| 93 | G |
| 94 | T |
| 95 | G |
| 96 | G |
| 97 | A |
| 98 | A |
| 99 | G |
| 100 | A |
| 101 | A |
| 102 | C |
| 103 | A |
| 104 | C |
| 105 | A |
| 106 | A |
| 107 | T |
| 108 | G |
| 109 | C |
| 110 | A |
| 111 | A |
| 112 | C |
| 113 | C |
| 114 | A |
| 115 | G |
| 116 | C |
| 117 | A |
| 118 | A |
| 119 | C |
| 120 | A |
| 121 | A |
| 122 | R (A: 50/G: 50) |
| 123 | K (G: 50/T: 50) |
| 124 | R (A: 50/G: 50) |
| 125 | A |
| 126 | A (A: 50/—: 50) |
| 127 | C |
| 128 | G |
| 129 | C |
| 130 | G |
| 131 | A |
| 132 | A |
| 133 | A |
| 134 | G |
| 135 | C |
| 136 | A |
| 137 | C |
| 138 | A |
| 139 | C |
| 140 | A |
| 141 | A |
| 142 | A |
| 143 | T |
| 144 | T |
| 145 | C |
| 146 | A |
| 147 | A |
| 148 | C |
| 149 | A |
| 150 | A |
| 151 | T |
| 152 | G |
| 153 | C |
| 154 | A |
| 155 | G |
| 156 | A |

TABLE 20-continued

SmOTOT00200480 Variation in ZB113

| | |
|---|---|
| 157 | T |
| 158 | T |
| 159 | A |
| 160 | T |
| 161 | T |
| 162 | G |
| 163 | A |
| 164 | A |
| 165 | A |
| 166 | G |
| 167 | A |
| 168 | A |
| 169 | A |
| 170 | G |
| 171 | T |
| 172 | G |
| 173 | Y (C: 50/T: 50) |
| 174 | G |
| 175 | A |
| 176 | G |
| 177 | G |
| 178 | C |
| 179 | T |
| 180 | C |
| 181 | A |
| 182 | A |
| 183 | A |
| 184 | A |
| 185 | G |
| 186 | G |
| 187 | G |
| 188 | T |
| 189 | G |
| 190 | C |
| 191 | T |
| 192 | G |
| 193 | G |
| 192 | |
| 0.55 | |

SUMMARY

The sequence analysis described above demonstrates that BAC ZB19 is enriched for CentC and BAC ZB113 is enriched for CentC and CRM. The frequency of these repeats is particular to the BACs of the invention and is not a representation of the natural occurrence of these repeats in the maize genome. The relative frequency of sequences within the entire maize genome database (TIGR web site) having homology to CentC or CRM was compared to the frequency in ZB19 and ZB113. CentC hit the maize genome (300 Mb) 530 times over a total aligned length of 70 kb. CRM hit the maize genome 860 times over a total aligned length of 336 kb. The proportion of CentC and CRM in ZB19 and ZB119 as compared to the maize genome is summarized in Table 21.

TABLE 21

| | centC | CrM |
|---|---|---|
| ZB19 | 28.91% | 0.00% |
| ZB113 | 47.55% | 31.73% |
| maize genome | 0.02% | 0.11% |

The invention is claimed as follows:

1. An isolated mini-chromosome comprising a centromere, wherein the centromere comprises:

(a) at least five first repeated nucleotide sequences that hybridize under conditions comprising 0.5×SSC and 0.25% SDS at 65° C. for 15 minutes, followed by a wash at 65° C. for a half hour to any one of: the nucleotide sequence of SEQ ID NO:70 or the nucleotide sequence of SEQ ID NO:71, and (b) at least a second nucleotide sequence comprising a nucleotide sequence that hybridizes under conditions comprising 0.5×SSC and 0.25% SDS at 65° C. for 15 minutes, followed by a wash at 65° C. for a half hour to any one of: the nucleotide sequence of SEQ ID NO:77 or the nucleotide sequence of SEQ ID NO:78, wherein the centromere that confers an ability to the minichromosome to segregate to daughter cells through cell division.

2. The mini-chromosome of claim 1, wherein the first repeated nucleotide sequence is selected from the group consisting of:
   (a) a nucleotide sequence at least 70% identical to SEQ ID NO:70,
   (b) a nucleotide sequence at least 70% identical to SEQ ID NO:71,
   (c) the nucleotide sequence of SEQ ID NO:70, or
   (d) the nucleotide sequence of SEQ ID NO:71.

3. The mini-chromosome of claim 1, wherein the second nucleotide sequence is selected from the group consisting of:
   (a) a nucleotide sequence at least 70% identical to a fragment of SEQ ID NO:77 at least 100 bp in length,
   (b) a nucleotide sequence at least 85% identical to a fragment of SEQ ID NO:77 at least 50 bp in length,
   (c) a fragment of the nucleotide sequence of SEQ ID NO:77 at least 50 bp in length,
   (d) a nucleotide sequence at least 70% identical to a fragment of SEQ ID NO:78 at least 100 bp in length,
   (e) a nucleotide sequence at least 85% identical to a fragment of SEQ ID NO:78 at least 50 bp in length, or
   (f) a fragment of the nucleotide sequence of SEQ ID NO:78 at least 50 bp in length.

4. The mini-chromosome of claim 1, wherein the second nucleotide sequence is at least 100 bp in length.

5. The mini-chromosome of claim 1, wherein the second nucleotide sequence is less than 3909 bp in length.

6. The mini-chromosome of claim 1, wherein the second nucleotide sequence ranges from 50 to 3909 bp in length.

7. The mini-chromosome of claim 1, wherein the centromere comprises at least two copies of the second nucleotide sequence.

8. The mini-chromosome of claim 1, wherein the centromere comprises at least 5 copies of the second nucleotide sequence.

9. The mini-chromosome of claim 1, wherein the centromere comprises n copies of the first repeated nucleotide sequence, wherein n is greater than or equal to 5, and less than 1000.

10. The mini-chromosome of claim 1, wherein the centromere comprises at least 20 copies of the first repeated nucleotide sequence within 3.5 kb of nucleotide sequence.

11. The mini-chromosome of claim 1, wherein at least 5 first repeated nucleotides sequences are in tandem.

12. The mini-chromosome of claim 1, wherein at least 5 first repeated nucleotide sequences are consecutive.

13. The mini-chromosome of claim 1, wherein at least 5 first repeated nucleotide sequences are each separated by less than n number of nucleotides, wherein n is 50.

14. The mini-chromosome of claim 1, further comprising a site for site-specific recombination.

15. The mini-chromosome of claim 1, further comprising at least one exogenous nucleic acid.

16. The mini-chromosome of claim 15, wherein the minichromosome comprises at least two exogenous nucleic acids.

17. The mini-chromosome of claim 15, wherein at least one exogenous nucleic acid is operably linked to a heterologous regulatory sequence functional in plant cells.

18. The mini-chromosome of claim 15, wherein at least one exogenous nucleic acid is operably linked to a plant promoter.

19. The mini-chromosome of claim 15, wherein the exogenous nucleic acid is selected from the group consisting of a herbicide resistance gene, a nitrogen fixation gene, an insect resistance gene, a disease resistance gene, a plant stress-induced gene, a nutrient utilization gene, a gene that affects plant pigmentation, a gene that encodes an antisense or ribozyme molecule, a gene encoding a secretable antigen, a toxin gene, a receptor gene, a ligand gene, a seed storage gene, a hormone gene, an enzyme gene, an interleukin gene, a clotting factor gene, a cytokine gene, an antibody gene, and a growth factor gene.

20. The mini-chromosome of claim 19, wherein the disease resistance gene confers resistance to a virus, bacteria, fungi or nematode.

21. The mini-chromosome of claim 19, wherein the enzyme gene is selected from the group consisting of a gene that encodes an enzyme involved in metabolizing biochemical wastes for use in bioremediation, a gene that encodes an enzyme for modifying pathways that produce secondary plant metabolites, a gene that encodes an enzyme that produces a pharmaceutical, a gene that encodes an enzyme that improves the nutritional content of a plant, a gene that encodes an enzyme involved in vitamin synthesis, a gene that encodes an enzyme involved in carbohydrate or starch synthesis, a gene that encodes an enzyme involved in mineral accumulation or availability, a gene that encodes a phytase, a gene that encodes an enzyme involved in fatty acid or oil synthesis, a gene that encodes an enzyme involved in synthesis of chemicals or plastics, a gene that encodes an enzyme involved in synthesis of a fuel and a gene that encodes enzyme involved in synthesis of a fragrance.

22. The mini-chromosome of claim 15, wherein the exogenous nucleic acid encodes a protein conferring resistance to drought, heat, chilling, freezing, excessive moisture, or salt stress.

23. The mini-chromosome of claim 15, wherein the exogenous nucleic acid is a phosphinothricin resistance gene.

24. The mini-chromosome of claim 23, wherein the phosphinothricin resistance gene is a phosphinothricin acetyltrasferase.

25. The mini-chromosome of claim 15, wherein the exogenous nucleic acid is a glyphosate resistance gene.

26. The mini-chromosome of claim 15, wherein the glyphosate resistance gene is a mutant EPSP synthase.

27. The mini-chromosome of claim 15, wherein the exogenous nucleic acid is a *Bacillus thuringiensis* toxin gene.

28. The mini-chromosome of claim 1, wherein the minichromosome is circular.

29. The mini-chromosome of claim 1, wherein the minichromosome exhibits a segregation efficiency in corn cells of at least 60%.

30. A corn plant cell comprising the mini-chromosome of claim 1.

31. A corn plant cell comprising a minichromosome of claim 1 that (i) is not integrated into the plant cell genome and (ii) confers an altered phenotype on the plant cell associated with at least one structural gene within the minichromo some.

32. The corn plant cell of claim 31, wherein the altered phenotype comprises increased expression of a native gene.

33. The corn plant cell of claim 31, wherein the altered phenotype comprises decreased expression of a native gene.

34. The corn plant cell of claim 31, wherein the altered phenotype comprises expression of an exogenous gene.

35. The corn plant cell of claim 30, further comprising an integrated exogenous structural gene.

36. Plant tissue comprising the corn plant cell of claim 30.

37. A corn plant comprising the corn plant cell of claim 30.

38. A corn plant part comprising the corn plant cell of claim 30.

39. A corn seed obtained from the corn plant of claim 37.

40. A corn plant progeny comprising a mini-chromosome, wherein the corn plant progeny is the result of breeding a corn plant of claim 37.

41. A method of using a plant of claim 37, the method comprising growing the plant to produce a recombinant protein encoded by a structural gene of the mini-chromosome.

42. The method of claim 41, further comprising the steps of harvesting or processing the plant and extracting the recombinant protein therefrom.

43. The method of claim 41, wherein the recombinant protein is a pharmaceutical.

44. The method of claim 41, wherein the plant produces a modified food product.

45. The method of claim 41, wherein the recombinant protein is an enzyme.

46. The method of claim 45, wherein the enzyme is selected from the group consisting of an enzyme involved in metabolizing biochemical wastes for use in bioremediation, an enzyme for modifying pathways that produce secondary plant metabolites, an enzyme that produces a pharmaceutical, an enzyme involved in vitamin synthesis, an enzyme involved in starch synthesis, an enzyme involved in mineral accumulation or availability, an enzyme involved in fatty acid synthesis, an enzyme involved in synthesis of chemicals or plastics, and enzyme involved in synthesis of a fragrance.

47. An isolated plant mini-chromosome comprising a centromere, wherein the centromere comprises
 (a) a first nucleic acid segment comprising at least 50 consecutive copies of a CentC repeated nucleotide sequence,
 (b) a second nucleic acid segment comprising at least 50 consecutive copies of a CentC repeated nucleotide sequence; and
 (c) at least one retrotransposon, wherein the retrotransposon is dispersed within the repeated nucleotide sequences,
 wherein the centromere that confers an ability to the mini-chromosome to segregate to daughter cells through cell division.

48. The mini-chromosome of claim 47, wherein the first and second nucleic acid segments are in head to head orientation or tail to tail orientation or head to tail orientation.

49. The mini-chromosome of claim 47, wherein the retrotransposon is CentA or CRM.

50. The mini-chromosome of claim 47, wherein said mini-chromosome further comprises at least one telomere.

51. A corn plant comprising the mini-chromosome of any one of claims 48-50.

52. A recombinant construct comprising a nucleic acid comprising:
 (a) a first nucleic acid segment comprising at least 10 consecutive copies of a CentC repeated nucleotide sequence,
 (b) a second nucleic acid segment comprising at least 10 consecutive copies of a CentC repeated nucleotide sequence; and
 (c) at least one retrotransposon, wherein the retrotransposon is dispersed within the repeated nucleotide sequences,
 wherein the recombinant construct confers an ability to segregate to daughter cells through cell division.

53. The recombinant construct of claim 52, wherein the retrotransposon is CentA or CRM.

54. A recombinant construct comprising a nucleic acid comprising:
 (a) a first nucleic acid segment comprising at least 10 consecutive copies of CentC, and
 (b) at least one retrotransposon, wherein the retrotransposon is CentA or CRM,
 wherein the recombinant construct confers an ability to segregate to daughter cells through cell division.

55. A recombinant construct comprising a nucleic acid comprising:
 (a) a first nucleic acid segment comprising at least 10 consecutive copies of a CentC repeated nucleotide sequence, and
 (b) at least one copy of CentA and at least one copy of CRM,
 wherein the isolated nucleic acid confers an ability to segregate to daughter cells through cell division.

56. The recombinant construct of any one of claims 52-55, further comprising a nucleic acid comprising at least 30 copies of telomeric repeats.

57. A transgenic corn plant comprising the recombinant construct of claim 56.

58. A method for making a transgenic corn plant comprising a plant mini-chromosome having a centromere, the method comprising:
 (a) contacting at least one corn plant cell with the recombinant construct of claim 56,
 (b) identifying at least one corn plant from step (a) comprising a plant mini-chromosome having a centromere,
 (c) regenerating a fertile corn plant from the corn plant cell of step (b) wherein said corn plant comprises a plant mini-chromosome having a centromere.

59. The method of claim 58, wherein step (a) further comprises contacting at least one plant cell with a polypeptide that stimulates cell growth.

60. The method of claim 59, wherein the polypeptide is wuschel or LecI.

* * * * *

UNITED STATES PATENT AND TRADEMARK OFFICE
CERTIFICATE OF CORRECTION

PATENT NO. : 8,222,028 B2
APPLICATION NO. : 12/066175
DATED : July 17, 2012
INVENTOR(S) : Helge Zieler et al.

It is certified that error appears in the above-identified patent and that said Letters Patent is hereby corrected as shown below:

In the Claims:

Column 332, Line 48, Claim 60, "wuscheI or LecI" should be "wuscheI or Lec1".

Signed and Sealed this
Twenty-third Day of September, 2014

Michelle K. Lee
*Deputy Director of the United States Patent and Trademark Office*

SEQUENCE LISTING

```
<160> NUMBER OF SEQ ID NOS: 89

<210> SEQ ID NO 1
<211> LENGTH: 2139
<212> TYPE: DNA
<213> ORGANISM: Drosophila melanogaster

<400> SEQUENCE: 1
gttgtccgca gcggagatgc aactgatgca acccacattt cagatcaccg acaacgtgca      60
gcgcggcaac tacgccactc tgaccgacaa ggatgtggcg catttcgagc agctcctggg     120
caagaacttc gtgctcactg aggacctgga gggatacaac atctgcttcc ttaagaggat     180
tcgaggtagg ttgtgtaacc aaattcattc acattcgtgt gccctttaat gaatttctcc     240
gatgaattgc ttcaaccagg caacagcaag ttggtgctta agcccggaag cacggcggag     300
gtggccgcca tcctgaagta ctgcaacgag cgtcgtttgg cggtggtgcc gcagggcggg     360
aacacaggtc tagtgggcgg atccgtgccg atctgcgacg agattgtcct ttctctagcg     420
cgcctgaaca aggtgttatc cgtggacgag gtcaccggca ttgctgtcgt ggaggcgggc     480
tgcatcctgg agaacttcga tcagagggcc agagaggtgg gcttgacggt gccactggac     540
ctgggcgcca aggccagttg ccacatcggg ggcaatgtgt ccacaaacgc gggcggagtg     600
cgggtggtgc gttacggcaa tctgcacggc tctgttttgg gcgtggaggc ggtgctggcc     660
accggtcagg tgctggacct tatgtccaac ttcaagaagg acaacaccgg ctaccacatg     720
aagcacttgt tcataggatc cgagggcact ctgggcgtgg tcacgaagct ttcgatgctc     780
```

```
tgcccccatt cctcgcgagc ggtgaacgtg gccttcatcg gcctgaactc cttcgacgat    840
gtgctgaaga cttttgtcag tgccaagcgt aatctgggcg agattctaag ctcctgcgag    900
ctgattgacg agcgggcctt gaacaccgcc ctcgagcagt tcaagttcct gaagtgagtt    960
gcgccacctt tgtcttctct gagcgttacc aatcctgttc acaaacttat ttcccatagc   1020
tcccccattt cgggatttcc cttctacatg ctcatcgaga cctcgggcag caacggtgac   1080
cacgacgagg agaagatcaa ccagttcatt ggggacggta tggagcgtgg cgagatccag   1140
gatggcaccg taaccggtga tcccggcaag gtgcaggaga tctggaagat ccgcgaaatg   1200
gtgccgctgg gtctgatcga aagagcttc tgcttcaagt acgacatctc gctgcctctg   1260
cgggacttct acaacattgt ggacgtgatg cgagagaggt gcggtcccct ggccacagtt   1320
gtctgcggat acggccatct gggggactct aatctgcacc tgaacgtctc ctgcgaggag   1380
tttaacggcg agatctacaa gcgggtcgaa cccttcgtct acgagtacac ctccaagctg   1440
aagggcagca ttagtgcgga gcacggcatt ggcttcctga agaaggacta cctgcactac   1500
tccaaggacc cggtggccat ggctacatg cgcgagatga agaagctgct ggaccccaac   1560
agcatcctca tccctataa ggtgcttaac tgaaggcttc tacctaatag attctatttt   1620
ttttgtttgt gtgtaattt cataaccta taatacagaa atggcattag aagtgaattt   1680
tgttaacttg tgaagttaaa aaggaccatc atatttggca cgaaaccaat gggcaaaact   1740
tacttataaa atagtccgaa aaatagtat ataccagttt ttacagtacc acattatagg   1800
tactcggagg taataataga aaaaacacta tctttgcatt tactgttaca ctacgaagca   1860
ctatatttag tagcagtact cattagagtc cactcacaaa attagcacca accggcagta   1920
attggtcaag gatcggcgat agcttcaaac tccgaagttc aaagtcaaac tgccgccctg   1980
cgaaagcttc gcgagtggag cttttctgca cttatcgata gctaacattg tggcgcgact   2040
atcgatcgac gagctgccgc ttaacagtgc catatataga ttgtaacatt agaagctcaa   2100
atcattgttg gagcacaaac cacaaagaac acacgaaac                          2139

<210> SEQ ID NO 2
<211> LENGTH: 2191
<212> TYPE: DNA
<213> ORGANISM: Drosophila melanogaster

<400> SEQUENCE: 2
aaaatatttc acctcatttt ccgcacacca tttataagca aagttacccc caacccataa     60
cttttatggt aagtaataca gaccctccaa gttcggcaaa tcgatacccca gcgaccttga    120 gcttgacatt tatatatatg ccagaatata acgaccacgt gctgtcaact gtgtcaggaa    180
aagctcaccc acactttctt tggaggagct gtgctcccta aacgaatttc attgtcaagg    240
tcgcacgcac aaaaatgaag aggaaaagct gaatgtgggt ggaaatgccg gccggcacga    300
ccttgaagcc agttgggtga gaaataaaaa gcttttgccg gtaggagact tgtgaacat     360 cacccacaag tggcggactt ggccttggcg atggccttgt tggagctccc tcagcaaaaa    420
tgttacatag ggggaggaaa taagctcaat tggctttatg ctttccgctc cctgaagtc     480 ctttctcgga atgttaaagt gttaaatgac atttattgaa catttgggac agaggaggag    540
ataatacaat atacttgtct aattaaaaaa aatcgttatt atgatttatt ccatatgtaa    600
gatttaattt catcatgatt gtaaataaat tatataaaac aaattcaata aatttacatt    660
attgataaaa tttatttttt catgaaatta tacccaaaaa ttattctcaa ttttttcttat   720 aatcagtttt gcataagtat actttcttca tacccctcta ccacagccac tgctttcttg    780
```

| | |
|---|---|
| actttgcaac tatccgggaa cagcttatca taatggatga gctgcagcta acggaaaatg | 840 |
| ggggagctgg gatcaaacat tttccaaggt tgaaattgtc gtcagcataa tgtttgaggg | 900 |
| agctggattc gcgttagctt gaaggtcaat ccatttgggt gcccttttgtt atggtcaagt | 960 |
| ttaaggctgc aataggggga atcttcaagg accattacgc aaggttttcg catcaaagat | 1020 |
| ttgccgtgca agcttttttga gttgaaggat gcttaacttg aaagcgggtt agtggttcca | 1080 |
| agagatttta ggtgaaggag actccgctgt tttgaaatat attaagtatg taagaagta | 1140 |
| tactataaat aacccaaagt gatacaatgt aagaaaagat ctcgttggtc cctggtataa | 1200 |
| atttgtttgc cattaatgaa tattgaaaat aataattata ctaataatag gtacaataag | 1260 |
| caagattaaa ttgcatttaa tcaccaaaaa tcagtttcta tgcgaaccaa aatgtcataa | 1320 |
| caaacaattg ttgattcatc cgtagtgaaa tccaagttcg aaattcgaaa tgagcatacg | 1380 |
| acgaccaaac ttcccctcaa aattgctaga ctcagctaga gcaagtacgc ccaagttaac | 1440 |
| ccctgaaatt cgaaatgaat tcgatgccgc gcttcgaaca acgaaatccc aaagagctta | 1500 |
| cgttttattt gacgtagcac tcttacgtga atgattttc cccaattccg ctctcatttc | 1560 |
| ccgagtctct caccgcttct cagccacttt cccacccccct ttctagttcc gaagtaaagg | 1620 |
| taacaaaggc agccgtgtct ttggggtggt aaactggcgg tggtggtggc acattgtcag | 1680 |
| tggtgtgggt tcctgtggtt ggtggttcaa ttggttggtt gttggcataa acaaagcaca | 1740 |
| cacacaatac acacaaactc ccgggggggtg gtggaaattg ggagggtgac attcactgcg | 1800 |
| agagaggaac tcgcttccta taggaaagta caaagagagc tatttataaa atgtgactgc | 1860 |
| agcaaggata tttacagtca gtccactctg aaacctcgac gagagaacat tgaataacaa | 1920 |
| gcggaagcga aaagcgcagt tgaaagttcg tcaaaaagcg acaagtttcc tcgttcgttt | 1980 |
| tcccgccaaa tgagtcagaa aaattttcca agtgctcgat acgaaacata aagacttaca | 2040 |
| agacttaaag tgcaagcagt gaatggaata tattattcct cagcgatatt gaaatcaaac | 2100 |
| attaaaaata tatgctacac taagttata tattttttta aagattcata cgttttgtaa | 2160 |
| aatcacattt tgtattaaat taaataccgc c | 2191 |

<210> SEQ ID NO 3
<211> LENGTH: 2035
<212> TYPE: DNA
<213> ORGANISM: Drosophila melanogaster

<400> SEQUENCE: 3

| | |
|---|---|
| tgggtgcgtc gcaggtttca ctggaaaaca atttgcactt tgtttgtgg agtcgacaac | 60 |
| aaaagcattc acttgtctaa gactctctca ttcataactc gcactttagt tcactgaacc | 120 |
| gcacgcaaaa ctttggggcg acaacatgt tttcgaggtg ccaaaagctt cataaaacta | 180 |
| ccaatccatt agattaaatt ccaggcggta catcttttgg ggatgattca tgtggcaggg | 240 |
| gttctctact cgtttacaat catatcatca tcttcaagat catatagttt atcatatcag | 300 |
| tagagtacta caatataatg cataaactaa gccaaataac tttatgacgc gtgcttatgc | 360 |
| gaaagtaaac tttattatca aatttactta accgtgaaat caaaaccttt atataaacac | 420 |
| gaatattatt atctttgcta aataaaactc tcgcttaaca aacaatgaca cttcaattcc | 480 |
| aacatagagt ttatcttaag ccaataacca aaaacggaac ttacataact tgccaacaaa | 540 |
| catatgaata tagctatttc ggatcgtggg agaccattat gcatacaagg cacgctccta | 600 |
| aaaccgtgt taaacaaata tatgtcaaat gtatatctta aaaagcgcg cacatatctt | 660 |
| ttgaaatatc ttcacccaga gtatgtatga gattaaactg gattagcact aagccacagc | 720 |

```
ttctgtagat agaaatttta tgcagagagt agattatttg gctgctgagc aatttgacca    780
ccacaagata gcagagaaca tctgacattt tctatatcca tataataaaa ctgacttaac    840
actaagctga agtggtatgt ttaaatcctc cagctaataa atcgagacta aacgccctat    900
cttatagtga tatataatag tatctatatg tgtattgtca tttactgttt atgagtattt    960
gaaaaaacca ttctatattt tataggttag ttaataaata ttttgatata catatgtaga   1020
ttggctcaca cgtacttatg acccactaca taataaaatt gttttgtttt ttaatagaat   1080
aatggtttat aaaaagttta gactcacacg gaaatgataa actctttgca aatacagctt   1140
tcattttatt acaaattgca ctctttcaga tctgcagttg ctatgccaac ctttattcc    1200 ctttactaaa agggtatact aggcttactg aacagtatgt aactggtaaa gtaaagcgtt   1260
tccgattcta taaattatat atctaaactt tgatcagtc gaatccatct gaacacattc    1320
tgtcacatta gattattcca gaaactcaac ttaaacatgt gtatttttta agaccattat   1380
caaggatatt aaaaatggtc tcctaaaatt taataaacaa aagtgtcaca tcaaatttaa   1440
gacgtaaatt aatattttt ttctatggtg aaataattgt tattttccaa tgttgtgaaa   1500
taataaatgt atcttttcaa cgcacacatt ttcaaggttt taataataat agtgactcgt   1560
gcgtgaataa gagagaaatt aagatttaa aaaagaataa aattcagaga tgtgatctgt   1620
aaaaattatt taccaatttt catttacccc cgaaagtgat gctaatggtt aaaacggcat   1680
ttgcgactta tctcctacgt aatattgcaa aataaggat ttggttagat gagtgtgaag   1740
taaacaagat gcaagttttt ggagataaa acatagcct tgagtcttgg tcatgtttac    1800
ttggcaccag gccgcgatta tcagcgctac tagtcgtaat ttgagttaga cctttaatac   1860
tctaagtgag agtgatgata tacgatttcc cagccacttg ctttctacga aatgcgctaa   1920
aaaaaatccc taactacaca aagatttgtg ttgttatcca ggtgttctga tataaaaggc   1980
ggcaaggaaa ttgatggcat catcagtatc aaagtgagag tgattgcagt cacac         2035

<210> SEQ ID NO 4
<211> LENGTH: 2136
<212> TYPE: DNA
<213> ORGANISM: Drosophila melanogaster

<400> SEQUENCE: 4
atgggacggt cctattctca gcaaaaattg acaagaacaa caacaatgtc tatggaaaat     60
cgaacttcat cccagcacct gcagaaatcc cgagcgagtc ggggaaaaag tatttaaccc    120
ccgaaagggt tttccccaaa ataatgaagt aatgaatgaa gcgaaaaaca ctggccgcca    180
atctacctaa tactaatgag cgggccaacc cgaccaggaa ttttgcaag tcaggtactt     240 caacggatat atgggttcga caagtgcgga ttttcccgcg acatcaatga ggacttggcc    300
gggttatccg cggtgctcat cgggcaattc cgcggccgag gacttcatcg tagtgatcat    360
taggtagata tgtgcatgga tgtgacatgg cgatcattgc gcggaataac acacgtaata    420
accgagatat ccgggatgac ccaccaggta ggatgtgagg acatatagaa aaccccagc     480 cagttttcc actcgtcgtg gcttgttttg cttgagtttc gctgactgcg taattggata    540
agatgggaaa ttactttaaa tccttcgctg atccacatcc ggacattcgt cgaaggaaaa   600
tccattgcag ggaaatacga aatggaaatg cggctgggtt attggctcga catttcccat   660
cttccctcac gccattggtt gcaggatcgc ggggaattgg aattccgcgc tggaattttt   720
tgtcacctct tgggtttatc aaaacttttg ggtttgctat ggattttttc caattttacc   780
accgcgcctg gttttttttt tttgacgacg cggaaaatcg gacttggcta tgcgggcttg   840
```

```
tctgttttc cgggtacaaa gtctgcatgt cagcctccat gcgggagtgg gagttgggaa    900
agtttcccat cgatagttgg aggggtggct tgaaagtctg gaggtgctag ctgggaaagt    960
tgtgtgtgcg cgatgaggca aggagtcaaa gatcagggga gttggaaagc gagaattgtg   1020
ggaatcgtcc aggactcagc tggatgctga ggggcagtat gatttttttt acgttatcaa   1080
tcgaattgat tttaagacag cagaacttca catactaata agatgaccat gggattagtt   1140
aaaatgtgta actcgtattc gaatcgtcat tctttcacgg accaatcgtg gaacaggag    1200
atctcttcga tccaagctca caggagactt gacactcttc gtctattcct tgtcaagttt   1260
ttaatgacat ctcctatgcc ctgagctatg ttttcctagc tctcatcgat cgctgccaat   1320
gagccactgg agatgatcca taagtcagcg tagagtgcac cccagagttg acacttggtg   1380
tctcggaatt cggctcatta tcagtgctat ttttggaaca cctctctgcg aaggtgtcat   1440
ttttgtcagt gcgtatcgct caggttcaac tccccaccaa aaaccgaatt tagagcatcg   1500
gcagatgtac ttgaagcact caatctaagt gaggaaacca ccccatgaac gaagagtact   1560
aggagtccta tttgactcgt gcttaaaaat agaaaattac ttagggtgat ccataggtag   1620
ggaggcgata ttgtaacttg catttcggac ccggacctgc acgagttatt acgggtgggt   1680
tgtgagcgta tcgggaaatt ggagagccac cagatctgtc ataacttata cggggatcc    1740
ttattcctgg gagggtgcgc ctgcgtctgc tcttccgaga gagaggtggg aaatggagga   1800
agagagagag agagagagtg agagagcagg tagagggaag tgagggaaat acgcaataag   1860
ggtatgggaa aagtgctgtt gttgttgcta ggtagcgacg cacacgtgcg agtgtttttc   1920
tgttttgaag aagaaccacc accaaatggc gacagcggcg tcggcagagg cgcagagttc   1980
cgggtataaa agagcgtgct cgactgttga cctgtcacag ccacctcagc tctcgttgag   2040
aacgcaacca ccgctctata ctcgatcccg aactatataa ctcgcctctc gatcgccgat   2100
ctcccgattt acccatctcg atcagtaccg gaaacc                             2136
```

<210> SEQ ID NO 5
<211> LENGTH: 2015
<212> TYPE: DNA
<213> ORGANISM: Drosophila melanogaster

<400> SEQUENCE: 5

```
atttggctcc ccatcgccat cggttgctcc aatgacacta gggaattgtg ggccgccgac     60
agctgtcctt aattacatgg aaatccacac tagattcgtg cccctcgccc cgtactcgca    120
gccgaagtcc ccacagagtc attcaccttg ccaccaccaa aaaaaaaacg aaagcaactg    180
aaggaaaagt tcgattcgaa ggctgaggga taccctttaaa ggcccatttc ccggcttcgt    240
aaatcacatt tagttagcca tttagactac agcaagtctt ttaagataca ctgcaaaata    300
aataccatta cattaataga agtgtcatgt catcggtctg tattttgtt accacagaat    360
agacttacat atatgataaa aaaatgttca acaataagtt acatcggtag ccaattctat    420
agatttaatt ccttacgaat atagtttcgt tggaatactc aatttgtaat tgtaattaat    480
tataattatt ataattttaa gaatttatat aagtaactaa aagacacggc agacacagaa    540
tgaaaacact ctatgttagg gaatgcaaaa aaacgtggcg gaagccaaaa ggcgcaagca    600
aaaatcgaaa ccaagtgaat ataacatatt atttcaacag gcaactcatt cagcatataa    660
tattaccacc catggagctt tatgtagttg atgtacgtag tctatgatgt ggagcccacg    720
ttggcggaac tggaatggg gattgggtt tgagagctgt ggtaaattgg ggggttgaag    780
tatcaagggt ttgggttctg tagacctgcg gaatcgaggt gaataagcga agaacacatt    840
```

-continued

| | |
|---|---|
| cacacacact aaaaggcaaa caaagggaaa tcaatctttg tacatactttt tagcatatgc | 900 |
| acacgtatga tctccaccca cttttccctc ccaatgaaac aaacacacac acacatgcaa | 960 |
| ggccgtacgt ttgtatatgt gtgcggttgt cggctttgcc gggaattggg gaatatttgc | 1020 |
| atgcctttgt gtactttttc catatgattt atgacctaaa ttgttgctgc tcgcgcacat | 1080 |
| ataattacac acacatcgct gtggccatgt gtgtgtgtgt cgtcttggga cgcgcgccaa | 1140 |
| agtatgctac acttttgtt ttatgagtta ataagtaggc gtggcccag cccaattgct | 1200 |
| acactctgat tatggcaccg gatacccaga tagacgccca tccaccccac tgtaagatgg | 1260 |
| gggaatttcc aaacctatat gtatgtgcag atcagatagg atagcacaga acttttaaa | 1320 |
| gtacactttt ggggcacgca atttagaaaa tgtacctcgg tgtcggagaa attatttaa | 1380 |
| aagtcgactg aaccacctcg ttccatatgg agaagtctac gagttcaagt ttaatggagc | 1440 |
| agctgactgc actgaatttt gtagtttaat acacaaatcc gcaaattgca tctcacttca | 1500 |
| aatagcctgg tacatagtat ctactaacat aactcatatt aaaataaagc aaccaaccag | 1560 |
| agggccgaag ttctattaat aaaactaata tttaactatt atatatacat tttatttact | 1620 |
| tggtacgctt atgataacct tcgaaagaga accaacacaa tacgctttgt catttgaaaa | 1680 |
| ataaatatgc tgtaactact ttacaaggtg aaactcttgt cagaagataa gaggctaggt | 1740 |
| aagttgatta ttcaatcagt ttacttactg caacccaaaa tggtcactgc actaaccttc | 1800 |
| agatgagctg cactcacccc tcaatcgaga atcaatgcaa acgcagtgcc agcgaaaatg | 1860 |
| tcagcaaggg attaggccaa tcccaaacgg gtaatcccgc tgcgacaatg ctaatccaat | 1920 |
| tccgatgggc cgtataaaag ccccaagctg ggctggctgt gatttcgtct tggcccgcag | 1980 |
| accggagcat ggagtccggt aacgtgtcgt cgagc | 2015 |

<210> SEQ ID NO 6
<211> LENGTH: 2082
<212> TYPE: DNA
<213> ORGANISM: Drosophila melanogaster

<400> SEQUENCE: 6

| | |
|---|---|
| atcgatgacg gcatcggctt gacctctcgg agtacgtttg atttataga acaagttttc | 60 |
| tcctttctta tactataagg aaaaattata aaaattgctg aaaatgaaac atggctagaa | 120 |
| ttcgtttttt aacattttt caatctgaga aaaaatttcc gattagtctt aaaataacta | 180 |
| aaccaattcg tatacccgtt aatcgtagaa gaaaaatgaa attcatataa taagtagatg | 240 |
| gatttgctga cccggtgagg tatatatgta ttcctgaaca tgatcagtaa acgagtcgat | 300 |
| ctggccttat ccgtatgaac gtcgagatct cgggaaatac aaaagctaga aggttgagat | 360 |
| taagtatgca gattctagaa gaagacgcag cgcaagtttg cgactacgct gaatctactg | 420 |
| ctaaaaactg ccacgcccac acttcttaag aatttgattt attttcacaa gctgaggaac | 480 |
| ggtagggtcg aggaactcga ctacaacgtt ctgccttgtt tatttcttaa caaaaactta | 540 |
| gtagccgttt ggggttggaaa ccacctgacc ttaggtctgg tagcagttat ttaatttatt | 600 |
| tttttattt tatacaactt gctcgctgtt tgttcccct agccctgaaa cacaagctgt | 660 |
| caaacggtgg aggtgataag tctaatgaat gcgataagct ttatttcaat tcgcaatttt | 720 |
| cgtgtggcat tttggcaaaa aaaaaaactc gtcggacata catgttgcca caaacataaa | 780 |
| gtgaatacat aatgttgggt gaacgactca tacacgattg tggcaaatca aattcttta | 840 |
| acacgggacg gggaaaggcg agtgaagata tttagcata tatttagcac atctgttaaa | 900 |
| tccattttt tactctccgt tttcggccag atatggttag aaaagaaaaa aattagtaca | 960 |

```
taccccccata tataataaga aaaaaagaga gagtcagcag aagtacgggg agcttaagtg    1020
tagcaatcag aacatcacaa atagtaaata aattaataat aataataatc atatccaaaa    1080
atatttttat tcctaaccta tcgcattgtt acatcgaggg tgaaattcaa aatagacaaa    1140
aagttgggga ataaaatgtg aaaaaagtgg taaaatgttt aatagtgtgg gcgttactgt    1200
tttgtcggtg tgaggtgcgt ggccaccaaa gtgtttttgg tataacgata gaaattggta    1260
agacaaacaa tattgcgaag aaaacccgaa gcatttttaa aaagtgcgaa cgtggcagtt    1320
ttaagggttt gtgggcgtgg caataatttt tggcaattcg ataaaaatgt acaggaccaa    1380
atatatgaag aaatataaaa tattttttcaa aatgacagcc agcaaccata catatatata    1440
aataaatgtc ggagacccctt ccttctacct gtaacatact tttccacgaa tctagtattg    1500
gttgatatat aattatgctg tgtataagac caaaatcagt gtacatttcc attggattca    1560
ccaaccggat ggttccggat ggtaatgcaa atatattcatc taagaaacga aaacacctag    1620
aattaaacct gaactgatat gacttatgca catatcagtg aggtgggcag ttcaaagcaa    1680
tcacgatgct ccaagttatt atcgcagtgc agtgaaaaat tcacagtcac cgtcgccaat    1740
tgccaataaa gatcggccat tatacaacag aaccgcgttg aagacgatcg acgaggtcgt    1800
gggtcttatc ttatcaccac ctgaattgag gcatgcctcc agaatgacga gggcatccga    1860
agataatgtg gcccgctatt ttcggccggg actggaccta tgcgacgacc tatgctgatg    1920
acgggagtct gccgctgata tggtgcaatg caaggctcca gtcgggggta taaaagaccc    1980
agtttcggtg cagtcaagac aacagacttt aggtgttggt cgttgagcga accaaagccg    2040
gagcagttga ggaaccaaag aatagcagcg agaggaccaa gg                      2082
```

<210> SEQ ID NO 7
<211> LENGTH: 1999
<212> TYPE: DNA
<213> ORGANISM: Saccharomyces cerevisia

<400> SEQUENCE: 7

```
tgtagggacc caaatccaat tgtagtagtt accttgatta tggttggctt gtccttcgat     60
agttttgcct tttccaaagc gctagaaatg gattccatat cgtcgtctcc tttatcgact    120
tccatgactt cccaaccata tgcctcgtat cgcttcaaaa catcttcgtc gaacgagtac    180
gaggttttac cgtcaatgga aatgctatta ctgtcataaa acgtaatcaa gttacccaat    240
tgcagatgtc ccgctaagga agaggtctcc gaagaaacac cctcttgtaa gcaaccatcc    300
cctacaatag caaacgtata tgagtcgaaa atgggaaagc catcctcgtt ataagtggcg    360
gcaaagttgg cctgcgctat tgccatacca acagcatttg agataccctg gcctagcgga    420
ccggaagtga tttccactcc cgctgagtgg aattctggat gacccggtgt ccttgagttt    480
acttgtctaa attgtctcaa gtcctcgata gagtaatcgt atcctaatag atggagcatt    540
gagtacagaa gagcgcatga gtgaccgttc gacagaacaa acctgtctct attgatccaa    600
tgttcattgt tagggttaca gcgcagttgc ttgaaaatta catgggcaac tggtgccaat    660
cctagtggtg cacctgggtg gccagattgt gcgctttcca cctggtcaac ggaaagtaat    720
cttaaagtgg aaaccgcaag tttatcaatg tcggagaact gtgccatttt tttgttcttt    780
ttttgattag taaggtataa tcgtctacgt agaggttaca aatcgaagac tacagtaaga    840
ggggacaagc caattgaata tacgactgaa ataaatggaa taattctgca ttattacact    900
cgtttatata tccaaacagg tgatctgta ttctcttgac aacgaatgaa gctccctata    960
ttcgacactc cttattcagg actcctccca acaaggagaa gtaggtgttc cttgagctac   1020
```

```
cctttaaagc tgggggagatg agcttgccct tcctgtcatc gccattatga cgagaaaagt    1080
aaaacatgta gaataaggtc cacccaaaca tgtccgagca atgacgttat atatcgtgtt    1140
ccctgttcaa agcatggcat atgtgccatt aaaggcgaat ttttgtccct agcaaaggag    1200
agacagcgag ccaccattaa gaagtgactt gaaagcaagc gaaatagct acacatatat    1260 atcaatatat tgacctataa acccaaaatg tgaaagaaat ttgataggtc aagatcaatg    1320
taaacaatta ctttgttatg tagagttttt ttagctacct atattccacc ataacatcaa    1380
tcatgcggtt gctggtgtat ttaccaataa tgtttaatgt atatatatat atatatatat    1440
ggggccgtat acttacatat agtagatgtc aagcgtaggc gcttcccctg ccggctgtga    1500
gggcgccata accaaggtat ctatagaccg ccaatcagca aactacctcc gtacattcat    1560
gttgcaccca cacatttata cacccagacc gcgacaaatt acccataagg ttgtttgtga    1620
cggcgtcgta caagagaacg tgggaacttt ttaggctcac caaaaagaa agaaaaaata    1680 cgagttgctg acagaagcct caagaaaaaa aaaattcttc ttcgactatg ctggaggcag    1740
agatgatcga gccggtagtt aactatatat agctaaattg gttccatcac cttcttttct    1800
ggtgtcgctc cttctagtgc tatttctggc ttttcctatt ttttttttttc cattttcttt    1860 tctctctttc taatatataa attctcttgc attttctatt tttctctcta tctattctac    1920
ttgtttattc ccttcaaggt tttttttttaa ggagtacttg tttttagaat atacggtcaa    1980
cgaactataa ttaactaaa                                                1999

<210> SEQ ID NO 8
<211> LENGTH: 2001
<212> TYPE: DNA
<213> ORGANISM: Saccharomyces cerevisia

<400> SEQUENCE: 8
tctgctatta ttgatgcttt gaagacctcc agacaaattt ttcacagaat gtactcttac      60
gttgtttacc gtattgcttt gtctctacat ttggaaatct tcttgggtct atggattgct     120
attttggata actctttgga cattgatttg attgttttca tcgctatttt cgctgatgtt     180
gctactttgg ctattgctta cgataatgct ccttactctc caaagcccgt taaatggaac     240
ctaccaagat tatggggtat gtctattatt ttgggcatag ttttagctat aggttcttgg     300
attaccttga ctactatgtt cttaccaaag ggtggtatta tccaaaactt cggtgctatg     360
aacggtatta tgttcttgca aatttccttg actgaaaact ggttgatttt cattaccaga     420
gctgctggtc cattctggtc ttctatccca tcctggcaat tggctggtgc cgtcttcgct     480
gtcgacatca tcgctaccat gtttaccctta ttcggttggt ggtctgaaaa ctggactgat     540
attgttactg tcgtccgtgt ctggatctgg tctatcggta tcttctgtgt tttgggtggt     600
ttctactacg aaatgtccac ttctgaagcc tttgacagat tgatgaacgg taagccaatg     660
aaggaaaaga gtctaccag aagtgtcgaa gacttcatgg ctgctatgca aagagtctct     720
actcaacacg aaaaggaaac ctaatcctgt tgaagtagca tttaatcata atttttgtca     780
cattttaatc aacttgattt ttctggttta attttttctaa ttttaatttt aatttttta     840 tcaatgggaa ctgatacact aaaaagaatt aggagccaac aagaataagc cgcttatttc     900
ctactagagt ttgcttaaaa tttcatctcg aattgtcatt ctaatatttt atccacacac     960
acaccttaaa attttttagat taaatggcat caactcttag cttcacacac acacacacac    1020
cgaagctggt tgttttattt gatttgatat aattggtttc tctggatggt acttttctct    1080
tcttggttat ttcctatttt aaaatatgaa acgcacacaa gtcataatta ttctaataga    1140
```

```
gcacaattca caacacgcac atttcaactt taatattttt ttagaaacac tttatttagt    1200
ctaattctta atttttaata tatataatgc acacacacta atttattcat taattttttta   1260 ttgagtagga tttgaaaata tttggtatct ttgcaagatg tttgtataga gggacaaaga    1320
atcgtcttta ttatggtcaa ggctttacgt cataatagtt cctgcccagc tcttctataa    1380
tactttaaag atctcttctc gtttgctcca tttggaagtc tcgcttacgt ttatgcgccc    1440
atacagacac tcaagataca cacttacatg aacgtataca aatttactaa cactacttga    1500
aaatatgaac cacagtacat catattaaga cgtagtattc gatgattgaa ggccgcctcc    1560
gcgaaatacc tttactgatt ttgccggtta atcgcatcga aatttcttca tcacaagaaa    1620
gcaaacaaat cgccaggcca ttctacaagt ttccttttct tatgaagatg taaaagctac    1680
taaggcgtca ttactctaga tgactcagtt tagtctgacc ttctatagta tactaccctg    1740
gcgctatgat gatgagcggt tcttttattg cggaaacgaa aattccggga ccggcgaaat    1800
ttgcccggtt ttgtccgtaa ccggcttcat gagtcggctt caatagtagt tgaatactta    1860
tttaaacagc agaacttaac tcactcatca cgctgtttcc gctgaatttt ctcaaaatat    1920
ctaagcagtc aacaaatata aagaatattg aaattgacag tttttgtcgc tatcgatttt    1980
tattatttgc tgttttaaat c                                               2001

<210> SEQ ID NO 9
<211> LENGTH: 2000
<212> TYPE: DNA
<213> ORGANISM: Saccharomyces cerevisia

<400> SEQUENCE: 9
ccaaatcatt cttattcggt ttccagacgg taacaatacc ctcgcccatc ccacacaaaa      60
gggtatctgc tacttcggga tcgacgaaac aaccacaaag aacttcgtcc tcctgatcat     120
cgctgatcaa aatttttacca tcctcgtttc cagctacgtt cggtttggca tctttgtcgc    180
gaacgtcaaa ataagctaac gttgtctggc ccaaagaaat gaatttatat gcagatcttt    240
tatcaaagtg gaaaatatcg ttgatagagt cgccaaaatg tatcgaacga atggaatttg    300
ataatgccaa gttttccgag tttattacgt gtatattacc ggattcatcg cctattaaaa    360
tgaatgggtg agtttgagag gcgcataatt tcgtaaattt atcattttt ttctcttcag     420 aattaaacag tgagcttaag tttacctttt tgacgacttt gccggtcata gtattggcct    480
tttttaaaac attatccgat ccaacagaaa aaatattgtc accttttagaa tcaaagcaca    540 tggcacggac actacctta tgtcttttag tcttccaaag tgtttttacg cccaagtctt     600
catcttttcc tgtttgcttt tgttgctgtt gttcttcaat atcaacaaat ttcaaatctc    660
cagtttctag gtctatatct aatctaatcc aagggcatac acctttcttt gcatccttgc    720
ctgtagttgc agtgtcaatt ctacgtctac gatctaggtg cgattgcaac ttagcggggt    780
cataacgatg gcacacaata tgtcctgtac caaagccagt tattataatg ggcagttcag    840
gatgtaaaag agactggaaa atgggagctt ttaatgatag taattctaga atgggcaggt    900
ttgttgaatc gacaacatct gttttttttt tgctctttgc catagctgat gcgtggattg    960
tttctaattt cccagctgct tcctcttcca attgtggcga tgatgccatg atttctatgt   1020
taaaattttt ctaaccatga aatttttttt ttctagcgag aaaaaaaatc agaaaaatta   1080
ctattagtga gtattggaga cattgtcaat gggagatgtt ctctttataa tatcttcaac   1140
aggttctttc aactctggaa attcatccac aatcttgtca gcaagtgaat ctcttaattg   1200
cttcaatcca tgcatcttgc ctctttgata ttggttggat cttcttatgg cttccacgaa   1260
```

-continued

```
ctctcttgtg taaatatctg gatttctacc gtcctcaatg tattgaacaa cttccaaggg      1320
aatgtccacc ttagacaagc tggattgagg atcgttgctt ctcacgttca gcttgtacaa      1380
gcgatccaca tttctttgca agttggtgat cattcccttg gtggcttctg gagtaccagg      1440
aaaatcatat atcgagacac ctaattcaac gaaggactca ataatcgaag ccacttggtc      1500
ttgagtagtg gccagttctt gctgcaattg ttcattgtta gtgctgtttc cattcatctt      1560
atcggtttat ttttctatat atttgcctct ttctcaaaca ggagttagta gttaaaagta      1620
cgaagttctt gttctttaat gcgcgctgac aaaagaattg gataaagag aatggtgggg       1680 ggacaagaag gaaatttgtc ctagtttaac atgaatggca tcttgttacc gggtggacat      1740
cacctattga ttctaaatat ctttacggtt tatcatactg ttctttattc cgtcgttatt      1800 cttttattt ttatcatcat ttcacgtggc tagtaaaaga aaagccacaa catgactcag        1860
caaatctcga caaagtaaaa gctcatagag atagtattat attgatataa aaaaagtata      1920
ctgtactgtt tgtaacctt tcaatgcttt aagatcaaaa ctaaggccag caaaggtatc       1980
aacccatagc aactcataaa                                                  2000

<210> SEQ ID NO 10
<211> LENGTH: 2001
<212> TYPE: DNA
<213> ORGANISM: Saccharomyces cerevisia

<400> SEQUENCE: 10
gaaaccatta atcatatttt aataaattgt tgcgacatgc aagaagttcg cggatggtca       60
tgcgtattta agaatagtca agtaacaatt tgcttattcg ttgatgatat gatattattc      120
agcaaagact taaatgcaaa taagaaaatc ataacaacac tcaagaaaca atacgataca      180
aagataataa atctgggtga aagtgataac gaaattcagt acgacatact tggattagag      240
atcaaatatc aaagaagcaa gtacatgaaa ttaggtatgg aaaaatccctt gacagaaaaa      300 ttacccaaac taaacgtacc tttgaaccca aaaggaaaga aacttagagc tccaggtcaa      360
ccaggtcatt atatagacca ggatgaacta gaaatagatg aagatgaata caaagagaaa      420
gtacatgaaa tgcaaaagtt gattggtcta gcttcatatg ttggatataa atttagattt      480
gacttactat actacatcaa cacattgctc aaccatatac tattcccctc taggcaagtt      540
ttagacatga catatgagtt aatacaattc atgtgggaca ctagagataa acaattaata      600
tggcacaaaa acaaacctac caagccagat aataaactag tcgcaataag cgatgcttca      660
tatggtaacc aaccatatta caagtcacaa attggtaaca ttttcctact caacggaaaa      720
gtgattggag gaaagtcgac aaaaggcttcg ttaacatgca cttcaactac agaagcagaa      780
atacacgcgg tcagtgaagc tattccgcta ttgaataacc tcagtcacct tgtgcaagaa      840
cttaacaaga aaccaattat taaaggctta cttactgata gtagatcaac gatcagtata      900
attaagtcta caaatgaaga gaaatttaga acagatttt ttggcacaaa ggcaatgaga       960
cttagagatg aagtatcagg taataattta tacgtatact acatcgagac caagaagaac     1020
attgctgatg tgatgacaaa acctcttccg ataaaaacat ttaaactatt aactaacaaa     1080
tggattcatt agatctatta cattatgggt ggtatgttgg aataaaaatc aactatcatc     1140
tactaactag tatttacgtt actagtatat tatcatatac ggtgttagaa gatgacgcaa     1200
atgatgagaa atagtcatct aaattagtgg aagctgaaac gcaaggattg ataatgtaat     1260
aggatcaatg aatattaaca tataaaatga tgataataat atttatagaa ttgtgtagaa     1320
ttgcagattc cctttttatgg attcctaaat cctcgaggag aacttctagt atatctacat    1380
```

```
acctaatatt attgccttat taaaaatgga atcccaacaa ttacatcaaa atccacattc      1440
tcttcaaaat caattgtcct gtacttcctt gttcatgtgt gttcaaaaac gttatattta      1500
taggataatt atactctatt tctcaacaag taattggttg tttggccgag cggtctaagg      1560
cgcctgattc aagaaatatc ttgaccgcag ttaactgtgg gaatactcag gtatcgtaag      1620
atgcaagagt tcgaatctct tagcaaccat tattttttc ctcaacataa cgagaacaca       1680
caggggcgct atcgcacaga atcaaattcg atgactggaa attttttgtt aatttcagag      1740
gtcgcctgac gcatataacct ttttcaactg aaaaattggg agaaaaagga aaggtgagag    1800
ccgcggaacc ggcttttcat atagaataga gaagcgttca tgactaaatg cttgcatcac     1860
aatacttgaa gttgacaata ttatttaagg acctattgtt ttttccaata ggtggttagc     1920
aatcgtctta ctttctaact tttcttacct tttacatttc agcaatatat atatatatat    1980
ttcaaggata taccattcta a                                                2001

<210> SEQ ID NO 11
<211> LENGTH: 2001
<212> TYPE: DNA
<213> ORGANISM: Saccharomyces cerevisia

<400> SEQUENCE: 11
cactaccacc actacggttg tccatgacgt atcctgcgat ttttgaatt aatgattcaa        60 tagttgacat ttgctcgtca ttggggttcg actgagctgc ggatgtcaac ttcgcaacag      120
cttctgcatg gtttccttga gaaaaatgag actcagcctc tgagattaac ttatccgtat      180
ccatttcaga tctttgctat acgtttgtat cgctatatgt acgttctttt aatgaacttt      240
ctcctttctt tatcgtgtag cttgcttggg tatctttaa tgagttgcgg acagtgagat       300
ttttcagaag ggcaattggc caagacacca aaaacgtttg gacgagacag gcatcaaagg      360
acaaggtaaa aggcgttgag ctgtggctgg ctgtgtatgc gtttgaaata ccatggatag      420
atatcaaaga aagataggat gtttcataca aatcccaaat ttggggcgcg gacaactgaa      480
atacgtgggt ccagtggaca cgaaagctgg aatgtttgct ggtgtagact tacttgccaa      540
cattggtaag aacgatggat cattcatggg gaagaagtat tttcaaacag gtatcctca       600 aagtggacta tttatccagt tgcaaaaagt cgcatcattg atcgagaagg catcgatatc      660
gcaaacctcg agaagaacga cgatggaacc gctatcaata cccaaaaaca gatctattgt      720
gaggctcact aaccagttct ctcccatgga tgatcctaaa tcccccacac ccatgagaag      780
tttccggatc accagtcggc acagcggtaa tcaacagtcg atggaccagg aggcatcgga      840
tcaccatcaa cagcaagaat ttggttacga taacagagaa gacagaatgg aggtcgactc      900
tatcctgtca tcagacagaa aggctaatca caacaccacc agcgattgga aaccggacaa      960
tggccacatg aatgacctca atagcagcga agttacaatt gaattacgag aagcccaatt     1020
gaccatcgaa aagctacaaa ggaaacaact acactacaaa aggctactcg atgaccaaag     1080
aatggtcctc gaagaagtgc aaccgacttt tgataggtat gaagccacaa tacaagaaag     1140
agagaaagag atagaccatc tcaagcaaca attggagctc gaacgcagac agcaagccaa     1200
acaaaagcag ttttttgacg ctgagaatga acagctactt gctgtcgtaa gccaactaca     1260
cgaagagatc aaagaaaacg aagagagaaa tctttctcat aatcaaccca ctggtgccaa     1320
cgaagatgtc gaactcctga aaaaacagct ggaacaatta cgcaacatag aagaccaatt     1380
tgagttacac aagacaaagt gggctaaaga acgcgaacaa ttgaaaatgc ataacgattc     1440
gctcagtaaa gaataccaaa atttgagcaa ggaactattt ttgacaaaac cacaagattc     1500
```

```
ctcatcggaa gaggtggcat ccttaacgaa aaaacttgaa gaggctaatg aaaaaatcaa    1560
acagttggaa caggctcaag cacaaacagc cgtggaatcg ttgccaattt tcgacccccc    1620
tgcaccagtc gataccacgg caggaagaca acagtggtgt gagcattgcg atacgatggg    1680
tcataataca gcagaatgcc cccatcacaa tcctgacaac cagcagttct tctaggcagt    1740
cgaactgact ctaatagtga ctccggtaaa ttagttaatt aattgctaaa cccatgcaca    1800
gtgactcacg tttttttatc agtcattcga tatagaaggt aagaaaagga tatgactatg    1860
aacagtagta tactgtgtat ataatagata tggaacgtta tattcacctc cgatgtgtgt    1920
tgtacataca taaaaatatc atagcacaac tgcgctgtgt aatagtaata caatagttta    1980 caaaatttt tttctgaata c                                               2001
```

```
<210> SEQ ID NO 12
<211> LENGTH: 2001
<212> TYPE: DNA
<213> ORGANISM: Saccharomyces cerevisia

<400> SEQUENCE: 12
acaatgagga agaacatgcc gttttacaag aattaaatag tttaacccaa agaattaatg      60
aactaggcat ggaaagtata aattcaaact ccgattcgga cagaataaac gggtcatatt     120
cacaagtgga ttttggtaac aataacgacg aggacgatat gaacctgttc gacccagatt     180
ttatggcaca agaccaattg cgtgctgaag aaagagacta caacaaggat gatagaacac     240
ccttagctaa ggtccctgcg gcctttcaat caactggatt gggcataacc cccgatgacg     300
atatcgagag acaatacata acggaacaca gatcacgaca tgaagtgcca aagcggtctc     360
ccgagaaacc ctccaacccg ctggaaatag gtaacccata cgcgaaacct ggcacaaggt     420
tgaataccac tcacacccac agcaaaactg atcgtagcat taccccctcag aggggccagc    480 cagtcccatc aggccagcag atttcctcct acgtgcagcc agcaaacatt aatagtccta     540
acaaaatgta tggtgcaaac aactcggcaa tgggttcgcc caggaatcca aagacgagag     600
cgccaccagg tccatacaat cagggatgga ataaccgccc ctcgccttca aatatttacc     660
aacgtcctca tccctcagat acacaaccac aagcatatca tctcccccgga aacccatact    720 caacggggaa caggccaaac atgcaagcgc aatatcaccc gcagcaggtg cccatgccta     780
tcctgcagca gcccaatcgc ccgtaccaac cttatgcgat gaatacgcac atgggctctc     840
ctggcggata tgctggggca gcaccaccat ttcagccagc taacgtcaac tacaatacta     900
ggcctcagca gccatggcct acacctaact caccatccgc acactaccgt ccgcccccta     960
acctgaacca gcctcaaaac ggtagtgctg gttactatcg tccgccggca ccacaattgc    1020
aaaactccca agcccgtcca caaagaaggg acggattctc acagttcatg ccatctgcaa    1080
ctacgaagaa cccatatgcc cagtaactcg accgactggt tgtaattta caaaagaga     1140 gacaattaag aaaagaaaca agcgccaggc ttccgtatcc cagttttca tctcactttc    1200 tgggcacgat tgtaataata cttcatgata taactaaac tatataagta gtgtctcatc    1260
cgtaaatata catttagaca gattcttgta ttttctccgg gcaatttta actttttttc    1320 tgttagggca catgacactt gcctattatg gacagccagt aaagatgtgc catatattgc    1380
cccctttacg ctctctgcca gtattagtgg gaaaaaaaa actgaaaaaa aaaaatcgc     1440 agactactaa taatcacgtg atatttcttt tcactctctt cataaagttg ctaaaaacac    1500
acaatcgaat gagcctctga gcagtataaa ttgtacttca aagcactagt catgaaaaac    1560
gcttacatta gttcagtttg tcaaggttat gctattactt gtacttattt cttgctattg    1620
```

-continued

| | |
|---|---|
| ttagtggctc cccacattga cgtattttca cgtgatgcgc ctcactgcgg aaggcgccac | 1680 |
| acattgcctg caaaaaattg tggatgcact catttgatag taaactaagt catgttaatc | 1740 |
| gtttggattt ggcacacacc cacaaatata cacattacat atatatatat attcaaaata | 1800 |
| cagctgcgtc caatagatga gcttccgctt cgttgtacaa cctacctgct atcttgttca | 1860 |
| cggatatttc ttgcttttaa taaacaaaag taactctaga acagtcaagt cttcgataat | 1920 |
| tttttttagtc acagggtccg tctaaagttt ctctttattt ggaataatag aaaagaaaga | 1980 |
| aaaaaacgta gtataaaagg a | 2001 |

<210> SEQ ID NO 13
<211> LENGTH: 2000
<212> TYPE: DNA
<213> ORGANISM: Saccharomyces cerevisia

<400> SEQUENCE: 13

| | |
|---|---|
| aaggatggca ataccccaat cggaggaact cgaacacttc agtatctgtg tcttctagtg | 60 |
| agtctttagc ggaagttatt cagccatctt ccttcaaaag tgggagtagt tcattgcatt | 120 |
| atctatcgtc ttctatctca agccaacctg gttcgtacgg ttcttggttc aacaaaaggc | 180 |
| caacaatttc tcagttcttt caaccaagcc cttctttaaa acacaacgag tcgtgggaga | 240 |
| ggctgcaaac aactgctgga atatgcaaa ggacttcaag ttcgtcttct ttgcagcaag | 300 |
| caacctccag gttatcacta accactccgc aacaatcacc gtctatcagc gaatatgatg | 360 |
| agtatccttg gatgggcaca cctggctctc ctaatgttgg agatgtgtct cacgcacccc | 420 |
| cattggttaa gaatatatca tataaatttc cactaaagaa cgttgagttg aaaagagatt | 480 |
| gccaaaggat ctctcaggat gatcttttgg atgaggcttt tgaaagaata tgtcagccct | 540 |
| ctttggctga ccttaattcc acttacgaaa ttttccagg taactcttct tatgcggata | 600 |
| ttttgactac tgattctgat attgatgatg cttgatgaa taaacctctg gaactattgc | 660 |
| cgaaatatac aatgtattta acccattta acaatttttt ccagttgcaa gcatgtcctg | 720 |
| ctggtcaaga atcagagagc agaataacaa attctatgaa gattgacctg ttaaaggcgg | 780 |
| attacacaag aagtctatta gtatcgttac gttcaaggga cattagggat gtcgcattga | 840 |
| aaagagagtt tactggcaat aacaacaata acagcaacca gaatatctat gatgagaatt | 900 |
| ttgtcggaaa aaggaagtac gtgttgaaac agaagaccag aaaaatcttt tcctgtggca | 960 |
| agattggcaa gctaagtact agtttggaaa actgcgttaa ttttgttgaa aatagtataa | 1020 |
| agagtgcaat gatgttatat gatgataatg gaatagatag tgagcttcgc gattcagaag | 1080 |
| ctttacggat ttttttcatct cttgttcatt attgtaatgc aggttaatgt tttctccttc | 1140 |
| tttacatgtt taatatattc caagttacct aagaggtgta cgatattttt ttcttttata | 1200 |
| tatatgattt tctctattca ttttttagtt tttttttgata cataagcgaa tcgcacattg | 1260 |
| cgcaacttca atttgttgat tcgccaaagt attcttacca taaacaacc attcgttgct | 1320 |
| ttacccttc gtaatcattt accgtgataa ccataatcag aaacttatta tttcagccta | 1380 |
| gtagaccggc caagcaggcc ttgtaatgtt tctcttgatt gcttgaatct tttaagcagc | 1440 |
| caaatctttc caaaaaaatg caattatcag aacaaaacta tttaaggtga cttctccgta | 1500 |
| tttacaccac cagaagcgtt ctggctcccc ttttctctaa acgttaaaca ttttacaatt | 1560 |
| gaaatgttac caatcctata ttattgtacc acattgccag atttatgaac tctgggtatg | 1620 |
| ggtgctaatt ttcgttagaa gcgctggtac aatttctct gtcattgtga cactaattag | 1680 |
| gaaacttctc gactatcaat gtgtaaatga aggaataatg gcggaaactt tgaaactttg | 1740 |

```
tcaataattg catcattgga tgcgtttcat ttggccgtta tcacggagag gcagagttct    1800
ctccacaatt tgggcagaag tcttttgaaa agacatatat atatatatat atgtatatga    1860
gtggatgctt aaggtaagaa taatttctga attcccaagt attcattttg tgcagtattc    1920
acatattcta ttttattgct ttttaacttt agaggcaatt aaatttgtgt aggaaaggca    1980
aaatactatc aaaatttttcc                                                2000

<210> SEQ ID NO 14
<211> LENGTH: 2001
<212> TYPE: DNA
<213> ORGANISM: Saccharomyces cerevisia

<400> SEQUENCE: 14
ttgccttcaa gatctacttt cctaagaaga tcattattac aaacacaact gcactcaaag      60
atgactgctc atactaatat caaacagcac aaacactgtc atgaggacca tcctatcaga     120
agatcggact ctgccgtgtc aattgtacat ttgaaacgtg cgcccttcaa ggttacagtg     180
attggttctg gtaactgggg gaccaccatc gccaaagtca ttgcggaaaa cacagaattg     240
cattcccata tcttcgagcc agaggtgaga atgtgggttt ttgatgaaaa gatcggcgac     300
gaaaatctga cggatatcat aaatacaaga caccagaacg ttaaatatct acccaatatt     360
gacctgcccc ataatctagt ggccgatcct gatcttttac actccatcaa gggtgctgac     420
atccttgttt tcaacatccc tcatcaattt ttaccaaaca tagtcaaaca attgcaaggc     480
cacgtggccc ctcatgtaag ggccatctcg tgtctaaaag ggttcgagtt gggctccaag     540
ggtgtgcaat tgctatcctc ctatgttact gatgagttag gaatccaatg tggcgcacta     600
tctggtgcaa acttggcacc ggaagtggcc aaggagcatt ggtccgaaac caccgtggct     660
taccaactac caaaggatta tcaaggtgat ggcaaggatg tagatcataa gatttttgaaa    720 ttgctgttcc acagacctta cttccacgtc aatgtcatcg atgatgttgc tggtatatcc     780
attgccggtg ccttgaagaa cgtcgtgca cttgcatgtg gtttcgtaga aggtatggga     840
tggggtaaca atgcctccgc agccattcaa aggctgggtt taggtgaaat tatcaagttc     900
ggtagaatgt ttttcccaga atccaaagtc gagacctact atcaagaatc cgctggtgtt     960
gcagatctga tcaccacctg ctcaggcggt agaaacgtca aggttgccac atacatggcc    1020
aagaccggta agtcagcctt ggaagcagaa aaggaattgc ttaacggtca atccgcccaa    1080
gggataatca catgcagaga agttcacgag tggctacaaa catgtgagtt gacccaagaa    1140
ttcccattat tcgaggcagt ctaccagata gtctacaaca acgtccgcat ggaagaccta    1200
ccggagatga ttgaagagct agacatcgat gacgaataga cactctcccc ccccctcccc    1260
ctctgatctt tcctgttgcc tcttttttccc ccaaccaatt tatcattata cacaagttct    1320
acaactacta ctagtaacat tactacagtt attataatttt tctattctct ttttctttaa    1380
gaatctatca ttaacgttaa tttctatata tacataacta ccattataca cgctattatc    1440
gtttacatat cacatcaccg ttaatgaaag atacgacacc ctgtacacta acacaattaa    1500
ataatcgcca taaccttttc tgttatctat agcccttaaa gctgttttct cgagcttttt    1560
cactgcagta attctccaca tgggcccagc cactgagata agagcgctat gttagtcact    1620
actgacggct ctccagtcat ttatgtgatt ttttagtgac tcatgtcgca tttgccccgt    1680
ttttttccgc tgtcgcaacc tatttccatt aacggtgccg tatggaagag tcatttaaag    1740
gcaggagaga gagattactc atcttcattg gatcagattg atgactgcgt acggcagata    1800
gtgtaatctg agcagttgcg agacccagac tggcactgtc tcaatagtat attaatgggc    1860
```

```
atacattcgt actcccttgt tcttgcccac agttctctct ctctttactt cttgtatctt   1920
gtctccccat tgtgcagcga taaggaacat tgttctaata tacacggata caaaagaaat   1980
acacataatt gcataaaata c                                             2001

<210> SEQ ID NO 15
<211> LENGTH: 1999
<212> TYPE: DNA
<213> ORGANISM: Saccharomyces cerevisia

<400> SEQUENCE: 15
ttttgtaaga aattattcac cgcatcttca tctggcaaac gaatgggaga ctttgaggaa     60
cccaatccat ttctgaataa cggagattta gaaatgtaaa aggtagcaaa tgtaaaaagt    120
gccaggacca tcacagcagt caatgccaac accaatttcc cttgccatga cactgttgga    180
tcttttgaag gagatttgta acctggaatc tcactataat gaacacattc accggattca    240
cacttcaaag taatataagg gtcaccaaac acggtcaata tcaaatcatt catagaaggc    300
tcactgaatt tacattgcct tgtttctaaa tcacagctga aatctcctgg ccctttatt     360 gtctctgtca ggaaatccga gatatctata gacccttag caccacacaa cacagtgtcg     420
ggaacgcatt tgcattgaac gtcattacac ttataatggg aggtattctg ttccaagtcg    480
tattcaaagg cacaatcact taagccacaa tagaagcttt ctaactgatc tatccaaaac    540
tgaaaattac attcttgatt aggtttatca caggcaaatg taatttgtgg tattttgccg    600
ttcaaaatct gtagaatttt ctcattggtc acattacaac ctgaaaatac tttatctaca    660
atcataccat tcttataaca tgtcccctta atactaggat caggcatgaa cgcatcacag    720
acaaaatctt cttgacaaac gtcacaattg atccctcccc atccgttatc acaatgacag    780
gtgtcatttt gtgctcttat gggacgatcc ttattaccgc tttcatccgg tgatagaccg    840
ccacagaggg gcagagagca atcatcacct gcaaaccctt ctatacactc acatctacca    900
gtgtacgaat tgcattcaga aaactgtttg cattcaaaaa taggtagcat acaattaaaa    960
catggcgggc atgtatcatt gcccttatct tgtgcagtta gacgcgaatt tttcgaagaa   1020
gtaccttcaa agaatggggt cttatcttgt tttgcaagta ccactgagca ggataataat   1080
agaaatgata atatactata gtagagataa cgtcgatgac ttcccatact gtaattgctt   1140
ttagttgtgt attttttagtg tgcaagtttc tgtaaatcga ttaattttt tttctttcct    1200 ctttttatta accttaattt ttattttaga ttcctgactt caactcaaga cgcacagata   1260
ttataacatc tgcataatag gcatttgcaa gaattactcg tgagtaagga aagagtgagg   1320
aactatcgca tacctgcatt taaagatgcc gatttgggcg cgaatccttt attttggctt   1380
caccctcata ctattatcag ggccagaaaa aggaagtgtt tccctccttc ttgaattgat   1440
gttaccctca taaagcacgt ggcctcttat cgagaaagaa attaccgtcg ctcgtgattt   1500
gtttgcaaaa agaacaaaac tgaaaaaacc cagacacgct cgacttcctg tcttcctatt   1560
gattgcagct tccaatttcg tcacacaaca aggtcctagc gacggctcac aggttttgta   1620
acaagcaatc gaaggttctg gaatggcggg aaagggttta gtaccacatg ctatgatgcc   1680
cactgtgatc tccagagcaa agttcgttcg atcgtactgt tactctctct ctttcaaaca   1740
gaattgtccg aatcgtgtga caacaacagc ctgttctcac acactctttt cttctaacca   1800
agggggtggt ttagtttagt agaacctcgt gaaacttaca tttacatata tataaacttg   1860
cataaattgg tcaatgcaag aaatacatat ttggtctttt ctaattcgta gttttttcaag  1920 ttcttagatg ctttctttt ctcttttta cagatcatca aggaagtaat tatctacttt     1980
```
ttacaacaaa tataaaaca 1999

<210> SEQ ID NO 16
<211> LENGTH: 1999
<212> TYPE: DNA
<213> ORGANISM: Saccharomyces cerevisia

<400> SEQUENCE: 16

| | | | | | |
|---|---|---|---|---|---|
| aaacaaatgg | caaaaataac | gggcttcacc | attgttcctg | tatggtgtat | tagaacatag | 60 |
| ctgaaaatac | ttctgcctca | aaaaagtgtt | aaaaaaaaga | ggcattatat | agaggtaaag | 120 |
| cctacaggcg | caagataaca | catcaccgct | ctccccctc | tcatgaaaag | tcatcgctaa | 180 |
| agaggaacac | tgaaggttcc | cgtaggttgt | ctttggcaca | aggtagtaca | tggtaaaaac | 240 |
| tcaggatgga | ataattcaaa | ttcaccaatt | tcaacgtccc | ttgtttaaaa | agaaaagaat | 300 |
| ttttctcttt | aaggtagcac | taatgcatta | tcgatgatgt | aaccattcac | acaggttatt | 360 |
| tagcttttga | tccttgaacc | attaattaac | ccagaaatag | aaattaccca | agtgggctc | 420 |
| tccaacacaa | tgagaggaaa | ggtgactttt | taaggggggcc | agaccctgtt | aaaaacctttt | 480 |
| gatggctatg | taataatagt | aaattaagtg | caaacatgta | agaaagattc | tcggtaacga | 540 |
| ccatacaaat | attgggcgtg | tggcgtagtc | ggtagcgcgc | tcccttagca | tgggagaggt | 600 |
| ctccggttcg | attccggact | cgtccaaatt | atttttact | ttccgcggtg | ccagatgca | 660 |
| gacgtggcca | actgtgtctg | ccgtcgcaaa | atgatttgaa | ttttgcgtcg | cgcacgtttc | 720 |
| tcacgtacat | aataagtatt | ttcatacagt | tctagcaaga | cgaggtggtc | aaaatagaag | 780 |
| cgtcctatgt | tttacagtac | aagacagtcc | atactgaaat | gacaacgtac | ttgactttc | 840 |
| agtattttct | ttttctcaca | gtctggttat | ttttgaaagc | gcacgaaata | tatgtaggca | 900 |
| agcattttct | gagtctgctg | acctctaaaa | ttaatgctat | tgtgcacctt | agtaacccaa | 960 |
| ggcaggacag | ttaccttgcg | tggtgttact | atggccggaa | gcccgaaaga | gttatcgtta | 1020 |
| ctccgattat | tttgtacagc | tgatgggacc | ttgccgtctt | cattttttt | tttttcacc | 1080 |
| tatagagccg | ggcagagctg | cccggcttaa | ctaagggccg | gaaaaaaaac | ggaaaaaaga | 1140 |
| aagccaagcg | tgtagacgta | gtataacagt | atatctgaca | cgcacgtgat | gaccacgtaa | 1200 |
| tcgcatcgcc | cctcacctct | cacctctcac | cgctgactca | gcttcactaa | aaaggaaaat | 1260 |
| atatactctt | tcccaggcaa | ggtgacagcg | gtccccgtct | cctccacaaa | ggcctctcct | 1320 |
| gggggtttgag | caagtctaag | tttacgtagc | ataaaaattc | tcggattgcg | tcaaataata | 1380 |
| aaaaaagtaa | ccccacttct | acttctacat | cggaaaaaca | ttccattcac | atatcgtctt | 1440 |
| tggcctatct | tgttttgtcc | tcggtagatc | aggtcagtac | aaacgcaaca | cgaaagaaca | 1500 |
| aaaaaagaag | aaaacagaag | gccaagacag | ggtcaatgag | actgttgtcc | tcctactgtc | 1560 |
| cctatgtctc | tggccgatca | cgcgccattg | tccctcagaa | acaaatcaaa | cacccacacc | 1620 |
| ccgggcaccc | aaagtcccca | cccacaccac | caatacgtaa | acggggcgcc | cctgcaggc | 1680 |
| cctcctgcgc | gcggcctccc | gccttgcttc | tctccccttc | cttttctttt | tccagttttc | 1740 |
| cctattttgt | ccctttttcc | gcacaacaag | tatcagaatg | ggttcatcaa | atctatccaa | 1800 |
| cctaattcgc | acgtagactg | gcttggtatt | ggcagtttcg | tagttatata | tatactacca | 1860 |
| tgagtgaaac | tgttacgtta | ccttaaattc | tttctccctt | taattttctt | ttatcttact | 1920 |
| ctcctacata | agacatcaag | aaacaattgt | atattgtaca | cccccccct | ccacaaacac | 1980 |
| aaatattgat | aatataaag | | | | | 1999 |

<210> SEQ ID NO 17

<211> LENGTH: 2009
<212> TYPE: DNA
<213> ORGANISM: Saccharomyces cerevisia

<400> SEQUENCE: 17

```
ggatgagaaa cgagtgcggt ttcgagagta gatattcaac ccacccgaag tagccttcag      60
gaactggttc cgttctctct tcctccggaa tagtctgaat gtccttaaga gaccgtggct     120
cgtatactct tctattcttg ggccgcaata gcaaaagag ccagacaaac acgacggcgg     180
taagaccgta gataatcagg gttgaaatga acgccgaagt cgaagaactg tcagccatag     240
tacgtatgtg ctataaatat ctaacctttc gctgctttga atatgatgtg ctcaaatata     300
acttaatata atagtataac aaaaaggagt actatttgct aaatatcgta gacgtagtag     360
acatagtaaa tacaataaag gatagataac caagaaccca catcaagcga atacatacat     420
atatatatac tcgatgtata catgtttcta agcacttgcg cacatacgta tttaaagtat     480
ttcagggaga ttaacgtatt aaaacaagaa gagggttgac tacatcacga tgaggggggat     540
cgaagaaatg atggtaaatg aaataggaaa tcaaggagca tgaaggcaaa agacaaatat     600
aagggtcgaa cgaaaaataa agtgaaaagt gttgatatga tgtatttggc tttgcggcgc     660
cgaaaaaacg agtttacgca attgcacaat catgctgact ctgtggcgga cccgcgctct     720
tgccggcccg gcgataacgc tgggcgtgag gctgtgcccg gcggagtttt ttgcgcctgc     780
attttccaag gtttaccctg cgctaagggg cgagattgga gaagcaataa gaatgccggt     840
tgggggttgcg atgatgacga ccacgacaac tggtgtcatt atttaagttg ccgaaagaac     900
ctgagtgcat ttgcaacatg agtatactag aagaatgagc caagacttgc gagacgcgag     960
tttgccggtg gtgcgaacaa tagagcgacc atgaccttga aggtgagacg cgcataaccg    1020
ctagagtact ttgaagagga aacagcaata gggttgctac cagtataaat agacaggtac    1080
atacaacact ggaaatggtt gtctgtttga gtacgctttc aattcatttg ggtgtgcact    1140
ttattatgtt acaatatgga agggaacttt acacttctcc tatgcacata tattaattaa    1200
agtccaatgc tagtagagaa gggggggtaac acccctccgc gctcttttcc gattttttc    1260
taaaccgtgg aatatttcgg atatccttt gttgtttccg ggtgtacaat atggacttcc    1320
tcttttctgg caaccaaacc catacatcgg gattcctata ataccttcgt tggtctccct    1380
aacatgtagg tggcggaggg gagatataca atagaacaga taccagacaa gacataatgg    1440
gctaaacaag actacaccaa ttacactgcc tcattgatgg tggtacataa cgaactaata    1500
ctgtagccct agacttgata gccatcatca tatcgaagtt tcactaccct ttttccattt    1560
gccatctatt gaagtaataa taggcgcatg caacttcttt tcttttttt tcttttctct    1620
ctcccccgtt gttgtctcac catatccgca atgacaaaaa aatgatgaa gacactaaag    1680
gaaaaaatta acgacaaaga cagcaccaac agatgtcgtt gttccagagc tgatgagggg    1740
tatctcgaag cacacgaaac tttttccttc cttcattcac gcacactact ctctaatgag    1800
caacggtata cggccttcct tccagttact tgaatttgaa ataaaaaaaa gtttgctgtc    1860
ttgctatcaa gtataaatag acctgcaatt attaatcttt tgtttcctcg tcattgttct    1920
cgttcccttt cttccttgtt tcttttttctg cacaatattt caagctatac caagcataca    1980
atcaactatc tcatatacaa tgtctatcc                                      2009
```

<210> SEQ ID NO 18
<211> LENGTH: 1943
<212> TYPE: DNA
<213> ORGANISM: Saccharomyces cerevisia -continued

```
<400> SEQUENCE: 18
ggcagtcatc aggatcgtag gagataagca ccctgacaag taacatgccg atgaagttgt      60
ttggttcatt gggcaaaaaa atcgggattc tagaaaaccc tgagttgaag attttttcga     120
cagttttatc gtctaggatg gtatcggcac tcattgtgaa cacgttttca atcggagtca     180
tgatttcctc aaccctcttt gcctttagat ccaaaacagc agagatgatt gtaacttcgt     240
ctttagtcaa ccgttccacc cccatggtcc tatgcaaggt gaccaaagtc tttaagccgg     300
attttttgta catcgtacca tgatcttcac ccagcatata gtccaggaga gtcgcgatcg     360
gatatgcgac tgggtacatc agatacatca gtacaagaac aaaggggcag aagaatgccc     420
caacttgcag cccgtattta acacagacac tctgcggaat aatttcaccg aagatcacaa     480
ttagaatagt tgacgacact acagcctgcc aaccacccc aagacacctg tccaaaacaa      540
taggcaatgt ttcgttggtt ataacattag aaagcagcag tgtgactaga acccaatgct     600
tcccctaga tattaggtca agcacccgct tggccagttt cttttcagaa ttcgagcctg      660
aagtgctgat taccttcagg tagacttcat cttgacccat caaccccagc gtcaatcctg     720
caaatacacc acccagcagc actaggatga tagagataat atagtacgtg gtaacgcttg     780
cctcatcacc tacgctatgg ccggaatcgg caacatccct agaattgagt acgtgtgatc     840
cggataacaa cggcagtgaa tatatcttcg gtatcgtaaa gatgtgatat aagatgatgt     900
atacccaatg aggagcgcct gatcgtgacc tagaccttag tggcaaaaac gacatatcta     960
ttatagtggg gagagtttcg tgcaaataac agacgcagca gcaagtaact gtgacgatat    1020
caactctttt tttattatgt aataagcaaa caagcacgaa tggggaaagc ctatgtgcaa    1080
tcaccaaggt cgtccctttt ttcccatttg ctaatttaga atttaaagaa accaaaagaa    1140
tgaagaaaga aaacaaatac tagccctaac cctgacttcg tttctatgat aatacccgct    1200
ttaatgaac ggtatgccct agggtatatc tcactctgta cgttacaaac tccggttatt     1260
ttatcggaac atccgagcac ccgcgccttc ctcaacccag gcaccgcccc caggtaaccg    1320
tgcgcgatga gctaatcctg agccatcacc caccccaccc gttgatgaca gcaattcggg    1380
agggcgaaaa ataaaaactg gagcaaggaa ttaccatcac cgtcaccatc accatcatat    1440
cgccttagcc tctagccata gccatcatgc aagcgtgtat cttctaagat tcagtcatca    1500
tcattaccga gtttgttttc cttcacatga tgaagaaggt ttgagtatgc tcgaaacaat    1560
aagacgacga tggctctgcc attgttatat tacgcttttg cggcgaggtg ccgatgggtt    1620
gctgagggga agagtgttta gcttacggac ctattgccat tgttattccg attaatctat    1680
tgttcagcag ctcttctcta ccctgtcatt ctagtatttt tttttttttt ttttggtttt    1740
acttttttt cttcttgcct ttttttcttg ttactttttt tctagttttt tttccttcca     1800
ctaagctttt tccttgattt atccttgggt tcttctttct actcctttag attttttttt    1860
tatatattaa ttttttaagtt tatgtatttt ggtagattca attctctttc cctttccttt    1920
tccttcgctc cccttcctta tca                                            1943

<210> SEQ ID NO 19
<211> LENGTH: 2001
<212> TYPE: DNA
<213> ORGANISM: Saccharomyces cerevisia

<400> SEQUENCE: 19
tgacaacgag taccaggaaa tcagtgcttc tgctttgaag aaggctcgta agggctgtga      60
tggtttgaag aaaaaggcag tcaagcaaaa ggaacaggag ttgaagaaac aacaaaaaga    120
```

```
ggcagaaaat gctgccaagc aattgtctgc tttgaatatc accattaagg aggacgaatc      180
gctaccagct gccattaaga ctagaattta tgactcttat tccaaggtcg acaaagagt       240 taaggtttcc ggttggatcc atagattacg ttctaacaag aaggttattt cgtcgtcct      300 cagagacgga tctggtttca ttcaatgtgt cttgtccggt gatttggcat ggctcaaca      360 aactttggac ctgactttgg aatccaccgt tactctgtac ggtaccatag tcaaattgcc     420
tgagggtaaa accgctccag gtggtgttga attgaatgtc gactattacg aagttgtagg     480
tttggccccc ggtggtgaag actcctttac aaacaaaatc gcagagggct cagacccttc     540
tttactgttg gaccaacgtc atttggcctt gagaggagag gccttgtctg cagtcatgaa     600
agtccgtgct gctctactga aaagcgttag acgtgtttat gatgaagaac atttgacaga     660
agttacccca ccatgtatgg tgcaaactca agtcgaaggt ggttccactt tgttcaagat     720
gaactattac ggcgaggaag cttacttgac ccaaagttcc caattatatt tagaaacctg     780 tttgcctcc ctaggtgatg tttataccat ccaagaatcc ttcagagctg aaaagtccca     840
cacaagaaga catttgtccg aatatacca tatcgaagct gaattggcct tcttgacttt     900
cgacgatcta ttacaacata ttgaaacttt gatcgtcaaa tccgtgcaat acgttttgga     960
agacccaatt gctggcccac tcgtaaaaca attgaatcca aactttaagg ctccaaaggc    1020
tccattcatg agattacagt acaaggatgc cattacctgg ttgaacgaac acgacatcaa    1080
gaacgaagag ggcgaagact ttaaatttgg tgacgatatt gcagaagctg ctgaaagaaa    1140
gatgaccgat accatcggcg tcccaatctt tttgacgaga ttcccagtag aaatcaagtc    1200
tttctacatg aagcgttgtt ctgacgaccc ccgcgtcact gaatccgtcg acgttttgat    1260
gccaaacgtt ggtgaaatca ctggtggttc tatgagaatc gacgcatgg acgaactaat    1320 ggcagggttt aagcgtgagg gtattgatac cgacgcctac tactggttca ttgaccaaag    1380
aaaatacggt acttgcccac atggtggtta cggtatcggt accgaacgta ttttagcctg    1440
gttgtgtgac agattcactg tcagagactg ttccttgtat ccacgtttca gcggtagatg    1500
taagccatga tctttagtta ctgaagagta cgtgagcgct cacatatata caaatattta    1560
taccgattaa tatttacgtt cctccctctc tctaattatt cattgattta ttcaagaatt    1620
agcgttataa caataaatgg ttggcgcagg caattaattt ttctttactc ttccaaaccc    1680
tctgttaacg acaatcaaat aacctgatct gccaaggctc catcatatct ggcctagaac    1740
agtttttttt tttcgattat ttgttcgttc ttgtggtggt tactcattgg cagaatcccg    1800
aaaatcatga ttagtagatg aatgactcac tttttggata agctggcgca aattgaaaca    1860
tgtgaaaaaa aaaaaaaagg attataaaag gtcagcgaag cacagaactc tgagataaga    1920
ctacctttct ttagctaggg gagaaatattc gcaattgaag agctcaaaag caggtaacta    1980
tataacaaga ctaaggcaaa c                                              2001
```

<210> SEQ ID NO 20
<211> LENGTH: 1999
<212> TYPE: DNA
<213> ORGANISM: Saccharomyces cerevisia

<400> SEQUENCE: 20

```
tcctaaggac atattccgtt cgtacttgag ttattggatc tatgaaatcg ctcgctatac       60
accagtcatg attttgtccc tggtaatagg ggttttggtt ttattaatta tattttttaa      120
tgacaacgaa gcttgtgttt tcaattctgc aatatttgct tttacttctc ttgtaggttt     180
gttaataata ttaagtgatg gtaatccaaa gctagtcagt cgtcgaaatt ttaggaccga     240
```

-continued

```
gcttttagtg gatgtcatca cacgtaaacc ggcggtagaa gggaaagaat ggaggatcat      300
cacatacaac atgaaccaat atttgtttaa tcatgggcaa tggcatactc cgtattactt      360
ttacagcgat gaggattgct accgttattt tctacgcctt gttgagggag taacccccaa      420
gaagcaaaca gccacgtcaa ttggcaattc tccggtcacc gctaagcctg aagatgccat      480
cgagtcagct tctcctagtt ccagactgaa ttatcaaaac tttttgctca aggcagcgga      540
gatcgaacga caagctcagg aaaattactg gcgaaggcgg catcccaata tcgatgcgct      600
tcttaaaaag acggaatagc ttagagacac taccatacgt aaagcgaaca taaactagag      660
tatgatatat aatcagcact aactggccgg aaaacggccg aaggaagcct cgaaaagtcg      720
attcgtgttg gacccatttg ctgaacaaag tggttcattg cctacctatt atggtagtag      780
tcgtgataat cgtgtggttg gttttgtcaa cggtgcattt gcattttcat gacaataaac      840
cttgcgtttt cgttctcggg atattacttt ccctccactt cttcgcctc aatagctcct      900 ataagcattc tcagggcgta tgtcggtgat cgagatttcc aagcaagctt ttagtggaaa      960
tcatcgcgcg caagccagcg gtaaagggaa agaacggag gacgattaca tacaagatga     1020
acgaataaat aaattaataa taataataa taaaagtac agtagcatta aatattatta     1080
agtttaatga ttaaaaattg gttaattgtc aagaaaatct aaggtattaa taaataaata     1140
atactatgac aacttgcagc gaaagcatca gccccaatga aaattaatca gaattgaatc     1200
tgagcgtatt tatttgataa cggtttacgt aactgttgga ataaaaatca actatcatct     1260
actaactagt gtttacgtta ctagtatatt atcatatacg gtgttagaag atgacgcaaa     1320
tgatgagaaa tagtcatcgt tttcaacgga agctgaaata caaggattga taatgtaata     1380
ggatcaatga atatcaacat ataaaacgat gataataata tttatagaat tgtgtagaat     1440
tgcagattcc ctttttatgga ttcctaaatc ctcgagaaga acttctagta tatctacgta     1500
cctaatatta ttgccttatt aaaaatggaa tcccaacaat tatctcaaaa ttcccccaat     1560
tctcatcagt aacaccccac cccgtattac ttttaccgtg atgaagattg gcatcgttac     1620
tttctaaacg taggacgtgc ggaatgacaa accatcagc agtgtcacga tctctccagt     1680
cacaatggca atcatgagtg catagtccaa agtaaagggg caaggaaaag catgattgaa     1740
aggactcccc atctggactc tatatgtcat cagcggctaa aaaaaagcat atagcacaac     1800
atcagcatca gcatcagcac tagagtcatc ggcccggcgg tccgcggtca tccccgcgga     1860 cttccgtcc gcccggcggg ctgtatcagc gtcaactgga acgcgcatat atatacaaga     1920
cacacataac atagaagcac acccacgaca ataaccacac gacaataacc acacccgccc     1980
accctccttc tccgtatac                                                  1999
```

<210> SEQ ID NO 21
<211> LENGTH: 1500
<212> TYPE: DNA
<213> ORGANISM: Zea mays

<400> SEQUENCE: 21

```
tgtcctattc atttataact tactaccccg cattacttac ttgaaaccta aggattgact       60
agctttacac tttactttat ccttgatgac cttatgggct gttatggtta gcactctgct      120
attgccttaa cttaatcaat gaacatgatg tgactattta tgatactgtt atcctgatga      180
tgttgatgat cttgtgatac tctaggggc tcaggctgtt tcctgagtac ctctccgtaa      240
ggacttgttc gttgagagac cacccgggat aacagtacaa ccatgagggt gaaatgggat      300 gccccttagct gattaattag atgaactaga ggtgtagttg cttagccgtc gtgccgtcaa      360
```

```
tggggtccag gcacagtgct tgctctgccg aggctgagtg ccgaggttct ttcgttttgc      420
tctttgttag tcactctcct gcggggaggg gtactgtgtt tatcaaactg gagaaaccta      480
acgggcagct atggtctcta gggaatcttt gtaaaagcta cgtagtgatg ccctgccgga      540
ccacctaggt agtggtcaat ggggattagc tctccccggg tagaaaggga atcatgactc      600
atgggtaaag tgtgcaacct ctgcagaggg tagtgaaact ggtatatcag ctgtgctcac      660
ggttaagagc agccttggga tcctctttga ttagagatac agatggttcg agatacaagg      720
attatgttat ggttttggtt cgactatgat gatgatgttc ctcgatgagg aaatggttta      780
cgggttgtta aatgctaaaa tctggcttct actaatgata aatacctgac caactaaaag      840
caactgcttg agcctaaccc cacataaagc tagtccactt cagccaaacg ggacatttgc      900
tgagtacgtt gatgtgtact catccttgct ttaccacaaa acaccaggt tgtccgcatt       960 gtaaccactg ctcaggagaa ggtgaagccg tggaaggaga cttccaggag ttccaagact     1020
acgacgaatt ctaggtgtgg gttggcggca accccccagtc agctacctgt gaaggcctta    1080
tctttactgc gtttcgctag cactttgatt tacctgttaa gacaatgact atgtggatgt     1140
ctatgactct gtgatgtaat aagttaatac tcttttatgt tattattcga gcactgtgcg     1200
atgatgttca tttatgtaat cgctgtgtac gtgagttctg atcctggcac gtacatagtt     1260
cgcattcggt ttaccttcca aaaccgggtg tgacataagt ggtatcaaag ccaggttgac     1320
tgtaggaccg ctgacctaga gtagcactgg tcgtactaag gactattgac ccttccctct     1380
caccttgacc tctgatgtta cttcaaaagt cggtcacctc gcccacccta tgttttacta     1440
catatatata ctatattata ccttggaaaa tttttttatct tatcctggct atgggttatt    1500
```

<210> SEQ ID NO 22
<211> LENGTH: 1708
<212> TYPE: DNA
<213> ORGANISM: Zea mays
<220> FEATURE:
<221> NAME/KEY: misc_feature
<222> LOCATION: (914)..(914)
<223> OTHER INFORMATION: n is a, c, g, or t
<220> FEATURE:
<221> NAME/KEY: misc_feature
<222> LOCATION: (973)..(973)
<223> OTHER INFORMATION: n is a, c, g, or t
<220> FEATURE:
<221> NAME/KEY: misc_feature
<222> LOCATION: (1693)..(1693)
<223> OTHER INFORMATION: n is a, c, g, or t
<220> FEATURE:
<221> NAME/KEY: misc_feature
<222> LOCATION: (1698)..(1698)
<223> OTHER INFORMATION: n is a, c, g, or t

<400> SEQUENCE: 22

```
gctgtctgag aatacgcttg aattcgttct gtgattttg gcacagaggt aggttattac        60
ccatagatgc catcaaaaat aacctctagt gcagaacccc aaccaaatga gggttgtagt      120
acaaagtaac catctaccct tactttttgtt attttttgcca agattatatc ctaattattc    180
ttaacctcaa atttgtagca taaacaacag tgaccaatag caaccaactg taattttttac    240 aacatttttg aaaatttttta aatcaatata gtagtacaag ttcccttttaa aagaacataa   300 atagaaaata aaaagggaa ttctggaagg aattaatatt acataactag atctccctaa      360
gtgcccacta aaacactaag aggatgacta aattcttact tccactcaaa acctaaacta     420
ggtaagtata aagcactaag agcatcatac gataaagaaa ccctagttta cccactgcct     480
taatattgct tcaccataca tcgtatttac taaattggca tatcattaac atgcacgtat     540
```

```
cttattcatt gcattcaata gattgtaacc tcgctgacgg agagtacgtc ctcattctag      600
agcaaggagt tgctcaagaa ggagtccagg agccagcacc agagactgcc actgaggatc      660
tccctgcccc agcttttgaa ggcaagcccc agttttatgc ataaccgtta tatatgctat      720
tttactgcac ttaatgattg taggcttgta ctgtgcactt aagtgtagga gttgccctaa      780
accatagttg catgaactca ggatcccttg agatggatac gagtatgcta ggtcgagtag      840
ctgctttact aattagggga tctcgtagaa atctagtgat ttttctagca ctcgcgcgag      900
gtcaggaatt ggtngtatcc attttatat cataataatg atggtaggtg gacacgatcc       960
atgaggatgc gtngtctacg ggacggaaat tgaataaagg attaaggtgt ggtatcgtgt     1020
gtcaagcgtt tgaacttact aaacacatgc cgagaaatat ggtaaatcgg caagcctagt    1080
acctgagtga acctgcccgc aaattgacct tctcacggga cctgagatgt ggtctcccat    1140
tccggttatg gtgggtacaa gtgcggtcac tgcacgacga cagtcggtgt cagtgatgca    1200
ttgtacgcca aggcggtgag cctcttctg ttgatgggga atcgatgggg acggttgatg    1260
tgtgtgggga cggagtgcct cgccacgtcg tgtgtttagg tttaccttgc aaggttaaaa    1320
actcgattcg aatcgtctgc ttctcgcagc taatgagact gcttgatcca tgctgctaca    1380
ttgagtgata agtgaaaatg aggtgactgg taaaagatgt tgattgataa aatgtttgat    1440
accatgtatg attagctagg ttctcatcta gttttttgta acacccagtt tgtaatatat    1500
aataaaagag gagaaaagtt atttttcctat attttatgtg tgttaaatct acttatcatc   1560
acatgtgaac accatattca aaaacaaata agtaataaaa aatatatgcc attaaattat    1620
gcatcatgct ggatattatt tttgtgtgtg cattttgtga caatataaaa ataaagagac    1680
aagaagacga atncctanat gtcaatcc                                       1708

<210> SEQ ID NO 23
<211> LENGTH: 118
<212> TYPE: DNA
<213> ORGANISM: Zea mays

<400> SEQUENCE: 23
ccacgtattt tgcaagctat ttaactggcg gcgattgcgt acccgacgac caaaattagg       60
gtcaacgcta cctgtaggaa gtgtccgcat aaagtgcacc gcatggaaat gaagacgg        118

<210> SEQ ID NO 24
<211> LENGTH: 194
<212> TYPE: DNA
<213> ORGANISM: Zea mays

<400> SEQUENCE: 24 cccttactt gaggataaat tatgtctaat attcaaactg gcgccgagcg tatgccgcat       60
gacctttccc atcttggctt ccttgctggt cagattggtc gtcttattac catttcaact    120
actccggtta tcgctggcga ctccttcgag atggacgccg ttggcgctct ccgtctttct    180
ccattgcgtc gtgg                                                      194

<210> SEQ ID NO 25
<211> LENGTH: 1176
<212> TYPE: DNA
<213> ORGANISM: Zea mays

<400> SEQUENCE: 25
ccgatgataa gcttgaattc tggtcgtatt atgttcttat gcggatgatg agagccaact      60
tgctttcctg cttggcatgt gctacaaatc ctgtctttct aaaatgaaca tttgttagtc     120
```

```
ctaaaatgtg ttctcccttt agaagcttgt gaagattctt catcccaaca tgggctagtc    180
ggcggtgcca gagccaaccc atgttagtct tagcaattaa gcaagtgtcg agttcagctc    240
tatcaaaatc taccaagtat agctgaccct ctaacactcc cttaaatgct attgaatcat    300
cacttcttct aaagacagta acacctacat cagtgaatag acagttgtag cccatttgac    360
acaattgaga tacggaaagc aaattgtaat ctaaagaatc tacaagaaaa acattggaaa    420
tagaatggtc aggagatata gcaattttac ccaaaccttt gaccaaacct tgatttccat    480
ccccgaatgt gatcgctctt tggggatttt ggtttttctc atatgaggag aacatctttt    540
tctccccagt catgtggttt gtgcacccgc tgtcgagtat ccaacttgag cccccggatg    600
cataaaccta caaaacaagt ttagttcttg actttaggta cccaaatggt tttgggtcct    660
ttggcattag acacaagaac tttgggtacc caaacacaag tctttgaccc cttgtgtttg    720
cccccaacat atttggcaac taatttgccg gattttttttg ttaaaacata agatgcatca    780
aaagttttaa atgaaatgct atgttcattt gatgcaatag gaattttctt cttaggcaac    840
ttggcacggg ttggttgcct agagctagat gtctcacttt tatacataaa agcatggtta    900
gaaccagagt gagacttcct agaatgaatt ttcctaattt tgtcctcggg ataaccggca    960
gggtataaaa tgtaaccctc gttatcctga ggcatgggag ccttgccctt aacaaaattg   1020
gacaatcttt taggaggggc actaagtttg acattgtctc ccctttggaa gccaatacca   1080
tccttaatgc ccgggcgtct cccattatag agcatacttc tagcaaattt aaatttttca   1140
ttctctaaag aattcaagcg tattctcgga gagtca                             1176
```

<210> SEQ ID NO 26
<211> LENGTH: 731
<212> TYPE: DNA
<213> ORGANISM: Zea mays

<400> SEQUENCE: 26

```
cgtaccaccg cacgaagatt tctattgttc ctgaaggcat attcaaatcg ttttcgttac     60
cgcttgcagg catcatgaca gaacactact tcctataaac gctacacagg ctcctgagat    120
taataatgcg gatctctacg ataatgggag attttcccga ctgtttcgtt cgcttctcag    180
tggataacag ccagcttctc tgtttaacag acaaaaacag catatccact cagttccaca    240
tttccatata aaggccaagg catttattct caggataatt gtttcagcat cgcaaccgca    300
tcagactccg gcatcgcaaa ctgcacccgg tgccgggcag ccacatccag cgcaaaaacc    360
ttcgtgtaga cttccgttga actgatggac ttatgtccca tcaggctttg cagaactttc    420
agcggtatac cggcatacag catgtgcatc gcataggaat ggcggaacgt atgtggtgtg    480
accggaacag agaacgtcac accgtcagca gcagcggcgg caaccgcctc cccaatccag    540
gtcctgaccg ttctgtccgt cacttcccag atccgcgctt tctctgtcct tcctgtgcga    600
cggttacgcc gctccatgag cttatcgcga ataaatacct gtgacggaag atcacttcgc    660
agaataaata aatcctggtg tccctgttga taccgggaag ccctgggcca acttttggcg    720
aaaatgagac g                                                        731
```

<210> SEQ ID NO 27
<211> LENGTH: 1325
<212> TYPE: DNA
<213> ORGANISM: Zea mays
<220> FEATURE:
<221> NAME/KEY: misc_feature
<222> LOCATION: (1148)..(1148)
<223> OTHER INFORMATION: n is a, c, g, or t

```
<400> SEQUENCE: 27
tggctgtccg agaatacgct tgaattctta gaccagtttt ggattcacga aggagcaaag    60
tggcaaccga aggccctctg gtctgggagc accggactgt ccggtgtaca ccggacagtg   120
tccggtgcac caccggacag tgtccggtgt accagaggca ttcaactcga actcgccacc   180
ttcgggaatt tccagaggca ctcgcgctat aattcaccgg actgtccggt gtacaccgga   240
cagtgtccgg tgcgccaagg aagatcagcc tcaggaactc gccagcttcg ggaaactcca   300
acggctagtc cgctataatt caccggactg tccggtgtgc accggactgt ccggtgcgac   360
tccagagcaa cggctagtcc acgccaacgg ctacctgcgg cgcattaaat gcgcgcgcag   420
cgcgcgcaga agtcaggcgc gcccatactg gcacaccgga caaggaacag tagatgtccg   480
gtgtgcaccg acacccagg cgggcccaca agtcagaagc tccaacggtc agaatccaac    540
ggcagtgatg acgtggcagg gggcaccgga ctgtctggtg tgcaccggac tgtccggtgc   600
accctctgcc aggtggggcc aggctggtcc ggggcagagg cttccctcc gcagaaaccc    660
gagagcgcag gtttgggagt tgaattttag tggtgcaccg acatcgcac cggactgccc    720
ggtgtgcacc ggacagtgac tgttcactgt ccggtgtgcc atgagtccaa cggctagctg   780
tcagaactag ccgttggaaa cgaccgttgg cgcaccggtg gcgcaccgtt ggcgcaccgg   840
tggcgcaccg gactgtccgg tgcgccattg cgcagtgagg tgcctgtaac ggctagttgg   900
tgggtgaggg ctatttatac cccttccacc caccatattc aatgtcttgc actccacatt   960
tattccagca cattgctaga gcattgcaac caccaaaagc ctagtgagga gattagagaa  1020
tcttaattcg cgtctgttcc tcattagcgc tagcgagagc cacctagagc acacaccact  1080
tgcattaggc ttctcttggt caagcaaaag tctacggctt gttactcttg gtgattggca  1140
tcacctanac ggcttgttgg cgttgggagc tcggtgatca ccgtgaagat cttgttggtg  1200
acccgactca agtttgtaag cggtcttgag ggatccaccg ggcccgaagt ggcaaagatc  1260
atctcgtagt gagcccctgg ttcttgcgag acaaggggg aacgataccc tggcccggtg   1320
cttca                                                              1325

<210> SEQ ID NO 28
<211> LENGTH: 77
<212> TYPE: DNA
<213> ORGANISM: Zea mays

<400> SEQUENCE: 28
aacggggccg cttttcaga aaccaagac cattaacggt tttggggaaa aattccacca    60
acttgggacc gggaata                                                  77

<210> SEQ ID NO 29
<211> LENGTH: 153
<212> TYPE: DNA
<213> ORGANISM: Zea mays

<400> SEQUENCE: 29
gcgttcaata tcatcgcgat gttcttcgtt atcgcgccag accagcaata cctgcgcttc    60
tcccggctgg cggttctctt ccgctttgtg atgacgtcgc caccagcgtc gtgccgcgct   120
ctgtccaggc aggttttcca gctcaaactg gag                                153

<210> SEQ ID NO 30
<211> LENGTH: 1424
<212> TYPE: DNA
<213> ORGANISM: Zea mays
<220> FEATURE:
```

<221> NAME/KEY: misc_feature
<222> LOCATION: (1261)..(1261)
<223> OTHER INFORMATION: n is a, c, g, or t
<220> FEATURE:
<221> NAME/KEY: misc_feature
<222> LOCATION: (1267)..(1267)
<223> OTHER INFORMATION: n is a, c, g, or t
<220> FEATURE:
<221> NAME/KEY: misc_feature
<222> LOCATION: (1275)..(1276)
<223> OTHER INFORMATION: n is a, c, g, or t
<220> FEATURE:
<221> NAME/KEY: misc_feature
<222> LOCATION: (1403)..(1403)
<223> OTHER INFORMATION: n is a, c, g, or t

<400> SEQUENCE: 30

| | | | | | |
|---|---|---|---|---|---|
| atgagcaatt | agagattcgt | gccttggttc | accaagtctt | gagccggttg | tacatgtgtt | 60 |
| gtggctcctc | ccctttgcga | agccggaacc | gactgagctc | ccctcgatc | atttcccgct | 120 |
| tggtgatctt | tgtaagctca | tctccctcgt | gcgcggtttt | gagcacatcc | caaacctcct | 180 |
| tggcgctctt | caaccttga | actttgttat | actcctctct | acttaaagag | gcgaggagta | 240 |
| ttgttgtcgc | ttgagagttg | aagtgctcga | tttgggctac | ctcatcctca | tcatagtctt | 300 |
| tatcccctat | agatggtacc | tgcgctccaa | actcaacaac | attccatata | cttttgtgga | 360 |
| gtgaggttag | atgaaatttc | attaaatcac | tccacctagc | ataatcttca | ccgtcaaaag | 420 |
| ttggcggttt | gcctaatgga | acggaaagta | atggagtatg | tctagatgta | cgagagtagt | 480 |
| gtaggggat | attactaaac | ttcttacgct | cttggcgttt | agaagttatg | gagggtgcat | 540 |
| cggagtcgga | ggtcgatgtt | gatgaagtgt | cggtctcgta | gtagaccact | ttcctcatcc | 600 |
| tcttttgctt | atctccactt | cgatgtggct | tgtgggaaga | agattttttcc | ttcttctctt | 660 |
| tgtggtgaga | agaagatttc | ttctccttcc | ctttgttgga | ggagatcttc | ttcttctccc | 720 |
| tcctcttggt | gcgggactct | tccgatgaag | tgctcccgtg | gcttagtg | ggcttttcgc | 780 |
| cggtctccat | ctccttcttg | gcgtgatctc | ccgacatcac | ttcgagcggt | taggctctaa | 840 |
| tgaagcaccg | ggctctgata | ccaattgaaa | gtcgcctaga | ggggggtga | atagggcgaa | 900 |
| actgaaattt | acaaatataa | acacaactac | aagccgggtt | agcgttagaa | atataaacga | 960 |
| gtccgcgaga | gagggcgcaa | aaacaaatcg | taagcgaata | agcaagtgag | acacgtggat | 1020 |
| ttgttttacc | gaggttcggt | tctcgcaaac | ctactccccg | ttgaggaggc | cacaaaggcc | 1080 |
| gggtctcttt | caacccttcc | ctctctcaaa | cggtccctcg | gaccgagtga | gcttttcttc | 1140 |
| ttctcaatca | aacgggaaca | aaacttcccc | gcaaggggcca | ccacacaatt | ggtgcctctt | 1200 |
| gccttggtta | caattgagtt | ttgatcacta | gaacaagtga | gaaagaaaga | aagcgatcca | 1260 |
| ngcgcangag | ctcannagac | cacggcaaat | ctctctcgct | agtcactaaa | agcttgagtg | 1320 |
| ggattggaga | ggatttgatc | tctttggtgt | gtctagaatt | tgatgctaga | gctcttgtag | 1380 |
| tagttgggaa | gtggaaaact | tgnatgccat | gatgttgggg | ttgg | | 1424 |

<210> SEQ ID NO 31
<211> LENGTH: 78
<212> TYPE: DNA
<213> ORGANISM: Zea mays

<400> SEQUENCE: 31

| | | | | | |
|---|---|---|---|---|---|
| tggctgtctg | agattaagct | tgattcgttg | ctctttcgct | ttaggcagag | tcgtcttgat | 60 |
| gatttcatga | cgaaccag | | | | | 78 |

<210> SEQ ID NO 32

```
<211> LENGTH: 1743
<212> TYPE: DNA
<213> ORGANISM: Zea mays

<400> SEQUENCE: 32
ggagccagtg tacctatcgg taaggcacag caccccttctg gttgttgtag tcgaatagca      60
caacgtcgac ctccacccta atcgtagtt atcaggagac ggtgtacctg tcgctcaagg      120
cgccacacca tcttggtgtg gtagtcgggc agccaacgtt gttctcaaac aagttttcca      180
cccccatcat ctctcatcga aagatcggac acccttcttg tgatagaccc tcccaagtca      240
ttaggcccac ctatagttgt ccttgtccaa cggacctcaa acaaccctgc aggtgcacct      300
gatcacttga caagttcggt atctgaattc cttaccttt ccaagagcgt ttcacctatc      360
acacagacat tacaattcat cggagatacg aaagtgtgga agcagttaca ataacttact      420
ttattgaaaa gtaagacaaa gttatatagt tatagaccag aacaaaatat atgagtgcag      480
agtattatta ttcataaca tgggaggcaa aaacccctcc caaataaaca gtaaaagttc      540
tcctaacgga ggacctttcg tcccgcagct ttagtcttga ttctcttctt tcggtaccac      600
cttggaacag aagcaacaaa agtttgttgt ttcttcacct aaaacaacat gggacaaagc      660
cctgagtatg aagtgtactt tcgcaatact tacccgacaa agtaaaagac tctcaaggat      720
atgctggctt aagggagtc aaggtaaggc ttatcaataa tcaatgactc tgttttgcag      780
aaatgcttac taatagtgga tccttaaaaa tccagtttta tttgtcaggt taagtaaaat      840
tacctgcaac tagagttctt tctatcctag ttcaatcact tgacctatac tagccaattt      900
cttaacaacc cttcttattc actggaatgc tacgtgtagg tcagtgacca agtcttcatg      960
tccgcgaagt tacggcgatc cgaatcgatt atactcagct gaggatctcc aatcacacga     1020
catatgtagc atttaaccct tgcatatgtc aactcgccac cgaggttctt aagaccagat     1080
caggttcagg ccaaccgaga gcatagatac accaccgtcc agcctcttgc cacggagggt     1140
acacgctact ctcgccatct ctccactccc attgcgtgtt atcttattct ggtattagtc     1200
tgcccgaggc aaagcttacc cgtgacgagg catgtgacca gttaaagggt cctcgatcat     1260
caagcctaca tcgagacggt ccttaatcga ctaagacgga gacactccac cgagactctc     1320
ttctcgtgca agtcacccgc ccggtctcag cttaatcatt tcaaacccaa agtttggtac     1380
ctggtagagg tacatatttt ccgatgttga acccatcatg gccatgatgg atccaccatc     1440
aagttttatt ttcgaaaaca ttccacccac tttgaagcat catcttttgt aaaagcaaaa     1500
tatttttatt tttctagagc aaagctaagc ataagaaaaa ccatttgtaa aacagggact     1560
taaggagaag taatcaaatc taaggaacgt gttggggcga aggcaaagac gctacccttc     1620
gcttgatgcc cttgccgatc tcgccgcacc aacggaggcg aagcgatcgg cagttttcac     1680
ccttcgtcca acacgctgca agacgaaggc ctacgacgag gtcgcccgt ctcgcgtcct     1740
cgt                                                                   1743

<210> SEQ ID NO 33
<211> LENGTH: 1528
<212> TYPE: DNA
<213> ORGANISM: Zea mays
<220> FEATURE:
<221> NAME/KEY: misc_feature
<222> LOCATION: (1308)..(1308)
<223> OTHER INFORMATION: n is a, c, g, or t

<400> SEQUENCE: 33
atgagcaatt agaaattcgt agttatgaat ttttcaagct ctctacttat ttaaaaagaa       60
```

```
taaatcttaa aggtttaaga aaaacagctt tgcgccaggg tccctgggtt atttcttaac    120
taaaacgttc aaaccgtgcc cttgaggaac tgtttcactg agtagtggac ttcgcgaata    180
ccccctggct tttccctctc ttaacccgag ctccctcctc gccggaacag tagccgcaga    240
gagaaatagc ggtggcgcgg cttaccgtgt gtaggagagg tccggtggac ggttgggtga    300
ggttcggtgg cttctagcgg tcacgtcgag gggcggatcg ccggcggtga tggccggagt    360
agggctggcc acgcgcgcag gcggtcgagc tcgtcggcga cgcgtgatcc ggcctgctca    420
cggcggtaga gttcaatcaa accgcacgag gagcttcatg ggaggtcact cgtgctgtat    480
gcacaaggaa tcgaagagcg gctcaccgtg tagctcggtc tacgcgcgac ggcggtcggg    540
cgaagtccgg cgacgtcaat ccggcacctc ctatgaggtg gtgttcggtc caagggctca    600
gggagcttca cttagctcta gggaggctag gcgagggttt ggatgggtg gcggaggact    660 ggagcggcca gtccatggtg gccggggcta gggcggccgc tggcacgccg tgcgcagagc    720
gattgccggt gaacttgtgc tcgggcgggg ttgagagcga gcggggtgt acggtcaagg    780 ccggggtcgg ctttataggc gtgggcactg gcgtgggcat gtgtggggga cagatatccc    840
ccgggttcac tggaaggata aaagacctca caaaaggccc aagggcccaa tagatcgtaa    900
ggtcactcct tcatgggcct cgggaggaac aatcagtaaa gcagattgac ataaggccgg    960
atcggtgcaa gcccggacgg ccccacaacg ttgagcaagc aaccacaaca gaagattcga   1020
ctttctcgcg ctggagcccc gtacgacaga accaggcgaa gataagtcgg cagaactata   1080
ggaagataga ctcaatcagt tcactttctc ttaggtgccg tttgttatct catccgcatg   1140
tattgcctca cggtcgaata tataaggcct aggggcacc ccttcaaatt gatcgatccc   1200
attactcagc catccacccc aactctctac gttctagctt tagagagctc ccttgtaacc   1260
cattacataa agcatactcg ccaggacgta gggtgttacg catctcanag cggcccgaac   1320
ctgtaaacac tgtccattgt tcttcgtgca tctggcacga accatttagc tatagtcggc   1380
gacaccgtcc tactcctaaa acaccttgag gggcaacccc gggtgtgcgg tcggacccaa   1440
aacatcgaca gctggcgcgc caggtagggg ggtgtgtcgc cgatctaagc tagctcaatt   1500
gccgtcaccc tttcacgcaa gatcaccc                                      1528

<210> SEQ ID NO 34
<211> LENGTH: 460
<212> TYPE: DNA
<213> ORGANISM: Zea mays

<400> SEQUENCE: 34
ctgaacggta gagaaacgta caaatactgg ggtgattttg ttcggatctg agaggaaatc     60
cgctttggta atatcgctta agcttttata tggctggaaa taccgtgag cggctgatcc    120 gcgtgcatga acaatacgtt ccggaatgcg ctcatggtca aagtgggtga ttttctcgcg    180
cagaataaaa tcttccagca gcgttggacc acgctaccg gcacgcagtg agttttgatc    240
gtcggcgatg cgcacgccct gattagtggt cagcgcataa ttttcactgc ctttgcgtac    300
gtcttccaga gaattaagtt tttcgttacg cgtatcaggg gctttcaggc tccctggggc    360
ggtaggttgt gcacctggcg gtgttggttc agccgctgga cgatgagagc cgtcctcagg    420
tgccagtgag tccatccccg gtttcgcttc gctggaatcg                          460

<210> SEQ ID NO 35
<211> LENGTH: 234
<212> TYPE: DNA
<213> ORGANISM: Zea mays
```

```
<400> SEQUENCE: 35
ccgtttgaat gttgacggga tgaacataat aagcaatgac ggcagcaata aactcaacag      60
gagcaggaaa gcgagggtat cctacaaagt ccagcgtacc ataaacgcaa gcctcaacgc     120
agcgacgagc acgagagcgg tcagtagcaa tccaaacttt gttactcgtc agaaaatcga     180
aatcatcttc ggttaaatcc aaaacggcag aagcctgaat gagcttaata gagg           234

<210> SEQ ID NO 36
<211> LENGTH: 2303
<212> TYPE: DNA
<213> ORGANISM: Zea mays
<220> FEATURE:
<221> NAME/KEY: misc_feature
<222> LOCATION: (876)..(876)
<223> OTHER INFORMATION: n is a, c, g, or t

<400> SEQUENCE: 36
atgagcaatt agaaattcgt aatttactgc aaagcacaac aaaatcgcaa agtcatcaaa      60
aaaccgcaaa gttgtttaaa ataagagcaa cactacaaaa ggagataaga agagcacata     120
cctcagtcac ttattatcac tagcgctcgc cgcagccgtg taaccgagca tagcgagcga     180
actggcgagg aagcaaagaa gaactgttct gtcagatagc tcttacgctc agcgcaagaa     240
gaaatatcca ccgtgggaaa aactccaggt agaggtacac acgcggatag ccaattcaga     300
gtaataaact gtgataatca accctcatca atgatgacga actaaccccc gatatcaggt     360
cacatgacga agggaaagag aaggaaatca actgtgacaa actgccctca aatttggctt     420
ccttaaaaat tacagttcaa aaagtatgag aaaatccatg caggctgaag gaaacagcaa     480
aactgtgaca aattaccctc agtaggtcag aacaaatgtg acgaaccacc ctcaaatctg     540
tgacagataa ccctcagact atcctgtcgt catggaagtg atatcgcgga aggaaaatac     600
gatatgagtc gtctggcggc ctttcttttt ctcaatgtat gagaggcgca ttggagttct     660
gctgttgatc tcattaacac agacctgcag gaagcggcgg cggaagtcag gcatacgctg     720
gtaactttga ggcagctggt aacgctctat gatccagtcg attttcagag agacgatgcc     780
tgagccatcc ggcttacgat actgacacag ggattcgtat aaacgcatgg catacggatt     840
ggtgatttct tttgtttcac taagccgaaa ctgcgntaac cggttctgta acccgataaa     900
gaagggaatg agatatgggt tgatatgtac actgtaaagc cctctggatg gactgtgcgc     960
acgtttgata aaccaaggaa aagattcata gcctttttca tcgccggcat cctcttcagg    1020
gcgataaaaa accacttcct tccccgcgaa actcttcaat gcctgccgta tatccttact    1080
ggcttccgca gaggtcaatc cgaatatttc agcatattta gcaacatgga tctcgcagat    1140
accgtcatgt tcctgtaggg tgccatcaga tttttctgatc tggtcaacga acagatacag    1200
catacgtttt tgatcccggg agagactata tgccgcctca gtgaggtcgt ttgactggac    1260
gattcgcggg ctatttttac gtttcttgtg attgataacc gctgtttccg ccatgacaga    1320
tccatgtgaa gtgtgacaag ttttttagatt gtcacactaa ataaaaaga gtcaataagc    1380 agggataact ttgtgaaaaa acagcttctt ctgagggcaa tttgtcacag ggttaagggc    1440
aatttgtcac agacaggact gtcatttgag ggtgatttgt cacactgaaa gggcaatttg    1500
tcacaacacc ttctctagaa ccagcatgga taaaggccta caaggcgctc taaaaagaa    1560 gatctaaaaa ctataaaaaa ataattata aaaatatccc cgtggataag tggataaccc    1620
caagggaagt tttttcaggc atcgtgtgta agcagaatat ataagtgctg ttccctggtg    1680
cttcctcgct cactcgaggg cttcgccctg tcgctcgact gcggcgagca ctactggctg    1740
```

```
taaaaggaca gaccacatca tggttctgtg ttcattaggt tgttctgtcc attgctgaca      1800
taatccgctc cacttcaacg taacaccgca cgaagatttc tattgttcct gaaggcatat      1860
tcaaatcgtt ttcgttaccg cttgcaggca tcatgacaga acactacttc ctataaacgc      1920
tacacaggct cctgagatta ataatgcgga tctctacgat aatgggagat tttcccgact      1980
gtttcgttcg cttctcagtg gataacagcc agcttctctg tttaacagac aaaaacagca      2040
tatccactca gttccacatt tccatataaa ggccaaggca tttattctca ggataattgt      2100
ttcagcatcg caaccgcatc agactccggc atcgcaaact gcaccgggtg ccgggcagcc      2160
acatccagcg caaaaacctt cgtgtagact tccgttgaac tgatggactt atgtcccatc      2220
aggctttgca gaactttcag cggtataccg gcatacagca tgtgcatcgc atagaacgaa      2280
tcaagcgtat tctcgacagc tca                                              2303

<210> SEQ ID NO 37
<211> LENGTH: 1638
<212> TYPE: DNA
<213> ORGANISM: Zea mays

<400> SEQUENCE: 37
catttagaaa ttcgtccaag taaggggcaa ggaaaagcat gattgaaagg actcccatc        60 tggactctat atgtcatcag cggctaaaaa aaagcatata gcacaacatc agcatcagca      120
tcagcactag agtcatcggc ccggcggtcc gcggtcatcc ccgcggactt tccgtccgcc      180
cggcgggctg tatcagcgtc aactggaacg cgcatatata tacaagacac acataacata      240
gaagcacacc cacgacaata accacacgac aataaccaca cccgcccacc cctcctttcc      300
gtatacaagg cctcggtacc tcttaaaaac tttctctcaa ttctctctac cgtgatcaag      360
gtaaatttct gtgttcctta ttctctcaaa atcttcgatt ttgttttcgt tcgatcccaa      420
tttcgtatat gttctttggt ttagattctg ttaatcttag atcgaagacg attttctggg      480
tttgatcgtt agatatcatc ttaattctcg attagggttt catagatatc atccgatttg      540
ttcaaataat ttgagttttg tcgaataatt actcttcgat ttgtgatttc tatctagatc      600
tggtgttagt ttctagtttg tgcgatcgaa tttgtcgatt aatctgagtt tttcttttc      660 tttttgcagg tagagttaac gctagccttg gtaccatacg taagaaaatg attgaacaag      720
atggattgca cgcaggttct ccggccgctt gggtggagag gctattcggc tatgactggg      780
cacaacagac aatcggctgc tctgatgccg ccgtgttccg gctgtcagcg caggggcgcc      840
cggttctttt tgtcaagacc gacctgtccg gtgccctgaa tgaactccaa gacgaggcag      900
cgcggctatc gtggctggcc acgacgggcg ttccttgcgc agctgtgctc gacgttgtca      960
ctgaagcggg aagggactgg ctgctattgg gcgaagtgcc ggggcaggat ctcctgtcat     1020
ctcaccttgc tcctgccgag aaagtatcca tcatggctga tgcaatgcgg cggctgcata     1080
cgcttgatcc ggctacctgc ccattcgacc accaagcgaa acatcgcatc gagcgagcac     1140
gtactcggat ggaagccggt cttgtcgatc aggatgatct ggacgaagag catcagggc      1200 tcgcgccagc cgaactgttc gccaggctca aggcgcggat gcccgacggc gaggatctcg     1260
tcgtgaccca tggcgatgcc tgcttgccga atatcatggt ggaaaatggc cgcttttctg     1320
gattcatcga ctgtggccgg ctgggtgtgg cggaccgcta tcaggacata gcgttggcta     1380
cccgtgatat tgctgaagag cttggcggcg aatgggctga ccgcttcctc gtgctttacg     1440
gtatcgccgc tcccgattcg cagcgcatcg ccttctatcg ccttcttgac gagttcttct     1500
gagcgggact ctgggtacgt atgtcgacac aattgcagcg cttgagctct cctaggtccg     1560
```

-continued

```
cggacaaagc tgggttttt ttttttcaat ttcgattcat ctcaaggtta agaattcaag    1620
cgtattctcg gacagcca                                                 1638

<210> SEQ ID NO 38
<211> LENGTH: 1869
<212> TYPE: DNA
<213> ORGANISM: Zea mays

<400> SEQUENCE: 38
gaattcgtca tcccgggccc cgctcagctt ccacctaacc atgcataccc acaccaccag     60
gaggtacaaa tcgtacctcc cccacccccg cctccacacc cgcaacagcc aaacatccac    120
caccccaacc accccaagc accaaaacaa gaagacttcg ccgatcagct gtatcgcaga    180
gtcattcaca tgatcaccgg ggggtccagc atcgacttcg atacgaagcg acagaagagg    240
gaccactacc gcagcatcaa ccacgttgcc gtcaccggtc cagtcgtgca gacaaagtgg    300
tccatgtgcc attgaccttc gacgcccgag acgtcgacct cgcagcgca ccccacatcg    360 acgccatggt tatcaactgc atcatggcag gctgggacct acacaaagtc ttagttgaca    420
acagcagcca gcggatatc atttttcctcc acgccttcga ccgcatgggc atcagccaca    480
gctttctcaa accctcggac aacccactat atggcttcgg cggcaagggc acctttcctg    540
tcggcaaaat agagctaccc ctctccttcg gtgtatcacc caatgcacga agcgagaaag    600
tcactttcga catcgtcgac atggtgtacc catacaacgc cataatgggt cgaggctcca    660
tcaacaagtt tgaggcagcc attcacagac tttacctgtg catgaagatc ccgggtccgc    720
aaggcgcgat cacagtctac gacaaccagc aggccgcacg caacatagaa agagacttcg    780
ttcctgggca aaggaacgta cactgcctca cggcgaagcg cgaggtcccc gagtctgcca    840
gcccaaccgc caaagaccat gaaaaggcac agctgcagag caacgatggg accaagactg    900 ttccctcga ccagacaacg cccaagcaaa cagtcatcat aagcgaagac ctcacttcgc    960
atgacgaggc gagactcctc tcctgtctat ccaaaaataa agacatcttc gcctggtccg   1020
ccctcgacct ggtcggagtc aatcgctcta tcatcaagca caacttggga tttgacccctt   1080 cggtgaggcc aagaagtag cggctgcgca agatgtctga tgagaagaca gaagccgcca   1140
aggccgaggt acaccgccta cttgaggcca actttatcga gccagtcgcc taccctacat   1200
ggctggccaa tgtagtaatg gtgtagaaga agagcggcaa gtggcgaatg tgcattgatt   1260
tcaatagcct caacaaggcc tgccccaagg acaacttccc gctgcctcgg attgacaaga   1320
tcgttgatag tgcagccggg tgcgaagtca tgtcactcct tgattgcttc tccggctacc   1380
accaaatata tatgaaggag gaagacaagg ccagcaccag tttcataaca cccttcggca   1440
cgtattgctt catcagaatg ccggagggac ttaagaacgc tgggtccaca ttctctcggc   1500
tcaccaaaat ggtgctcgag agccaagtcg gcagaaacat atttacgtat gtggacgaca   1560
tcgtcgtcgc catcagaagc aaggaagacc atctggctga cctcgcagaa acgttcgcaa   1620
acatgcggga cgcacaactt cgcctaaacc ccgaaaagtg tgtattcgac gttcgctagg   1680
gtaaatactg ggctacctgg tgtcgcaccg cgggatcgaa cccaatccga caaaatccag   1740
ccatcatcaa catgacgccc ccgcatcagc taaaaacttc aacgactgac cagtaaatgg   1800
cccgcctcaa cagattattt tcaagtccga aagcgagcct actttcctaa aaacttcgtg   1860
gcgaaaaaa                                                          1869

<210> SEQ ID NO 39
<211> LENGTH: 2133
<212> TYPE: DNA
```

<213> ORGANISM: Zea mays

<400> SEQUENCE: 39

```
aatttggaac caatgaggta ttagtaagga cacaagaaga tgcagatgag tggatagaag      60
gaaagaggct cagaatgtaa ggaaagcacc aaccacaaca ccgtcgggac agacgagaaa     120
catgggaagc tccaccacaa tcttgggtta agtgcaactt tgatggggca tggccaacag     180
aaggattaaa atgtggctta gggtgggtgc ttcgcgatca tacagggaag gtgttatggt     240
taggtgcacg agctgtggta aaagtaagaa gcgtgctgga agtagaagtg gaggctctta     300
gatgggctgt gctgtcatta tcccgattca attataggaa gatcattttt gaggtggatt     360
ctcagcaact tgtgtctttg gttacatgaa agttatgctt gtcaagtctc aatccaatta     420
tccaagacat aaagtatcta cttagcaagt ttgaggattt tatgcttgtg catacaagcc     480
gagaaggaaa tggagtggca gatagaatag ctaaggaatc tctttctttt gagaattatg     540
atctaaagtt gtattctatt gtaccaattt gggttaaaag ctctgttgag ctagactgtg     600
tatccataaa tgggtgaatg gaaagtttgt tgttgagccc accggtggcg cgccataact     660
tcgtatagca tacattatac gaagttatat tcgatgcggc cgcaaggggt tcgcgtcagc     720
gggtgttggc gggtgtcggg gctggcttaa ctatgcggca tcagagcaga ttgtactgag     780
agtgcaccat atgcggtgtg aaataccgca cagatgcgta aggagaaaat accgcatcag     840
gcgccattcg ccattcagct gcgcaactgt tgggaagggc gatcggtgcg ggcctcttcg     900
ctattacgcc agctggcgaa aggggggatgt gctgcaaggc gattaagttg ggtaacgcca     960
gggttttccc agtcacgacg ttgtaaaacg acggccagtg aattgtaata cgactcacta    1020
tagggcgaat tcgagctcgg tacccgggga tcccttcgg ggtatccccc tttcccggtc    1080
cctgttgcaa gagatagaga aagaggaaaa cggaaaagga tacgaaatcg gacgacgtgg    1140
cgtaccttt ctgacgcggt tattacggcg aaggtgaagc gtcgcgcgct cctcccgtca    1200
gaggcgccgc ctgtcccgcc gcggagttaa tgcgacgggg cgagtggttg gcggggcggc    1260
cgttacgcgt gtgcgagccg tttcgaggaa cggctgtgcc gcttcgcgct tttcgaatct    1320
tgcgtccggt ccaggcggcg tgctggaaac ggtttcgccc tggccttcat atacttgaga    1380
gggggtccgg tgacggttct tcgctctgct cccttctttt ccctttaggt tttcgcaacc    1440
cgggaaactt tagtcggagg agagagaaac cgcccttcct gccccccgcg ccgccatctt    1500
ctccatcttg gtgatggcgg atcgagtggc tataatcccc ccgcgcgatc cgtggccctt    1560
ctccagggta acgcgagtg atctggagga gctggtcggc gaaggtttgc tccgcccct    1620
caccgacaag cagcggctag agtggattcc tcccgtgggc ggagccgctc cgtccccacc    1680
gccgggtat gtcgtgagct tcgtctcctt ccatgagcgg ggatttggtg tgccggcggg    1740
ccgctttatg cgggccatcc tattccacta cggggtggag ttgcacaacc tctcccccaa    1800
ctccatctcg caggccgcta ttttcgtagc gttatgcgaa gggtacttgg ggatcgctcc    1860
tcattgggat ttgtggactt acttctttct cgccgagcct ttcgccttgt cgacggggga    1920
gaggaggatc cgtgcagcgg tgcgggccgg cggctgcatt ctcttgttga ggcagtcgcg    1980
ggcgttgcag tacattcctg ccattcttgc gtcttcgaac aagggggtggc agcgccggtg    2040
gttctacctc cggaatgacg gtgagttgct cccaccgttt tcccagcgag tagttacggc    2100
tgccaccgaa cgaatcaagc ttatcatcgg cca                                 2133
```

<210> SEQ ID NO 40
<211> LENGTH: 1536
<212> TYPE: DNA

<213> ORGANISM: Zea mays

<400> SEQUENCE: 40

```
gatgaccatt tagaaattcg tctattcagc aatgacctag gtgcctaagg gcacatgcgt     60
ccttaatcca agatgctggg tactcaggca cctataaata ccctcgcaca gtgcccttga    120
gaggctagat taatagagca attgccttcc tgagctaaaa ccttgtttgc attactttca    180
ctcccccgtt ggatcatctt gctcgggaga gcaagttcca acatttggcg cccaccgttc    240
gtgttacgaa aaaaccaccc acgatggcac caagagagc tagctcgaag gcagccccat     300
ccgttgacga agcagcgaag gcagcgctgt tggccgagaa aaagggcaat gcccttgtcg    360
acgccaccca ccacgaagcc tgcgaagacg acgcactcag caagaggcag cgcaatgaac    420
aacccacacc cgaaggcagt ctccgcacct gcagctccgg aggacaaccg caacctcccc    480
caggcttcac tccccggagg gcgcggacgc cactgaggat ggcggagtca tcggtgtttc    540
agcagaggaa caactacaac tgcgggcctt gcgcatcaag aaccgcaacc tccagaagca    600
aaaggagatc ctcaaggcca agcgccaacg tgtctctgcg caggccaagg tgcgccagat    660
gatacacgac gaggagcaga aggctcagga gcttgagcaa gagattgcgc tcatgcagag    720
cgaaggccaa cttggtctac aacaaggacc acccctccaa cagcgtgcgc cattcgaaga    780
cctgttcatt catcagcgtg gacccatccc gcacgccaca gcgttccaag gtgtcaacta    840
ccttgacgag cgaagtccac tggcgccgca cctgcaagtg tcaccatggc ccgccaactt    900
cagggcgggg atctacccca gtacaacgcg cagcacagac ccagcacaat atatcatgag    960
ctaccaagtc gtcgttgcat catccggagg ggacgacgcc acgatggcca aatcattcat   1020
catcgccctc caaggcccgg ctctcacttg gtacaccagg ttgccccgt tgttcatcga   1080
ctcctggaga ggtctgtggg acaaattttt gctcaacttc caagggtact gccagacacc   1140
gacgccttgg ctgaactgtc actctgcaag cagctggaaa gacagactct gcggagtac    1200
taccgcatgt ttctgactct caagtcgcaa ctgccttcgg ttgatgacca aatcgccatt   1260
cactacgcca tcagtggcct tcaggctggc gttctttaca gccgctgcat cagagatcca   1320
cccaagaacc tccaggagct gtatcagctg ttcgaaaaat atgccagatc tgaagagctc   1380
caccagcgca aagtcgagtc ccagaggaaa cccaaagacc ctccgtagtc tagccatacg   1440
tggatgagac cttcgcaagc agactccggt cgggatggcc gcagtcagca gcaggtgcac   1500
aacatcgcac gaatcaagct gaatctcaga cgctca                             1536
```

<210> SEQ ID NO 41
<211> LENGTH: 1614
<212> TYPE: DNA
<213> ORGANISM: Zea mays

<400> SEQUENCE: 41

```
gaagataggc gattaatgaa agatcgtagg cgggtagaat tggaaaagat gacaaggtgg     60
tgaaaaccta gaatgcaaat ttgaggggca aaatggagac cggggaaatg gtggaacatt    120
aaaaatatag gacaccagcg gaaggagcc gtttcgggaa ttcttctggg cgatttttga    180
agaagggcgc ccaatagggc aaattcagga gttaggaagt tatcggcggg tttcttgccc    240
ggcaccaaat tgcgaggaag ggtgagcaag gtggttccca aaaccccac cagggcgagc     300
gagttgatgg acatcgccac caagttcgcc tctggccagg aggcggtcga ggctatcttc    360
cgaaaggaca agcagcccca gggtcgccca tcggaagaag ctcccgaggc gtctgctccg    420
cgcggcgcca agaagaaagg caagaagaag tcgcaatcga aacgcgacgc cgctgacgcg    480
```

| | |
|---|---|
| gaccttgtcg ccgccgccga gtataagaac cctcggaagc cccccggagg tgcaaacctc | 540 |
| ttcgacaaga tgctcaagga gccgtgcccc taccatcagg ggcccgtcaa gcacaccctc | 600 |
| gaggagtgcg ttatgcttcg gcgtcacttc cacagggccg ggccacccgc cgagggtggc | 660 |
| agggcccgcg acgaggacaa gaacgaagat cacctagcag gagagttccc cgaggtccgc | 720 |
| gactgcttca tgatctatgg agggcatgcg gcgaatacct cggctcggca ccgcaagcaa | 780 |
| gagcgccggg aggtctgctc ggtgaaggtg cggcgccag tctacctaga ctggtccgac | 840 |
| aagcccatca ctttcgacca ggccgaccac cccgatcatg tgccgagccc ggggaaatac | 900 |
| ccgctcgtcg tcgaccccgt tgtcggcgat gtcaggctca ccaaggtcct gatggatggg | 960 |
| ggcagctgcc tcaacatcat ctacgccgag accctcaagc tcctgcgcgt cgatctgtcc | 1020 |
| tccgtctgag caggcgctgc gcccttccac gggatcatcc ctgggaagcg cgtccagccc | 1080 |
| ctcgggcgac tcgacctccc cgtctgcttc gggacaccct ccaacttccg aagggagacc | 1140 |
| ctgacgttcg aggtggtcgg gttccgagga acctaccacg ccgtgctagg gaggccatgc | 1200 |
| tacgcgaagt tcatggccgt ccccaactac acctacttga agctcaagat gtcgggcccc | 1260 |
| aacggggtca tcaccgtcgg ccccacgtac aaacacgcgt tcgaatgcga cgtggagtgc | 1320 |
| gtggagtacg ccgaggccct cgccgagtcc gaggccctca tcgtcgacct ggagaacctc | 1380 |
| tccaaggagg tgccagacgt gaagcgccat gccggcaact tcgagccagc ggagacggtc | 1440 |
| aaggccgtcc ctctcgaccc cagtggcgac accaccaagc aggtccggat tggttccggg | 1500 |
| cttgacccca ataagaagc agtgctcgtc gacttttcc gcgcaaacgc cgacgttttg | 1560 |
| ggccggatcc cttcgactgc cccggcttcc cgaggaatgt ccccaaacct tcct | 1614 |

<210> SEQ ID NO 42
<211> LENGTH: 2563
<212> TYPE: DNA
<213> ORGANISM: Zea mays
<220> FEATURE:
<221> NAME/KEY: misc_feature
<222> LOCATION: (739)..(739)
<223> OTHER INFORMATION: n is a, c, g, or t

<400> SEQUENCE: 42

| | |
|---|---|
| tgtcgatgat tacgcttgat tcatcagaat tggttaattg gttgtaacac tggcagagca | 60 |
| ttacgctgac ttgacgggac ggcggctttg ttgaataaat cgatacggtc cgagtttaaa | 120 |
| cactcgagag gccacgtggg ccaacctgca ggaactagtg atatcacatt tagggtcagt | 180 |
| ttttttggtc gacaaaacga ggaaagagaa acataacgtc agttttattg gatgccttaa | 240 |
| accgacgtta aagtccatat tatttgtagt gaatgttgac aactaggtgt gtaatagcgg | 300 |
| attctgacac atttggtctc acaaacagtt aatgagctat aatgtctcca aaaccacaa | 360 |
| tcgtagcaaa gcaaactgaa gaagaagata cagcaaacaa caagtgtgaa tagtacaaga | 420 |
| gaagagagac atgcaacgaa aattataacc aaaaacgagg ttctacatat taaagacatc | 480 |
| ccatcttaaa agaagctgat atcccgcgga cctaggagag ctcaagcgct gcaattgcat | 540 |
| tcattttatg tttcaggttc aggggggaggt gtggaggtt ttttaaagca agtaaaacct | 600 |
| ctacaaatgt ggtatggctg attatgatca gttatctaga tccggtggat cctacctttc | 660 |
| tcttcttttt tggatctacc tttctcttct tttttggatc taccttctc ttctttttg | 720 |
| gatcagctcg agatctcang aacaggtggt ggcggccctc ggtgcgctcg tactgctcca | 780 |
| cgatggtgta gtcctcgttg tgggaggtga tgtccagctt ggcgtccacg tagtagtagc | 840 |
| cgggcagctg cacgggcttc ttggccatgt agatggactt gaactccacc aggtagtggc | 900 |

```
cgccgtccctt cagcttcagg gccttgtggg tctcgcccctt cagcacgccg tcgcgggggt    960
acaggcgctc ggtggaggcc tcccagccca tggtcttctt ctgcatcacg gggccgtcgg   1020
aggggaagtt cacgccgatg aacttcacct tgtagatgaa gcagccgtcc tgcagggagg   1080
agtcctgggt cacggtcgcc acgccgccgt cctcgaagtt catcacgcgc tcccacttga   1140
agccctcggg gaaggacagc ttcttgtagt cggggatgtc ggcggggtgc ttcacgtaca   1200
ccttggagcc gtactggaac tgggggggaca ggatgtccca ggcgaagggc aggggggccgc   1260 ccttggtcac cttcagcttc acggtgttgt ggccctcgta ggggcggccc tcgccctcgc   1320
cctcgatctc gaactcgtgg ccgttcacgg tgccctccat gcgcaccttg aagcgcatga   1380
actcggtgat gacgttctcg gaggaggcca tggtggcgac cggtagcgct agctggtacc   1440
tgttaactct acctgcaaaa agaaaaagaa aaactcagat taatcgacaa attcgatcgc   1500
acaaactaga aactaacacc agatctagat agaaatcaca aatcgaagag taattattcg   1560
acaaaactca aattatttga acaaatcgga tgatatctat gaaaccctaa tcgagaatta   1620
agatgatatc taacgatcaa acccagaaaa tcgtcttcga tctaagatta acagaatcta   1680
aaccaaagaa catatacgaa attgggatcg aacgaaaaca aaatcgaaga ttttgagaga   1740
ataaggaaca cagaaattta ccttgatcac ggtagagaga attgagagaa agttttttaag   1800 atttttgagaa attgaaatct gaattgtgaa gaagaagagc tctttgggta ttgtttttata   1860 gaagaagaag aagaaaagac gaggacgact aggtcacgag aaagctaagg cggtgaagca   1920
atagctaata ataaaatgac acgtgtattg agcgttgttt acacgcaaag ttgttttttgg   1980 ctaattgcct tatttttagg ttgaggaaaa gtatttgtgc tttgagttga taaacacgac   2040
tcgtgtgtgc cggctgcaac cactttgacg ccgtttatta ctgactcgtc gacaaccaca   2100
atttctaacg gtcgtcataa gatccagccg ttgagattta acgatcgtta cgatttatat   2160
ttttttagca ttatcgtttt attttttaaa tacggtgg agctgaaaat tggcaataat   2220
tgaaccgtgg gtcccactgc attgaagcgt atttcgtatt ttctagaatt cttcgtgctt   2280
tatttctttt ccttttttgtt tttttttgcc atttatctaa tgcaagtggg cttataaaat   2340
cagtgaattt cttggaaaag taacttcttt atcgtataac atattgtgaa attatccatt   2400
tcttttattt tttagtgtta ttggatattt tggatgatta ttgatttgca taggataatg   2460
acttttgtat cagttggtga acaagtctcg ttaaaaaagg cagtgtttgg tgactcgatt   2520
tattcctgta attaattcat aataaatgga tcttatttgg ggc                      2563
```

<210> SEQ ID NO 43
<211> LENGTH: 2753
<212> TYPE: DNA
<213> ORGANISM: Zea mays
<220> FEATURE:
<221> NAME/KEY: misc_feature
<222> LOCATION: (2505)..(2505)
<223> OTHER INFORMATION: n is a, c, g, or t
<220> FEATURE:
<221> NAME/KEY: misc_feature
<222> LOCATION: (2549)..(2549)
<223> OTHER INFORMATION: n is a, c, g, or t

<400> SEQUENCE: 43

```
tcgagattac gcttgattcg tttgtgctat tccggcttca cccgtaggtg acttttgcac     60
ggagtgtcgc acgcgagggt agttagcgct gcccctcgcg atgactttgg tgtggtcgaa    120
tgccgaagac catcgatgcg gtcttttttcg acattggctt agttttttgc ggggggatttt    180 tgcttgtata ttacatggcg ccgcctcatt aaaaaccctca ccccccctggg aggaaaagag   240
```

```
tgcgggccgg aataataata tttggtgaat tacaagggcg tgatggccct gaggattcaa    300
acaaaaaatt tgcgaagatt atctatattc caggaatgtt ccaggtcttc gccagattgt    360
gttgtcagtc cgtacgcgct gggagacgac ttcgtcttga cgataaatgg tccttcccac    420
tttggttcca gcttacccg tgactctgtc cgggttgtgc ggacaagtac gaggtcccct     480
tcgttgaatt ctcttgggac gactgcgtgg tcgcgccagg ccttcgtttg tgcttgatat    540
ttgtcgagga cctgcagggc gaagacacag tctccgtcaa tgaggtcttt ggaagttggc    600
tcgtcgacgt cgggtactgc taaagcgctt gtccgcgggg acccatgttt gattttttgc    660
ggtgtcatgg cctccgatcc aggggggtgaa atcggtcgcc cgacactcgg tcgtgttcag   720
tgcccagact gcttcaggta gcaggtcggc ccatttgcgc ttcttgtcgt cgaggagcat    780
tttcttgatc accgtgaaaa tcttgccatt ggcgcgctcc acgacgccgt tggattgtgg    840
gtggtacatt gaggcgaagg caagcttggt gccaatggag aagcagaaat ccttgaagtc    900
ttggctgtca aattgcttgc cattatcgac tgtgagctcg gacgggactc cgaatcgaca    960
aacaatgttt tgccagaaga atttctaggc agtcttcgat gttatcgtgg atactgccct    1020
cgcctcgatc cacttggtaa aatactcgac ggtgatgaag gtgaacttga ggttcccttg    1080
ggccgtgggt agtggcccga caatgtctag gccccagcgc taaggggcc atgtgtgggc     1140 gattagcttt gtgaattgcg aagggcttcc cgagcgtgga gaaaacttct ggcaggcttc    1200
gcatgacctt gtgacacgat tgtggtgca gatcatggcg ggccagtaga agccttgacg     1260
gatcaccttt gcagctaggg ccctaggccc tgcgtgagag ccccaagtcc cgtttggact    1320
tccgcaggat ttgacgcctt tcgttttggt gacacattta agcatgggtg gcctgattcc    1380
ttcttgtaaa gctggccttc gatgagtgcg aagtcccggc ttcggtgttt gaggcgctgg    1440
gcttcgttga tgtcggttgg atgatagtac ccctgcagga acagggttat tggtgcccgc    1500
cagtcttcga tcataatgag gttgactatg cggtggccct cgctgtcatt ggttatttgg    1560
aggccctctg ggctgcggac ggctggcgtg ccgatgacat ggtagaatac gtcgaagggc    1620
agggcctcgc ctctagcggc tgccttggcc aatgcgtcgg cctcctcatt cttggctcga    1680
tccacgtgct gcaaggtgaa gcctttgaat tgcctctcga gactgcggat agccgcgaga    1740
tactgcatga gtgcggggtc cttcgctgcg aaatatttct cgacttggcc ggcgactacc    1800
ttggagtccg ttctgatgat acaggtagtg acgccaagtg cccttagctt gcgaaggccg    1860
aggatgatag cttcgtattc ttctatattg ttggtgcatc tgtcagactc caaagcaaag    1920
ctgaggcgtc ctgcatattt gtgcttgacc cctgtgggtg aagtaatgac tgcagctgcg    1980
cctgcccccg catggcacca tgcgccgtcg caatggatgg tccacacctt ctctgcggac    2040
gtgtccggct gcgttattgg cccgatccag tcgacgatga agtctgccag gacttgtgac    2100
ttgatggttg tcctgggctc taaggtgata tggtagccgg aaagctcggc tgcccacttg    2160
gcaatccgaa cagatgcctc cggattttta aacaattcgc cgagtcccct gtctaaggtg    2220
acccgtacct tgaacgcttc aaaataatgg cgcaatttgc gtgaagccat aacaactgcg    2280
taggcgattt tttccagttc cgtcatgttg cattttgatg tcgtgagtac ttcggagaca    2340
taataaactg gacattgcct gatcgtgccc tctctgtcct gctcttgaac cagtgctgcg    2400
ctgatcgcat gcggcgaagc tgcgatgtag agcaataggg gtagcgaggg gttgggcctt    2460
gtaagaatcg ccaactctga cagatgctgc tttaatgaag cgaangccgc cgcttgctct    2520
ggtccccatg cgaagtcttt tacgcacgna gtgttttgag aaaaggtagg ctcgctctgc    2580
cgacttggag atgaatctgt tgagggcggc ccatctacct gtcagttcgt ggacgtctct    2640
```

```
agctgactgc gggggcgtca ttgtgatgat ggcctggatt ttggtcggat gggctccaat    2700
ccgcggtgcc acaccagtaa cccagttttt accctaacga acgtcgatac cac           2753

<210> SEQ ID NO 44
<211> LENGTH: 2816
<212> TYPE: DNA
<213> ORGANISM: Zea mays

<400> SEQUENCE: 44
ggggccaacc ccggggggtt cttccctccc gaaatacgtg aaatttgctc ccccggttt      60 tcccacggag taagtaaggg ttgccccccaa acgccggggc catggggccc cggcacgaaa   120
gccaaaaaat tcccaagccc cttttttccgg ccccgaagga atttcgggga gggggactta   180
```

```
agctgactgc gggggcgtca ttgtgatgat ggcctggatt ttggtcggat gggctccaat    2700
ccgcggtgcc acaccagtaa cccagttttt accctaacga acgtcgatac cac           2753

<210> SEQ ID NO 44
<211> LENGTH: 2816
<212> TYPE: DNA
<213> ORGANISM: Zea mays

<400> SEQUENCE: 44
ggggccaacc ccggggggtt cttccctccc gaaatacgtg aaatttgctc ccccggttt      60 tcccacggag taagtaaggg ttgccccccaa acgccggggc catggggccc cggcacgaaa   120
gccaaaaaat tcccaagccc ctttttccgg ccccgaagga atttcgggga ggggactta    180 ccgctgcggg aatgaatgcc gctatccacc gtcggagggt gctcccattg gcggaccgcc    240
ggctgccgct ctgggagatg accccggaaa actgactggg agggctcatg aatgtcccct    300
gatcctctcc ccttcaacgc cctccaatgg cgggtgtcgg ccgcgatggg gaagccggac    360
ccccacgcat attcccagct tcggatgcgc cccgaccagg ggtgcgtgac tttggtgagc    420
gtttgctcct cccttcttcg tatatctggt cgctccgggt ccttatgatc gagttcttt     480 ctcccctcct tttaggatgt ggggtgtcac aaaccctccc tgccacgggt cccggaggac    540
gcggtggacc gtgcagcgcg gcgggtcgcc gcggaggaga agaagaaaaa gaaggacgcg    600
gagaaggccc gggcccgcga gcggaggcgg gctcgggacg ccttggagaa gcgccgccgc    660
cagcaggagc gggacggact cccgagggag ccgtcgccgg agacgcccga cgacgatgac    720
gacgatgacg atgataatga tgacgacatg gccgcccgtc tcggccttag cctcggcccg    780
gggtgtggcc aggagccgtc gagccagccc ccgagcgagc cgactccgtc agccccgaa     840 gtcggggcgt cgggctcccg acccgaggcg cgggggcgaa ccgagaggtc acctgacccc    900
tcagccggag gagctgaagt agttccggag gtccaggcca aggcgtctgt tcccaggggg    960
ccgccgcttg tgtcggtggc gcatggggt gaccctcagg tcgtcgcggt cgtgcccggg    1020
gaatctgcct cccaggcgcc ccaagcgccg gtgaagcgga cctcggcggc cgttccgaga   1080
gccaggatac aagaaggctc tccccaggcg cggtggatca tggcccggag tgggtgagta   1140
cctcggaacg tcttcgtctt ggcctcccat tcgtatgtct cggttgtgat cccctttctt   1200
tttcatccag caagcgaagt catggccaga ctgacctggc acctcggaag gccctcaaga   1260
cggcgccgaa ctgtgcggcc agcgccattc agccgaccct ttcgcggggt actccgacat   1320
cgggggctcg ggcgtcgcca atctcggagg agcaggctcc cgaggccggc tcttcagccg   1380
aagcggcgat cgtggttgag gaggcggctg acgcccacgc ggctctgagt tcgcctgtcg   1440
tgtcggtcat gccggcgcct gccaccgccg aggttgccgc cgtccctgtc gaagggtgtc   1500
cagttgccgc cagcgccagg gtggctgatg cgtcggcgcc cgagacctca gaagaggtgg   1560
gcgcggtcgc gcaatccgtc cagccgggtg acagcctcat cgctgtgcgg cggagccccg   1620
aggcccggcg cccattgctc tgattccgga cccgcgaggc ctcggacccc gtcttcgttc   1680
ttgatgatga gcaggaggac cagtcctggg gtgagctcca cgagtgcgca gaggcaacgg   1740
tggggtcgct ccgggcgtcg ctggaggttt tctgcagaga cgtccccaaa atccttcagg   1800
tagcgatttc gggcatacct ttttcccttc tgtgagatac tcgctgtgac gccctgtttc   1860
ctttcccagg atctgacgga ccggagcgcc gccaagtcgt cgttcatccg ccgtgaggtt   1920
gatgtctggg gctcgctgcg atccctgagg tcttcgcttg ccggggctac cacgcgcctt   1980
tctcagcagg atgccaaggt ggcggacctc cagctgctct gcgccgacct gagagccgag   2040
```

| | | | | |
|---|---|---|---|---|
| gcggcagcag | cgcgtgcgga | ggcgcaacag | cagcgatcgg | agctcgtcca ggtcgtcgag | 2100 |
| gaatggaacc | gacttcaggg | ccgggctgcc | gaggccgaaa | gccgagccga gaccctcgag | 2160 |
| gctgacctag | ccgcgaccca | ggtcgcggcc | tcggagcacc | gtgcccgagc cggaagtacg | 2220 |
| tcttcgtcct | ccctagttct | ttttcttgtc | cgtttcccctt | gcttgtgctt gaggtatttc | 2280 |
| tcctggctac | ttgcagagct | tgagtccgcc | ctcgacgagt | ccgccaaggc gcttgctgag | 2340 |
| gcgcttgccg | gagccgccga | gcagagggag | cggacctcg | cggccatgtc cgaggccgtc | 2400 |
| tcggactttt | atcgtgtcct | cggctccggc | gacgtccctt | caggaagctc ccctcagagc | 2460 |
| cgccttcgag | ccttaggtgg | ccacgcccgc | ggcagagtcc | gcgaagcgct acaccacggc | 2520 |
| gtcaggcggg | ccttcgccgt | gctcgcttct | cactacgttg | tggacctgga gcgggttagt | 2580 |
| gaggggtact | gtcttcctga | cgaggacgat | gctgctctgg | cggaggtgca gcggcttgac | 2640 |
| gcggtcgccg | cgggtccgag | cgcggtgctg | gcgaccacct | ttgaggcgga ggtccttcct | 2700 |
| cctgcgacgt | caccggaggc | cgagatggac | cccaccgatg | gcggggtgg agctgaaggc | 2760 |
| gcggctcctt | cccaaggcgg | cgcctgatag | aattcaagcg | tattctcgga cagcca | 2816 |

<210> SEQ ID NO 45
<211> LENGTH: 2997
<212> TYPE: DNA
<213> ORGANISM: Zea mays
<220> FEATURE:
<221> NAME/KEY: misc_feature
<222> LOCATION: (918)..(918)
<223> OTHER INFORMATION: n is a, c, g, or t

<400> SEQUENCE: 45

| | | | | |
|---|---|---|---|---|
| atgagcattt | aggaattcgt | caaattagga | attagaataa | acaaaatttt tctgcaaagt | 60 |
| ataatatata | taataaaaca | taaaattggt | cgatatgacc | aaccttttgaa gggataccaa | 120 |
| agtcaaggtg | ataatagagg | tctatagtcc | ttagaacgac | catcctactc taggttagtg | 180 |
| gtcctacagt | cagcacgact | ttgataccac | ctatgtcaca | cccggtttta gaaggcaaac | 240 |
| cgaatgcgaa | ccatgtacgt | gcccaggatc | agcaattcac | gtacacaaca attacataac | 300 |
| tggacatcat | cacacagtgc | tcaaataata | acataaaaga | tagtaatagt cgattacatc | 360 |
| atgatgtccg | agacatccac | attgtcatta | atagttatca | aagtgcaaga aagaaacgta | 420 |
| gatacacaca | gccttcacaa | gcagccgact | gggggtttgc | cgctaaccca cgcctagaac | 480 |
| tcatcgcact | cttggaactc | ctggaagtcc | tcctccacga | cttcatcttc tcctgagcag | 540 |
| tggttgcaac | atggacaacc | tggggggctt | tggtgtgtaa | agcaagggtg agtacacatc | 600 |
| aacatactca | gcaattgtcc | cgttttgctg | tagtggacta | gctttatgtg gggttaagcc | 660 |
| aagtagttgc | ttttagttgg | tcaggttatt | attactagta | gagagccaga ttttagcatt | 720 |
| aacccaagtt | gttaacccaa | aagtaccctt | tccaaatgga | aaggatacca gaaacattac | 780 |
| cataagcata | atcaaaacca | tcatcctcgt | caccacctgt | aaaccaacca tctctaatca | 840 |
| aagtatctct | aatcaatgga | gctcccttgc | cactcataac | catgagcaca actgattaat | 900 |
| cagtttaata | acactcgnaa | agagttgggc | accttaccca | caagccgtga ttccctcttg | 960 |
| cctggggccg | atcaaacctt | taacactgcc | atggtgaata | ggcagggttt tactacgtag | 1020 |
| cctttacaaa | gattccctga | ggctatagcc | gcccattagg | ttttctaaat gtaccacact | 1080 |
| cctccccaag | gggcaatcca | ccctcggtag | agcgagccgc | atacactgag ccccattgac | 1140 |
| ggcacgacgg | cgaagcgaac | tacaccccag | ttcctctaat | tattcagcta agggcgtccc | 1200 |
| ataccaccct | catggttgca | ctttttttccc | gggcggtcat | ccaacgaacc aatccttatg | 1260 |

```
gagaggcact cgagaaacca ctcgagtccc cttaaatgtc acagtatcat catcataatc    1320
aaaaggaaaa atagcgtatg ataaataatc tcatcctgtt cattgattaa tgtgaagcac    1380
tagcataaag ctaaaccaaa ataacccaac caaataggta aacaaggaca agataaacaa    1440
aagctagtca atccttaggt ataaattgtg taaatgcggg gagtgaatta taatgtgagt    1500
aggacataga tgggtcaagg gacacttgcc ttcaccaacc agctgctgct cagggtcttc    1560
acctacaact ccttcagact ctgccaactg accgttatct ataagagttc aaacatacat    1620
tccacaaatt caatataaaa gaacagtaca ccatgcatta aaatagagta aataagtaga    1680
tactcggcgc agggctcgca cctacgacta agcgagaaag agaaagcaac ggtcaaggct    1740
atggtcgatg gacgatcacg ttaagcgatt atagattaaa gtactcgtct aaacataata    1800
gtattaattt gacaatcacg ttatgcatag gataaagtca cgctacagtt taattattat    1860
aaacaattca agtaaatttt aaaaagattg ttgcccagcg aaacgcacga cgacaaacgc    1920
aaacgaaact tagaataaaa tgagtcgtcg cgcggcgaag cgcgcgacac aacacttaga    1980
ctaaaatgaa cataaaacga atcatcgcgt gacgaagcgc gccatgagac acttgaatta    2040
attatgaaaa taacgtcaag cgtcgcgcga cgaagtgcac gacaggatat gtcacttaaa    2100
atgaaattaa aacaaaacgt catgcgacca gacacgcaac gccacacatt aaataattta    2160
agatgaaccg tcgcgtgaca aagtgcgcga cgtagcactt taattaaaact aaattcgaaa    2220 ctaattaaac tgaaatttga tcaccgcgcg cgcggaaacg cgctgggcga ccacgagggg    2280
gctgcgcgcc gggtcgggt cgcgcgcact ggagccggga cggccgcgcg caagggccag    2340
gatggccgcg caccaggggt cgggaacgac cgtgcgcagg ggcgccggga cgaccgcgct    2400
cagggggcta ggaacggcca caccgagggg cgccgggaac agccacacat aggggggccag    2460 ggcggccgcg cgcagggggc caaggtgccg caccgctagg acacgcgggc ggtgggaaga    2520
gaaagggaag ggagagggag agagaggggg aggtgaggct cacctggga tccaaaatcc    2580 ggcgataact gtcaccggat cacacctagg gcacgaggtg ggagagaggt ggaagagagg    2640
gagagggagt tgctgtgcag gaaaaataaa atgagaggaa gggagaggcg ggcgcgcatg    2700 gggggtttg gggcgccagg ggcacgcggg ggcgcgcagg gccgggacaa gctgggtcac    2760
gagccgggat agaagcccac aacgcacacg accactgatc ggaatccagt tgcgaatcga    2820
aatccaaaac gaggcgagat gaacgcgtga ttaaacaaaa catcagacaa aataaaaatg    2880
ctttggcatg atgcaacacc catgtcaact taggttttg tttacacgcg atacgtacac    2940
cagtcgctat actggtttaa aatgaagaa cgaatcaagc gtattctcgg acactca    2997
```

<210> SEQ ID NO 46
<211> LENGTH: 2897
<212> TYPE: DNA
<213> ORGANISM: Zea mays

<400> SEQUENCE: 46

```
tggctctccg agaatacgct tgaattctta tgctttagag gtcagcatta tgtcaccgat     60
attatgcttt agaggtcagc atgtattttg tcttttgcgg ccgagttcgt gatccgccca    120
tatcttgcta ggtggtgcaa tttatttgct ctgtgactga ttggacattt gatggacgtt    180
ccctggctag tcttcatgtc gcttctgtcg ttcagatttt gtacttcacc ggctatattt    240
ggctttcctt tgatccttac tgatatctca tttttgtctt gaggtattca ttgcatgccc    300
tgcacggatg tgcagttttt gaaaatata ctgataattc ctgggcgtcc ctcccaatgg    360
gtgtgggcaa gggacggctt ggtacgctga gtgttttagc cggctgcttc tgagtagtaa    420
```

```
tgtgatgtga cggtgggtgt aatcatatcg cccgcgcggt tgatctctgt cgtgatattt    480
attgcaccgt cttaagtcgt tgccgactta agccgattgc tccgttagca gggcatagtg    540
gtcacctcga gttaagtaag cgcgagcatg ttgcaccgtc ttaagtcatt gccgacttaa    600
gccgattgct ccgttagcag ggcatagtgg tcaccccgag ttaagtaaga atgccggtca    660
atcgtgaaca aactgagtat tcttgaagcc cttttttatt gatgacatat ttcccatttt    720
acaaagtaca ttatcgtccc gatagctttt gaaatacaac tagggataaa acttcctgag    780
gtgttctata ttccaggagt tcccaattcc tgtgtcgtcc atttgagtga gacgatatga    840
tcccggccga gtgacttctg ctactatgaa tggtccttcc catgagggcg acaacttgtg    900
ccgtccctcc cccgttagaa ttcggcggag gacgagatct cccactgtaa aggatcgttg    960
tcgcacggcc ttgtcgtgat agcatctcag agtctgctgg tatcgtgctg attgaattac   1020
tgcattcagc cgttcttctt cgagtacatc aatgtcctcc agcctagtag cttcggcttc   1080
tgctatgctt tcgaaaatca accttggcgc cccaaacttg agatcagcgg gtaatactgc   1140
ctctgaccca tagaccatga agaaaggagt gtttccatgc agagctcggc taggttgggt   1200
tcttaggctc caaacgacat agggcaattc cctttatcat tttcctgcga acttttcatt   1260
cttatcaaag accttttttcc tgagtgcttc ccatatcatc ccgtttgctc gttcaacctg   1320
cccgttggct ctggggtgtg ctactgaagc atacttgatc tgaatgcttt tttgctcgca   1380
gaaatcgaag aactctgaaa cttgtgaagt tggatcctaa ggtcagttat gatatggttt   1440
cggtatcccg accctgaata ataagttctg ttatgaattc cacgggcctt agctgaggtt   1500
aaagaagtga tgggtttgaa ctctatccat ttagtgaatt tgtcgattgc taccagtaca   1560
tgagtgtatc ctccttgagc tttcttgaac ggtccaatca tatccagtcc ccagcatgcg   1620
aagggccaag ttactggtat ggtctgcagc tgttgtgctg gtagatgttg ttgctttgat   1680
aagtactggc aagcctcgca cctttgaact aactgggctg cgtcacttt tgctgttggc    1740 caatagaatc ctgacctgaa gaccttcccg actagtgtct tggatgctgc gtgtattcca   1800
cattgcccag catggatctc atctaaaagt cgcttcccag tagatgagag aatgcacttc   1860
atgaggacgc ctgatgcacc ccttctgtat aatgtctccc caatgagtgt gtagtgagct   1920
gactgtctag cgatgcgctc ggctgcattt ttgtcatctg gttcctcttc attctttata   1980
tatttgatga tcggccttct ccagtcatca gagtctgact ctggttgatt cacgatatta   2040
cactcttctg cctgatccat tgagatgctt gattgtggta tttcttgtac aaagactcca   2100
ggtgggacct cagttcgact ggatcctagc ttggacagta catcggctgc cgtgtttcga   2160
tctctttcca cgtgatgaaa ttccagacct tcaaatttat cttctagttt tcggacggca   2220
gtgcagtact ttcccattga atcgcttgaa caatcccatt ctttgtttat ctggcttatg   2280
actaccaaag aatccccgta caccatcagt ctcttgatgc ctagtgatat agcaatgttc   2340
agtccatgaa ttagggcttc atactcggct gcgttgttgg aggctggaaa tagcaactgg   2400
agggcatatt tgaggtgctc gcctccaggt gcggtgaaga gaattcccgc gcctgctccc   2460
tgcagcctca gcgagccatc aaaatacatt cgccatactt ctgcagtttc tgggttatct   2520
ggtacttgtt gttcagtcca ttctgatacg aagtcaacca acgcttgagt tttgatggca   2580
gtgcgaggtc gaaattcgat gtcatgagat cccagttcac aggcccactt ggctattcgg   2640
ccaatggctt ccttgttgtg aggaatatcc ccaatcggaa aaccagtgac tactatgact   2700
ttgtggtcgt caaagtagtg acatagcttg cgggcagtta gaagtactgc atataatagc   2760
tcctgaactt gaggatactt tttctttgag ggacccagaa cttcactgat gaaataaaca   2820
```

-continued

```
ggatgttgta ctgggtaggc atgtccttct tctgctcgct caaatacaac gaattcaagc    2880
ttattctcag acagcca                                                   2897

<210> SEQ ID NO 47
<211> LENGTH: 2845
<212> TYPE: DNA
<213> ORGANISM: Zea mays

<400> SEQUENCE: 47
tgagtgtccg agattaagct tgattcgttc gattcgccgt aaactgttga aaaccagctg      60
taagtcttcg atgaagtttt ctgagttctc cgttttgatt accacatcat ctacataggc     120
ttccacacgc ttgccccagt gatcggttaa gcatgtttga atggccctct gataagtcgc     180
tccagcgttt ttgaggccaa acaacatgga ggtatagcag aaagcaccga acggagtgat     240
gaacgctgtt ttttcctcat cttcccttgc caagctaatc tgatgatatc cggagtagca     300
atccagaaaa gacagcacaa acatccagc ggtggagtct accacctggt ctatccttgg      360
gagcccgaag ggatcctttg acaattttt gttgagatcc gtatagtcga cgcacatgcg      420
ccaatccact ttattctttt tgattacaag aacagggttg gctaaccact cgggatgtaa     480
cacctctcta ataaacccag ccgcgaccaa gcgagccagc ttagcgcgaa tggcctctct     540
cttgtcgggc gtgaagcgac gtagttttg ccgaatcggc cttgcctggg ggtagacctt      600
cagtttgtgc tcggccagtt ctctcgggac tcccggcata tccgcaggtt gccatgcgaa     660
tacgtctcgg ttatcttgca gaaactggac gagcgcgcct tcctatttat cgcccaggct     720
ggagctgatg atggcaatct tgcgctcatc agcaaacccc aggttgatcc ttttagtttc     780
ttcagtcggt cgcatagagg tcgcggcttg agcttcattc gccggtgctg caaggtcttc     840
ctcaggctta gagtttgcct gcgttgaaga agttgccgat ggtttggtgg tgagggccgc     900
ctggatggcc actcggaaac attatgccgc gccttggaag tcagcgcgca cagttatgat     960
tccttgtggt cctagcatct ttaatatcat gtacgtgtaa tgcggaatgg ccatgaattt    1020
tgccaatccc ggcctcccga tgatggcgtt gtacccgcag tcgaagttcg ccacttcgaa    1080
ccttaggaac tcgattctgt agttatccgg agttccgaag gtgacaggca tgtagatgtg    1140
gcccagcggg tattcccctt cagtcagcat gatgccgaag aaaggagtat ctgacttgtg    1200
gagctctttg aggtgaactc ccaagccttg gagtgtccgg gggaaggtga cgttgatgct    1260
gctccccccc gtccactaac accttcttca ccctgctctc tcggatcacc agatcgacga    1320 ggagggata tttgcctggg tggtcgaagt tgagccattg gtctgcccga gtgaaagtga     1380
tcgggtgctc cgaccatcgg tacggagcgg gaggaccggt ggtcgccacc aatatctggc    1440
gatcgttgag cttttgttgt cttctgttct cctgcgatcc gtgtccgttg aagatgacgt    1500
tgacctccct atcaacgcgt gggaaggctc cacctcctcc ctcctcctgc tgctagggtt    1560
gtcgtggttc ttctggtcct cccccgcggcg gaggaggagg tagaggttgg aagggtcggc    1620
cgtgtccgac ggagtgcttg aagtccctgc agttccgaag ggtgtggcgc atgtccttgt    1680
ggtacgggca ctgggcgtcg aggatgtcgt ccagcgtgcg ctcgcctccg cgaggtcctc    1740
cccaggcgcg agaggcaggt ggtccagcgg cgtgcacttc ttcgcgaggt ctcttctccc    1800
agcgtttgtc gggttgctgg ttcgcgtcgc gtcgtggtgc tgccggtgcg ggcttcgctc    1860
ccccgatgag gtcctgagct cgctcgtcgg cggtgatgta gaggtcggct tcccggaaca    1920
gctgctcgga ggtagtcggc gccttctgca atatggctcg gacgaaggcc gagtcattgg    1980
atcctctgta gaagtcctcg atcacgaccg cctccgtaac ctcggggata cgatttctca    2040
```

```
tggtctggaa cctttgagg tacgaccgga gagtttcgtc ccccggcgct tgatggattt    2100
gaggtcccat ggttgcgctg gtttgtcaga gagggattga agttggcgg tgaagcgtcg    2160 actgaagtcg caccagtcgt cgatgcagtg tcggggtaga tgtcgcagcc attgaagtgc    2220
gtcttgcccg aggacaatgg gtaagtatgt agtcatcacg tcctcggacg ctccagcggc    2280
tcgagcggtg gtggtgtaga cggccagcca gccccctgga tcctgcttag gttcatattt    2340
gtcgacattg gataccttga agttaggcgg ccattgaatg gccctaaggc gtggagtaag    2400
ggcagacact ccacacgtat cttcctgtcg tcagggatga tgtctgtccc ggggagggga    2460
gtagttgttg tggttcctcg actgtccccg ggtagtaccg ccagtcgagg tcgtcgttga    2520
ctcggttctg gtggcctgac tccgagctgg gatgccgtga tccctgtcgt actcctcccg    2580
gcgactgatc tcgttctcat gtcgtcgttc acgcgaagca ttgatggagc ttcgcgcgtc    2640
ccggcgactg ttgatggcgt gtcgtagatc gttcggtggg tgagcaagag gtagatggtt    2700
ggctgcttgg gtgaacaatc gtcgatagcc ctcggcgtcg ggagtccgag ggagtccatc    2760
agctatccga gctagtaacc ctccgacttc actcggcgtg ttcaggctcg ggcgaagtcg    2820
ggaaacgaat caagcttaat ctcga                                          2845

<210> SEQ ID NO 48
<211> LENGTH: 3308
<212> TYPE: DNA
<213> ORGANISM: Zea mays

<400> SEQUENCE: 48
tgactctctg agaatacgct tgattcgtag ctctggctcc ctctccctcc tctctatttc      60
ttttgagcag agcactccat tcctcccctt tttgcccaaa ttccaaatcc tgtgaaatct     120
tgtgcaacct tgttgtgaaa tgtgttcccc tgtactcctt gagtactcct gcaggttctc     180
agctccttcg ggagggtttt cacaccttaa atggccattt ctccgaaacc ctaattcctc     240
gccctccaag tgctcggtga atgcccaaa ctagccaaaa atgcttcaat tgaacccaaa     300
tttttcaggc accttcacaa cacttccagc aatatacttg tcaaatttca cgccaatccg     360
agtttccagg cttcaatttc actcaattct ccgtttcgag cgatcgtttc cgagccgagt     420
gcccaaatct cttttcttc gcctaaatte aaaccaagca cacacttcac tcatattcac     480
ctatataaac ctattcatga agtatcggct caattccatg tcgtttcgtg cctcaattcg     540
aattccaaac ctcctatggc actatttatc gttcaaacat cgttttcac gccgtttgac     600 ctatcgatct tctcgtctcg tgtttttctgt gccatatctc tctgtgtgtg tatttatta     660 catttcatat acttatgact atgtgactaa tacgtgctca cctctttgt catttcagtg     720 accttgattg cccgtgtgcc gtctcctgtc ctgcctggat cgtcacctct cgtgtgagct     780
ttccaggtag tcatctcatc ttttgctaat ctatcggtca ttttcgctct gtgcttagtc     840
actctctctc atttgcagac atcagttcag gatgccgcgc acgaagaatg tgtcggcgcc     900 aggggaggc gatgacgagg atcctcgtcg ccccttcagg caggtcaagg gcaagaccgt     960
ttacttggag cagcaagaag gccgcaagaa gcggcgtaca gacagagcag cccgtgcagc    1020
ggcagcggct acagcagccg cagcgcaggc cgagcttgga gatcagccgc agactccgtc    1080
agatcagatc gcataccgtg ttcgtcgtct cgcctcccgg cctcgctcct ccactcacac    1140
ctccgcttcc actccgccac ccactctgcc tgctcccgtc actcctattg ctccatccac    1200
ctccacagcc ataccgcta cctccactac gccagcttcc actgctcctc ctcctcccgc    1260
tcccgcttta gctcctcctg tccctccacc tcgattccgg gagcgcgatg agactgaggt    1320
```

| | |
|---|---|
| tcgaccectg gctacggatc ctcgactgtt tgaccttcag cgtgctacag cggcacgggt | 1380 |
| acgtaggttc agatacgtac ctgtggagtc ttggctacca gctcagagag accctgcagc | 1440 |
| aggtgaccta ttcagcacac ggattcagga gtcgtttttc agagctcaga tgtctgctca | 1500 |
| gatagctctg cgagtgcacc ggcttttgga tcttccagcc tttctgcttg cagccggtgc | 1560 |
| tgactctcag gcgcacctca aatatctgcc tggccttctg acccttttga ctaccagcgg | 1620 |
| caggtatgtt gaggagtggg ttcgagtctt ctacgcctct gtatggatag acccggatca | 1680 |
| tcactggatg aggtttcgtt tgagcgcga ggatgtcacc attactgccg gtcagatccg | 1740 |
| ccagcttttt ggatttcccg agtcgacgac tcgtcttcac agcctctgct acggcacttc | 1800 |
| tgatcctcct cgtcgccctc acggcggtgt ggctccgggt acagctcacg tcgcggctct | 1860 |
| cttccgcccc cccttctcag atgggtcgcg acgttcaccg gcatatttta ctacagcagc | 1920 |
| caagtattta tatgagctga tcagacgaac tcttctgccg aggatgggat acagggaggc | 1980 |
| taccacacat atacagctct ggctccttgg tgccctggtc tctcactcta agtttgacgt | 2040 |
| tgtggacttc ctgattttg agatcgagga caccgttttg gatgggatct gtgctcgtcg | 2100 |
| gcagttgccc tatgctcact acttgtgcca catctttgcg cagctgattc agcctcctcg | 2160 |
| gtttcagggc acccttgagg cctcccgcct cgttttgga tcctaccgtc ctgtgcctga | 2220 |
| gattcctgtg ccagcttctg ctcctgtttt tgactcttag gccgaggatg cagctcttcg | 2280 |
| tcagttcgac actcaggttc cagcagctga tgatgatgat tttggggttc ctcctccgcc | 2340 |
| tccgcctcct atgcctccac gctcacatga tcctctagag tcgacctgca ggcatgcaag | 2400 |
| cttgagtatt ctatagtgtc acctaaatag cttggcgtaa tcatggtcat agctgtttcc | 2460 |
| tgtgtgaaat tgttatccgc tcacaattcc acacaacata cgagccggaa gcataaagtg | 2520 |
| taaagcctgg ggtgcctaat gagtgagcta actcacatta attgcgttgc gctcactgcc | 2580 |
| cgctttccag tcgggaaacc tgtcgtgcca gctgcattaa tgaatcggcc aacgcgaacc | 2640 |
| ccttgcggcc gcccgggccg tcgaccaatt ctcatgtttg acagcttatc atcgaatttc | 2700 |
| tgccattcat ccgcttatta tcacttattc aggcgtagca accaggcgtt taagggcacc | 2760 |
| aataactgcc ttaaaaaaat tacgccccgc cctgccactc atcgcagtac tgttgtaatt | 2820 |
| cattaagcat tctgccgaca tggaagccat cacaaacggc atgatgaacc tgaatcgcca | 2880 |
| gcggcatcag caccttgtcg ccttgcgtat aatatttgcc catggtgaaa acggggggcga | 2940 |
| agaagttgtc catattggcc acgtttaaat caaaactggt gaaactcacc cagggattgg | 3000 |
| ctgagacgaa aaacatattc tcaataaacc ctttagggaa ataggccagg ttttcaccgt | 3060 |
| aacacgccac atcttgcgaa tatatgtgta gaaactgccg gaaatcgtcg tggtattcac | 3120 |
| tccagagcga tgaaaacgtt tcagtttgct catggaaaac ggtgtaacaa gggtgaacac | 3180 |
| tatcccatat caccagctca ccgtctttca ttgccatacg aaattccgga tgagcattca | 3240 |
| tcaggcgggc aagaatggaa taaaggccgg ataaaactgt agaattcaag cttatcatcg | 3300 |
| gacactca | 3308 |

```
<210> SEQ ID NO 49
<211> LENGTH: 4998
<212> TYPE: DNA
<213> ORGANISM: Zea mays

<400> SEQUENCE: 49
```

| | |
|---|---|
| tggctgtctg agattacgct tgaattctct gcaccgcacc gtgtccggtc agtcgagtca | 60 |
| cctggagaga ctgcaccacc gcctgcgtga ggagcaggaa cgccggcgcc agcacagaga | 120 |

```
gcagcagggc tcttcttccc cacctcaacg agaggtggag tccgcgaggc cccgttcctc    180
tgtggcccag ctggaggcgc cccctgcccc gccgcggagc gttccagctg ttggaggagc    240
tactggagga gatcctggag gagaccccga cgacgacgac tcagaccaca gcacggagtc    300
ttctgagccg caggaggcgg aaggatgggt cgcccgaccc atcacccgtg acgccgctcg    360
cggttgtcac ttccacgacg cactcgacac cttgctgcgc caggctttcg accgacacac    420
ctggtcgatc gagtatcgtt gtgtagtcta ccagcacaat cgcgggaggt acccggaccg    480
ctgggaggct acctgcctag ttcgccgtcc ggaggatgac ctccggggtg cggaggccat    540
ttcggagcac tattccatct ccgagaggga cactgcagag gcggctatgc aggatgcagc    600
acgacgtgca ctctctcagt actgttcttt gttcggtggc gtggccgacg gtcttaacct    660
tcggtactac ccccgccgcc ctactagcag caccgagagt gtggttgtct cacccgttgg    720
tgaggctaac cctaggttga gcagcacagt caacctagtc gcagtgctta acactgagct    780
ggaccactct ctggacgagc taagcagggc tcgaacggag attgcggagt tgcgtgctga    840
gctggcagag cgccatcacc aggagggtgg ttctcccgct cctgttggga ctcagcaccc    900
ataccgctca ccgccacgtg gtcaccacac ttatggttcc cctgtctgta agaccaggat    960
agatctggat ccttagatcg ttagcgtcgt agtttgtaat aattcttaag tcagatgtct    1020
cagtcttagg tagtcagttt agtttgctta tcagttgctt ccatttaggt tagtttgctt    1080
atcagttgct ttcatgcttg ttatgatgaa cttgtgctgg attcgaatct ttgtaatgac    1140
tgttgccaac ctgtgggttt ctgaaaggga attaggctta cacctagtcc ctaattaatt    1200
ttggtggttg aattgcccaa cacaaataat tggactaact agtttgccca agtgtataga    1260
ttatacaggt gtaaaaggtt cacactcagc caataaaaag accaagtttt ggattcaacg    1320
aaggagcaaa gtggcaaccg aaggccctct ggtctgggag caccggactg tccggtgtac    1380 acggacagt gtccggtgca ccaccggaca gtgtccggtg taccagaggt gtcgggggacc    1440 ataattaggg gtaccctcaa gacgcctaat tctcagctgg taaccccat cagcataaag    1500 ctgcaaaggc ctgatgggta cgattaagtc agggatcagt ccacacgagt gactcgatca    1560
cgcttcaccc gagcctagcc tcggccaagg gcagccgacc tcgagagact tccgtctcgc    1620
ccgaggcccc cttttatgg cggacacatc accggctcgc ccgaggcctt ggcttcgctc    1680
agaagcaacc ttgactaaat cgccacaccg actgaccaaa ttgcagggc atttaacgca    1740 aaggtggcct gacaccttca tcctgacacg cgccccggc agagccgaag tgaccgccgt    1800
cactccaccc ctccactggc cagtctgaca gaaggacagc gccgcctgcg ccactccgac    1860
tgcagtgcca ctcgacagag tgagtctgac aggcagtcag gccttgccaa aggcaccacg    1920
gcgaactccg ccctgcccga ccccagggct cggactcggg ctaagacccg gaagacggag    1980
aactccgctc cgcccgaccc cagggctcgg actcggcta agaccccggaa gacggcgaac    2040 tccgctccgc ccaccctagg gctcggactc gggctaagac ccggaagacg gcgaactccg    2100
ctccgcccga cccctagggct cggactcagg ctaagacccg gaagacggcg aactccgctc    2160
cgcccgaccc cagggctcgg actcggcta agacccggaa gacggcgaac tccgctccgc    2220
ccgaccccag ggctcggact cgggctaaga cccggaagac ggcgaactcc gctccgcccg    2280
accccagggc tcggactcgg gctaagaccc ggaagacggc gaactccgct ccgcccgacc    2340
ccagggctcg gactcgggct aagacccgga agacgacgaa actccgcttc gcccgacccc    2400
agggctcgga ctcgggctaa gacccggaag acgacgaaac tccgcctcgc ccgacccag    2460 ggctcggact ccgccctggc ctcggccgaa cgacttccgc ctcgcccgac cccatggctc    2520
```

-continued

```
gggctcggcc acggcaacgg aaggcagact caacctcggc ttcggaggaa ccccacgtc      2580 gccctgccta gggcacagac cgccacgcca acaggaagcg ccatcatcat cctaccccga      2640
atcgactcgg gtcacggaga acaagaccgg cgtcccatcc ggccagctcc gccggagggg      2700
caatgatggc gctccacaag ctctatgacg acggcggccc ccagctctct tacggaagca      2760
ggacgacgtc agcagggact cgaccgctcc aacagctgtc cctccgccag gctccgccgc      2820
acctccgaca gccacgacat cacgccagca gggtgcccag atctctccgg ctgccacatt      2880
ggcatgtacc tagggcgcta gctctccctc cgctagacac gtagcactct gctacacccc      2940
ccattgtaca cctggatcct ctccttacga ctataaaagg gaggaccagg gccttcttag      3000
agaaggttgg ccgcgcggga ccgaggacgg gacaggcgct ctcttgggc cgctcgcttc       3060 cctcacccgc gtggacgctt gtaaccccc tactgcaagc gcacctgacc tgggcgcggg       3120
acgaacacga aggccgcggg acttccacct ctctcacgct cgactccggc cacctcgcct      3180
ctcccccctt cgcgctcgcc cacgcgctcg acccatctgg gctggggcac gcagcacact      3240
cactcgtcgg cttagggacc ccctgtctc gaaacgccga cagttggcgc gccaggtagg       3300
ggcctgctgc gtgctgacga acagctcccc gtcaagctcc agatgggcag tctccagcaa      3360
cctctccggc ccgggacggt gcttcgtttc gggactcttg agttcatgtc cttcgacggc      3420
agctacgaca tgatacttct tccaccgccg cgcgactacg acaatggcga ccgacaaccc     3480
gcccgccggc ggcggaatcg acgacgtctt ccccgcgtgg tggaagggca acattcgggc      3540
tcgctccgtt ctctccccg ccaacggagg aggaggcggg gccgtcaagg ccaggtggga       3600
ggccgcgctt cgtcggccgt cgagcgaatc gacgcccccg acgccccgac ggaaggcacg     3660
ccggacgtcg acctcgcgtt caagacggag gcaagcgccg tcccccgcg gcacgctgac      3720 cccgagcaag aagacgacgc cggcgcgctc gcggaaagcc tgcaggacgt cgccctcgaa      3780
ccagagttga cggtgcaacc agtccccgat gtgactacgt cgctcctcgt cgacaaaaag     3840
gtaccaacta actcccatct tgcgtcattt cgactcggcc tcaacccgcc aaacgacctc     3900
gttttggcgg gcgctctcat tgaggcgagt gcaaccccac tgaggttccg tatgcggtcg     3960
ccttgggacc gactgacgga cgtctcgacc tacgggccct ctgggtccga ggaagatgac     4020
gatcccagca tcgcttggga tttctccgga ctcggcaacc ccagtgccgt gcgggacttc     4080
atgaccgcat gtgactactg cctatccgac tgttccgatg gaagccgcag ccttggcgac    4140
gagagctgcg gcccaagccg cgaatgtttc cacatcgagc tagggatcc ctccgaaggc      4200 aaccatcttg gcatgccgga ggacagtgat ctccctaggc cggtgcctcg cgccgacatc     4260
ccacgggagc tagctgtagt ccccgctccg gcgggggtt acgacccaca actcgagcaa      4320
gtccgcgagg cgcaggccag gctcaacgag ggaacaggag cgcttgagcc gatccgtcgg     4380
gacgtcggac aagcatgggt gggccaaccc ctgcccggag aaatacgtca cttgccccaa     4440
ggtctccagc accgcgtcgc caacgatgtc aggatcaggc cgccgcccgc atccagcggg     4500
gttggtcaga acctggcaac cgcagcaatg ctcatccgcg cgatgccgga gccgtcaacc    4560
accgagggtc ggcgaatcca gggagaactc aagaatctcc tggaaggcgc tgcggcccgg     4620
cgggccgaga gcactgcctc ccgaaggcaa ggttatccct cggaacctca tgccgcgact     4680
tcccgattca tgcgggaagc ctcggtctac accgggcgca cgcgcaacac cgcgcctgcg     4740
gccccgggcc acctcggcaa cgagcaccat cgacgcgacc gtcgggctca cctcgacgaa     4800
agggtgcgcc gaggctacca ccccaggcgt gggggcgct acgacagcgg ggaggatcgg      4860
agtccctcgc ccgaaccacc cggtccgcag gccttcagtc gggccatccg acgggcgcca     4920
```

| | |
|---|---|
| ttcccgaccc ggttccgacc cccgactact atcacgaagt acttcggggg aaacgagacc | 4980 |
| ggaactgtgg ctcgggga | 4998 |

<210> SEQ ID NO 50
<211> LENGTH: 8151
<212> TYPE: DNA
<213> ORGANISM: Zea mays

<400> SEQUENCE: 50

| | |
|---|---|
| tgagctgtcg agaataagct tgattcgttg tgaaactcac attcaattca aacttgattc | 60 |
| aaaataatta tataagataa cagaaaataa aaaaggaaaa gcttaaccgg gcctcagatt | 120 |
| cacacttggc ccaccatgaa aacccctccg cgcggcccaa cttgaatccc cccccgcgca | 180 |
| tgactcattg tcaggtgggg ccgtgttgtt ggtcgccgag gcgcgcgcgc tcacgaccgc | 240 |
| gtttcgccgc ctggtgggac cccatgttg gctgttcctt cgaccttcag ctcggtgtgt | 300 |
| cggttgcaac cactcgccga agattccgcg aatagctcgg gattgacctg accgattccg | 360 |
| cgaataactt tgaatgcacc ccgaaatccg ttttcggaat gggtgacgtg cggcaacgaa | 420 |
| attgcgcgaa acaaccccaa acatgagttt tggacctaaa gtaatggatt gggcatgttc | 480 |
| gttgcgctaa atgaagaaat ggttccggtg gcaaaaactc gtgcttatat gcaccccgac | 540 |
| acccgttttc ggaatgggtg atgtgcggca acgaaattgc gcgaaaccac cccaaacatg | 600 |
| ggttttggac ctaaagtagt ggattgggca tgttcgttgc gaaaaacgaa gaaatgattc | 660 |
| cagtggcaaa aactcgtgct tttatgcaac ccgacacccg ttttcggaat gggtgacgtg | 720 |
| cggcaacgaa attgcgcgaa accaccccaa acatgagttt tggacctaaa gtagtttagt | 780 |
| gggcatattt tttgcgaaaa acgaagaaat ggttccggtg gccaaaactt gtgctttgaa | 840 |
| tgcaccccga aatccgtttt cggaatgggt gacgtgcggc aacgaaattg cgcgaaacaa | 900 |
| ccccaaacat gagttttgga cctaaagtaa tggattgggc atgttcgttg cgctaaatga | 960 |
| agaaatggtt ccggtggcaa aaactcgtgc ttatatgcac cccgacaccc gttttcggaa | 1020 |
| tgggtgatgt gcggcaacaa aattgcgcga accaccccca acatggggtt ttggacctaa | 1080 |
| agtagtggat tgggcatgtt cgttgcgaaa acgaagaaa tgattccagt ggcaaaaact | 1140 |
| cgtgctttta tgcaacccga cacccgtttt cgaaatgggt gacgtgcggc aacgaaattg | 1200 |
| cgtgaaacca ccccaaacat tagttttgga cctaaagtag tgtattgggc atgttcgttg | 1260 |
| tgaaaaacga gaaatggttc cggtggcaa aaacacgtcc ttttatgcac cccgacaccc | 1320 |
| gttttcggaa tgggtgacgt gctgcaacaa aattgcgtga accaccccca acatgagtt | 1380 |
| ttggacctta agtagtggat tgggcatgtt cgttgcgaaa aagaagaaa tggttctggt | 1440 |
| ggcaaaaact cgtgctttta tgcactcccg acacccgttt tcggaatggt tgacgtgcgg | 1500 |
| caacgaaatt gcgcgaaacc acccaaaaca tgagttttgg acctaaagta gtttagtggg | 1560 |
| catatttttt gcgaaaaacg aagaaatggt tccgtggcc aaaacttgtg ctttgaatgc | 1620 |
| accccgaaat ccgttttcgg aatgggtgac gtgcggcaac gaaattgcgc gaaacaaccc | 1680 |
| caaacatgag ttttggacct aaagtaatgg attgggcatg ttcgttgcgc taatgaaga | 1740 |
| aatggttccg gtggcaaaaa cttgtgctta tatgcacccc gacaccgtt tcggattgg | 1800 |
| gtgatgtgcg gcaacgaaat tgcgggaaac caccccaaac atgggttttg gacctaaagt | 1860 |
| agtggattgg gcatgttcgt tgcgaaaaac gaagaaatga ttccagtggc aaaaactcgt | 1920 |
| gcttttatgc accccgacac ccgttttcga atgggtgac gtgcggcaac gaaattgcgc | 1980 |
| gaaaccaccc caaacatgag ttttggacct aaagtagtgt attgggcatg ttcgttgcga | 2040 |

```
aaaacgaaga aatggttccg gtggcaaaaa ctcgtgcttt tatgcacccc gacacccgtt    2100
ttcggaatgg gtgacgcgcg gcaacgaaat tgcgcgaaac cacccaaat atgggttttg     2160 gacctaaagt agtggattgg acatgttcgt tgcgaaaaac gaagaaatga ttctggtggc    2220
aaaaactcat gcttttatgc accccgacac ccttttcgg aatgggtgac gtgcggcaac     2280
gaaattgcgc gaaaccaccc caaacatgag ttttggacct aaagtactgg attgggcatg    2340
ttcgttgcga aaaatgaaga aatggttccg gtggcaaaaa ctcgtgctta tatgcacccc    2400
gacacccgtt ttcggaatgg gtgacgtgcg gcaacgaaat tgcgcgaaac caccccaaac    2460
atgggttttg gacctaaagt agtggattgg gcattttcgt tgcgaaaaaa gaagaaatgg    2520
ttctggtggc aaaaactcgt gcttttatgc accccgaca cccgttttta gaatgggtga     2580
cgtgcggcaa cgaaattgcg cgaaaccacc caaacatgg gttttggacc taaagtagtg     2640
gattgtgcat gttcgttgcg aaaaacgaag aaatggttct ggtggcaaaa actcgtgctt    2700
ttatgcaacc cgacacccgt tttcggaatg ggtgacgtgc ggcaacgaaa ttgcgcgaaa    2760
ccaccacaaa catgagtttt ggacctaaag tagtggattg gcatgttcg ttgcgaaaaa     2820 tgaagaaatg gttccggtgg caaaaactcg tgcttttatg caccccgaca cccgttttcg    2880
gaatgggtga cgtgcggcaa cgaaattaag cgaaaccacc ccaaacatgg gttttggacc    2940
taaagtagtg gattgggcat gttcgttgcg aaaaacaaag aaatgattcc agtggcaaaa    3000
actcgtgctt ttatgcaccc cgacacccgt tttcgaaatg ggtgacgtgc ggcaacgaaa    3060
ttgcgcgaaa ccaccccaaa catgcgtttt ggacctaaag tagtgtattg gcatgttcg     3120 ttgcgaaaaa cgaagaaatg gttccggtgg caaaaactcg tgcattgtat gcaccccgac    3180
acccgttttc ggaatgggtg acgtgcggca acgaaattgc gcgaaaccac cccaaacatg    3240
ggttttggac ctaaagtagt ggattgggca tgttcgttgc gaaaaacgaa gaatggttc     3300 cggtggcaaa actcgtgcat tgtatgcacc ccgacacccg ttttcggaat gggtgacgtg    3360
cggcaaccga aattgcgcga aaccacccca acatgagtt tttggacctaaa agtagtgga    3420 ttgggcatgt tcgttgcgaa aaacaaagaa atgattccag tggcaaaaac tcgtgctttt    3480
atgcaccccg acacccgttt tcgaaatggg tgacgtgcgg caacgaaatt gcgcgaaacc    3540
accccaaaca tgcgttttgg acctaaagta gtgtattggg catgttcgtt gcgaaaaacg    3600
aagaaatggt tccggtggca aaaactcgtg cattgtatgc accccgacac ccgttttcgg    3660
aatgggtgac gtgcggcaac gaaattgcgc gaaaccaccc caaacatggg ttttggacct    3720
aaagtagtgg attgggcatg ttcgttgcga aaacgaaga aatgattctg gtggcaaaaa     3780
cacatgcttt tatgcacccc gacacccttt tcggaatgg gtgacgtgcg gcaacgaaat     3840
tgcgcgaaac caccccaaac atgagttttg gacctaaagt agtggattgg gcatgttcgt    3900
tgcgaaaaat gaagaaatgg ttccggtggc aaaaactcgt gcttatatgc accccgacac    3960
ccgttttcgg aatgggtgac gtgcggcaac gaaattgcgc gaaccaccc caaacatggg     4020 ttttggacct aaagtagtgg attgggcatg ttcgttgcga aaacgaaga aatggttccg     4080 gtggcaaaac tcgtgcattg tatgcaccca cacccgttt tcggaatggg tgacgtgcgg     4140
caacgaaatt gcgcgaaacc accccaaaca tgagttttgg acctaaagta ggggattggg    4200
catgttcgtt gcgaaaaatg aagaaatggt tccggtggca aaaactcgtg gttttatgca    4260
ccccgacacc cgttttcgga atgggtgacg cgcggcaacg aaattgcgcg aaaccaccca    4320
aaacatgagt tttgggccta agtagtgga ttgggcatgt tcgttgcgaa aaacaaagaa     4380
atggtttcgg tggcaaaaac tcgtgcattg tatgcacccc gacacccgtt ttcggaatgg    4440
```

```
gtgacgtgcg gcaacgaaat tgcgcgaaac caccccaaac atgggttttg gacctaaagt    4500
agtggattgg gcatgttcgt tgcgaaaaac gaagaaatga ttctggtggc aaaaactcat    4560
gcttttatgc accccgacac cctttttcgg aatgggtgac gtgcggcaac gaaattgcgc    4620
gaaaccaccc caaacatgag ttttggacct aaagtagtgg attgggcatg ttcgttgcga    4680
aaaatgaaga atggttccg gtggcaaaaa ctcgtgctta tatgcacccc gacacccgtt    4740
ttcggaatgg gtgacatgcg gcaacgaaat tgcgcgaaac caccccaaac atggttttg    4800 gacctaaagt agtggattgg gcatgttcgt tgcgaaaaac gaagaaatgg ttccggtggc    4860
aaaaactcgt gcttttaagc accccgacac ccgttttcga atgggtgac gtgcggcaac    4920 gaaattgcgc gaaaccaccc caaacattag ttttggacct aaagtagtgt attgggcatg    4980
ttcgttgcga aaaacgaaga atggttttcg gtggcaaaaa cacgtcctttt tatgcacccc    5040 gacacccgtt ttcggaatgg gtgacgtgct gcaacaaaat tgcgtgaaac caccccaaac    5100
atgagttttg gaccttaagt agtggattgg gcatgttcgt tgcgaaaaaa gaagaaatgg    5160
ttctggtggc aaaaactcgt gcttttatgc actcccgaca cccgttttcg gaatggttga    5220
cgtgcggcaa cgaaattgcg cgaaacaacc ccaaacatga gttttggacc taaagtaata    5280
gattgggcat gttcgttgcg caaaatgaag aaatggttcc agtggaaaaa actcgtgctt    5340
atatgcaccc cgacacccgt tttcggaatg ggtgatgtgc ggcaacgaaa ttgcgcgaaa    5400
ccaccccaaa catgggtttt ggacctaaag tagtggattg gcatgttcg ttgcaaaaac    5460 gaagaaatgg tttcggtggc aaaaactcgt gaattgtatg caccccgaca cccgttttcg    5520
gaataggtga cgtgtggcaa cgaaattgcg cgaaaccacc ccaaacatga gttttgacc    5580 taaagtagtg tattgggcat gttcgttgcg aaaaatgaag aaatggttcc ggtggcaaaa    5640
actcgtgctt ttatgcaccg cgataccgt tttcggaatg gatgacgtgc ggcaacgaaa    5700
ttgcgcgaaa ccaccccaaa catgggtttt ggacctaaag tagtggattg gcatgttcg    5760 ttgcgaaaaa cgaagaaatg attccagtgg caaaaactcg tgcttttatg caacccgaca    5820
cccgttttcg gaatgggtga cgtgcggcaa cgaaattgcg cgaaaccacc caaacatga    5880 gttttggacc taaagtagtg gattgggcat gttcgttgcg aaaaatgaag aaatggttct    5940
ggtggcaaaa actcgtgctt ttatgcaccc cgacacccgt tttcggaatg ggtgacgtgc    6000
ggcaacgaaa ttaagcgaaa ccaccccaaa catgggtttt ggacctaaag tagtggattg    6060
ggcatgttcg ttgcgaaaaa caaagaaatg attccagtgg caaaaactcg tgcttttatg    6120
caccccgaca cccgttttcg aaatgggtga cgtgcggcaa cgaaattgcg cgaaaccacc    6180
ccaaacatga ggtttggacc taaagtagtg tattgggcat gttcgttgcg aaaaacgaag    6240
aaatggttcc gatggcaaaa actcgtgctt ttatgcaccc caacaccgt tttcggaatg    6300 ggtgacgcgc ggcaacgaaa ttgcgcgaaa ccacccaaaa catgagtttt gggcctaaag    6360
tagtggattg gcatgttcg ttgcgaaaaa caaagaaatg gtttcggtgg caaaaactcg    6420
tgcattgtat gcaccccgac accgttttc ggaatgggtg acgtgcagca acgaaattgc    6480
gcgaaaccac cccaaacatg ggttttggac ctaaagtagt ggattgggca tgttcgttgc    6540
gaaaaacgaa gaaatgattc tggtggcaaa aactcatgct tttaagcacc ccgacaccct    6600
ttttcggaat gggtgacgtg cggcaacgaa attgcgcgaa accacccaa acatgagttt    6660 tggacctaaa gtagtggatt gggcatgttc gttgcgaaaa atgaagaaat ggttccggtg    6720
gcaaaaactc gtgcttatat gcaccccgac accgttttc ggaatgggtg acgtgcggca    6780
acgaaattgc gcgaaaccac cccaaacatg ggttttggac ctaaagtagt ggattgggca    6840
```

```
tgttcgttgc gaaaaacgaa gaaatggttc cggtggcaaa aactcgtgct tttaagcacc    6900
ccgacacccg ttttcgaaat gggtgacgtg cggcaacgaa attgcgcgaa accaccccaa    6960
acattagttt tggacctaaa gtagtgtatt gggcatgttc gttgcgaaaa acgaagaaat    7020
ggtttcggtg gcaaaaactc gtgaattgta tgcaccccga cacccgtttt cggaataggt    7080
gacgtgtggc aacgaaattg cgcgaaacca ccccaaacat gagttttgac ctaaagtagt    7140
gtattgggca tgttcgttgc gaaaaatgaa gaaatggttc cggtggcaaa aactcgtgct    7200
tttatgcacc ccgatacccg ttttcggaat ggatgacgtg cggcaacgaa attgcgcgaa    7260
accaccccaa acatgggttt tggacctaaa gtagtggatt gggcatgttc gttgcgaaaa    7320
acgaagaaat gattccagtg gcaaaaactc gtgcttttat gcaacccgac accgttttc    7380
ggaatgggtg acgtgcggca acgaaattgc gcgaaaccac cacaaacatg agttttggac    7440
caaaagtagt ggattgggca tgttcgttgc gaaaaacaaa taaatggttc cggtggcaaa    7500
aactcgtgct tttatgcacc cccgacaccc gttttggaa tgggtgacgt gcggcgacga    7560
aattgcacga aaccacccca acatgagtt ttggacctaa agtagtgtat tgggactgtt    7620
cgttgcgaaa acgaagaaa gggttccggt ggcaaaaact cgtgctttta tgcaccccga    7680
cacccgattt cggaatgggt gacgtgcgac aacgaaattg cgcgaaacca cccaaaacat    7740
gagttttgga cctaaagtag tggattgggc atgttcgttg cgaaaaacaa agaaatggtt    7800
tcggtggcaa aaactcgtgc attgtatgca ccccgacacc cgttttcgga tgggtgacg    7860
tgcggcaacg aaattgcgtg aaaccacccc aaacatgagt tttggaccta agcagtgga    7920
ttgggcatgt tcgttgtgaa aaatgaagaa atggttccgg tggcaaaact cgtgcttta    7980
tgcacctcga cacccgtttt cggaatgggt gatgtgcggc aacgaaattg tgcgaaacca    8040
cccccgaaca tgggttttgg acttaaagta gtgcattggg catgttcgtt gtgaaaaacg    8100
aagaaatgat tccagggcaa aaactaagaa ttcaagctta ttctcagaca c             8151

<210> SEQ ID NO 51
<211> LENGTH: 10813
<212> TYPE: DNA
<213> ORGANISM: Zea mays

<400> SEQUENCE: 51
gactctccga gaataagctt gattcgttaa cgaacatgcc caatacacta ctttaggtca      60
aaaactcatg tttggggtgg tttcgcgcaa tttcgttgcc acacgtcacc tattccgaaa     120
acgggtgtcg gggtgcatac aattcacgag ttttgtccac cgaaaccatt tcttcgtttt     180
tcgcaacgaa catgcccaat acactacttt aggtccaaaa ctaatgtttg ggtggtttc      240
gcgcaattc gttgccgcac gtcacccatt tcgaaaacgg gtgtcggggt gcttaaaagc     300
acgagttttt gccaccggaa ccacttcttc gttttttcgca acgaacatgc caatccact      360
actttaggtc caaaacccat gtttggggtg gtttcgcgca atttcgttgc cgcacgtcac     420
ccattccgaa aacgggtgtc ggggtgcata taagcacgag ttttgtccac cggaaccatt     480
tcttcatttt tcgcaacgaa catgcccaat ccactacttt aggtccaaaa ctcatgtttg     540
ggtggtttc gcgcaatttc gttgccgcac gtcacccatt ccgaaaagg tgtcgggt      600
gcataaaagc atgagttttt gccaccgaaa tcatttcttc gtttttgca acgaacatgc     660
ccaatccact actttaggtc caaaacccat atttggggtg gtttcgcgca atttcgttgc     720
cgcacgtcac ccattccgaa aacgggtgtc ggggtgcata caatgcacga ttttgtcca      780
ccggaaccat ttcttcgttt ttcgcaacga acatgcccaa tacactactt taggtccaaa     840
```

| | |
|---|---|
| actcatgttt ggggtggttt cgcgcaattt cgttgccgca cgtcacccat ttcgaaaacg | 900 |
| ggtgtcgggg tgcataaaag cacgagtttt tgccactgga atcatttctt tgttttttcgc | 960 |
| aacgaacatg cccaatccac tactttaggt ccaaaaccca tgtttggggt ggtttcgctt | 1020 |
| aatttcgttg ccgcacgtca cccattccga aaacgggtgt cggggtgcat aaaagcacga | 1080 |
| gttttttgcca ccgggaccca tttcttcatt tttcgcaacg aacatgccca atccactact | 1140 |
| ttaggtccaa aactcatgtt tgtggtggtt tcgcgcaatt tcgttgccgc acgtcaccca | 1200 |
| ttccgaaaac gggtgtcggg ttgcataaaa gcacgagttt ttgccactgg aatcatttct | 1260 |
| tcgttttttcg caacgaacat gcccaatcca ctactttagg tccaaaaccc atgtttgggg | 1320 |
| tggtttcgcg caatttcgtt gccgcacgtc atccattccg aaaacgggta cggggtgca | 1380 |
| taaaagcacg agttttttgcc accggaacca tttcttcatt tttcgcaacg aacatgccca | 1440 |
| atacactact ttaggtcaaa aactcatgtt tggggtggtt tcgcgcaatt tcgttgccac | 1500 |
| acgtcaccta ttccgaaaac gggtgtcggg gtgcatacaa ttcacgagtt tttgccaccg | 1560 |
| aaaccatttc ttcgtttttc gcaacgaaca tgcccaatac actactttag gtccaaaact | 1620 |
| aatgtttggg gtggtttcgc gcaatttcgt tgccgcacgt cacccatttc gaaaacgggt | 1680 |
| gtcggggtgc ttaaaagcac gagttttttgc caccggaacc acttcttcgt ttttcgcaac | 1740 |
| gaacatgccc aatccactac tttaggtcca aaacccatgt ttggggtggt ttcgcgcaat | 1800 |
| ttcgttgccg cacgtcaccc attccgaaaa cgggtgtcgg ggtgcatata agcacgagtt | 1860 |
| tttgccaccg gaaccatttc ttcattttttc acaacgaaca tgcccaatcc actgctttag | 1920 |
| gtccaaaact catgtttggg gtggtttcac gcaatttcgt tgccgcacgt cacccattcc | 1980 |
| gaaaacgggt gtcggggtgc atacaatgca cgagttttttg ccaccgaaac catttctttg | 2040 |
| tttttcgcaa cgaacatgcc caatccacta ctttaggtcc aaaactcatg ttttgggtgg | 2100 |
| tttcgcgcaa tttcgttgcc gcacgtcacc cattccgaaa acgggtgtcg gggtgcataa | 2160 |
| aagcacgagt ttttgccacc agaaccattt cttcgttttt cgcaacgaac atgcccaata | 2220 |
| cactacttaa ggtccaaaac tcatgtttgg ggtggtttcg cgcaatttcg ttgccgcacg | 2280 |
| tcatccattc cgaaaacgga tgccggggtg catacaatgc acgagttttt gccactggaa | 2340 |
| ccatttctttt cttttttcgca acgaacatgc ccaatccact actttaggtc caaaacccat | 2400 |
| gtttggggtg gtttcgcgca atttcgttgc cgcacgtcac ccattccaaa acgggtgtc | 2460 |
| ggggtgcaga aaagcacggg tttttgccac cggaaccatt tcttcgtttt tcgcaacgaa | 2520 |
| catgccaaat acactacttt aggtccaaaa ctcatgtttg ggtggtttc gcgcaatttc | 2580 |
| gttgcagcac gtcacccatt tcaaaaacgg gtgtggtgca taaaagcacg agttttttgcc | 2640 |
| accgaaacca tttcttcgtt tttcgcaacg aacatgccca atccactagt ttaggtccaa | 2700 |
| aaccaatgtt tggggtggtt tcgcgcaatt tcgttgccgc acgtcaccca ttccgaaaac | 2760 |
| gggtgtcggg gtgcataaaa gcacgagttt ttgccaccgg aaccatttct tcatttttcg | 2820 |
| caacgaacat gcacaatcca ctactttagg tccaaaactc atgtttgggg tggtttcgcg | 2880 |
| caatttcgtt gccgcacgtc acccattccg aaaacgggtg tcggggtgca taaaagcacg | 2940 |
| agttttttgcc accggaacca tttcatcatt tttcgcaacg aacatgccca atacactact | 3000 |
| ttaggtctaa aactcatgtt tggggtggtt tcgcacaatt tcgttgtcgc acgtcaccca | 3060 |
| tttcgaaaac gggtgtcggg gtgcataaaa gcacgagttt ttgccaccag aaccatttct | 3120 |
| tcgttttttcg caacgaacat gcccaataca ctacttaggg tccaaaactc atgtgtttggg | 3180 |
| gtggtttcgc gcaatttcgt tgccgcacgt cacccattcc gaaaacgggt gtcgggtgca | 3240 |

```
tacaatgcac gagttttgc caccgatacc atttctttgt ttttcgcaac gaacatgccc   3300
aatccactac tttaggtcca aaactcatgt tttgggtggt tcgcgcaat ttcgttaccg    3360
cacgtcaccc attccgaaaa cgggtgtcgg ggtgcataaa agcacgagtt tttgccacgg   3420
gaaccatttc ttcattttc gcaacgaaca tgcccaatcc actactttag gtccaaaact    3480
catgtttggg gttgtttcgc gcaatttcgt tgccgcacgt cacacattcc gaaaacgggt   3540
gtcgggggtgc ataaaagcac gagttttgc caccggaacc atttcttcat ttttcacaac   3600
gaacatgccc aatccactgc tttaggtcca aaactcatgt ttggggtggt tcacgcaat    3660
ttcgttgccg cacatcaccc attccgaaaa cgggtgtcga ggtgcataaa agcacgagtt   3720
ttgccaccgg aaccatttct tcattttca caacgaacat gcccaatcca ctgctttagg   3780
tccaaaactc atgtttgggg tggtttcacg caatttcgtt gccgcacgtc acccattccg   3840
aaaacgggtg tcgggtgca tacaatgcac gagttttgc caccgaaacc atttctttgt   3900
ttttcgcaac gaacatgccc aatccactac tttaggtcca aaactcatgt tttgggtggt   3960
ttcgcgcaat ttcgttgtcg cacgtcaccc attccgaaat cgggtgtcgg ggtgcataaa   4020
agcacgagtt tttgccaccg gaacccttc ttcgttttc gcaacgaaca gtcccaatac   4080
actactttag gtccaaaact catgtttggg gtggtttcgt gcaatttcgt cgccgcacgt   4140
cacccattcc aaaaacgggt gtcggggtg cataaaagca cgagttttg ccaccggaac   4200
catttatttg ttttcgcaa cgaacatgcc caatccacta cttttggtcc aaaacccatg   4260
tttgggtgg tttcgcgcaa tttcgttgcc gcacgtcacc cattccgaaa acgggtgtcg   4320
gggtgcataa aagcacgagt ttttgccacc agaaccattt cttcgttttt cgcaacgaac   4380
atgcccaata cactacttta ggtccaaaac tcatgtgttg ggtggttc gcgcaatttc    4440
gttgccgcac gtcacccatt ccgaaaacgg gtgtcgggg gcattcaaag cacagttttt    4500
tgccaccgga accatttctt cgttttcgc aacaaacatg ccgactaaac tactttaggt    4560
ccaaaactca gttttgggt ggtttcgcgc aatttcgttg ccgcacgtca cccattccga    4620
aaacgggtgt cggggtgcat aacaacacga gttttgcca ccggaaccat ttcttcattt    4680
ttcgcaacga acatgcccaa tccactactt taggtccaaa actcatgttt ggggtggttt   4740
cgcgcaattt cgttgctgca cgtcacccat tccgaaaacg ggtgtcgggt gcatacaatg   4800
cacgagtttt tgccaccgaa accatttctt tgttttcgc aacgaacatg accaatccac   4860
tactttaggt ccaaaactca tgttttgtat ggtttcgcgc aatttcgttg ccgcacgtca   4920
cccataccga aaacgggtgt cggggtgcat aaaagcaaga gttttgcca ccggaaccat    4980
ttttcattt ttcgcaacga acatgcccac taaactactt taggtccaaa actcatgttt    5040
ggggtggttt cgcgcaattt cgttgtcgca cgtcacccat tccgaaatcg ggtgtcgggg   5100
tgcataaaag cacgagtttt tgccaccgga acctttctt cgttttcgc aacgaacagt   5160
cccaatacac tactttaggt ccaaaactca tgtttgggt ggtttcgtgc aatttcgtcg    5220
ccgcacgtca cccattccaa aaacgggtgt cggggtgca taaaagcacg agttttgcc    5280
accggaacca tttatttgtt tttcgcaacg aacatgccca atccactact tttggtccaa   5340
aacccatgtt tgggtggtt tcgcgcaatt tcgttgccgc acgtcaccca ttccgaaaac   5400
gggtgtcggg gtgcataaaa gcacgagttt ttgccaccag aaccatttct tcgttttcg   5460
caacgaacat gcccaataca ctactttagg tccaaaactc atgtgttggg gtggtttcgc   5520
gcaatttcgt tgccgcacgt cacccattcc gaaaacgggt gtcggggtgc attcaaagca   5580
caagttttg ccaccggaac catttcttcg ttttcgcaa caaacatgcc gactaaacta    5640
```

-continued

```
ctttaggtcc aaaactcaag ttttgggtgg tttcgcgcaa tttcgttgcc gcacgtcacc    5700
cattccgaaa acgggtgtcg gggtgcataa caacacgagt ttttgccacc ggaaccattt    5760
cttcattttt cgcaacgaac atgcccaatc cactacttta ggtccaaaac tcatgttttgg   5820
ggtggtttcg cgcaatttcg ttgctgcacg tcacccattc cgaaaacggg tgtcgggtgc    5880
atacaatgca cgagttttg ccaccgaaac catttctttg tttttcgcaa cgaacatgac    5940
caatccacta ctttaggtcc aaaactcatg ttttgtatgg tttcgcgcaa tttcgttgcc    6000
gcacgtcacc cataccgaaa acgggtgtcg gggtgcataa aagcaagagt ttttgccacc    6060
ggaaccattt ttcattttt cgcaacgaaca tgcccaatct actactttag gtccaaaact    6120
catgtttggg gtggtttcgc gcaatttcgt tgccgcacgt cacccattcc gaaaacgggt    6180
gtcggggtgc atacaatgca cgagttttg ccaccgaaac catttctttg tttttcgcaa    6240
cgaacatgcc caatccacta ctttaggtcc aaaactcatg ttttttagtgg tttcgcgcaa   6300
tttcgttgcc gcatgtcacc cattccgaaa acgggtgtcg gggtgcataa aagcacgagt    6360
ttttgccacc ggaaccattt cttcgttttt cgcaacgaac acgcccaata cactactata    6420
ggtccaaaac tcattttttt gggtggtttc gcgcaatttc gttgccgcac gtcaaccatt    6480
ccgaaacgg tgtcaaggg tgcataaaag cacgagtttt tgccaccaga accatttctt     6540
tttttcgcaa cgaacatgct caatccacta cttaaggtcc aactcatgtt tggggtggtt    6600
tcgcgcaatt tcgttgcagc acgtcaccca ttccgacaac aggtgtcggg ggtgcataca    6660
atgcacgagt ttttgccatc ggaaccattt cttcgttttt cgcaatgaac atgcccaatc    6720
cactactta ggtccaaaac acatgttttg ggtggtttcg cgcaatttcg ttgccacatg    6780
tcacccattc cgaaatgggt gtcggggtgc ataaaagcac gagttttgc caccggaacc    6840
atttcatcat ttttcgcaac gaacatgccc aatacactac tttaggtcta aaactcatgt    6900
ttggggtggt ttcgcacaat ttcgttgtcg cacgtcaccc atttcgaaaa cgggtgtcgg    6960
ggtgcataaa agcacgagtt tttgccaccg gaaccatttc ttcgtttttc gcaacgaaca   7020
tgcccaatcc actactttag gtccaaaacc catgtttggg gtggtttcgc gcaatttcgt    7080
tgccgcacgt cacccattct aaaaacggtt gtcggggtgc ataaaagcac gagtttctgc    7140
caccggaacc atttcttcat ttttcgcaac gaacatgccc aatccactac tttaggtcca    7200
aaactcatgt tttgggtggt ttcacgcaat ttcgttgccg cacgtcaccc attccgaaaa    7260
cgggtgtcgg ggtgcataaa agcacgagtt tttgccaccg gaatcatttc ttcgtttttc    7320
acaacgaaca tgcccaatcc actactttag gtccaaaacc catgtttggg gtggtttcgc    7380
acaatttcgt tgccgcacgt cacccattcc gaaaacgggt gtcggggtgc ataaaagcac    7440
gagttttgc caccggaacc atctcttcat ttttcgcaac gaacatgccc aatccactac    7500
tttaggtcca aaactcatgt ttgggttggt ttcgcgcaat ttcgtcgccg cacgtcaccc    7560
attccgaaaa cgggtgtcgg ggtgcataca atgcacgagt ttttgccacc gaaaccattt    7620
ctttgttttt cgcaacgaac atgcccaatc cactacttta ggtccaaaac tcatgttttg    7680
ggtggtttcg cgcaatttcg ttgccgcacg tcacccattc caaaaacggg tgttggggtg    7740
cataaatgca cgagttttg ccaccggaac catttcttcg tttttcgcaa cgaacatgcc    7800
caatacacta ctttaggtcc aaaactcatg tttggggtgg ttatcgcaat ttcgtcgccg    7860
cacgtcaccc attccgaaaa cgggtgtcgg ggtgcataaa agcacgagtt tttgccaccg    7920
gaaccatttc ttcgttttttc gcaacgaaca tgcccaatcc actactttag gtccaaaact    7980
catgtttggg gtggtttcgc gcaatttcgt tgcagcacgt cacccattcc gaaaacgggt    8040
```

```
gtcggggtac atacaatgca cgagtttttg ccaccggaac cgtttcttcg ttttttcgcaa    8100
tgaacatgcg caatccacta ctttaggtcc aaaacacatg ttttgagtgg tttcgcgcaa    8160
tttcgttgcc gcacgtcacc cattccgaaa acgggtgtcg gggtgcataa aagcacaagt    8220
ttttgccacc ggaaccattt cttcgttttt tgcaacgaac atgcccaata cactacttta    8280
tgtccaaaac tcatgtttgg agtggtttct cgcaatttcg ttgccgcacg tcaaccattc    8340
cgaaaacggg tgtcggggt gcataaaagc acgagttttt gccaccagaa ccatttcttc    8400
tttttcgcaa cgaacatgcc caatccacta cttaaggtcc aaaactcatg tttggggtgg    8460
tttcgcgcaa tttcgttgcc ccacgtcacc cattccgaaa acgggtgtcg gggtgcatac    8520
aatgcacgag ttttttgccac gggaaccatt tcttcgtttt tcgcaacgaa catgcccaat    8580
ccactacttt aggtccaaaa catatgtttt gggtggtttc gcgcaatttc gttgccgcac    8640
gtcacccatt ccgaaaatgg gtgtcggggt gcattcaaag cacaagtttt tgccaccgga    8700
accatttctt cgttttttcgc aacgaacatg cccaatccac tacttaaagt ccaaaactca    8760
tgtttttgggt ggttttgcgc aatttcgttg tcgcacgtca accattccga aaacgggtgt    8820
cgggggtgca taaaagcacg agttttttgcc accagaacca tttcttcttt tttcgcaacg    8880
aaaatgccca atccactact taaagtccaa aactcatgtt tggggtggtt tcgcgcaatt    8940
tcgttgcagc acgtcaccca ttccgaaaac gggtgtcggg gtgcatacaa tgcacgagtt    9000
tttgccaccg gaaccatttc ttcgtttttc gcaacgaaca tgcccaatcc actactttag    9060
gtccaaaaca catgttttgg gtggtttcgc gcaatttctt tgccgcacgt cacccattcc    9120
gaaaacgggt gtcagggtgc gtaaaagcac gagttttttgc caccggaacc atttcttcgt    9180
ttttcgcaac gaacatgccc aatacactac tttaggtcta aaactcatgt ttggtggtt    9240
tcgcgcaatt tcgttgccgc acgtcaccca tttcgaaaac aggtgtcggg gtgcataaaa    9300
gcacgagttt ttgccaccag aaccatttct tcgttttttcg caacgaacat gcccaatcca    9360
ctactttagg tccaaaaccc atgtttgggg tggtttcgtg taatttcgtt gccgcacgtc    9420
acccattcta aaaacgggtg tcggggtgca taaaagcacg agttttttgcc accggaatca    9480
tttcttcgtt tttcgcaacg aacatgccca atccactact ttaggtccaa aacccatgtt    9540
tggggtggtt tcgcgcaatt tcgttgccgc atgtcaccca ttccaaaaac gggtgtcggg    9600
gtgcatataa gcacgagttt ttgccaccgg aaccatttct tcattttttcg caacgaacat    9660
gcccaatcca ctactttagg tccaaaactc atgtttgggg tggtttcgcg caatttcgtt    9720
gccgcacgtc acccattccg aaaacgggtg tggggtgcat acaatgcacg agttttttgcc    9780
accggaacca tttcttcgtt tttcgcaacg aacatgccca atccactact ttaggtccaa    9840
aacacatgtt ttgggtggtt tcgcgcaatt tcgttgccgc acgtcaccca ttccaaaaac    9900
gggtgtccgg gtgcatattg ggtggtttcg cgcaatttcg ttgccgcacg tcacccattc    9960
caaaaacggg tgtccgggtg cataaaagca cgagttttttg ccaccggaac catttcttcg   10020
ttttttcgcaa cgaacatgcc caatacacta ctttaggtcc aaaactcatg tttggggtgg   10080
tttcgcgcaa tttcgtcgcc gcacgtcacc cattccgaaa acgggtgttg gggtgcataa   10140
aagcacgagt ttttgccacc ggaacgattt cttcgttttt cgcaacgaac atgcccaatc   10200
cactactttta ggtccaaaac ccatgtttgg ggtggtttcg cgcaatttcg ttgccgcacg   10260
tcacccattc cgaaaacggg tgtcgggtgc ataaaaggac gagttttttgc caccagaacc   10320
attacttctt ttttcgcaac gaacatgccc gatccactac tttaggtcca aaactcatgt   10380
ttggggtggt ttcgcgcaat ttcgttgccg cacgtcaccc attccgaaaa acgggtgtcg   10440
```

```
gggtgcataa aagcatgagt ttttgccacc agaaccattt cttcgttttt cgcaacgaac    10500
atgcccaata cactacttta ggtccaaaac tcatgtttgg ggtgggttcg cgcaatttcg    10560
ttgccgcacg tcacccattt cgaaaacggg tgtcggggtg cataaaagca cgagttttg     10620 ccaccggaac catttcttca ttttcgcaa cgaacatgcc caatcccta cttcaggtcc     10680 aaaactcatg tttggggtgg ttttgcgcaa tttcgttgcc gcacgtcacc catttcgaaa    10740
acgggtgttg ggtgcataca atgcacgagt ttttgccacc ggaacacgaa tcaagcttaa    10800
tctcggacac tca                                                       10813

<210> SEQ ID NO 52
<211> LENGTH: 864
<212> TYPE: DNA
<213> ORGANISM: Zea mays

<400> SEQUENCE: 52
acgaatcgaa gattcatcgc cactgtgctg gaagcatcag actccggcat cgcaaactgc      60
acccggtgcc gggcagccac atccagcgca aaaaccttcg tgtagacttc cgttgaactg     120
atggacttat gtcccatcag gctttgcaga actttcagcg gtataccggc atacagcatg     180
tgcatcgcat aggaatggcg gaacgtatgt ggtgtgaccg gaacagagaa cgtcacaccg     240
tcagcagcag cggcggcaac cgcctcccca atccaggtcc tgaccgttct gtccgtcact     300
tcccagatcc gcgctttctc tgtccttcct gtgcgacggt tacgccgctc catgagctta     360
tcgcgaataa atacctgtga cggaagatca cttcgcagaa taaataaatc ctggtgtccc     420
tgttgatacc gggaagccct gggccaactt ttggcgaaaa tgagacgttg atcggcactc     480
cgcttattat cacttattca ggcgtagcaa ccaagcgttt aagggcacca ataactgcct     540
taaaaaaatt acgcccgcc ctgccactca tcgcagtact gttgtaattc attaagcatt     600
ctgccgacat ggaagccatc acaaacgaaa tgatgaacct gaatcgccag cggcatcagc     660
acccttgtcg ccttggcgta atatatttgc ccctggtgaa aaacgggggg gaacaagttg     720
gccattttgg gccacgtttt aatccaaacc tgggtgaaac tcccccccagg tattggctga    780 aaaacaaaaa acctaattct ccaataaacc ccttaaggga aatagggcc cggttttca     840 ccgtaacacc accccacctt ttgt                                            864

<210> SEQ ID NO 53
<211> LENGTH: 835
<212> TYPE: DNA
<213> ORGANISM: Zea mays

<400> SEQUENCE: 53
acttctgaag ataatcagct tgattcgctg aagctccaat gtgctggaaa ggttttgaaa      60
tccatgtttt gtagctgtat tgttccttaa ggcaataatt ctatcctcca cgtaatttgt     120
aacctgcaca cgaatttaat acccgacttt gggtttctga tttcaccaca aaccgagtca     180
acatcgtttc cttatttttc tccttcggtt acgtcaaaaa aaaacagaaa aaacaaaccg     240
agtcaacggc cgtttccttg attttctcct tcggttacga aaaaaaaaca gcaaaaaaaa     300
acaaaccgag tcaaccttcc ttgttttttct ccttcggtta cgtcaaaaaa acagaaaaaa    360
aagataacga aggagaaagg atacggttgt ttcatcccgg tcgttttttag aacataacttt    420 gaggtacctt ccgtaaaccg ggcataactt ttcgctcggg tgtccaaaaa atctgaaatt     480
tttataggag ctagttgaca ccattctgag gccggccaaa ctcacctacg gtctgtttgg     540
ggttcgacaa aattgtcaaa aaaattcagg aaaataaaga aaaaaatccg tcaaagttct     600
```

```
cgcacgcttt tcagagaact tcctgatttt ctgtagacca catctgatat ctgttttagg    660
tgaaacttcg tgtagctcct atcttgttgc ttccttgtgct gagaaaaata tcaaaagaat   720
catacaaaaa agcaaaacaa aatcacctgt gatttctact agtggctttt ttgcatcact    780
agtacaatat ttacggtact ggccttcctg ctagtttcca tcctcccttt gcacc         835
```

```
<210> SEQ ID NO 54
<211> LENGTH: 903
<212> TYPE: DNA
<213> ORGANISM: Zea mays

<400> SEQUENCE: 54
cgattctaga tatcatcgcc actcgtgctg gaaaggacca gacaaacaca gaaaaattcc    60
agacatattc ctacttattc agtacagtcc ctgaactaaa cccccactat agctctatca    120
ctgttcagtc gccagaatgt cttcgtcaaa acagcctcac caggaggacc atcccgattc    180
ggagcctgaa atgctcgcgg aggatgatgc tcttgaggag attgacgctt ccgaggacgt    240
cgacgttccc atggacagcg acgatgaggg ggagcccgaa gagatcaacc tgcacaacga    300
cggcgtcgcc tactttgacc tacacaagga ctcggttttc gccattgccc aacatccaac    360
ccgcccgaca ctgatcgcaa cgggtggatc agaaggagac tcggacgacg cgccaggcaa    420
gggctacgtc tttgacaccg cacacgttcc ccagcgccct ctattaccac caaactttag    480
cggcgaacct ccgaaccccc cggtagcgct ggaccgtctg tttgagattg atgggcatac    540
cgacagcatc aatgctttga cgttcaccta ccccgaggga gagtatctct tgagcggagg    600
tatggacggc aagcttcgcg cgtacgccgg caaggcggca ccatttcaac cgggagccgc    660
ccatgtcacc agtcgcacaa atccccccttc cttgccgagt cccaggaagt cccccaaatc    720
aacttcctat cttcccttgc cccattgctc catcgtcctc ccttgtcctt agaccttggc    780
tggcatcctg accggctccg tctggtgtgt acccatggaa gaacgcaggc tccccaatcc    840
cggcgctggt ctaatcccga aagacatttt ccttcttccc taatatgggc cccggaccca    900
cta                                                                  903
```

```
<210> SEQ ID NO 55
<211> LENGTH: 1110
<212> TYPE: DNA
<213> ORGANISM: Zea mays

<400> SEQUENCE: 55
ctccggaatg attcaagctt ggattcgctg aagctccaat gtgctggaaa gatgttcgtt    60
gagaaaaacg aagaaatggt tcctgtggca aaaactcgtg ctttgtatgc accatgacac    120
ccgttttcag aatgggtgac gtgcgacaac gaaattgtgc gaaaccaccc caaacatgag    180
ttttggacct aaagtagtgg attgggcatg ttcgttgcga aaaacgaaga aatggttccg    240
gtggcaaaaa ttcgtgcttt gtatgcacca tgacacccgt tttcggaatg ggtgacgtgc    300
gacaacgaaa ttgtgcgaaa cgacctaaag tagtggattg ggcatgtttg ttacgaaaaa    360
cgaagaaatg gttccggtgg caaaaactcg tgcttttatg caccccgata cccgttttca    420
gaataggtga cgtgtgacaa cgaaattgcg cgaaaccacc tcaaacatga gttttggacc    480
taaagtagtg gattgggcat gttcgttgcg aaaaacgaag aaatggttcc ggtgcaaaac    540
actcgtgctt ttatgcaccc gacactcgtt ttcagaatga gtgacgtgcg caacgaaat    600 tgcgtgaaac cacccaaaac atgagttttt acctaaagt agtggattgg gcatgttcgt    660
tgagaaaaac gaagaaatgg ttccagtggc aaaaactcgt gctttgtatg cacccgacac    720
```

| | |
|---|---|
| ccgttttcgg aatgggtgac gtgcgacaac gaaattgtgc gaaaccaccc caaacatgag | 780 |
| ttttggacct aaagtagtgg attgggcatg tttgttacga aaaacgaaga aatggttccg | 840 |
| gtggcaaaaa ctcgtgcttt tatgcacccc gatacccgtt ttcagaatgg gtgacgtgcg | 900 |
| acaacgaaat tgcgcgaaac cacctcaaat atgagttttg gacctaaagt agtggattgg | 960 |
| gcatgttcgt tgcgaaaaac gaagaaatgg ttccggtggc aaacactcgt gcttttatgc | 1020 |
| acccgacact cgttttcgga atgagtgacg tgcggcaacg ctttccagca cattggagct | 1080 |
| tcagcgaatc aagcttgata ccattctgta | 1110 |

<210> SEQ ID NO 56
<211> LENGTH: 586
<212> TYPE: DNA
<213> ORGANISM: Zea mays

<400> SEQUENCE: 56

| | |
|---|---|
| ggcctttta cggttcctgg ccttttgctg gccttttgct cacatgttct ttcctgcgtt | 60 |
| atccctgat tctgtggata accgtattac cgcctttgag tgagctgata ccgctcgccg | 120 |
| cagccgaacg accgagcgca gcgagtcagt gagcgaggaa gcggaagagc gcccaatacg | 180 |
| caaaccgcct ctccccgcgc gttggccgat tcattaatgc agctggcacg acaggtttcc | 240 |
| cgactggaaa gcgggcagtg agcgcaacgc aattaatgtg agttagctca ctcattaggc | 300 |
| accccaggct ttacactta tgctcccggc tcgtatgttg tgtggaattg tgagcggata | 360 |
| acaatttcac acaggaaaca gctatgacca tgattacgcc aagcgcgcaa ttaaccctca | 420 |
| ctaaagggaa caaaagctgg gtaccgggcc cccctcgag gtcgacggta tcgataagct | 480 |
| tgatagagtg aagttgtcgc atgtatcaag tgatccagaa tcgtactgca actttacttt | 540 |
| taatggagct atcagcgaat cagagctgat tctcagtagt acaaaa | 586 |

<210> SEQ ID NO 57
<211> LENGTH: 857
<212> TYPE: DNA
<213> ORGANISM: Zea mays
<220> FEATURE:
<221> NAME/KEY: misc_feature
<222> LOCATION: (827)..(827)
<223> OTHER INFORMATION: n is a, c, g, or t
<220> FEATURE:
<221> NAME/KEY: misc_feature
<222> LOCATION: (847)..(847)
<223> OTHER INFORMATION: n is a, c, g, or t

<400> SEQUENCE: 57

| | |
|---|---|
| agaaaaataa gcacaagttt tatccggcct ttattcacat tcttgcccgc ttgatgaatg | 60 |
| ctcatccgga attacgtatg gcatgaaaag acggtgagtc ggtgatatgg gatagtgttc | 120 |
| acccttgtta caccgttttc catgagcaaa ctgaaacgtt ttcatcgctc tggagtgaat | 180 |
| accacgacga tttccggcag tttctacaca tatattcgca agatgtggcg tgttacggtg | 240 |
| aaaacctggc ctatttccct aaagggttta ttgagaatat gttttcgtc tcagccaatc | 300 |
| cctgggtgag tttcaccagt tttgatttaa acgtggccaa tatggacaac ttcttcgccc | 360 |
| ccgttttcac catgggcaaa tattatacgc aaggcgacaa ggtgctgatg ccgctggcga | 420 |
| ttcaggttca tcatgccgtt tgtgatggct tccatgtcgg cagaatgctt aatgaattac | 480 |
| aacagtactg cgatgagtgg cagggcgggg cgtaattttt ttaaggcagt tattggtgcc | 540 |
| cttaaacgcc tggttgctac gcctgaataa gtgataataa gcggatgaat ggcagaaatt | 600 |
| cgaaagcaaa ttcgacccgg tcgtcggttc agggcagggt cgttaaatag ccgcttatgt | 660 |

| | | |
|---|---|---|
| ctattgctgg tttaccggtt tattgactac cggaagcagt gtgaccgtgt gcttctcaaa | 720 | |
| tgcctgaggc cagtttgctc aggctctccc cgtggaggta ataattgacg atatgatcct | 780 | |
| tttttctga tcaaaaagga tctaggtgaa gatccttttt gcttccnagc acagtggcga | 840 | |
| tgatatncta gaattcg | 857 | |

<210> SEQ ID NO 58
<211> LENGTH: 119
<212> TYPE: DNA
<213> ORGANISM: Zea mays

<400> SEQUENCE: 58

| | |
|---|---|
| agctccaatg tgctggaaag gcaacggtgc acttggcgga aaggccttgg gtgcttgctg | 60 |
| gcggattgca gtgtcgtttt gcgtggggat aaatcctttc cagcacagtg gcgatgata | 119 |

<210> SEQ ID NO 59
<211> LENGTH: 1510
<212> TYPE: DNA
<213> ORGANISM: Zea mays
<220> FEATURE:
<221> NAME/KEY: misc_feature
<222> LOCATION: (1491)..(1491)
<223> OTHER INFORMATION: n is a, c, g, or t

<400> SEQUENCE: 59

| | |
|---|---|
| ggaagattgg gcatgtcctt gcgaaaaacg aagaaatggt tccggtggca aaaactcgtg | 60 |
| ctttgtatgc acccgacacc cgttttcgga atgggtgacg tgcgacaacg aaattgtgcg | 120 |
| aaaccacccc aaacatgagt tttggaccta agtagtggga ttcggcatgt tcgttacgaa | 180 |
| aaacgaagaa atggttccgg tggcaaaaac tcgtgctttt atgcaccccg atacacgttt | 240 |
| tcagaatggg tgacgtgcga caacaaaatt gcgcgaaacc accccaaaca tgagttttgg | 300 |
| acctaaagta gtggattggg catgtccttg cgaaaaacga gaaatggtt ccggtggcaa | 360 |
| aaactcgtgc tttgtatgca cccgacaccc gttttcggaa tgggtgacgt gcgacaacga | 420 |
| aattgtgcga aaccacccca aacatgagtt ttggacctaa agtagtggat tcggcatgtt | 480 |
| cgttacgaaa acgaagaaa tggttccggt ggcaaaaact cgtgctttta tgcacccga | 540 |
| tacacgtttt cagaatgggt gacgtgcgac aacaaaattg cgcgaaacca ccccaaacat | 600 |
| gagttttgga cctaaagtag tggaattggg catgtccttg cgaaaaacga gaaatggtt | 660 |
| ccggtggcaa aaactcgtgc tttgtatgca cccgacaccc gttttcggaa tgggtgacgt | 720 |
| gcgacaacga aattgcgaga accacccca aacatgagtt ttggacctaa agtactggat | 780 |
| taggcatgtt cgttgcgaaa acgaagaaa tggttccggt ggcaaaaact cgtgctttgt | 840 |
| atgcacccga taccgttttt cggaatgggt gacgtgcgac aactaaattg tgtgaaacca | 900 |
| ccccaaacat gagttttgga cctaaagtag tggattgggc atgttcgtta cgaaaaacga | 960 |
| agaaatggtt ccggtggcaa aaactcgtgc tttgtatgca accccacact cgttttcgga | 1020 |
| atgagtgacg tgcggcaacg aaattgcgca aaaccaccca aaacatgagt tttgtaccta | 1080 |
| aagtagtgga ttgggcatgt tcgttgagaa aaacgaagaa atggttcctg tggcaaaaac | 1140 |
| tcgtgctttg tatgcaaccc cacacccgtt ttcagaatgg gtgacgtgcg gcaacgaaat | 1200 |
| tgcgcgaaac caccccaaaac atgagttttg gacctaaagt agtggattgg catgttcgtt | 1260 |
| gcgaaaaaca agaaatagt tccggtggca aaaactcgtg ctttgtatgc accatgacac | 1320 |
| ccgttttcag aatgggtgac gtgcgacaac gaaattgtgc gaaaccaccc caaacatgag | 1380 |
| ttttggaccct aaagtagtgg attgggcatg ttcgttgcga aaaacgaaga atggttccg | 1440 |

| | | |
|---|---|---|
| gtggcaaaaa ctcgtgcttt ctttccagca cattggagct tcagcgaatc naagctgata | 1500 |
| catacaggga | 1510 |

<210> SEQ ID NO 60
<211> LENGTH: 1785
<212> TYPE: DNA
<213> ORGANISM: Zea mays

<400> SEQUENCE: 60

| | |
|---|---|
| gggttttggg gccgaggatc agcgagctga ttcgtcgcca ctgtgctgga aaggtcatct | 60 |
| aaattgaaac cgccctttta tgttatttga attccagtca tgttcttttt tccccttcg | 120 |
| ttttacaagc cttcatttgt tcagcatatt cattaattta tgatggatag aacttagaag | 180 |
| tagtagcagt aacaagtacg caaataataa acatgtatga caataagtga atgtgttaac | 240 |
| tatatactga ccattatgaa tgtgacataa gaaatagaga aatttcaaag actccatccc | 300 |
| atcatgaatt catggtttac ttacattaaa caagaatagt atacatttgt atagtggtaa | 360 |
| cagaaaaata tggcacagag cagcaattct gctcaagtcc ctagtgttac attataacaa | 420 |
| agaatattca cgttatgcga gtccatttca gctgataaga acaacaagaa gaattcctag | 480 |
| tcaggaactt actcgtggca atagcaattg gtgcagttgt tggccaatgt tccttccatc | 540 |
| ggactagctt agcacttgac agttcaaagc tgcaacactc actcgtccaa cctttcccag | 600 |
| cacattggag cttcagctgc tcgagggggg ggcccggtac ccaattcgcc ctatagtgag | 660 |
| tcgtattacg cgcgctcact ggccgtcgtt ttacaacgtc gtgactggga aaaccctggc | 720 |
| gttacccaac ttaatcgcct tgcagcacat ccccctttcg ccagctggcg taatagcgaa | 780 |
| gaggcccgca ccgatcgccc ttcccaacag ttgcgcagcc tgaatggcga atgggacgcg | 840 |
| ccctgtagcg gcgcattaag cgcggcgggt gtggtggtta cgcgcagcgt gaccgctaca | 900 |
| cttgccagcg ccctagcgcc cgctcctttc gctttcttcc cttcctttct cgccacgttc | 960 |
| gccggctttc cccgtcaagc tctaaatcgg gggctcccct tagggttccg atttagtgct | 1020 |
| ttacggcacc tcgaccccaa aaaacttgat tagggtgatg gttcacgtag tgggccatcg | 1080 |
| ccctgataga cggtttttcg ccctttgacg ttggagtcca cgttctttaa tagtggactc | 1140 |
| ttgttccaaa ctggaacaac actcaaccct atctcggtct attcttttga tttataaggg | 1200 |
| attttgccga tttcggccta ttggttaaaa aatgagctga tttaacaaaa atttaacgcg | 1260 |
| aattttaaca aaatattaac gcttacaatt taggtggcac ttttcgggga aatgtgcgcg | 1320 |
| gaacccctat ttgtttattt ttctaaatac attcaaatat gtatccgctc atgagacaat | 1380 |
| aaccctgata aatgcttcaa taatattgaa aaaggaagag tatgagtatt caacatttcc | 1440 |
| gtgtcgccct tattcccttt tttgcggcat tttgccttcc tgtttttgct cacccagaaa | 1500 |
| cgctggtgaa agtaaaagat gctgaagatc agttgggtgc acgagtgggt tacatcgaac | 1560 |
| tggatctcaa cagcggtaag atccttgaga gttttcgccc cgaagaacgt tttccaattg | 1620 |
| atgagcactt tttcgaccga taaatacct gtgacgggaa gatcacttcg caaaaataaa | 1680 |
| taaaatcctg ggtgtccctg ttgataccgg gaaagccctg ggccaactt ttggcgaaaa | 1740 |
| tgaaaacgtt gatccggcac gtaagtttct tccccctttc ctcta | 1785 |

<210> SEQ ID NO 61
<211> LENGTH: 867
<212> TYPE: DNA
<213> ORGANISM: Zea mays

<400> SEQUENCE: 61

```
gtaggcagga cttttcaagt cttgggaagg gttttttcaa tttgcatttc gcttcgaatt      60
agatattaac aagttgtttg ggtgttcgaa tttcaacagg taaagttagt tgctagaacc     120
catggctcct ttgccgacgc tgagtagatt ttaggtgacg ggtggtgaca atgagtccgt     180
gtcgagcgct gattttttcg gcctttagag cgagatttat acaatagaat ttggcatgag     240
attggattgc ttttagtcag cctcttatag cctaaagtct ttgagtgact agatgacata     300
tcatgtaagt tgctgatagg tttccagttt tccgctccta ggtctgcata ttgtactttt     360
cctcttactc gacttaacca gtaccaaccc agcttctcaa cggatttata ccatggcact     420
ttaaagccag catcactgac aatgagcggt gtggtgttac tcggtagaat gctcgcaagg     480
tcggctagaa attggtcatg agctttcttt gaacattgct ctgaaagcgg gaacgctttc     540
tcataaagag taacagaacg accgtgtagt gcgactgaag ctcgcaatac cataagtcgt     600
ttttgctcac gaatatcaga ccagtcaaca agtacaatgg gcatcgtatt gcccgaacag     660
ataaagctag catgccaacg gtatacagcg agtcgctctt tgtggaggtg acgattacct     720
aacaatcggt cgattcgttt gatgttatgt tttgttctcg ctttggttgg caggttacgg     780
ccaagttcgg taagagtgag agttttacag tcaagtaatg cgtggcaagc cctttccagc     840
acagtggcga tgatatctag attcgcg                                         867
```

`<210>` SEQ ID NO 62
`<211>` LENGTH: 3369
`<212>` TYPE: DNA
`<213>` ORGANISM: Zea mays
`<220>` FEATURE:
`<221>` NAME/KEY: misc_feature
`<222>` LOCATION: (3353)..(3354)
`<223>` OTHER INFORMATION: n is a, c, g, or t

`<400>` SEQUENCE: 62

```
cttcagaatg aatcaaagct tgattcgctg aagctccaat gtgctggaaa gatgcacccg      60
acacccgttt tcggaatggg tgacgtgcga caacaaaatt gcgcgaaacc accccaaaca     120
tgagttttgg acctaaagta gtggattggg catgttcatt gcgaaaaacg aagaaatggt     180
tccggtggca aaaactcgag ctctgtatgc acccgacacc cgttttcgga atgggtgacg     240
tgcgacaacg aaattgcgtg aaaccacccc aaacatgagt tttggaccta agtagtgga     300 ttgggcatgt tcgttgcgaa aaacgaagaa atggttccgg tggcaaaaac tcgtgctttg     360
tatgcacccg acacccgttt tcggaatggg tgacgtgcga caacgaaatt gcgagaaacc     420
acctcaaaca tgagtttgga cctaaagtag tggattgggc atgttcgtta cgaaaaacga     480
agaaatggtt ccggtggcaa aaactcgtgc tttgtatgca cccgacaccc gttttcggaa     540
tgggtgacgt gcgacaacga aattgtgcga accacccca aacatgagtt ttggacctaa     600
agtagtggat tgggcatgtt tgttgcgaaa acaaagaaa tggttccggt ggcaaaaact     660
cgtgctttgt atgcaccatg acacccgttt tcggaatggg taacgtgcga caacaaaatt     720
gcgagaaacc accccaaaca tgagttttgg acctaaagta gtggattagg catgttcgtt     780
gcgaaaaacg aagaaatggt tccggtggca aaaactcgtg ctttgtatgc actccgacac     840
ccgttttcgg aatgggtgac gcgtgacaac aaaattgcgc gaaaccaccc caaacatgag     900
ttttgaacct aaagaagtgg attgggcatg ttccgttaca aaaacgaag aaatggtttc     960 cggtggcaaa aactcgtgct tttgtatgcc accccgacac ccgttttcg aaatgggtgg    1020 acttgcgaca accaaatttc gagaaatccc cccaacatg agtttggac taaagtagt     1080 ggattgagca tgttcgttgc gaaaaacgaa gaaatggttc cggtggcaaa aactcgtgct    1140
```

```
ttttattcac ccgacacccg ttttcggaat gggtgacgtg cgacaacgaa attgcgcgaa    1200
accaccccaa acatgagttt tggatgtaaa gtagtggatt gggcatgttc gttgcgaaaa    1260
acgaagaaat ggttccggtg gcaaaaactc gtgctttgta tgcacccgac accgttttc     1320
ggaatgggtg acgtgcgaca acgaaattgt gcgaaaccac cccaaacatg agttttggac    1380
ctaaagtagt ggattcggca tgttcgttac gaaaaacgaa gaaatggttc cggtggcaaa    1440
aactcgtgct tttatgcacc cgacacccgt tttcagaatg ggtgacgtgc gacaacaaaa    1500
ttgcgcgaaa ccaccccaaa catgagtttt ggacctaaag tagtggattc ggcatgttcg    1560
ttgcgaaaaa cgaagaaatg gttccggtgg caaaaactcg tgctttttat gcaccccgat    1620
acccgttttc agaatgggtg acatgcgaca caaaattgc acgaaaccac cccaaacatg     1680
agttttggac ctaaagtagt ggattgggca tgttcgttgc gaaaaacgaa gaaatggttc    1740
cggtggcaaa aactcgtgct tttatgcacc ccgataccct ttttcagaat gggtgacgtg    1800
cgacaacgaa actgtgcgaa accaccccaa acatgagttt tggacctata gtagtggatt    1860
gggcatgttc gttgtgaaaa acgaagaaat ggttccggtg gcaaaaactc gtgctttgta    1920
tgcacccga caaccgtttt cggaatgggt gacgtgcggc aacgaaattg cgcgaaacca    1980
ccccaaacat gagttttgga cctaaagtag tggattgggc atgttcgttg cgaaaaacga    2040
agaaatggtt ccggtggcaa aaactcgtgc ttttatgcac cccgatacca gttttcagaa     2100
tgggtgacgt gcgacaacga aattgtgcga acctcccca acatgagtt ttggacctaa       2160
agtagtggat tggcatgtt cgttgcgaaa acgaagaaa tggttccggt ggcaaaaact       2220
cgtgctttgt atgcacccccc gacaaccgtt ttcggaatgg gtgacgtgcg gcaacgaaat    2280
tgcgcgaaac cactccaaac atgagttttg gacctaaagt agtggattgg gcatgttcat    2340
tgcgaaaaac gaagaaatgg ttccggtggc aaaaactcgt gctttttatt cacccgacac    2400
ccgtttcgg aatgggtgac gtgcgacaac gaaattgcgc gaaaccaccc caaacatgag     2460
ttttggatgt aaagtagtgg attgggcatg ttcgttgcga aaaacgaaga atgggttccg    2520
gtggcaaaaa ctcgtgcttt gtatgcaccc gacaccgtt ttcggaatgg gtgacgtgcg     2580
acaaagaaat tgcgcgaaaa ccaccccaaa catgagtttt ggatgtaaag tagtggatgg    2640
ggcatgttcg ttgcgaaaaa cgaagaaatg gttccggtgg caaaaactcg tgcttttatg    2700
caccccgata cccgttttca gaatgggtga cgtgcgacaa cgaaattgcg cgaaaccacc    2760
ccaaacatga gttttggacc taaagtagtg gattgggcat gttcgttgcg aaaaacgaag    2820
aaatggttcc ggtggcaaaa actcgtgctt ttatgcaccc cgatacccgt tttcagaatg    2880
ggtgacgtgc gacaacgaaa ctgtgcgaaa ccaccccaaa catgagtttt ggacctaaag    2940
tagtggattg gcatgttcg ttatgaaaaa cgaagaaatg gttccggtgg caaaaactcg     3000
tgctttgtat gcaccccgac aaccgttttc ggaatgggtg acgtgcggca acgaaattgc    3060
gcgaaaccac cccaaacatg agttttggac ctaaagtagt ggattgggca tgttcgttgc    3120
gaaaaacgaa gaaatggttc cggtggcaaa aactcgtgct ttatcacc cgacacccg       3180
ttttcggaat gggtgacgtg cgacaacgaa attgcgcgaa accaccccaa acatgagttt    3240
tggatgtaaa gtagtggatt gggcatgttc gttgcgaaaa acgaagaaat ggttccggtg    3300
gcaaaaactc gtgctttctt tccagcacat tggagcttca gcgaatcaag ctnngatatc    3360
attcggaag                                                            3369
```

<210> SEQ ID NO 63
<211> LENGTH: 5594
<212> TYPE: DNA

<213> ORGANISM: Zea mays

<400> SEQUENCE: 63

```
cgatatctag aatcatcgcc actgtgctgg aaaggagtgt atagagaaaa ttgaggccat      60
tcttaaggaa cttgaaaagc cagcaccctg atgcgaccac gttttagtct acgtttatct     120
gtctttactt aatgtccttt gttacaggcc agaaagcata actggcctga atattctctc     180
tgggcccact gttccacttg tatcgtcggt ctgataatca gactgggacc acggtcccac     240
tcgtatcgtc ggtctgatta ttagtctggg accacggtcc cactcgtatc gtcggtctga     300
ttattagtct gggaccacgg tcccactcgt atcgtcggtc tgataatcag actgggacca     360
cggtcccact cgtatcgtcg gtctgattat tagtctggga ccatggtccc actcgtatcg     420
tcggtctgat tattagtctg gaccacggt cccactcgta tcgtcggtct gattattagt     480
ctggaaccac ggtcccactc gtatcgtcgg tctgattatt agtctgggac cacggtccca     540
ctcgtatcgt cggtctgatt attagtctgg gaccacgatc ccactcgtgt tgtcggtctg     600
attatcggtc tgggaccacg gtcccacttg tattgtcgat cagactatca gcgtgagact     660
acgattccat caatgcctgt caagggcaag tattgacatg tcgtcgtaac ctgtagaacg     720
gattaacctc ggtgtgcggt tgtatgcctg ctgtggattg ctgctgtgtc ctgcttaatc     780
cacaacattt tgcgcacggt ttatgtggac aaaatacctg gttacccagg ccgtgccggc     840
acgttaaccg ggctgcatcc gatgcaagtg tgtcgctgtc gacgagctcg cgagctcgga     900
catgaggttg ccccgtattc agtgtcgctg atttgtattg tctgaagttg tttttacgtt     960
aagttgatgc agatcaatta atacgatacc tgcgtcataa ttgattattt gacgtggttt    1020
gatggcctcc acgcacgttg tgatatgtag atgataatca ttatcacttt acgggtcctt    1080
tccggtgatc cgacaggtta cggggcggcg acctcgcggg ttttcgctat ttatgaaaat    1140
tttccggttt aaggcgtttc cgttcttctt cgtcataact taatgttttt atttaaaata    1200
ccctctgaaa agaaaggaaa cgacaggtgc tgaaagcgag cttttttggcc tctgtcgttt    1260
cctttctctg tttttgtccg tggaatgaac aatggaagtc cgagctcatc gctaataact    1320
tcgtatagca tacattatac gaagttatag cggccgcaca ccgtgttcc taaggacata    1380
ttccgttcgt acttgagtta ttggatctat gaaatcgctc gctatacacc agtcatgatt    1440
ttgtccctgg taatagggt tttggtttta ttaattatat ttttttaatga caacgaagct    1500
tgtgttttca attctgcaat atttgctttt acttctcttg taggtttgtt aataatatta    1560
agtgatggta atccaaagct agtcagtcgt cgaaattta ggaccgagct tttagtggat    1620
gtcatcacac gtaaaccggc ggtagaaggg aaagaatgga ggatcatcac atacaacatg    1680
aaccaatatt tgtttaatca tgggcaatgg catactccgt attacttta cagcgatgag    1740
gattgctacc gttatttct acgccttgtt gagggagtaa cccccaagaa gcaaacagcc    1800
acgtcaattg gcaattctcc ggtcaccgct aagcctgaag atgccatcga gtcagcttct    1860
cctagttcca gactgaatta tcaaaacttt ttgctcaagg cagcggagat cgaacgacaa    1920
ggtcaggaaa attactggtg aaggcggcat cccaatatcg atgcgcttct taaaaagatg    1980
gaatagctta gagacattgc cttacgtaaa gggaacataa actagagtat gatatttaat    2040
cagcactaac tggccggaaa acggccgaag gaagcctcga aaagtcgatt cgtgttggac    2100
ccatttgctg aacaaagtgg ttcattgcct acctattatg gtagtagtcg tgataatcgt    2160
gtggttggtt ttgtcaacgg tgcatttgca ttttcatgac aataaaccct tgcgttttcgt    2220
tctcgggata ttactttccc tccacttctt tcgcctcaat agctcctata agcattctca    2280
```

```
gggcgtatgt cggtgatcga gatttccaag caagctttta gtggaaatca tcgcgcgcaa    2340
gccagcggta aagggaaaag aacggaggac gattacatac aagatgaacg aataaataaa    2400
ttaataataa ataataataa aaagtacagt agcattaaat attattaagt ttaatgatta    2460
aaaattggtt aattgtcaag aaaatctaag gtattaataa ataaataata ctatgacaac    2520
ctgcagcgaa agcatcagcc ccaatgaaaa ttaatcagaa ttgaatctga gcgtatttat    2580
ttgataacgg tttacgtaac tgttggaata aaaatcaact atcatctact aactagtgtt    2640
tacgttacta gtatattatc atatacggtg ttagaagatg acgcaaatga tgagaaatag    2700
tcatcgtttt caacggaagc tgaaatacaa ggattgataa tgtaatagga tcaatgaata    2760
tcaacatata aaacgatgat aataatattt atagaattgt gtagaattgc agattccctt    2820
ttatggattc ctaaatcctc gagaagaact tctagtatat ctacgtacct aatattattg    2880
ccttattaaa aatggaatcc caacaattat ctcaaaattc ccccaattct catcagtaac    2940
accccacccc gtattacttt taccgtgatg aagattggca tcgttacttt ctaaacgtag    3000
gacgtgcgga atgacaaaac catcagcagt gtcacgatct ctccagtcac aatggcaatc    3060
atgagtgcat agtccaaagt aaaggggcaa ggaaaagcat gattgaaagg actccccatc    3120
tggactctat atgtcatcag cggctaaaaa aaagcatata gcacaacatc agcatcagca    3180
tcagcactag agtcatcggc ccggcggtcc gcggtcatcc ccgcggactt tccgtccgcc    3240
cggcgggctg tatcagcgtc aactggaacg cgcatatata tacaagacac acataacata    3300
gaagcacacc cacgacaata accacacgac aataaccaca cccgcccacc cctccttttcc    3360 gtatacaagg cctcggtacc tcttaaaaac tttctctcaa ttctctctac cgtgatcaag    3420
gtaaatttct gtgttcctta ttctctcaaa atcttcgatt ttgttttcgt tcgatcccaa    3480
tttcgtatat gttctttggt ttagattctg ttaatcttag atcgaagacg attttctggg    3540
tttgatcgtt agatatcatc ttaattctcg attagggttt catagatatc atccgatttg    3600
ttcaaataat ttgagttttg tcgaataatt actcttcgat ttgtgatttc tatctagatc    3660
tggtgttagt ttctagtttg tgcgatcgaa tttgtcgatt aatctgagtt tttcttttc    3720 tttttgcagg tagagttaac gctagccttg gtaccatacg taagaaaatg attgaacaag    3780
atggattgca cgcaggttct ccggccgctt gggtggagag gctattcggc tatgactggg    3840
cacaacagac aatcggctgc tctgatgccg ccgtgttccg gctgtcagcg caggggcgcc    3900
cggttctttt tgtcaagacc gacctgtccg gtgccctgaa tgaactccaa gacgaggcag    3960
cgcggctatc gtggctggcc acgacgggcg ttccttgcgc agctgtgctc gacgttgtca    4020
ctgaagcggg aagggactgg ctgctattgg gcgaagtgcc ggggcaggat ctcctgtcat    4080
ctcaccttgc tcctgccgag aaagtatcca tcatggctga tgcaatgcgg cggctgcata    4140
cgcttgatcc ggctacctgc ccattcgacc accaagcgaa acatcgcatc gagcgagcac    4200
gtactcggat ggaagccggt cttgtcgatc aggatgatct ggacgaagag catcaggggc    4260
tcgcgccagc cgaactgttc gccaggctca aggcgcggat gcccgacggc gaggatctcg    4320
tcgtgaccca tggcgatgcc tgcttgccga atatcatggt ggaaaatggc cgcttttctg    4380
gattcatcga ctgtggccgg ctgggtgtgg cggaccgcta tcaggacata gcgttggcta    4440
cccgtgatat tgctgaagag cttggcggcg aatgggctga ccgcttcctc gtgctttacg    4500
gtatcgccgc tcccgattcg cagcgcatcg ccttctatcg ccttcttgac gagttcttct    4560
gagcgggact ctgggtacgt atgtcgacac aattgcagcg cttgagctct cctaggtccg    4620
cggacaaagc tgggtttttt tttttttcaat ttcgattcat ctcaaggttt ttggagtttt    4680
```

```
tgattatgga cttgtgagac tcttagaatt tctgttttat gatttattgg ataactgtga    4740
ttctccaaga acttatgtct tatatgattt tgtcttcatt tcgttgcttc ttatttcttg    4800
cctgtgatgt attgcatctg catagttgga ttgaaagtta ggttcttggg tttataagaa    4860
ggctgtgact tgatgttact tagccatagc tgatcaaata tcgtctaaca aagtggtctg    4920
ttactctgtt atattggttc gcgtaaattt tggttacagt ttgtttccga gttggtatct    4980
cgtaagtcgt aacgtttgtg tacttattca ctggaagcaa gttgtattgt tgttagtctt    5040
ttgttacctc tcctggtacg atttttttg tttgtgaaca agatcagaaa ctgggactgt    5100
gaatttgacc gataaactag tcttaattaa gatttaaatg cgagctcagc ccgggcagcg    5160
atcgcaggcc ggccatcgat ttattcaaca aagccacgtt gtgtctcaaa atctctgatg    5220
ttacattgca caagataaaa atatatcatc atgaacaata aaactgtctg cttacataaa    5280
cagtaataca agggtgtta tgacgatgga ccgcgcttgt gtgtcgcgtt cagtttggct    5340
tttgccaagc agtagggtag cttcccgcgt cggtaattat atggtatgaa ccatcacctt    5400
ttggctctac atggtatgaa cgtaagatac aaattccaac tacctctagc tcgccgcact    5460
agttcctgca ggttggccca cgtggcctct cgagtgttta aactcggacc gtatcgattt    5520
attcaacaaa gccgccgtcc cgtcaagtca gcgtaatgct ctgccagtgt acaaccaat    5580 taaccaaatt ctga                                                     5594

<210> SEQ ID NO 64
<211> LENGTH: 5111
<212> TYPE: DNA
<213> ORGANISM: Zea mays

<400> SEQUENCE: 64
ctccggaaga aattaagctt gaatttcgct gaagctcaat gtgctggaaa gtggaacacg      60
agacctgtcc aggttaagca ccattttatc gcccttatac aatactgtcg ctccaggagc     120
aaactgatgt cgtgagctta aactagttct tgatgcagat gacgttttaa gcacagaagt     180
taaaagagtg ataacttctt cagcttcaaa tatcacccca gcttttttct gctcatgaag     240
gttagatgcc tgctgcttaa gtaattcctc tttatctgta aaggcttttt gaagtgcatc     300
acctgaccgg gcagatagtt caccggggtg agaaaaaaga gcaacaactg atttaggcaa     360
tttggcggtg ttgatacagc gggtaataat cttacgtgaa atattttccg catcagccag     420
cgcagaaata tttccagcaa attcattctg caatcggctt gcataacgct gaccacgttc     480
ataagcactt gttgggcgat aatcgttacc caatctggat aatgcagcca tctgctcatc     540
atccagctcg ccaaccagaa cacgataatc actttcggta agtgcagcag ctttacgacg     600
gcgactccca tcggcaattt ctatgacacc agatactctt cgaccgaacg ccggtgtctg     660
ttgaccagtc agtagaaaag aagggatgag atcatccagt gcgtcctcag taagcagctc     720
ctggtcacgt tcattacctg accatacccg agaggtcttc tcaacactat cacccggag      780 cacttcaaga gtaaacttca catcccgacc acatacaggc aaagtaatgg cattaccgcg     840
agccattact cctacgcgcg caattaacga atccaccatc gggcagctg gtgtcgataa     900 cgaagtatct tcaaccggtt gagtattgag cgtatgtttt ggaataacag gcgcacgctt     960
cattatctaa tctcccagcg tggtttaatc agacgatcga aatttcatt gcagacaggt    1020 tcccaaatag aaagagcatt tctccaggca ccagttgaag agcgttgatc aatggcctgt    1080
tcaaaaacag ttctcatccg gatctgacct ttaccaactt catccgtttc acgtacaaca    1140 tttttttagaa ccatgcttcc ccaggcatcc cgaatttgct cctccatcca cggggactga    1200
```

```
gagccattac tattgctgta tttggtaagc aaaatacgta catcaggctc gaacccttta    1260
agatcaacgt tcttgagcag atcacgaagc atatcgaaaa actgcagtgc ggaggtgtag    1320
tcaaacaact cagcaggcgt gggaacaatc agcacatcag cagcacatac gacattaatc    1380
gtgccgatac ccaggttagg cgcgctgtca ataactatga catcatagtc atgagcaaca    1440
gtttcaatgg ccagtcggag catcaggtgt ggatcggtgg gcagtttacc ttcatcaaat    1500
ttgcccatta actcagtttc aatacggtgc agagccagac aggaaggaat aatgtcaagc    1560
cccggccagc aagtgggctt tattgcataa gtgacatcgt ccttttcccc aagatagaaa    1620
ggcaggagag tgtcttctgc atgaatatga agatctggta cccatccgtg atacattgag    1680
gctgttccct gggggtcgtt accttccacg agcaaaacac gtagccccctt cagagccaga    1740 tcctgagcaa gatgaacaga aactgaggtt ttgtaaacgc cacctttatg ggcagcaacc    1800
ccgatcaccg gtggaaatac gtcttcagca cgtcgcaatc gcgtaccaaa cacatcacgc    1860
atatgattaa tttgttcaat tgtataacca acacgttgct caacccgtcc tcgaatttcc    1920
atatccgggt gcggtagtcg ccctgctttc tcggcatctc tgatagcctg agaagaaacc    1980
ccaactaaat ccgctgcttc acctattctc cagcgccggg ttattttcct cgcttccggg    2040
ctgtcatcat taaactgtgc aatggcgata gccttcgtca tttcatgacc agcgtttatg    2100
cactggttaa gtgtttccat gagtttcatt ctgaacatcc tttaatcatt gctttgcgtt    2160
tttttattaa atcttgcaat ttactgcaaa gcaacaacaa aatcgcaaag tcatcaaaaa    2220
accgcaaagt tgtttaaaat aagagcaaca ctacaaaagg agataagaag agcacatacc    2280
tcagtcactt attatcacta gcgctcgccg cagccgtgta accgagcata gcgagcgaac    2340
tggcgaggaa gcaaagaaga actgttctgt cagatagctc ttacgctcag cgcaagaaga    2400
aatatccacc gtgggaaaaa ctccaggtag aggtacacac gcggatagcc aattcagagt    2460
aataaactgt gataatcaac cctcatcaat gatgacgaac taaccccccga tatcaggtca    2520 catgacgaag ggaaagagaa ggaaatcaac tgtgacaaac tgccctcaaa tttggcttcc    2580
ttaaaaatta cagttcaaaa agtatgagaa aatccatgca ggctgaagga acagcaaaa    2640 ctgtgacaaa ttaccctcag taggtcagaa caaatgtgac gaaccaccct caaatctgtg    2700
acagataacc ctcagactat cctgtcgtca tggaagtgat atcgcggaag gaaaatacga    2760
tatgagtcgt ctggcggcct ttcttttttct caatgtatga gaggcgcatt ggagttctgc    2820
tgttgatctc attaacacag acctgcagga agcggcggcg gaagtcaggc atacgctggt    2880
aactttgagg cagctggtaa cgctctatga tccagtcgat tttcagagag acgatgcctg    2940
agccatccgg cttacgatac tgacacaggg attcgtataa acgcatggca tacggattgg    3000
tgatttcttt tgtttcacta agccgaaact gcgtaaaccg gttctgtaac ccgataaaga    3060
agggaatgag atatggggttg atatgtacac tgtaaagccc tctggatgga ctgtgcgcac    3120
gtttgataaa ccaaggaaaa gattcatagc cttttttcatc gccggcatcc tcttcagggc    3180
gataaaaaac cacttccttc cccgcgaaac tcttcaatgc ctgccgtata tccttactgg    3240
cttccgcaga ggtcaatccg aatatttcag catatttagc aacatggatc tcgcagatac    3300
cgtcatgttc ctgtagggtg ccatcagatt ttctgatctg gtcaacgaac agatacagca    3360 tacgttttttg atcccgggag agactatatg ccgcctcagt gaggtcgttt gactggacga    3420
ttcgcgggct attttttacgt ttcttgtgat tgataaccgc tgtttccgcc atgacagatc    3480
catgtgaagt gtgacaagtt tttagattgt cacactaaat aaaaaagagt caataagcag    3540
ggataacttt gtgaaaaaac agcttcttct gagggcaatt tgtcacaggg ttaagggcaa    3600
```

```
tttgtcacag acaggactgt catttgaggg tgatttgtca cactgaaagg gcaatttgtc    3660
acaacacctt ctctagaacc agcatggata aaggcctaca aggcgctcta aaaaagaaga    3720
tctaaaaact ataaaaaaaa taattataaa aatatccccg tggataagtg gataacccca    3780
agggaagttt tttcaggcat cgtgtgtaag cagaatatat aagtgctgtt ccctggtgct    3840
tcctcgctca ctcgagggct tcgccctgtc gctcgactgc ggcgagcact actggctgta    3900
aaaggacaga ccacatcatg gttctgtgtt cattaggttg ttctgtccat tgctgacata    3960
atccgctcca cttcaacgta acaccgcacg aagatttcta ttgttcctga aggcatattc    4020
aaatcgtttt cgttaccgct tgcaggcatc atgacagaac actacttcct ataaacgcta    4080
cacaggctcc tgagattaat aatgcggatc tctacgataa tgggagattt tcccgactgt    4140
ttcgttcgct tctcagtgga taacagccag cttctctgtt taacagacaa aaacagcata    4200
tccactcagt tccacatttc catataaagg ccaaggcatt tattctcagg ataattgttt    4260
cagcatcgca accgcatcag actccggcat cgcaaactgc acccggtgcc gggcagccac    4320
atccagcgca aaaaccttcg tgtagacttc cgttgaactg atggacttat gtcccatcag    4380
gctttgcaga actttcagcg gtataccggc atacagcatg tgcatcgcat aggaatggcg    4440
gaacgtatgt ggtgtgaccg gaacagagaa cgtcacaccg tcagcagcag cggcggcaac    4500
cgcctcccca atccaggtcc tgaccgttct gtccgtcact tcccagatcc gcgctttctc    4560
tgtccttcct gtgcgacggt tacgccgctc catgagctta tcgcgaataa atacctgtga    4620
cggaagatca cttcgcagaa taaataaatc ctggtgtccc tgttgatacc gggaagccct    4680
gggccaactt ttggcgaaaa tgagacgttg atcggcactg cccgctttcc agtcgggaaa    4740
cctgtcgtgc cagctgcatt aatgaatcgg ccaacgcgaa cccttgcgg ccgcccgggc    4800
cgacgaccaa ttctcatgtt tgacagctta tcatcaaatt tctgccattc ctccgcttta    4860
ttattcaact tattccggcg aagccactat ggcgtttaag ggcaccaata actgccttaa    4920
aaaatttacc cccccccctg cccctcctt cgcagtactg tttgaaatca ttaaacatttt    4980
ttgccgaact ggaaacccat aaaaacgggc aggatgaacc ttaatccgcc cccggccttc    5040
ccacccttgg caccttgggg taaaattatt tcccaaggga gaaacagggg cgccaaaaaa    5100
atcctcccaa t                                                        5111
```

<210> SEQ ID NO 65
<211> LENGTH: 8559
<212> TYPE: DNA
<213> ORGANISM: Zea mays
<220> FEATURE:
<221> NAME/KEY: misc_feature
<222> LOCATION: (8221)..(8222)
<223> OTHER INFORMATION: n is a, c, g, or t
<220> FEATURE:
<221> NAME/KEY: misc_feature
<222> LOCATION: (8225)..(8225)
<223> OTHER INFORMATION: n is a, c, g, or t
<220> FEATURE:
<221> NAME/KEY: misc_feature
<222> LOCATION: (8227)..(8228)
<223> OTHER INFORMATION: n is a, c, g, or t
<220> FEATURE:
<221> NAME/KEY: misc_feature
<222> LOCATION: (8230)..(8230)
<223> OTHER INFORMATION: n is a, c, g, or t
<220> FEATURE:
<221> NAME/KEY: misc_feature
<222> LOCATION: (8234)..(8236)
<223> OTHER INFORMATION: n is a, c, g, or t
<220> FEATURE:
<221> NAME/KEY: misc_feature
<222> LOCATION: (8241)..(8241)

```
<223> OTHER INFORMATION: n is a, c, g, or t
<220> FEATURE:
<221> NAME/KEY: misc_feature
<222> LOCATION: (8244)..(8245)
<223> OTHER INFORMATION: n is a, c, g, or t
<220> FEATURE:
<221> NAME/KEY: misc_feature
<222> LOCATION: (8250)..(8250)
<223> OTHER INFORMATION: n is a, c, g, or t
<220> FEATURE:
<221> NAME/KEY: misc_feature
<222> LOCATION: (8256)..(8256)
<223> OTHER INFORMATION: n is a, c, g, or t
<220> FEATURE:
<221> NAME/KEY: misc_feature
<222> LOCATION: (8258)..(8258)
<223> OTHER INFORMATION: n is a, c, g, or t
<220> FEATURE:
<221> NAME/KEY: misc_feature
<222> LOCATION: (8269)..(8269)
<223> OTHER INFORMATION: n is a, c, g, or t
<220> FEATURE:
<221> NAME/KEY: misc_feature
<222> LOCATION: (8274)..(8274)
<223> OTHER INFORMATION: n is a, c, g, or t
<220> FEATURE:
<221> NAME/KEY: misc_feature
<222> LOCATION: (8278)..(8278)
<223> OTHER INFORMATION: n is a, c, g, or t
<220> FEATURE:
<221> NAME/KEY: misc_feature
<222> LOCATION: (8290)..(8290)
<223> OTHER INFORMATION: n is a, c, g, or t
<220> FEATURE:
<221> NAME/KEY: misc_feature
<222> LOCATION: (8300)..(8301)
<223> OTHER INFORMATION: n is a, c, g, or t
<220> FEATURE:
<221> NAME/KEY: misc_feature
<222> LOCATION: (8304)..(8304)
<223> OTHER INFORMATION: n is a, c, g, or t
<220> FEATURE:
<221> NAME/KEY: misc_feature
<222> LOCATION: (8315)..(8315)
<223> OTHER INFORMATION: n is a, c, g, or t
<220> FEATURE:
<221> NAME/KEY: misc_feature
<222> LOCATION: (8319)..(8319)
<223> OTHER INFORMATION: n is a, c, g, or t
<220> FEATURE:
<221> NAME/KEY: misc_feature
<222> LOCATION: (8321)..(8321)
<223> OTHER INFORMATION: n is a, c, g, or t
<220> FEATURE:
<221> NAME/KEY: misc_feature
<222> LOCATION: (8323)..(8323)
<223> OTHER INFORMATION: n is a, c, g, or t
<220> FEATURE:
<221> NAME/KEY: misc_feature
<222> LOCATION: (8343)..(8343)
<223> OTHER INFORMATION: n is a, c, g, or t
<220> FEATURE:
<221> NAME/KEY: misc_feature
<222> LOCATION: (8356)..(8356)
<223> OTHER INFORMATION: n is a, c, g, or t
<220> FEATURE:
<221> NAME/KEY: misc_feature
<222> LOCATION: (8361)..(8361)
<223> OTHER INFORMATION: n is a, c, g, or t
<220> FEATURE:
<221> NAME/KEY: misc_feature
<222> LOCATION: (8372)..(8372)
<223> OTHER INFORMATION: n is a, c, g, or t
<220> FEATURE:
<221> NAME/KEY: misc_feature
<222> LOCATION: (8383)..(8383)
<223> OTHER INFORMATION: n is a, c, g, or t
<220> FEATURE:
<221> NAME/KEY: misc_feature
<222> LOCATION: (8386)..(8387)
```

```
<223> OTHER INFORMATION: n is a, c, g, or t
<220> FEATURE:
<221> NAME/KEY: misc_feature
<222> LOCATION: (8391)..(8391)
<223> OTHER INFORMATION: n is a, c, g, or t
<220> FEATURE:
<221> NAME/KEY: misc_feature
<222> LOCATION: (8397)..(8397)
<223> OTHER INFORMATION: n is a, c, g, or t
<220> FEATURE:
<221> NAME/KEY: misc_feature
<222> LOCATION: (8400)..(8400)
<223> OTHER INFORMATION: n is a, c, g, or t
<220> FEATURE:
<221> NAME/KEY: misc_feature
<222> LOCATION: (8404)..(8404)
<223> OTHER INFORMATION: n is a, c, g, or t
<220> FEATURE:
<221> NAME/KEY: misc_feature
<222> LOCATION: (8408)..(8408)
<223> OTHER INFORMATION: n is a, c, g, or t
<220> FEATURE:
<221> NAME/KEY: misc_feature
<222> LOCATION: (8413)..(8413)
<223> OTHER INFORMATION: n is a, c, g, or t
<220> FEATURE:
<221> NAME/KEY: misc_feature
<222> LOCATION: (8421)..(8421)
<223> OTHER INFORMATION: n is a, c, g, or t
<220> FEATURE:
<221> NAME/KEY: misc_feature
<222> LOCATION: (8424)..(8424)
<223> OTHER INFORMATION: n is a, c, g, or t
<220> FEATURE:
<221> NAME/KEY: misc_feature
<222> LOCATION: (8427)..(8427)
<223> OTHER INFORMATION: n is a, c, g, or t
<220> FEATURE:
<221> NAME/KEY: misc_feature
<222> LOCATION: (8433)..(8433)
<223> OTHER INFORMATION: n is a, c, g, or t
<220> FEATURE:
<221> NAME/KEY: misc_feature
<222> LOCATION: (8435)..(8435)
<223> OTHER INFORMATION: n is a, c, g, or t
<220> FEATURE:
<221> NAME/KEY: misc_feature
<222> LOCATION: (8461)..(8461)
<223> OTHER INFORMATION: n is a, c, g, or t
<220> FEATURE:
<221> NAME/KEY: misc_feature
<222> LOCATION: (8463)..(8465)
<223> OTHER INFORMATION: n is a, c, g, or t
<220> FEATURE:
<221> NAME/KEY: misc_feature
<222> LOCATION: (8472)..(8472)
<223> OTHER INFORMATION: n is a, c, g, or t
<220> FEATURE:
<221> NAME/KEY: misc_feature
<222> LOCATION: (8479)..(8479)
<223> OTHER INFORMATION: n is a, c, g, or t
<220> FEATURE:
<221> NAME/KEY: misc_feature
<222> LOCATION: (8482)..(8483)
<223> OTHER INFORMATION: n is a, c, g, or t

<400> SEQUENCE: 65
gggttctcgt tactgatgat cagcttgatt cgctgaagct ccaatgtgct ggaaagtatg      60
gattttgtgc tgggattgcc taggactagg aagggacgtg atagtgtgtt tgtggttgtt     120
gatagatttt ctaagatggc acatttcata ccatgtcata aaactgacga tgctactcat     180
attgctgatt tgttctttcg tgaaattgtt cgcttgcatg gtgtgcccaa cacaatcgtt     240
tctgatcgtg atgctaaatt tcttagtcat ttttggagga ctttgtgggc aaaattgggg     300
actaagcttt tattttctac tacatgtcat cctcaaactg atggtcaaac tgaagttgtg     360
```

-continued

| | |
|---|---|
| aatagaactt tgtctactat gttaagggca gttctaaaga agaatattaa gatgtgggag | 420 |
| gactgtttgc ctcatgttga atttgcttat aatcgatcat tgcattctac tacaaagatg | 480 |
| tgcccatttc agattgtata tggtttgttg cctcgtgctc ctattgattt aatgcctttg | 540 |
| ccatcttctg aaaaactaaa ttttgatgct actaggcgtg ctgaattgat gttaaaactg | 600 |
| catgaaacta ctaaagaaaa catagagcgt atgaatgcta gatataagtt tgctagtgat | 660 |
| aaaggtagaa aggaaataaa ttttgaacct ggagatttag tttggttgca tttgagaaag | 720 |
| gaaaggtttc ctgaattgcg aaaatctaag ttgttgcctc gagccgatgg accgtttaaa | 780 |
| gtgctagaga aaattaacga caatgcatat aggctagatc tgcctgcaga ctttggggtt | 840 |
| agccccacat ttaacattgc agatttaaag ccctacttgg gagaggaagt taagcttgag | 900 |
| tcgaggacga ctcaaatgca agaagggag aatgatgaag acatccacac tactgatgca | 960 |
| tctataccaa tacaagtacc aatttctggt cccattactc gcgctcgtgc tcgtcaactc | 1020 |
| aaccatcagg tgattacact cttgagttca tgtccatcat atttagacca tggagacccg | 1080 |
| tgcactcttg ttttgcttag gaatcaggga gaagaccgaa agggaaaagg atttgaacat | 1140 |
| gctggattcg gactgcagaa gaacaccaac ttgtgacggt caccacggtc agatgcgggc | 1200 |
| tcggattgga atgttcaagc acaacatgga aagcttatca agtctactt catatggatc | 1260 |
| cggaattata gtcatatctg ttctgaggcc gccgtaatca ttgttttatt accgagacat | 1320 |
| ttcctgcctt ttctgcccat ggtgctgcgt caccctattt tgcccaatg ggtcgtgtat | 1380 |
| caagttaggt ccattaggga cgcatcctag ggttgcagca cgaccccaat acccttgtgg | 1440 |
| tcgtcctccc atgtttataa accccctagc cgccaccaag aacagcgggt tttgtttaga | 1500 |
| tcaagtttag ctctcgctac ttgcttgcaa gcgcgcgtgc tagttcagcc gcccgtcttc | 1560 |
| ttgtcttcgg aaccccacca tattgtagtt tgatctttaa acctacattt agatctggta | 1620 |
| attcagtact tgttctactt gttcttgcta gttcttcgat tgcttgcagg acgagtgccc | 1680 |
| tagtggccag ggtgtcacgc tccacaagat cgtgacagcc ataggaggtg gtgtatcggt | 1740 |
| tgctaaggcg cagcgtcttt ggaaggctgt agtcgggccg tgaacgtcgt ctcctccccc | 1800 |
| aatcgagtta ttccacaccc tctcatcgaa agatcgggca atcacccaac gggtgcacat | 1860 |
| cactgaatat cccgtgtacg tcctgtggaa gaagcggcgc ctttggcagg gggcgccact | 1920 |
| ggcttggtcg tccctgtgcg cgatgtagtg ctaggcgtag aaggtgcagg gctggaagga | 1980 |
| gttgagctgt gtgttggacc ccggcctgca agagagttag tatatgtctt tgatcgtcgt | 2040 |
| ccctgcactt cacgttcagc tttgcaagca tattcaaaca atgtggttat atcaaaataa | 2100 |
| tccttataat caagtatatc ctgaatttcc ctgttcaaac caccacgaaa acgcgccata | 2160 |
| gcagcgtcat ccgactcaac taaaccacaa cgaagcatac ccttttgtaa ctcctggtaa | 2220 |
| taatcctcaa cagactgtga accttgttga aaacgctgca ttttgttaag caaatcacga | 2280 |
| gcataatagg aaggaacaaa tctgtggcgc atggcagttt ttaattgggt ccaagtaatg | 2340 |
| acactgttaa tgggaagttt tgttttatac tcacgccacc aaattaaagc aaaatcagta | 2400 |
| aattcactaa tggcagcctt cacttggcta ttagcaggaa tatcatggca tgaaaatttc | 2460 |
| tgttctacct ctaattccca atcaagatat gcagcaggat catatttacc attaaaagat | 2520 |
| ggaattttaa atttaatctt agaaaataag tcattagggg gatgacgaac cacacgacgt | 2580 |
| gcacgaccac ggcgatctcc atcgtcctgc tcagtgtcaa cgccgtattc ctgctccatc | 2640 |
| tttgtggtca gtgcatcaag gcgtgccagg atggtgtcga gtgtggtgcg agtcgccgtt | 2700 |
| tgagcaaggt caagttggtt gaaacgctcg gtcgtcgaag tgatcgttga atcaagccgt | 2760 |

```
tcatgcatcg tcctaatgtc agcagcaagt ccatcaactt gtcccctta  ttcctgcaac   2820 tgggcatcca ccatgtcgtg tgctcctgcc atagttagcg caaacaccaa aaggagaaaa   2880
accaacgaca caacaggggg tgtactgctc acaaggcgct cacactagtg ctgttatcaa   2940
gttcttatcc gttcttacca agccacagtg gtgaactgca accaacaggt ggaaccggtg   3000
aaagattgga tgagcgattg cgtggagaaa cagaaacctg ctcgtcgtag aaatatgtgg   3060
agttgtgggt aggctgcact caagtcaagg attagcacga tcaaacaata atgcaaagta   3120
gaattatagt gcaaaacacg aaactatatt gctggccaca ggtgcaaagg atggatggaa   3180
ctagcagaat ggcagtaccg taaatattgt actagtgatg ccaaaaaggc actagtagaa   3240
atcacaggtg attttgtttt tcttttttgt atgatttttt tgatatttt  ctcagcacaa   3300 gaagcaacaa gataggagct acacgaagtt tcacctaaaa cagatatcag atgtggtcta   3360
cagaaaatca ggaagttctc tgaaaagcgt gcgagaactt tgacggattt ttttctttat   3420
tttcctgaat ttttttgaca attttgtcga accccaaaca gaccgtaggt gagtttggcc   3480
ggcctcagaa tggtgtcaac tagctcctat aaaaatttca gattttttgg acacccgagc   3540
gaaaagttat gcccggttta cggaaggtac ctcaagttat gttctaaaaa cgaccgggat   3600
gaaacaaccg tatcctttct ccttcgttat cttttttttc tgtttttttg acgtaaccga   3660
aggagaaaaa caaggaaggt tgactcggtt tgtttttttt tgctgttttt ttttcgtaac   3720
cgaaggagaa aatcaaggaa acggccgttg actcggtttg tttttttctgt ttttttttga   3780 cgtaaccgaa ggagaaaaat aaggaaacga tgttgactcg gtttgtggtg tgatcaaatg   3840
ggagatggtg gcggcgctag ggtttgaatg gtggaagaac acaatgcaac cagcaacaaa   3900
tgacgcgaaa gcacacaaat tcaacaatgc agattattga agaaagtgt  gaggctcaaa   3960 agggtgctgg gataagatct aacctgaatt tttatgtggt tttgtggact gtaggaaaaa   4020
aaacgctcga taaactcacc gatcaacctg gaaatctgat accaattgat gaagctgagg   4080
tgcccgatct ttcggcaagt agagataatt ccgatttggc ggaagatgac ccttgcgatc   4140
cgactacgac gagcaagccc gaggcgccaa tgcaatcgct gaaccaactc cctgtggtta   4200
ccgaccttgc tgatgcgaga tcggcctgat cacgaagatc gtttcctgtg cgcaatcgaa   4260
gaacgaacaa gaacaagatg cgagcaatct aatctattac tcgagggtgg agttctgaat   4320
acacgaagac agcgcagatt tgcgcgtgtt cgagagtagc taaggctaat gtaaaacaaa   4380
actcaggaaa taaaggaggc gcagctcctg aataaataga gagggggcgc agcccctagg   4440
ggcggccaac cctagtcgt  ccattatggg ccgcaattgg gctggtcgtc tattctttcg   4500
ggccttcgtt cttaacaac  atgatgtagt tcaattctct tgcacgggcc cgagtcactg   4560
gcccaggtgg aagggtggc gcctgggctg gagaaggtgc tgctggtgta gatgtgctcg   4620
tgttggtgtt gatgtccgca tcacttgggt tttgtttgat gtaagtttag cctttgctac   4680
ttccttgtaa acgcgtgtgt cggctagacc acccgaatac ttgaaacggg accccaactt   4740
tatcagatcc gtgcgtgttt gcttgttatc ttgttcttgc ttgttctcga ttgcttgcag   4800
gttcaaggct gttcttggca cggcaagagc agcaacaaca ggagccggtg taactatcgc   4860
taaggcgcag caccttgtg  gttgttgtag tcggatagca caacgtcgac ctccacccca   4920
aatcgtagtt atcaggagat ggtgtacctg tcgctcaagg cgccacacca tcttggttgt   4980
ggtagtcggg cagccaacgt cgttctccaa caagttttcc acctccatca tctctcatcg   5040
aaagatcggg caccctttcta cccgttgggt tcatcagttc cggtggcaaa aactcgtgct   5100
ttgtatgcac catgacaccc gttttcggaa tgggtgagac gtgcgacaac gaaattgtgc   5160
```

| | |
|---|---|
| gaaaccaccc caacacatga gttttggacc taaagtagtg gattgggcat gttcgttgca | 5220 |
| aaaaacaaag aaatggttcc ggtggcaaaa actcgtgctt tgtatgcacc atgacacccg | 5280 |
| ttttcggaat gggtgacgtg cgacaacgaa attgcgagaa accaccccaa acatgagttt | 5340 |
| tggacctaaa gtactggatt aggcatgttc gttgcgaaaa acgaagaaat ggttccggtg | 5400 |
| gcaaaaactc gtgctttgta tgcacccgac accgttttc ggaatgggtg acgtgcgaca | 5460 |
| acgaaattgt gtgaaccac cccaaacatg agttttggac ctaaagtagt ggattgggca | 5520 |
| tgttcgttac gaaaaacgaa gaaatggttc cggtggcaaa aactcgtgct tttatgcacc | 5580 |
| ccgatacccg ttttcagaat gggtgacatg cgacaacaaa attgcgcgaa accaccccaa | 5640 |
| acatgagttt tggacctaaa gtagtggatt gggcatgttc gttgcgaaaa acgaaggaat | 5700 |
| ggttccggtg gcaaaaactc gtgcttttat gcaccccgat accgttttc agaatgggtg | 5760 |
| acgtgcgaca acgaaactgt gcgaaaccac cccaaacatg agttttggac ctatagtagt | 5820 |
| ggattgggca tgttcgttgt gaaaaacgaa gaaatggttc cggtgaaaaa actcgtgct | 5880 |
| ttgtatgcac cccgacaacc gttttcggaa tgggtgacgt gcggcaacga aattgcgcga | 5940 |
| aaccacccca acatgagtt ttggacctaa agtagtggat tgggcatgtt cgttgcgaaa | 6000 |
| aacgaagaaa tggttccggt ggcaaaaact cgtgcttttt attcacccga cacccgtttt | 6060 |
| cggaatgggt gacgtgcgac aaagaaattg cgcgaaacca ccccaaacat gagttttgga | 6120 |
| tgtaaagtag tggattgggc atgttcgttg tgaaaaacga agaaatggtt ccggtggcaa | 6180 |
| aaactcgtgc tttgtatgca cccgacaccc gttttcggaa tgggtgacgt gcgacaacga | 6240 |
| aattgtgcga aaccacccca acatgagtt ttggacctaa agtagtggat tcggcatgtt | 6300 |
| cgttacgaaa aacgaagaaa tggttccggt ggcaaaaact cgtgcttta tgcaccccga | 6360 |
| tacccgtttt cagaatgggt gacgtgcgac aacaaaattg cgcgaaacca ccccaaacat | 6420 |
| gagttttgga cctaaagtag tggattgggc atgttcgttg cgaaaacga agaaatggtt | 6480 |
| ccggtggcaa aaactcgtgc ttttatgcac cccgatacccc gttttcagaa tgggtgacgt | 6540 |
| gcgacaacga aactgtgcga accaccccca acatgagtt ttggacctat agtagtggat | 6600 |
| tgggcatgtt cgttgtgaaa aacgaagaaa tggttccggt ggcaaaaact cgtgctttgt | 6660 |
| atgcaccccg acaaccgttt tcggaatggg tgacgtgcgg caacgaaatt gcgcgaaacc | 6720 |
| accccaaaca tgagttttgg acctaaagta gtggattggg catgttcgtt gcgaaaaacg | 6780 |
| aagaaatggt tccggtggca aaaactcgtg cttttatgca ccccgatacc gttttcgga | 6840 |
| atgggtgaca tgcgacaaca aaattgcgcg aaaccacccc aaacatgagt tttggaccta | 6900 |
| aagtagtgga ttgggcatgt tcgttgcgaa aaacgaagaa atggttccgg tgcaaaaac | 6960 |
| tcgtgctttg tatgcacccg acaccgtttt cggaatggg tgacgtgcga caagaaatt | 7020 |
| gcgcgaaacc accccaaaca tgagttttgg atgtaaagta gtggattggg catgttcgtt | 7080 |
| gcgaaaaacg aagaaatggt tccggtggca aaaactcgtg ctttgtatgc acccgacacc | 7140 |
| cgttttcgga atgggtgacg tgcgacaacg aaattgtgcg aaaccacacc aaacatgagt | 7200 |
| tttggaccta agtagtgga ttgggcatgt tcgttacgaa aaacgaagaa atggttccgg | 7260 |
| tggcaaaaac tcgtgctttg tatgcacccc cgacaaccgt tttcggaatg ggtgacgtgc | 7320 |
| ggcaacgaaa ttgcgcgaaa ccactccaaa catgagtttt ggacctaaag tagtggattg | 7380 |
| ggcatgttcg ttgtgtaaaa cgaagaaatg gttccggtgg caaaaactcg tgctttgtat | 7440 |
| gcaccccgac aaccgtttc ggaatgggtg acgtgcggca acgaaattgc gcgaaaccac | 7500 |
| cccaaacatg agttttggac ctaaagtagt ggattgggca tgttcgttgc gaaaaacgaa | 7560 |

-continued

| | |
|---|---|
| gaaatggttc cggtggcaaa aactcgtgct ttgtatgcac ccgacacccg ttttcggaat | 7620 |
| gggtgacgtg cgacaaagaa attgcgcgaa accaccccaa acatgagttt tggatgtaaa | 7680 |
| gtagtggatt gggcatgttc gttgcgaaaa acgaagaaat ggttccggtg caaaaactc | 7740 |
| gtgctttgta tgcacccgac acccgttttc ggaatgggtg acgtgcgaca acgaaattgt | 7800 |
| gcgaaaccac accaaacatg agttttggac ctaaagtagt ggattgggca tgttcgttac | 7860 |
| gaaaaacgaa gaaatggttc cggtggcaaa aactcgtgct tttatgcacc ccgatacccg | 7920 |
| ttttcggaat gggtgatgat gaagacatcc acactactga tgcatctata ccaatacaag | 7980 |
| taccaatttc tggtcccatt actcgcgctc gtgctcgtca actcaaccat caggtgatta | 8040 |
| cactcttgag ttcatgtcca tcatatttag accatggaga cccgtgcact cttgttttgc | 8100 |
| ttaggaatca gggagaagac cgaaagggaa aaggatttga acatgctgga ttcggactgc | 8160 |
| agaagaacac caacttgtga cggtcaccac ggtcagatgc gggctcggat tggaatgttc | 8220 |
| nngcncnncn tggnnngctt ntcnngtctn ctttcntntg gatccggant tatngtcntt | 8280 |
| tctgttctgn ggccgccgtn ntcnttgttt tcttnccgng ncntttcctg ccttttctgc | 8340 |
| ccntggtgct gcgtcnccct nttttggccc antgggtcgt gtntcnngtt nggtccnttn | 8400 |
| gggncgcntc ctnggggttgc ngcncgnccc ccntncccctt gtggtcgtcc taaggtgttt | 8460 |
| ntnnncccc tngccgtcnc cnngccccg aaatgtgttt agatcaagtt tctttccagc | 8520 |
| agatggagct tcagcgaatc aagcttgatt catcaggag | 8559 |

<210> SEQ ID NO 66
<211> LENGTH: 10771
<212> TYPE: DNA
<213> ORGANISM: Zea mays

<400> SEQUENCE: 66

| | |
|---|---|
| cgtcctcatg atatcaagct tgattcgctg aagctccaat gtgctggaaa gacgaagaaa | 60 |
| tggttccggt ggcaaaaact cgtgctttgt gtgcacccga cacccgtttt cggaatgggt | 120 |
| gacgtgcgac aacgaaattg cgagaaatca ccccaaacat gagttttgga cctaaagtag | 180 |
| tggattgggc atgttcgttg cgaaaaacga agaaatggtt ccggtggcaa aaactcgtgc | 240 |
| tttgtatgca accgacaccc gttttcggaa tgggtgacgt gcgacaacga aattgcgcga | 300 |
| aaccacccca acatgagtt ttggatctaa agtagtggat tgggcatgtt cgttgcgaaa | 360 |
| aacgaagaaa tggttccggt ggcaaaaact cgtgctttgt atgcacccga cacccgtttt | 420 |
| cggattgggt gatgtgcgac aacgaaatta cgcgaaacca ccccaaacat gagttttgga | 480 |
| tgtaaagtag tggattgggc atgttcgttg cgaaaaacga agaaatggtt ctggtggcaa | 540 |
| aaactcgtgc tttgtatgca accgacaccc gttttcggaa tgggtgacgt gcgacaacga | 600 |
| aattgcgcga aaccatccca acatgagtt tttggatcta agtagtgga ttgggcatgt | 660 |
| tcgttgcgaa aaacgaagaa atggttccgg tggcaaaaac tcgtgctttt atgcaccccg | 720 |
| atgcccgttt tcagaatggg tgacgtgcga caacgaaact gtgcgaaacc accccaaaca | 780 |
| tgagttttgg acctaaagta atggattggg catgttcgtt gcgaaaaacg aagaaatggt | 840 |
| tccggtggca aaaactcgtg ctttgtatgc accccgaca accgttttcg gaatgggtga | 900 |
| cgtgcggcaa cgaaattgcg cgaaaccacc caaacatga ttttggacc tatagtagtg | 960 |
| gattgggcat gttcgttgtg aaaacgaag aaatggttcc ggtggaaaaa actcgtgctt | 1020 |
| tgtatgcacc ccgacaaccg ttttcggaat gggtgacgtg cggcaacgaa attgcgcgaa | 1080 |
| accaccccaa acatgagttt tggacctaaa gtagtggatt gggcatgttc gttgcgaaaa | 1140 |

-continued

```
acgaagaaat ggttccggtg gcaaaaactc gtgcttttta ttcacccgac acccgttttc      1200
ggaatgggtg acgtgcgaca aagaaattgc gcgaaaccac cccaaacatg agttttggat      1260
gtaaagtagt ggattgggca tgttcgttgc gaaaaacgaa gaaatggttc cggtggcaaa      1320
aactcgtgct ttgtatgcac ccgacacccg ttttcggaat gggtgacgtg cgacaacgaa      1380
attgtgcgaa accacaccaa acatgagttt tggacctaaa gtagtggatt gggcatgttc      1440
gttacgaaaa acgaagaaat ggttccggtg gcaaaaactc gtgcttttat gcaccccgat      1500
acccgttttc agaatgggtg acatgcgaca caaaattgc acgaaaccac cccaaacatg       1560
agttttggac ctaaagtagt ggattgggca tgttcgttgc gaaaaacgaa gaaatggttc      1620
cggtggcaaa aactcgtgct tttatgcacc ccgatacccg ttttcagaat gggtgacgtg      1680
cgacaacgaa actgtgcgaa accaccccaa acatgagttt tggacctaaa gtagtggatt      1740
gggcatgttc gttgtgaaaa acgaagaaat ggttccggtg gcaaaaactc gtgctttgta      1800
tgcaccccga caaccgtttt cggaatgggt gacgtgcggc aacgaaattg cgcgaaacca      1860
ccccaaacat gagttttgga cctaaagtag tggattgggc atgttcgttg cgaaaaacga      1920
agaaatggtt ccggtggcaa aaactcgtgc tttttattca cccgacaccc gttttcggaa      1980
tgggtgacgt gcgacaacga aattgcgcga accaccccca aacatgagtt ttggatgtaa      2040
agtagtggat tggcatgtt cgttgcgaaa acgaagaaa tggttccggt ggcaaaaact        2100
cgtgctttgt atgcacccga cacccgtttt cggaatgggt gacgtgcgac aacgaaattg      2160
tgcgaaacca ccccaaacat gagttttgga cctaaagtag tggattcggc atgttcgtta      2220
cgaaaaacga agaaatggtt ccggtggcaa aaactcgtgc ttttatgcac cccgatacac      2280
gttttcagaa tgggtgacgt gcgacaacga aactgtgcga accaccccca aacatgagtt      2340
ttggacctaa agtagtggat tggcatgtt cgttatgaaa acgaagaaa tggttccggt        2400 ggcaaaaact cgtgctttgt atgcaccccg acaaccgttt tcggaatggg tgacgtgcgg      2460
caacgaaatt gcgcgaaacc accccaaaca tgagttttgg acctaaagta gtggattggg      2520
catgttcgtt gcgaaaaacg aagaaatggt tccggtggca aaaactcgtg cttttttattc    2580 acccgacacc cgttttcgga atgggtgacg tgcgacaacg aaattgcgcg aaaccacccc      2640
aaacatgagt tttggatgta agtagtgga ttgggcatgt tcgttgcgaa aaacgaagaa       2700
atggttccgg tggcaaaaac tcgtgctttg tatgcacccg acaccgttt tcggaatggg       2760 tgacgtgcga caacgaaatt gtgcgaaacc accccaaaca tgagttttgg acctaaagta      2820
gtggattcgg catgttcgtt acgaaaacg aagaaatggt tccggtggca aaaactcgtg       2880
cttttatgca ccccgatacc cgttttcaga tgggtgacg tgcgacaaca aaattgcgcg       2940
aaaccacccc aaacatgagt tttggaccta agtagtgga ttgggcatgt tcgttgcgaa       3000
aaacgaagaa atggttccgg tggcaaaaac tcgtgctttt atgcaccccg atacccgttt     3060
tcagaatggg tgacgtgcga caacgaaact gtgcgaaacc accccaaaca tgagttttgg     3120
acctaaagta gtggattggg catgttcgtt gtgaaaaacg aagaaatggt tccggtggca      3180
aaaactcgtg ctttgtatgc accccgacaa ccgttttcgg aatgggtgac gtgcggcaac     3240
gaaattgcgc gaaaccaccc caaacatgag ttttggacct aaagtagtgg attgggcatg     3300
ttcgttgcga aaaacgaaga atggttccg gtggcaaaaa ctcgtgcttt gtatgcaccc      3360
gacacccgtt ttcggaatgg gtgacgtgcg acaagaaat gcgcgaaac caccccaaac       3420 atgagttttg gatgtaaagt agtggattgg gcatgttcgt tgcgaaaaac gaagaaatgg     3480
ttccggtggc aaaaactcgt gctttgtatg cacccgacac ccgttttcgg aatgggtgac     3540
```

```
gtgcgacaac gaaattgtgc gaaaccacac caaacatgag ttttggacct aaagtagtgg   3600
attgggcatg ttcgttacga aaaacgaaga aatggttccg gtggcaaaaa ctcgtgcttt   3660
tatgcacccc gatacccgtt ttcagaatgg gtgacgtgcg acaacaaaat tgcgcgaaac   3720
caccccaaac atgagttttg gacctaaagt agtggattgg gcatgttcgt tgcgaaaaac   3780
gaagaaatgg ttccggtggc aaaaactcgt gcttttatgc accccgatac ccgttttcag   3840
aatgggtgac gtgcgacaac gaaactgtgc gaaaccaccc caaacatgag ttttggacct   3900
aaagtagtgg attgggcatg ttcgttgtga aaaacgaaga aatggttccg gtggcaaaaa   3960
ctcgtgcttt gtatgcaccc cgacaaccgt tttcggaatg ggtgacgtgc ggcaacgaaa   4020
ttgcgcgaaa ccaccccaaa catgagtttt ggacctaaag tagtggattg agcatgttcg   4080
ttgcgaaaaa cgaagaaatg gttccggtgg caaaaactcg tgcttttttat tcacccgaca   4140 cccgttttcg gaatgggtga cgtgcgacaa cgaaattgcg cgaaaccacc caaacatga   4200 gttttggatg taaagtagtg gattgggcat gttcgttgcg aaaacgaag aaatggttcc   4260 ggtggcaaaa actcgtgctt tgtatgcacc cgacacccgt tttcggaatg ggtgacgtgc   4320
gacaacgaaa ttgtgcgaaa ccaccccaaa catgagtttt ggacctaaag tagtggattc   4380
ggcatgttcg ttacgaaaaa cgaagaaatg gttccggtgg caaaaactcg tgcttttatg   4440
caccccgata cccgttttca gaatgggtga cgtgcgacaa caaaattgcg cgaaaccacc   4500
ccaaacatga gttttggacc taaagtagtg gattgggcat gttcgttgcg aaaacgaag   4560 aaatggttcc ggtggcaaaa actcgtgctt tgtatgcacc cgacacccgt tttcggaatg   4620
ggtgacgtgc gacaacgaaa ttgtgcgaaa ccaccccaaa catgagtttt ggacctaaag   4680
tagtggattg ggcatgttcg ttgcgaaaaa cgaagaaatg gttccggtgg caaaaactcg   4740
tgcttttatg caccccgata cccgttttca gaatgggtga catgcgacaa caaaattgca   4800
cgaaaccacc caaacatga gttttggacc taaagtagtg gattgggcat gttcgttgcg   4860
aaaaacgaag aaatggttcc ggtggcaaaa actcgtgctt ttatgcaccc cgatacccgt   4920
tttcagaatg ggtgacgtgc gacaacgaaa ctgtgcgaaa ccaccccaaa catgagtttt   4980
ggacctatag tagtggattg ggcatgttcg ttgtgaaaaa cgaagaaatg gttccggtgg   5040
caaaaactcg tgctttgtat gcaccccgac aaccgttttc ggaatggatg acgtgcggca   5100
acgaaattgc gcgaaaccac cccaaacatg agttttggac ctaaagtagt ggattgggca   5160
tgttcgttgc gaaaaacgaa gaaatggttc cggtggcaaa aactcgtgct ttttattcac   5220
ccgacacccg ttttcggaat gggtgacgtg cgacaacgaa attgcgcgaa accaccccaa   5280
acatgagttt tggatgtaaa gtagtggatt gggcatgttc gttgcaaaaa acgaagaaat   5340
ggttccggtg gcaaaaactc gtgctttgta tgcacccgac acccgttttc ggaatgggtg   5400
acgtgcgaca acgaaattgt gcgaaaccac cccaaacatg agttttggac ctaaagtagt   5460
ggattaggca tgttcgttgc gaaaaacgaa gaaatggttc cgctggcaaa aactcgtgct   5520
ttgtatgcac tccgacaccc ttttcggaat gggtgacgtg tgacaacgaa attgcgcgaa   5580
accaccccaa catgagtttt gtacctaaag tagtggattg gcatgttcg ttgcgaaaaa   5640 cgaagaaatg gttccggtgg caaaaacgcg tgctttgtat gcaccccga caaccgtttt   5700 cggaatgggt gacgtgcggc aacgaaattg cgcgaaacca ccccaaacat gagttttgga   5760
cctaaagtag tggattgggc atgttcgttg cgaaaaacga gaaatggtt ccggtggcaa   5820 aaactcgtgc tttgtatgca cccgacaccc gttttcggaa tggtgacgt gcgacaacga   5880 aattgtgtga aaccaccccca aacatgagtt ttggacctaa agtagtggat tgggcatgtt   5940
```

```
cgttacgaaa aacgaagaaa tggttccggt ggcaaaaact cgtgctttta tgcacctgac    6000
actcgttttc ggaatgagtg acgtgcggca acgaaattgc gcaaaaccac ccaaaacatg    6060
agttttgtac ctaaagtagt ggattgggca tgttcgttga aaaaacgaa gaaatggttc     6120
ctgtggcaaa aactcgtgct ttgtatgcaa ccccacaccc gttttcagaa tgggtgacgt    6180
gcggcatcga aattgcgcga accaccccaa acatgagtt ttggacctaa agtagtggat     6240
tggcatgttc gttgcgaaaa acaaagaaat agttccggtg gcaaaaactc gtgctttgta    6300
tgcaccatga cacccgtttt cagaatgggt gacgtgcgac aacgaaattg tgcgaaacca    6360
ccccaaacat gagttttgga cctaaagtag tggattgggc atgttcgttg cgaaaaatga    6420
agaaatggtt ccggtggcaa aaactcgtgc tttgtatgca cccgacaccc gttttcggaa    6480
tgggtgacgt gcgacaacga aattgtgcga accaccccca aacatgagtt ttggacctaa    6540
agtagtggat tgggcatgtt cgttgcgaaa aacaaagaaa tggttccggt ggcaaaaact    6600
cgtgctttgt atgcaccatg acaccgtttt cggatgggta acgtgcga caacaaaatt      6660
gcgagaaacc accccaaaca tgagttttgg acctaaagta gtgtattagg catgttcgtt    6720
gcgaaaaacg aagaaatggt tccgctggca aaaactcgtg ctttgtatgc actccgacac    6780
ccttttcgga atgggtgacg tgtgacaacg aaattgcgcg aaaccaccca acatgagtt    6840
ttgtacctaa agtagtggat tgggcatgtt cgttgcgaaa aacgaagaaa tggttccggt    6900
ggcaaaaacg cgtgctttgt atgcaccccc gacaaccgtt ttcggaatgg gtgacgtgcg    6960
gcaacgaaat tgcgcgaaac caccccaaac atgagttttg acctaaagt agtggattgg    7020
gcatgttcgt tgcgaaaaac gaagaaatgg ttccggtggc aaaaactcgt gctttgtatg    7080
cacccgacac ccgttttcgg aatgggtgac gtgcgacaac gaaattgcgc aaaaccaccc    7140
caaacatgag ttttggacct aaagtagtgg attgggcatg ttcattgcga aaaacgaaga    7200
aatggttccg gtggcaaaaa ctcgtgcttt gtatgcaccc gacaccgtt tcggaatga    7260
gtgacatgcg acaacgaaat tgcgcgaaac caccccaaac atgagttttg acctaaagt    7320
agtggattgg gcatgttcgt tgcgaaaaac gaagaaatgg ttccagtggc aaaaactcgt    7380
gctttgtatg cacccgacac ccgttttcgg aatgggtgac gtgcgacaac gaaattgcgc    7440
gaaaccacct caaacatgag ttttggacct aaagtagtgg attgggcatg ttcgttacga    7500
aaaacaaga aatggttccg gtggcaaaaa ctcgtgcttt gtatgcaccc gacaccgtt     7560
ttcggaatgg gtgacgtgcg acaacgaaat tgcgagaaac caccccaaac atgagttttg    7620
gacctaaagt agtggattgg gcatgttcgt tgcgaaaaac gaagaaatgg ttccggtggc    7680
aaaaactcgt gctttgtatg cacccccgac aaccgttttc ggaatgggtg acgtgcggca    7740
acgaaattgc gcgaaaccac tcaaacatg agttttggac ctaaagtagt ggattgggca    7800
tgttcgttgc gaaaaacgaa gaaatggttc cggtggcaaa aactcgtgct ttttattcac    7860
ccgacacccg ttttcggaat gggtgacgtg cgacaacgaa attgcgcgaa accaccccaa    7920
acatgagttt tggatgtaaa gtagtggatt gggcatgttc gttgcgaaaa acgaagaaat    7980
ggttccggtg gcaaaaactc gtgctttgta tgcacccgac accgttttc ggaatgggtg    8040
acgtgcgaca agaaattgc gcgaaaccac cccaaacatg agttttggat gtaaagtagt    8100
ggattgggca tgttcgttgc gaaaaacgaa gaaatggttc cggtggcaaa aactcgtgct    8160
ttgtatgcac ccgacacccg ttttcggaat gggtgacgtg cgacaacgaa attgtgcgaa    8220
accaccccaa acatgagttt tggacctaaa gtagtggatt ggcatgttc gttacgaaaa    8280
acgaagaaat ggttccggtg gcaaaaactc gtgctttat gcaccccgat accgttttc     8340
```

```
agaatgggtg acgtgcgaca acaaaattgc gcgaaaccat cccaaacatg agttttggac    8400
ctaaagtagt ggattgggca tgttcgttgc gaaaaacgaa gaaatggttc cggtggcaaa    8460
aactcgtgct tttatgcacc ccgatgcccg ttttcagaat gggtgacgtg cgacaacgaa    8520
actgtgcgaa accaccccaa acatgagttt tggacctaaa gtaatggatt gggcatgttc    8580
gttgcgaaaa acgaagaaat ggttccggtg gcaaaaactc gtgctttgta tgcacccccg    8640
acaaccgttt tcggaatggg tgacgtgcgg caacgaaatt gcgcgaaacc accccaaaca    8700
tgagttttgg acctaaagta gtggattggg catgttcgtt gcgaaaaacg aagaaatggt    8760
tccggtggca aaaactcgtg ctttttattc acccgacacc cgttttcgga atgggtgacg    8820
tgcgacaacg aaattgcgcg aaaccacccc aaacatgagt tttggatgta agtagtgga    8880 ttgggcatgt tcgttgcgaa aaacgaagaa atggttccgg tggcaaaaac tcgtgctttg    8940
tatgcacccg acaccgtttt cggaatgggt gacgtgcga caacgaaatt gtgcgaaacc    9000
accccaaaca tgagttttgg acctaaagta gtggattcgg catgttcgtt acgaaaaacg    9060
aagaaatggt tccggtggca aaaactcgtg cttttatgca ccccgatacc cgttttcaga    9120
atgggtgacg tgcgacaaca aaattgcgcg aaaccacccc aaacatgagt tttggaccta    9180
aagtaataaa gttgggcatg ttcgttgcga aaacgaaga atggttcca gtggcaaaaa    9240 ctcgtgcttt gtatgcaccc gacacccgtt tcggaatgg gtgacgtgcg acaacgaaat    9300
tgcgcgaaac cacctcaaac atgagttttg gacctaaagt agtggattgg gcatgttcgt    9360
tacgaaaaac aaagaaatgg ttccggtggc aaaaactcgt gctttgtatg cacccgacac    9420
ccgttttcgg aatgggtgac gtgcgacaac gaaattgcga gaaaccaccc caaacatgag    9480
ttttgtacct aaagtactgg attaggcatg ttcgttgcga aaacgaaga atggttccg    9540 gtggcaaaaa ctcgtgcttt gtatgcaccc gacacccgtt tcggaatgg gtgacgtgcg    9600 acaacaaaat tgtgtgaaac cacccccaaac atgagttttg gacctaaagt agtggattgg    9660
gcatgttcgt tacgaaaaac gaagaaatgg ttccggtggc aaaaactcgt gcttttatgc    9720
acctgacact cgttttcgga atgagtgacg tgcggcaacg aaattgcgca aaaccaccca    9780
aaacatgagt tttgtaccta aagtagtgga ttgggcatgt tcgttgagaa aaacgaagaa    9840
atggttcctg tggcaaaaac tcgtgctttg tatgcacccc acacccgttt tcagaatgg    9900 gtgacgtgcg gcaacgaaat tgcgcgaaac cacccaaaac atgagttttg gacctaaagt    9960
agtggattgg catgttcgtt gcgaaaaaca agaaatagt tccggtggca aaaactcgtg    10020
ctttgtatgc accatgacac ccgttttcag aatgggtgac gtgcgacaac gaaattgtgc    10080
gaaaccaccc caaacatgag ttttggacct aaagtagtgg attgggcatg ttcgttgcga    10140
aaaactaaga aatggttccg gtggcaaaaa ctcgtgcttt gtatgcaccc gacacccgtt    10200
ttcggaatgg gtgacgtgcg acaacgaaat tgtgcgaaac caccccaaac atgagttttg    10260
gacctaaagt agtggattgg gcatgttcgt tgcgaaaaac aaagaaatgg ttccggtggc    10320
aaaaactcgt gctttgtatg caccatgaca cccgttttcg gaatgggtga cgtgcgacaa    10380
cgaaattgtg cgaaaccacc ccaaacatga gttttggacc taaagtagtg gattgggcat    10440
gttcgttgcg aaaaacgaag aaatggttcc ggtggcaaaa actcgtgctt tgtatgcacc    10500
cgacacccgt tttcggaatg ggtgacgtgc gacaacgaaa ttgtgcgaaa ccacccaaaa    10560
catgagtttt gtacctaaag tagtggattg gcatgttcg ttgagaaaaa cgaagaaatg    10620
gttccggtgg caaaaactcg tgctttgtat gcacccgaca cccgttttcg gaatgggtga    10680
cgtgcggcaa cgaaattgcg cgaaaccacc cgaaacatga gtttctttcc agcacatgga    10740
```
gctcagcgaa tcaagcttga ttctcagggc c                          10771

<210> SEQ ID NO 67
<211> LENGTH: 15540
<212> TYPE: DNA
<213> ORGANISM: Zea mays

<400> SEQUENCE: 67

| | | | | | |
|---|---|---|---|---|---|
| ccgaaatcta | gaatcatcgc | cactgctgca | tggaagatga | acatattagg | tctttaatcg     60 |
| tctctaatcc | aaagattttg | tagtcaagtt | gattcagcaa | agtatatctc | ctagacaaag    120 |
| cgtcagcaat | gatattctct | tttcctttct | tgtgcttaat | aacataagga | aacgattcga    180 |
| taaattcaac | ccacttagca | tgtctacggt | tcagttttcc | ttgactacga | atatgtttca    240 |
| aagattcatg | atcagaatga | ataacaaact | ctttgggcca | caataatgc  | tgccatgttt    300 |
| ctaatgttcg | cacaagagca | tataattcct | tatcataagt | agaataattt | agaacagacc    360 |
| cactcaattt | ttcactaaaa | tatgcaacag | gtttgccttc | ttgtaacaaa | acaccaccca    420 |
| atccaattcc | actagcatca | cattcaagct | caaaagtctt | attaaaatca | ggaagttgga    480 |
| ggagaggtgc | atgtgtcaac | ttatctttca | gcacgttgaa | agcgtgctct | tgtactttgc    540 |
| cccaactaaa | atgcactccc | ttcttcgtaa | gctcattcaa | aggtgcagca | atggtgctaa    600 |
| agtccttcac | aaaacggcga | tagaagccag | caagtcctag | gaaactccgc | acctgtgtga    660 |
| tagtctttgg | cataggccat | ccatgtatcg | cttctacctt | ggcttgatca | acctcaattc    720 |
| cctgtggagt | cacaacataa | ccaagaaacg | aaactcgatc | ggtgcaaaat | gtgcacttct    780 |
| caaggttacc | aaataaacgt | gcatctcgta | aagcattaaa | aacagcacgc | atgtgatcaa    840 |
| catgttcatc | catagatttg | ctgtagatca | atatatcatc | aaagtatact | accacaaatt    900 |
| ttccaatgaa | ggcacgcaaa | acctcgttca | ttaatctcat | gaaagtgcta | ggtgcattag    960 |
| ttaacccaaa | aggcatgact | aaccactcat | acaatccgaa | cttagttttg | aaagcagttt   1020 |
| tccattcatc | tcccaatttc | atacgaatct | ggtggtaccc | actacgcaaa | tcaactttag   1080 |
| aaaagacaat | ggcaccactc | aattcatcaa | gcatatcatc | taaacgtgga | atagggtgtc   1140 |
| gataacgtat | ggtgatatta | ttaatagccc | tacaatcaac | acacatacgc | catgttccat   1200 |
| ctttcttagg | cactaaaata | accggaacag | cacacggact | aagagactca | cgcacgtaac   1260 |
| cttttgtcgag | tagttcttgc | acttgtcgct | gaatttcttt | tgtttcctct | ggatttgtcc   1320 |
| tatatggcgc | acgattcggc | aaagatgcac | caggaataag | atcaatttgg | tgctcaatcc   1380 |
| ctcgtatagg | tggcagcccc | tctggtatct | cacttggaaa | tacatcagaa | tactcctgca   1440 |
| aaatgttagt | aataacagga | ggcaaagaat | gctgcatatc | ttgaattgaa | atcaaaacat   1500 |
| ccttgcatac | caaggcgtag | gcaacagtag | tggaagcaaa | taattcatta | acatcagttt   1560 |
| ttgttgcaag | caagcaatgt | cctttcaatt | ttatcccatc | tttgttatta | ccaacagctt   1620 |
| taatattctt | gttgttctca | gttttagctt | tggtagcttt | agcaacatca | tcacacacaa   1680 |
| tagcctcagg | ggacatggga | agcaaaataa | ttttcttatc | atggtgtatg | agagaatatt   1740 |
| tatttgatct | accatgatgc | atacaatctg | aatcaaattg | ccatggtcta | cctagcagaa   1800 |
| tattacaagc | atccataggc | acaacatcac | agtcaacaac | atcacgatat | gaaccaatag   1860 |
| caaaattaat | tcgtaccagc | ttggttacct | tgaccttacc | actattgtta | agccattgaa   1920 |
| tgtgatatgg | atgcgggtgc | ggtttggtcg | taagtgcaag | cttctccacc | atgtcgctgc   1980 |
| tagccaagtt | gttgcagcta | cctccatcaa | tgatcaaacg | acatgaacgc | tccttaatga   2040 |
| cacactttgt | ttgaaacaac | gtatgtcgct | gattctgctc | tgccttctcc | atttgtgcac   2100 |

```
taagcacacg ctgtacaatg aggctctcat aatgctctgc atcatctgca ccaatctgtt    2160
cttcgggtgg ttccttagtg cctgcatcat cagccgcaag caaagcaagt gtagcttcat    2220
ccaaatcact agcagaggaa tacccaccat cgtctttac caccaaaaca cgctgattag     2280
gacaatcacg ctgcacgtgt ccatagccct tgcatcgata acacagaaca tctcttgttc    2340
tacccgtgga ggctactgaa gaggcactac ctgctggttt ctgggcagat tggttgctg     2400 aatttgtgga agatgcacgt ggtttgtcgc cggaggaagg cggggggtgct ggtcgacttg   2460 gcgagggagt tggtgctggt gtacggccgg tcatggacgt agtcgtgcgc tgttgccatg    2520
gtgtagattt tcctgcagaa acattagacc ttgcactagc acgtcgtccc tgcacttccc    2580
tttcagcttt gcaagcaaga tgaaacaatc gggttacatt agcataatct ttataagcaa    2640
ggatgtcctg aatttcccta tttaacccgc ccaaaaatct agccatagca gattcctcac    2700
actcctctat gttacaacgc aacatacca tttgtaattc ctgataatat tcttctacac     2760
ttttagtacc ctgtctcaat tgttgcaact tgtttaacat atcacgtgca taataagaag    2820
gaacaaatct agcccgcatg acccgtttca acgcatccca agtttgtggc atgttattag    2880
gattcttctt accatgttct atccaccaaa cagaagcaaa ttcagtaaac tcactagtag    2940
cagctctaac ccgcacattc tcaggaaatt catggcatgc aaactttga tcaaccgcaa     3000 tctcccaagt aatgtaagca tcagggtcat atttaccatc aaaaggaggt attttaaatt    3060
taaccttact aaaagcatca tcattaccat gtacctcacg tcggtgaaaa ccacccatac    3120
ctctacggtt agtacgtagt cgccggcgat taggtgcttc ttggtcatct tgttcagtat    3180
cagcaacata gtcatcccag ttaccttcgg cgccctcatc acgcccacca ttgatattag    3240
catgcatctc atcaaaccgc ctcaagagtg cgacaaggct cttgtcaata tgagcaactg    3300
tcatttccac atttgcaagt ttggtgttcg tgtcgatctg tgtggcctcc aattgcccca    3360
tcttttcatt cgtcacctgc atgtcattat caagaccttc cgtgtgcgtc ttcactagcc    3420
ttacaaagtg ttgtatgata ccettggtgc gaggagagtg tggcatatta cgagaagcat    3480
catcaacctc caatcctgcc atggttagac gaacagaggc aacaagaaaa aaaaacgtga    3540
aggaatgaaa actctacaac tattaggatg tagctactgc aaggcgctca ctctcaacct    3600
gccacacaag ctcttaccaa ttcttacctt gcacaacagg aggggtcagc aaccaacaag    3660
tctgcaaccg tggaataagt gtatcggtgc cgcagcaaca cgacctgtca aactgtagtc    3720
gaaatatgta gagttgtagg tgggctgaag caaggaatac actagtacca cgttagttac    3780
aaaagcaagc tgaataatcg ttcaacggtg gtactgtgct ggtcctaggc taaaccaggt    3840
tagagacgtg agcctaggca caaaggtagt cactgaaaaa gaacaactag cacagcacaa    3900
agagaaacaa cagatttaga gattcagccc ccttcttctt ctttccttt ttttttctat     3960 tctttttttt tcttcttctt cttctgtttt tttttgcagg ggcttaaacc cttttttcac    4020
tatgacaacc caaacaataa agatattgct aacagcccct ttaaatcaga tttaacaaat    4080
cttgttaata tagaaagtcc agaaatctct acgatgattg cggagcgctc agaacgaatt    4140
ttgagataag gtcagatccg ttggaaagaa gataagataa gctttctaga ttgtatttaa    4200
acttccaaat cggatatgat atgtatccgt ggtggcaaaa acgaaccaga tatgttttg    4260 gtgatggtgg atctcgtggt gaccaaaacg tggtagaact caaaactcta aaggaataaa   4320
ctaagaccag caactcgaca caaccgatgc aaccaaaaac tcaacaagcc ctaactaagt    4380
agtactagta aatgctcaat ggtttatagg attgcggtaa aactaatcta ctatttttt    4440 ggcttttttct ggactatagg agataagaaa acagcgaaga aaagtaaatc tctcaccgat   4500
```

```
aaaccttgct ctgattacca actgatgtgc acccgttggg tgattgcccg atctttcgat   4560
gagagggtgt ggaataactc gattggggga ggagacgacg ttcacggccc gactacagcc   4620
ttccaaagac gctgcgcctt agcaaccgat acaccacctc ctatggctgt cacgatcttg   4680
tggagcgtga caccctggcc actagggcac tcgtcctgca agcaatcgaa gaactagcaa   4740
gaacaagtag aacaagtact gaattaccag atctaaatgt aggtttaaag atcaaactac   4800
aatatggtgg ggttccgaag acaagaagac gggcggctga actagcacgc gcgcttgcaa   4860
gcaagtagcg agagctaaac ttgatctaaa caaaacccgc tgttcttggt ggcagctagg   4920
gggtttataa acatgggagg acgaccacaa gggtattggg gtcgtgctgc aaccctagga   4980
tgcgtcccta atggacctaa cttgatacac gacccattgg gccaaaatag ggtgacgcag   5040
caccatgggc agaaaaggca ggaaatgtct cggtaataaa acaatgatta cggcggcctc   5100
agaacagata tgactataat tccggatcca tatgaaagta gacttgataa gctttccatg   5160
ttgtgcttga acattccaat ccgagcccgc atctgaccgt ggtgaccgtc acaagttggt   5220
gttcttctgc agtccgaatc cagcatgttc aaatcctttt ccctttcggt cttctccctg   5280
attcctaagc aaaacaagag tgcacgggtc tccatggtct aaatatgatg gacatgaact   5340
caagagtgta atcacctgat ggttgagttg acgagcacga gcgcgagtaa tgggaccaga   5400
aattggtact tgtattggta tagatgcatc agtagtgtgg atgtcttcat cattcagtgc   5460
catcgttgta gagggtttgg gcatatgatt cgggactgcc caaacaagcg taccttgctt   5520
atacgtgaca atggtgagta ctcttcagcc agtgattctg aggaaactag tcatgctatg   5580
attgccacta accatgcaga aaatgaggaa gtccacgttg atcctatcga cgccgatagg   5640
tatgagagtc ttgttgtgca gcgtgttctc agcacacagg ttgcccaggc cgaaaaaaat   5700
cagcgacaca ctctattcca taccaagggc gtcgtgcacg aacggtcgat tcgcatcatc   5760
atcgatagtg gcagctgcaa caatttggca agtacagcgt tggtagagaa attatccttg   5820
cccactcgca cacatccaca tccgtatcac attcaatggc ttaatgatgg tggtaaaata   5880
aaggtaacac gttcggtacg tgtccccttt tcgctgggtt cttattctga ttatgctgat   5940
tgcgatgtta ttcctatgga agcatgctct ttgttattag gtcgaccttg gcaatatgat   6000
actgatagtt tacatcatgg tcgttcaaat cattattctt tcatgtttaa aggccagaaa   6060
ataattatac atccaatgac ccctgaccaa attttgaaag atgatcttac tagggctgct   6120
aaaactgcac aacaagtcaa atcgacatca gccgcaccta ttaaatctga aatcaagttg   6180
cactctcctg ttttacttgc tacacgtgct gattttgatg atctccatga agctcatatg   6240
ccctgttatg cacttgtatg ctcgcgaatg attgttccgc ttgatgatgc aacgtctttg   6300 gatataccccc ctgctgttgt taaccttttg caggagtatg ctgatgttta tcctacggac   6360
ttaccaccgg gtcttcctcc cctccgtggc attgagcatc agatcgatct catccccggc   6420
gcttctcttc cgaaccgcgc cccgtaccgt acaaatccag atgagacgaa ggagatccag   6480
cgccaggtgc agacgctgct tgataagggt tacattcgtg agtctcttag cccttgctcg   6540
gttcctgttt tactcgtccc aaagaaagat gggtcatggc gtatgtgcgt agattgtcgt   6600
gctattaata acatcacagt tcgttatcga tatcctattc cacgccttga tgatatgcta   6660
gatgagctta gtggtgccgt tattttctct aaggttgatt tgcgtagcgg ttaccatcag   6720
attagaatga aactcggtga tgaatggaaa acggctttta aaacgaaatt tggtttatat   6780
gaatggttgg ttatgccatt tggattgact aatgctccca gcacctttat gcgtttaatg   6840
aacgaagttc tacgggcctt cataggtttg tttgttgttg tttatttcga tgatatcctt   6900
```

```
atttacagca agtctataga ggagcattta gaacatttgc gtgctgtttt tgacgctttg    6960
cgtgctgctc gcttgtttgg taacatggaa aagtgcacat tttgcacgca acgtgtctcg    7020
tttcttggtt atgtggttac tccgcagggc attgaggtgg atagcagcaa gattgctgcc    7080
attcgggagt ggcctacacc gacgacggtc acacaaattc ggagctttct tggacttgcc    7140
ggtttctacc gcagatttgt tcgtgatttt agctccattg cagcgcctct acatgagctt    7200
acaaagaaag atgtgccgtt tgcttggagt gattcgcagg aggtagcgtt cagcactttg    7260
aaagataagt taacccaagc tcccctattg caattgcctg attttaataa agtgtttgag    7320
cttgaatgcg atgctagcgg tattgggcta ggtgctgttt tgttacaaga aggaaaacca    7380
gttgcttatt ttagtgaaaa attaagcggt gctagtctga aatattctac ttatgataag    7440 gagcttacg ctttagtgcg cactttgcat acatggcagc actatctttg gcatcgtgag    7500
tttataatcc attctgatca tgaggcttta aaacatattc gtacccaaac aaatctgaac    7560
cgtcgtcatg ctaaatgggt agaattcatt gagtcctttc cttacattat aaacacaag    7620 aacgggaagg acaatgttat tgctgatgct ttgtctcgtc gctataccat gctgtcacag    7680
ttagatttta aaatctttgg tttggacact gtgaaggatc aatatgttga cgatgctgat    7740
tttaaagatg ctttcggtca ttgtattaat gggaaaccat ggggcaaatt tcacatacag    7800
gatgggttcc tgtttcgcgc taacaagctg tgtgttccag ctagctcggt tcgtcttttg    7860
ttgttacagg aagcgcatgg aggcggtctc atggggcatt tcggcctcta caagacacat    7920
gaggttttgg ctgcccattt cttttggcct cggatgcgcg ctgatgtgga gcgccttgtt    7980
gcacgctgca ctacttgtca gaaagctaag tcacggttga caaccatgg tttgtatatg    8040 cctttgcctg tcccttcttc tccttggctt gatatctcta tggactttgt tttgggcttg    8100
cctagaacta agaaggggag ggatagtatt tttgtggttg ttgatagatt ctctaaaatg    8160 gctcactta taccttgtca taaaactgat gatgctagca ttgttgctga attgttcttt    8220
agagaaatta ttcgtttaca tggtattcca aaaacaatag tctctgatcg cgatgctaag    8280
tttctaagcc attttggag atctcttgg aataaattgg gaactaaatt gttgtttagc    8340
actacttgtc accctcagac tgatggacaa actgaggtag taaatagaac tttatctacc    8400
atgcttaggg ctgttttaga caagaatttg agacgttggg aggattgctt gcctcatgtt    8460
gaatttgctt acaatcatgc cacgcattct tctacaaaga tgtgcccttt ccagattgtt    8520
tatggttaca ttcctagggc acctattgat ttgatttcac ttaatgctgc gaacgcccca    8580
catgtagatg cttctgcaca tgttgaacaa atgattacca tacatgaaca aacgaaacag    8640
aacattgctg ctactaatac aaaaaatcag gttgctggta gtaaaggaag aaaacatgtt    8700
acttttgaac ctggtgatat ggtttggttg catttgagaa aggatcgttt tcctactttg    8760
cgccgttcta aattgatgcc tcgtgctgct ggtccttta agatactaac caagattaat    8820
gataatgctt atacctcga cctacctgcg gagtttggtg tttccactag ttttaatgtt    8880
gcagatttga aaccgtatgc gggagaagat gaggagttgc cgtcgaggac gacttcagtt    8940
caagaagggg aggatgatgc ggacatcaac accaacacga gcacatctac accagcagca    9000
ccttctccag cccaggcgcc accccttcca cctgggccag tgactcgggc ccgtgcaaga    9060
gaattgaact acatcatgtt gttaaagaac gaaggcccgg aagaatagac gaccagccca    9120
attgcggccc ataatggacg acctagggtt ggccgcccct aggggctgcg cccctctct    9180 atttattcag gagctgcgcc tcctttattt cctgagtttt gttttacatt agccttagct    9240
actctcgaac acgcgcaaat ctgcgctgtc ttcgtgtatt cagaactcca ccctcgagta    9300
```

```
atagattaga ttgctcgcat cttgttcttg ttcattcttc gattgcgcac aggaaacgat   9360
cttcgtgatc aggccgatct cgcatcagca aggtcggtaa ccacagggag ttggttcagc   9420
gattgcattg gcgcctcggg cttgctcgtc gtagtcggat cgcaagggtc atcttccgcc   9480
aaatcggaat tatctctact tgccgaaaga tcgggcacct cagcttcatc accaagttct   9540
ttggtggctg ctagttgctt aaatagagaa ataggaagaa ggaattctgg tggagtcatg   9600
aagttccctc ggcagtttct ggacgcctcg ggtgtagtct cccattaatt cttgatccac   9660
cagcaagtag acgaagggag cttttccaaca agtatttatt tgcattaaac ggccttggaa   9720
gttggaagat atgccccatt taaacttgta tttggtgctg ttacgaaatc ctctcgggtg   9780
cagcagcctt tattgccttg ttgccttctc cagtccaaga tggttcacct cccaaacacc   9840
tgagcataat aaagtcatcg caaggcttta gtacctcatt taaagaagaa ttagcttcaa   9900
tagcaaagaa cgagttcacc tgataattaa gtttacgtgc acgggctcgt gtcattggtc   9960
cttgattagc tacgaatggt gaagtggtca ctggtatggt tgtatcaatg atagtgatgt  10020
cctcatcatc ctccccttct tgcaacaaag tcgtcctcga ctcaaacgtg tcattctctc  10080
ccaagtatgg tgttaaatct gcaatgttaa aagaggaact cacccaaaa tctgcaggca  10140 actgaacttt atatgcatta tcattaattt tgtgaagcac tttgaagggt ccagcagctc  10200
ttggttgtaa tttagatttg cgcatatcag ggaatctatc tttccttaaa tgcacccata  10260
ctaaatcacc aggttcaaag gtaatatgct ttctacccctt gctacctgct tcttcatact  10320
tagcattcat ggctttaata tttgctttag tttgttcatg cagctttata atcagttcag  10380
cacgacgaga agcatcaaaa ttcattattt cagaatgtgg gatggcgata agatcaatag  10440
gagcacgagg gacaaaacca tacacaattt taaaagggca tagtttagtt gtagaatgct  10500
gagaacgatt ataagcaaat tcaatgtgag gcaaacattc ttcccacaat ttgatgttat  10560
gtttcagaac agccctaagc atggtagata aactacggtt tacgacttcg gtttgtccat  10620
cggtttgagg gtgacaagta gtagaaaaga gcaatttagt tcccaactta gcccataacg  10680
ttttccaaaa atgactaaga aatttggtat cccgatcgga cacaatagtg tttggaaccc  10740
catgcaaacg aacaacttca cgaaagaaca aatcagcaac atgggtagcg tcatcagttt  10800
tgtgacatgg tataaagtgt gccattttttg aaaatctgtc cacaacaaca aaaatactat  10860
ccctcccctt ctttgttcta ggtattccta aaacaaagtc catagaaata tcctcccatg  10920
gtgcactggg aactgggaga ggcatgtata aaccatgtga attaaggcga gacttagctt  10980
tttgacatgt agtgcagcga gcaacaaatc gctccacgtc tcttctcatc ttcggccaaa  11040
agaaatggct ggccaggatg tcttatgtct tcttcacacc aaagtgtccc atcaacccac  11100
cgccatgtgc ttgctgtaat aataatatac gcacggaacc agctggaatg cataatttgt  11160
tagcccgaaa cacaaagcca tcagtgagaa caaatttgtt ccatgtcctt ccttctttac  11220
aatgtaatag cacatctttg aaatcagcat cgaaaacata ttcttgttta attgtttcca  11280
agccaaaaat cttaaaatca agttgagaca gcatggtata acggcgagac aaggcatctg  11340
caatgacatt atcttttcct ttcttatgtt tgatgacata gggaaaagat tcaataaatt  11400
cgacccactt ggcatgccta cggttcagat ttgtttggct ccttagatgc tttaaagatt  11460
catgatcaga atgtataaca aattcttag gccataagta gtgttgccat gtttccaaag  11520
ttcgaactaa ggcatataat tctttatcat aagtggaata gttcagactg gtccattca  11580 gtttctcact aaaataagca acaggcttcc cttcttgcaa caagacacca cccaaaccaa  11640
taccactagc atcacattcc aattcaaaag tcttactaaa atcaggtaat tggagaaggg  11700
```

```
gtgtatgagt taacctatcc ttcaatgttt caaatgcaac ctcttgtgcc ttgccccaag   11760
aaaaaggagc acccttctta gtaagctcgt gcaatggccc tgcgatggtg ctgaaatctt   11820
tcacaaatcg acgatagaac cccgcaagcc cgagaaagct tcggacttgc gtgaccgtgg   11880
tagggactgg ccagctatgt atggcctcca ccttagcctg atcaacttca attccctgcg   11940
gtgtcacaac atagccaaga aaagagacac ggtctgtgca aaatgtgcac ttgtcaaggt   12000
tatcaaataa gcgtgcttca cgtaaagcat tgaaaacaac acgtagatga tcaagatggt   12060
ctactagaca tttgttatag atccccgggt accgagctcg aattcgccct atagtgagtc   12120
gtattacaat tcactggccg tcgttttaca cgtcgtgac tgggaaaacc ctggcgttac   12180
ccaacttaat cgccttgcag cacatccccc tttcgccagc tggcgtaata gcgaagaggc   12240
ccgcaccgat cgcccttccc aacagttgcg cagctgaatg gcgaatggcg cctgatgcgg   12300
tattttctcc ttacgcatct gtgcggtatt tcacaccgca tatggtgcac tctcagtaca   12360
atctgctctg atgccgcata gttaagccag ccccgacacc cgccaacacc cgctgacgcg   12420
aaccccttgc ggccgcatcg aatataactt cgtataatgt atgctatacg aagttatggc   12480
gcgccaccgg tgggatccaa acagtcactt aggatatgtt tggaagcaca ccgacatgtt   12540
tggaagcaca ccagttttaa aaaactattt tctatcctca ctttcttgaa aatgttttat   12600 gaaaaaatt gggtgggtg tttggaacct agtttctagt tttttttataa ggagaatagc   12660 ttcttggttt tagttatggg agagtagctt cttggttttt aagaaactaa gaatccagtt   12720
tttataaact gagacataaa caagtatatt tggaatcact ctagtttgta caaaccaatt   12780
tcttagaaat tggatgctta taaataggcc ctcaatgtcc ttgttgggtt tatgaaattt   12840
acatctatta ccattatttt aaaaatagac gaagaatatg ttagtaatta tgtataaaaa   12900
actagaaact attttaaaaa aaactgagtt ccagttacct ttatctaatt cttttataag   12960
ctaattttta gacactgagg atagaaactg ttttaaaaa actggtgtgc ttctgtttaa   13020
ctcttcgtaa gaacagtggt acgtcccgtg tctatatttg gcttttgtta aagccaacag   13080
tacatgcttg cgtgggtgaa aatgtgaaat gccatcgctg tgctacaact tttcggctcc   13140
ctcctgcttc ggtgcttcca catgcccctg cacggcgtct agaaatccta atgatttagc   13200
agcacacctg tccgcctagc cgcctacgcg tacacagaaa acaatttttt tgtccacaca   13260
cgcgcgcgct ccgagccgca gatccgagct agcgcggcgc atccgacggc cacgacagcg   13320
cagtgccgtc ctccgccgcc accgcttggc gattgtccgc accccaccag tccaccacct   13380
cccccacgag cgaaaccac ggtccacgga ccacggctat gttccactcc aggtggaggc   13440 tgcagcccg gtttcgcaag ccgcgccgtg gtttgcttgc ccacaggcgg ccaaaccgca   13500
ccctccttcc cgtcgtttcc catctcttcc tcctttagag ctaccactat ataaatcagg   13560
gctcattttc tcgctcctca caggctcatc tcgctttgga tcgattggtt tcgtaactgg   13620
tgagggactg agggtctcgg agtggattga tttggggttc tgttcggaga tttgcggagg   13680
gaggccttgg taccggtgat caagtgcaaa ggtccgcctt gtttctcctc tgtctcttga   13740
tctgactaat cttggtttat gattcgttga gtaattttgg ggaaagcttc gtccacagtt   13800
ttttttcgat gaacagtgcc gcagtggcgc tgatcttgta tgctatcctg caatcgtggt   13860
gaacttattt cttttatatc ctttactccc atgaaaaggc tagtaatctt tctcgatgta   13920
acatcgtcca gcactgctat taccgtgtgg tccatccgac agtctggctg aacacatcat   13980
acgatctatg gagcaaaaat ctatcttccc tgttctttaa tgaaggacgt catttttcatt   14040 agtatgatct aggaatgttg caacttgcaa ggaggcgttt ctttctttga atttaactaa   14100
```

```
ctcgttgagt ggccctgttt ctcggacgta aggcctttgc tgctccacac atgtccattc    14160
gaattttacc gtgtttagca agggcgaaaa gtttgcatct tgatgattta gcttgactat    14220
gcgattgctt tcctggaccc gtgcagctgc ggtggcaagg gaggccggca agcgctagcg    14280
ctaccggtcg ccaccatggc ctcctccgag aacgtcatca ccgagttcat gcgcttcaag    14340
gtgcgcatgg agggcaccgt gaacggccac gagttcgaga tcgagggcga gggcgagggc    14400
cgcccctacg agggccacaa caccgtgaag ctgaaggtga ccaagggcgg ccccctgccc    14460
ttcgcctggg acatcctgtc ccccagttc cagtacggct ccaaggtgta cgtgaagcac    14520
cccgccgaca tccccgacta caagaagctg tccttccccg agggcttcaa gtgggagcgc    14580
gtgatgaact tcgaggacgg cggcgtggcg accgtgaccc aggactcctc cctgcaggac    14640
ggctgcttca tctacaaggt gaagttcatc ggcgtgaact tccctccga cggccccgtg    14700 atgcagaaga agaccatggg ctgggaggcc tccaccgagc gcctgtaccc ccgcgacggc    14760
gtgctgaagg gcgagaccca aaggccctg aagctgaagg acggcggcca ctacctggtg    14820
gagttcaagt ccatctacat ggccaagaag cccgtgcagc tgcccggcta ctactacgtg    14880
gacgccaagc tggacatcac ctcccacaac gaggactaca ccatcgtgga gcagtacgag    14940
cgcaccgagg gccgccacca cctgttcctg agatctcgag ctgatccaaa aagaagaga    15000 aaggtagatc caaaaaagaa gagaaaggta gatccaaaaa agaagagaaa ggtaggatcc    15060
accggatcta gataactgat cataatcagc cataccacat ttgtagaggt tttacttgct    15120
ttaaaaaacc tcccacacct cccctgaac ctgaaacata aatgaatgc aattgcagcg    15180 cttgagctct cctaggtccg cggaggcaat gccagcctgc cctttcgatg aggaggtaca    15240
tacacgctgg cgatggaccg cgcttgtgtg tcgcgttcag tttggctttt gccaagcagt    15300
agggtagctt cccgcgtcgg taattatatg gtatgaacca tcacctttg gctctacatg    15360 gtatgaacgt aagatacaaa ttccaactac ctctagctcg ccgcactagt tcctgcaggt    15420
tggcccacgt ggcctctcga gtgttaaac tcggaccgta tcgatttatt caacaaagcc    15480
gccgtcccgt caagtcagcg taatgctctg ccagtgttac aaccaattaa ccaattctga    15540
```

<210> SEQ ID NO 68
<211> LENGTH: 14443
<212> TYPE: DNA
<213> ORGANISM: Zea mays

<400> SEQUENCE: 68

```
ggaagctttc cagcaatttc gttgccgcac gtcactcatt ccgaaaacga gtgtcaggtg      60
cataaaagca cgagttttg ccaccggaac catttcttcg ttttcgtaa cgaacatgcc     120 caatccacta ctttaggtcc aaaactcatg tttggggtgg tttcacacaa tttcgttgtc     180
gcacgtcacc cattccgaaa acgggtgtcg ggtgcataca aagcacgagt ttttgccacc     240
ggaaccattt cttcgttttt cgcaacgaac atgcctaatc cagtacttta ggtccaaaac     300
tcatgtttgg ggtggtttct cgcaatttcg ttgtcgcacg tcacccattc cgaaaactgg     360
tgtcatggtg catacaaagc acgagttttt gccaccggaa ccatttcttt gttttttgca     420
acgaacatgc ccaatccact actttaggtc caaaactcat gtgttggggt ggtttcgcac     480
aatttcgttg tcgcacgtct cacccattcc gaaaacgggt gtcatggtgc atacaaagca     540 cgagttttg ccaccggaac catttctttg ttttcgcaa cgaacatgcc caatccacta     600
ctttaggtcc aaaactcatg tttggggtgg tttcgcgcaa tttcgttgcc gcacgtcacc     660
cattccgaaa acgggtgtcg ggtgcataca aagcacgagt ttttgccact ggaaccattt     720
```

```
cttcgttttt ctcaacgaac atgcccaatc cactacttta ggtacaaaac tcatgttttg      780
ggtggtttca cgcaatttcg ttgccgcacg tcactcattc tgaaaacgag tgtcgggtgc      840
ataaaagcac gagtgtttgc caccggaacc atttcttcgt ttttcgcaac gaacatgccc      900
aatccactac tttaggtcca aaactcatgt ttgaggtggt tcgcgcaat ttcgttgtca       960
cacgtcacct attctgaaaa cgggtatcgg ggtgcataaa agcacgagtt tttgccaccg     1020
gaaccatttc ttcgtttttc gtaacaaaca tgcccaatcc actactttag gtcgtttcgc     1080
acaatttcgt tgtcgcacgt cacccattcc gaaaacgggt gtcatggtgc atacaaagca     1140
cgaattttg ccaccggaac catttcttcg ttttcgcaa cgaacatgcc caatccacta       1200
ctttaggtcc aaaactcatg tttggggtgg tttcgcacaa tttcgttgtc gcacgtcacc     1260
cattctgaaa cgggtgtca tgtgcatac aaagcacgag tttttgccac cggaaccatt      1320
tctttgtttt tcgcaacgaa catgcccaac ccactacttt aggtccaaaa ctcatgtttg     1380
gggtggtttc gcgcaatttc gttgtcgcac gtcaccccatt ccgaaaacgg tgtcgggtg    1440
catacaaagc acgagttttt gccaccggaa ccatttcttc gttttcgca acgaacatgc     1500
ccaatccact actttaggtc caaaactcat gtttggggtg tttcacgca atttcgttgt     1560
cgcacgtcac ccattccgaa aacgggtgtc gggtgcatac agagctcgag tttttgccac     1620
cggaaccatt tcttcgtttt tcgcaatgaa catgcccaat ccactacttt aggtccaaaa    1680
ctcatgtttg gggtggtttc gcgcaatttc gttgtcgcac gtcacccatt ccgaaaacgg     1740
gtgtcgggtg catacaaagc acgagttttt gccaccggaa ccatttcttc gttttcgca     1800
acgaacatgc ccaatccact actttaggtc caaaactcat gtttggggtg atttctcgca    1860
atttcgttgt cgcacgtcac ccattccgaa aacgggtgtc gggtgcatac aaagcacgag    1920
tttttgccac cggaaccatt tcttcgtttt ttgtaacgaa catgcccaat ccactacttt    1980
aggtccaaaa ctcatgtttg ggtggtttc gcgcaatttc gttgtcacgc gtcacccatt     2040
ccgaaaacgg gtgtcggagt gcatacaaag cacgagtttt tgccaccgga accatttctt    2100
tgttttttcgc aacgaacatg cccaatccac tatttaggt ccaaaactca tgtttggggt    2160
ggtttcgcac aatttcgttg tcgcacgtca cctattccga aaacaggtgt catggtgcat    2220
acaaagcacg agttttttgcc accggaacca tttcttcgtt tttcgcaacg aacatgccca   2280
atccactact ttaggtccaa aactcatgtt tggggtggtt tcgaacaatt tcgttgtcgc    2340
acgtcaccca ttccgaaaac gggtgtcatg gtgcatacaa agcacgagtt tttgccaccg    2400
gaaccatttc tttgttttc gcaacgaaca tgcccaatcc actactttag gtccaaaact     2460
catgtttggg gtggtttcgc gcaatttcgt tgccgcatgt cacccattcc gaaaacgggt    2520
atcgggtgc ataaaagcac gagttttttgc caccggaacc atttcttcgt ttttcgcaac    2580
gaacatgccc aatccactac tttaggtcca aaactcatgt ttggggtggt tcgcgcaat    2640
ttcgttgtcg cacgtcaccc attccgaaaa cgggtgtcgg gtgcatacaa agcacgagtt    2700
tttgccaccg gaaccatttc ttcgttttc gtaacgaaca tgcccaatcc actactttac    2760
atccaaaact catgtttggg gtggtttcgc gcaatttcgt tgtcgcacgt cacccattcc    2820
gaaaacgggt gtcgggtgaa taaaaagcac gagttttttgc caccggaacc atttcttcgt    2880
ttttcgcaac gaacatgctc aatccactac tttaggtcca aaactcatgt ttggggtgat    2940
ttcgcacaat ttcgttgtcg cacgtcaccc attccgaaaa cgggtgtcgg gtgcatacaa    3000
agcacgagtt tttgccaccg gaaccatttc ttcgtttttt gtaacgaaca tgcccaatcc    3060
actactttag gtccaaaact catgtttggg gtggtttcgc gcaatttcgt tgtcgcacgt    3120
```

```
cacccattcc gaaaacgggt gtcgggtgaa taaaaagcac gagttttttgc caccggaacc   3180
atttcttcgt ttttcgcaat gaacatgccc aatccactac tttaggtcca aaactcatgt   3240
ttggagtggt ttcgcgcaat ttcgttgccg cacgtcaccc attccgaaaa cggttgtcgg   3300
gggtgcatac aaagcacgag ttttttgccac cggaaccatt tcttcgtttt tcgcaacgaa   3360
catgcccaat ccactacttt aggtccaaaa ctcatgtttg gggaggtttc gcacaatttc   3420
gttgtcgcac gtcacccatt ctgaaaacgg gtatcggggt gcataaaagc acgagttttt   3480
gccaccggaa ccatttcttc gttttttcgca acgaacatgc ccaatccact actttaggtc   3540
caaaactcat gtttggggtg gtttcgcgca attttgttgt cgcacgtcac ccattctgaa   3600
aacgtgtatc ggggtgcata aaagcacgag ttttttgccac cggaaccatt tcttcgtttt   3660
tcgtaacgaa catgccgaat ccactacttt aggtccaaaa ctcatgtttg ggtggtttc   3720
gcacaatttc gttgtcgcac gtcacccatt ccgaaaacgg gtgtcgggtg catacaaagc   3780
acgagttttt gccaccggaa ccatttcttc gttttttcgca acgaacatgc ccaatccact   3840
actttacatc caaaactcat gtttggggtg gtttcgcgca atttcgttgt cgcacgtcac   3900
ccattccgaa aacgggtgtc gggtgaataa aaagcacgag ttttttgccac ctgaaccatt   3960
tcttcgtttt tcgcaacgaa catgcccaat ccactacttt aggtccaaaa ctcatgtttg   4020
gggtggtttc gcgcaatttc gttgccgcac gtcacccatt ccgaaaacgg ttgtcggggg   4080
tgcatacaaa gcacgagttt ttgccaccgg aaccatttct tcgttttttcg caacgaacat   4140
gcccaatcca ctactttagg tccaaaactc atgtttgggg tggttcgca cagtttcgtt   4200
gtcgcacgtc acccattctg aaaacgggta tcggggtgca taaaagcacg agttttttgcc   4260
accggaacca tttcttcgtt tttcgcaacg aacatgccca atccactact ttaggtccaa   4320
aactcatgtt tgggatggtt tcgcgcaatt ttgttgtcgc acgtcaccca ttctgaaaac   4380
gggtatcggg gtgcataaaa gcacgagttt ttgccaccgg aaccatttct tcgttttttcg   4440
taacgaagat gcagaatcca ctactttagg tccaaaactc atgtttgggg tggtttagca   4500
caatttagtc gttgcacgtc acccattccg aaaacgggtg tcgggtgcat acaaagcacg   4560
agttttttgcc accggaacca tttcttcgtt tttcgcaacg aacatgccga atccactact   4620
ttaggtccaa aactcatgtt tggggtgatt tctcgcaatt tcgttgtcgc acgtcaccca   4680
ttccgaaaac gggtgtcggg tgcatacaaa gcacgagttt ttgccaccgg aaccatttct   4740
tcgttttttcg caacgaacat gcccaaccca ctactttagg tccaaaactc atgtttgggg   4800
tggtttcgcg caatttcgtt gccgcacgtc acccattctg aaaacggttg tcggggtggg   4860
gtgcatacaa agcacgattt tgccaccgg aaccatttct tcgttttttag caacgaacat   4920
gcccaatcca ctactttagg tacaaaactc ttgtttgggg tggttcgcg caatttcgtt   4980
gccgcacgtc acccattccg aaaacgggtg tcgggtgcat acaaagcacg agttttttgcc   5040
accggaacca tttcttcgtt tttcgcaacg aacatgccca atccactact ttaggtccaa   5100
aactcatgtt tggggtggtt tcgcgcaatt tcgttgtcgc acgtcaccca ttctgaaaaa   5160
gggtatcggg gtgcataaaa gcacgagttt ttgccaccgg aaccatttct tcgttttttcg   5220
caacgaacat gcccaatcca ctactttagg tccaaaactc atgtttgggg tggttcgcg   5280
caatttttgtt gtcgcacgtc acccattctg aaaacgggta tcggggtgca taaaagcacg   5340
agttttttgcc accggaacca tttcttcgtt tttcgcaacg aacatgccga atccactact   5400
ttaggtccaa aactcatgtt tggggtggtt tcgcacaatt tcgttgtcgc acgtcaccca   5460
ttccgaaaac gggtgtcggg gtgcatacaa agcacgagtt tttgccaccg gaaccatttc   5520
```

-continued

```
ttcgtttttc acaacgaaca tgcccaatcc actactttag gtccaaaact catgtttggg      5580
gtggtttcgc acagtttcgt tgtcgcacgt cacccattct gaaaacgggt atcggggtgc      5640
ataaaagcac gagttttgc caccggaacc atttcttcgt ttttcgcaac gaacatgccc       5700
aatccactac tttaggtcca aaactcatgt ttggggtggt tcgcgcaat ttcgttgccg       5760 cacgtcaccc attccgaaaa cggttgtcgg ggtgcataca aagcacgagt ttttgccacc     5820
ggaaccattt cttcgttttt cacaacgaac atgcccaatc cactactttta ggtccaaaac    5880 tcatgtttgg ggtggtttcg cacagtttcg ttgtcgcacg tcacccattc tgaaaacggg     5940
tatcggggtg cataaaagca cgagttttg ccaccggaac catttcttcg ttttcgcaa       6000 cgaacatgcc caatccacta ctttaggtcc aaaactcatg tttggggtgg tttcgcgcaa     6060
ttttgttgtc gcatgtcacc cattccgaaa acgggtatcg gggtgcataa aagcacgagt     6120
ttttgccacc ggaaccattt cttcgttttt cgcaacgaac atgcccaatc cactactttta   6180 ggtccaaaac tcatgtttgg ggtggtttcg cgcaatttcg ttgccgcacg tcacccattc    6240
cgaaaacggt tgtcggggtg catacaaagc acgagttttt gccaccggaa ccatttcttc    6300
gtttttcaca acgaacatgc ccaatccact actttaggtc caaaactcat gtttggggtg    6360
gtttcgcaca gtttcgttgt cgcacgtcac ccattctgaa acgggtatc ggggtgcata      6420 aaagcacgag ttttgccac cggaaccatt cttcgtttt tcgcaacgaa catgcccaat      6480 ccactactt aggtccaaaa ctcatgtttg ggtggtttc gcgcaattt gttgtcgcac       6540 gtcacccatt ctgaaaacgg gtatcggggt gcataaaagc acgagttttt gccaccggaa    6600
ccatttcttc gtttttcgta acgaacatgc ccaatccact acttaggtc caaaactcat     6660 gtttggtgtg gtttcgcaca atttcgttgt cgcacgtcac ccattccgaa acgggtgtc     6720 gggtgcatac aaagcacgag ttttgccac cggaaccatt cttcgtttt tcgcaacgaa      6780 catgcccaat ccactactt acatccaaaa ctcatgtttg ggtggtttc gcgcaatttc      6840 gttgtcgcac gtcacccatt ccgaaacgg gtgtcgggtg catacaaagc acgagttttt    6900
gccaccggaa ccatttcttc gtttttcgca acgaacatgc ccaatccact actttacatc   6960
caaaactcat gtttggggtg gtttcgcgca atttcgttgt cgcacgtcac ccattccgaa    7020
aacgggtgtc ggtgaataa aaagcacgag ttttgccac cggaaccatt cttcgtttt       7080 tcgcaacgaa catgcccaat ccactacttt aggtccaaaa ctcatgtttg gagtggtttc    7140
gcgcaatttc gttgccgcac gtcacccatt ccgaaaacgg ttgtcggggg tgcatacaaa    7200
gcacgagttt tgccaccgg aaccattct tcgtttttcg caacgaacat gcccaatcca      7260
ctactttagg tccaaaactc atgtttgggg tggtttcgcg caatttcgtt gtcgcacgtc   7320
acccattctg aaaacgggta tcggggtgca taaaagcacg agttttgcc accggaacca    7380 tttcttcgtt tttcgcaagg acatgcccaa tccactactt taggtccaaa actcatgttt    7440
ggggtggttt cgcgcaattt tgttgtcgca cgtcacccat tctgaaaacg tgtatcgggg    7500
tgcataaaag cacgagtttt tgccaccgga accatttctt cgttttcgt aacgaacatg     7560 ccgaatccac tactttaggt ccaaaactca tgtttgggt ggtttcgcac aatttcgttg     7620
tcgcacgtca cccattccga aaacgggtgt cgggtgcata caaagcacga ttttttgcca    7680
ccggaaccat ttcttcgttt tcgcaacga acatgcccaa tccactactt tacatccaaa     7740
actcatgttt ggggtggttt cgcgcaattt cgttgtcgca cgtcacccat tccgaaacg     7800 ggtgtcgggt gaataaaaag cacgagtttt tgccaccgga accatttctt cgttttcgc    7860 aacgaacatg cccaatccac tactttaggt ccaaaactca tgtttggggt ggtttcgcac   7920
```

```
aatttcgttg tcgcacgtca cccattctga aaacgggtgt catggtgcat acaaagcacg   7980 agttttttgcc accggaacta tttctttgtt tttcgcaacg aacatgccaa tccactactt   8040
taggtccaaa actcatgttt tgggtggttt cgcgcaattt cgttgccgca cgtcacccat   8100
tctgaaaacg ggtgtggggt tgcatacaaa gcacagagtt ttgccacagg aaccatttct   8160
tcgtttttct caacgaacat gcccaatcca ctactttagg tacaaaactc atgttttggg   8220
tggttttgcg caatttcgtt gccgcacgtc actcattccg aaaacgagtg tggggttgca   8280
tacaaagcac gagttttttgc caccggaacc atttcttcgt ttttcgtaac gaacatgccc   8340
aatccactac tttaggtcca aaactcatgt ttggggtggt ttcacacaat ttagttgtcg   8400
cacgtcaccc attccgaaaa cgggtatcgg gtgcatacaa agcacgagtt tttgccaccg   8460
gaaccatttc ttcgttttttc gcaacgaaca tgcctaatcc agtactttag gtccaaaact   8520
catgtttggg gtggtttctc gcaatttcgt tgtcgcacgt cacccattcc gaaaacgggt   8580
gtcatggtgc atacaaagca cgagttttttg ccaccggaac catttcttttg ttttttgcaa   8640 cgaacatgcc caatccacta ctttaggtcc aaaactcatg tgttggggtg gtttcgcaca   8700
atttcgttgt cgcacgtctc acccattccg aaaacgggtg tcatggtgca tacaaagcac   8760 gagttttttgc caccggaacc atttctttgt ttttcgcaac gaacatgccc aatccactac   8820
tttaggtcca aaactcatgt ttcgggtggt ttcgcgcaat ttcgttgccg cacgtcaccc   8880
attccgaaaa cgggtgtcgg gtgcatacaa agcacgagtt tttgccaccg gaaccatttc   8940 ttcgttttttc tcaacgaaca tgcccaatcc actactttag gtacaaaact catgttttgg   9000
gtggtttcgc gcaatttcgt tgccgcacgt cactcattcc gaaaacgagt gtcgggtgca   9060
taaaagcacg agtgtttgcc accggaacca tttcttcgtt tttcgcaacg aacatgccca   9120
atccactact ttaggtccaa aactcatgtt tgaggtggtt tcgcgcaatt tcgttgtcgc   9180
acgtcaccca ttctgaaaac gggtatcggg gtgcataaaa gcacgagttt ttgccaccgg   9240
aaccatttct tcgttttttcg taacaaacat gcccaatcca ctactttagg tccaaaactc   9300
atgtttgggg tggtttcgca caatttcgtt gtcgcacgtc acccattccg aaaacgggtg   9360
tcgggtgcat acaaagcacg agttttttgcc accggaacca tttctttgtt tttcgtaacg   9420
aacatgccca atccactact ttaggtccaa aactcatgtt tgaggtggtt tcgcgcaatt   9480
tcgttgtcgc acgtcaccca ttccgaaaac gggtgtcggg tgcatacaaa gcacgagttt   9540
ttgccaccgg aaccatttct tcgttttttcg caacgaacat gcccaatcca ctactttagg   9600
tccaaaactc atgtttgggg tggtttcgcg caatttcgtt gtcgcatgtc actcattccg   9660
aaaacgggtg tcgggtgcat acagagcacg agttttttgcc accggaacca tttcttcgtt   9720
tttcgcaatg aacatgccca atccactact ttaggtccaa aactcatgtt tggggtggtt   9780
tcgcgcaatt tcgttgtcgc acgtcaccca ttccgaaaac gggtgtcggg tgcatacaaa   9840
gcacgagttt ttgccaccgg aaccatttct tcgttttttgc gaacatgccc aatccactac   9900
tttaggtcca aaactcatgt ttgggtggt ttcgcgcaat ttcgttgccg cacgtcaccc   9960
attccgaaaa cggttgtcgg gggtgcatac aaagcacgcg ttttttgccac cggaaccatt   10020 tcttcgttttt tcgcaacgaa catgcccaat ccactacttt aggtacaaaa ctcatgtttg   10080
ggtggtttcg cgcaatttcg ttgtcacacg tcacccattc cgaaaagggt gtcggagtgc   10140
atacaaagca cgagttttttg ccagcggaac catttcttcg ttttttcgcaa cgaacatgcc   10200 taatccacta ctttaggtcc aaaactcatg tttggggtgg tttctcgcaa ttttgttgtc   10260
gcacgttacc cattccgaaa acgggtgtca tggtgcatac aaagcacgag ttttttgccac   10320
```

```
cggaaccatt tctttgtttt tcgcaacgaa catgcccaac ccactacttt aggtccaaaa    10380
ctcatgtttg gggtggtttc gcgcaatttc gttgtcgcac gtcacccatt ccgaaaacgg    10440
gtgtcgggtg catacagagc acgagttttt gccaccagaa ccatttcttc gttttcgca     10500
atgaacatgc ccaatccact actttaggtc caaaactcat gtttggggtg gtttcgcgca    10560
atttcgttgt cgcacgtcac ccattccgaa acgggtgtc  gggtgcatac aaagcacgag    10620
ttttgccac  cggaaccatt tcttcgtttt tcgcaacgaa catgcccaat ccactacttt    10680
aggtccaaaa ctcatgtttg ggtggtttc  gcgcaatttc gttgccgcac gtcacccatt    10740
ccgaaaacgg ttgtcggggg tgcatacaaa gcacgcgttt tgccaccgg  aaccatttct    10800
tcgtttttcg caacgaacat gcccaatcca ctactttagg tacaaaactc atgtttgggt    10860
ggtttcgcgc aatttcgttg tcacacgtca cccattccga aagggtgtc  ggagtgcata    10920
caaagcacga gttttttgcca gcggaaccat ttcttcgttt ttcgcaacga catgcctaa    10980
tccactactt taggtccaaa actcatgttt ggggtggttt ctcgcaattt tgttgtcgca    11040
cgttacccat tccgaaaacg ggtgtcatgg tgcatacaaa gcacgagttt tgccaccgg     11100
aaccatttct ttgtttttcg caacgaacat gcccaatcca ctactttagg tccaaaactc    11160
atgtttgggg tggtttcgca caatttcgtt gtcgcacgtc acccattccg aaaacgggtg    11220
tcgggtgcat acaaagcacg agttttttgcc accggaacca tttcttcgtt tttcgcaacg    11280
aacatgccca atccactact ttaggtccaa aactcatgtt tggggtggtt tcgcacaatt    11340
tcgttgtcgc acgtcaccca ttctgaaaac gggtgtcatg gtgcatacaa agcacgagtt    11400
tttgccaccg gaactatttc tttgtttttc gcaacgaaca tgccaatcca ctactttagg    11460
tccaaaactc atgttttggg tggtttcgcg caatttcgtt gccgcacgtc acccattctg    11520
aaaacgggtg tggggttgca tacaaagcac gagtttttgc cacaggaacc atttcttcgt    11580
ttttctcaac gaacatgccc aatccactac tttaggtaca aaactcatgt tttgggtggt    11640
tttgcgcaat ttcgttgccg cacgtcactc attccgaaaa cgagtgtcag gtgcataaaa    11700
gcacgagttt ttgccaccgg aaccatttct tcgtttttcg taacgaacat gcccaatcca    11760
ctactttagg tccaaaactc atgtttgggg tggtttcaca caatttcgtt gtcgcacgtc    11820
acccattccg aaaacgggtg tcgggtgcat acaaagcacg agttttttgcc accggaacca    11880
tttcttcgtt tttcgcaacg aacatgccta atccagtact ttaggtccaa aactcatgtt    11940
tggggtggtt tctcgcaatt tcgttgtcgc acgtcaccca ttccgaaaac gggtgtcatg    12000
gtgcatacaa agcacgagtt tttgccaccg gaaccatttc tttgtttttt gcaacgaaca    12060
tgcccaatcc actactttag gtccaaaact catgtgttgg ggtggtttcg cacaatttcg    12120
ttgtcgcacg tctcacccat tccgaaaacg gtgtcatgg  tgcatacaaa gcacgagttt    12180
ttgccaccgg aaccatttct ttgtttttcg caacgaacat gcccaatcca ctactttagg    12240
tccaaaaatc atgtttgggg gggtttcgca caatttcgtt gccgcacgtc acccattccg    12300
aaaacggttg tcggggtgc  atacaaagca cgagtttttg ccaccggaac catttcttcg    12360
ttttttcgcaa cgaacatgcc caatccacta ctttaggtcc aaaactcatg tttgggtgg    12420
tttcgcacag tttcgttgtc gcacgtcacc cattctgaaa acgggtatcg ggtgcataa     12480
aagcacgagt ttttgccacc ggaaccattt cttcgttttt cgcaacgaac atgcccaatc    12540
cactacttta ggtccaaaac tcatgtttgg gatggtttcg cgcaattttg ttgtcgcacg    12600
tcacccattc tgaaacggg  tatcggggtg cataaaagca cgagttttg  ccaccggaac    12660
catttcttcg tttttcgtaa cgaagatgca gaatccacta ctttaggtcc aaaactcatg    12720
```

-continued

| | | |
|---|---|---|
| tttggggtgg tttcgcacaa tttcgttgtc gcacgtcacc cattccgaaa acgggtgtcg | 12780 |
| ggtgcataca aagcacgagt tttttgccacc ggaaccattt cttcgttttt cgcaacgaac | 12840 |
| atgcccaatc cactacttta catccaaaac ccatgtttgg ggtggtttct cgcaatttcg | 12900 |
| ttgtcgcacg ttgaaagctc tcttgtgagt tttggtgttt ggatgacaac tcaattaaag | 12960 |
| gactaacaag agtactaagt gttgaacagg tgcttaaggt aaagcctaca gggttcaaca | 13020 |
| caagtgaaca aatgtgatgg tccaagaact ggattatgga tacataatgg acatcacaag | 13080 |
| taagttggac attgcaaaag tgatactcgg gtgcgtagct cggagacaac tgatcaagcc | 13140 |
| aaggacggag gaagaaaagc ttcgaggtac caagtgcacg ggagaaggtc aaggaggctg | 13200 |
| aggaacccaa agccaagggc gaagaagaag gcttgcaaag tcaagggtga tcgagttgag | 13260 |
| aacagctacg gcacatcaag gatcactata taaggacgcg acttacaacc aatgaggtaa | 13320 |
| cagctacagt tatgtggtgt aagtcataag gctcaagacc aagctctaag aaggagatcc | 13380 |
| tctagagtcg acctgcaggc atgcaagctt gagtattcta tagtgtcacc taaatagctt | 13440 |
| ggcgtaatca tggtcatagc tgtttcctgt gtgaaattgt tatccgctca caattccaca | 13500 |
| caacatacga gccggaagca taaagtgtaa agcctgggt gcctaatgag tgagctaact | 13560 |
| cacattaatt gcgttgcgct cactgcccgc tttccagtcg ggaaacctgt cgtgccagct | 13620 |
| gcattaatga atcggccaac gcgaaccect tgccggccgcc cgggccgtcg accaattctc | 13680 |
| atgtttgaca gcttatcatc gaatttctgc cattcatccg cttattatca cttattcagg | 13740 |
| cgtagcaacc aggcgtttaa gggcaccaat aactgcctta aaaaaattac gccccgccct | 13800 |
| gccactcatc gcagtactgt tgtaattcat taagcattct gccgacatgg aagccatcac | 13860 |
| aaacggcatg atgaacctga atcgccagcg gcatcagcac cttgtcgcct tgcgtataat | 13920 |
| atttgcccat ggtgaaaacg ggggcgaaga agttgtccat attggccacg tttaaatcaa | 13980 |
| aactggtgaa actcacccag ggattggctg agacgaaaaa catattctca ataaacccttt | 14040 |
| tagggaaata ggccaggttt tcaccgtaac acgccacatc ttgcgaatat atgtgtagaa | 14100 |
| actgccggaa atcgtcgtgg tattcactcc agagcgatga aaacgtttca gtttgctcat | 14160 |
| ggaaaacggt gtaacaaggg tgaacactat cccatatcac cagctcaccg tctttcattg | 14220 |
| ccatacgaaa ttccggatga gcattcatca ggcgggcaag aatgtgaata aaggccggat | 14280 |
| aaaacttgtg cttatttttc tttacggtct ttaaaaaggc cgtaatatcc agctgaacgg | 14340 |
| tctggttata ggtacattga gcaactgact gaaatgcctc aaaatgttct ttacgatgcc | 14400 |
| attgggatat atcaacggtg gtatatccag tgatttttttt ctc | 14443 |

<210> SEQ ID NO 69
<211> LENGTH: 20048
<212> TYPE: DNA
<213> ORGANISM: Zea mays

<400> SEQUENCE: 69

| | | |
|---|---|---|
| cgaatcctag atatcatcgc cactgtgctg gaagttcgtt gtgaaaacga agaaatggtt | 60 |
| ccggtggcaa aaactcgtgc tttgtatgca ccccgacaac cgttttcgga atgggtgacg | 120 |
| tgcggcaacg aaattgcgcg aaaccacccc aaacatgagt tttggaccta agtagtggag | 180 |
| ttgggcatgt tcgttgcgaa aaacgaagaa atggttccgg tggcaaaaac tcgtgctttt | 240 |
| tattcacccg acaccgtttt cggaatgggt gacgtgcga caacgaaatt gcgcgaaacc | 300 |
| accccaaaca tgagttttgg atgtaaagta gtggattggg catgttcatt gcgaaaaacg | 360 |
| aagaaatggt tccggtggca aaaactcgtg ctttgtatgc acccgacacc cgttttcgga | 420 |

```
atgggtgacg tgcgacaacg aaattgtgcg aaaccacccc aaacatgagt tttggaccta       480
aagtagtgga ttcggcatgt tcgttacgaa aaacgaagaa atggttctgg tggcaaaaac       540
tcgtgctttt atgcaccccg atacccgttt tcagaatggg tgacgtgcga caacaaaatt       600
gcgcgaaacc accccaaaca tgagttttgg acctaaagta gtggattggg catgttcgtt       660
gcgaaaaacg aagaaatggt tccggtggca aaaactcgtg cttttatgca ccccgatacc       720 cttttcaga atgggtgacg tgcgacaacg aaactgtgcg aaaccacccc aaacatgagt       780
tttggaccta tagtagtgga ttgggcatgt tcgttgtgaa aaacgaagaa atggttccgg       840
tggcaaaaac tcgtgctttg tatgcacccc gacaaccgtt ttcggaatgg gtgacgtgcg       900
gcaacgaaat tgcgcgaaac caccccaaac atgagttttg gacctaaagt agtggattgg       960
gcatgttcgt tgcgaaaaac gaagaaatgg ttccggtggc aaaaactcgt gcttttatt      1020 cacccgacac ccgttttcgg aatgggtgac gtgcgacaac gaaattgcgc gaaaccaccc      1080
caaacatgag ttttggatgt aaagtagtgg attgggcatg ttcattgcga aaaacgaaga      1140
aatggttccg gtggcaaaaa ctcgtgcttt gtatgcaccc gacacccgtt tcggaatgg      1200 gtgacgtgcg acaacgaaat tgtgcgaaac caccccaaac atgagttttg gacctaaagt      1260
agtggattgg gcatgttcgt tgagaaaaac gaagaaatgg ttccagtggc aaaaactcgt      1320
gctttgtatg cacccgacac ccgttttcgg aatgggtgac gtgcggcaac gaaattgcgc      1380
gaaaccaccc gaaacatgag ttttggacct aaagtagtgg attgggcatg ttcgttgcga      1440
aaaacaaaga atggttccg gtggcaaaaa ctcgtgcttt gtatgcacca tgacacccgt      1500
tttcggaatg ggtgacgtgc gacaacgaaa ttgttcgaaa ccaccccaaa catgagtttt      1560
ggacctaaag tagtggattg gcatgttcg ttgcgaaaaa cgaagaaatg gttccggtgg      1620
caaaaactcg tgctttgtat gcaccatgac acctgttttc ggaataggtg acgtgcgaca      1680
acgaaattgt gcgaaaccac cccaaacatg agttttggac taaagtagt ggattgggca      1740 tgttcgttgc gaaaaataaa gaaatggttc cggtggcaaa aactcgtgct ttgtatgcac      1800
catgacaccc gttttcggaa tgggtgacgt gcgacaacga aattgcgaga accaccccca      1860
aacatgagtt tttggaccta a agtagtggat taggcatgtt cgttgcgaaa acgaagaaa      1920 tggttccggt ggcaaaaact cgtgctttgt atgcactccg acaccgtt tcggaatggg      1980 tgacgcgtga caacgaaatt gcgcgaaacc accccaaaca tgagttttgg acctaaagta      2040
gtggattggg catgttcgtt acaaaaaacg aagaaatggt tccggtggca aaaactcgtg      2100
ctttgtatgc acccgacacc cgttttcgga atgggtgacg tgcgacaacg aaatatcgag      2160
aaatcacccc aaacatgagt tttggaccta agtagtgga ttgggcatgt tcgttgcgaa      2220
aaacgaagaa atggttccgg tggcaaaaac tcgtgctttg tatgcacccg acacccgttt      2280
tcggaatggg tgacgtgcga caacgaaatt gcgcgaaacc accccaaaca tgagttttgg      2340
acctaaagta gtggattggg catgttcatt gtgaaaaacg aagaaatggt tccggtggca      2400
aaaactcgag ctctatatgc acccgacacc cgttttcgga atgggtgacg tgcgacaacg      2460
aaattgcgtg aaaccacccc aaacatgagt tttggaccta aagtagtgga ttgggcatgt      2520
tcgttgcgaa aaacgaagaa atggttccgg tggcaaaaac tcgtgctttg tatgcacccg      2580
acacccgttt tcggaatggg tgacgtgcga caacgaaatt gcgagaaacc acctcaaaca      2640
tgagttttgg acctaaagta gtggattggg catgttcgtt acgaaaaacg aagaaatggt      2700
tccggtggca aaaactcgtg ctttgtatgc acccgacacc cgttttcgga atgggtgacg      2760
tgcgacaacg aaattgtgcg aaaccacccc aaacatgagt tttggaccta aagtagtgga      2820
```

```
ttgggcatgt tgttacgaa aaacgaagaa atggttccgg tggcaaaaac tcgtgctttt   2880 atgcacccg ataccgttt tcagaatggg tgacgtgcga caacgaaatt gcgcgaaacc    2940
acctcaaaca tgagttttgg acctaaagta gtggattggg catgttcgtt gcgaaaaacg   3000
aagaaatggt tccggtggca aacactcgtg cttttatgca cccgacactc gtttcggaa    3060 tgagtgacgt gcggcaacga aattgcgcga aaccacccaa acatgagtt ttgtacctaa    3120 agtagtggat tgggcatgtt cgttgagaaa acgaagaaa tggttccggt ggcaaaaact   3180
cgtgctttgt atgcaccccc acaccggttt ttagaatggg tgacgtgcgg caacgaaatt   3240
gcgcgaaacc acccgaaaca tgagttttgg acctaaagta gtggattggg catgttcgtt   3300
gcgaaaaaca agaaatggt tccggtggca aaaactcgtg ctttgtatgc accatgacac    3360
ccgttttcgg aatgggtgac gtgcgacaac gaaattgcga gaaaccaccc caaacatgag   3420
ttttggacca aaagtagtgg attaggcatg ttcgttgcga aaaacgaaga aatggttccg   3480
gtggcaaaaa ctcgtgcttt gtatgcactc cgacacccgt tttcggaatg ggtgacgtgt   3540
gacaacgaaa ttgcgcgaaa ccaccccaaa catgagtttt ggacctaaag tagtggcttg   3600
ggcatgttcg ttacaaaaaa cgaagagatg gttccggtgg caaaaactcg tgctttgtat   3660
gcacccgaca cccgttttcg gaatgggtga cgtgcgacaa cgaaattgcg agaaagcacc   3720
ccaaacatga gttttggacc taaagtagtg gattgggcat ttcgttgcg aaaaacgaag    3780 aaatggttcc ggtggcaaaa actcgtgctt tgtatgcacc ccgacacccg ttttcggaat   3840
gggtgacgtg cgacaacgaa attgcgcgaa accaccccaa acatgagttt tggacctaaa   3900
gtagtggatt gggcatgttc gttgcgaaaa acgaagaaat ggttccggtg gcaaaaactc   3960
gtgctttgta tgcaccccga caaccgtttt cagaatgggt gacgtgcggc aacgaaattg   4020
cgcgaaacca ccctaaacat gagttttgga cctaaagtag tggattgggc atgttcgttg   4080
cgaaaaacga gaaatggtt ccggtggcaa aaactcgtgc tttgtatgca cccgacaccc   4140
gttttcggaa tgggtgacgt ccgacaacga attgtgcga aaccacccca aacatgagtt    4200
ttggacctaa agtagtggat tgggcatgtt cgttgcgaaa acgaagaaa tggttccggt    4260 ggcaaaaatt gtgctttgta tgcaccccga caaccgtttt cagaatgggt gacgtgcggc   4320
aacgaaattg cgcgaaacca ccccaaacat gagttttgga cctaaagtag tgggttgggc   4380
atgttcgttg cgaaaaacaa agaaatggtt ccggtggcaa aaactcgtgc tttgtatgca   4440
ccatgacacc cgttttcaga atgggtgacg tgcgacaacg aaattgtgcg aaaccacccc   4500
aaacatgagt tttggaccta agtagtgga ttggcatgt tcgttgcgaa aaacgaagaa    4560
atggttccgg tggcaaaaat tcgtgctttg tatgcaccat gacaccgtt tcggaatgg    4620 gtgacgtgcg acaacgaaat tgtgcgaaac caccccaaac atgagtttg acctaaagt    4680 agtggattgg gcatgttcgt tgcgaaaaac aaagaaatgg ttccggtggc aaaaactcgt   4740
gctttgtatg caccatgaca cccgttttcg gaatgggtga cgtgcgacaa cgaaattgcg   4800
agaaaccacc ccaaacatga gttttggacc taaagtagtg gattaggcat gttcgttgcg   4860
aaaaacgaag aaatggttcc gctggcaaaa actcgtgctt tgtatgcact ccgacaccct   4920
tttcggaatg gctgacgtgt gacaacgaaa ttgcggaaac cacccaaaca tgagttttgt   4980
acctaaagta gtggattggg catgttcgtt gcgaaaaacg aagaaatggt tccggtggca   5040
aaaacgcgtg ctttgtatgc accccgacaa ccgttttcgg aatgggtgac gtgcggcaac   5100
gaaattgcgt gaaccaccc caaacatgag ttttggacct aaagtagtgg attgggcatg   5160
ttcgttgcga aaacgaaga aatggttccg gtggaaaaaa actcgtgctt tgtatgcacc    5220
```

```
cgacacccgt tttcggaatg ggtgacgtgc gacaacgaaa ttgcgcgaaa ccaccccaaa    5280
catgagtttt ggacctaaag tagtggattg gcatgttca ttgcgaaaaa cgaagaaatg    5340
gttccggtgg caaaaactcg tgctctgtat gcacccgaca cccgttttcg gaatgggtga    5400
cgtgcgacaa cgaaattgcg cgaaaccacc ccaaacatga ttttggacc taaagtagtg    5460 gattgggcat gttcgttgcg aaaaacgaag aaatggttcc ggtggcaaaa actcgtgctt    5520
tgtatgcacc cgacacccgt tttcggaatg ggtgacgtgc gacaacgaaa ttgtgcgaaa    5580
ccaccccaaa catgagtttt ggacctaaag tagtggattg gcatgttcg ttgcgaaaaa    5640 cgaagaaatg gttccggtgg caaaaatcgt gctttgtatg caccccgaca ccgttttca    5700 gaatgggtga cgtgcggcaa cgaaattgcg cgaaaccacc ccaaacatga ttttggacc    5760 taaagtagtg ggttgggcat gttcgttgcg aaaaacgaag aaatggttcc ggtggcaaaa    5820
actcgtgctt tgtgtgcacc cgacacccgt tttcggaatg ggtgacgtgc gacaacgaaa    5880
ttgcgagaaa tcaccccaaa catgagtttt ggacctaaag tagtggattg gcatgttcg    5940 ttgcgaaaaa cgaagaaatg gttccggtgg caaaaactcg tgctttgtat gcaccccgac    6000
acccgttttc ggaatgggtg acgtgttaca cgaaattgc gcaaaaccac cccaaacatg    6060
agttttgtac ctaaagtagt ggattgggca tgttcgttgc gaaaaacgaa gaaatggttc    6120
cggtggcaaa aactcgtgct ttgtatgcac cccaacaccc gttttcggca tgggtgacgt    6180
gcggaaacga aattgcgcga aaccacccca aacctgagtt ttggacctaa agtagtggat    6240
tgggcatgtt cgttgcgaaa aacgaagaaa tggttccggt ggcaaaaact cgtgctttgt    6300
atgcacccga cacccgtttt cggaatgggt gacgtgcgac aacgaaatta cgcgaaacca    6360
ctccaaacat gagttttgga tgtaaagtag tggattgggc atgttcgttg cgaaaaacga    6420
agaaatggtt ccagtggcaa aaatcgtgct ttgtatgcac cccgacaacc gttttcagaa    6480
tgggtgatgt gcggcaacga aattgcgcga accaccccca aacatgagtt ttgtacctaa    6540
agtagtggat tgggcatgtt cgttgagaaa acgaagaaa tggttccggt ggcaaaaact    6600
cgtgctttgt atgcacccg acacccgttt tcgaatgggt gacgtgctg caacgaaatt    6660 gcacgaaacc acccccaaaca tgagttttgg acctaaagta gtggattggg catgttcgtt    6720
gcgaaaaacg aagaaatggt tccggtggca aaaactcgtg ctttgtatgc acccgacacc    6780
cgttttcgga ttgggtgatg tgcgacaacg aaattacgcg aaaccacccc aaacatgagt    6840
tttggatgta aagtagtgga ttgggcatgt tcgttgcgaa aaacgaagaa atggttctgg    6900
tggcaaaaac tcgtgctttg tatgcaaccg acacccgttt tcggaatggg tgacgtgcga    6960
caacgaaatt gcgcgaaacc accccaaaca tgagttttgg atctaaagta gtggattggg    7020
catgttcgtt gcgaaaaacg aagaaatggt tccggtggca aaaactcgtg ctttgtatgc    7080
acccgacacc cgttttcgga atgagtgacg tgcgaaaacg aaattgtgcg aaaccacccc    7140
aaacatgagt tttggaccta aaaagtgga ttggcatttt cgttacgaa aaacgaagaa    7200 atggttccgg tggcaaaaac tcgtgctttt atgcaccccg atacccgttt tcagaatggt    7260
ttatgcaccc gacactcgtt ttcggaatgg gtgacgtgcg gcaacgaaat tgcgcgaaac    7320
caccccaaac aagagttttg tacctaaagt agtggattgg gcatgttcgt tgctaaaaac    7380
gaagaaatgt tccggtggc aaaaatcgtg ctttgtatgc accccacccc gacaccgtt    7440 ttcagaatgg gtgacgtgcg gcaacgaaat tgcgcgaaac caccccaaac atgagttttg    7500
gacctaaagt agtgggttgg gcatgttcgt tgcgaaaaac gaagaaatgg ttccggtggc    7560
aaaaactcgt gctttgtatg cacccgacac ccgttttcgg aatgggtgac gtgcgacaac    7620
```

```
gaaattgcga gaaatcaccc caaacatgag ttttggacct aaagtagtgg attcggcatg    7680
ttcgttgcga aaaacgaaga aatggttccg gtggcaaaaa ctcgtgcttt gtatgcaccc    7740 gacaccgtt ttcggaatgg gtgacgtgtg acaacgaaat tgcgcaaaac caccccaaac    7800
atgagttttg tacctaaagt agtggattgg gcatgttcgt tgcgaaaaac gaagaaatgg    7860
ttccggtggc aaaaactcgt gctttgtatg cacccgacac ccgttttcgg attgggtgat    7920
gtgcgacaac gaaattacgc gaaccaccc ctgatgagga catcaacacc aacacgagca    7980
catctacacc agcagcacct tctccagccc aggcaccatc ttccccagtc caggcgccac    8040
cccttccacc tgggccagtg actcgggccc gtgcaagaga attgaactac attatgctgt    8100
taaagaacga aggcccggaa gaatagacga ccagcccaac tgcggcccat aatggacgac    8160
ctagggttgg ccgcccctag ggctgcgcc cctctctatt tatccaggag ctgcgcctcc    8220
tttatttctg gagttttgtt ttacgttagc cttagctact ctcgaacacg cgcaaatctg    8280
cgctgtcttc gtgtattcag aactccaccc tcgagtaata gattagattg ctcgcctctt    8340
tttcttgttc gttcttcgat tgcgcacagg aaacgatctt cgtgatcagg ccgatctcgc    8400
atcagcaagg tcggtaacca cagggagttg gttcagcgat tgcattggcg cctcgggctt    8460
gctcgtcgta gtcggatcgc aagggtcatc ttccgccaaa tcggaattat ctctactcgc    8520
cgaaagatcg ggcacctcag ctacatcaat tggtatcaga tttccaggtt gatcggtgag    8580
tttatcgagc gttttttttcc tacagtccac aaaaccacat aaaaattcag gttagatctt    8640
atcccagcac ccttttgagc ctcgcacttt cttttcaataa tctgcattgt tgaatttgtg    8700
tgctttcgcg tttccttgtt gctggttgca ttgtgttctt ccaccattca aatcctagcg    8760
ccgccatcat cttccgtttg atcacgccac aaaccgagtc aacatcgtct ccttgttttt    8820
ctccttcggt tacgaaaaaa aaacagaaaa aaaaaacaaa ccgagtcaac gaccgcttcc    8880
ttgtttttct ccttcggtta cataaaaaaa acagaaacaa aaaaaagaa acgaaggag      8940 aagggatacg gttgtttcat cccggtcgtt tttaaaacat aacttgaggt accttccgta    9000
aaccgggcat aacttttcgc tcgggtgtcc aaaaaatctg aaatttttac aggagcttgt    9060
tgacaccatt cggaggccgg ccaaactgac ctttggtctg tttggattcg acaaaattgt    9120
caaaaaaatt caggaaaata agaaaaaaa tccgtcaaag ttctcgcacg cttttcagag    9180
aacttcctga ttttctgtag accacatctg atctctgttt tcggtgaaac ttcgtctagc    9240 tcctatttg ttgcttcttg tgctgagaaa aatatcaaaa aatcatacaa aaaagaaaa     9300 acaaaatcac ttgtgattcc tactagtggc ctcgctagta caatatttac ggtactgcca    9360
ttctgctagt tccatccgtc ctttgcactt gtggccagca atatagtttc gtgttctgca    9420
ctataattca actttgcatt attgtttgat cgtgctaatc cttgacttga gtgcagccta    9480
cccaaaactc cacatatttc tacgacgaga cggtttctgt ttctccaggc aatcgctaat    9540
ccaatctttc accggttcca cctgttgatt gcagttcacc actgtggctt ggtaagaacg    9600
gataagaact tgataacaac actagtgtga gcgccttgtg agcagtacac ccctgttttt    9660
gtcgttggtt tttctcctttt tggtgttttg gtgtttgcgc taactatggc aggagcacac    9720
gacatggtgg atgcccagtt gcaggaagta aggggacaag ttgatggact tgctgctgac    9780
attcggacga tgcatgaacg gcttgattca acgatcactt cgacgaccga gcgtttcaac    9840
caacttgacc ttgctcaaac ggcgactcgc accacactcg acaccatcct ggcacgcctt    9900
gatgcattga ccacaaagat ggagcaggaa tacggcggtg acactgagca ggacgatgga    9960
gatcgccgtg gtcgtgcacg tcgtgtggtt cgtcatcccc ctaatgactt attttctaag   10020
```

```
attaaattta aaattccatc ttttaatggt aaatatgatc ctgctgcata tcttgattgg    10080
gaattagagg tagaacagaa attttcatgc catgatattc ctgctcatag ccaagtgaag    10140
gctgccatta gtgaatttac tgattttgct ttaatttggt ggcgcgagta taatcaaaaa    10200
cttcccatta acaatgtcat tacttggacc caattaaaaa ctgccatgcg ccacagattt    10260
gttccttcct attatgctcg tgatttgctt aacaaaatgc agcgttttca acaaggttca    10320
cagtctgttg aggaatatta ccaggagtta caaaagggta tgcttcgttg tggtttagtt    10380
gagtcggatg acgctgctat ggcgcgtttt cgtggtggtt tgaacaggga aattcaggat    10440
atacttgatt ataaggatta ttttgatata accacattat ttgaatatgc ttgcaaagct    10500
gaacgtgaag tgcagggacg ccgctcgaag ccatattcta acccttttgc aggacgaagc    10560
tcgacatcca cctcagcacc agttccccct gcgccatcga cgtccaccac tacttcacgc    10620
gagaagacga ccaaaccagc cagcactgcc ccacccacag gtcgtacacg ggatattcag    10680
tgtcatcgct gtagaggatt tggccatgtg attcgggact gcccaaacaa gcgcactttg    10740
ctcattcgtg acgatggtga gtactcttcc gctagtgatt ctgaagaaat tgaacatgca    10800
ctacttgcca cttaccatgc agctaaggcg gaggtacatg tcaacccgag cgacgctgat    10860
aggtatgaaa gtcttgttgt gcagcgtgtt ctcagtacac aggtcgcttt gcccgagaag    10920
aatcagcgac acactctgtt ccatacaaag ggtgttgtgc aggagcggtc aattcgcatc    10980
attatcgaca gtggcagttg caacaatttg gcgagtacca tgctggtcga caagttatcg    11040
ttacccactc gtaagcatcc aaacccatat cacattcaat ggcttaatga tggtggtaaa    11100
ataaaaatca cacgttccgt gcgtgttcct ttctccatgg gtgcttattc tgattttgtt    11160
gattgtgatg ttattcccat ggaagcatgc tctttgttac ttggtcgacc ttggcaatat    11220
gatactgata gcttgcatca tggtcgttcg aatcattatt ctttcatttt taagggtcag    11280
aaaataatta tacatccaat gacacccgaa caaattgtta agatgatct tgcccgagct    11340 gctataactg ctaaacaact tgatccatcg ccctctgttc cttctgaaat caagttgaag    11400
gctcctgttt tacttgctac acgtgctgat tttgatgatc tacacggtgc tcatttgcca    11460
tgctatgcac ttatatgctc tagtgtcctc atttcacttg atgatgcacc atctttggct    11520
attcccccta tggttgctaa cctttttgcaa gagtacgctg atgtcttttcc caaagactta    11580 ccaccgggtc tcccaccact tcgtggcatt gagcaccaga tcgacctcat tcccggcgca    11640
cagcttccga accgcgcacc gtaccgtaca aatccggatg agacgaagga gattcagcgc    11700
caggtacagg cgttgcttga caagggatac attcgtgagt ctcttagccc ttgctctgtt    11760
cctgtgttac ttgttcccaa gaaagatggg tcatggcgta tgtgtgtaga ctgtcgtgct    11820
attaataaca tcactattcg ttatcgatat cctataccac gccttgatga tatgctagat    11880
gagcttagtg gtgccattat tttcactaag attgatttgc gtagtggtta ccaccagatt    11940
agaatgaaac tgggtgatga atggaaaacg gcttttaaaa cgaaatttgg tttatatgaa    12000
tggttggtta tgccgtttgg attgactaat gctcccagca cttttatgcg agtgatgaat    12060
gaagttctaa ggcccttcat aggattgttt gtggttgttt attttgatga tattcttatt    12120
tacagcaaat ctacgaaaga gcatttggaa catttacgtg ctgtttttga tgcattgcgt    12180
gctgctcagt tatttgctaa catggaaaaa tgcatgtttt gtacgacgcg tgtctcgttt    12240
cttggttatg ttgttactcc acagggcatt gaggtggata gcagcaagat tgctgccatt    12300
cgggagtggc ctacaccgac gacggtcaca caaatttgga gctttcttgg acttgccggt    12360
ttctaccgca gatttgttcg tgattttagc tccattgcag cgcctctaca tgagcttaca    12420
```

```
aagaaagatg tgccatttgc ttggagtgat tcccaggagg aagcgttcag cactttgaaa    12480
gataagttaa cccaagctcc cctattgcaa ttgcctgatt ttaataaagt gtttgagctt    12540
gaatgcgatg ctagcggtat tgggctaggt gctgttttgt tacaagaagg aaaaccagtt    12600
gcttatttta gtgaaaaatt aagcggtgct agtctgaaat attctactta tgataaggag    12660
ctttacgctt tagtgcgcac tttgcataca tggcagcact atctttggca tcgtgagttt    12720
ataatccatt ctgatcatga ggcttttaaaa catattcgta cccaaacaaa tctgaaccgt    12780
cgtcatgcta aatgggtaga attcattgag tcctttcctt acattattaa acacaagaac    12840
gggaaggaca atgttattgc tgatgctttg tctcgtcgct ataccatgct gtcacagtta    12900
gattttaaaa tctttggttt gcacactctg aaagatcaat atgttgatga tgctgatttt    12960
aaagatgctt tcggccattg tattaatggg aaaccatggg gcaaatttca catacaggat    13020
gggttcctgt ttcgcgctaa caagctgtgt gttccagcta gctcggttcg tcttttgttg    13080
ttacaggaag cacatggagg cggtctcatg gggcactttg gcgtctacaa gacacatgag    13140
gtgttggctg cccacttctt ttggcctcgg atgcgcgctg atgttgagcg ccttgttgca    13200
cgctgcacta cttgtcagaa agctaagtca cggttgaaca accattgttt gtatatgcct    13260
ttgcctgttc ctactttccc ttggattgat atttcgatgg attttgtttt gggattgcct    13320
agaactaaga aggggaggga tagcattttt gtggttgttg atcgattctc caaaatggct    13380
catttcatac cttgtcataa gactgatgat gctagcaatg ttgctgaatt gttttttaga    13440
gagattattc gtttgcacgg tattcccaat acaatagtct cggatcgtga tgctaagttt    13500
ctgagtcatt tttggagatc tctgtggaat aaattgggaa ctaaattgct gtttagcacc    13560
acttgtcacc ctcagactga tggtcaaact gaggtagtta atcgaacttt gtctaccatg    13620
cttagggctg ttttagacaa aaatttgaaa cgttgggagg attgcttgcc tcatgttgag    13680
tttgcttata atcatgcaac ccattcttct acaaagatgt gccctttca aattgtttat    13740 ggttacattc ctagggcgcc tattgctttg ttttcgcttg atgctgcgga cgccccacac    13800
atagcttcct cctcccaagt taagcgaggt gggataattc tgaggctcac acggtcaccg    13860
tccgactaca attgggccaa ctggccaatt gcgtctttgc caacgggtaa tagtggagga    13920
tgtcctcatc aaacatcatc acgcacaata gcctcagggg acatgggaag caaaataatt    13980
ttcttatcat ggtgtatgag agaatattga tttgatctac catgatgcat acaatctgaa    14040
tcatattgcc atggtctacc tagcagaata ttacaagcat ccataggcac aacatcacag    14100
tcaacaacat cacgatatga accaaatagca aaattaattc gtaccagctt ggttaccttg    14160
accttaccac tattgttgag ccattgaatg tgatatggat gcgggtgtgg tttggtcgta    14220
agtgcaagct tctccaccat gtcgctgcta gccaagttgt tgcagctacc tccatcaatg    14280
atcaaacgac atgaacgctc cttaatgaca cactttgttt gaaacaacgt atgtcgctga    14340
ttctgctctg ccttctccat ttgtgcacta agcacacgct gtacaatgag gctctcataa    14400
tgctctgcat catctgcacc aatctgttct tcgggtggtt ccttagtgcc tgcatcatca    14460
gccgcaagca aagcaagtgt agcttcatcc aaatcactag cagaggaata cccaccatcg    14520
tcttttacca ccaaaacacg ctgattagga caatcacgct gcacgtgtcc atagcccttg    14580
catcgataac acagaacatc tcttgttcta cctgtggaag ctactgaaga ggccctacct    14640
gcgggttcct gggcagattt ggttgctgaa tttatggaag atgcacgtgg tttgtcgctg    14700
gaggaaggcg ggggtgctgg tcgacttggc gaaggagttg gtgctggtgt acggccggtc    14760
atggacgtag tcgtgcgctg ttgccatggt gtagattttc ctgcagaaac attagacctt    14820
```

```
gcactagcac gtcgtccctg cacttccctt tcagctttgc aagcaagatg aaacaatcgg    14880
gttacattag cataatcttt ataagcaagg atgtcctgaa tttccctatt taacccgccc    14940
aaaaatctag ccatagcaga ttcctcaccc tcctctatgt tacaacgcag catacccatt    15000
tgtaattcct gataatattc ttctacactt ttagtaccct gtctcaattg ttgcaacttg    15060
tttaacatat cacgtgcata ataagaagga acaaatctag cccgcatgac ccgtttcaac    15120
gcatcccaag tttgtggcat gttattagga ttcttcttac catgttctat ccaccaaaca    15180
aaagcaaatt cagtaaactc actagtagca gctctaaccc gcgcattctc aggaaattca    15240
tggcatgcaa acttttgatc aaccgcaatc tcccaagtaa tgtaagcatc agggtcatat    15300
ttaccatcaa aaggaggtat tttaaattta accttactaa aagcatcatc attaccatgt    15360
acctcacgtc ggcgaaaacc atccatacct ctacggttag tacgtagtcg ccggcgatta    15420
ggtgcttctt ggtcatcttg ttcagtatca gcaacatagt catcccagtt accttcggcg    15480
ccctcatcac gcccaccatt gatattagca tgcatctcat caaaccgcct caagagtgcg    15540
acaaggctct tgtcaatatg agcaactgtc atttccactt ttgcaagttt ggtgtttgtg    15600
tcgatctgtg tggcctccaa ttgccccatc tttttattcg tcacctgcat gtcattatca    15660
agaccttccg tgtgcgtctt caccagcctt acaaagtgtt gtatgatacc cttggtgcga    15720
ggagagtgtg gcatattatg agaagcatca tcaacctcca atcctgccat ggttagacga    15780
atagaggcaa caagaaaaaa aacgtgaagg aatgaaaact ctacaactat taggatgtag    15840
ctactgcaag gcgctcactc tcaacctgcc acacaagctc ttaccaattc ttaccttgca    15900
caacaggagg ggtcagcaac caacaagtct gcaactgtgg aataagtgta tcggtgccgc    15960
agcaacacga cctgtcaaac tgtagtcgaa atatgtagag ttgtaggtgg gctgaagcaa    16020
ggaatacact agtaccacgt tagttacaaa agcaagctga ataatcgttc aacggtggta    16080
ctgtgctggt cctaggctaa accaggctag agacgtgagc ctaggcacaa aggtagtcac    16140 tgaaaagaa caactagcac agcacaaaga gaaacaacag atttagagat tcagcccct    16200 tcttcttctt ttccttttttt ttcttttcta ttcttttttt ttcttcttct tctgtttttt    16260
tttgcagggg cctaaacccct ttttttcact atgcaacccc aaacaataaa gatattgcta    16320 acagccctt taaatcagat ttaacaaatc ttgttaatat agaaagtcca gaatctcta    16380 cgatgattgc ggagcgctca gaacgaattt tgagataagg tcagatccat tggaaagaag    16440
ataagataag cttccagat tgtatttaaa cttccaaatc ggatatgata tgtatccgtg    16500
gtggcaaaaa cgaaccagag atgttttttgg tgatggtgaa tctcgtggtg accaaaacgt    16560
ggtagaactc aaaactctaa aggaataaac taagaccagc aactcgacac aaccgatgca    16620
accaaaaact caacagcccc taactaagta gtactagtaa atgctcaatg gtttatagga    16680
ttgcggtaaa actaatctac tattttttgg cttttctgg actataggag ataagaaaac    16740
agcgaagaaa agtaaatctc tcaccgataa accttgttct gataccaact gatgtgcacc    16800
cgttgggtga ttgcccgatc tttcgatgag agggtgtgga ataactcgat tggggggagga    16860 gacgacgttc acgccccgac tacagccttc caaagacgct gcgccttagc aaccgataca    16920
ccacctccta tggctgtcac gatcttgtgg agcgtgacac cctggccact agggcactcg    16980
tcctgcaagc aatcgaagaa ctagcaagaa caagtagaac aagtactgaa ttaccagatc    17040
taaatgtagg tttcaaaatc aaactccaat atggtggggt tccgaagaca agaagacggg    17100
cggctgaact agcacgcgcg cttgcaagca agtagcgaga gctaaacttg atctaaacaa    17160
aacccgctgt tcttggtgac ggctagggggg tttataaaca tgggaggacg accacaaggg    17220
```

| | |
|---|---|
| tattggggtc gtgctgcaac cctaggatgc gtccctaatg gacctaactt gatacacgac | 17280 |
| ccattgggcc aaaatagggt gacgcagcac catgggcaga aaaggcagga aatgtctcgg | 17340 |
| taagaaaaca atgattacgg cggcctcaga acagatatga ctataattcc ggatccatat | 17400 |
| gaaagtagac ttgataagct ttccatgttg tgcttgaaca ttccaatccg agcccgcatc | 17460 |
| tgaccgtggt gaccgtcaca agttggtgtt cttctgcagt ccgaatccag catgttcaaa | 17520 |
| tccttttccc tttcggtctt ctccctgatt cctaagcaaa acaagagtgc acgggtctcc | 17580 |
| atggtctaaa tatgatggac atgaactcaa gagtgtaatc acctgatggt tgagttgacg | 17640 |
| agcacgagcg cgagtaatgg gaccagaaat tggtacttgt attggtatag atgcatcagt | 17700 |
| agtgtggatg tcttcatcat cacccattcc gaaaacgggt gtcgggtgaa taaaaagcac | 17760 |
| gagttttgc caccggaacc atttcttcgt ttttcgcaac gaacatgccc aatccactac | 17820 |
| tttaggtcca aaactcatgt ttggggtggt ttcgcgcaat ttcgttgccg cacgtcaccc | 17880 |
| attccgaaaa cggttgtcgg ggtgcataca aagcacgagt ttttccacc agaaccattt | 17940 |
| cttcgttttt cacaacgaac atgcccaatc cactactata ggtccaaaac tcatgtttgg | 18000 |
| ggtggtttcg cacagtttcg ttgtcgcacg tcacccattc tgaaaacggg tatcggggtg | 18060 |
| cataaaagca cgagttttg ccaccggaac catttcttcg tttttcgtaa cgaacatgcc | 18120 |
| caatccacta ctttaggtcc aaaactcatg tttggtgtgg tttcgcacaa tttcgttgtc | 18180 |
| gcacgtcacc cattccgaaa acgggtgtcg ggtgcataca aagcacgagt ttttgccacc | 18240 |
| ggaaccattt ctttgttttt cgtaacgaac atgcccaatc cactactttA ggtccaaaac | 18300 |
| tcatgtttga ggtggtttcg cgcaatttcg ttgtcgcacg tcacccattc cgaaaacggg | 18360 |
| tgtcgggtgc atacaaagca cgagttttg ccaccggaac catttcttcg tttttcgcaa | 18420 |
| cgaacatgcc caatccacta ctttaggtcc aaaactcatg tttggggtgg tttcgcgcaa | 18480 |
| tttcgttgtc gcatgtcact cattccgaaa acgggtgtcg ggtgcataca gagcacgagt | 18540 |
| ttttgccacc agaaccattt cttcgttttt cgcaatgaac atgcccaatc cactacttta | 18600 |
| ggtccaaaac tcatgtttgg ggtggtttcg cgcaatttcg ttgtcgcacg tcacccattc | 18660 |
| cgaaaacggg tgtcgggtgc atacaaagca cgagttttg ccaccggaac catttcttcg | 18720 |
| tttttcgcaa cgaacatgcc caatccacta ctttaggtcc aaaactcatg tttggggtgg | 18780 |
| tttcgcgcaa tttcgttgcc gcacgtcacc cattccgaaa acggttgtcg ggggtgcata | 18840 |
| caaagcacgc gttttgcca ccggaaccat tcttcgtttt tcgcaacga acatgcccaa | 18900 |
| tccactactt taggtacaaa actcatgttt gggtggtttc gcgcaatttc gttgtcacac | 18960 |
| gtcacccatt ccgaaagggg tgtcggagtg catacaaagc acgagttttt gccagcggaa | 19020 |
| ccatttcttc gttttcgca acgaacatgc ctaatccact actttaggtc caaaactcat | 19080 |
| gtttggggtg gtttctcgca atttcgttgc cgcacgtcac ccattccgaa acgggtgtc | 19140 |
| gggtgcatac aaagcacgag ttttgccac cggaaccatt tcttcgtttt ttgtaacgaa | 19200 |
| catgcccaat ccactacttt aggtccaaaa ctcatgtttg gggtggtttc gcgcaatttc | 19260 |
| gttgtcacgc gtcacccatt ccgaaaacgg gtgtcggagt gcatacaaag cacgagtttt | 19320 |
| tgccaccgga accatttctt cgttttttcgc aacgaacatg cctaatccag tactttaggt | 19380 |
| ccaaaactca tgtttgggt ggtttctcgc aatttcgttg tcgcacgtca cccattccga | 19440 |
| aaacgggtgt catggtgcat acaaagcacg agttttgcc accggaacca tttctttgtt | 19500 |
| ttttgcaacg aacatgccca atccactact taggtccaa aactcatgtg ttggggtggt | 19560 |
| ttcgcgcaat tttcgttgcc gcacgtcacc cattctgaaa acgggtgtgg ggttgcatac | 19620 |

```
aaagcacgag ttttgccac aggaaccatt tcttcgtttt tctcaacgaa catgcccaat    19680
ccactacttt aggtacaaaa ctcatgtttt gggtggtttt gcgcaatttc gttgtcgcac    19740
gtcacccatt ccgaaaacgg gtgtcgggtg catacaaagc acgagttttt gccaccggaa    19800
ccatttcttc gttttcgca acgaacatgc ctaatccagt actttaggtc caaaactcat    19860
gtttggggtg gtttctcgca atttcgttgt cgcacgtcac ccattccgaa aacgggtgtc    19920
atggtgcata caaagcacga ttttgcca ccggaaccat ttctttgttt ttgcaacgaa    19980
catgcccaat ccactacttt cttccagca catggagctt cagcgaattc aagcttgaat    20040
cttcagga                                                             20048
```

<210> SEQ ID NO 70
<211> LENGTH: 172
<212> TYPE: DNA
<213> ORGANISM: Zea mays

<400> SEQUENCE: 70

```
tggttccggt ggcaaaaact cgtgchttdw mttgcacycc cgacaccgg ttttcgggaa       60 tgggtgacgt gcggcaacga aattgcgcga accaccccca acacaatgag ttttggacct    120
aaagtagtgg attgggcatg ttcgttgcga aaacgaaga aatgrttcyg gt             172
```

<210> SEQ ID NO 71
<211> LENGTH: 188
<212> TYPE: DNA
<213> ORGANISM: Zea mays
<220> FEATURE:
<221> NAME/KEY: misc_feature
<222> LOCATION: (46)..(46)
<223> OTHER INFORMATION: n is a, c, g, or t

<400> SEQUENCE: 71

```
ccatttcttc gttttkcgc maaacgaacv mmatgcccbh aatccnactw actttwaagg       60
dtccaaaaac tcatkgtttg gggdtggdtt tcgcgcaart ttcgrtttgt cgcacgtctc    120
acccatttcc gaaaamcggg tgtcgggkkt gcatacaaag cacgagtttt tgtccaccgg    180
aaccatct                                                             188
```

<210> SEQ ID NO 72
<211> LENGTH: 158
<212> TYPE: DNA
<213> ORGANISM: Zea mays

<400> SEQUENCE: 72

```
tttcatcccg gtcgttttta gaacataact tgaggtacct tccgtaaacc gggcataact       60
tttcgctcgg gtgtccaaaa aatctgaaat ttttatagga gctagttgac accattctga    120
ggccggccaa actcacctac ggtctgtttg gggttcga                            158
```

<210> SEQ ID NO 73
<211> LENGTH: 176
<212> TYPE: DNA
<213> ORGANISM: Zea mays

<400> SEQUENCE: 73

```
acaaaccgag tcaacggycg tttccttgtt tttctccttc ggttaaccga aaaaaaaaca       60
gvaaaaaaaa aamcaaaccg agtcmaacga ccggcccttc cttgttttc tccttcggtt    120 acdtaaaaaa aacagaaaca aaaaaaaaga aaacgaagga aagggatac ggttgt         176
```

<210> SEQ ID NO 74

```
<211> LENGTH: 193
<212> TYPE: DNA
<213> ORGANISM: Zea mays

<400> SEQUENCE: 74
gacgtaaccg aaggagaaaa ayaaggarac gatgttgact cggtttgtgg ygtgatcaaa     60
yggragatgr tggcggcgct aggrtttgaa tggtggaaga acacaatgca accagcaaca    120
arkraacgcg aaagcacaca aattcaacaa tgcagattat tgaaagaaag tgygaggctc    180
aaaagggtgc tgg                                                       193

<210> SEQ ID NO 75
<211> LENGTH: 147
<212> TYPE: DNA
<213> ORGANISM: Zea mays

<400> SEQUENCE: 75
gcagggacga cgatcaaaga catatactaa ctctcttgca ggccggggtc caacacacag     60
ctcaactcct tccagccctg caccttctac gcctagcact acatcgcgca cagggacgac    120
caagccagtg gcgccccctg ccaaagg                                        147

<210> SEQ ID NO 76
<211> LENGTH: 466
<212> TYPE: DNA
<213> ORGANISM: Zea mays

<400> SEQUENCE: 76
ggttcaggta gtaaaaactc gtgctttgta tgcaccccga tacccgtttt cggaatgggt     60
gacgtgaggc aacgaaattg cgcgaaacca acccaaacat gagttttgga cctaaagtag    120
tggattgggc atgttcgttg caaaaaacaa agaaatggtt ccggtggcaa aaactcgtgc    180
tttgtatgca cccgacaccc gttttcggaa tgggtgacgt gcggcaacga aattgcgaga    240
aaccacctca aacctgagtt ttggacctaa agtagtggat tgggcatgtt tgttgcgaaa    300
aacgaagaaa tggttccggt ggcaaaaact cgtgctttgt atgcacccga cacccgtttt    360
cggaatgggt gacgtgcgac aacaaaattg cgcgaaacct ccccaaacat gagttttgga    420
cctaaagtag tggattaggc atgttcattg cgaaaaacga agaaat                   466

<210> SEQ ID NO 77
<211> LENGTH: 7572
<212> TYPE: DNA
<213> ORGANISM: Zea mays

<400> SEQUENCE: 77
tgatgaagac atccacacta ctgatgcatc tataccaata caagtaccaa tttctggtcc     60
cattactcgc gctcgtgctc gtcaactcaa ccatcaggtg attacactct tgagttcatg    120
tccatcatat ttagaccatg gagacccgtg cactcttgtt ttgcttagga atcagggaga    180
agaccgaaag ggaaaaggat ttgaacatgc tggattcgga ctgcagaaga acaccaactt    240
gtgacggtca ccacggtcag atgcgggctc ggattggaat gttcaagcac aacatggaaa    300
gcttatcaag tctactttca tatggatccg gaattatagt catatctgtt ctgaggccgc    360
cgtaatcatt gttttcttac cgagacattt cctgcctttt ctgcccatgg tgctgcgtca    420
ccctattttg gcccaatggg tcgtgtatca agttaggtcc attagggacg catcctaggg    480
ttgcagcacg accccaatac ccttgtggtc gtcctcccat gtttataaac cccctagccg    540
ccaccaagaa cagcgggttt tgtttagatc aagtttagct ctcgctactt gcttgcaagc    600
```

```
gcgcgtgcta gttcagccgc ccgtcttctt gtcttcggaa ccccaccata ttggagtttg    660
atctttaaac ctacatttag atctggtaat tcagtacttg ttctacttgt tcttgctagt    720
tcttcgattg cttgcaggac gagtgccta gtggccaggg tgtcacgctc cacaagatcg     780
tgacagccat aggaggtggt gtatcggttg ctaaggcgca gcgtctttgg aaggctgtag    840
tcgggccgtg aacgtcgtct cctcccccaa tcgagttatt ccacaccctc tcatcgaaag    900
atcgggcaat cacccaacgg gtgcacatca gttggtaatc agagcaaggt ttatcggtga    960
gagatttact tttcttcgct gttttcttat ctcctatagt ccagaaaaag ccaaaaaaat   1020
agtagattag ttttaccgca atcctataaa ccattgagca tttactagta ctacttagtt   1080
agggcttgtt gagttttttgg ttgcatcggt tgtgtcgagt tgctggtctt agtttattcc  1140
tttagagttt tgagttctac cacgttttgg tcaccacgag atccaccatc accaaaaaca   1200
tctctggttc gttttttgcca ccacggatac atatcatatc cgatttggaa gtttaaatac  1260
aatctggaaa gcttatctta tcttctttcc aacggatctg accttatctc aaaattcgtt   1320
ctgagcgctc cgcaatcatc gtagagattt ctggactttc tatattaaca agatttgtta   1380
aatctgattt aaagggggttg ttagcaatat ctttattgtt tgggttgtca tagtgaaaaa  1440
aagggtttag gccccctgcaa aaaaaaacag aagaagaaga aaaaaaaaga atagaaaaga  1500
aaaaaaagga aaagaagaag aagggggctg aatctctaaa tctgttgttt ctctttgtgc   1560
tgtgctagtt gttctttttc agtgactacc tttgtgccta ggctcacgtc tctagcctgg   1620
tttagcctag gaccagcaca gtaccaccgt tgaacgatta ttcagcttgc ttttgtaact   1680
aacgtggtac tagtgtattc cttgcttcag cccacctaca actctacata tttcgactac   1740
agtttgacag gtcgtgttgc tgcggcaccg atacacttat tccacggttg cagacttgtt   1800
ggttgctgac ccctcctgtt gtgcaaggta agaattggta agagcttgtg tggcaggttg   1860
agagtgagcg ccttgcagta gctacatcct aatagttgta gagttttat tccttcacat    1920 ttttttttct tgttgcctct gttcgtctaa ccatggcagg attggaggtt gatgatgctt   1980
ctcgtaatat gccacactct cctcgcacca agggtatcat acaacacttt gtaaggctgg   2040
tgaaaacgca cacggaaggt cttgataatg acatgcaggt gacgaatgaa agatggggc    2100 aattggaggc cacacagatc gacacaaaca ccaaacttgc aaatgtggaa atgacagttg   2160
ctcatattga caagagcctt gtcgcactct tgaggcgatt tgatgagatg catgctaata   2220
ccaatggtgg gcgtgatgag ggcgccgaag gtaactggga tgactatgtt gctgatactg   2280
aacaagatga ccaagaagca cctaatcgcc ggcgactacg tactaaccgt agaggtatgg   2340
gtggttttca ccgacgtgag gtacatggta atgatgatgc ttttagtaag gttaaattta   2400
aaatacctcc ttttgatggt aaatatgacc ctgatgctta cattacttgg gagattgcgg   2460
ttgatcaaaa gtttgcatgc catgaatttc ctgagaatgc gcgggttaga gctgctacta   2520
gtgagtttac tgaatttgct tctgtttggt ggatagaaca tggtaagaag aatcctaata   2580
acatgccaca aacttgggat gcgttgaaac gggtcatgcg ggctagattt gttccttctt   2640
attatgcacg tgatatgtta aacaagttgc aacaattgag acagggtact aaaagtgtag   2700
aagaatatta tcaggaatta caaatgggta tgctgcgttg taacatagag gagggtgagg   2760
aatctgctat ggctagattt ttgggcgggt taaataggga aattcaggac atccttgctt   2820
ataaagatta tgctaatgta acccgattgt ttcatcttgc ttgcaaagct gaaagggaag   2880
tgcagggacg acgtgctagt gcaaggtcta atgtttctgc aggaaaatct acaccatggc   2940
aacagcgcac gactacgtcc atgaccggcc gtacactagc accaactccc tcgccaagtc   3000
```

```
gaccagcacc cccgccttcc tccagcgaca aaccacgtgc atcttccaca aattcagcaa    3060
ccaaatctgc ccagaaacca gcaggtagtg cctcttcagt agcctccacg ggtagaacaa    3120
gagatgttct gtgttatcga tgcaagggct atggacacgt gcagcgtgat tgtcctaatc    3180
agcgtgtttt ggtggtaaaa gacgatgtg ggtattcctc tgctagtgat ttggatgaag    3240
ctacacttgc tttgcttgcg gctgatgatg caggcactaa ggaaccaccc gaagaacaga    3300
ttggtgcaga tgatgcagag cattatgaga gcctcattgt acagcgtgtg cttagtgcac    3360
aaatggagaa ggcagagcag aatcagcgac atacgttgtt tcaaacaaag tgtgtcatta    3420
aggagcgttc atgtcgtttg atcattgatg aggtagctg caacaacttg gctagcagcg    3480
acatggtgga gaagcttgca cttacgacca aaccgcaccc gcatccatat cacattcaat    3540
ggctcaacaa tagtggtaag gtcaaggtaa ccaagctggt acgaattaat tttgctattg    3600
gttcatatcg tgatgttgtt gactgtgatg ttgtgcctat ggatgcttgt aatattctgc    3660
taggtagacc atggcaattt gattcagatt gtatgcatca tggtagatca aatcaatatt    3720
ctctcataca ccatgataag aaaattattt tgcttcccat gtcccctgag gctattgtgc    3780
gtgatgatgt tgctaaagct accaaagcta aaactgagaa caacaagaat attaaagttg    3840
ttggtaataa caaagatggg ataaaattga aggacattg cttgcttgca acaaaaactg    3900
atgttaatga attatttgct tccactactg ttgcctacgc cttggtatgc aaggatgctt    3960
tgatttcaat tcaagatatg cagcattctt tgcctcctgt tattactaac attttgcagg    4020
agtattctga tgtatttcca agtgagatac cagagggct gccacctata cgagggattg    4080
agcaccaaat tgatcttatt cctggtgcat cttttgccgaa tcgtgcgcca tataggacaa    4140
atccagagga acaaaagaa attcagcgac aagtgcaaga actactcgac aaaggttacg    4200
tgcgtgagtc tcttagtccg tgtgctgttc cggttatttt agtgcctaaa aaagatggaa    4260
catggcgtat gtgtgttgat tgtagggcta ttaataatat cacgatacgt tatcgacacc    4320
ctattccacg tttagatgat atgcttgatg aattgagtgg tgccattgtc ttttctaaag    4380
ttgatttgcg tagtgggtac caccagattc gtatgaaatt gggagatgaa tggaaaactg    4440 cttttcaaaac taagttcgga ttgtatgagt ggttagtcat gccttttggg ttaactaatg    4500
cacctagcac tttcatgaga ttaatgaacg aggttttgcg tgccttcatt ggaaaatttg    4560
tggtagtata ctttgatgac atattaatct acagcaaatc tatggatgaa catgttgatc    4620
acatgcgtgc tgttttaat gctttacgag atgcacgttt atttggtaac cttgagaagt    4680
gcacattttg caccgatcga gtttcgtttc ttggttatgt tgtgactcca cagggaattg    4740
aggttgatca agccaaggta gaagcgatac atggatggcc tatgccaaag actatcacac    4800
aggtgcggag tttcctagga cttgctggct tctatcgccg ttttgtgaag gactttagca    4860
ccattgctgc acctttgaat gagcttacga agaagggagt gcatttagt tggggcaaag    4920 tacaagagca cgctttcaac gtgctgaaag ataagttgac acatgcacct ctcctccaac    4980
ttcctgattt taataagact tttgagcttg aatgtgatgc tagtggaatt ggattgggtg    5040
gtgttttgtt acaagaaggc aaacctgttg catatttag tgaaaaattg agtgggtctg    5100
ttctaaatta ttctacttat gataaggaat tatatgctct tgtgcgaaca ttagaaacat    5160
ggcagcatta tttgtggccc aaaagagtttg ttattcattc tgatcatgaa tctttgaaac    5220
atattcgtag tcaaggaaaa ctgaaccgta gacatgctaa gtgggttgaa tttatcgaat    5280
cgtttcctta tgttattaag cacaagaaag gaaaagagaa tatcattgct gacgctttgt    5340
ctaggagata tactttgctg aatcaacttg actacaaaat ctttggatta gagacgatta    5400
```

```
aagaccaata tgttcatgat gctgatttta aagatgtgtt gctgcattgt aaagatggga   5460
aaggatggaa caaatatatc gttagtgatg ggtttgtgtt tagagctaac aagctatgca   5520
ttccagctag ctccgttcgt tgttgttgt tacaggaagc acatggaggt ggcttaatgg    5580
gacattttgg agcaaagaaa acggaggaca tacttgctgg tcatttcttt tggcccaaga   5640
tgagaagaga tgtggtgaga ttggttgctc gttgcacgac atgccaaaag gcgaagtcac   5700
ggttaaatcc acacggtttg tatttgcctc tacccgttcc tagtgctcct tgggaagata   5760
tttctatgga ttttgtgctg ggattgccta ggactaggaa gggacgtgat agtgtgtttg   5820
tggttgttga tagattttct aagatggcac atttcatacc atgtcataaa actgacgatg   5880
ctactcatat tgctgatttg ttctttcgtg aaattgttcg cttgcatggt gtgcccaaca   5940
caatcgtttc tgatcgtgat gctaaatttc ttagtcattt ttggaggact ttgtgggcaa   6000
aattggggac taagctttta ttttctacta catgtcatcc tcaaactgat ggtcaaactg   6060
aagttgtgaa tagaactttg tctactatgt taagggcagt tctaaagaag aatattaaga   6120
tgtgggagga ctgtttgcct catattgaat ttgcttataa tcgatcattg cattctacta   6180
caaagatgtg cccatttcag attgtatatg gtttgttacc tcgtgctcct attgatttaa   6240
tgcctttgcc atcttctgaa aaactaaatt ttgatgctac taggcgtgct gaattgatgt   6300
taaaactgca cgaaactact aaagaaaaca tagagcgtat gaatgctaga tataagtttg   6360
ctagtgataa aggtagaaag gaaataaatt ttgaacctgg agatttagtt tggttgcatt   6420
tgagaaagga aaggtttcct gaattacgaa aatctaaatt gttgcctcga gccgatggac   6480
cgtttaaagt gctagagaaa attaacgaca atgcatatag gctagatctg cctgcagact   6540
ttggggttag ccccacattt aacattgcag atttaaagcc ctacttggga gaggaagttg   6600
agcttgagtc gaggacgact caaatgcaag aaggggagaa tgatgaagac atccacacta   6660
ctgatgcatc tataccaata caagtaccaa tttctggtcc cattactcgc gctcgtgctc   6720
gtcaactcaa ccatcaggtg attacactct tgagttcatg tccatcatat ttagagccat   6780
ggagacccgt gcactcttgt tttgcttagg aatcagggag aagaccgaaa gggaaaagga   6840
tttgaacatg ctggattcgg actgcagaag aacaccaact tgtgacggtc accacggtca   6900
gatgcgggct cggattggaa tgttcaagca caacatggaa agcttatcaa gtctactttc   6960
atatggatcc ggaattatag tcatatctgt tctgaggccg ccgtaatcat tgttttctta   7020
ccgagacatt tcctgccttt tctgcccatg gtgctgcgtc accctatttt ggcccaatgg   7080
gtcgtgtatc aagttaggtc cattagggac gcatcctagg gttgcagcac gaccccaata   7140
cccttgtggt cgtcctccca tgtttataaa cccccctagcc gccaccaaga acagcgggtt   7200
ttgtttagat caagtttagc tctcgctact tgcttgtaag cgcgcgtgct agttcagccg   7260
cccgtcttct tgtcttcgga accccaccat attggagttt gattttgaaa cctacattta   7320
gatctggtaa ttcagtactt gttctacttg ttccttgctag ttcttcgatt gcttgcagga   7380
cgagtgccct agtggccagg gtgtcacgct ccacaagatc gtgacagcca taggaggtgg   7440
tgtatcggtt gctaaggcgc agcgtctttg gaaggctgta gtcgggccgt gaacgtcgtc   7500
tcctccccca atcgagttat tccacaccct ctcatcgaaa gatcgggcaa tcacccaacg   7560
ggtgcacatc ag                                                      7572
```

<210> SEQ ID NO 78
<211> LENGTH: 6682
<212> TYPE: DNA
<213> ORGANISM: Zea mays

<400> SEQUENCE: 78

```
ggttccggtg gcaaaaactc gtgctttata tgcaccccgt tcaaatcatt attctttcat        60
gtttaaaggc cagaaaataa ttatacatcc aatgacccct gaccaaattt tgaaagatga       120
tcttactagg gctgctaaaa ctgcacaaca agtcaaatcg acatcagccg cacctattaa       180
atctgaaatc aagttgcact ctcctgtttt acttgctaca cgtgctgatt ttgatgatct       240
ccatgaagct catatgccct gttatgcact tgtatgctcg cgcatgcttg ttccgcttga       300
tgatgcaccg tctttggata tacccccctgc tgttgttaac cttttgcagg agtatgctaa       360
tgtttatcct acggacttac caccgggtct tcctcccctc cgtggcattg agcatcagat       420
cgatctcatc cccggcgctt ctcttccgaa ccgcgccccg taccgtacaa atccagagga       480
gacgaaggag atccagcgcc aggtgcagac gctgcttgat aagggttaca ttcgtgagtc       540
tcttagccct tgctcggttc ctgttttact cgttccaaag aaagatgggt catggcgaat       600
gtgcgtagat tgtcgtgcta ttaataacat cacagttcgt tatcgatatc ctattccacg       660
ccttgatgat atgttagatg aacttagtgg tgccgttatt ttctctaagg ttgatttgcg       720
tagcggttac catcagatta gaatgaaact cggtgatgaa tggaaaacgg cttttaaaac       780
aaaatttggt ttatatgaat ggttggttat gccatttgga ttgactaatg ctcccagcac       840
ctttatgcgt ttaatgaacg aagttctacg ggccttcata ggtttgtttg ttgttgttta       900
tttcgatgat atccttatttt acagcaagtc tatagaggag catttagaac atttgcgtgc       960
tggttttgat gctttgcgtg ctgctcgctt ggttggtaac atggaaaagt gcacattttg      1020
cacgcaacgt gtcttgtttc ttggttatgt ggttactccg cagggcattg aggggatagc      1080
agcaagattg ctgccatcgg gagggcctac accaacgacg gtcacacaaa ttcggagctt      1140
tcttggactt gccggtttct accgcagatt tgttcgtgat tttagctcca ttgcagcgcc      1200
tctacatgag cttacaaaga aagatgtgcc gtttgcttgg agtgattcac aggaggtagc      1260
gttcagcact ttgaaagata gttaaccca agcttccctc ttgcaattgt gatgagaaca      1320
taacccgcac agatatgacc atgttaatgg ctcctgctac aaagacattg aggaacaaag      1380
aagttgattg gggaccaagt aatgatattt ccaacatttc caacaaagca agcacatcat      1440
caaatttaaa gatatacttg ggtgaggagc atacactaga gtcgaggacg actctattac      1500
aagaagggga ggatgatgag gacatcactg ccatcaatac accacaccag cgacctcctt      1560
caccatttaa taatggacca gtaaacgagt ccgtgcacgt aaatttttatt atcaggtgaa      1620
ctcgttcctt attgttgaag ctaatcattc cttaaatgag gtactaatac cttgtgatta      1680
ctttattaat ctaaggtgtt tgggaggtga accatctaga atttgagaag gcaacaaggc      1740
aataaaagct gctccacttg aggggatttc gaaactacaa caagtgcaag tttaagaggg      1800
catatctttc agctcctaag gttgtttaat gcaaataagc acttgttgga aaggtctctt      1860
tgtctacttt ctagtggatc aagaatcaac gagagatcag acactaagtg tccagaaact      1920
gccgagtgaa ctcctgctct acccaagtca atttcgtaac tgcagcatgc accaaattaa      1980
atggagcata actttccact cccaaggttg tttagtgcaa ataactactt gttggaaagc      2040
tctcttcgtc tactttcatg tgcatcaata atcaatgaca gaaaccaaac gaggcgtcca      2100
gaaactgccg agagagtttc gttctccatt agaactcctt tctattcctc tatttaagca      2160
actagcagcc accaaagaac ttgggttttt gtttgatgta agtttagcct ttgctacttc      2220
cttgtaaacg catgtgtcgg ctagaccacc cggatacttg aaacagaacc ccaactctat      2280
cagatccgtg agtgtctgct ttttatcttg ttcttgcttg ttctcgattg cttgcaggtt      2340
```

```
caaggctgtt cttggcacgg caagggcagc aacaacagga gccgatgtaa ctatcgctaa    2400
ggcgcagcac ccttgtggtt gttgtagtcg gatagcacaa cgtcgacctc cacccccaaat   2460 cgtagttatc aggagacggt gtacctgtcg ctcaaggcgc cacaccatct tggttgtggt    2520
agtcgggcag ccaacgtcgt tctccaacaa gtttccacct ccatcatctc tcatcgaaag    2580
atcgggcacc cttctacccg ttgggtttat caagtggtat caaatttcag gttgctcggt    2640
gagagatctc aatcttcctt gttttgttta cctacagtcc acttttgccc aaagatatat    2700
ttagagcaga aattcaccta aaaacagttt gagcctttgc tttactactt agttttcgac    2760
ttgttgaatt ccggtagctg catttgggtc gagttgctgg tctaaagttt tcttaccgct    2820
agagtttcga gttcgcgcca ccttgtttca atcaccagtt tagacctctt gctgcaattc    2880
aaccaaaaag aagagaaagc aaaggcgag tgcacaaaaa aagccgcact aatcagcaaa     2940
acaaaaaaag acacgtgcaa aacaaaagag agagaaaaaa accagttctg aattttggta    3000
gataaaattt gtaagtgcaa caaaacaaaa ggcagtttgt gtgccttctt tttatagttt    3060
cagaaatcag attgttgttc tgagcttttg gtgatactat ttgtgtaacg gctcgcgtct    3120
ctattacggt ttggactagg accagcacaa caccttgtgg aacgtttatt caacttgttg    3180
tggctaacgt ggtactagct attccttgga actattgttt aaacagccac ctataaatcc    3240
acaaaatttt ctacaacacc accaggttgt gctagcagcc actgttgttg ttgttcgtgc    3300
tgtttgccag cgcctcctgc tttgcgtggt gagaacttgt aagaacttgt ttaaccagtt    3360
tgagagtgag agattacaac aatgattcct agtagtttat agaatcaaag atatttttta    3420
ttgtttcttg tctttactaa acatggcagg tgatatggac atttttgacc caaccgaacg    3480
ttatattgga ggcatcattc aacacttgcc tttatatgcc ggtaaattcg atcctcatgc    3540
atacattgat tgggagctaa agctagataa ggaatttgat aagcatgatc tatctcaaaa    3600
acaaaagatt tatattgcct ctaatttgtt aactgagcac gcattgatgg aatggaaata    3660
catttgtagg cacaacaaag ttccacaatc ttgggaagac ttcaaacttc attttagaga    3720
tgcattcatt cctgcatact atgctgatca tttgcttttct aaattagaca ccttaaagca    3780
gggtgctagg actgtgaaag attattatta tgattttaaa attttttacca tgtttgctcg    3840 tttagatgaa tgcatggaag atgtcatgac taggttcatg aaaggactca attctgaaat    3900
tcagactata gtcatgcatg aagcatacaa acacatttct cacttgtttt tgcttgcatg    3960
taaagctgaa aatgagattc tattatacaa ttatacaagc actgaacatg tgagccataa    4020
ttcctctttt gcatcttctc tacatgctga tcaagaacac aaaataatga aaccagctgt    4080
tgtttttcca tcatcacaag aagaattgat tgctgacact tgtgatagtg aagatttgtg    4140
ggataatgat tcacatgtac taagacaaca actagtaaat gaacatgtta catctattat    4200
tgaaccaaac attttggcta aaaaggaaca tgtaatttgt attgcaaacg aaactgaaga    4260
aataaatttg ctctcttctt taaatacttg gggctatatt gaatttgatg atcttttttga   4320 gctcggtaat ttggaaaata ttttatttgc tagattcaac tataccatgt ccttctcatg    4380 atatattta tattgctggc aagtacaaca acataggaca atttcttgtg catagaattt    4440
ctatttcatc tagatatgtt gtttcttcac tttgtgcaaa taagatattg gtatgttctc    4500
aagaagaaaa gaatctcttg tttccatgta ctttagttga agtttcaggt ttatatttga    4560
aagacattaa taaaagctta gtcatcaaca tcaatcatga tgcaaaaccg aggacggttt    4620
gctatcaaga aggggagaat gatgagaaca taacccgcac agatatgacc atgttaatgg    4680
ctcctgctac aaagacatta aggaacaaag aagttgattg gggaccaagt aatgatattt    4740
```

```
tcaacatttc caacaaagca agcacatcat caaatttaaa gatatacttg ggtgaggagc    4800
atacactaga gtcgaggacg actctattac aagaagggga ggacgatgag gacatcactg    4860
ccatcaatac accacaccag cgacctcctt caccatttaa taatggacca gtaaacgagt    4920
ccgtgcacgt aaatttaatt atcaggtgaa ctcgttcctt gttgttgaag ctaatcattc    4980
cttaaatgag gtactaatac cttgtgatta ctttattatt ctaaggtgtt tgggaggtga    5040
accatctaga atttgagaag gcaacaaggc aataaaagtt gctccacttg agggatttc     5100 gaaactacaa caagtgcaag tttaagaggg catatctttc agctcctaag gttgtttaat    5160
gcaaataagc acttgttgga aaggtctctt tgtctacttt ctagtggatc aagaatcaac    5220
gagagatcag acactaagtg tccagaaact gccgagtgaa ctcctgctct acccaagtca    5280
atttcgtaac tgcagcatgc accaaattaa atggagcata actttccact cccaaggttg    5340
tttagtgcaa ataactactt gttggaaagc tctcttcgtc tactttcatg tgcatcaata    5400
atcaatgaca gaaaccaaac gaggcgtcca gaaactgccg agagagtttc gttctccatt    5460
agaactcctt tctattcctc tatttaagca actagcagcc accaaagaac ttgggttttt    5520
gtttgatgta agtttagcct ttgctacttc cttgtaaact catgtgtcgg ctagaccacc    5580
cggatacttg aaacaaaacc ccaactctat cagatccgtg agtgtctgct ttttatcttg    5640
ttcttgcttg ttctcgattg cttgcaggtt caaggctgtt cttggcacgg caagagcagc    5700
aacaacagga gccggtgtaa ctatcgctaa ggcgcagcac ccttgtggtt gttgtagtcg    5760
gatagcacaa cgtcgacctc cacccccaaat cgtagttatc aggagacggt gtacctgtcg    5820
ctcaaggcac cacaccatct tggttgtggt agtcgggcag ccaacgtcgt tctccaacaa    5880
gttttccacc tccatcatct ctcatcgaaa gatcgggcac ccttctaccc gttgcgttta    5940
tcaaattgcc tgattttaat gaagttttg agcttgaatg cgatgctagc ggtattgggc    6000
taggtgctgt tttgttacaa gaaggaaaac cagttgctta ttttagtgaa aaattaagcg    6060
gtgctagtct gaaatattct acttatgata aggagcttta cgctttagtg cgcactttgc    6120
atacatggca gcactatctt tggcatcgtg agttcataat tcattctgat catgaggctt    6180
taaaacatat tcgtacccaa acaaatctga accgtcgtca tgctaaatgg gtcgaattca    6240
ttgagtcctt tccttacatt attaaaccca agaccagtaa ggacaacgtt attgctgatg    6300 cttttgtctcg tcgctatacc atgctgtcac aattagattt taaaatcttt ggtttggaca    6360
ctgtgaagga tcaatatgtt gacgatgctg attttaaaga tgctttcggc cattgtatta    6420
atgggatacc atggggcaaa tttcacatac aggatgggtt cctgtttcgc gctaacaagt    6480
tgcgtgttcc agctagttcg gttcgtcttt tgttgttaca ggaggcgcat ggaggcggtc    6540 tcatgggca ttttggcgtc tacaaaacgc atgaggtgtt ggctgcccac ttctttggc     6600 ctcggatgcg cgctgatgtt gagcgccttg ttgcacgctg aaagtcgcct agagggggg    6660 tgaatagggc gaaactgaaa tt                                             6682
```

<210> SEQ ID NO 79
<211> LENGTH: 118
<212> TYPE: DNA
<213> ORGANISM: Zea mays

<400> SEQUENCE: 79

```
ccacgtattt tgcaagctat ttaactggcg gcgattgcgt acccgacgac caaaattagg    60
gtcaacgcta cctgtaggaa gtgtccgcat aaagtgcacc gcatggaaat gaagacgg     118
```

<210> SEQ ID NO 80

```
<211> LENGTH: 194
<212> TYPE: DNA
<213> ORGANISM: Zea mays

<400> SEQUENCE: 80
ccccttactt gaggataaat tatgtctaat attcaaactg gcgccgagcg tatgccgcat      60
gacctttccc atcttggctt ccttgctggt cagattggtc gtcttattac catttcaact     120
actccggtta tcgctggcga ctccttcgag atggacgccg ttggcgctct ccgtctttct     180
ccattgcgtc gtgg                                                      194

<210> SEQ ID NO 81
<211> LENGTH: 234
<212> TYPE: DNA
<213> ORGANISM: Zea mays

<400> SEQUENCE: 81
ccgtttgaat gttgacggga tgaacataat aagcaatgac ggcagcaata aactcaacag      60
gagcaggaaa gcgagggtat cctacaaagt ccagcgtacc ataaacgcaa gcctcaacgc     120
agcgacgagc acgagagcgg tcagtagcaa tccaaacttt gttactcgtc agaaaatcga     180
aatcatcttc ggttaaatcc aaaacggcag aagcctgaat gagcttaata gagg           234

<210> SEQ ID NO 82
<211> LENGTH: 400
<212> TYPE: DNA
<213> ORGANISM: Zea mays
<220> FEATURE:
<221> NAME/KEY: misc_feature
<222> LOCATION: (74)..(233)
<223> OTHER INFORMATION: n is a, c, g, or t
<220> FEATURE:
<221> NAME/KEY: misc_feature
<222> LOCATION: (368)..(400)
<223> OTHER INFORMATION: n is a, c, g, or t

<400> SEQUENCE: 82
tgagctgtcg agaataagct tgattcgttg tgaaactcac attcaattca aacttgattc      60
aaaataatta tatnnnnnnn nnnnnnnnnn nnnnnnnnnn nnnnnnnnnn nnnnnnnnnn     120
nnnnnnnnnn nnnnnnnnnn nnnnnnnnnn nnnnnnnnnn nnnnnnnnnn nnnnnnnnnn     180
nnnnnnnnnn nnnnnnnnnn nnnnnnnnnn nnnnnnnnnn nnnnnnnnnn nnncgaccgc     240
gtttcgccgc ctggtgggac ccccatgttg gctgttcctt cgaccttcag ctcggtgtgt     300
cggttgcaac cactcgccga agattccgcg aatagctcgg gattgacctg accgattccg     360
cgaataannn nnnnnnnnnn nnnnnnnnnn nnnnnnnnnn                           400

<210> SEQ ID NO 83
<211> LENGTH: 903
<212> TYPE: DNA
<213> ORGANISM: Zea mays

<400> SEQUENCE: 83
cgattctaga tatcatcgcc actcgtgctg gaaaggacca gacaaacaca gaaaaattcc      60
agacatattc ctacttattc agtacagtcc ctgaactaaa cccccactat agctctatca     120
ctgttcagtc gccagaatgt cttcgtcaaa acagcctcac caggaggacc atcccgattc     180
ggagcctgaa atgctcgcgg aggatgatgc tcttgaggag attgacgctt ccgaggacgt     240
cgacgttccc atgacagcg acgatgaggg ggagcccgaa gagatcaacc tgcacaacga     300
cggcgtcgcc tactttgacc tacacaagga ctcggttttc gccattgccc aacatccaac     360
```

```
ccgcccgaca ctgatcgcaa cgggtggatc agaaggagac tcggacgacg cgccaggcaa        420
gggctacgtc tttgacaccg cacacgttcc ccagcgccct ctattaccac caaactttag        480
cggcgaacct ccgaaccccc cggtagcgct ggaccgtctg tttgagattg atgggcatac        540
cgacagcatc aatgctttga cgttcaccta ccccgaggga gagtatctct tgagcggagg        600
tatggacggc aagcttcgcg cgtacgccgg caaggcggca ccatttcaac cgggagccgc        660
ccatgtcacc agtcgcacaa atccccttc cttgccgagt cccaggaagt cccccaaatc        720
aacttcctat cttcccttgc cccattgctc catcgtcctc ccttgtcctt agaccttggc        780
tggcatcctg accggctccg tctggtgtgt acccatggaa gaacgcaggc tcccaatcc        840 cggcgctggt ctaatcccga aagacatttt ccttcttccc taatatgggc cccggaccca        900
cta                                                                     903
```

```
<210> SEQ ID NO 84
<211> LENGTH: 857
<212> TYPE: DNA
<213> ORGANISM: Zea mays
<220> FEATURE:
<221> NAME/KEY: misc_feature
<222> LOCATION: (1)..(603)
<223> OTHER INFORMATION: n is a, c, g, or t
<220> FEATURE:
<221> NAME/KEY: misc_feature
<222> LOCATION: (779)..(821)
<223> OTHER INFORMATION: n is a, c, g, or t
<220> FEATURE:
<221> NAME/KEY: misc_feature
<222> LOCATION: (827)..(827)
<223> OTHER INFORMATION: n is a, c, g, or t
<220> FEATURE:
<221> NAME/KEY: misc_feature
<222> LOCATION: (847)..(847)
<223> OTHER INFORMATION: n is a, c, g, or t

<400> SEQUENCE: 84
```

```
nnnnnnnnnn nnnnnnnnnn nnnnnnnnnn nnnnnnnnnn nnnnnnnnnn nnnnnnnnnn         60
nnnnnnnnnn nnnnnnnnnn nnnnnnnnnn nnnnnnnnnn nnnnnnnnnn nnnnnnnnnn        120
nnnnnnnnnn nnnnnnnnnn nnnnnnnnnn nnnnnnnnnn nnnnnnnnnn nnnnnnnnnn        180
nnnnnnnnnn nnnnnnnnnn nnnnnnnnnn nnnnnnnnnn nnnnnnnnnn nnnnnnnnnn        240
nnnnnnnnnn nnnnnnnnnn nnnnnnnnnn nnnnnnnnnn nnnnnnnnnn nnnnnnnnnn        300
nnnnnnnnnn nnnnnnnnnn nnnnnnnnnn nnnnnnnnnn nnnnnnnnnn nnnnnnnnnn        360
nnnnnnnnnn nnnnnnnnnn nnnnnnnnnn nnnnnnnnnn nnnnnnnnnn nnnnnnnnnn        420
nnnnnnnnnn nnnnnnnnnn nnnnnnnnnn nnnnnnnnnn nnnnnnnnnn nnnnnnnnnn        480
nnnnnnnnnn nnnnnnnnnn nnnnnnnnnn nnnnnnnnnn nnnnnnnnnn nnnnnnnnnn        540
nnnnnnnnnn nnnnnnnnnn nnnnnnnnnn nnnnnnnnnn nnnnnnnnnn nnnnnnnnnn        600
nnnaagcaaa ttcgacccgg tcgtcggttc agggcagggt cgttaaatag ccgcttatgt        660
ctattgctgg tttaccggtt tattgactac cggaagcagt gtgaccgtgt gcttctcaaa        720
tgcctgaggc cagtttgctc aggctctccc cgtggaggta ataattgacg atatgatcnn        780
nnnnnnnnnn nnnnnnnnnn nnnnnnnnnn nnnnnnnnnn ncttccnagc acagtggcga        840
tgatatncta gaattcg                                                      857
```

```
<210> SEQ ID NO 85
<211> LENGTH: 119
<212> TYPE: DNA
<213> ORGANISM: Zea mays
```

```
<400> SEQUENCE: 85
agctccaatg tgctggaaag gcaacggtgc acttggcgga aaggccttgg gtgcttgctg      60
gcggattgca gtgtcgtttt cgtgggggat aaatcctttc cagcacagtg gcgatgata     119

<210> SEQ ID NO 86
<211> LENGTH: 1802
<212> TYPE: DNA
<213> ORGANISM: Zea mays
<220> FEATURE:
<221> NAME/KEY: misc_feature
<222> LOCATION: (643)..(834)
<223> OTHER INFORMATION: n is a, c, g, or t
<220> FEATURE:
<221> NAME/KEY: misc_feature
<222> LOCATION: (1282)..(1765)
<223> OTHER INFORMATION: n is a, c, g, or t

<400> SEQUENCE: 86
gggttttggg gccgaggatc agcgagctga ttcgtcgcca ctgtgctgga aaggtcatct      60
aaattgaaac cgcccttttta tgttatttga attccagtca tgttcttttt tccccttcg    120 ttttacaagc cttcatttgt tcagcatatt cattaattta tgatggatag aacttagaag    180
tagtagcagt aacaagtacg caaataataa acatgtatga caataagtga atgtgttaac    240
tatatactga ccattatgaa tgtgacataa gaaatagaa aatttcaaag actccatccc    300
atcatgaatt catggtttac ttacattaaa caagaatagt atacatttgt atagtggtaa    360
cagaaaaata tggcacagag cagcaattct gctcaagtcc ctagtgttac attataacaa    420
agaatattca cgttatgcga gtccatttca gctgataaga acaacaagaa gaattcctag    480
tcaggaactt actcgtggca atagcaattg gtgcagttgt tggccaatgt tccttccatc    540
ggactagctt agcacttgac agttcaaagc tgcaacactc actcgtccaa cctttcccag    600
cacattggag cttcagctgc tcgagggggg ggcccggtac ccnnnnnnnn nnnnnnnnnn    660
nnnnnnnnnn nnnnnnnnnn nnnnnnnnnn nnnnnnnnnn nnnnnnnnnn nnnnnnnnnn    720
nnnnnnnnnn nnnnnnnnnn nnnnnnnnnn nnnnnnnnnn nnnnnnnnnn nnnnnnnnnn    780
nnnnnnnnnn nnnnnnnnnn nnnnnnnnnn nnnnnnnnnn nnnnnnnnnn nnnngacgcg    840
ccctgtagcg gcgcattaag cgcggcgggt gtggtggtta cgcgcagcgt gaccgctaca    900
cttgccagcg ccctagcgcc cgctcctttc gctttcttcc cttcctttct cgccacgttc    960
gccggctttc cccgtcaagc tctaaatcgg gggctccctt tagggttccg atttagtgct   1020
ttacggcacc tcgaccccaa aaaacttgat tagggtgatg gttcacgtag tgggccatcg   1080
ccctgataga cggttttttcg cccctttgacg ttggagtcca cgttctttaa tagtggactc   1140
ttgttccaaa ctgaacaac actcaaccct atctcggtct attcttttga tttataaggg   1200 atttttgccga tttcggccta ttggttaaaa aatgagctga tttaacaaaa atttaacgcg   1260
aattttaaca aaatattaac gnnnnnnnnn nnnnnnnnnn nnnnnnnnnn nnnnnnnnnn   1320
nnnnnnnnnn nnnnnnnnnn nnnnnnnnnn nnnnnnnnnn nnnnnnnnnn nnnnnnnnnn   1380
nnnnnnnnnn nnnnnnnnnn nnnnnnnnnn nnnnnnnnnn nnnnnnnnnn nnnnnnnnnn   1440
nnnnnnnnnn nnnnnnnnnn nnnnnnnnnn nnnnnnnnnn nnnnnnnnnn nnnnnnnnnn   1500
nnnnnnnnnn nnnnnnnnnn nnnnnnnnnn nnnnnnnnnn nnnnnnnnnn nnnnnnnnnn   1560
nnnnnnnnnn nnnnnnnnnn nnnnnnnnnn nnnnnnnnnn nnnnnnnnnn nnnnnnnnnn   1620
nnnnnnnnnn nnnnnnnnnn nnnnnnnnnn nnnnnnnnnn nnnnnnnnnn nnnnnnnnnn   1680
nnnnnnnnnn nnnnnnnnnn nnnnnnnnnn nnnnnnnnnn nnnnnnnnnn nnnnnnnnnn   1740
```

```
nnnnnnnnnn nnnnnnnnnn nnnnntttct tccccctttc ctctatgata tctagattcg    1800
cg                                                                    1802

<210> SEQ ID NO 87
<211> LENGTH: 294
<212> TYPE: DNA
<213> ORGANISM: Zea mays
<220> FEATURE:
<221> NAME/KEY: misc_feature
<222> LOCATION: (1)..(3)
<223> OTHER INFORMATION: n is a, c, g, or t
<220> FEATURE:
<221> NAME/KEY: misc_feature
<222> LOCATION: (157)..(294)
<223> OTHER INFORMATION: n is a, c, g, or t

<400> SEQUENCE: 87
nnncgatgga ccgcgcttgt gtgtcgcgtt cagtttggct tttgccaagc agtagggtag      60
cttcccgcgt cggtaattat atggtatgaa ccatcacctt ttggctctac atggtatgaa     120
cgtaagatac aaattccaac tacctctagc tcgccgnnnn nnnnnnnnnn nnnnnnnnnn     180
nnnnnnnnnn nnnnnnnnnn nnnnnnnnnn nnnnnnnnnn nnnnnnnnnn nnnnnnnnnn     240
nnnnnnnnnn nnnnnnnnnn nnnnnnnnnn nnnnnnnnnn nnnnnnnnnn nnnn          294

<210> SEQ ID NO 88
<211> LENGTH: 2540
<212> TYPE: DNA
<213> ORGANISM: Zea mays
<220> FEATURE:
<221> NAME/KEY: misc_feature
<222> LOCATION: (1)..(13)
<223> OTHER INFORMATION: n is a, c, g, or t
<220> FEATURE:
<221> NAME/KEY: misc_feature
<222> LOCATION: (1274)..(2203)
<223> OTHER INFORMATION: n is a, c, g, or t
<220> FEATURE:
<221> NAME/KEY: misc_feature
<222> LOCATION: (2404)..(2540)
<223> OTHER INFORMATION: n is a, c, g, or t

<400> SEQUENCE: 88
nnnnnnnnnn nnntgtttaa ctcttcgtaa gaacagtggt acgtcccgtg tctatatttg      60
gcttttgtta aagccaacag tacatgcttg cgtgggtgaa aatgtgaaat gccatcgctg     120
tgctacaact tttcggctcc ctcctgcttc ggtgcttcca catgcccctg cacggcgtct     180
agaaatccta atgatttagc agcacacctg tccgcctagc cgcctacgcg tacacagaaa     240 acaattttt tgtccacaca cgcgcgcgct ccgagccgca gatccgagct agcgcggcgc     300
atccgacggc cacgacagcg cagtgccgtc ctccgccgcc accgcttggc gattgtccgc     360
accccaccag tccaccacct cccccacgag cgaaaaccac ggtccacgga ccacggctat     420
gttccactcc aggtggaggc tgcagccccg gtttcgcaag ccgcgccgtg gtttgcttgc     480
ccacaggcgg ccaaaccgca ccctccttcc cgtcgtttcc catctcttcc tcctttagag     540
ctaccactat ataaatcagg gctcattttc tcgctcctca caggctcatc tcgctttgga     600
tcgattggtt tcgtaactgg tgagggactg agggtctcgg agtggattga tttggggttc     660
tgttcggaga tttgcggagg gaggccttgg taccggtgat caagtgcaaa ggtccgcctt     720
gtttctcctc tgtctcttga tctgactaat cttggtttat gattcgttga gtaattttgg     780
ggaaagcttc gtccacagtt ttttttcgat gaacagtgcc gcagtggcgc tgatcttgta     840
tgctatcctg caatcgtggt gaacttattt cttttatatc ctttactccc atgaaaaggc     900
```

```
tagtaatctt tctcgatgta acatcgtcca gcactgctat taccgtgtgg tccatccgac    960
agtctggctg aacacatcat acgatctatg gagcaaaaat ctatcttccc tgttctttaa   1020
tgaaggacgt cattttcatt agtatgatct aggaatgttg caacttgcaa ggaggcgttt   1080
ctttctttga atttaactaa ctcgttgagt ggccctgttt ctcggacgta aggcctttgc   1140
tgctccacac atgtccattc gaattttacc gtgtttagca agggcgaaaa gtttgcatct   1200
tgatgattta gcttgactat gcgattgctt tcctggaccc gtgcagctgc ggtggcaagg   1260
gaggccggca agcnnnnnnn nnnnnnnnnn nnnnnnnnnn nnnnnnnnnn nnnnnnnnnn   1320
nnnnnnnnnn nnnnnnnnnn nnnnnnnnnn nnnnnnnnnn nnnnnnnnnn nnnnnnnnnn   1380
nnnnnnnnnn nnnnnnnnnn nnnnnnnnnn nnnnnnnnnn nnnnnnnnnn nnnnnnnnnn   1440
nnnnnnnnnn nnnnnnnnnn nnnnnnnnnn nnnnnnnnnn nnnnnnnnnn nnnnnnnnnn   1500
nnnnnnnnnn nnnnnnnnnn nnnnnnnnnn nnnnnnnnnn nnnnnnnnnn nnnnnnnnnn   1560
nnnnnnnnnn nnnnnnnnnn nnnnnnnnnn nnnnnnnnnn nnnnnnnnnn nnnnnnnnnn   1620
nnnnnnnnnn nnnnnnnnnn nnnnnnnnnn nnnnnnnnnn nnnnnnnnnn nnnnnnnnnn   1680
nnnnnnnnnn nnnnnnnnnn nnnnnnnnnn nnnnnnnnnn nnnnnnnnnn nnnnnnnnnn   1740
nnnnnnnnnn nnnnnnnnnn nnnnnnnnnn nnnnnnnnnn nnnnnnnnnn nnnnnnnnnn   1800
nnnnnnnnnn nnnnnnnnnn nnnnnnnnnn nnnnnnnnnn nnnnnnnnnn nnnnnnnnnn   1860
nnnnnnnnnn nnnnnnnnnn nnnnnnnnnn nnnnnnnnnn nnnnnnnnnn nnnnnnnnnn   1920
nnnnnnnnnn nnnnnnnnnn nnnnnnnnnn nnnnnnnnnn nnnnnnnnnn nnnnnnnnnn   1980
nnnnnnnnnn nnnnnnnnnn nnnnnnnnnn nnnnnnnnnn nnnnnnnnnn nnnnnnnnnn   2040
nnnnnnnnnn nnnnnnnnnn nnnnnnnnnn nnnnnnnnnn nnnnnnnnnn nnnnnnnnnn   2100
nnnnnnnnnn nnnnnnnnnn nnnnnnnnnn nnnnnnnnnn nnnnnnnnnn nnnnnnnnnn   2160
nnnnnnnnnn nnnnnnnnnn nnnnnnnnnn nnnnnnnnnn nnnaggcaat gccagcctgc   2220
cctttcgatg aggaggtaca tacacgctgg cgatggaccg cgcttgtgtg tcgcgttcag   2280
tttggctttt gccaagcagt agggtagctt cccgcgtcgg taattatatg gtatgaacca   2340
tcaccttttg gctctacatg gtatgaacgt aagatacaaa ttccaactac ctctagctcg   2400
ccgnnnnnnn nnnnnnnnnn nnnnnnnnnn nnnnnnnnnn nnnnnnnnnn nnnnnnnnnn   2460
nnnnnnnnnn nnnnnnnnnn nnnnnnnnnn nnnnnnnnnn nnnnnnnnnn nnnnnnnnnn   2520
nnnnnnnnnn nnnnnnnnnn                                               2540

<210> SEQ ID NO 89
<211> LENGTH: 153
<212> TYPE: DNA
<213> ORGANISM: Zea mays

<400> SEQUENCE: 89
cgatggaccg cgcttgtgtg tcgcgttcag tttggctttt gccaagcagt agggtagctt     60
cccgcgtcgg taattatatg gtatgaacca tcaccttttg gctctacatg gtatgaacgt    120
aagatacaaa ttccaactac ctctagctcg ccg                                 153
```